(12) United States Patent
Buckmelter et al.

(10) Patent No.: US 10,399,980 B2
(45) Date of Patent: *Sep. 3, 2019

(54) PURINONES AS UBIQUITIN-SPECIFIC PROTEASE 1 INHIBITORS

(71) Applicant: FORMA Therapeutics, Inc., Watertown, MA (US)

(72) Inventors: Alexandre Joseph Buckmelter, Acton, MA (US); Stephanos Ioannidis, Natick, MA (US); Bruce Follows, Littleton, MA (US); Gary Gustafson, Ridgefield, CT (US); Minghua Wang, Acton, MA (US); Justin A. Caravella, Cambridge, MA (US); Zhongguo Wang, Lexington, MA (US); Edward L. Fritzen, Niantic, CT (US); Jian Lin, Acton, MA (US)

(73) Assignee: FORMA Therapeutics, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/051,879

(22) Filed: Aug. 1, 2018

(65) Prior Publication Data

US 2018/0339986 A1    Nov. 29, 2018

Related U.S. Application Data

(63) Continuation of application No. 15/355,887, filed on Nov. 18, 2016, now Pat. No. 10,189,841.

(60) Provisional application No. 62/258,162, filed on Nov. 20, 2015.

(51) Int. Cl.
*C07D 473/00* (2006.01)
*A61K 31/522* (2006.01)

(52) U.S. Cl.
CPC .......... *C07D 473/00* (2013.01); *A61K 31/522* (2013.01)

(58) Field of Classification Search
None
See application file for complete search history.

(56) References Cited

U.S. PATENT DOCUMENTS

| | | | |
|---|---|---|---|
| 4,859,672 A | 8/1989 | Spada et al. |
| 5,955,610 A | 9/1999 | Nguyen-Ba et al. |
| 6,372,740 B1 | 4/2002 | Murata et al. |
| 6,376,501 B1 | 4/2002 | Isobe et al. |
| 6,444,656 B1 | 9/2002 | Nguyen-Ba et al. |
| 6,552,192 B1 | 4/2003 | Hanus et al. |
| 6,630,478 B2 | 10/2003 | Diamond et al. |
| 6,630,490 B2 | 10/2003 | Diamond et al. |
| 6,734,187 B1 | 5/2004 | Tanaka et al. |
| 7,247,621 B2 | 7/2007 | Hong et al. |
| 7,285,658 B2 | 10/2007 | Cook et al. |
| 7,291,736 B2 | 11/2007 | Cole et al. |
| 7,371,857 B2 | 5/2008 | Ramasamy et al. |
| 7,884,109 B2 | 2/2011 | Ohlmeyer et al. |
| 7,919,498 B2 | 4/2011 | Chen et al. |
| 7,951,810 B2 | 5/2011 | Critchley et al. |
| 7,989,459 B2 | 8/2011 | Roughton et al. |
| 8,383,634 B2 | 2/2013 | Mortensen et al. |
| 8,404,856 B2 | 3/2013 | Tucker et al. |
| 8,415,321 B2 | 4/2013 | Schinazi et al. |
| 8,541,192 B2 | 9/2013 | D'Andrea |
| 8,703,778 B2 | 4/2014 | Ren et al. |
| 8,735,586 B2 | 5/2014 | Alonso et al. |
| 8,846,672 B2 | 9/2014 | Cooymans et al. |
| 8,921,560 B2 | 12/2014 | Cooymans et al. |
| 8,927,720 B2 | 1/2015 | Cooymans et al. |
| 8,946,257 B2 | 2/2015 | Solana |
| 8,987,473 B2 | 3/2015 | Nagai et al. |
| 9,518,032 B2 | 12/2016 | D'Andrea et al. |
| 9,573,939 B2 | 2/2017 | McComas et al. |
| 10,189,841 B2 | 1/2019 | Buckmelter et al. |

(Continued)

FOREIGN PATENT DOCUMENTS

EP      0385850 A2      9/1990
JP      S63199347       8/1988

(Continued)

OTHER PUBLICATIONS

Areias, F. et al. In silico directed chemical probing of the adenosine receptor family, Bioorganic & Medicinal Chemistry, 18(9): 3043-3052 (2010).
Banker, G., Modern Pharmaceutics, 3rd Edition, Marcel Dekker, Inc., 3 pages (retrieved Nov. 8, 2007).
Cohn, M. A., et al., A UAF I-Containing Multisubunit Protein Complex Regulates the Fanconi Anemia Pathway. Mol. Cell 28, 786-797 (2007).
Cole, A. et al. 2-Benzimidazolyl-9-(chroman-4-yl)-purinone derivatives as JAK3 inhibitors, Bioorganic & Medicinal Chemistry Letters, 19(23): 6788-6792 (2009).

(Continued)

*Primary Examiner* — Emily A Bernhardt
*Assistant Examiner* — Laura M Daniel
(74) *Attorney, Agent, or Firm* — Choate, Hall & Stewart LLP; Michael A. Shinall; Nicholas J. Pace

(57) ABSTRACT

The application relates to inhibitors of USP1 useful in the treatment of cancers, and other USP1 associated diseases and disorders, having the Formula:

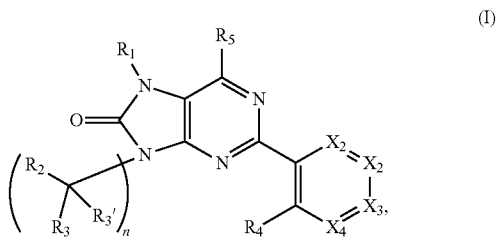

where $R_1$, $R_2$, $R_3$, $R_{3'}$, $R_4$, $R_5$, $X_1$, $X_2$, $X_3$, $X_4$, and n are described herein.

11 Claims, No Drawings

(56) References Cited

U.S. PATENT DOCUMENTS

| | | |
|---|---|---|
| 2002/0040031 A1 | 4/2002 | Glasky et al. |
| 2002/0040032 A1 | 4/2002 | Glasky et al. |
| 2002/0091133 A1 | 7/2002 | Taylor |
| 2002/0128264 A1 | 9/2002 | Taylor |
| 2002/0156277 A1 | 10/2002 | Fick et al. |
| 2003/0187261 A1 | 10/2003 | Havlicek et al. |
| 2004/0166137 A1 | 8/2004 | Lackey |
| 2005/0043239 A1 | 2/2005 | Douangpanya et al. |
| 2005/0054614 A1 | 3/2005 | Diacovo et al. |
| 2005/0239809 A1 | 10/2005 | Watts et al. |
| 2006/0079538 A1 | 4/2006 | Hallahan et al. |
| 2006/0106038 A1 | 5/2006 | Bouscary et al. |
| 2007/0021443 A1 | 1/2007 | Ohlmeyer et al. |
| 2008/0119496 A1 | 5/2008 | Ohlmeyer et al. |
| 2008/0254029 A1 | 10/2008 | Yanni et al. |
| 2008/0287469 A1 | 11/2008 | Diacovo et al. |
| 2009/0005560 A1 | 1/2009 | Oka et al. |
| 2009/0023723 A1 | 1/2009 | Cole et al. |
| 2009/0118301 A1 | 5/2009 | Lu et al. |
| 2009/0182035 A1 | 7/2009 | Yanni et al. |
| 2010/0144738 A1 | 6/2010 | Bornmann et al. |
| 2011/0257167 A1 | 10/2011 | Chopra et al. |
| 2011/0269780 A1 | 11/2011 | Emmanuel et al. |
| 2013/0089512 A1 | 4/2013 | Eastwood et al. |
| 2013/0102613 A1 | 4/2013 | Xu et al. |
| 2013/0137694 A1 | 5/2013 | Batist et al. |
| 2013/0165426 A1 | 6/2013 | Ruel et al. |
| 2013/0253005 A1 | 9/2013 | D'Andrea et al. |
| 2013/0267556 A1 | 10/2013 | Cooymans et al. |
| 2014/0005164 A1 | 1/2014 | Varrone et al. |
| 2014/0030425 A1 | 1/2014 | Owei et al. |
| 2014/0113904 A1 | 4/2014 | Mortensen et al. |
| 2014/0148433 A1 | 5/2014 | Follmann et al. |
| 2014/0275011 A1 | 9/2014 | Mastracchio et al. |
| 2014/0275033 A1 | 9/2014 | Li et al. |
| 2015/0045368 A1 | 2/2015 | Bregman et al. |
| 2016/0008356 A1 | 1/2016 | Hege |
| 2016/0159801 A1 | 6/2016 | Quinn et al. |
| 2017/0145012 A1 | 5/2017 | Buckmelter et al. |

FOREIGN PATENT DOCUMENTS

| | | |
|---|---|---|
| JP | 2001048882 A | 2/2001 |
| JP | 2001213867 A | 8/2001 |
| JP | 2004217582 A | 8/2004 |
| JP | 2011136925 A | 7/2011 |
| JP | 2012012332 A | 1/2012 |
| JP | 6024979 B2 | 11/2016 |
| WO | WO-2005016348 A1 | 2/2005 |
| WO | WO-2005120511 A1 | 12/2005 |
| WO | WO-2006108103 A1 | 10/2006 |
| WO | WO-2008030744 A2 | 3/2008 |
| WO | WO-2008045529 A1 | 4/2008 |
| WO | WO-2008051494 A1 | 5/2008 |
| WO | WO-2008060301 A1 | 5/2008 |
| WO | WO-2008117796 A1 | 10/2008 |
| WO | WO-2008131501 A2 | 11/2008 |
| WO | WO-2008131502 A2 | 11/2008 |
| WO | WO-2008143674 A1 | 11/2008 |
| WO | WO-2009062059 A2 | 5/2009 |
| WO | WO-2011/137320 A2 | 11/2011 |
| WO | WO-2012009258 A2 | 1/2012 |
| WO | WO-2013025628 A1 | 2/2013 |
| WO | WO-2013034048 A1 | 3/2013 |
| WO | WO-2014043246 A1 | 3/2014 |
| WO | WO-2014134240 A1 | 9/2014 |
| WO | WO-2015002754 A2 | 1/2015 |
| WO | WO-2017/087837 A1 | 5/2017 |

OTHER PUBLICATIONS

Dexheimer, T.S. et al., Synthesis and Structure—Activity Relationship Studies of N-Benzyl-2-phenylpyrimidin-4-amine Derivatives as Potent USP1/UAF1 Deubiquitinase Inhibitors with Anticancer Activity against Nonsmall Cell Lung Cancer, J. Med. Chem., 57: 8099-8110 (2014).

Huang, T. T. et al., Regulation of monoubiquitinated PCNA by DUB autocleavage. Nat. Cell Biol. 8, 339-347 (2006).

Hussain, S. et. al., DUBs and cancer: The role of deubiquitinating enzymes as oncogenes, non-oncogenes and tumor suppressors. Cell Cycle 8, 1688-1697 (2009).

International Search Report for PCT/US2016/062837, 4 pages (dated Jan. 25, 2017).

Lee, J.-K. et al. USP1 targeting impedes GBM growth by inhibiting stem cell maintenance and radioresistance. Neuro. Oncol. 18(1) 37-47 (2015).

Mistry, H. et al., Small-Molecule Inhibitors of USP1 Target ID1 Degradation in Leukemic Cells, Mol Cancer Ther., 12(12): 2651-2662 (2013).

Nagarajan, Shanthi et al. Receptor-Ligand Interaction-Based Virtual Screening for Novel Eg5/Kinesin Spindle Protein Inhibitors, Journal of Medicinal Chemistry, vol. 55, No. 6, p. 2561-2573, (2012).

Numan, S. M. B., et al. The deubiquitinating enzyme USP1 regulates the fanconi anemia pathway Mol. Cell 17, 331-339 (2005).

Oestergaard, V. H. et al. Deubiquitination of FANCD2 Is Required for DNA Crosslink Repair, Mol. Cell 28, 798-809 (2007).

STN Accession No. 1999: 425755 to Isobe et al. (corresponds to U.S. Pat. No. 6,376,501 B2 dated Apr. 2002).

Villamil, M. A., et al., Serine phosphorylation is critical for the activation of ubiquitin-specific protease 1 and its interaction with WD40-repeat protein UAFI Biochem. 51, 9112-9123 (2012).

Williams, S. A. et al., USP1 deubiquitinates ID proteins to preserve a mesenchymal stem cell program in osteosarcoma Cell 146, 918-930 (2011).

Written Opinion for PCT/US2016/062837, 6 pages (dated Jan. 25, 2017).

Zaki, M. et al. Synthesis of 6-cyano and 6-unsubstituted 2-aryl-8-oxopurine from a common 2-oxoimidazole precursor, Tetrahedron, 67(4): 755-762 (2011).

PURINONES AS UBIQUITIN-SPECIFIC PROTEASE 1 INHIBITORS

RELATED APPLICATIONS

This application is a continuation of U.S. application Ser. No. 15/355,887, filed Nov. 18, 2016 know U.S. Pat. No. 10,189,841), which claims the benefit of and priority to U.S. provisional application No. 62/258,162, filed Nov. 20, 2015, the entire contents of each of which are incorporated herein by reference in its entirety.

FIELD OF DISCLOSURE

The present application is directed to inhibitors of ubiquitin-specific protease 1 (USP1) useful in the treatment of diseases or disorders associated with USP1 enzymes. Specifically, the application is concerned with compounds and compositions thereof, which inhibit USP1, methods of treating diseases or disorders associated with USP1, and methods of synthesis of these compounds.

BACKGROUND OF THE APPLICATION

Ubiquitination is a reversible process which involves a family of deubiquitinating enzymes (DUBs) that regulate a variety of cellular processes by deconjugating ubiquitin from the substrate. DUBs are encoded by approximately 100 human genes and are classified into six families, with the largest family being the ubiquitin-specific proteases (USPs) that has more than 50 members. DUBs and their substrate proteins are often deregulated in cancers, supporting the hypothesis that targeting specific DUB family members may result in antitumor activity through enhancing the ubiquitination and subsequent degradation of oncogenic substrates and the activity of other key proteins involved in tumor growth, survival, differentiation and maintenance of the tumor microenvironment. (Hussain, S., et. al., "DUBs and cancer: The role of deubiquitinating enzymes as oncogenes, non-oncogenes and tumor suppressors." *Cell Cycle* 8, 1688-1697 (2009))

USP1 is a cysteine isopeptidase of the USP subfamily of DUBs. (Nijman, S. M. B., et al. "The deubiquitinating enzyme USP1 regulates the fanconi anemia pathway. *Mol. Cell* 17, 331-339 (2005)) Full-length human USP1 is composed of 785-amino acids, including a catalytic triad composed of Cys90, His593 and Asp751. (Villamil, M. A., et al., "Serine phosphorylation is critical for the activation of ubiquitin-specific protease 1 and its interaction with WD40-repeat protein UAF1." *Biochem.* 51, 9112-9113 (2012)) USP1 is relatively inactive on its own and full enzymatic activity is achieved only when bound in a heterodimeric complex with UAF1, a cofactor which also binds to and regulates the activity of USP12 and USP46. (Cohn, M. A., et al., "A UAF1-Containing Multisubunit Protein Complex Regulates the Fanconi Anemia Pathway." *Mol. Cell* 28, 786-797 (2007))

USP1 deubiquitinates a variety of cellular targets involved in different processes related to cancer. For example, USP1 deubiquitinates PCNA (proliferating cell nuclear antigen), a key protein in translesion synthesis (TLS), and FANCD2 (Fanconi anemia group complementation group D2, a key protein in the Fanconi anemia (FA) pathway. (Nijman, S. M. B. et al. "The deubiquitinating enzyme USP1 regulates the Fanconi anemia pathway." *Mol. Cell* 17, 331-339 (2005); Huang, T. T. et al., "Regulation of monoubiquitinated PCNA by DUB autocleavage." *Nat. Cell Biol.* 8, 339-347 (2006)) These DNA damage response (DDR) pathways are essential for repair of DNA damage induced by DNA cross-linking agents such as cisplatin, mitomycin C, diepoxybutane, ionizing radiation and ultraviolet radiation.

In vivo studies in mouse embryonic fibroblasts (MEFs) from USP1-deficient mice show increased levels of Ub-PCNA and Ub-FANCD2 in chromatin, demonstrate impaired FANCD2 foci assembly and are defective in homologous recombination repair. Disruption of the USP1 gene in chicken cells (DT40) has been shown to result in DNA crosslinker hypersensitivity. (Oestergaard, V. H. et al. Deubiquitination of FANCD2 Is Required for DNA Crosslink Repair. *Mol. Cell* 28, 798-809 (2007)) Moreover, depletion of USP1 in human cell lines by siRNA results in elevated Ub-PCNA levels with increased recruitment of DNA polymerases specialized for translesion synthesis. (Cohn, M. A. et al., "A UAF1-Containing Multisubunit Protein Complex Regulates the Fanconi Anemia Pathway." *Mol. Cell* 28, 786-797 (2007); Huang, T. T. et al., "Regulation of monoubiquitinated PCNA by DUB autocleavage." *Nat. Cell Biol.* 8, 339-347 (2006))

In addition to regulating protein dynamics in DDR pathways, USP1 promotes tumor stem cell maintenance and radioresistance in glioblastoma via stabilization of ID1 and CHEK1 and plays a role in regulating proliferation and differentiation through deubiquitinating and stabilizing inhibitors of DNA binding (IDs) that antagonize basic helix-loop-helix (bHLH) transcription factors. (Lee, J.-K. et al., "USP1 targeting impedes GBM growth by inhibiting stem cell maintenance and radioresistance." *Neuro. Oncol.* 1-11 (2015). doi: 10.1093/neuonc/nov091) shRNA knockdown of USP1 in U2OS cells induces cell cycle arrest via ID proteins and shRNA knockdown of USP1 in 143B human osteosarcoma xenografts inhibits tumor growth result. (Williams, S. A. et al., "USP1 deubiquitinates ID proteins to preserve a mesenchymal stem cell program in osteosarcoma." *Cell* 146, 918-930 (2011))

Inhibition of USP1 with small molecule inhibitors therefore has the potential to be a treatment for cancers and other disorders. For this reason, there remains a considerable need for potent small molecule inhibitors of USP1.

SUMMARY OF THE APPLICATION

A first aspect of the application relates to compounds of Formula (I):

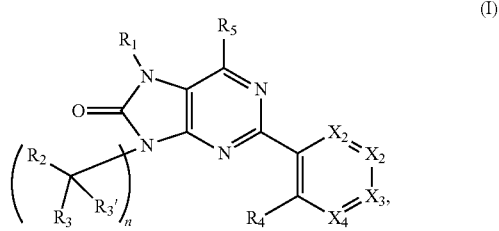

and pharmaceutically acceptable salts, hydrates, solvates, isotopes, prodrugs, stereoisomers, and tautomers thereof, wherein:
$X_1$ is $CR_6$ or N;
$X_2$ is $CR_7$ or N;
$X_3$ is $CR_8$ or N;
$X_4$ is $CR_9$ or N;

$R_1$ is H, —$CD_3$, $(C_1-C_6)$ alkyl, $(C_2-C_6)$ alkenyl, $(C_2-C_6)$ alkynyl, $(C_1-C_6)$ haloalkyl, $(C_2-C_6)$ hydroxyalkyl, $(C_3-C_8)$ cycloalkyl, or heterocycloalkyl, wherein the alkyl, alkenyl, alkynyl, cycloalkyl, and heterocycloalkyl are optionally substituted with one or more substituents selected from halogen, —$OR_{20}$, —$C(O)R_{20}$, —$CO_2R_{20}$, —$NR_{18}R_{19}$, —$NR_{20}C(O)R_{21}$, —$C(O)NR_{20}R_{21}$, —$NR_{20}C(O)NR_{21}R_{22}$, —$NR_{20}S(O)_rR_{21}$, —$S(O)_rNR_{20}R_{21}$, —$NR_{20}S(O)_rNR_{21}R_{22}$, —$S(O)_rR_{20}$, —$P(O)R_{20}R_{21}$, oxo, and —$Si((C_1-C_4) \text{ alkyl})_3$;

$R_2$ is $(C_6-C_{14})$ aryl, heteroaryl, $(C_3-C_{10})$ cycloalkyl, or heterocycloalkyl, wherein the aryl, heteroaryl, cycloalkyl, and heterocycloalkyl are substituted with one or more $R_{10}$;

$R_3$ is H, D, $(C_1-C_6)$ alkyl, $(C_1-C_6)$ haloalkyl, $(C_1-C_6)$ hydroxyalkyl, $(C_1-C_6)$ aminoalkyl, heterocycloalkyl, halogen —$C(O)OH$, —$C(O)NH_2$, or CN;

$R_{3'}$ is H, D, $(C_1-C_6)$ alkyl, $(C_1-C_6)$ haloalkyl, $(C_1-C_6)$ hydroxyalkyl, $(C_1-C_6)$ aminoalkyl, heterocycloalkyl, halogen, —$C(O)OH$, —$C(O)NH_2$, or CN; or $R_3$ and $R_{3'}$ together with the carbon atom to which they are attached form a $(C_3-C_7)$ cycloalkyl ring; $R_3$ and $R_{3'}$ together with the carbon atom to which they are attached form a heterocycloalkyl ring;

$R_4$ is $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_3-C_8)$ cycloalkyl, —O—$(C_0-C_2)$-alkylene-$(C_3-C_8)$ cycloalkyl, heterocycloalkyl, —O—$(C_0-C_2)$-alkylene-heterocycloalkyl, halogen, —OH, —$NH_2$, CN, —$C(O)(C_1-C_4)$ alkyl, —$C(O)O(C_1-C_4)$ alkyl, —$NR_{20}C(O)O(C_1-C_4)$ alkyl, —$Si(CH_3)_3$, —$SF_5$, —$S(O)_p(C_1-C_4)$alkyl, —$S(O)_p(NH)(C_1-C_4)$ alkyl, —$NH(C_1-C_4)$ alkyl, —$N((C_1-C_4) \text{ alkyl})_2$, —NH—$(C_0-C_2)$-alkylene-$(C_3-C_8)$ cycloalkyl, or —NH—$(C_0-C_2)$-alkylene-heterocycloalkyl, wherein the alkyl, alkenyl, alkynyl, and alkoxy are optionally substituted with one or more substituents selected from $(C_1-C_6)$ alkyl, $(C_1-C_6)$ alkoxy, $(C_3-C_8)$ cycloalkyl, halogen, —OH, —$S(O)_r(C_1-C_4)$ alkyl, —$S(O)_r(NH)(C_1-C_4)$ alkyl, —$SF_5$, —$Si(CH_3)_3$, —$NH_2$, —$NH(C_1-C_4)$ alkyl, —$N((C_1-C_4) \text{ alkyl})_2$, —$C(O)NH_2$, —$C(O)NH(C_1-C_4)$ alkyl, and —$C(O)N((C_1-C_4) \text{ alkyl})_2$; and the cycloalkyl, heterocycloalkyl, aryl and heteroaryl are optionally substituted with one or more substituents selected from $(C_1-C_6)$ alkyl, $(C_1-C_6)$ haloalkyl, and halogen; or $R_4$ and $X_4$ together with the atoms to which they are attached form a $(C_6-C_{14})$ aryl ring optionally substituted with one or more $R_{17}$; or $R_4$ and $X_4$ on adjacent atoms together with the atoms to which they are attached form a heteroaryl ring optionally substituted with one or more $R_{17}$; or $R_4$ and $X_4$ together with the atoms to which they are attached form a $(C_5-C_7)$ cycloalkyl ring optionally substituted with one or more $R_{17}$; or $R_4$ and $X_4$ on adjacent atoms together with the atoms to which they are attached form a heterocycloalkyl ring optionally substituted with one or more $R_{17}$;

$R_5$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ hydroxyalkyl, $(C_1-C_6)$ haloalkoxy, halogen, $(C_3-C_6)$ cycloalkyl, heterocycloalkyl, —$C(O)O(C_1-C_4)$ alkyl, —$C(O)(C_1-C_4)$ alkyl, —$C(O)NR_{13}R_{14}$, —OH, —$NH_2$, CN, —$NH(C_1-C_4)$ alkyl, —$N((C_1-C_4) \text{ alkyl})_2$ or —$NR_{13}C(O)R_{14}$; or $R_1$ and $R_5$ together with the atoms to which they are attached form a heterocycloalkyl ring;

each $R_6$, $R_7$, $R_8$, and $R_9$ is independently, at each occurrence, H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, $(C_3-C_8)$ cycloalkyl ring, heterocycloalkyl, or halogen, wherein the alkyl is optionally substituted with one or more $(C_1-C_6)$ alkoxy;

each $R_{10}$ is independently at each occurrence D, —$CD_3$, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, halogen, —$C(O)R_{14}$, —$C(O)OR_{13}$, —$NR_{13}R_{14}$, —$NR_{13}C(O)R_{14}$, —$NR_{13}C(O)NR_{13}R_{14}$, —$C(O)NR_{13}R_{14}$, —$S(O)_pR_{14}$, —$NR_{13}S(O)_pR_{14}$, —$S(O)_pNR_{13}R_{14}$, —CN, —$(C_0-C_2)$-alkylene-$(C_6-C_{14})$ aryl, —$(C_0-C_2)$-alkylene-heteroaryl, —$(C_0-C_2)$-alkylene-$(C_3-C_8)$ cycloalkyl, —$(C_0-C_2)$-alkylene-heterocycloalkyl, —O—$(C_0-C_2)$-alkylene-aryl, —O—$(C_0-C_2)$-alkylene-heteroaryl, —O—$(C_0-C_2)$-alkylene-$(C_3-C_8)$ cycloalkyl, or —O—$(C_0-C_2)$-alkylene-heterocycloalkyl, wherein the aryl, heteroaryl, cycloalkyl and heterocycloalkyl are optionally substituted with one or more $R_{11}$ and the alkyl, alkenyl, alkynyl, and alkoxy are optionally substituted with one or more $R_{12}$; or two $R_{10}$ on adjacent atoms together with the atoms to which they are attached form a $(C_6-C_{14})$ aryl ring optionally substituted with one or more $R_{11}$; or two $R_{10}$ on adjacent atoms together with the atoms to which they are attached form a heteroaryl ring optionally substituted with one or more $R_{11}$; or two $R_{10}$ on adjacent atoms together with the atoms to which they are attached form a $(C_3-C_8)$ cycloalkyl ring optionally substituted with one or more $R_{11}$; or two $R_{10}$ on adjacent atoms together with the atoms to which they are attached form a heterocycloalkyl ring optionally substituted with one or more $R_{11}$; or two $R_{10}$ on the same atom to which they are attached form a spirocycloalkyl ring optionally substituted with one or more $R_{11}$; or two $R_{10}$ on the same atom to which they are attached form a spiroheterocycloalkyl ring optionally substituted with one or more $R_{11}$;

each $R_{11}$ is independently at each occurrence D, —$CD_3$, $(C_1-C_6)$ alkyl, $(C_1-C_6)$ alkoxy, $(C_1-C_6)$ haloalkyl, $(C_1-C_6)$ haloalkoxy, halogen, CN, —OH, —$NH_2$, —$NH(C_1-C_4)$ alkyl, —$N((C_1-C_4) \text{ alkyl})_2$, —$C(O)O(C_1-C_4)$ alkyl, —$S(O)_q(C_1-C_4)$ alkyl, —$C(O)NH_2$, —$C(O)NH(C_1-C_4)$ alkyl, —$C(O)N((C_1-C_4) \text{ alkyl})_2$, —$NHC(O)(C_1-C_4)$ alkyl, —$N((C_1-C_4) \text{ alkyl})C(O)(C_1-C_4)$ alkyl, $(C_6-C_{14})$ aryl, heteroaryl, $(C_3-C_8)$ cycloalkyl, or heterocycloalkyl, wherein the alkyl, alkoxy, $(C_3-C_8)$ cycloalkyl, heterocycloalkyl, aryl, and heteroaryl are optionally substituted with one or more substituents selected from $(C_1-C_6)$ alkyl, $(C_1-C_6)$ alkoxy, $(C_1-C_6)$ haloalkyl, —$C(O)OH$, —$C(O)O(C_1-C_4)$ alkyl, —$C(O)(C_1-C_4)$ alkyl, —$S(O)_q(C_1-C_4)$ alkyl, —$C(O)NH(C_1-C_4)$ alkyl, —$C(O)N((C_1-C_4) \text{ alkyl})_2$, —OH, —$NH_2$, —CN, —$NH(C_1-C_4)$ alkyl, and —$N((C_1-C_4) \text{ alkyl})_2$; or two $R_{11}$ on adjacent atoms together with the atoms to which they are attached form a heterocycloalkyl ring; or two $R_{11}$ on adjacent atoms together with the atoms to which they are attached form a $(C_5-C_8)$ cycloalkyl ring; or two $R_{11}$ on adjacent atoms together with the atoms to which they are attached form a $(C_6-C_{14})$ aryl ring; or two $R_{11}$ on adjacent atoms together with the atoms to which they are attached form a heteroaryl ring; or two $R_{11}$ together with the atom to which they are attached form a C=O;

each $R_{12}$ is independently at each occurrence $(C_1-C_6)$ alkoxy, —$NR_{15}R_{16}$, —$NR_{15}C(O)NR_{15}R_{16}$, —$NR_{15}C(O)R_{16}$, —$NR_{15}S(O)_mR_{16}$, or —$C(O)NH(C_3-C_8)$ cycloalkyl;

each $R_{13}$ is independently at each occurrence H or $(C_1-C_4)$ alkyl;

each $R_{14}$ is independently at each occurrence H, $(C_1-C_6)$ alkyl, $(C_2-C_6)$ alkenyl, $(C_2-C_6)$ alkynyl, $(C_1-C_6)$ haloalkyl, —$(C_0-C_2)$-alkylene-$(C_3-C_8)$ cycloalkyl, —$(C_0-C_2)$-alkylene-heterocycloalkyl, —$(C_0-C_2)$-alkylene-$(C_6-C_{14})$ aryl, or —$(C_0-C_2)$-alkylene-heteroaryl, wherein the alkyl, cycloalkyl, heterocycloalkyl, aryl, and heteroaryl is optionally substituted with one or more substituents selected from ($C_1$-$C_4$) alkyl optionally substituted with ($C_1$-$C_4$) alkoxy, ($C_1$-$C_4$) alkoxy, ($C_1$-$C_4$) haloalkyl, ($C_1$-$C_4$) haloalkoxy, ($C_6$-$C_{14}$) aryl, heteroaryl, halogen, —OH, —NH$_2$, CN, —C(O)NH$_2$, —C(O)NH($C_1$-$C_4$) alkyl, —C(O)N(($C_1$-$C_4$) alkyl)$_2$, —NH($C_1$-$C_4$) alkyl, and —N(($C_1$-$C_4$) alkyl)$_2$; or $R_{13}$ and $R_{14}$ together with the nitrogen atom to which they are attached form a heterocycloalkyl ring optionally substituted with one or more $R_{23}$;

each $R_{15}$ is independently at each occurrence H or ($C_1$-$C_4$) alkyl;

each $R_{16}$ is independently at each occurrence H, ($C_1$-$C_6$) alkyl, ($C_2$-$C_6$) alkenyl, ($C_2$-$C_6$) alkynyl, ($C_2$-$C_6$) haloalkyl, ($C_3$-$C_8$) cycloalkyl, or —($C_0$-$C_2$)-alkylene-heteroaryl, wherein the alkyl, alkenyl, alkynyl, cycloalkyl, and heteroaryl are optionally substituted with one or more substituents independently selected from ($C_1$-$C_4$) alkyl, ($C_1$-$C_4$) alkoxy, ($C_1$-$C_4$) haloalkyl, ($C_1$-$C_4$) haloalkoxy, and halogen;

each $R_{17}$ is independently at each occurrence ($C_1$-$C_6$) alkyl, ($C_2$-$C_6$) alkenyl, ($C_2$-$C_6$) alkynyl, ($C_1$-$C_6$) alkoxy, ($C_1$-$C_6$) haloalkyl, ($C_1$-$C_6$) haloalkoxy, ($C_1$-$C_6$) hydroxyalkyl, halogen, —OH, —NH$_2$, or CN;

each $R_{18}$ and $R_{19}$ is independently at each occurrence H or ($C_1$-$C_4$) alkyl; or $R_{18}$ and $R_{19}$ together with the nitrogen atom to which they are attached form a heterocycloalkyl ring;

each $R_{20}$, $R_{21}$ and $R_{22}$ is independently at each occurrence H, ($C_1$-$C_4$) alkyl, or ($C_6$-$C_{14}$) aryl;

each $R_{23}$ is independently selected from ($C_1$-$C_4$) alkyl, ($C_1$-$C_4$) alkoxy, ($C_1$-$C_4$) haloalkoxy, halogen, —C(O)($C_1$-$C_4$) alkyl, —C(O)O($C_1$-$C_4$) alkyl, —C(O)($C_3$-$C_8$) cycloalkyl, —C(O)heterocycloalkyl, —OH, —NH$_2$, and CN, wherein the alkyl and alkoxy are optionally substituted with one or more substituents selected from ($C_1$-$C_4$) alkoxy and —OH; or two $R_{23}$ on the same atom to which they are attached form a spiroheterocycloalkyl ring; and each m, n, p, q, and r is independently 0, 1, or 2.

Another aspect of the application relates to a method of treating or preventing a disease or disorder associated with the inhibition of ubiquitin specific protease 1 (USP1). The method comprises administering to a patient in need of a treatment for diseases or disorders associated with modulation of ubiquitin specific protease 1 (USP1) an effective amount of a compound of Formula (I), or a pharmaceutically acceptable salt, hydrate, solvate, prodrug, stereoisomer, or tautomer thereof.

Another aspect of the application is directed to a method of inhibiting ubiquitin specific protease 1 (USP1). The method involves administering to a patient in need thereof an effective amount of a compound of Formula (I), or a pharmaceutically acceptable salt, hydrate, solvate, prodrug, stereoisomer, or tautomer thereof.

Another aspect of the application relates to a method of treating or preventing cancer. The method comprises administering to a patient in need of a treatment for cancer an effective amount of a compound of Formula (I), or a pharmaceutically acceptable salt, hydrate, solvate, prodrug, stereoisomer, or tautomer thereof.

Another aspect of the application relates to a method of treating cancer. The method comprises administering to a patient in need thereof of a treatment for cancer an effective amount of a compound of Formula (I), or a pharmaceutically acceptable salt, hydrate, solvate, prodrug, stereoisomer, or tautomer thereof.

Another aspect of the application relates to a method of treating or preventing a disease or disorder associated with DNA damage. The method comprises administering to a patient in need of a treatment for diseases or disorders associated with DNA damage an effective amount of a compound of Formula (I), or a pharmaceutically acceptable salt, hydrate, solvate, prodrug, stereoisomer, or tautomer thereof.

Another aspect of the application relates to a method of inhibiting or reducing DNA repair activity modulated by ubiquitin specific protease 1 (USP1). The method comprises administering to a patient in need thereof an effective amount of a compound of Formula (I), or a pharmaceutically acceptable salt, hydrate, solvate, prodrug, stereoisomer, or tautomer thereof.

Another aspect of the application is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the present application relates to a compound of Formula (I), or a pharmaceutically acceptable salt, hydrate, solvate, prodrug, stereoisomer, or tautomer thereof, for use in a method of treating or preventing a disease associated with inhibiting USP1.

Another aspect of the present application relates to a compound of Formula (I), or a pharmaceutically acceptable salt, hydrate, solvate, prodrug, stereoisomer, or tautomer thereof, for use in a method for treating or preventing cancer.

Another aspect of the present application relates to a compound of Formula (I), or a pharmaceutically acceptable salt, hydrate, solvate, prodrug, stereoisomer, or tautomer thereof, for use in a method of treating or preventing a disease or disorder associated with DNA damage.

Another aspect of the present application relates to a compound of Formula (I), or a pharmaceutically acceptable salt, hydrate, solvate, prodrug, stereoisomer, or tautomer thereof, for use in a method of inhibiting or reducing DNA repair activity modulated by ubiquitin specific protease 1 (USP1).

Another aspect of the present application relates to the use of a compound of Formula (I), or a pharmaceutically acceptable salt, hydrate, solvate, prodrug, stereoisomer, or tautomer thereof, in the manufacture of a medicament for treating or preventing a disease associated with inhibiting USP1.

Another aspect of the present application relates to the use of a compound of Formula (I), or a pharmaceutically acceptable salt, hydrate, solvate, prodrug, stereoisomer, or tautomer thereof, in the manufacture of a medicament for treating or preventing cancer.

Another aspect of the present application relates to the use of a compound of Formula (I), or a pharmaceutically acceptable salt, hydrate, solvate, prodrug, stereoisomer, or tautomer thereof, in the manufacture of a medicament for treating or preventing a disease or disorder associated with DNA damage.

Another aspect of the present application relates to the use of a compound of Formula (I), or a pharmaceutically acceptable salt, hydrate, solvate, prodrug, stereoisomer, or tautomer thereof, in the manufacture of a medicament for inhibiting or reducing DNA repair activity modulated by ubiquitin specific protease 1 (USP1).

The present application further provides methods of treating a disease or disorder associated with modulation of ubiquitin specific protease 1 (USP1) including, but not limited to, cancer comprising, administering to a patient suffering from at least one of said diseases or disorder a compound of Formula (I), or a pharmaceutically acceptable salt, hydrate, solvate, prodrug, stereoisomer, or tautomer thereof.

The present application provides inhibitors of USP1 that are therapeutic agents in the treatment of diseases such as cancer and other disease associated with the modulation of ubiquitin specific protease 1 (USP1).

The present application further provides compounds and compositions with an improved efficacy and safety profile relative to known USP1 inhibitors. The present disclosure also provides agents with novel mechanisms of action toward USP1 enzymes in the treatment of various types of diseases including cancer. Ultimately the present application provides the medical community with a novel pharmacological strategy for the treatment of diseases and disorders associated with USP1 enzymes.

DETAILED DESCRIPTION OF THE APPLICATION

The present application relates to compounds and compositions that are capable of inhibiting the activity USP1. The application features methods of treating, preventing or ameliorating a disease or disorder in which USP1 plays a role by administering to a patient in need thereof a therapeutically effective amount of a compound of Formula (I), or a pharmaceutically acceptable salt, hydrate, solvate, prodrug, stereoisomer, or tautomer thereof. The methods of the present application can be used in the treatment of a variety of USP1 dependent diseases and disorders by inhibiting the activity of USP1 enzymes. Inhibition of USP1 provides a novel approach to the treatment, prevention, or amelioration of diseases including, but not limited to, cancer.

In a first aspect of the application, the compounds of Formula (I) are described:

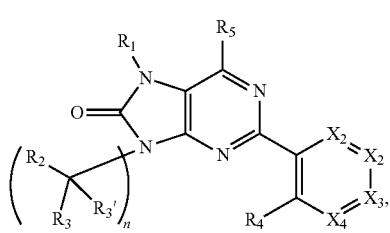

(I)

and pharmaceutically acceptable salts, hydrates, solvates, isotopes, prodrugs, stereoisomers, and tautomers thereof, wherein $R_1$, $R_2$, $R_3$, $R_3'$, $R_4$, $R_5$, $X_1$, $X_2$, $X_3$, $X_4$, and n are as described herein above.

The details of the application are set forth in the accompanying description below. Although methods and materials similar or equivalent to those described herein can be used in the practice or testing of the present application, illustrative methods and materials are now described. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, $C_1$-$C_6$ alkoxy, ($C_1$-$C_6$) haloalkyl, $C_1$-$C_6$ haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$) alkyl, and S(O)N(($C_1$-$C_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, NH$_2$, NH(($C_1$-$C_6$) alkyl), N(($C_1$-$C_6$) alkyl)$_2$, —S(O)$_2$—($C_1$-$C_6$) alkyl, —S(O)NH($C_1$-$C_6$) alkyl, and S(O)N(($C_1$-$C_6$) alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b] pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b] pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5] oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d] thiazolyl, imidazo[2,1-b][1,3,4]thiadiazolyl, thieno[2,3-b] pyrrolyl, 3H-indolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include, without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

The term "aminoalkyl" as used herein refers to an alkyl group, as defined herein, which is substituted one or more amino. Examples of aminoalkyl groups include, but are not limited to, aminomethyl, diaminomethyl, aminoethyl, 1,2-aminoethyl, etc.

"Cycloalkyl" means monocyclic or polycyclic saturated carbon rings (e.g., fused, bridged, or spiro rings) containing 3-18 carbon atoms (e.g., $C_3$-$C_{10}$). Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2] octenyl.

"Heterocyclyl" or "heterocycloalkyl" means monocyclic or polycyclic rings (e.g., fused, bridged, or spiro rings) containing carbon and heteroatoms taken from oxygen, nitrogen, or sulfur and wherein there is not delocalized π electrons (aromaticity) shared among the ring carbon or heteroatoms. The heterocycloalkyl can be a 3-, 4-, 5-, 6-, 7-, 8-, 9-10-, 11-, or 12-membered ring. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl. In accordance with the present application, 3- to 10-membered heterocyclyl refers to saturated or partially saturated non aromatic rings structures containing between 3 and 10 atoms in which there is at least one heteroatoms selected from the group N, O, or S.

The term "hydroxyalkyl" means an alkyl group as defined above, where the alkyl group is substituted with one or more —OH groups. Examples of hydroxyalkyl groups include HO—$CH_2$—, HO—$CH_2$—$CH_2$— and $CH_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary (R—NH$_2$, R≠H), secondary (R$_2$—NH, R$_2$≠H) and tertiary (R$_3$—N, R≠H) amines. A substituted amine is intended to mean an amine where at least one of the hydrogen atoms has been replaced by the substituent.

The term "amino" as used herein means a substituent containing at least one nitrogen atom. Specifically, NH$_2$, —NH(alkyl) or alkylamino, —N(alkyl)$_2$ or dialkylamino, amide-, carbamide-, urea, and sulfamide substituents are included in the term "amino".

The term "dialkylamino" as used herein refers to an amino or NH$_2$ group where both of the hydrogens have been replaced with alkyl groups, as defined herein above, i.e., —N(alkyl)$_2$. The alkyl groups on the amino group can be the same or different alkyl groups. Example of alkylamino groups include, but are not limited to, dimethylamino (i.e., —N(CH$_3$)$_2$), diethylamino, dipropylamino, diiso-propylamino, di-n-butylamino, di-sec-butylamino, di-tert-butylamino, methyl(ethyl)amino, methyl(butylamino), etc.

The term "oxo" as used herein refers to an "=O" group.

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A (C$_3$-C$_{12}$) spirocycloalkyl is a spirocycle containing between 3 and 12 carbon atoms. One or more of the carbon atoms can be substituted with a heteroatom.

The term "spiroheterocycloalkyl" or "spiroheterocyclyl" is understood to mean a spirocycle wherein at least one of the rings is a heterocycle (e.g., at least one of the rings is furanyl, morpholinyl, or piperadinyl).

The term "solvate" refers to a complex of variable stoichiometry formed by a solute and solvent. Such solvents for the purpose of the application may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The term "cancer" includes, but is not limited to, the following cancers: adrenocortical carcinoma, AIDS-related lymphoma, AIDS-related malignancies, anal cancer, cerebellar astrocytoma, extrahepatic bile duct cancer, bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, liver cancer, non-small cell lung cancer, small cell lung cancer, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (e.g., renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodennal and pineal tumors, cutaneous t-celllymphoma, testicular cancer, malignant thymoma, thyroid cancer, gestational trophoblastic tumor, urethral cancer, uterine sarcoma, vaginal cancer, vulvar cancer, and Wilms' tumor. In a preferred embodiment, the cancer is a non-small cell lung cancer.

In any of the embodiments of the application, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

The present application relates to compounds or pharmaceutically acceptable salts, hydrates, solvates, prodrugs, stereoisomers, or tautomers thereof, capable of inhibiting USP1, which are useful for the treatment of diseases and disorders associated with modulation of a USP1 enzyme. The application further relates to compounds, or pharmaceutically acceptable salts, hydrates, solvates, prodrugs, stereoisomers, or tautomers thereof, which are useful for inhibiting USP1.

In one embodiment, the compounds of Formula (I) have the structure of Formula (Ia):

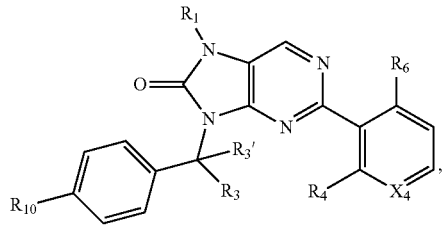

(Ia)

and pharmaceutically acceptable salts, hydrates, solvates, isotopes, prodrugs, stereoisomers, and tautomers thereof.

In another embodiment, the compounds of Formula (I) have the structure of Formula (Ib):

(Ib)

and pharmaceutically acceptable salts, hydrates, solvates, isotopes, prodrugs, stereoisomers, and tautomers thereof.

In one embodiment, the compounds of Formula (I) have the structure of Formula (Ic) or (Id):

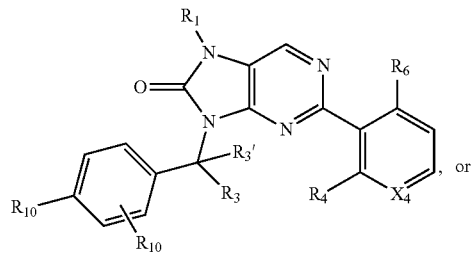

(Ic)

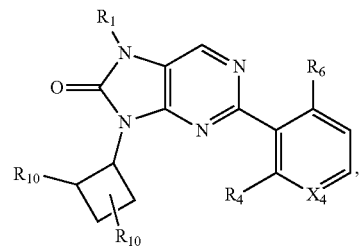

(Id)

and pharmaceutically acceptable salts, hydrates, solvates, isotopes, prodrugs, stereoisomers, and tautomers thereof.

In another embodiment, the compounds of Formula (I) have the structure of Formula (Ie), Formula (If), Formula (Ig), or Formula (Ih):

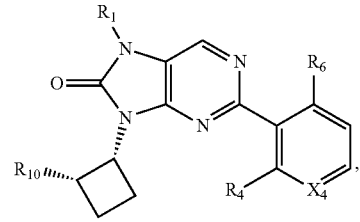

(Ie)

-continued (If)
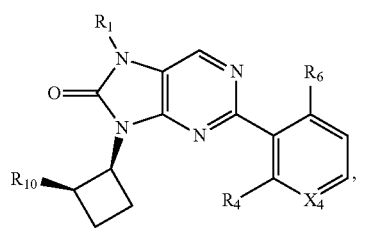

(Ig)
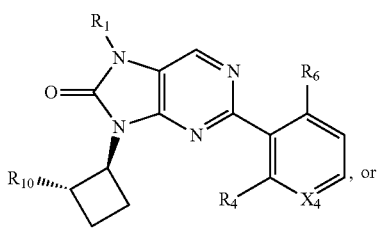

(Ih)
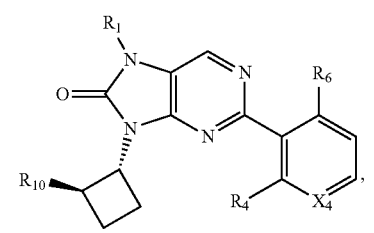

and pharmaceutically acceptable salts, hydrates, solvates, isotopes, prodrugs, stereoisomers, and tautomers thereof.

In another embodiment, the compounds of Formula (I) have the structure of Formula (Ix), Formula (Ij), Formula (Ik), or Formula (Iz):

(Ix)
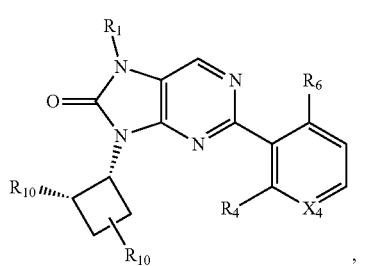

(Ij)
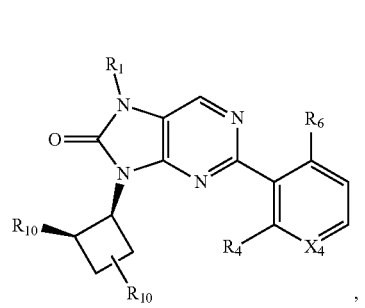

(Ik)
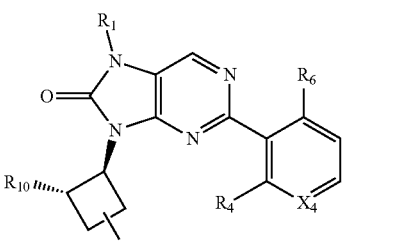

, or (Iz)
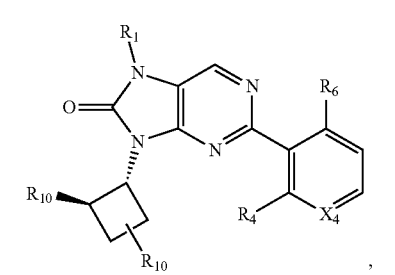

and pharmaceutically acceptable salts, hydrates, solvates, isotopes, prodrugs, stereoisomers, and tautomers thereof.

In another embodiment, the compounds of Formula (I) have the structure of Formula (Im) or Formula (Io):

(Im)
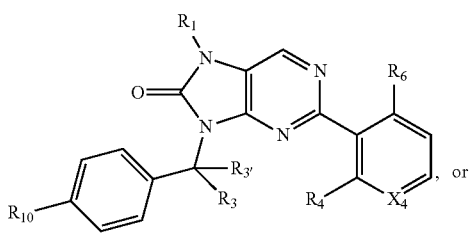

, or (Io)
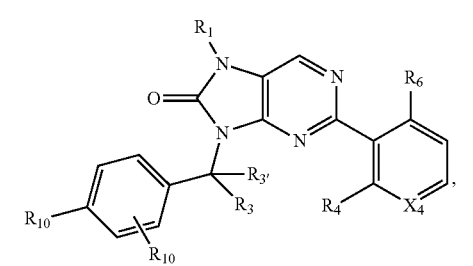

and pharmaceutically acceptable salts, hydrates, solvates, isotopes, prodrugs, stereoisomers, and tautomers thereof, wherein $R_3$ is $(C_1\text{-}C_6)$ alkyl, $(C_1\text{-}C_6)$ haloalkyl, $(C_1\text{-}C_6)$ hydroxyalkyl, $(C_1\text{-}C_6)$ aminoalkyl, heterocycloalkyl, —C(O)OH, —C(O)NH$_2$, or CN.

In another embodiment, the compounds of Formula (I) have the structure of Formula (Ip), Formula (Iq), Formula (Ir), or Formula (Iu):

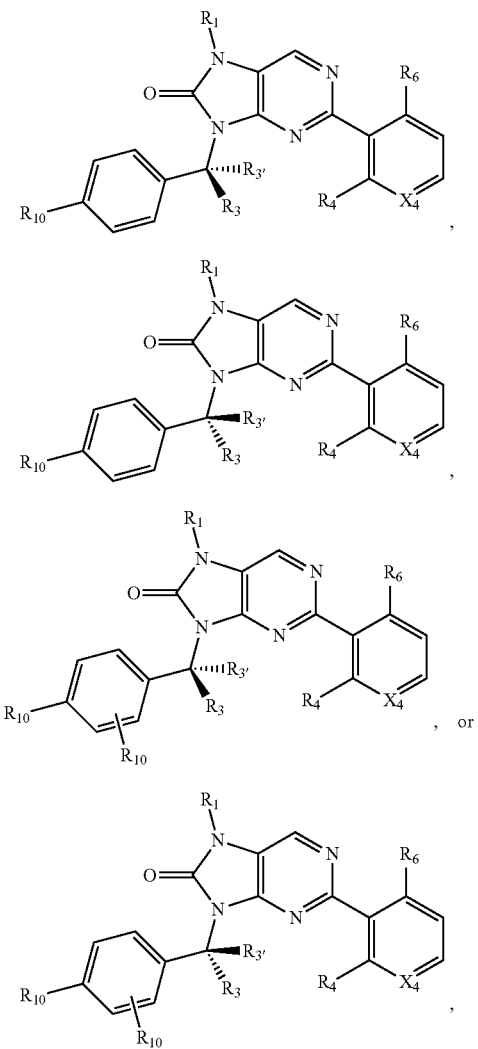

and pharmaceutically acceptable salts, hydrates, solvates, isotopes, prodrugs, stereoisomers, and tautomers thereof, wherein $R_3$ is $(C_1-C_6)$ alkyl, $(C_1-C_6)$ haloalkyl, $(C_1-C_6)$ hydroxyalkyl, $(C_1-C_6)$ aminoalkyl, heterocycloalkyl, —C(O)OH, —C(O)NH$_2$, or CN.

In some embodiments of the Formulae above:

$R_1$ is H, $(C_1-C_6)$ alkyl, $(C_2-C_6)$ alkenyl, $(C_2-C_6)$ alkynyl, $(C_1-C_6)$ haloalkyl, $(C_1-C_6)$ hydroxyalkyl, or heterocycloalkyl, wherein the alkyl, alkenyl, alkynyl, and heterocycloalkyl are optionally substituted with one or more substituents selected from halogen, —OR$_{20}$, —C(O)R$_{20}$, —CO$_2$R$_{20}$, —NR$_{18}$R$_{19}$, —NR$_{20}$C(O)R$_{21}$, —C(O)NR$_{20}$R$_{21}$, —NR$_{20}$C(O)NR$_{21}$R$_{22}$, —NR$_{20}$S(O)$_r$R$_{21}$, —S(O)$_r$NR$_{20}$R$_{21}$, —NR$_{20}$S(O)$_r$NR$_{21}$R$_{22}$, —S(O)$_r$R$_{20}$, —P(O)R$_{20}$R$_{21}$, and —Si((C$_1$-C$_4$) alkyl)$_3$;

$R_2$ is $(C_6-C_{14})$ aryl, heteroaryl, $(C_3-C_{10})$ cycloalkyl, heterocycloalkyl, wherein the aryl, heteroaryl, cycloalkyl, and heterocycloalkyl are substituted with one or more R$_{10}$;

$R_3$ is H, D, $(C_1-C_6)$ alkyl, $(C_1-C_6)$ haloalkyl, $(C_1-C_6)$ hydroxyalkyl, $(C_1-C_6)$ aminoalkyl, heterocycloalkyl, halogen —C(O)OH, —C(O)NH$_2$, or CN;

$R_{3'}$ is H, $(C_1-C_6)$ alkyl, $(C_1-C_6)$ haloalkyl, $(C_1-C_6)$ hydroxyalkyl, $(C_1-C_6)$ aminoalkyl, heterocycloalkyl, —C(O)OH, —C(O)NH$_2$, or CN; or $R_3$ and $R_{3'}$ together with the carbon atom to which they are attached may form a $(C_3-C_7)$ cycloalkyl ring; $R_3$ and $R_{3'}$ together with the carbon atom to which they are attached may form a heterocycloalkyl ring;

$R_4$ is $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_3-C_8)$ cycloalkyl, —O—$(C_0-C_2)$-alkylene-$(C_3-C_8)$ cycloalkyl, halogen, —OH, —NH$_2$, CN, —C(O)(C$_1$-C$_4$) alkyl, —NH(C$_1$-C$_4$) alkyl, or —N((C$_1$-C$_4$) alkyl)$_2$, wherein the alkyl, alkenyl, alkynyl, and alkoxy are optionally substituted with one or more substituents selected from $(C_1-C_6)$ alkyl, $(C_1-C_6)$ alkoxy, $(C_3-C_8)$ cycloalkyl, —OH, —NH$_2$, —NH(C$_1$-C$_4$) alkyl, and —N((C$_1$-C$_4$) alkyl)$_2$; or $R_4$ and $X_4$ together with the atoms to which they are attached may form a $(C_6-C_{14})$ aryl ring optionally substituted with one or more R$_{17}$; or $R_4$ and $X_4$ on adjacent atoms together with the atoms to which they are attached may form a heteroaryl ring optionally substituted with one or more R$_{17}$; or $R_4$ and $X_4$ together with the atoms to which they are attached may form a $(C_5-C_7)$ cycloalkyl ring optionally substituted with one or more R$_{17}$; or $R_4$ and $X_4$ on adjacent atoms together with the atoms to which they are attached may form a heterocycloalkyl ring optionally substituted with one or more R$_{17}$;

$R_5$ is H, $(C_1-C_4)$ alkyl, $(C_2-C_4)$ alkenyl, $(C_2-C_4)$ alkynyl, $(C_1-C_4)$ alkoxy, $(C_1-C_4)$ hydroxyalkyl, $(C_1-C_4)$ haloalkoxy, halogen, $(C_3-C_6)$ cycloalkyl, heterocycloalkyl, —OH, —NH$_2$, CN, —NH(C$_1$-C$_4$) alkyl, —N((C$_1$-C$_4$) alkyl)$_2$ or —NR$_{13}$C(O)R$_{14}$;

each $R_6$, $R_7$, $R_8$, and $R_9$ is independently, at each occurrence, H, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, or halogen, wherein the alkyl is optionally substituted with one or more $(C_1-C_6)$ alkoxy;

each $R_{10}$ is independently at each occurrence $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, halogen, —C(O)R$_{14}$, —C(O)OR$_{13}$, —NR$_{13}$R$_{14}$, —NR$_{13}$C(O)R$_{14}$, —NR$_{13}$C(O)NR$_{13}$R$_{14}$, —C(O)NR$_{13}$R$_{14}$, —S(O)$_p$R$_{14}$, —NR$_{13}$S(O)$_p$R$_{14}$, —S(O)$_p$NR$_{13}$R$_{14}$, —CN, —(C$_0$-C$_2$)-alkylene-(C$_6$-C$_{14}$) aryl, —(C$_0$-C$_2$)-alkylene-heteroaryl, —(C$_0$-C$_2$)-alkylene-(C$_3$-C$_8$) cycloalkyl, —(C$_0$-C$_2$)-alkylene-heterocycloalkyl, —O—(C$_0$-C$_2$)-alkylene-aryl, —O—(C$_0$-C$_2$)-alkylene-heteroaryl, —O—(C$_0$-C$_2$)-alkylene-(C$_3$-C$_8$) cycloalkyl, or —O—(C$_0$-C$_2$)-alkylene-heterocycloalkyl, wherein the aryl, heteroaryl, cycloalkyl and heterocycloalkyl are optionally substituted with one or more R$_{11}$ and the alkyl, alkenyl, alkynyl, and alkoxy are optionally substituted with one or more R$_{12}$; or two $R_{10}$ on adjacent atoms together with the atoms to which they are attached may form a $(C_6-C_{14})$ aryl ring optionally substituted with one or more R$_{11}$; or two R$_{10}$ on adjacent atoms together with the atoms to which they are attached may form a heteroaryl ring optionally substituted with one or more R$_{11}$; or two R$_{10}$ on adjacent atoms together with the atoms to which they are attached may form a $(C_3-C_8)$ cycloalkyl ring optionally substituted with one or more R$_{11}$; or two R$_{10}$ on adjacent atoms together with the atoms to which they are attached may form a heterocycloalkyl ring optionally substituted with one or more R$_{11}$; or two R$_{10}$ on the same atom to which they are attached may form a spirocycloalkyl ring optionally substituted with one or more R$_{11}$; or two R$_{10}$ on the same atom to which they are attached may form a spiroheterocycloalkyl ring optionally substituted with one or more R$_{11}$;

each $R_{11}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, CN, —OH, —NH$_2$, —NH(C$_1$-C$_4$) alkyl, —N((C$_1$-C$_4$) alkyl)$_2$, —C(O)O(C$_1$-C$_4$) alkyl, —S(O)$_q$ (C$_1$-C$_4$) alkyl, —C(O)NH$_2$, —C(O)NH(C$_1$-C$_4$) alkyl, —C(O)N((C$_1$-C$_4$) alkyl)$_2$, —NHC(O)(C$_1$-C$_4$) alkyl, —N((C$_1$-C$_4$) alkyl)C(O)(C$_1$-C$_4$) alkyl, (C$_6$-C$_{14}$) aryl, heteroaryl, (C$_3$-C$_8$) cycloalkyl, or heterocycloalkyl, wherein the alkyl, alkoxy, (C$_3$-C$_8$) cycloalkyl, heterocycloalkyl, aryl, and heteroaryl are optionally substituted with one or more substituents selected from (C$_1$-C$_6$) alkyl, (C$_1$-C$_6$) alkoxy, (C$_1$-C$_6$) haloalkyl, —C(O)OH, —C(O)O(C$_1$-C$_4$) alkyl, —C(O)(C$_1$-C$_4$) alkyl, —S(O)$_q$(C$_1$-C$_4$) alkyl, —C(O)NH (C$_1$-C$_4$) alkyl, —C(O)N((C$_1$-C$_4$) alkyl)$_2$, —OH, —NH$_2$, —CN, —NH(C$_1$-C$_4$) alkyl, and —N((C$_1$-C$_4$) alkyl)$_2$; or two R$_{11}$ on adjacent atoms together with the atoms to which they are attached may form a heterocycloalkyl ring; or two R$_{11}$ on adjacent atoms together with the atoms to which they are attached may form a (C$_5$-C$_8$) cycloalkyl ring; or two R$_{11}$ on adjacent atoms together with the atoms to which they are attached may form a (C$_6$-C$_{14}$) aryl ring; or two R$_{11}$ on adjacent atoms together with the atoms to which they are attached may form a heteroaryl ring; or two R$_{11}$ together with the atom to which they are attached may form a C=O;

each R$_{12}$ is independently at each occurrence (C$_1$-C$_6$) alkoxy, —NR$_{15}$R$_{16}$, —NR$_{15}$C(O)NR$_{15}$R$_{16}$, —NR$_{15}$C(O)R$_{16}$, —NR$_{15}$S(O)$_m$R$_{16}$, or —C(O)NH(C$_3$-C$_8$) cycloalkyl;

each R$_{13}$ is independently at each occurrence H or (C$_1$-C$_4$) alkyl;

each R$_{14}$ is independently at each occurrence H, (C$_1$-C$_6$) alkyl, (C$_2$-C$_6$) alkenyl, (C$_2$-C$_6$) alkynyl, (C$_1$-C$_6$) haloalkyl, —(C$_0$-C$_2$)-alkylene-(C$_3$-C$_8$) cycloalkyl, —(C$_0$-C$_2$)-alkylene-heterocycloalkyl, —(C$_0$-C$_2$)-alkylene-(C$_6$-C$_{14}$) aryl, or —(C$_0$-C$_2$)-alkylene-heteroaryl, wherein the alkyl, cycloalkyl, heterocycloalkyl, aryl, and heteroaryl is optionally substituted with one or more substituents selected from (C$_1$-C$_4$) alkyl optionally substituted with (C$_1$-C$_4$) alkoxy, (C$_1$-C$_4$) alkoxy, (C$_1$-C$_4$) haloalkyl, (C$_1$-C$_4$) haloalkoxy, (C$_6$-C$_{14}$) aryl, heteroaryl, halogen, —OH, —NH$_2$, CN, —C(O) NH$_2$, —C(O)NH(C$_1$-C$_4$) alkyl, —C(O)N((C$_1$-C$_4$) alkyl)$_2$, —NH(C$_1$-C$_4$) alkyl, and —N((C$_1$-C$_4$) alkyl)$_2$; or R$_{13}$ and R$_{14}$ together with the nitrogen atom to which they are attached may form a heterocycloalkyl ring optionally substituted with one or more R$_{23}$;

each R$_{15}$ is independently at each occurrence H or (C$_1$-C$_4$) alkyl;

each R$_{16}$ is independently at each occurrence H, (C$_1$-C$_6$) alkyl, (C$_2$-C$_6$) alkenyl, (C$_2$-C$_6$) alkynyl, (C$_2$-C$_6$) haloalkyl, (C$_3$-C$_8$) cycloalkyl, or —(C$_0$-C$_2$)-alkylene-heteroaryl, wherein the alkyl, alkenyl, alkynyl, cycloalkyl, and heteroaryl are optionally substituted with one or more substituents independently selected from (C$_1$-C$_4$) alkyl, (C$_1$-C$_4$) alkoxy, (C$_1$-C$_4$) haloalkyl, (C$_1$-C$_4$) haloalkoxy, and halogen;

each R$_{17}$ is independently at each occurrence (C$_1$-C$_6$) alkyl, (C$_2$-C$_6$) alkenyl, (C$_2$-C$_6$) alkynyl, (C$_1$-C$_6$) alkoxy, (C$_1$-C$_6$) haloalkyl, (C$_1$-C$_6$) haloalkoxy, (C$_1$-C$_6$) hydroxyalkyl, halogen, —OH, —NH$_2$, or CN;

each R$_{18}$ and R$_{19}$ is independently at each occurrence H or (C$_1$-C$_4$) alkyl; or R$_{18}$ and R$_{19}$ together with the nitrogen atom to which they are attached may form a heterocycloalkyl ring;

each R$_{20}$, R$_{21}$ and R$_{22}$ is independently at each occurrence H, (C$_1$-C$_4$) alkyl, or (C$_6$-C$_{14}$) aryl;

each R$_{23}$ is independently selected from (C$_1$-C$_4$) alkyl, (C$_1$-C$_4$) alkoxy, (C$_1$-C$_4$) haloalkoxy, halogen, —C(O)(C$_1$-C$_4$) alkyl, —C(O)O(C$_1$-C$_4$) alkyl, —C(O)(C$_3$-C$_8$) cycloalkyl, —C(O)heterocycloalkyl, —OH, —NH$_2$, and CN, wherein the alkyl and alkoxy are optionally substituted with one or more substituents selected from (C$_1$-C$_4$) alkoxy and —OH; or two R$_{23}$ on the same atom to which they are attached may form a spiroheterocycloalkyl ring; and each m, n, p, q, and r is independently 0, 1, or 2.

In some embodiments of the Formulae above:

R$_1$ is H, (C$_1$-C$_6$) alkyl, (C$_2$-C$_6$) alkenyl, (C$_2$-C$_6$) alkynyl, (C$_1$-C$_6$) haloalkyl, (C$_2$-C$_6$) hydroxyalkyl, or heterocycloalkyl, wherein the alkyl, alkenyl, alkynyl, and heterocycloalkyl are optionally substituted with one or more substituents selected from halogen, —OR$_{20}$, —C(O)R$_{20}$, —CO$_2$R$_{20}$, —NR$_{18}$R$_{19}$, —NR$_2$OC(O)R$_{21}$, —C(O)NR$_{20}$R$_{21}$, —NR$_{20}$C(O)NR$_{21}$R$_{22}$, —NR$_{20}$S(O)$_r$R$_{21}$, —S(O)$_r$NR$_{20}$R$_{21}$, —NR$_{20}$S(O)$_r$NR$_{21}$R$_{22}$, —S(O)$_r$R$_{20}$, —P(O)R$_{20}$R$_{21}$, and —Si((C$_1$-C$_4$) alkyl)$_3$ R$_2$ is (C$_6$-C$_{14}$) aryl, heteroaryl, (C$_3$-C$_8$) cycloalkyl, or heterocycloalkyl, wherein the aryl, heteroaryl, cycloalkyl, and heterocycloalkyl are substituted with one or more R$_{10}$;

R$_3$ is H, (C$_1$-C$_6$) alkyl, (C$_1$-C$_6$) haloalkyl, (C$_1$-C$_6$) hydroxyalkyl, (C$_1$-C$_6$) aminoalkyl, heterocycloalkyl, —C(O)OH, —C(O)NH$_2$, or CN;

R$_{3'}$ is H, (C$_1$-C$_6$) alkyl, (C$_1$-C$_6$) haloalkyl, (C$_1$-C$_6$) hydroxyalkyl, (C$_1$-C$_6$) aminoalkyl, heterocycloalkyl, —C(O)OH, —C(O)NH$_2$, or CN; or R$_3$ and R$_{3'}$ together with the carbon atom to which they are attached form a (C$_3$-C$_7$) cycloalkyl ring; R$_3$ and R$_{3'}$ together with the carbon atom to which they are attached form a heterocycloalkyl ring;

R$_4$ is (C$_1$-C$_6$) alkyl, (C$_2$-C$_6$) alkenyl, (C$_2$-C$_6$) alkynyl, (C$_1$-C$_6$) alkoxy, (C$_1$-C$_6$) haloalkyl, (C$_1$-C$_6$) haloalkoxy, (C$_3$-C$_8$) cycloalkyl, halogen, —OH, —NH$_2$, CN, —C(O)(C$_1$-C$_4$) alkyl, —NH(C$_1$-C$_4$) alkyl, or —N((C$_1$-C$_4$) alkyl)$_2$, wherein the alkyl, alkenyl, alkynyl, and alkoxy are optionally substituted with one or more substituents selected from (C$_1$-C$_6$) alkyl, (C$_1$-C$_6$) alkoxy, (C$_3$-C$_8$) cycloalkyl, —OH, —NH$_2$, —NH(C$_1$-C$_4$) alkyl, and —N((C$_1$-C$_4$) alkyl)$_2$; or R$_4$ and X$_4$ together with the atoms to which they are attached form a (C$_6$-C$_{14}$) aryl ring optionally substituted with one or more R$_{17}$; or R$_4$ and X$_4$ on adjacent atoms together with the atoms to which they are attached form a heteroaryl ring optionally substituted with one or more R$_{17}$; or R$_4$ and X$_4$ together with the atoms to which they are attached form a (C$_5$-C$_7$) cycloalkyl ring optionally substituted with one or more R$_{17}$; or R$_4$ and X$_4$ on adjacent atoms together with the atoms to which they are attached form a heterocycloalkyl ring optionally substituted with one or more R$_{17}$;

R$_5$ is H;

each R$_6$, R$_7$, R$_8$, and R$_9$ is independently, at each occurrence, H, (C$_1$-C$_6$) alkyl, (C$_2$-C$_6$) alkenyl, (C$_2$-C$_6$) alkynyl, (C$_1$-C$_6$) alkoxy, (C$_1$-C$_6$) haloalkyl, (C$_1$-C$_6$) haloalkoxy, (C$_1$-C$_6$) hydroxyalkyl, or halogen, wherein the alkyl is optionally substituted with one or more (C$_1$-C$_6$) alkoxy;

each R$_{10}$ is independently at each occurrence (C$_1$-C$_6$) alkyl, (C$_2$-C$_6$) alkenyl, (C$_2$-C$_6$) alkynyl, (C$_1$-C$_6$) alkoxy, (C$_1$-C$_6$) haloalkyl, (C$_1$-C$_6$) haloalkoxy, (C$_1$-C$_6$) hydroxyalkyl, halogen, —C(O)R$_{14}$, —C(O)OR$_{13}$, —NR$_{13}$R$_{14}$, —NR$_{13}$C(O)R$_{14}$, —NR$_{13}$C(O)NR$_{13}$R$_{14}$, —C(O)NR$_{13}$R$_{14}$, —S(O)$_p$R$_{14}$, —NR$_{13}$S(O)$_p$R$_{14}$, —S(O)$_p$NR$_{13}$R$_{14}$, —CN, —(C$_0$-C$_2$)-alkylene-(C$_6$-C$_{14}$) aryl, —(C$_0$-C$_2$)-alkylene-heteroaryl, —(C$_0$-C$_2$)-alkylene-(C$_3$-C$_8$) cycloalkyl, —(C$_0$-C$_2$)-alkylene-heterocycloalkyl, —O—(C$_0$-C$_2$)-alkylene-aryl, —O—(C$_0$-C$_2$)-alkylene-heteroaryl, —O—(C$_0$-C$_2$)-alkylene-(C$_3$-C$_8$) cycloalkyl, or —O—(C$_0$-C$_2$)-alkylene-heterocycloalkyl, wherein the aryl, heteroaryl, cycloalkyl and heterocycloalkyl are optionally substituted with one or more $R_{11}$ and the alkyl, alkenyl, alkynyl, and alkoxy are optionally substituted with one or more $R_{12}$; or two $R_{10}$ on adjacent atoms together with the atoms to which they are attached form a $(C_6-C_{14})$ aryl ring optionally substituted with one or more $R_{11}$; or two $R_{10}$ on adjacent atoms together with the atoms to which they are attached form a heteroaryl ring optionally substituted with one or more $R_{11}$; or two $R_{10}$ on adjacent atoms together with the atoms to which they are attached form a $(C_5-C_7)$ cycloalkyl ring optionally substituted with one or more $R_{11}$; or two $R_{10}$ on adjacent atoms together with the atoms to which they are attached form a heterocycloalkyl ring optionally substituted with one or more $R_{11}$; or two $R_{10}$ on the same atom to which they are attached form a spirocycloalkyl ring optionally substituted with one or more $R_{11}$; or two $R_{10}$ on the same atom to which they are attached form a spiroheterocycloalkyl ring optionally substituted with one or more $R_{11}$;

each $R_{11}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, CN, —OH, —NH$_2$, —NH$(C_1-C_4)$ alkyl, —N$((C_1-C_4)$ alkyl$)_2$, —C(O)O$(C_1-C_4)$ alkyl, —S(O)$_q$ $(C_1-C_4)$ alkyl, —C(O)NH$_2$, —C(O)NH$(C_1-C_4)$ alkyl, —C(O)N$((C_1-C_4)$ alkyl$)_2$, —NHC(O)$(C_1-C_4)$ alkyl, —N$((C_1-C_4)$ alkyl)C(O)$(C_1-C_4)$ alkyl, $(C_6-C_{14})$ aryl, heteroaryl, $(C_3-C_8)$ cycloalkyl, or heterocycloalkyl, wherein the alkyl, alkoxy, $(C_3-C_8)$ cycloalkyl, heterocycloalkyl, aryl, and heteroaryl are optionally substituted with one or more substituents selected from $(C_1-C_6)$ alkyl, $(C_1-C_6)$ alkoxy, $(C_1-C_6)$ haloalkyl, —C(O)OH, —C(O)O$(C_1-C_4)$ alkyl, —C(O)$(C_1-C_4)$ alkyl, —S(O)$_q(C_1-C_4)$ alkyl, —C(O)NH $(C_1-C_4)$ alkyl, —C(O)N$((C_1-C_4)$ alkyl$)_2$, —OH, —NH$_2$, —CN, —NH$(C_1-C_4)$ alkyl, and —N$((C_1-C_4)$ alkyl$)_2$; or two $R_{11}$ on adjacent atoms together with the atoms to which they are attached form a heterocycloalkyl ring; or two $R_{11}$ on adjacent atoms together with the atoms to which they are attached form a $(C_5-C_8)$ cycloalkyl ring; or two $R_{11}$ on adjacent atoms together with the atoms to which they are attached form a $(C_6-C_{14})$ aryl ring; or two $R_{11}$ on adjacent atoms together with the atoms to which they are attached form a heteroaryl ring; or two $R_{11}$ together with the atom to which they are attached form a C=O;

each $R_{12}$ is independently at each occurrence $(C_1-C_6)$ alkoxy, —NR$_{15}$R$_{16}$, —NR$_{15}$C(O)NR$_{15}$R$_{16}$, —NR$_{15}$C(O) R$_{16}$, —NR$_{15}$S(O)$_m$R$_{16}$, or —C(O)NH$(C_3-C_8)$ cycloalkyl;

each $R_{13}$ is independently at each occurrence H or $(C_1-C_4)$ alkyl;

each $R_{14}$ is independently at each occurrence H, $(C_1-C_6)$ alkyl, $(C_2-C_6)$ alkenyl, $(C_2-C_6)$ alkynyl, $(C_1-C_6)$ haloalkyl, —$(C_0-C_2)$-alkylene-$(C_3-C_8)$ cycloalkyl, —$(C_0-C_2)$-alkylene-heterocycloalkyl, —$(C_0-C_2)$-alkylene-$(C_6-C_{14})$ aryl, or —$(C_0-C_2)$-alkylene-heteroaryl, wherein the alkyl, cycloalkyl, heterocycloalkyl, aryl, and heteroaryl is optionally substituted with one or more substituents selected from $(C_1-C_4)$ alkyl optionally substituted with $(C_1-C_4)$ alkoxy, $(C_1-C_4)$ alkoxy, $(C_1-C_4)$ haloalkyl, $(C_1-C_4)$ haloalkoxy, $(C_6-C_{14})$ aryl, heteroaryl, halogen, —OH, —NH$_2$, CN, —C(O) NH$_2$, —C(O)NH$(C_1-C_4)$ alkyl, —C(O)N$((C_1-C_4)$ alkyl$)_2$, —NH$(C_1-C_4)$ alkyl, and —N$((C_1-C_4)$ alkyl$)_2$; or $R_{13}$ and $R_{14}$ together with the nitrogen atom to which they are attached form a heterocycloalkyl ring optionally substituted with one or more $R_{23}$;

each $R_{15}$ is independently at each occurrence H or $(C_1-C_4)$ alkyl;

each $R_{16}$ is independently at each occurrence H, $(C_1-C_6)$ alkyl, $(C_2-C_6)$ alkenyl, $(C_2-C_6)$ alkynyl, $(C_2-C_6)$ haloalkyl, $(C_3-C_8)$ cycloalkyl, or —$(C_0-C_2)$-alkylene-heteroaryl, wherein the alkyl, alkenyl, alkynyl, cycloalkyl, and heteroaryl are optionally substituted with one or more substituents independently selected from $(C_1-C_4)$ alkyl, $(C_1-C_4)$ alkoxy, $(C_1-C_4)$ haloalkyl, $(C_1-C_4)$ haloalkoxy, and halogen;

each $R_{17}$ is independently at each occurrence $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, halogen, —OH, —NH$_2$, or CN;

each $R_{18}$ and $R_{19}$ is independently at each occurrence H or $(C_1-C_4)$ alkyl; or $R_{18}$ and $R_{19}$ together with the nitrogen atom to which they are attached form a heterocycloalkyl ring;

each $R_{20}$, $R_{21}$, and $R_{22}$ is independently at each occurrence H or $(C_1-C_4)$ alkyl;

each $R_{23}$ is independently selected from $(C_1-C_4)$ alkyl, $(C_1-C_4)$ alkoxy, $(C_1-C_4)$ haloalkoxy, halogen, —C(O)$(C_1-C_4)$ alkyl, —C(O)O$(C_1-C_4)$ alkyl, —C(O)$(C_3-C_8)$ cycloalkyl, —C(O)heterocycloalkyl, —OH, —NH$_2$, and CN, wherein the alkyl and alkoxy are optionally substituted with one or more substituents selected from $(C_1-C_4)$ alkoxy and —OH; or two $R_{23}$ on the same atom to which they are attached form a spiroheterocycloalkyl ring; and each m, n, p, q, and r is independently 0, 1, or 2.

In some embodiments of the Formulae above:

$R_1$ is H, $(C_1-C_6)$ alkyl, $(C_2-C_6)$ alkenyl, $(C_2-C_6)$ alkynyl, $(C_1-C_6)$ haloalkyl, $(C_2-C_6)$ hydroxyalkyl, or heterocycloalkyl, wherein the alkyl, alkenyl, alkynyl, and heterocycloalkyl are optionally substituted with one or more substituents selected from halogen, —OR$_{20}$, —C(O)R$_{20}$, —CO$_2$R$_{20}$, —NR$_{18}$R$_{19}$, —NR$_2$OC(O)R$_{21}$, —C(O) NR$_{20}$R$_{21}$, —NR$_{20}$C(O)NR$_{21}$R$_{22}$, —NR$_{20}$S(O)$_r$R$_{21}$, —S(O)$_r$ NR$_{20}$R$_{21}$, —NR$_{20}$S(O)$_r$NR$_{21}$R$_{22}$, —S(O)$_r$R$_{20}$, —P(O) R$_{20}$R$_{21}$, and —Si$((C_1-C_4)$ alkyl$)_3$ $R_2$ is $(C_6-C_{14})$ aryl, heteroaryl, $(C_3-C_8)$ cycloalkyl, or heterocycloalkyl, wherein the aryl, heteroaryl, cycloalkyl, and heterocycloalkyl are substituted with one or more $R_{10}$;

$R_3$ is H, $(C_1-C_6)$ alkyl, $(C_1-C_6)$ haloalkyl, $(C_1-C_6)$ hydroxyalkyl, $(C_1-C_6)$ aminoalkyl, heterocycloalkyl, —C(O)OH, —C(O)NH$_2$, or CN;

$R_{3'}$ is H, $(C_1-C_6)$ alkyl, $(C_1-C_6)$ haloalkyl, $(C_1-C_6)$ hydroxyalkyl, $(C_1-C_6)$ aminoalkyl, heterocycloalkyl, —C(O)OH, —C(O)NH$_2$, or CN; or $R_3$ and $R_{3'}$ together with the carbon atom to which they are attached form a $(C_3-C_7)$ cycloalkyl ring; $R_3$ and $R_{3'}$ together with the carbon atom to which they are attached form a heterocycloalkyl ring;

$R_4$ is $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_3-C_8)$ cycloalkyl, halogen, —OH, —NH$_2$, CN, —C(O)$(C_1-C_4)$ alkyl, —NH$(C_1-C_4)$ alkyl, or —N$((C_1-C_4)$ alkyl$)_2$, wherein the alkyl, alkenyl, alkynyl, and alkoxy are optionally substituted with one or more substituents selected from $(C_1-C_6)$ alkyl, $(C_1-C_6)$ alkoxy, $(C_3-C_8)$ cycloalkyl, —OH, —NH$_2$, —NH$(C_1-C_4)$ alkyl, and —N$((C_1-C_4)$ alkyl$)_2$; or $R_4$ and $X_4$ together with the atoms to which they are attached form a $(C_6-C_{14})$ aryl ring optionally substituted with one or more $R_{17}$; or $R_4$ and $X_4$ on adjacent atoms together with the atoms to which they are attached form a heteroaryl ring optionally substituted with one or more $R_{17}$; or $R_4$ and $X_4$ together with the atoms to which they are attached form a $(C_5-C_7)$ cycloalkyl ring optionally substituted with one or more $R_{17}$; or $R_4$ and $X_4$ on adjacent atoms together with the atoms to which they are attached form a heterocycloalkyl ring optionally substituted with one or more $R_{17}$;

$R_5$ is H;

each $R_6$, $R_7$, $R_8$, and $R_9$ is independently, at each occurrence, H, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, or halogen, wherein the alkyl is optionally substituted with one or more $(C_1-C_6)$ alkoxy;

each $R_{10}$ is independently at each occurrence $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, halogen, —C(O)$R_{14}$, —C(O)O$R_{13}$, —N$R_{13}R_{14}$, —N$R_{13}$C(O)$R_{14}$, —N$R_{13}$C(O)N$R_{13}R_{14}$, —C(O)N$R_{13}R_{14}$, —S(O)$_p$$R_{14}$, —N$R_{13}$S(O)$_p$$R_{14}$, —S(O)$_p$N$R_{13}R_{14}$, —CN, —(C$_0$-C$_2$)-alkylene-(C$_6$-C$_{14}$) aryl, —(C$_0$-C$_2$)-alkylene-heteroaryl, —(C$_0$-C$_2$)-alkylene-(C$_3$-C$_8$) cycloalkyl, —(C$_0$-C$_2$)-alkylene-heterocycloalkyl, —O—(C$_0$-C$_2$)-alkylene-aryl, —O—(C$_0$-C$_2$)-alkylene-heteroaryl, —O—(C$_0$-C$_2$)-alkylene-(C$_3$-C$_8$) cycloalkyl, or —O—(C$_0$-C$_2$)-alkylene-heterocycloalkyl, wherein the aryl, heteroaryl, cycloalkyl and heterocycloalkyl are optionally substituted with one or more $R_{11}$ and the alkyl, alkenyl, alkynyl, and alkoxy are optionally substituted with one or more $R_{12}$; or two $R_{10}$ on adjacent atoms together with the atoms to which they are attached form a $(C_6-C_{14})$ aryl ring optionally substituted with one or more $R_{11}$; or two $R_{10}$ on adjacent atoms together with the atoms to which they are attached form a heteroaryl ring optionally substituted with one or more $R_{11}$; or two $R_{10}$ on adjacent atoms together with the atoms to which they are attached form a $(C_5-C_7)$ cycloalkyl ring optionally substituted with one or more $R_{11}$; or two $R_{10}$ on adjacent atoms together with the atoms to which they are attached form a heterocycloalkyl ring optionally substituted with one or more $R_{11}$; or two $R_{10}$ on the same atom to which they are attached form a spirocycloalkyl ring optionally substituted with one or more $R_{11}$; or two $R_{10}$ on the same atom to which they are attached form a spiroheterocycloalkyl ring optionally substituted with one or more $R_{11}$;

each $R_{11}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, CN, —OH, —NH$_2$, —NH$(C_1-C_4)$ alkyl, —N$((C_1-C_4)$ alkyl$)_2$, —C(O)O$(C_1-C_4)$ alkyl, —S(O)$_q$$(C_1-C_4)$ alkyl, —C(O)NH$_2$, —C(O)NH$(C_1-C_4)$ alkyl, —C(O)N$((C_1-C_4)$ alkyl$)_2$, —NHC(O)$(C_1-C_4)$ alkyl, —N$((C_1-C_4)$ alkyl)C(O)$(C_1-C_4)$ alkyl, $(C_6-C_{14})$ aryl, heteroaryl, $(C_3-C_8)$ cycloalkyl, or heterocycloalkyl, wherein the alkyl, alkoxy, $(C_3-C_8)$ cycloalkyl, heterocycloalkyl, aryl, and heteroaryl are optionally substituted with one or more substituents selected from $(C_1-C_6)$ alkyl, $(C_1-C_6)$ alkoxy, $(C_1-C_6)$ haloalkyl, —C(O)OH, —C(O)O$(C_1-C_4)$ alkyl, —C(O)$(C_1-C_4)$ alkyl, —S(O)$_q$$(C_1-C_4)$ alkyl, —C(O)NH$(C_1-C_4)$ alkyl, —C(O)N$((C_1-C_4)$ alkyl$)_2$, —OH, —NH$_2$, —CN, —NH$(C_1-C_4)$ alkyl, and —N$((C_1-C_4)$ alkyl$)_2$; or two $R_{11}$ on adjacent atoms together with the atoms to which they are attached form a heterocycloalkyl ring; or two $R_{11}$ on adjacent atoms together with the atoms to which they are attached form a $(C_5-C_8)$ cycloalkyl ring; or two $R_{11}$ on adjacent atoms together with the atoms to which they are attached form a $(C_6-C_{14})$ aryl ring; or two $R_{11}$ on adjacent atoms together with the atoms to which they are attached form a heteroaryl ring; or two $R_{11}$ together with the atom to which they are attached form a C=O;

each $R_{12}$ is independently at each occurrence $(C_1-C_6)$ alkoxy, —N$R_{15}R_{16}$, —N$R_{15}$C(O)N$R_{15}R_{16}$, —N$R_{15}$C(O)$R_{16}$, —N$R_{15}$S(O)$_m$$R_{16}$, or —C(O)NH$(C_3-C_8)$ cycloalkyl;

each $R_{13}$ is independently at each occurrence H or $(C_1-C_4)$ alkyl;

each $R_{14}$ is independently at each occurrence H, $(C_1-C_6)$ alkyl, $(C_2-C_6)$ alkenyl, $(C_2-C_6)$ alkynyl, $(C_1-C_6)$ haloalkyl, —(C$_0$-C$_2$)-alkylene-(C$_3$-C$_8$) cycloalkyl, —(C$_0$-C$_2$)-alkylene-heterocycloalkyl, —(C$_0$-C$_2$)-alkylene-(C$_6$-C$_{14}$) aryl, or —(C$_0$-C$_2$)-alkylene-heteroaryl, wherein the alkyl, cycloalkyl, heterocycloalkyl, aryl, and heteroaryl is optionally substituted with one or more substituents selected from $(C_1-C_4)$ alkyl optionally substituted with $(C_1-C_4)$ alkoxy, $(C_1-C_4)$ alkoxy, $(C_1-C_4)$ haloalkyl, $(C_1-C_4)$ haloalkoxy, $(C_6-C_{14})$ aryl, heteroaryl, halogen, —OH, —NH$_2$, CN, —C(O)NH$_2$, —C(O)NH$(C_1-C_4)$ alkyl, —C(O)N$((C_1-C_4)$ alkyl$)_2$, —NH$(C_1-C_4)$ alkyl, and —N$((C_1-C_4)$ alkyl$)_2$; or $R_{13}$ and $R_{14}$ together with the nitrogen atom to which they are attached form a heterocycloalkyl ring optionally substituted with one or more $R_{23}$;

each $R_{15}$ is independently at each occurrence H or $(C_1-C_4)$ alkyl;

each $R_{16}$ is independently at each occurrence H, $(C_1-C_6)$ alkyl, $(C_2-C_6)$ alkenyl, $(C_2-C_6)$ alkynyl, $(C_2-C_6)$ haloalkyl, $(C_3-C_8)$ cycloalkyl, or —(C$_0$-C$_2$)-alkylene-heteroaryl, wherein the alkyl, alkenyl, alkynyl, cycloalkyl, and heteroaryl are optionally substituted with one or more substituents independently selected from $(C_1-C_4)$ alkyl, $(C_1-C_4)$ alkoxy, $(C_1-C_4)$ haloalkyl, $(C_1-C_4)$ haloalkoxy, and halogen;

each $R_{17}$ is independently at each occurrence $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, halogen, —OH, —NH$_2$, or CN;

each $R_{18}$ and $R_{19}$ is independently at each occurrence H or $(C_1-C_4)$ alkyl; or $R_{18}$ and $R_{19}$ together with the nitrogen atom to which they are attached form a heterocycloalkyl ring;

each $R_{20}$, $R_{21}$, and $R_{22}$ is independently at each occurrence H or $(C_1-C_4)$ alkyl;

each $R_{23}$ is independently selected from $(C_1-C_4)$ alkyl, $(C_1-C_4)$ alkoxy, $(C_1-C_4)$ haloalkoxy, halogen, —C(O)$(C_1-C_4)$ alkyl, —C(O)O$(C_1-C_4)$ alkyl, —C(O)$(C_3-C_8)$ cycloalkyl, —C(O)heterocycloalkyl, —OH, —NH$_2$, and CN, wherein the alkyl and alkoxy are optionally substituted with one or more substituents selected from $(C_1-C_4)$ alkoxy and —OH; or two $R_{23}$ on the same atom to which they are attached form a spiroheterocycloalkyl ring; and each m, p, q, and r is independently 0, 1, or 2.

In some embodiments of the Formulae above, $X_1$ is $CR_6$, $X_2$ is $CR_7$, $X_3$ is $CR_8$, and $X_4$ is $CR_9$. In other embodiments, $X_1$ is $CR_6$, $X_2$ is $CR_7$, $X_3$ is $CR_8$, and $X_4$ is N. In other embodiments, $X_1$ is $CR_6$, $X_2$ is $CR_7$, $X_3$ is N, and $X_4$ is $CR_9$. In other embodiments, $X_1$ is $CR_6$, $X_2$ is N, $X_3$ is $CR_8$, and $X_4$ is $CR_9$. In other embodiments, $X_1$ is N, $X_2$ is $CR_7$, $X_3$ is $CR_8$, and $X_4$ is $CR_9$.

In some embodiments of the Formulae above, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —O$R_{20}$, —C(O)$R_{20}$, —CO$_2R_{20}$, and —N$R_{18}R_{19}$. In another embodiment, $R_1$ is H, methyl, —CH$_2$CH$_2$OH, —CH$_2$CH$_2$NH$_2$, —CH(CH$_3$)C(O)OH, or piperidinyl optionally substituted with —C(O)$R_{20}$. In yet another embodiment, $R_1$ is H or methyl.

In some embodiments of the Formulae above, $R_3$ is H, $(C_1-C_3)$ alkyl, $(C_1-C_3)$ haloalkyl, $(C_1-C_3)$ hydroxyalkyl, $(C_1-C_3)$ aminoalkyl, heterocycloalkyl, —C(O)OH, —C(O)NH$_2$, or CN. In yet another embodiment, $R_3$ is H, $(C_1-C_2)$ alkyl, $(C_1-C_2)$ hydroxyalkyl, —C(O)OH, —C(O)NH$_2$, or CN. In another embodiment, $R_3$ is H or $(C_1)$ alkyl.

In some embodiments of the Formulae above, $R_{3'}$ is H, $(C_1-C_3)$ alkyl, $(C_1-C_3)$ haloalkyl, $(C_1-C_3)$ hydroxyalkyl, $(C_1-C_3)$ aminoalkyl, heterocycloalkyl, halogen, —C(O)OH, —C(O)NH$_2$, or CN. In another embodiment, $R_{3'}$ is H, $(C_1-C_2)$ alkyl, $(C_1-C_2)$ hydroxyalkyl, —C(O)OH, —C(O)NH$_2$, or CN. In yet another embodiment, $R_{3'}$ is H or methyl.

In another embodiment, $R_3$ and $R_{3'}$ together with the carbon atom to which they are attached form a $(C_3-C_7)$ cycloalkyl ring. In yet another embodiment, $R_3$ and $R_{3'}$ together with the carbon atom to which they are attached form a heterocycloalkyl ring. In another embodiment, $R_3$ and $R_{3'}$ together with the carbon atom to which they are attached form a $(C_3-C_4)$ cycloalkyl ring In some embodiments of the Formulae above, $R_4$ is $(C_1-C_4)$ alkyl, $(C_1-C_4)$ alkoxy, $(C_1-C_4)$ haloalkyl, $(C_1-C_4)$ haloalkoxy, $(C_3-C_6)$ cycloalkyl, halogen, —NH$_2$, —C(O)$(C_1-C_4)$ alkyl, —O—$(C_0-C_2)$-alkylene-$(C_3-C_8)$ cycloalkyl, —NH$(C_1-C_4)$ alkyl, or —N$((C_1-C_4)$ alkyl$)_2$, wherein the alkyl and alkoxy are optionally substituted with one to three substituents selected from $(C_1-C_4)$ alkyl, $(C_1-C_4)$ alkoxy, —OH, —NH$_2$, —NH$(C_1-C_4)$ alkyl, and —N$((C_1-C_4)$ alkyl$)_2$. In another embodiment, $R_4$ is $(C_1-C_4)$ alkyl, $(C_1-C_4)$ alkoxy, $(C_1-C_4)$ haloalkyl, $(C_1-C_4)$ haloalkoxy, $(C_3-C_6)$ cycloalkyl, halogen, —NH$_2$, or —C(O)$(C_1-C_4)$ alkyl, wherein the alkyl is optionally substituted with one to three substituents $(C_1-C_4)$ alkoxy. In other embodiments, $R_4$ is heterocycloalkyl. In another embodiment, $R_4$ is pyrrolidinyl, piperazinyl, or piperidinyl.

In another embodiment, $R_4$ and $X_4$ together with the atoms to which they are attached form a $(C_6-C_{14})$ aryl ring optionally substituted with one or more $R_{17}$. In yet another embodiment, $R_4$ and $X_4$ on adjacent atoms together with the atoms to which they are attached form a heteroaryl ring optionally substituted with one or more $R_{17}$. In another embodiment, $R_4$ and $X_4$ together with the atoms to which they are attached form a $(C_5-C_7)$ cycloalkyl ring optionally substituted with one or more $R_{17}$. In yet another embodiment, $R_4$ and $X_4$ on adjacent atoms together with the atoms to which they are attached form a heterocycloalkyl ring optionally substituted with one or more $R_{17}$.

In some embodiments of the Formulae above, $R_5$ is H, $(C_1-C_4)$ alkyl, $(C_2-C_4)$ alkenyl, $(C_2-C_4)$ alkynyl, $(C_1-C_4)$ alkoxy, $(C_1-C_4)$ hydroxyalkyl, $(C_1-C_4)$ haloalkoxy, halogen, —OH, —NH$_2$, CN, —NH$(C_1-C_4)$ alkyl, —N$((C_1-C_4)$ alkyl$)_2$ or —NR$_{13}$C(O)R$_{14}$. In another embodiment, $R_5$ is H.

In some embodiments of the Formulae above, $R_6$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, or halogen, wherein the alkyl is optionally substituted with one to three $(C_1-C_6)$ alkoxy. In another embodiment, $R_6$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, or halogen, wherein the alkyl is optionally substituted with one to three $(C_1-C_6)$ alkoxy. In another embodiment, $R_6$ is H, $(C_1-C_4)$ alkyl, or halogen.

In some embodiments of the Formulae above, $R_7$ is H, $(C_1-C_4)$ alkyl, $(C_1-C_4)$ alkoxy, $(C_1-C_4)$ haloalkyl, $(C_1-C_4)$ haloalkoxy, or halogen, wherein the alkyl is optionally substituted with one to three $(C_1-C_6)$ alkoxy. In another embodiment, $R_7$ is H, $(C_1-C_4)$ alkyl, $(C_1-C_4)$ haloalkyl, or halogen. In yet another embodiment, $R_7$ is H, $(C_1-C_4)$ haloalkyl, or halogen.

In some embodiments of the Formulae above, $R_8$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, or halogen, wherein the alkyl is optionally substituted with one to three $(C_1-C_6)$ alkoxy. In another embodiment, $R_8$ is H, $(C_1-C_4)$ alkoxy, or halogen.

In some embodiments of the Formulae above, $R_9$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, or halogen, wherein the alkyl is optionally substituted with one to three $(C_1-C_4)$ alkoxy. In another embodiment, $R_9$ is H, $(C_1-C_4)$ alkyl, $(C_1-C_4)$ alkoxy, or halogen.

In some embodiments of the Formulae above, $R_{10}$ is $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, —C(O)R$_{14}$, —C(O)OR$_{13}$, —NR$_{13}$R$_{14}$, —NR$_{13}$C(O)R$_{14}$, —NR$_{13}$C(O)NR$_{13}$R$_{14}$, —C(O)NR$_{13}$R$_{14}$, —S(O)$_p$R$_{14}$, —NR$_{13}$S(O)$_p$R$_{14}$, —S(O)$_p$NR$_{13}$R$_{14}$, or CN, wherein the alkyl, alkenyl, alkynyl, and alkoxy are optionally substituted with one to three $R_{12}$. In another embodiment, $R_{10}$ is —C(O)R$_{14}$, —C(O)OR$_{13}$, —NR$_{13}$R$_{14}$, —NR$_{13}$C(O)R$_{14}$, —NR$_{13}$C(O)NR$_{13}$R$_{14}$, —C(O)NR$_{13}$R$_{14}$, —S(O)$_p$R$_{14}$, —NR$_{13}$S(O)$_p$R$_{14}$, —S(O)$_p$NR$_{13}$R$_{14}$, or CN. In another embodiment, $R_{10}$ is —(C$_0$-C$_2$)-alkylene-(C$_6$-C$_{14}$) aryl, —(C$_0$-C$_2$)-alkylene-heteroaryl, —(C$_0$-C$_2$)-alkylene-(C$_3$-C$_8$) cycloalkyl, —(C$_0$-C$_2$)-alkylene-heterocycloalkyl, —O—(C$_0$-C$_2$)-alkylene-aryl, —O—(C$_0$-C$_2$)-alkylene-heteroaryl, —O—(C$_0$-C$_2$)-alkylene-(C$_3$-C$_8$) cycloalkyl, or —O—(C$_0$-C$_2$)-alkylene-heterocycloalkyl, wherein the aryl, heteroaryl, cycloalkyl and heterocycloalkyl are optionally substituted with one to three $R_{11}$.

In another embodiment, two $R_{10}$ on adjacent atoms together with the atoms to which they are attached form a $(C_6-C_{14})$ aryl ring optionally substituted with one or more $R_{11}$. In yet another embodiment, two $R_{10}$ on adjacent atoms together with the atoms to which they are attached form a heteroaryl ring optionally substituted with one or more $R_{11}$. In another embodiment, two $R_{10}$ on adjacent atoms together with the atoms to which they are attached form a $(C_3-C_8)$ cycloalkyl ring optionally substituted with one or more $R_{11}$. In yet another embodiment, two $R_{10}$ on adjacent atoms together with the atoms to which they are attached form a heterocycloalkyl ring optionally substituted with one or more $R_{11}$. In another embodiment, two $R_{10}$ on the same atom to which they are attached form a spirocycloalkyl ring optionally substituted with one or more $R_{11}$. In yet another embodiment, two $R_{10}$ on the same atom to which they are attached form a spiroheterocycloalkyl ring optionally substituted with one or more $R_{11}$.

In some embodiments of the Formulae above, $R_{11}$ is $(C_1-C_6)$ alkyl, $(C_1-C_6)$ alkoxy, $(C_1-C_6)$ haloalkyl, $(C_1-C_6)$ haloalkoxy, halogen, CN, —OH, —NH$_2$, —NH$(C_1-C_4)$ alkyl, —N$((C_1-C_4)$ alkyl$)_2$, —C(O)O$(C_1-C_4)$ alkyl, —S(O)$_q$ $(C_1-C_4)$ alkyl, —C(O)NH$_2$, —C(O)NH$(C_1-C_4)$ alkyl, —C(O)N$((C_1-C_4)$ alkyl$)_2$, —NHC(O)$(C_1-C_4)$ alkyl, —N$((C_1-C_4)$ alkyl$)$C(O)$(C_1-C_4)$ alkyl, $(C_6-C_{14})$ aryl, heteroaryl, $(C_3-C_8)$ cycloalkyl, or heterocycloalkyl, wherein the alkyl, alkoxy, $(C_3-C_8)$ cycloalkyl, heterocycloalkyl, aryl, and heteroaryl are optionally substituted with one to three substituents selected from $(C_1-C_6)$ alkyl, $(C_1-C_6)$ alkoxy, $(C_1-C_6)$ haloalkyl, —C(O)OH, —C(O)O$(C_1-C_4)$ alkyl, —C(O)$(C_1-C_4)$ alkyl, —S(O)$_q$$(C_1-C_4)$ alkyl, —C(O)NH $(C_1-C_4)$ alkyl, —C(O)N$((C_1-C_4)$ alkyl$)_2$, —OH, —NH$_2$, CN, —NH$(C_1-C_4)$ alkyl, and —N$((C_1-C_4)$ alkyl$)_2$. In another embodiment, $R_{11}$ is $(C_1-C_6)$ alkyl, $(C_1-C_6)$ alkoxy, $(C_1-C_6)$ haloalkyl, $(C_1-C_6)$ haloalkoxy, or halogen, wherein the alkyl and alkoxy, are optionally substituted with one to three substituents selected from $(C_1-C_6)$ alkyl, $(C_1-C_6)$ alkoxy, $(C_1-C_6)$ haloalkyl, —C(O)OH, —C(O)O$(C_1-C_4)$ alkyl, —C(O)$(C_1-C_4)$ alkyl, —S(O)$_q$$(C_1-C_4)$ alkyl, —C(O)NH$(C_1-C_4)$ alkyl, —C(O)N$((C_1-C_4)$ alkyl$)_2$, —OH, —NH$_2$, CN, —NH$(C_1-C_4)$ alkyl, and —N$((C_1-C_4)$ alkyl$)_2$. In another embodiment, $R_{11}$ is CN, —OH, —NH$_2$, —NH$(C_1$-

$C_4$) alkyl, —N(($C_1$-$C_4$) alkyl)$_2$, —C(O)O($C_1$-$C_4$) alkyl, —S(O)$_q$($C_1$-$C_4$) alkyl, —C(O)NH$_2$, —C(O)NH($C_1$-$C_4$) alkyl, —C(O)N(($C_1$-$C_4$) alkyl)$_2$, —NHC(O)($C_1$-$C_4$) alkyl, or —N(($C_1$-$C_4$) alkyl)C(O)($C_1$-$C_4$) alkyl. In another embodiment, $R_{11}$ is ($C_6$-$C_{14}$) aryl, heteroaryl, ($C_3$-$C_8$) cycloalkyl, or heterocycloalkyl, wherein the ($C_3$-$C_8$) cycloalkyl, heterocycloalkyl, aryl, and heteroaryl are optionally substituted with one to three substituents selected from ($C_1$-$C_6$) alkyl, ($C_1$-$C_6$) alkoxy, ($C_1$-$C_6$) haloalkyl, —C(O)OH, —C(O)O($C_1$-$C_4$) alkyl, —C(O)($C_1$-$C_4$) alkyl, —S(O)$_q$ ($C_1$-$C_4$) alkyl, —C(O)NH($C_1$-$C_4$) alkyl, —C(O)N(($C_1$-$C_4$) alkyl)$_2$, —OH, —NH$_2$, CN, —NH($C_1$-$C_4$) alkyl, and —N(($C_1$-$C_4$) alkyl)$_2$.

In another embodiment, two $R_{11}$ on adjacent atoms together with the atoms to which they are attached form a heterocycloalkyl ring. In yet another embodiment, two $R_{11}$ on adjacent atoms together with the atoms to which they are attached form a ($C_5$-$C_8$) cycloalkyl ring. In another embodiment, two $R_{11}$ on adjacent atoms together with the atoms to which they are attached form a ($C_6$-$C_{14}$) aryl ring. In yet another embodiment, two $R_{11}$ on adjacent atoms together with the atoms to which they are attached form a heteroaryl ring.

In another embodiment, two $R_{11}$ together with the atom to which they are attached form a C=O.

In some embodiments of the Formulae above, $R_{12}$ is —NR$_{15}$R$_{16}$, —NR$_{15}$C(O)NR$_{15}$R$_{16}$, —NR$_{15}$C(O)R$_{16}$, —NR$_{15}$S(O)$_m$R$_{16}$, or —C(O)NH($C_3$-$C_8$) cycloalkyl. In another embodiment, $R_{12}$ is —NR$_{15}$R$_{16}$, —NR$_{15}$C(O)NR$_{15}$R$_{16}$, —NR$_{15}$C(O)R$_{16}$, or —NR$_{15}$S(O)$_m$R$_{16}$. In yet another embodiment, $R_{12}$ is ($C_1$-$C_6$) alkoxy or —C(O)NH ($C_3$-$C_8$) cycloalkyl.

In some embodiments of the Formulae above, $R_{13}$ is H, methyl, ethyl, n-propyl, i-propyl, n-butyl, s-butyl, or i-butyl.

In some embodiments of the Formulae above, $R_{14}$ is H, ($C_1$-$C_6$) alkyl, ($C_2$-$C_6$) alkenyl, ($C_2$-$C_6$) alkynyl, ($C_1$-$C_6$) haloalkyl, —($C_0$-$C_2$)-alkylene-($C_3$-$C_8$) cycloalkyl, —($C_0$-$C_2$)-alkylene-heterocycloalkyl, —($C_0$-$C_2$)-alkylene-($C_6$-$C_{14}$) aryl, or —($C_0$-$C_2$)-alkylene-heteroaryl, wherein the alkyl, cycloalkyl, heterocycloalkyl, aryl, and heteroaryl is optionally substituted with one to three substituents selected from ($C_1$-$C_4$) alkyl optionally substituted with ($C_1$-$C_4$) alkoxy, ($C_1$-$C_4$) alkoxy, ($C_1$-$C_4$) haloalkyl, ($C_1$-$C_4$) haloalkoxy, ($C_6$-$C_{14}$) aryl, heteroaryl, halogen, —OH, —NH$_2$, CN, —C(O)NH$_2$, —C(O)NH($C_1$-$C_4$) alkyl, —C(O)N(($C_1$-$C_4$) alkyl)$_2$, —NH($C_1$-$C_4$) alkyl, and —N(($C_1$-$C_4$) alkyl)$_2$. In another embodiment, $R_{14}$ is H, ($C_1$-$C_6$) alkyl, ($C_2$-$C_6$) alkenyl, ($C_2$-$C_6$) alkynyl, or ($C_1$-$C_6$) haloalkyl, wherein the alkyl is optionally substituted with one to three substituents selected from ($C_1$-$C_4$) alkyl optionally substituted with ($C_1$-$C_4$) alkoxy, ($C_1$-$C_4$) alkoxy, ($C_1$-$C_4$) haloalkyl, ($C_1$-$C_4$) haloalkoxy, ($C_6$-$C_{14}$) aryl, heteroaryl, halogen, —OH, —NH$_2$, CN, —C(O)NH$_2$, —C(O)NH($C_1$-$C_4$) alkyl, —C(O)N(($C_1$-$C_4$) alkyl)$_2$, —NH($C_1$-$C_4$) alkyl, and —N(($C_1$-$C_4$) alkyl)$_2$. In yet another embodiment, $R_{14}$ is —($C_0$-$C_2$)-alkylene-($C_3$-$C_8$) cycloalkyl, —($C_0$-$C_2$)-alkylene-heterocycloalkyl, —($C_0$-$C_2$)-alkylene-($C_6$-$C_{14}$) aryl, or —($C_0$-$C_2$)-alkylene-heteroaryl, wherein the cycloalkyl, heterocycloalkyl, aryl, and heteroaryl is optionally substituted with one to three substituents selected from ($C_1$-$C_4$) alkyl optionally substituted with ($C_1$-$C_4$) alkoxy, ($C_1$-$C_4$) alkoxy, ($C_1$-$C_4$) haloalkyl, ($C_1$-$C_4$) haloalkoxy, ($C_6$-$C_{14}$) aryl, heteroaryl, halogen, —OH, —NH$_2$, CN, —C(O)NH$_2$, —C(O)NH($C_1$-$C_4$) alkyl, —C(O)N(($C_1$-$C_4$) alkyl)$_2$, —NH($C_1$-$C_4$) alkyl, and —N(($C_1$-$C_4$) alkyl)$_2$.

In another embodiment, $R_{13}$ and $R_{14}$ together with the nitrogen atom to which they are attached form a heterocycloalkyl ring optionally substituted with one or more $R_{23}$. In another embodiment, $R_{13}$ and $R_{14}$ together with the nitrogen atom to which they are attached form a heterocycloalkyl ring optionally substituted with one to three $R_{23}$.

In some embodiments of the Formulae above, $R_{15}$ is H, methyl, ethyl, n-propyl, i-propyl, n-butyl, s-butyl, or i-butyl.

In some embodiments of the Formulae above, $R_{16}$ is H, ($C_1$-$C_6$) alkyl, ($C_2$-$C_6$) haloalkyl, ($C_3$-$C_8$) cycloalkyl, or —($C_0$-$C_2$)-alkylene-heteroaryl, wherein the alkyl, cycloalkyl, and heteroaryl are optionally substituted with one to three substituents independently selected from ($C_1$-$C_4$) alkyl, ($C_1$-$C_4$) alkoxy, ($C_1$-$C_4$) haloalkyl, ($C_1$-$C_4$) haloalkoxy, and halogen.

In some embodiments of the Formulae above, $R_{17}$ is ($C_1$-$C_6$) alkyl, ($C_2$-$C_6$) alkenyl, ($C_2$-$C_6$) alkynyl, ($C_1$-$C_6$) alkoxy, ($C_1$-$C_6$) haloalkyl, ($C_1$-$C_6$) haloalkoxy, ($C_1$-$C_6$) hydroxyalkyl, halogen, —OH, —NH$_2$, or CN.

In some embodiments of the Formulae above, $R_{18}$ is H, methyl, ethyl, n-propyl, i-propyl, n-butyl, s-butyl, or i-butyl.

In some embodiments of the Formulae above, $R_{19}$ is H, methyl, ethyl, n-propyl, i-propyl, n-butyl, s-butyl, or i-butyl.

In another embodiment, $R_{18}$ and $R_{19}$ together with the nitrogen atom to which they are attached form a heterocycloalkyl ring.

In some embodiments of the Formulae above, $R_{20}$ is H, methyl, ethyl, n-propyl, i-propyl, n-butyl, s-butyl, or i-butyl.

In some embodiments of the Formulae above, $R_{21}$ is H, methyl, ethyl, n-propyl, i-propyl, n-butyl, s-butyl, or i-butyl.

In some embodiments of the Formulae above, $R_{22}$ is H, ($C_1$-$C_4$) alkyl, or ($C_6$-$C_{10}$) aryl. In yet another embodiment, $R_{22}$ is H, methyl, ethyl, n-propyl, i-propyl, n-butyl, s-butyl, or i-butyl. In another embodiment, $R_{22}$ is ($C_6$-$C_{10}$) aryl.

In some embodiments of the Formulae above, $R_{23}$ is selected from ($C_1$-$C_4$) alkyl, ($C_1$-$C_4$) alkoxy, ($C_1$-$C_4$) haloalkoxy, halogen, —C(O)($C_1$-$C_4$) alkyl, —C(O)O($C_1$-$C_4$) alkyl, —C(O)($C_3$-$C_8$) cycloalkyl, —C(O)heterocycloalkyl, —OH, —NH$_2$, and CN, wherein the alkyl and alkoxy are optionally substituted with one to three substituents selected from ($C_1$-$C_4$) alkoxy and —OH. In yet another embodiment, $R_{23}$ is selected from ($C_1$-$C_4$) alkyl, ($C_1$-$C_4$) alkoxy, ($C_1$-$C_4$) haloalkoxy, and halogen, wherein the alkyl and alkoxy are optionally substituted with one or more substituents selected from ($C_1$-$C_4$) alkoxy and —OH. In another embodiment, $R_{23}$ is selected from —C(O)($C_1$-$C_4$) alkyl, —C(O)O($C_1$-$C_4$) alkyl, —C(O)($C_3$-$C_8$) cycloalkyl, —C(O)heterocycloalkyl, —OH, —NH$_2$, and CN.

In another embodiment, two $R_{23}$ on the same atom to which they are attached form a spiroheterocycloalkyl ring.

In some embodiments of the Formulae above, m is 0 or 1. In yet another embodiment, m is 1 or 2. In another embodiment, m is 0. In yet another embodiment, m is 1. In another embodiment, m is 2.

In some embodiments of the Formulae above, n is 0 or 1. In yet another embodiment, n is 1 or 2. In another embodiment, n is 0. In yet another embodiment, n is 1. In another embodiment, n is 2.

In some embodiments of the Formulae above, p is 0 or 1. In yet another embodiment, p is 1 or 2. In another embodiment, p is 0. In yet another embodiment, p is 1. In another embodiment, p is 2.

In some embodiments of the Formulae above, q is 0 or 1. In yet another embodiment, q is 1 or 2. In another embodiment, q is 0. In yet another embodiment, q is 1. In another embodiment, q is 2.

In some embodiments of the Formulae above, r is 0 or 1. In yet another embodiment, r is 1 or 2. In another embodiment, r is 0. In yet another embodiment, r is 1. In another embodiment, r is 2.

In some embodiments of the Formulae above, $R_1$ is H, —$CD_3$, ($C_1$-$C_6$) alkyl, ($C_2$-$C_6$) alkenyl, ($C_2$-$C_6$) alkynyl, ($C_1$-$C_6$) haloalkyl, ($C_2$-$C_6$) hydroxyalkyl, ($C_3$-$C_8$) cycloalkyl, or heterocycloalkyl, wherein the alkyl, alkenyl, alkynyl, cycloalkyl, and heterocycloalkyl are optionally substituted with one or more substituents selected from halogen, —$OR_{20}$, —$C(O)R_{20}$, —$CO_2R_{20}$, —$NR_{18}R_{19}$, —$NR_{20}C(O)R_{21}$, —$C(O)NR_{20}R_{21}$, —$NR_{20}C(O)NR_{21}R_{22}$, —$NR_{20}S(O)_rR_{21}$, —$S(O)_rNR_{20}R_{21}$, —$NR_{20}S(O)_rNR_{21}R_{22}$, —$S(O)_rR_{20}$, —$P(O)R_{20}R_{21}$, and —$Si((C_1$-$C_4)$ alkyl$)_3$; and $R_4$ is ($C_1$-$C_6$) alkyl, ($C_2$-$C_6$) alkenyl, ($C_2$-$C_6$) alkynyl, ($C_1$-$C_6$) alkoxy, ($C_1$-$C_6$) haloalkyl, ($C_1$-$C_6$) haloalkoxy, ($C_3$-$C_8$) cycloalkyl, —O—($C_0$-$C_2$)-alkylene-($C_3$-$C_8$) cycloalkyl, heterocycloalkyl, halogen, —OH, —$NH_2$, CN, —$C(O)(C_1$-$C_4)$ alkyl, —$C(O)O(C_1$-$C_4)$ alkyl, —$NR_{20}C(O)O(C_1$-$C_4)$ alkyl, —$Si(CH_3)_3$, —$SF_5$, —$S(O)_p(C_1$-$C_4)$alkyl, —$S(O)_p(NH)(C_1$-$C_4)$ alkyl, —$NH(C_1$-$C_4)$ alkyl, or —$N((C_1$-$C_4)$ alkyl$)_2$, wherein the alkyl, alkenyl, alkynyl, and alkoxy are optionally substituted with one or more substituents selected from ($C_1$-$C_6$) alkyl, ($C_1$-$C_6$) alkoxy, ($C_3$-$C_8$) cycloalkyl, —OH, —$S(O)_r(C_1$-$C_4)$ alkyl, —$S(O)_r(NH)(C_1$-$C_4)$ alkyl, —$SF_5$, —$Si(CH_3)_3$, —$NH_2$, —$NH(C_1$-$C_4)$ alkyl, and —$N((C_1$-$C_4)$ alkyl$)_2$; or $R_4$ and $X_4$ together with the atoms to which they are attached form a ($C_6$-$C_{14}$) aryl ring optionally substituted with one or more $R_{17}$; or $R_4$ and $X_4$ on adjacent atoms together with the atoms to which they are attached form a heteroaryl ring optionally substituted with one or more $R_{17}$; or $R_4$ and $X_4$ together with the atoms to which they are attached form a ($C_5$-$C_7$) cycloalkyl ring optionally substituted with one or more $R_{17}$; or $R_4$ and $X_4$ on adjacent atoms together with the atoms to which they are attached form a heterocycloalkyl ring optionally substituted with one or more $R_{17}$.

In some embodiments of the Formulae above, $R_2$ is

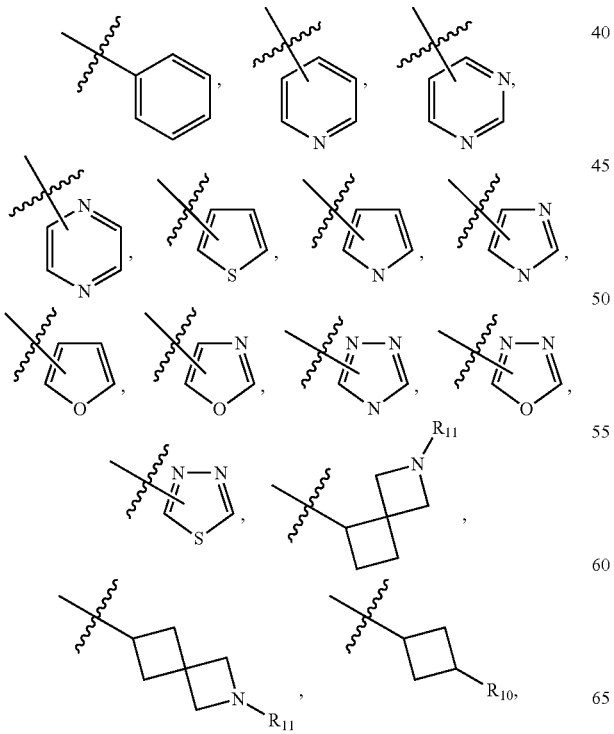

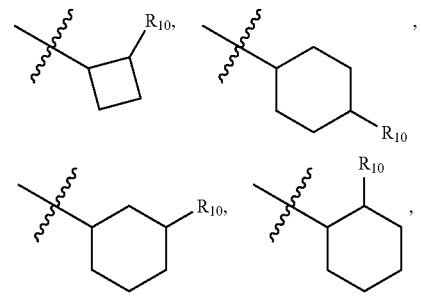

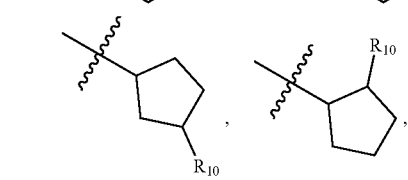

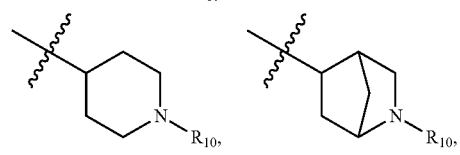

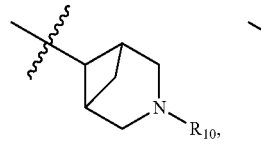

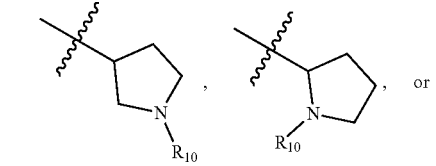

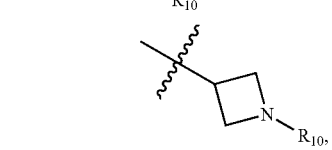

wherein each $R_2$ is substituted with one or more $R_{10}$.

In some embodiments of the Formulae above, $R_2$

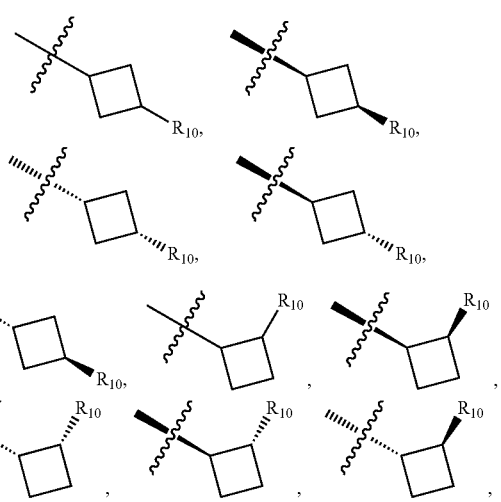

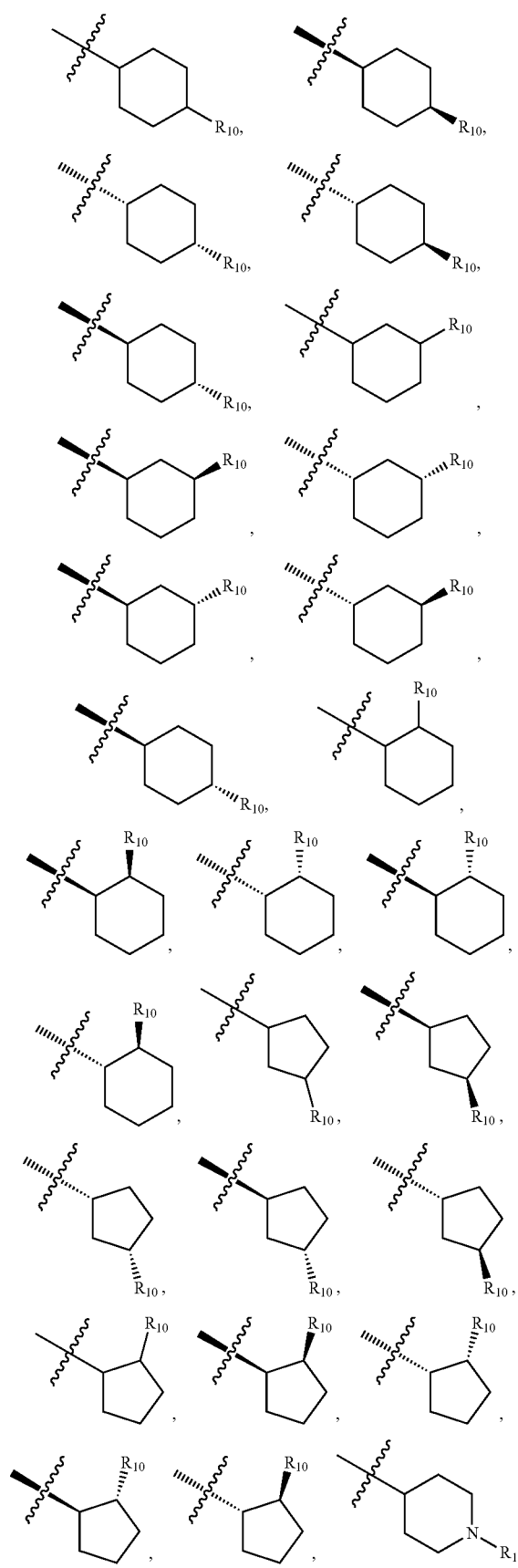
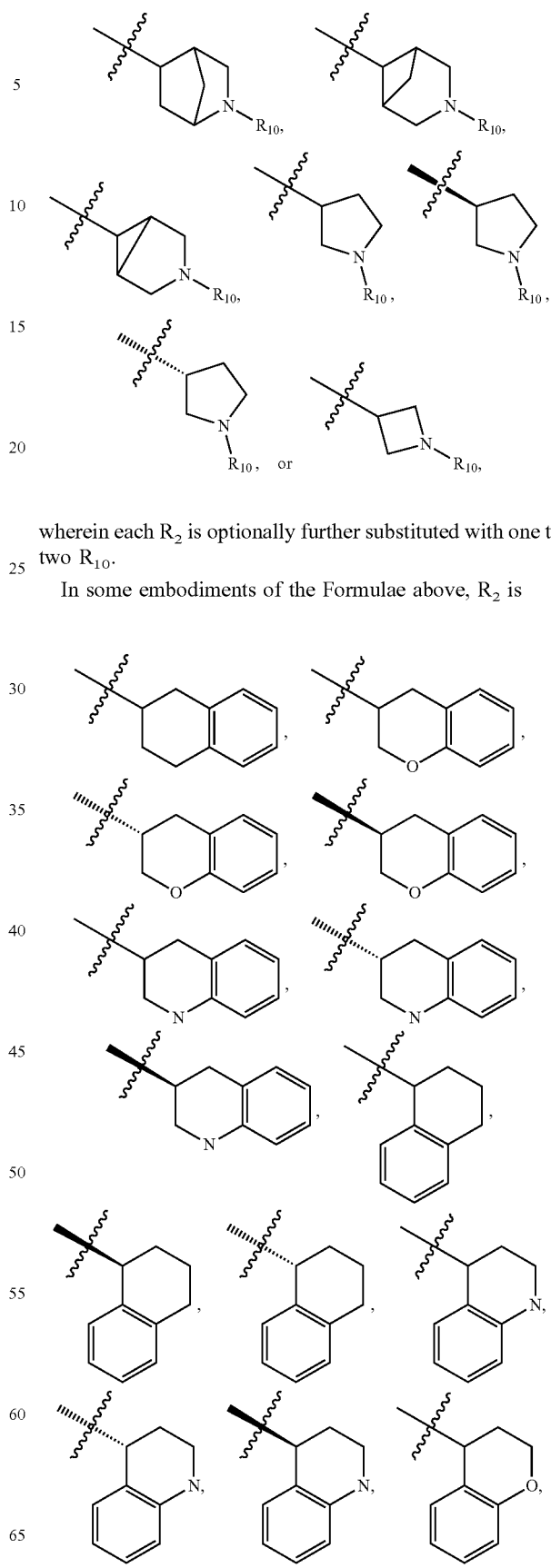
wherein each $R_2$ is optionally further substituted with one to two $R_{10}$.
In some embodiments of the Formulae above, $R_2$ is

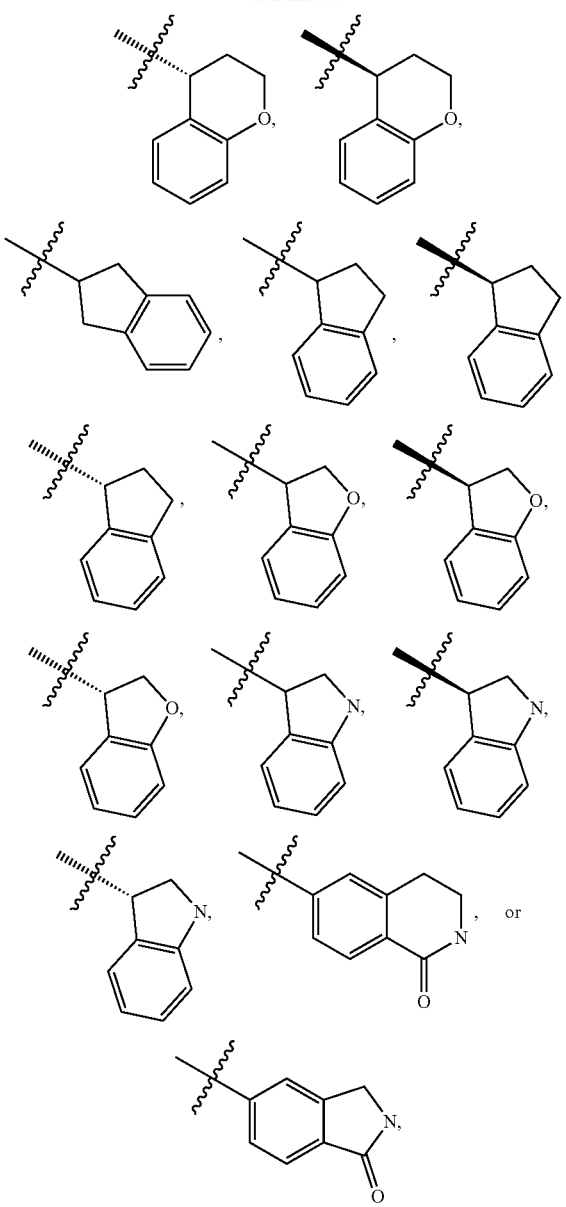
wherein each is optionally further substituted with one to two $R_{11}$.
In some embodiments of the Formulae above, $R_2$ is
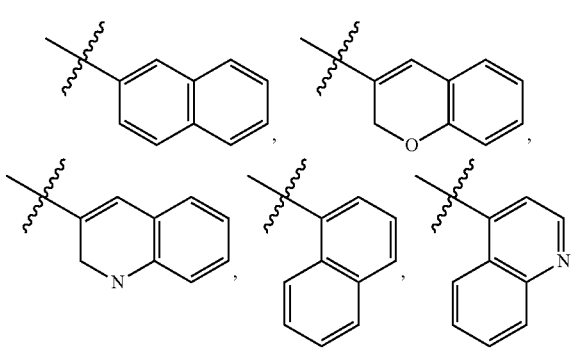
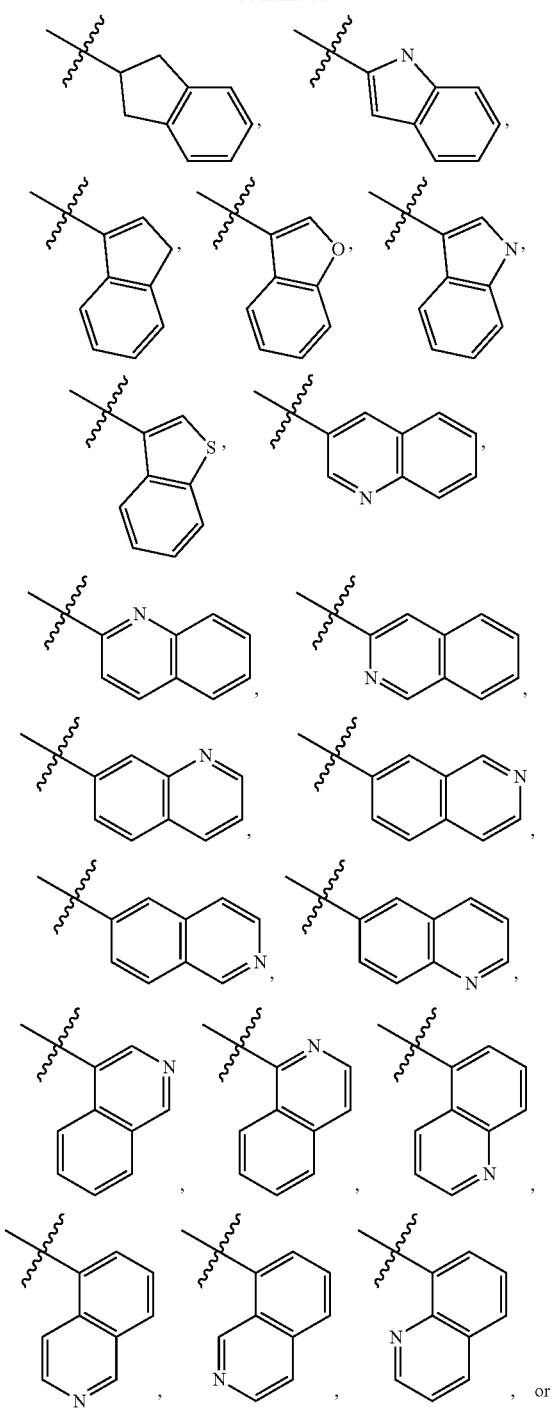
wherein each is optionally further substituted with one to two $R_{11}$.

In some embodiments of the Formulae above, $R_2$ is

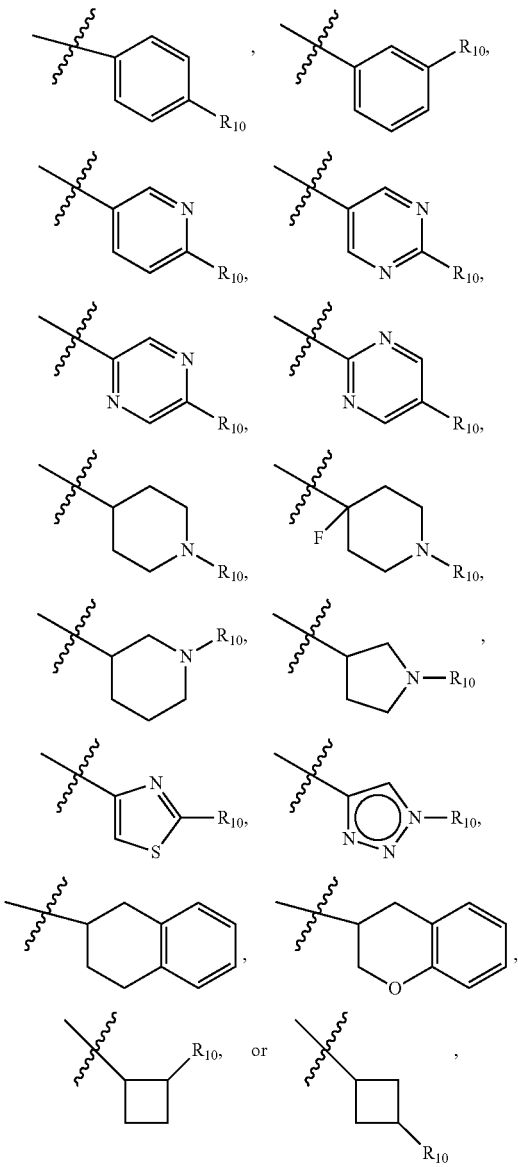

wherein each is optionally further substituted with one to two $R_{10}$.

In some embodiments of the Formulae above, n is 1 and $R_2$ is

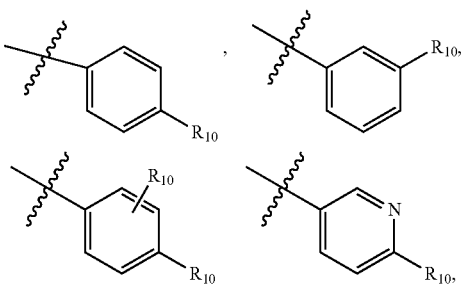

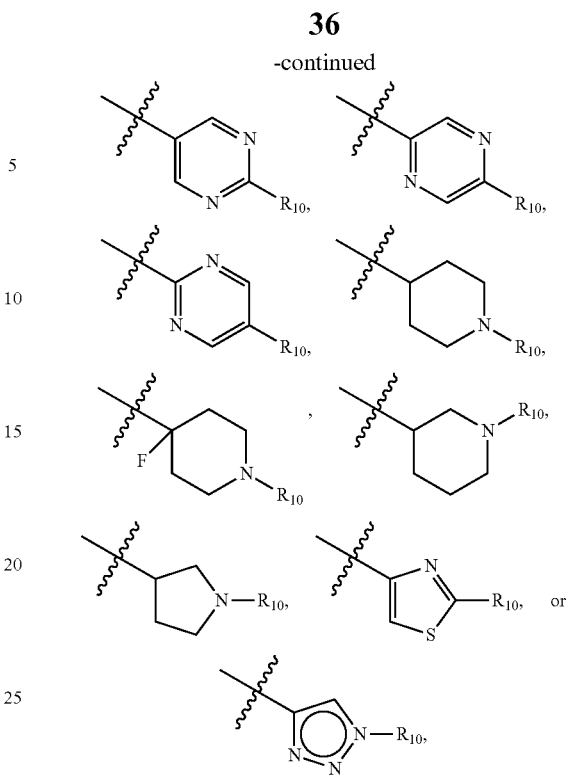

wherein each is optionally further substituted with one to two $R_{10}$.

In some embodiments of the Formulae above, n is 0 and $R_2$ is

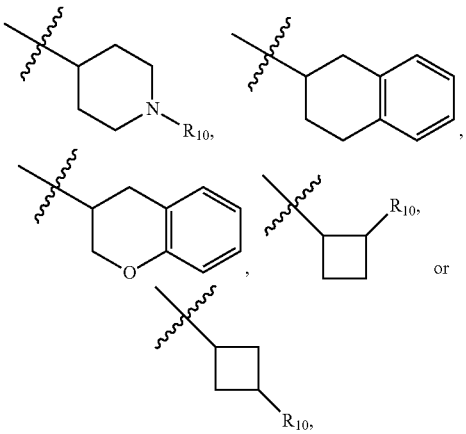

wherein each is optionally further substituted with one to two $R_{10}$.

In some embodiments of the Formulae above, n is 2 and $R_2$ is

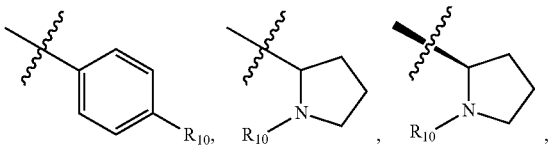

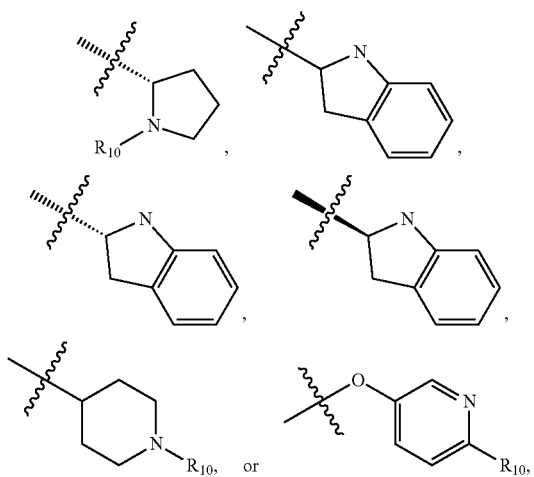
wherein each is optionally further substituted with one to two $R_{10}$.
In some embodiments of the Formulae above, $R_{10}$ is
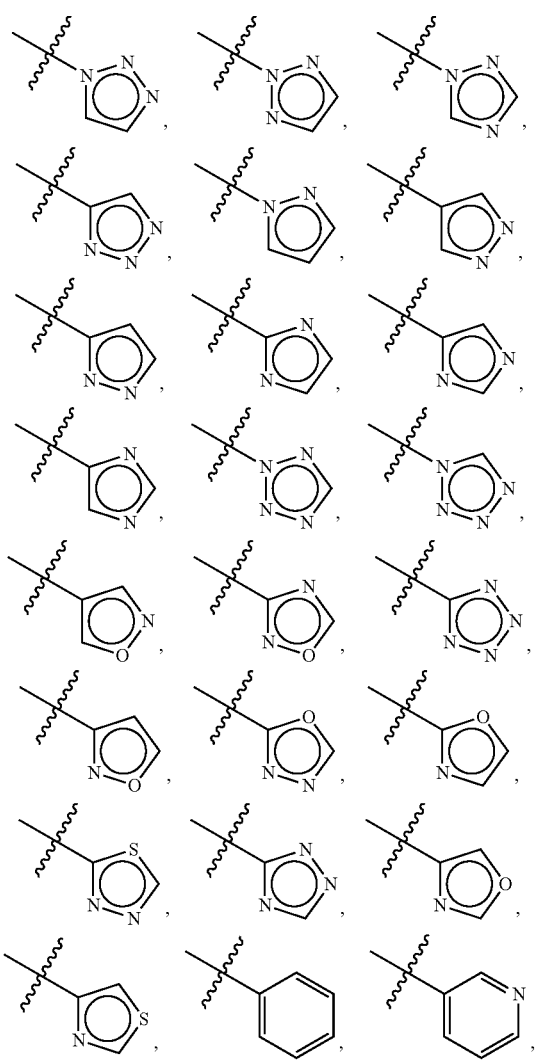
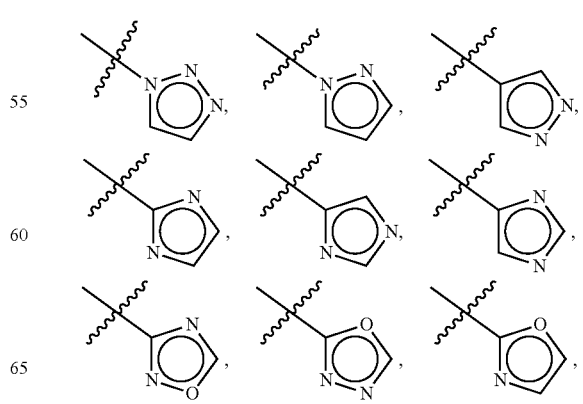
wherein each $R_{10}$ is optionally substituted with one to three $R_{11}$.
In some embodiments of the Formulae above, $R_{10}$ is

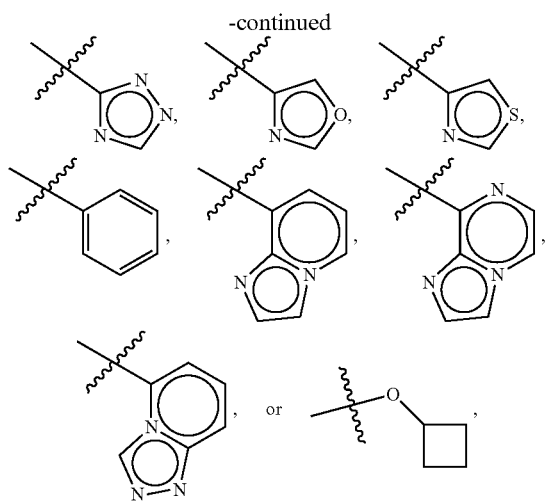

wherein each $R_{10}$ is optionally substituted with one to three $R_{11}$.

In some embodiments of Formula (I), $X_1$ is $CR_6$. In another embodiment, $X_1$ is $CR_6$ and $X_2$ is $CR_7$. In yet another embodiment, $X_1$ is $CR_6$, $X_2$ is $CR_7$, and $X_3$ is $CR_8$. In another embodiment, $X_1$ is $CR_6$, $X_2$ is $CR_7$, $X_3$ is $CR_8$, and $X_4$ is $CR_9$. In another embodiment, $X_1$ is $CR_6$, $X_2$ is $CR_7$, $X_3$ is $CR_8$, $X_4$ is $CR_9$, and $R_5$ is H. In yet another embodiment, $X_1$ is $CR_6$, $X_2$ is $CR_7$, $X_3$ is $CR_8$, $X_4$ is $CR_9$, $R_5$ is H, and $R_6$ is H, $(C_1-C_6)$ alkyl, or halogen. In another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, and $R_7$ is H, $(C_1-C_6)$ alkyl, $(C_1-C_6)$ haloalkyl, or halogen. In yet another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, and $R_8$ is H, $(C_1-C_6)$ alkyl, $(C_1-C_6)$ alkoxy, or halogen.

In another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, and $R_9$ is H, $(C_1-C_6)$ alkyl, $(C_1-C_6)$ alkoxy, or halogen. In another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_9$ is H, $(C_1-C_6)$ alkyl, $(C_1-C_6)$ alkoxy, or halogen, and $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$. In yet another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_9$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, and $R_{3'}$ is H.

In another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_9$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, and $R_3$ is H, $(C_1-C_6)$ alkyl, $(C_1-C_6)$ hydroxyalkyl, —$C(O)OH$, —$C(O)NH_2$, or CN. In another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_9$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, $R_3$ is H, $(C_1-C_6)$ alkyl, $(C_1-C_6)$ hydroxyalkyl, —$C(O)OH$, —$C(O)NH_2$, or CN, and $R_2$ is $(C_6-C_{14})$ aryl substituted with one or more $R_{10}$.

In another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_9$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, $R_3$ is H, $(C_1-C_6)$ alkyl, $(C_1-C_6)$ hydroxyalkyl, —$C(O)OH$, —$C(O)NH_2$, or CN, and $R_2$ is $(C_6-C_{14})$ aryl substituted with one or more $R_{10}$. In another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_9$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, $R_3$ is H, $(C_1-C_6)$ alkyl, $(C_1-C_6)$ hydroxyalkyl, —$C(O)OH$, —$C(O)NH_2$, or CN, $R_2$ is $(C_6-C_{14})$ aryl substituted with one or more $R_{10}$, and $R_{10}$ is $(C_6-C_{14})$ aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_9$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, $R_3$ is H, $(C_1-C_6)$ alkyl, $(C_1-C_6)$ hydroxyalkyl, —$C(O)OH$, —$C(O)NH_2$, or CN, and $R_2$ is heteroaryl substituted with one or more $R_{10}$. In yet another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_9$ is H, $(C_1-C_6)$ alkyl, $(C_1-C_6)$ alkoxy, or halogen, $R_1$ is H, $(C_1-C_6)$ alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, $R_3$ is H, ($C_1$-$C_6$) alkyl, ($C_1$-$C_6$) hydroxyalkyl, —C(O)OH, —C(O)$NH_2$, or CN, $R_2$ is heteroaryl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, $R_3$ is H, ($C_1$-$C_6$) alkyl, ($C_1$-$C_6$) hydroxyalkyl, —C(O)OH, —C(O)$NH_2$, or CN, and $R_2$ is ($C_3$-$C_8$) cycloalkyl substituted with one or more $R_{10}$.

In another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, $R_3$ is H, ($C_1$-$C_6$) alkyl, ($C_1$-$C_6$) hydroxyalkyl, —C(O)OH, —C(O)$NH_2$, or CN, $R_2$ is ($C_3$-$C_8$) cycloalkyl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, $R_3$ is H, ($C_1$-$C_6$) alkyl, ($C_1$-$C_6$) hydroxyalkyl, —C(O)OH, —C(O)$NH_2$, or CN, and $R_2$ is heterocycloalkyl substituted with one or more $R_{10}$. In yet another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, $R_3$ is H, ($C_1$-$C_6$) alkyl, ($C_1$-$C_6$) hydroxyalkyl, —C(O)OH, —C(O)$NH_2$, or CN, $R_2$ is heterocycloalkyl, substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, and $R_8$ is H, ($C_1$-$C_6$) alkyl, ($C_1$-$C_6$) alkoxy, or halogen. In another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, and $R_3$ and $R_{3'}$ together with the carbon atom to which they are attached form a ($C_3$-$C_7$) cycloalkyl ring.

In yet another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a ($C_3$-$C_7$) cycloalkyl ring, and $R_2$ is ($C_6$-$C_{14}$) aryl substituted with one or more $R_{10}$.

In another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a ($C_3$-$C_7$) cycloalkyl ring, $R_2$ is ($C_6$-$C_{14}$) aryl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In yet another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a ($C_3$-$C_7$) cycloalkyl ring, and $R_2$ is heteroaryl, substituted with one or more $R_{10}$. In another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a ($C_3$-$C_7$) cycloalkyl ring, $R_2$ is heteroaryl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a ($C_3$-$C_7$) cycloalkyl ring and $R_2$ is ($C_3$-$C_8$) cycloalkyl substituted with one or more $R_{10}$.

In yet another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a ($C_3$-$C_7$) cycloalkyl ring, $R_2$ is ($C_3$-$C_8$) cycloalkyl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a ($C_3$-$C_7$) cycloalkyl ring and $R_2$ is heterocycloalkyl substituted with one or more $R_{10}$. In yet another embodiment, $X_1$ is $CR_6$, $X_2$ is $CR_7$, $X_3$ is $CR_8$, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a ($C_3$-$C_7$) cycloalkyl ring, $R_2$ is heterocycloalkyl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In some embodiments of Formula (I), $X_1$ is $CR_6$. In another embodiment, $X_1$ is $CR_6$ and $X_2$ is $CR_7$. In yet another embodiment, $X_1$ is $CR_6$, $X_2$ is $CR_7$, and $X_3$ is $CR_8$. In another embodiment, $X_1$ is $CR_6$, $X_2$ is $CR_7$, $X_3$ is $CR_8$, and $X_4$ is N. In another embodiment, $X_1$ is $CR_6$, $X_2$ is $CR_7$, $X_3$ is $CR_8$, $X_4$ is N, and $R_5$ is H. In yet another embodiment, $X_1$ is $CR_6$, $X_2$ is $CR_7$, $X_3$ is $CR_8$, $X_4$ is N, $R_5$ is H, and $R_6$ is H, ($C_1$-$C_6$) alkyl, or halogen. In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, and $R_7$ is H, ($C_1$-$C_6$) alkyl, ($C_1$-$C_6$) haloalkyl, or halogen.

In yet another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, and $R_8$ is H, ($C_1$-$C_6$) alkyl, ($C_1$-$C_6$) alkoxy, or halogen. In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, and $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, and $R_{3'}$ is H.

In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, and $R_3$ is H, ($C_1$-$C_6$) alkyl, ($C_1$-$C_6$) hydroxyalkyl, —$C(O)OH$, —$C(O)NH_2$, or CN. In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, $R_3$ is H, ($C_1$-$C_6$) alkyl, ($C_1$-$C_6$) hydroxyalkyl, —$C(O)OH$, —$C(O)NH_2$, or CN, and $R_2$ is ($C_6$-$C_{14}$) aryl substituted with one or more $R_{10}$.

In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, $R_3$ is H, ($C_1$-$C_6$) alkyl, ($C_1$-$C_6$) hydroxyalkyl, —$C(O)OH$, —$C(O)NH_2$, or CN, $R_2$ is ($C_6$-$C_{14}$) aryl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, $R_3$ is H, ($C_1$-$C_6$) alkyl, ($C_1$-$C_6$) hydroxyalkyl, —$C(O)OH$, —$C(O)NH_2$, or CN, and $R_2$ is heteroaryl substituted with one or more $R_{10}$. In yet another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_{3'}$ is H, $R_3$ is H, ($C_1$-$C_6$) alkyl, ($C_1$-$C_6$) hydroxyalkyl, —$C(O)OH$, —$C(O)NH_2$, or CN, $R_2$ is heteroaryl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$, is H, $R_3$ is H, ($C_1$-$C_6$) alkyl, ($C_1$-$C_6$) hydroxyalkyl, —$C(O)OH$, —$C(O)NH_2$, or CN, and $R_2$ is ($C_3$-$C_8$) cycloalkyl substituted with one or more $R_{10}$. In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$, is H, $R_3$ is H, ($C_1$-$C_6$) alkyl, ($C_1$-$C_6$) hydroxyalkyl, —$C(O)OH$, —$C(O)NH_2$, or CN, $R_2$ is ($C_3$-$C_8$) cycloalkyl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$, is H, $R_3$ is H, ($C_1$-$C_6$) alkyl, ($C_1$-$C_6$) hydroxyalkyl, —$C(O)OH$, —$C(O)NH_2$, or CN, and $R_2$ is heterocycloalkyl substituted with one or more $R_{10}$. In yet another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$, is H, $R_3$ is H, ($C_1$-$C_6$) alkyl, ($C_1$-$C_6$) hydroxyalkyl, —$C(O)OH$, —$C(O)NH_2$, or CN, $R_2$ is heterocycloalkyl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, and $R_8$ is H, ($C_1$-$C_6$) alkyl, ($C_1$-$C_6$) alkoxy, or halogen. In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, and $R_3$ and $R_3$, together with the carbon atom to which they are attached form a ($C_3$-$C_7$) cycloalkyl ring.

In yet another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_3$, together with the carbon atom to which they are attached form a ($C_3$-$C_7$) cycloalkyl ring, and $R_2$ is ($C_6$-$C_{14}$) aryl substituted with one or more $R_{10}$. In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_3$, together with the carbon atom to which they are attached form a ($C_3$-$C_7$) cycloalkyl ring, $R_2$ is ($C_6$-$C_{14}$) aryl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In yet another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_3$, together with the carbon atom to which they are attached form a ($C_3$-$C_7$) cycloalkyl ring, and $R_2$ is heteroaryl substituted with one or more $R_{10}$. In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_3$, together with the carbon atom to which they are attached form a ($C_3$-$C_7$) cycloalkyl ring, $R_2$ is heteroaryl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_3$, together with the carbon atom to which they are attached form a ($C_3$-$C_7$) cycloalkyl ring and $R_2$ is ($C_3$-$C_8$) cycloalkyl substituted with one or more $R_{10}$. In yet another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_3$, together with the carbon atom to which they are attached form a ($C_3$-$C_7$) cycloalkyl ring, $R_2$ is ($C_3$-$C_8$) cycloalkyl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is N, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_1$ is H, ($C_1$-$C_6$)

alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a $(C_3-C_7)$ cycloalkyl ring and $R_2$ is heterocycloalkyl substituted with one or more $R_{10}$. In yet another embodiment, $X_1$ is $CR_6$, $X_2$ is $CR_7$, $X_3$ is $CR_8$, $X_4$ is N, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a $(C_3-C_7)$ cycloalkyl ring, $R_2$ is heterocycloalkyl substituted with one or more $R_{10}$, and $R_{10}$ is $(C_6-C_{14})$ aryl, heteroaryl, or heterocycloalkyl, wherein the aryl, heteroaryl, and heterocycloalkyl are optionally substituted with one or more $R_{11}$.

In yet another embodiment, $X_1$ is $CR_6$, $X_2$ is $CR_7$, $X_3$ is $CR_8$, $X_4$ is N, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a $(C_3-C_7)$ cycloalkyl ring, and $R_2$ is heteroaryl substituted with one or more $R_{10}$. In another embodiment, $X_1$ is $CR_6$, $X_2$ is $CR_7$, $X_3$ is $CR_8$, $X_4$ is N, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a $(C_3-C_7)$ cycloalkyl ring, $R_2$ is heteroaryl substituted with one or more $R_{10}$, and $R_{10}$ is $(C_6-C_{14})$ aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is N, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a $(C_3-C_7)$ cycloalkyl ring and $R_2$ is $(C_3-C_8)$ cycloalkyl substituted with one or more $R_{10}$. In yet another embodiment, $X_1$ is $CR_6$, $X_2$ is $CR_7$, $X_3$ is $CR_8$, $X_4$ is N, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a $(C_3-C_7)$ cycloalkyl ring, $R_2$ is $(C_3-C_8)$ cycloalkyl substituted with one or more $R_{10}$, and $R_{10}$ is $(C_6-C_{14})$ aryl, heteroaryl, or heterocycloalkyl, wherein the aryl, heteroaryl, and heterocycloalkyl are optionally substituted with one or more $R_{11}$.

In another embodiment, $X_1$ is $CR_6$, $X_2$ is $CR_7$, $X_3$ is $CR_8$, $X_4$ is N, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a $(C_3-C_7)$ cycloalkyl ring and $R_2$ is heterocycloalkyl substituted with one or more $R_{10}$. In yet another embodiment, $X_1$ is $CR_6$, $X_2$ is $CR_7$, $X_3$ is $CR_8$, $X_4$ is N, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ and $R_{3'}$ together with the carbon atom to which they are attached form a $(C_3-C_7)$ cycloalkyl ring, $R_2$ is heterocycloalkyl substituted with one or more $R_{10}$, and $R_{10}$ is $(C_6-C_{14})$ aryl, heteroaryl, or heterocycloalkyl, wherein the aryl, heteroaryl, and heterocycloalkyl are optionally substituted with one or more $R_{11}$.

In some embodiments of Formula (I), $X_1$ is $CR_6$. In another embodiment, $X_1$ is $CR_6$ and $X_2$ is $CR_7$. In yet another embodiment, $X_1$ is $CR_6$, $X_2$ is $CR_7$, and $X_3$ is N. In another embodiment, $X_1$ is $CR_6$, $X_2$ is $CR_7$, $X_3$ is N, and $X_4$ is $CR_9$. In another embodiment, $X_1$ is $CR_6$, $X_2$ is $CR_7$, $X_3$ is N, $X_4$ is $CR_9$, and $R_5$ is H. In yet another embodiment, $X_1$ is $CR_6$, $X_2$ is $CR_7$, $X_3$ is N, $X_4$ is $CR_9$, $R_5$ is H, and $R_6$ is H, $(C_1-C_6)$ alkyl, or halogen. In another embodiment, $X_1$ is $CR_6$, $X_2$ is $CR_7$, $X_3$ is N, $X_4$ is $CR_9$, $R_5$ is H, $R_6$ is H, $(C_1-C_6)$ alkyl, or halogen, and $R_7$ is H, $(C_1-C_6)$ alkyl, $(C_1-C_6)$ haloalkyl, or halogen. In another embodiment, $X_1$ is $CR_6$, $X_2$ is $CR_7$, $X_3$ is N, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, and $R_9$ is H, $(C_1-C_6)$ alkyl, $(C_1-C_6)$ alkoxy, or halogen. In another embodiment, $X_1$ is $CR_6$, $X_2$ is $CR_7$, $X_3$ is N, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_9$ is H, $(C_1-C_6)$ alkyl, $(C_1-C_6)$ alkoxy, or halogen, and $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$.

In yet another embodiment, $X_1$ is $CR_6$, $X_2$ is $CR_7$, $X_3$ is N, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_9$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, and $R_{3'}$ is H, $R_3$ is H, $(C_1-C_6)$ alkyl, $(C_1-C_6)$ hydroxyalkyl, —$C(O)OH$, —$C(O)NH_2$, or CN or $R_3$ and $R_{3'}$ together with the carbon atom to which they are attached form a $(C_3-C_7)$ cycloalkyl ring. In another embodiment, $X_1$ is $CR_6$, $X_2$ is $CR_7$, $X_3$ is N, $X_4$ is $CR_9$, $R_5$ is H, $R_6$ is H, $(C_1-C_6)$ alkyl, or halogen, $R_7$ is H, $(C_1-C_6)$ alkyl, $(C_1-C_6)$ haloalkyl, or halogen, $R_9$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from —$OR_{20}$, —$C(O)R_{20}$, —$CO_2R_{20}$, and —$NR_{18}R_{19}$, $R_3$ is H, $R_{3'}$ is H, ($C_1$-$C_6$) alkyl, ($C_1$-$C_6$) hydroxyalkyl, —C(O)OH, —C(O)NH$_2$, or CN or $R_3$ and $R_{3'}$ together with the carbon atom to which they are attached form a ($C_3$-$C_7$) cycloalkyl ring, and $R_2$ is ($C_6$-$C_{14}$) aryl, heteroaryl, ($C_3$-$C_8$) cycloalkyl, heterocycloalkyl, wherein the aryl, heteroaryl, cycloalkyl, and heterocycloalkyl substituted with one or more $R_{10}$.

In another embodiment, $X_1$ is $CR_6$, $X_2$ is $CR_7$, $X_3$ is N, $X_4$ is $CR_9$, $R_5$ is H, $R_6$ is H, ($C_1$-$C_6$) alkyl, or halogen, $R_7$ is H, ($C_1$-$C_6$) alkyl, ($C_1$-$C_6$) haloalkyl, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —OR$_{20}$, —C(O)R$_{20}$, —CO$_2$R$_{20}$, and —NR$_{18}$R$_{19}$, $R_3$ is H, $R_3$ is H, ($C_1$-$C_6$) alkyl, ($C_1$-$C_6$) hydroxyalkyl, —C(O)OH, —C(O)NH$_2$, or CN or $R_3$ and $R_{3'}$ together with the carbon atom to which they are attached form a ($C_3$-$C_7$) cycloalkyl ring, $R_2$ is ($C_6$-$C_{14}$) aryl, heteroaryl, ($C_3$-$C_8$) cycloalkyl, heterocycloalkyl, wherein the aryl, heteroaryl, cycloalkyl, and heterocycloalkyl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In some embodiments of Formula (I), $X_1$ is $CR_6$. In another embodiment, $X_1$ is $CR_6$ and $X_2$ is N. In yet another embodiment, $X_1$ is $CR_6$, $X_2$ is N, and $X_3$ is $CR_8$. In another embodiment, $X_1$ is $CR_6$, $X_2$ is N, $X_3$ is $CR_8$, and $X_4$ is $CR_9$. In another embodiment, $X_1$ is $CR_6$, $X_2$ is N, $X_3$ is $CR_8$, $X_4$ is $CR_9$, and $R_5$ is H. In yet another embodiment, $X_1$ is $CR_6$, $X_2$ is N, $X_3$ is $CR_8$, $X_4$ is $CR_9$, $R_5$ is H, and $R_6$ is H, ($C_1$-$C_6$) alkyl, or halogen. In another embodiment, $X_1$ is $CR_6$, $X_2$ is N, $X_3$ is $CR_8$, $X_4$ is $CR_9$, $R_5$ is H, $R_6$ is H, ($C_1$-$C_6$) alkyl, or halogen, and $R_8$ is H, ($C_1$-$C_6$) alkyl, ($C_1$-$C_6$) alkoxy, or halogen. In another embodiment, $X_1$ is $CR_6$, $X_2$ is N, $X_3$ is $CR_8$, $X_4$ is $CR_9$, $R_5$ is H, $R_6$ is H, ($C_1$-$C_6$) alkyl, or halogen, $R_8$ is H, ($C_1$-$C_6$) alkyl, ($C_1$-$C_6$) alkoxy, or halogen, and $R_9$ is H, ($C_1$-$C_6$) alkyl, ($C_1$-$C_6$) alkoxy, or halogen. In another embodiment, $X_1$ is $CR_6$, $X_2$ is N, $X_3$ is $CR_8$, $X_4$ is $CR_9$, $R_5$ is H, $R_6$ is H, ($C_1$-$C_6$) alkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, and $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —OR$_{20}$, —C(O)R$_{20}$, —CO$_2$R$_{20}$, and —NR$_{18}$R$_{19}$.

In another embodiment, $X_1$ is $CR_6$, $X_2$ is N, $X_3$ is $CR_8$, $X_4$ is $CR_9$, $R_5$ is H, $R_6$ is H, ($C_1$-$C_6$) alkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —OR$_{20}$, —C(O)R$_{20}$, —CO$_2$R$_{20}$, and —NR$_{18}$R$_{19}$, and $R_{3'}$ is H, $R_3$ is H, ($C_1$-$C_6$) alkyl, ($C_1$-$C_6$) hydroxyalkyl, —C(O)OH, —C(O)NH$_2$, or CN, and $R_{3'}$ is H, $R_3$ is H, ($C_1$-$C_6$) alkyl, ($C_1$-$C_6$) hydroxyalkyl, —C(O)OH, —C(O)NH$_2$, or CN or $R_3$ and $R_{3'}$ together with the carbon atom to which they are attached form a ($C_3$-$C_7$) cycloalkyl ring. In another embodiment, $X_1$ is $CR_6$, $X_2$ is N, $X_3$ is $CR_8$, $X_4$ is $CR_9$, $R_5$ is H, $R_6$ is H, ($C_1$-$C_6$) alkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —OR$_{20}$, $R_3$ is H, $R_3$ is H, ($C_1$-$C_6$) alkyl, ($C_1$-$C_6$) hydroxyalkyl, —C(O)OH, —C(O)NH$_2$, or CN or $R_3$ and $R_{3'}$ together with the carbon atom to which they are attached form a ($C_3$-$C_7$) cycloalkyl ring, and $R_2$ is ($C_6$-$C_{14}$) aryl, heteroaryl, ($C_3$-$C_8$) cycloalkyl, heterocycloalkyl, wherein the aryl, heteroaryl, cycloalkyl, and heterocycloalkyl substituted with one or more $R_{10}$.

In another embodiment, $X_1$ is $CR_6$, $X_2$ is N, $X_3$ is $CR_8$, $X_4$ is $CR_9$, $R_5$ is H, $R_6$ is H, ($C_1$-$C_6$) alkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —OR$_{20}$, —C(O)R$_{20}$, —CO$_2$R$_{20}$, and —NR$_{18}$R$_{19}$, $R_{3'}$ is H, $R_3$ is H, ($C_1$-$C_6$) alkyl, ($C_1$-$C_6$) hydroxyalkyl, —C(O)OH, —C(O)NH$_2$, or CN or $R_3$ and $R_{3'}$ together with the carbon atom to which they are attached form a ($C_3$-$C_7$) cycloalkyl ring, $R_2$ is ($C_6$-$C_{14}$) aryl, heteroaryl, ($C_3$-$C_8$) cycloalkyl, heterocycloalkyl, wherein the aryl, heteroaryl, cycloalkyl, and heterocycloalkyl substituted with one or more $R_{10}$, and $R_{10}$ is ($C_6$-$C_{14}$) aryl, heteroaryl, or heterocycloalkyl, wherein the aryl, heteroaryl, and heterocycloalkyl are optionally substituted with one or more $R_{11}$.

In some embodiments of Formula (I), $X_1$ is N. In another embodiment, $X_1$ is N and $X_2$ is $CR_7$. In yet another embodiment, $X_1$ is N, $X_2$ is $CR_7$, and $X_3$ is $CR_8$. In another embodiment, $X_1$ is N, $X_2$ is $CR_7$, $X_3$ is $CR_8$, and $X_4$ is $CR_9$. In another embodiment, $X_1$ is N, $X_2$ is $CR_7$, $X_3$ is $CR_8$, $X_4$ is $CR_9$, and $R_5$ is H. In yet another embodiment, $X_1$ is N, $X_2$ is $CR_7$, $X_3$ is $CR_8$, $X_4$ is $CR_9$, $R_5$ is H, and $R_7$ is H, ($C_1$-$C_6$) alkyl, ($C_1$-$C_6$) haloalkyl, or halogen. In yet another embodiment, $X_1$ is N, $X_2$ is $CR_7$, $X_3$ is $CR_8$, $X_4$ is $CR_9$, $R_5$ is H, $R_7$ is H, ($C_1$-$C_6$) alkyl, ($C_1$-$C_6$) haloalkyl, or halogen, and $R_8$ is H, ($C_1$-$C_6$) alkyl, ($C_1$-$C_6$) alkoxy, or halogen.

In another embodiment, $X_1$ is N, $X_2$ is $CR_7$, $X_3$ is $CR_8$, $X_4$ is $CR_9$, $R_5$ is H, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, and $R_9$ is H, ($C_1$-$C_6$) alkyl, ($C_1$-$C_6$) alkoxy, or halogen. In another embodiment, $X_1$ is N, $X_2$ is $CR_7$, $X_3$ is $CR_8$, $X_4$ is $CR_9$, $R_5$ is H, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, and $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —OR$_{20}$, —C(O)R$_{20}$, —CO$_2$R$_{20}$, and —NR$_{18}$R$_{19}$. In yet another embodiment, $X_1$ is N, $X_2$ is $CR_7$, $X_3$ is $CR_8$, $X_4$ is $CR_9$, $R_5$ is H, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —OR$_{20}$, —C(O)R$_{20}$, —CO$_2$R$_{20}$, and —NR$_{18}$R$_{19}$, and $R_{3'}$ is H, $R_3$ is H, ($C_1$-$C_6$) alkyl, ($C_1$-$C_6$) hydroxyalkyl, —C(O)OH, —C(O)NH$_2$, or CN or $R_3$ and $R_{3'}$ together with the carbon atom to which they are attached form a ($C_3$-$C_7$) cycloalkyl ring.

In another embodiment, $X_1$ is N, $X_2$ is $CR_7$, $X_3$ is $CR_8$, $X_4$ is $CR_9$, $R_5$ is H, $R_7$ is H, ($C_1$-$C_6$) alkyl, ($C_1$-$C_6$) haloalkyl, or halogen, $R_8$ is H, ($C_1$-$C_6$) alkyl, ($C_1$-$C_6$) alkoxy, or halogen, $R_9$ is H, ($C_1$-$C_6$) alkyl, ($C_1$-$C_6$) alkoxy, or halogen, $R_1$ is H, ($C_1$-$C_6$) alkyl, ($C_2$-$C_6$) hydroxyalkyl, or heterocycloalkyl, wherein the alkyl and heterocycloalkyl are optionally substituted with one or more substituents selected from —OR$_{20}$, —C(O)R$_{20}$, —CO$_2$R$_{20}$, and —NR$_{18}$R$_{19}$, $R_{3'}$ is H, $R_3$ is H, ($C_1$-$C_6$) alkyl, ($C_1$-$C_6$) hydroxyalkyl, —C(O)OH, —C(O)NH$_2$, or CN or $R_3$ and $R_{3'}$ together with the carbon atom to which they are attached form a ($C_3$-$C_7$) cycloalkyl ring, and $R_2$ is $(C_6-C_{14})$ aryl, heteroaryl, $(C_3-C_8)$ cycloalkyl, heterocycloalkyl, wherein the aryl, heteroaryl, cycloalkyl, and heterocycloalkyl substituted with one or more $R_{10}$.

In another embodiment, $X_1$ is N, $X_2$ is $CR_7$, $X_3$ is $CR_8$, $X_4$ is $CR_9$, $R_5$ is H, $R_7$ is H, $(C_1-C_6)$ alkyl, $(C_1-C_6)$ haloalkyl, or halogen, $R_8$ is H, $(C_1-C_6)$ alkyl, $(C_1-C_6)$ alkoxy, or halogen, $R_9$ is H, $(C_1-C_6)$ alkyl, $(C_1-C_6)$ alkoxy, or halogen, $R_1$ is H, $(C_1-C_6)$ alkyl, $(C_2-C_6)$ hydroxyalkyl, or heterocycloalkyl, wherein the alkyl and heterocycloalkyl are optionally substituted with one or more substituents selected from $-OR_{20}$, $-C(O)R_{20}$, $-CO_2R_{20}$, and $-NR_{18}R_{19}$, $R_3$ is H, $R_3$ is H, $(C_1-C_6)$ alkyl, $(C_1-C_6)$ hydroxyalkyl, $-C(O)OH$, $-C(O)NH_2$, or CN or $R_3$ and $R_{3'}$ together with the carbon atom to which they are attached form a $(C_3-C_7)$ cycloalkyl ring, $R_2$ is $(C_6-C_{14})$ aryl, heteroaryl, $(C_3-C_8)$ cycloalkyl, heterocycloalkyl, wherein the aryl, heteroaryl, cycloalkyl, and heterocycloalkyl substituted with one or more $R_{10}$, and $R_{10}$ is $(C_6-C_{14})$ aryl, heteroaryl, or heterocycloalkyl, wherein the aryl, heteroaryl, and heterocycloalkyl are optionally substituted with one or more $R_{11}$.

In some embodiments of the Formulae above, $X_1$ is $CR_6$, $X_2$ is $CR_7$, $X_3$ is $CR_8$, $X_4$ is N, $R_5$ is H, $R_6$ is H, $(C_1-C_6)$ alkyl, or halogen, $R_7$ is H, $(C_1-C_6)$ alkyl, or halogen, $R_8$ is H, $(C_1-C_6)$ alkyl, or halogen, and $R_1$ is H or $(C_1-C_6)$ alkyl. In another embodiment, $X_1$ is $CR_6$, $X_2$ is $CR_7$, $X_3$ is $CR_8$, $X_4$ is N, $R_5$ is H, $R_6$ is H, $(C_1-C_6)$ alkyl, or halogen, $R_7$ is H, $(C_1-C_6)$ alkyl, or halogen, $R_8$ is H, $(C_1-C_6)$ alkyl, or halogen, $R_9$ is H, $(C_1-C_6)$ alkyl, or halogen, $R_1$ is H or $(C_1-C_6)$ alkyl, and $R_3$ is H or $(C_1-C_6)$ alkyl. In another embodiment, $X_1$ is $CR_6$, $X_2$ is $CR_7$, $X_3$ is $CR_8$, $X_4$ is N, $R_5$ is H, $R_6$ is H, $(C_1-C_6)$ alkyl, or halogen, $R_7$ is H, $(C_1-C_6)$ alkyl, or halogen, $R_8$ is H, $(C_1-C_6)$ alkyl, or halogen, $R_9$ is H, $(C_1-C_6)$ alkyl, or halogen, $R_1$ is H or $(C_1-C_6)$ alkyl, $R_3$ is H or $(C_1-C_6)$ alkyl, and $R_{3'}$ is H or $(C_1-C_6)$ alkyl. In another embodiment, $X_1$ is $CR_6$, $X_2$ is $CR_7$, $X_3$ is $CR_8$, $X_4$ is N, $R_5$ is H, $R_6$ is H, $(C_1-C_6)$ alkyl, or halogen, $R_7$ is H, $(C_1-C_6)$ alkyl, or halogen, $R_8$ is H, $(C_1-C_6)$ alkyl, or halogen, $R_9$ is H, $(C_1-C_6)$ alkyl, or halogen, $R_1$ is H or $(C_1-C_6)$ alkyl, $R_3$ is H or $(C_1-C_6)$ alkyl, $R_{3'}$ is H or $(C_1-C_6)$ alkyl, and $R_4$ is $(C_1-C_6)$ alkyl, $(C_1-C_6)$ alkoxy, $-O-(C_0-C_2)$-alkylene-$(C_3-C_8)$ cycloalkyl, $-O-(C_0-C_2)$-alkylene-heterocycloalkyl, $-NH-(C_0-C_2)$-alkylene-$(C_3-C_8)$ cycloalkyl, or $-NH-(C_0-C_2)$-alkylene-heterocycloalkyl.

In another embodiment, $X_1$ is $CR_6$, $X_2$ is $CR_7$, $X_3$ is $CR_8$, $X_4$ is N, $R_5$ is H, $R_6$ is H, $(C_1-C_6)$ alkyl, or halogen, $R_7$ is H, $(C_1-C_6)$ alkyl, or halogen, $R_8$ is H, $(C_1-C_6)$ alkyl, or halogen, $R_9$ is H, $(C_1-C_6)$ alkyl, or halogen, $R_1$ is H or $(C_1-C_6)$ alkyl, $R_3$ is H or $(C_1-C_6)$ alkyl, $R_{3'}$ is H or $(C_1-C_6)$ alkyl, and $R_4$ is $-O-(C_0-C_2)$-alkylene-$(C_3-C_8)$ cycloalkyl, $-O-(C_0-C_2)$-alkylene-heterocycloalkyl, $-NH-(C_0-C_2)$-alkylene-$(C_3-C_8)$ cycloalkyl, or $-NH-(C_0-C_2)$-alkylene-heterocycloalkyl.

In some embodiments of the Formulae above, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, or halogen, $R_8$ is H, $(C_1-C_6)$ alkyl, or halogen, $R_9$ is H, $(C_1-C_6)$ alkyl, or halogen, and $R_1$ is H or $(C_1-C_6)$ alkyl. In another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, or halogen, $R_8$ is H, $(C_1-C_6)$ alkyl, or halogen, $R_9$ is H, $(C_1-C_6)$ alkyl, or halogen, $R_1$ is H or $(C_1-C_6)$ alkyl, and $R_3$ is H or $(C_1-C_6)$ alkyl. In another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, or halogen, $R_8$ is H, $(C_1-C_6)$ alkyl, or halogen, $R_9$ is H, $(C_1-C_6)$ alkyl, or halogen, $R_1$ is H or $(C_1-C_6)$ alkyl, $R_3$ is H or $(C_1-C_6)$ alkyl, $R_{3'}$ is H or $(C_1-C_6)$ alkyl, and $R_4$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, or halogen, $R_8$ is H, $(C_1-C_6)$ alkyl, or halogen, $R_9$ is H, $(C_1-C_6)$ alkyl, or halogen, $R_1$ is H or $(C_1-C_6)$ alkyl, $R_3$ is H or $(C_1-C_6)$ alkyl, $R_{3'}$ is H or $(C_1-C_6)$ alkyl, and $R_4$ is $(C_1-C_6)$ alkyl, $(C_1-C_6)$ alkoxy, $-O-(C_0-C_2)$-alkylene-$(C_3-C_8)$ cycloalkyl, $-O-(C_0-C_2)$-alkylene-heterocycloalkyl, $-NH-(C_0-C_2)$-alkylene-$(C_3-C_8)$ cycloalkyl, or $-NH-(C_0-C_2)$-alkylene-heterocycloalkyl.

In another embodiment, $X_1$ is $CR_6$, $X_2$ is $CR_7$, $X_3$ is $CR_8$, $X_4$ is $CR_9$, $R_5$ is H, $R_6$ is H, $(C_1-C_6)$ alkyl, or halogen, $R_7$ is H, $(C_1-C_6)$ alkyl, or halogen, $R_8$ is H, $(C_1-C_6)$ alkyl, or halogen, $R_9$ is H, $(C_1-C_6)$ alkyl, or halogen, $R_1$ is H or $(C_1-C_6)$ alkyl, $R_3$ is H or $(C_1-C_6)$ alkyl, $R_{3'}$ is H or $(C_1-C_6)$ alkyl, and $R_4$ is $-O-(C_0-C_2)$-alkylene-$(C_3-C_8)$ cycloalkyl, $-O-(C_0-C_2)$-alkylene-heterocycloalkyl, $-NH-(C_0-C_2)$-alkylene-$(C_3-C_8)$ cycloalkyl, or $-NH-(C_0-C_2)$-alkylene-heterocycloalkyl.

Non-limiting illustrative compounds of the application include:

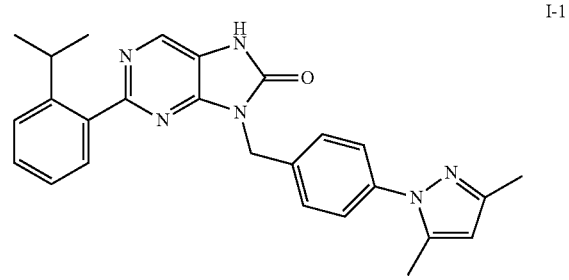

I-1

8-(4-[3,5-dimethyl-1H-pyrazol-1-yl]benzyl)-2-(2-isopropylphenyl)-7,8-dihydro-8H-purin-8-one

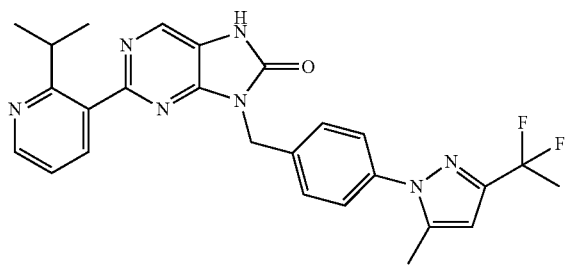

I-2

2-(2-isopropylpyridin-3-yl)-8-(4-(1-methyl-4-(trifluoromethyl)-1H-imidazol-2-yl)benzyl)-7,5-dihydro-8H-purin-8-one

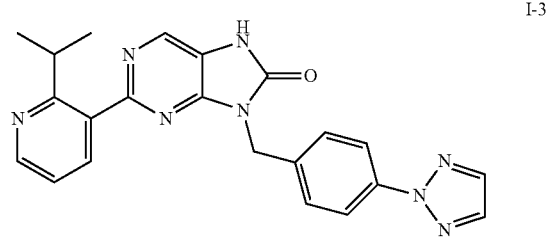

I-3

9-(4-(2H-1,2,3-triazol-2-yl)benzyl)-2-(2-ispropylpyridin-3-yl)-7,8-dihydro-8H-purin-8-one

I-4

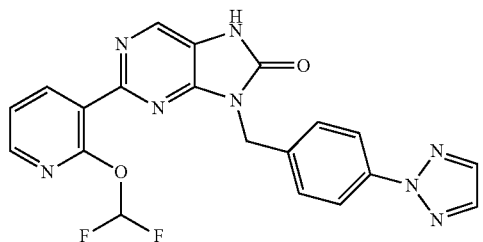

9-(4-(2H-1,2,3-triazol-2-yl)benzyl)-2-(2-(dihydromethoxy)
pyridin-3-yl)-7,9-dihydro-8H-purin-8-one

I-5

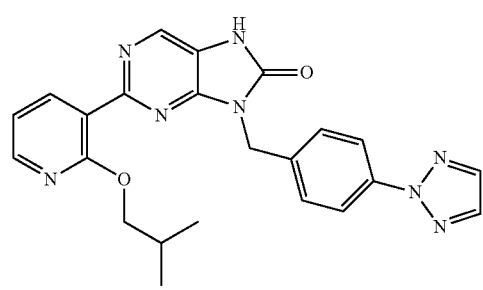

S-(4-(2H-1,2,3-triazol-2-yl)benzyl)-2-(2-isobutoxypyridin-
3-yl)-7,9-dihydro-8H-purin-8-one

I-6

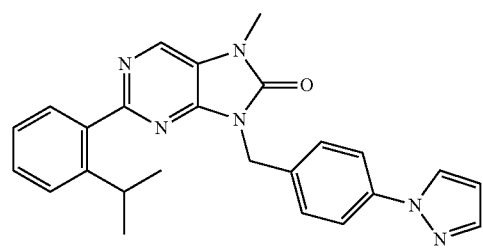

9-(4-(1H-pryazol-1-yl)benzyl)-2-(2-isopropylphenyl)-7-
methyl-7,8-dihydro-8H-purin-8-one

I-7

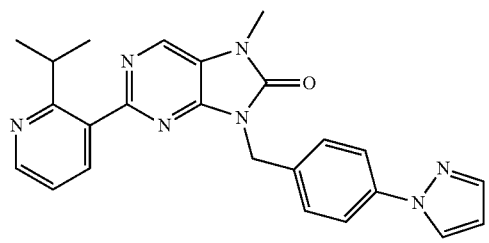

9-(4-(1H-pyrazol-1-yl)benzyl)-2-(2-isopropylpyridin-3-yl)
-7-methyl-7,5-dihydro-8H-purin-8-one

I-8

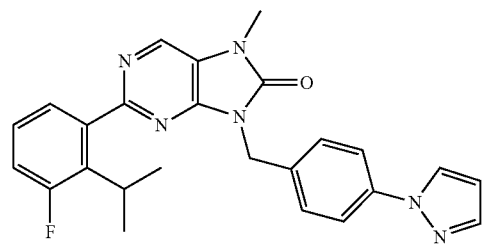

8-(4-(8H-pyrazol-1-yl)(benzyl)-2-(3-fluoro-2-iso-
propy)phenyl)-7-methyl)-7,8-thyoro-8H-purin-8-one

I-9

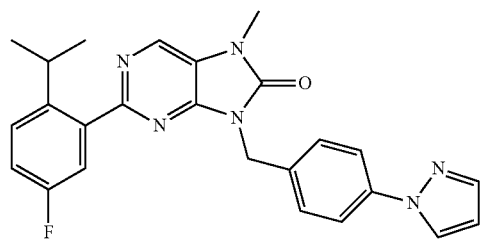

9-(4-(1H-pyrazol-1-yl)(benzyl)-2-(5-fluoro-2-des
propylphenyl)-7-methyl(-7,9-dihydro-8H)-purin-8-one

I-10

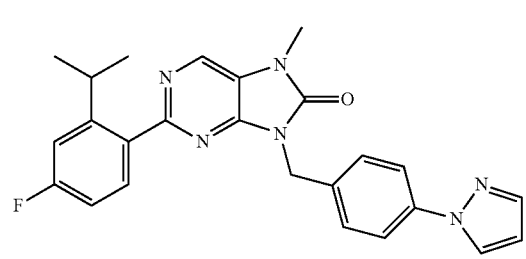

9-(4-(1H-pyrazol-1-yl)(benzyl)-2-(4-fluoro-2-des
propylphenyl)-7-methyl-7,9-dihydro-8H-purin-8-one

I-11

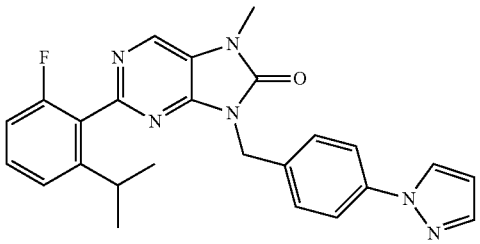

9-(4-(1H-pyrazol-1-yl)(benzyl)-2-(2-fluoro-8)-heopropyhenyl)-
7-methyl-7,8-dihydro-8H-purin-8-one

I-12

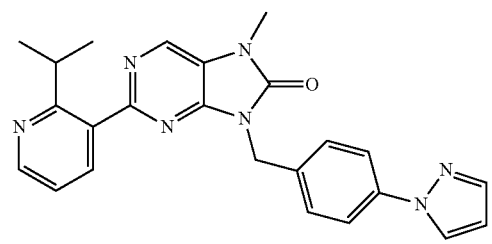

9-(4-(1H-pyrazol-1-yl)(benzyl)-2-(2-isoprophypurin-3-yl)1-7,8-
dihydro-8H-purin-8-one

I-13

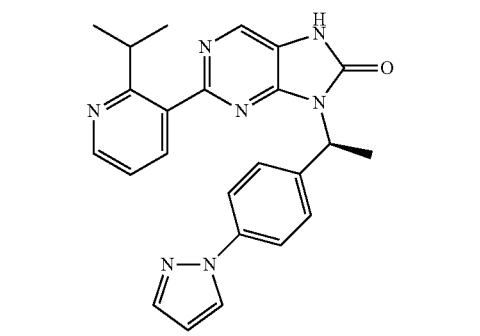

(S)-3-(1-(4-(1H-pyrazol-1-yl)phenyl)ethyl)-2-
(2-isopropylpyridin-3-yl)-7,8-dihydro-8H-purin-8-one -continued

I-14

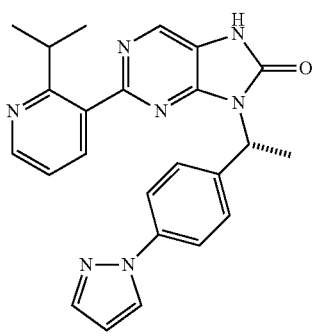

(R)-3-(1-(4-(1H-pyrazol-1-yl)phenyl)ethyl)-2-(2-isopropylpyridin-3-yl)-7,8-dihydro-8H-purin-8-one

I-15

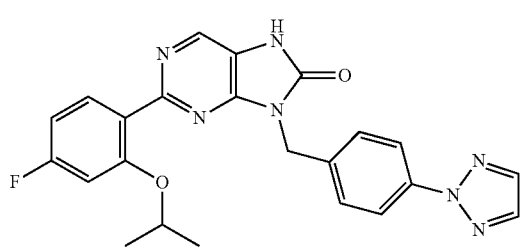

9-(4-(2H-1,2,3-trazol-2-yl)benzyl)-2-(4-fluoro-2-isopropyphenyl-7,5-dihydro-8H-purin-8-one

I-16

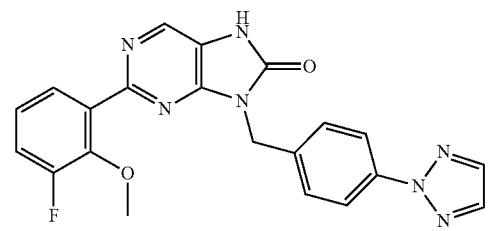

9-(4-(2H-1,2,3-trazol-2-yl)benzyl)-2-(3-fluoro-2-methoxyphenyl)-7,9-dihydro-8H-purin-8-one

I-17

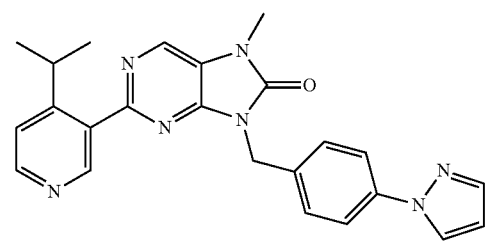

8-(4-(1H-pyrazol-1-yl)benzyl)-2-(4-isopropy(pyridin-3-yl)-7-methyl-7,8-dihydro-8H-purin-8-one -continued

I-18

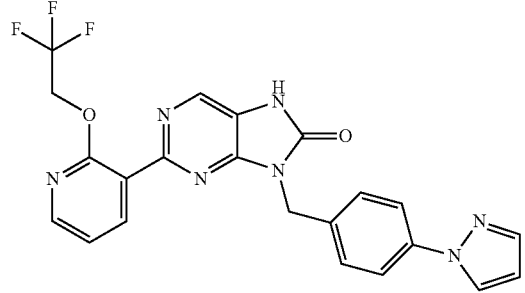

9-(4-(1H-pyrazol-1-yl)benzyl)-2-(2-(2,2,2-irifherothoxy)pyridin-3-yl)-7,9-dihydro-8H-purin-8-one

I-19

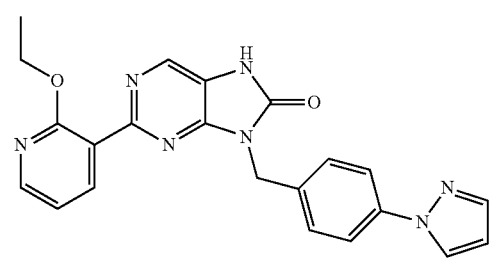

9-(4-(1H-pyrazol-1-yl)benzyl)-2-(2-ethyoxypyridin-3-yl)-7,8-dihydro-8H-purin-3-one

I-20

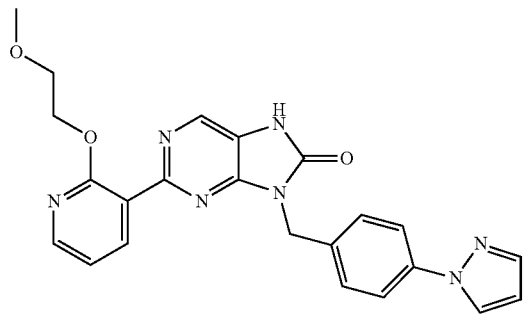

9-(4-(1H-pyrazol-1-yl)benzyl)-2-(2-(2-methoxyethoxy)phenyl)-7,8-dihydro-8H-purin-8-one

I-21

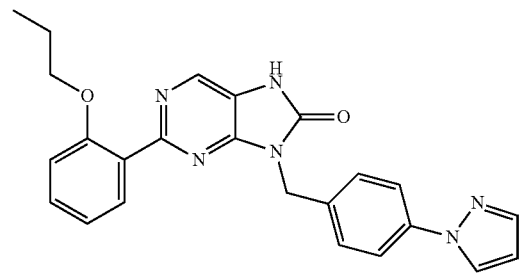

8-(4-(1H-pyrazol-1-yl)benzyl-1-(2-propyphenyl)-7,9-dihydro-8H-purin-8-one

I-22

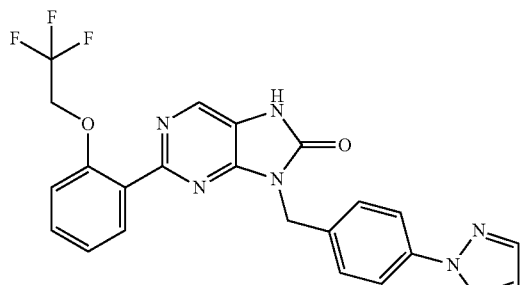

9-(4-(1H-pyrazol-1-yl)benzyl)-2-(2-(2,2,2-toluoroethoxy)phenyl)-7,9-dihydro-8H-purin-8-one

I-23

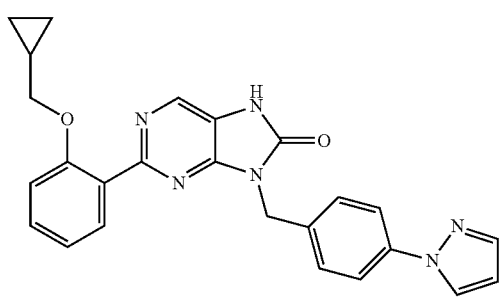

9-(4-(1H-pyrazol-1-yl)benzyl)-2-(2-(cyclopropy)methoxy)phenyl)-7,9-dihydro-8H-purin-8-one

I-24

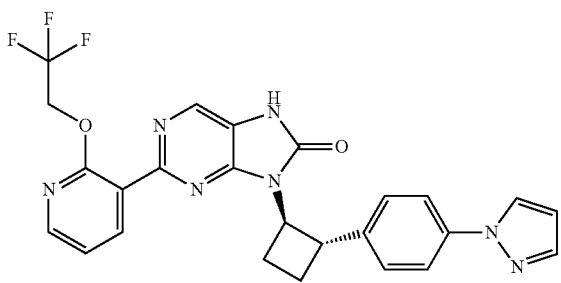

9-((1R,2S)-2-(4-(1H-pyrazzol-1-yl)phenyl)pyrothutyl-2-(2-(2,2,2-trifluomethoxy)pyridin-3-yl)-7,9-dihydro-8H-purin-8-one)

I-25

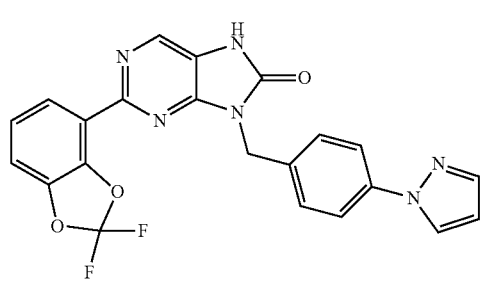

6-(4-(1H-pyrazol-1-yl)(benzyl)-2-(2,2-difluorbenzo)(1,3)dibuol-4-yl)-7,8-dihydro-8H-purin-8-one

I-26

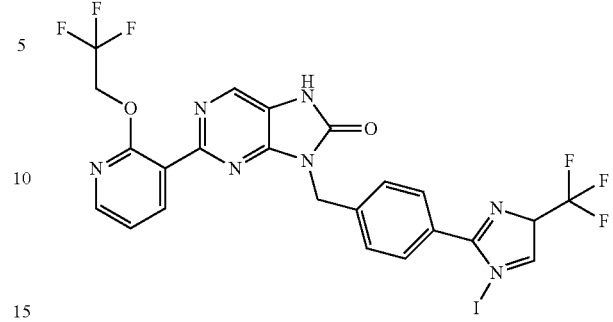

9-(4-(1-methyl-4-(trifluoromethyl)-1H-imidazol-2-yl)benzyl)-2-(2,2,2-trifluoroethoxy)pyridin-3-yl)-7,9-dihydro-8H-purin-8-one

I-27

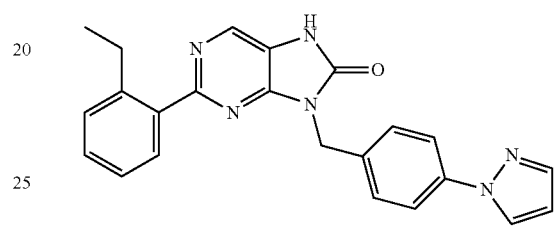

9-(4-1H-pyrazol-1-yl)(benzyl)-2-(2-ethylphenyl)-7,9-dihydro-8H-purin-8-one

I-28

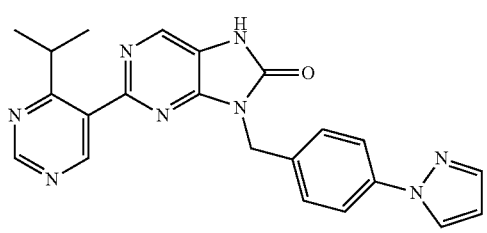

9-(4-1H-pyrazol-1-yl)(benzyl)-2-(2-isopropyl)pyrimidin-5-yl)-7,8-dihydro-8H-purin-8-one

I-29

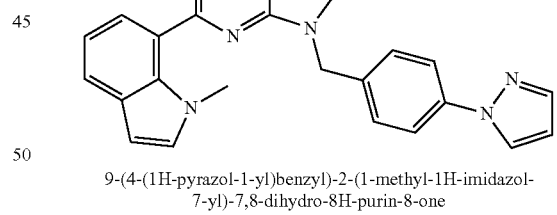

9-(4-(1H-pyrazol-1-yl)benzyl)-2-(1-methyl-1H-imidazol-7-yl)-7,8-dihydro-8H-purin-8-one

I-30

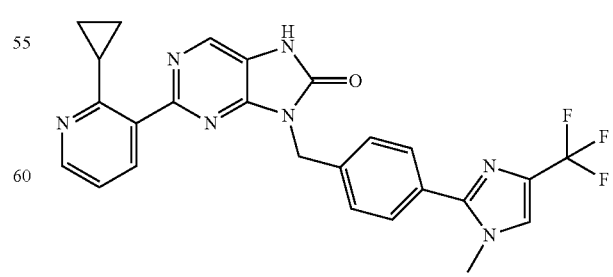

2-(2-cyclopropylpyridin-3-yl)-3-(4-(1-methyl)4-trifluoromethyl)-1H imidazol-2-yl)benzyl-7,5-dihydro-3H-purin-8-one

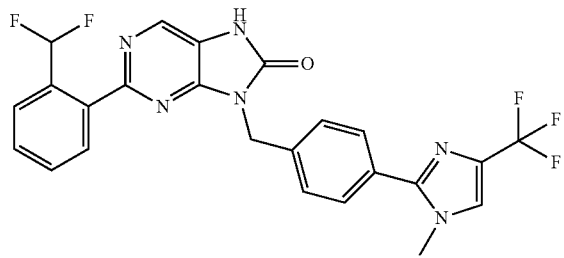

I-31

2-(2-(difluoromethyl)phenyl)-9-(4-(1-methyl-4-trifluoromethyl)-1H-imidazol-2-yl)benzyl)-7,8-dihydro-8H-purin-8-one

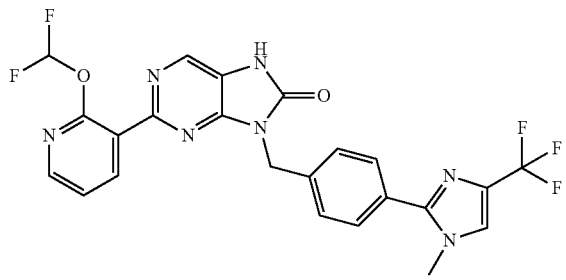

I-35

2-(2-(difluoromethoxy)pyridin-3-yl)-9-(4-(1-methyl-4-trifluormethyl)-1H-imidazol-2-yl)benzyl)-7,9-dihdro-8H-purin-8-one

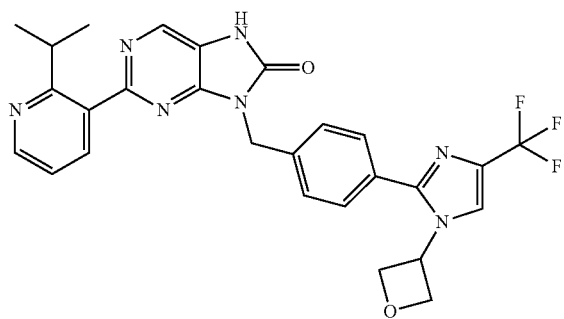

I-32

2-(2-(isopropylpyridin-3-yl)-9-(4-(1-oxetan-3-yl)-4-(trifluoromethyl)-1H-imidazol-2-yl)benzyl)-7,9-dihydro-8H-purin-8-one

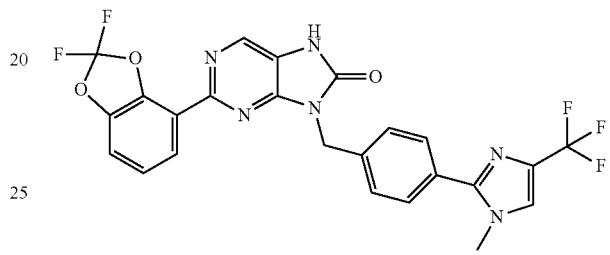

I-36

2-(2,2-difluorobenzo)d(1,3)diaxol-4-yl)-8-(4-yl-methyl-4-trifluormethyl)-1H-imidazol-2-yl)benzyl)-7,2-dihydro-8H-purin-8-one

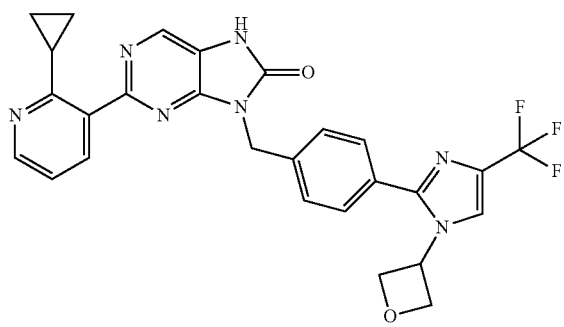

I-33

2-(2-cyclopropylpyridin-3-yl)-3-(4-1-joxetan-3-yl)-4-(trifluoromethyl)-1H-imidazol-2-yl)benzyl)-7,9-dihydro-8H-purin-8-one

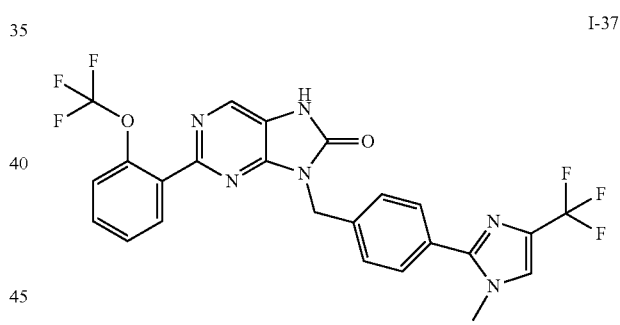

I-37

9-(4-(1-methyl-4-(trifluoromethyl)-1H-imidazol-2-yl)benzyl)-2-(2-(trifluoromethoxy)phenyl)-7,8-dihydro-8H-purin-8-one

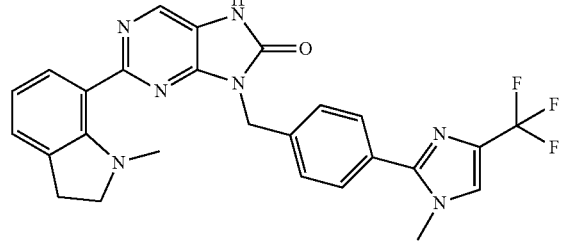

I-34

9-(4-(1-methyl-4-(trifluoromethyl)-1H-imidazol-2-yl)benzyl)-2-(1-methylindolin-7-yl)-7,9-dihydro-8H-purin-8-one

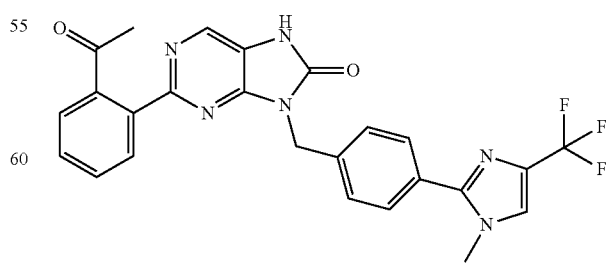

I-38

2-(2-acetylphenyl)-8-(4-(1H-methyl-4-(trifluoromethyl)-1H-imidazol-2-yl)benzyl)-7,8-dihydro-8H-purin-8-one -continued

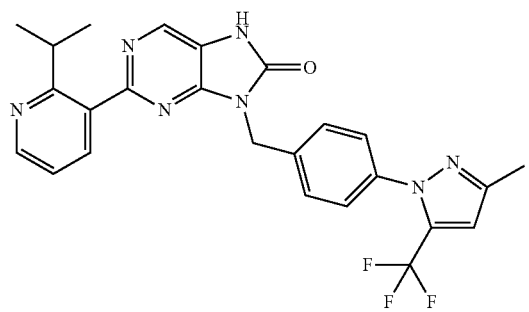

2-(2-isopropypyridin-3-yl)-8-(4-(3-methyl-5-(trifluormethyl)-
1H-pyrazol-1-yl)benzyl-7,8-dihydro-8H-purin-8-one

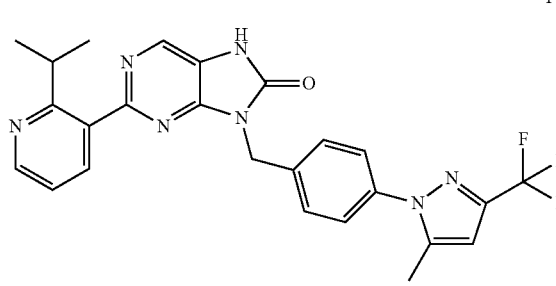

2-(2-isopropylpyridin-3-yl)-3-(-4-(5-methyl-3-trifluoromethyl)-1H-
pyrrazzol-1-yl)benzyl)-7,8-dihydro-8H-purin-8-one

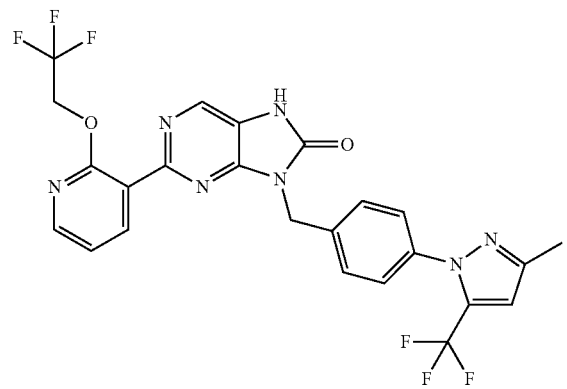

3-(4-(3-methyl)-5-(trifluoromethyl)-1H-pyrazol-1-yl)benzyl-2-
(2-(2,2,2-trifluorohoxy)pyridin-3-yl)-7,3-dihydro-8H-purinin-8-one

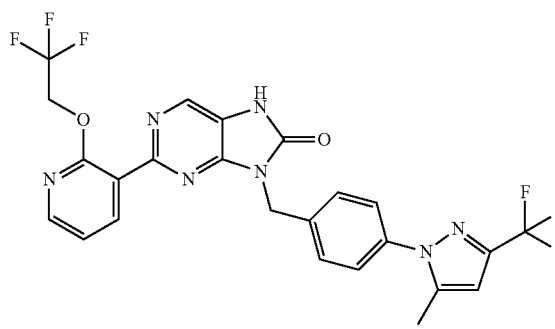

3-(4-(5-methyl)-3-(trifluoromethyl)-1H-pyrazol-1-yl)benzyl-2-
(2-(2,2,2-trifluorohoxy)pyrolin-3-yl)-7,9-dihydro-8H-purinin-8-one -continued

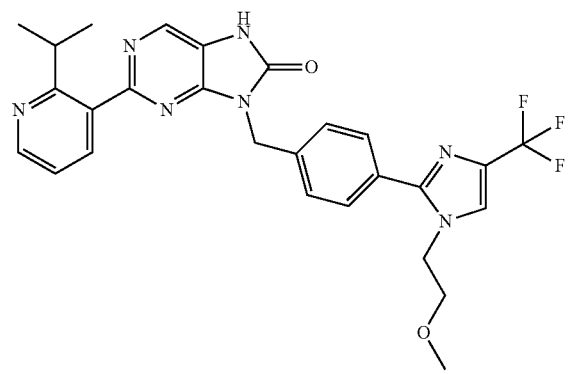

2-(2-isopropyl)pyridin-3-yl)-9-(4-(1-(2-methoxy
ethyl)-4-(trifluoromethyl)-1H-imidazol-2-yl)benzyl)-
7,9-dihydro-8H-purin-8-one

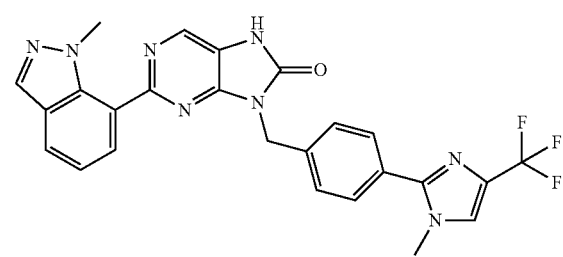

2-(1-methyl-1H-imdazol-7-yl)-3-(4-1H-methyl-4-(trifluoromethyl)-
1H-imidazol-2-yl)benzyl)-7,8-dihydro-8H-purin-8-one

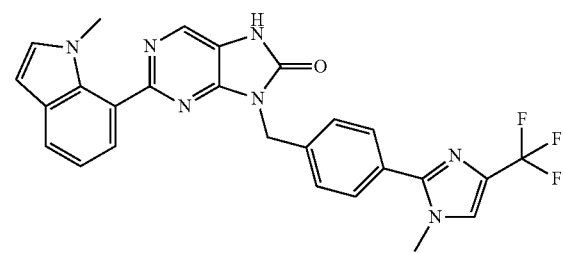

2-(1-methyl-1H-indol-7-yl)-8-(4-(1-methyl-4-(trifluoromethyl)-1H-
imidazol-2-yl)benzyl)-7,8-dihydro-8H-purin-8-one

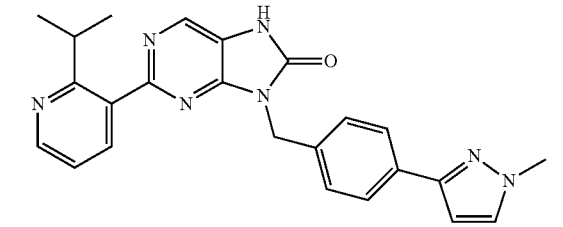

2-(2-isopropylpyridin-3-yl)-8-(3-methyl-1H-pyrazol-3-yl)benzyl)-
7,8-dihydro-8H-punin-8-one

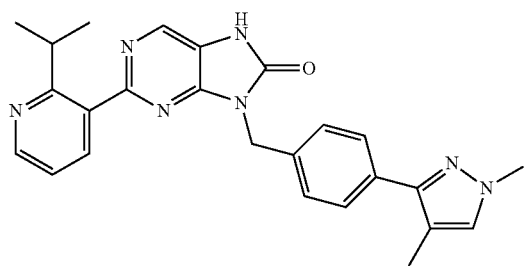

9-(4-(1,4-dimethyl-1H-pyrazol-3yl)benzyl-2-(2-isopropylpyridin-3-yl)-7,3-dihydro-8H-purini-8-one

I-47

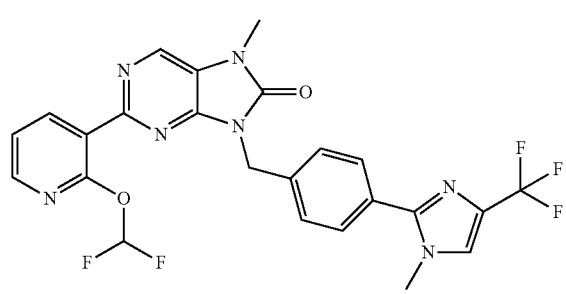

2-(2-(difluoromethoxy)pyridin-3-yl)-7-methyl-9-(4-(trifluoromethyl)-1H-imidazol-2-yl)benzyl)-7,3-dihydro-8H-purin-8-one

I-48

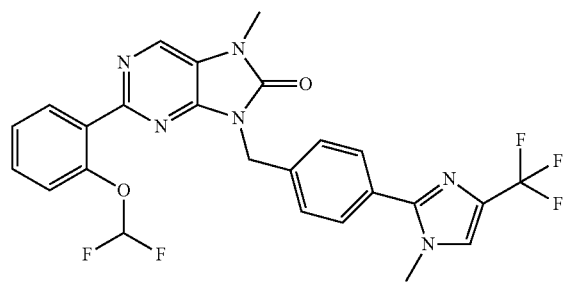

7-methyl-8-(4-(1-methyl-4-(trifluoromethyl)-1H-imitazol-2-yl)-2-benzyl)-2-(2-(trifluoromethoxy)phenyl)-7,9-dihydro-8H-purin-8-one

I-49

7-methyl-9-(4-(1-methyl-4-(trifluoromethyl)-1H-imitazol-2-yl)benzyl)-2-(2-2,2,2-trifluoromethoxy)pyridin-3-yl)-7,8-dihydro-8H-purin-8-one

I-50

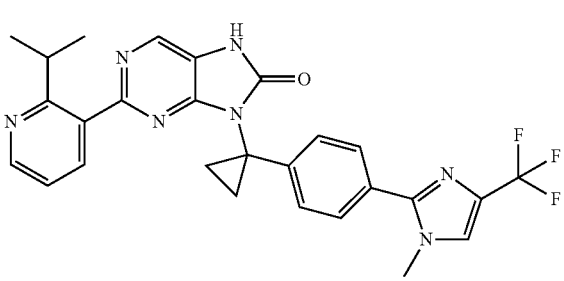

2-(2-isopropylpyridin-3-yl)-9-(1-(4-(1-methyl-4-(trifluoromethyl)-1H-imidazol-2-yl)phenyl)cycipropyl)-7,9-dihydro-8H-purin-8-one

I-51

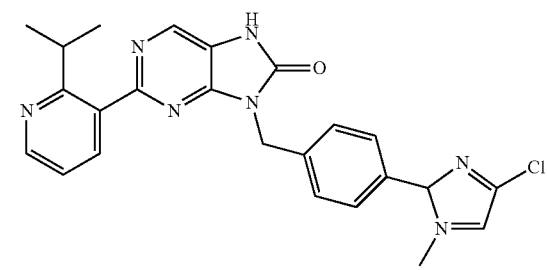

9-(4-(2-chloro-5-methyl-1H-pyrazol-1-yl)benzyl)-2-(2-isopropylpyridin-3-yl)-7,9-dihydro-8H-purin-8-one

I-52

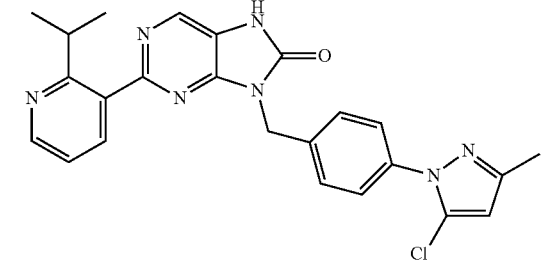

9-(4-(5-chloro-3-methyl-1H-pyrazol-1-yl)benzyl)-2-(2-isopropylpyridin-3-yl)-7,9-dihydro-8H-purin-8-one

I-53

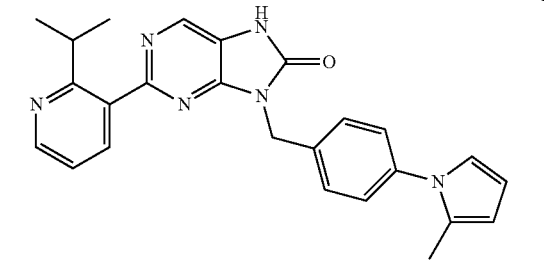

2-(2-isopropylpyridin-3-yl)-3-(4-(2-methyl-1H-pyrrol-1-yl)benzyl)-7,8-dihydro-8H-purin-8-one

I-54

I-55

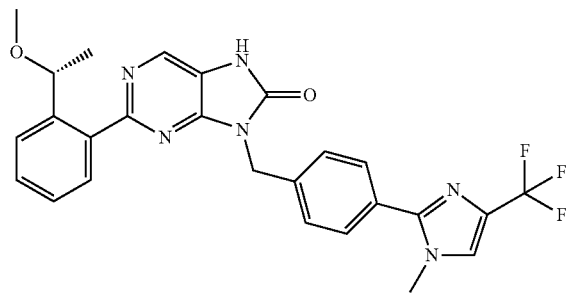

(R)-2-(2-(1-methoxyethyl)-8-(4-(1-methyl-4-(trifluoromethyl)-1H-imidazol-2-yl)benzyl)-7,9-dihydro-8H-purin-8-one

I-56

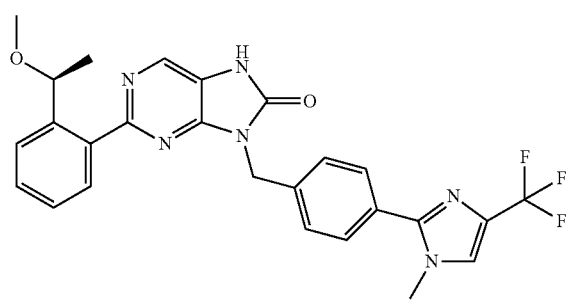

(S)-2-(2-(1-methoxyethyl)-8-(4-(1-methyl-4-(trifluoromethyl)-1H-imidazol-2-yl)benzyl)-7,9-dihydro-8H-purin-8-one

I-57

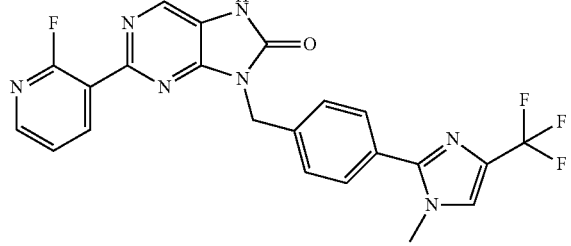

2-(2-fluoropyridin-3-yl)-8-(4-(1-methyl-4-(trifluoromethyl)-1H-imidazol-2-yl)benzyl)-7,8-dihydro-8H-purin-8-one

I-58

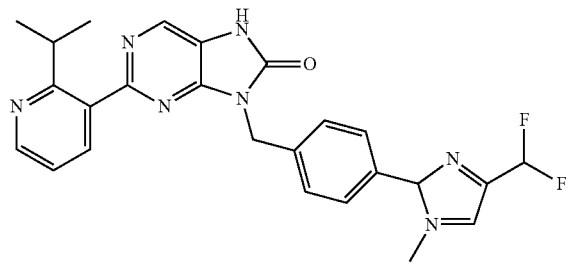

9-(4-(2-(dibromethyl)-5-methyl-1H-pyrazzol-1-yl)benzyl-2-(2-isopropylocyridin-3-yl)-7,8-dihydro-8H-purin-8-one

I-59

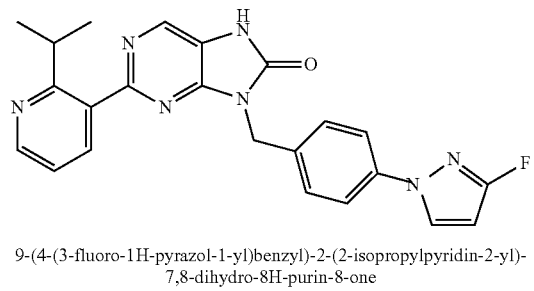

9-(4-(3-fluoro-1H-pyrazol-1-yl)benzyl)-2-(2-isopropylpyridin-2-yl)-7,8-dihydro-8H-purin-8-one

I-60

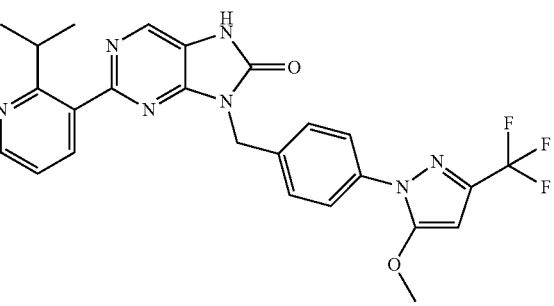

2-(2-isopropylpyridin-3-yl)-9-(4-(5-methoxy-3-(trifluoromethyl)-1H-pyrazol-1-yl)benzyl-7,9-dihydro-8H-purin-8-one

I-61

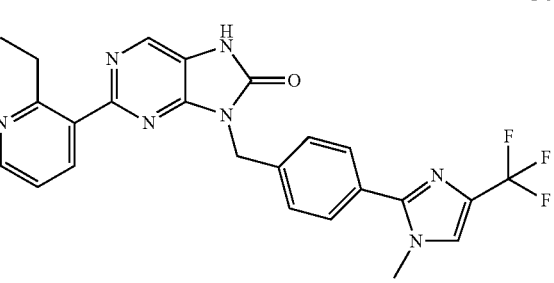

2-(2-ethylpyridin-3-yl)-7-methyl-8-(4-(1-methyl-4-(trifluoromethyl)-1H-imidazol-2-yl)benzyl)-7,8-dihydro-8H-purin-8-one

I-62

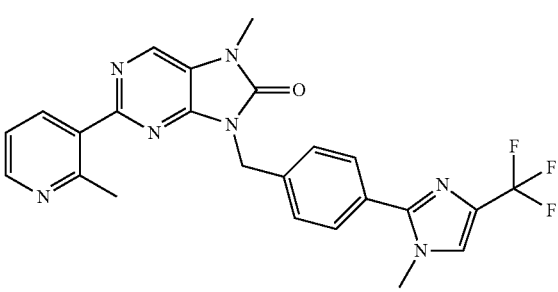

7-methyl-8-(4-(1-methyl-4-(trifluoromethyl)-1H-imidazol-2-yl)benzyl)-2-(2-methylpyridin-3-yl)-7,8-dihydro-8H-purin-8-one

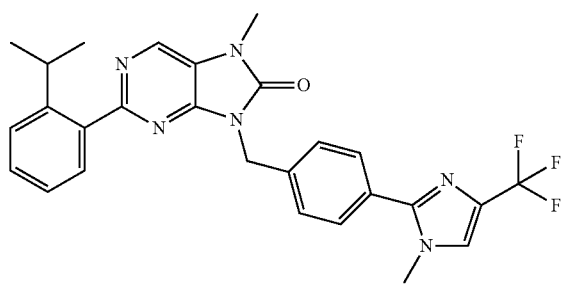

2-(2-isopropylphenyl)-7-methyl-5-(4-(1-methyl-4-(trifluoromethyl)-1H-imitazol-2-yl)benzyl)-7,9-dihydro-8H-purin-8-one

I-63

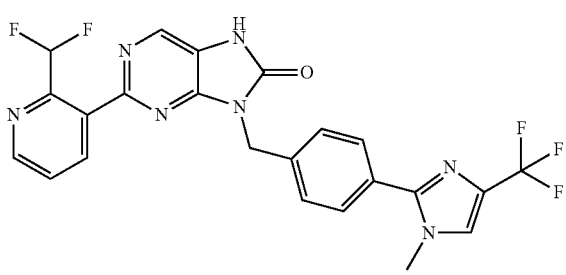

2-(2-difluoromethyl)pyridin-3-yl)-9-(4-(1-methyl-4-(trifluoromethyl)-1H-imidazol-2-yl)-benzyl-7,9-dihydro-8H-purin-8-one

I-64

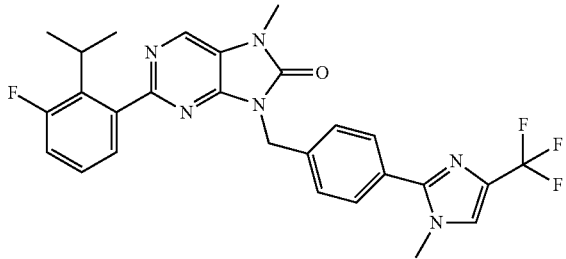

2-(3-fluoro-2-isopropylphenyl)-7-methyl-8-(4-(1-methyl-4-trifluoromethyl)-1H-imidazol-2-yl)-benzyl)-7,9-dihydro-8H-purin-8-one

I-65

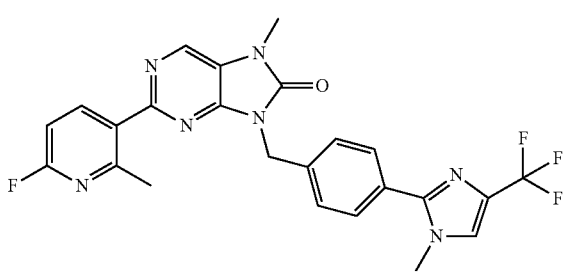

2-(6-fluoro-2-methylpyridin-3-yl)-7-methyl-9-(4-(1-methyl-4-(trifluoromethyl)-1H-imidazol-2-yl)-benzyl)-7,8-dihydro-8H-purin-8-one

I-66

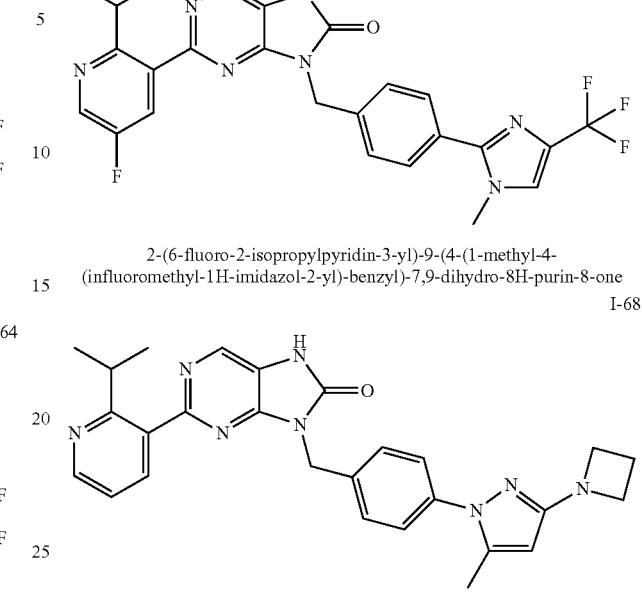

2-(6-fluoro-2-isopropylpyridin-3-yl)-9-(4-(1-methyl-4-(influoromethyl-1H-imidazol-2-yl)-benzyl)-7,9-dihydro-8H-purin-8-one

I-67

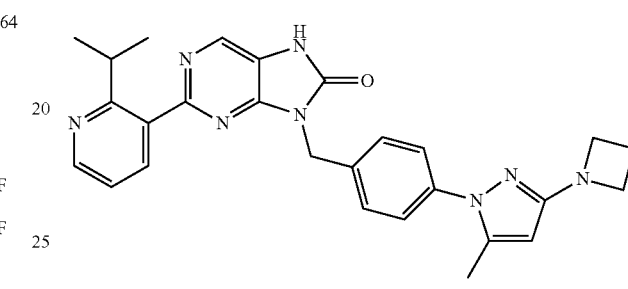

8-(4-(3-(azetioin-1-yl)-5-methyl-1H-pyrazol-1-yl)benzyl)-2-(2-isopropylpyridin-2-yl)-7,9-dihydro-8H-purine-8-one

I-68

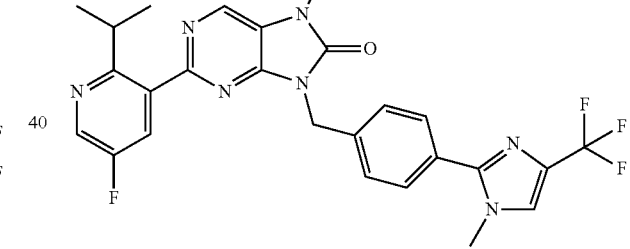

2-(5-fluoro-2-isopropylpyridin-3-yl)-7-methyl-9-(4-(1-methyl-4-(trifluoromethyl)-1H-imidazol-2-yl)-benzyl)-7,9-dihydro-8H-purin-8-one

I-69

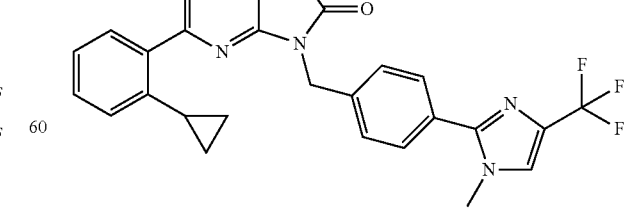

2-(2-cyclopropylphenyl)-7-methyl-8-(4-(t-methyl-4-(trifluoromethyl-1H-imidazol-2-yl)benzyl)-7,3-dihydro-8H-purin-8-one

I-70

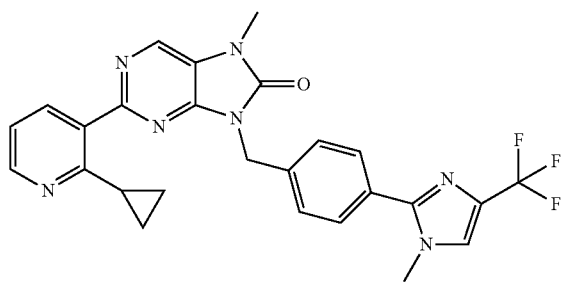

I-71

2-(2-cyclopropylpyridin-3-yl)-7-methyl-9-(4-(1-methyl-4-(trifluoromethyl)-1H-imidazol-2-yl)-benzyl)-7,9-dihydro-8H-purin-8-one

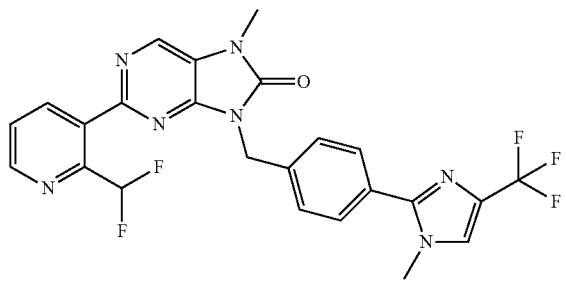

I-72

2-(2-(difluoromethylpyridin-3-yl)-7-methyl-9-(4-(1-methyl-4-(trifluoromethl)-1H-imidazol-2-yl)-benzyl)-7,9-dihydro-8H-purin-8-one

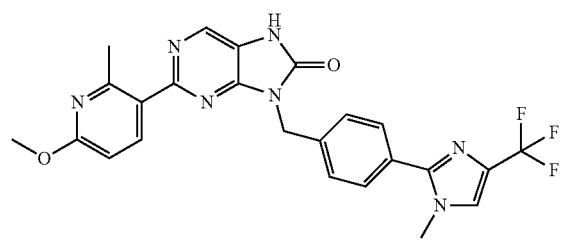

I-73

2-(6-methyoxy-2-methylpyridin-3-yl)-9-(4-(1-methyl-4-trifluoromethyl)-1H-imidazol-2-yl)benzyl)-7,9-dihydro 8H-purin-8-one

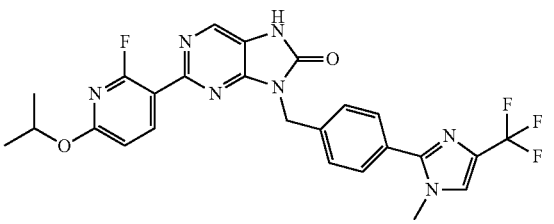

I-74

2-(2-fluoro-6-isopropyxypyridin-3-yl)-9-(4-(1-methyl-4-(trifluoromethyl-1H-imidazol-2yl)benzyl)-7,9-dihydro-8H-purin-8-one

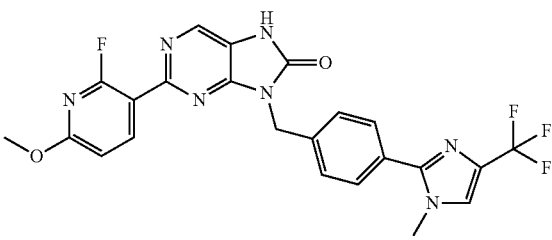

I-75

2-(2-fluoro-8-methoxypyridin-3-yl)-8-(4-(t-methyl-4-(trifluoromethyl)-1H-imidazol-2-yl)benzyl)-7,9-dihydro-8H-purini-8-one

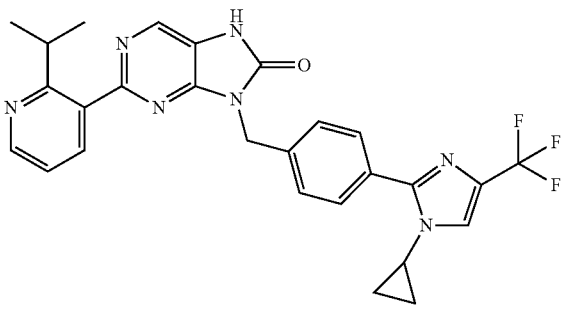

I-76

9-(4-(1-cyclopropyl-4-(trifluoromethyl)-1H-imidazol-2-yl)benzyl)-2-(2-isopropylpyridin-3-yl)-7,9-dihydro-8H-purinin-8-one

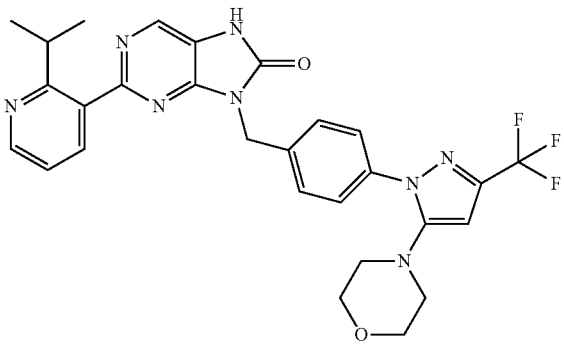

I-77

2-(2-isopropylpyridin-3-yl)-8-(4-(5-morpholino-3-(trifluoromethyl)-1H-pyrazol-1-yl)benzyl-7,9-dihydro-8H-purin-8-one

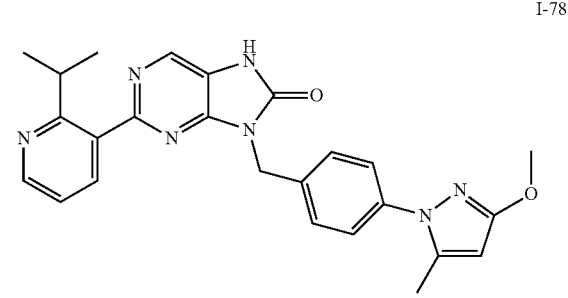

I-78

2-(2-isopropylpyridin-3-yl)-9-(4-(3-methoxy-5-methyl-1H-pyrazol-1-yl)benzyl)-7,9-dihydro-8H-purin-8-one

I-79

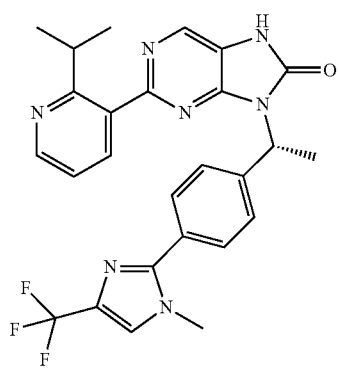

(R)-2-(2-isopropylpyridin-3-yl)-9-(1-(4-(1-methyl-
4-(trifluoromethyl)-1H-imidazol-2-yl)phenyl)ethyl)-
7,9-dihydro-8H-purin-8-one

I-80

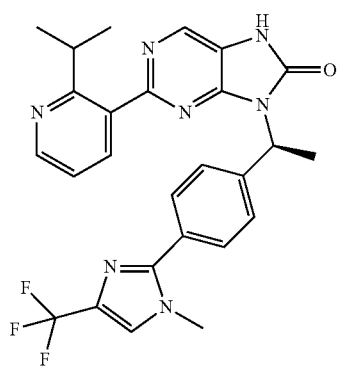

(S)-2-(2-isopropylpyridin-3-yl)-9-(1-(4-(1-methyl-
4-(trifluoromethyl)-1H-imidazol-2-yl)phenyl)ethyl)-
7,9-dihydro-8H-purin-8-one

I-81

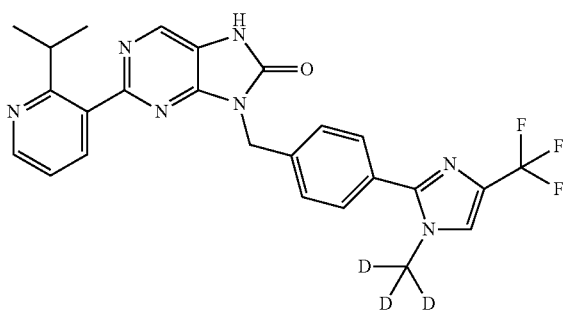

2-(2-isopropylpyridin-3-yl)-9-(4-(1-methyl-d3)-4-(trifluoromethyl)-1H-
imidazol-2-yl)benzyl)-7,9-dihydro-8H-purin-8-one

I-82

9-(3,5-difluro-4-(1-methyl-4-(trifluoromethyl)-1H-imidazol-2-yl)
benzyl)-2-(2-isopropylpyridin-3-yl)-7,9-dihydro-8H-purin-8-one

I-83

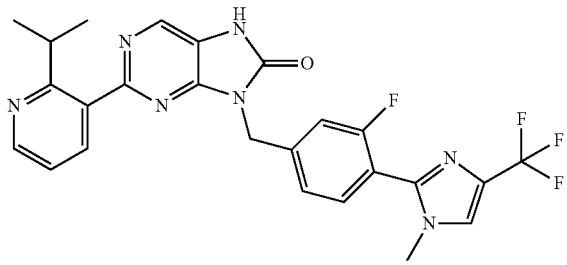

9-(3-fluoro-4-(1-methyl-4-(trifluoromethyl)-1H-imidazol-2-yl)
benzyl)-2-(2-isopropylpyridin-3-yl)-7,9-dihydro-8H-purin-8-one

I-84

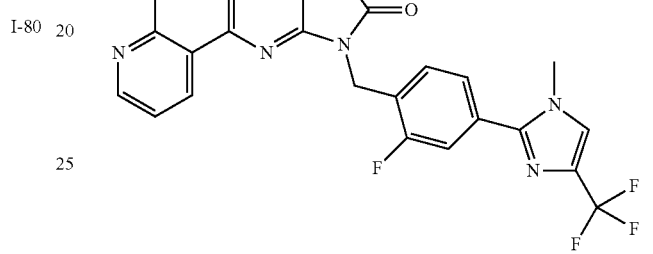

9-(2-fluoro-4-(1-methyl-4-(trifluoromethyl)-1H-imidazol-2-yl)
benzyl)-2-(2-isopropylpyridin-3-yl)-7,9-dihydro-8H-purin-8-one

I-85

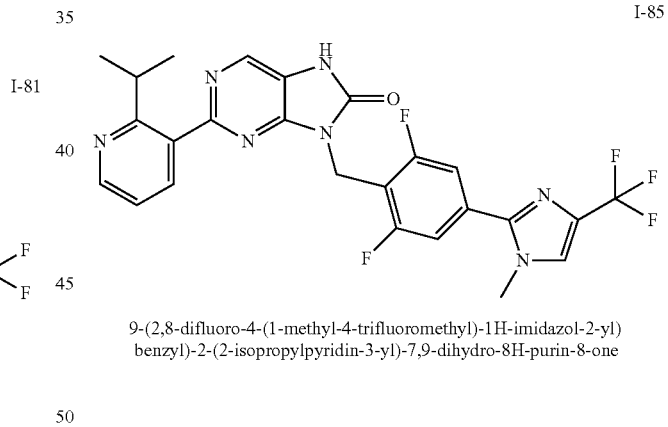

9-(2,8-difluoro-4-(1-methyl-4-trifluoromethyl)-1H-imidazol-2-yl)
benzyl)-2-(2-isopropylpyridin-3-yl)-7,9-dihydro-8H-purin-8-one

I-86

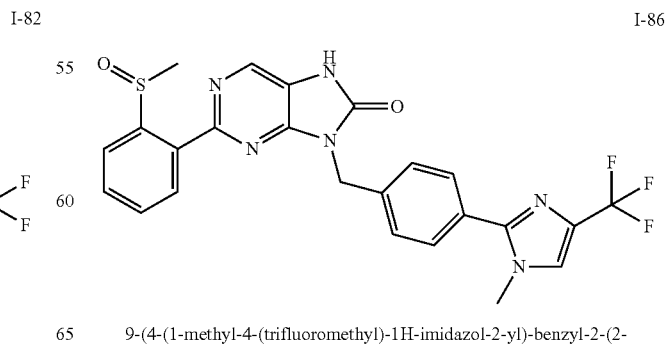

9-(4-(1-methyl-4-(trifluoromethyl)-1H-imidazol-2-yl)-benzyl-2-(2-
(methylsulfinyl)phenyl)7,9-dihydro-8H-purin-8-one

I-87

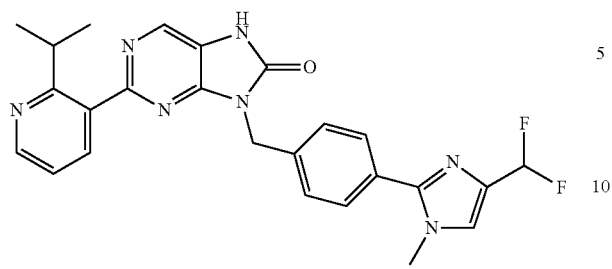

9-(4-(4-difluoromethyl-1-methyl-1H-imidazol-2-yl)benzyl-2-(2-isopropylpyridin-3-yl)-7,9-dihydro-8H-purin-8-one

I-88

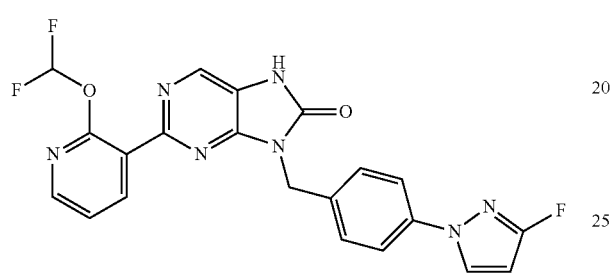

2-(2-difluoromethyoxy)pyridin-3-yl)-9-(4-(3-tifluoro-1H-pyrazol-1-yl)benzyl)-7,9-dihydro-8H-purin-8-one

I-89

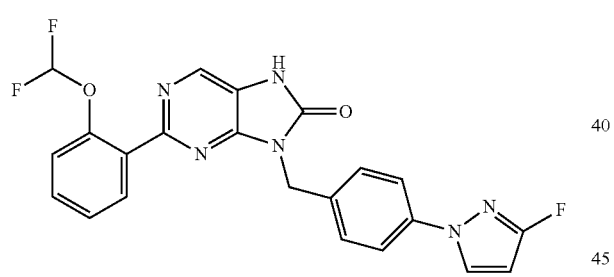

2-(2-difluoromethoxy)phenyl)-9-(4-(3-fluoro-1H-pyrazol-1-yl)benzyl-7,9-dihydro-8H-purin-8-one

I-90

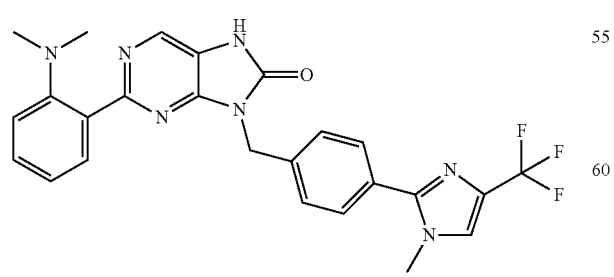

2-(2-(dimethylaminophenyl)-8-(4-(t-methyl-4-(trifluoromethyl)-1H-imidazol-2-yl)benzyl)-7,9-dihydro-8H-purin-8-one

I-91

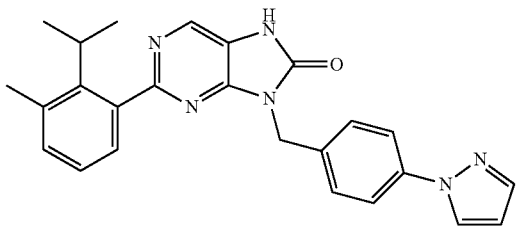

9-(4-1H-pyrazol-1-yl)benzyl)-2-(2-isopropyl-3-methylphenyl)-7,9-dihydro-8H-purin-8-one

I-92

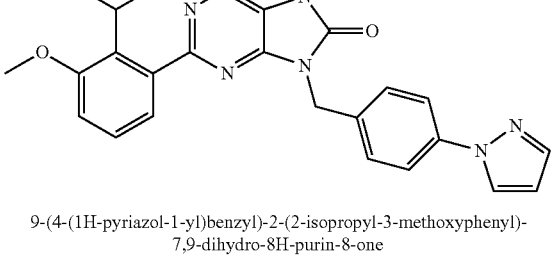

9-(4-(1H-pyriazol-1-yl)benzyl)-2-(2-isopropyl-3-methoxyphenyl)-7,9-dihydro-8H-purin-8-one

I-93

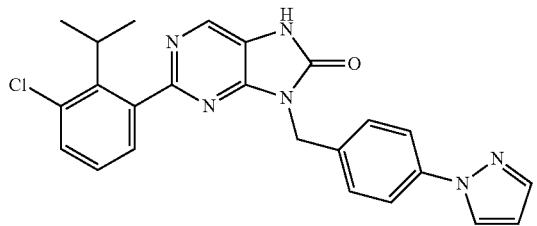

9-(4-(1H-pyrazol-1-yl)benzyl)-2-(3-chloro-2-isopropylphenyl)-7,9-dihydro-8H-purin-one

I94

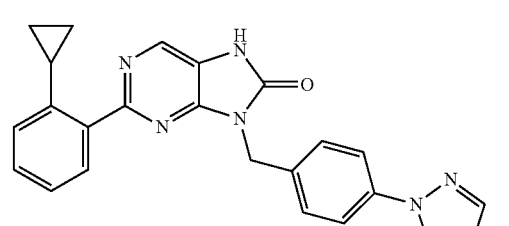

9-(4-(1H-pyrazol-1-yl)benzyl)-2-(2-cyclopropylphenyl)-7,9-dihydro-8H-purin-8-one

I-95

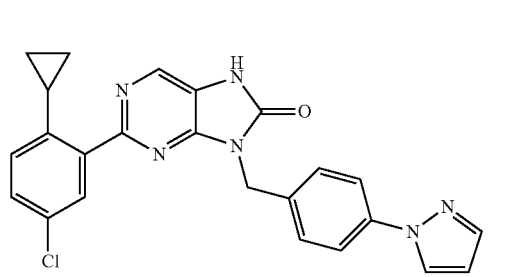

9-(4-(1H-pyrazol-1-yl)benzyl)-2-(5-chloro-2-cyclopropylphenyl)-7,9-dihydro-8H-purin-8-one

I-96

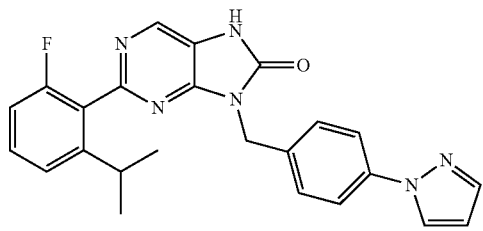

9-(4-(1H-pyrazol-1-yl)benzyl)-2-(2-fluoro-6-isopropylphenyl)-7,9-dihydro-8H-purin-8-one

I-97

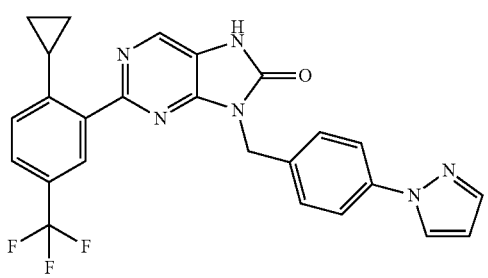

9-(4-(1H-pyrazol-1-yl)benzyl-2-(2-cyclopropyl-5-(trifluoromethyl)phenyl)-7,9-dihydro-8H-purin-8-one

I-98

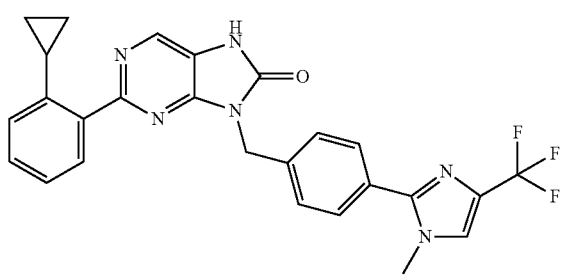

2-(2-cyclopropyl(phenyl)-3-(4-(1-methyl-4-(trifluoromethyl)-1H-imidazol-2-yl)benzyl)-7,9-dihydro-8H-purin-8-one

I-99

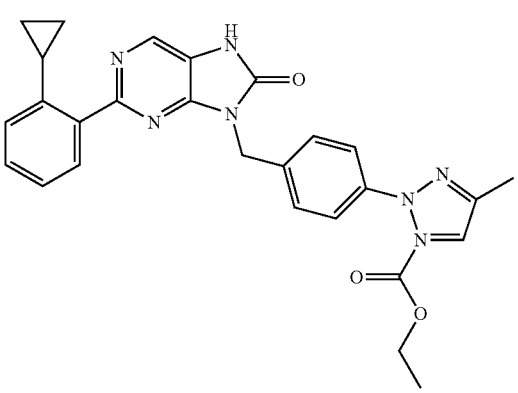

ethyl 1-(4-((2-(2-cyclopropylphenyl)-8-oxo-7,9-dihydro-9H-purin-9-yl)methylphenyl)-3-methyl-1H-pyrazol-5 oatoxylate

I-100

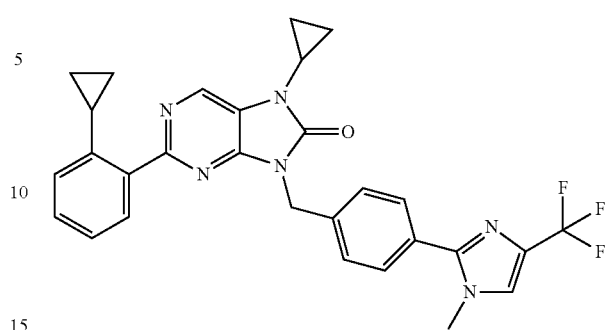

7-cyproply-2-(2-cyclopropylphenyl)-8-(4-(1-methyl-4-(trifluoromethyl)-1H-imidazol-2-yl)benzyl)-7,9-dihydro-8H-purin-8-one

I-101

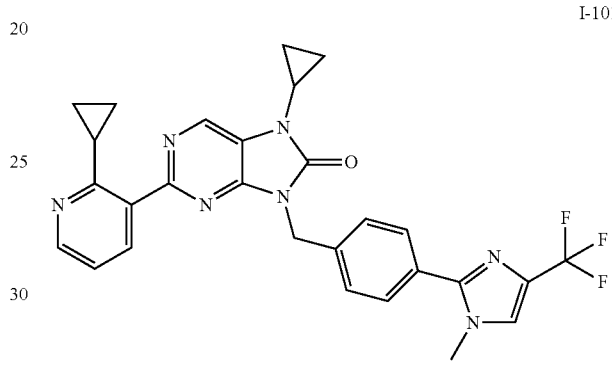

7-cyclopropyl-2-(2-cyclopropylpyridin-3-yl)-9-(4-(1-methyl-4-(trifluoromethyl)-1H-imifazol-2-yl)benzyl-7,9-dihydro-8H-purin-8-one

I-102

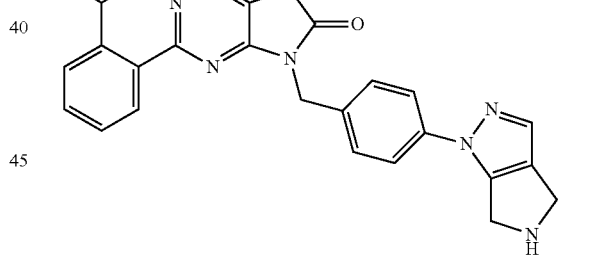

9-(4-(5,6-dihydropyrrolo)-4-pyrazol-1-(4H)-yl)benzyl)-2-(2-isopropylphenyl)-7,9-dihydro-8H-purin-8-one

I-103

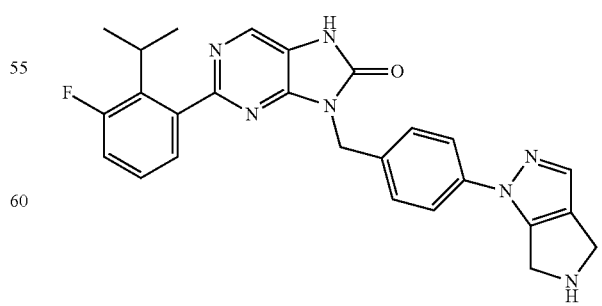

9-(4-(5,6-dihydropyrrolo)-[3,4-o]pyrazol-(4H)-yl)benzyl)-2-(3-fluoro-2-isopropylphenyl)-7,9-dihydro-8H-purin-8-one

I-104

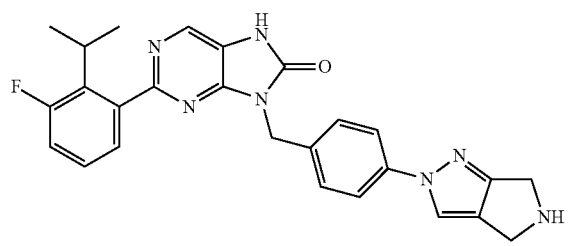

9-(4-(5,6-dihydropyrrolo[3,4-c]pyrazol-2(4H)-yl)benzyl)-2-(3-fluoro-2-isopropylphenyl-7,9-dihydro-8H-purin-8-one

I-105

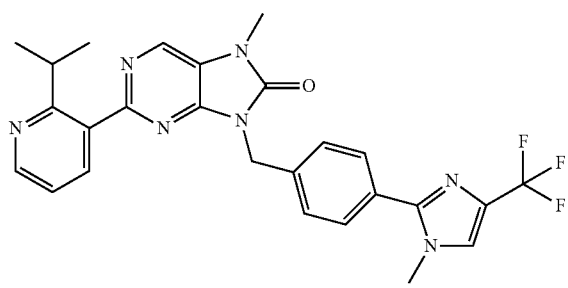

2-(2-isopropylpyridin-3-yl)-7-methyl-9-(4-(1-methyl-4-trifluoromethyl-1H-imidazol-2-yl)-benzyl)-7,9-dihydro-8H-purin-8-one

I-106

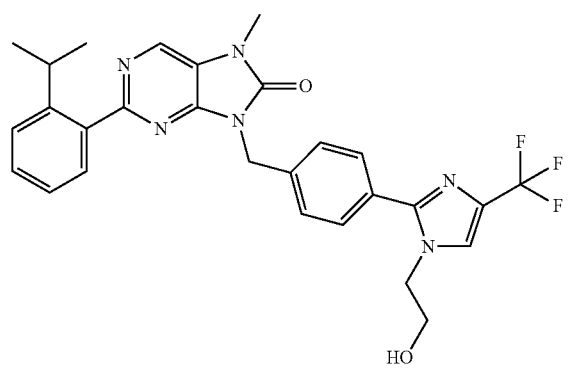

9-(4-(1-(2-hydroxyethyl)-4-trifluoromethyl)-1H-imidazol-2-yl)benzyl)-2-(2-isopropylphenyl)-7-methyl-7,8-dihydro-8H-purin-8-one

I-107

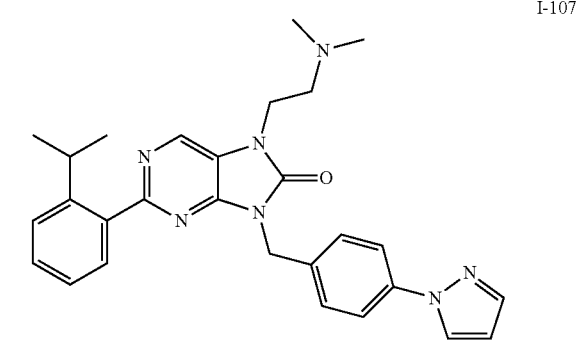

9-(4-(1H-pyrazol-2lyl)benzyl)-7-(2-(dimethylminoethyl)-2-(2-isopropylphenyl)7,9-dihydro-8H-purin-8-one

I-108

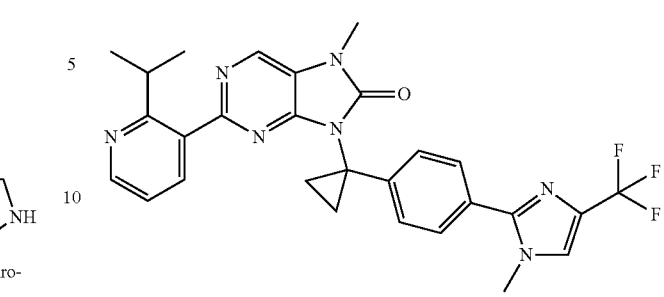

2-(2-isopropylpyridin-3-yl)-7-methyl-6-(1-(4-(t-methyl-4-(trifluoromethyl)-1H-imidazol-2-yl)phenyl-cyclopropyl)-7,8-dihydro-8H-purin-8-one

I-109

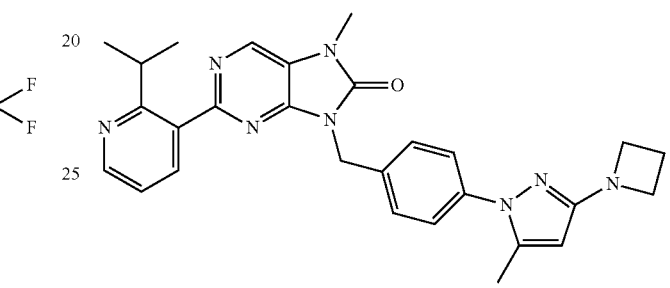

9-(4-(3-(azetitin-1-yl)-5-methyl-1H-pyrazol-1-yl)benzyl-2-(2-isopropylphridin-3-yl)-7-methyl-7,8-dihydro-8H-purin-8-one

I-110

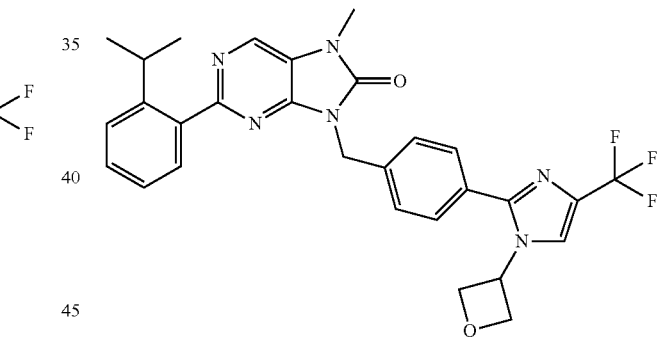

2-(2-isopropylphenyl)-7-methyl-9-(4-(1-axeten-3-yl)-4-(trifluoromethyl-1H-imidazol-2-yl)benzyl)-7,9-dihydro-8H-purin-8-one

I-111

9-(((1s,4s)-4-(3,5-dimethyl-1H-pyrazol-1-ylioyofohexyl)methyl)-2-(2-isopropyl)phenyl)-7-methyl-7,8-dihydro-8H-purin-8-one

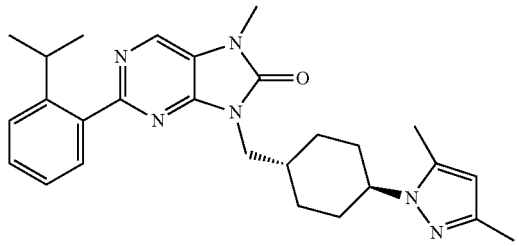

I-112

5-(((1t,4r)-4-(3,5-dimethyl-1H-pyrazol-1-yl)-cyclohexyl)
methyl)-2-(2-isopropylphenyl)-7-methyl-7,8-dihydro-8H-
purin-8-one

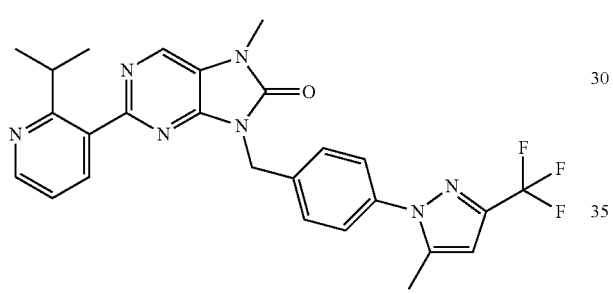

I-113

2-(2-isopropylphridin-3-yl)-7-methyl-8-(4-(5-methyl-3-
(trifluoromethyl)-1H-pyrazol-1-yl)benzyl)-7,8-dihydro-
8H-purin-8-one

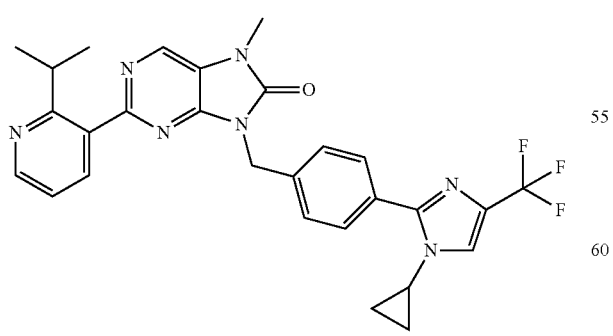

I-114

8-(4-t-cyclopropyl)4-(trifluoromethyl)-1H-imidazol-2-yl)
benzyl)-2-(2-isopropylpyridin-3-yl)-7-methyl-
7,9-dihydro-8H-purin-8-one

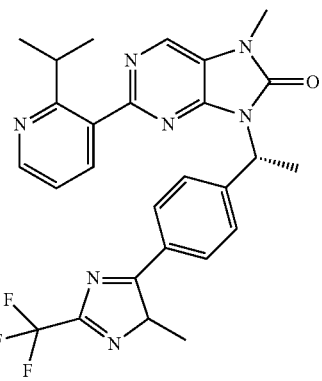

I-115

(R)-2-(2-isopropylpyridin-3-yl)-7-methyl-9-(1-(4-
(1-methyl-4-(trifluoromethyl)-1H-imidazol-2-yl)
phenyl)ethyl)-7,9-dihydro-8H-purin-8-one

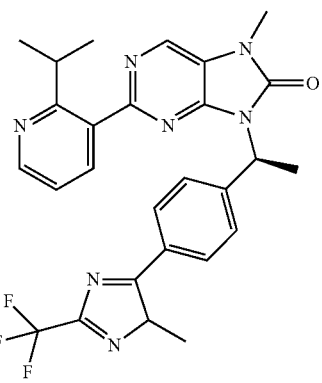

I-116

(S)-2-(2-isopropylpyridin-3-yl)-7-methyl-9-(1-(4-
(1-methyl-4-trifluoromethyl)-1H-imidazol-2-yl)
phenyl)ethyl)-7,9-dihydro-8H-purin-8-one

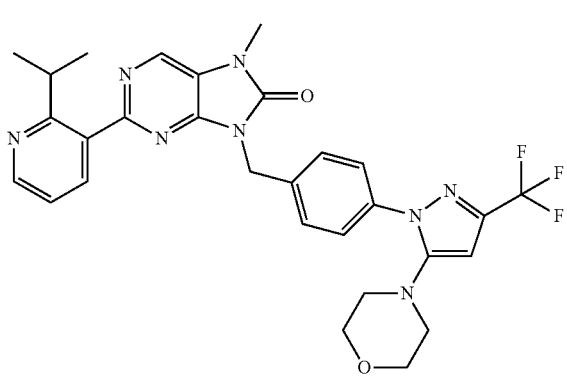

I-117

2-(2-isopropylpyridin-3-yl)-7-methyl-9-(4-(5-morpholine-3-
(trifluoromethyl)-1H-pyrazol-1-yl)benzyl)-7,9-dihydro-
8H-purin-8-one -continued

I-118

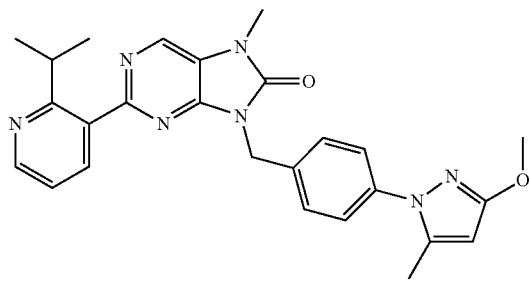

2-(2-isopropylpyridin-3-yl)-8-(4-(2-methoxy-5-methyl-1H-pyrazol-1-yl)benzyl)-7-methyl-7,8-dihydro-8H-purin-8-one

I-121

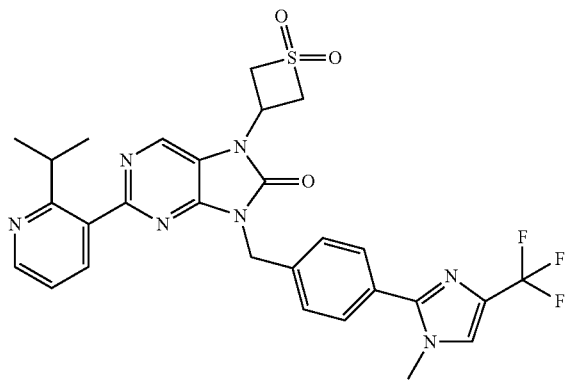

7-(1,1-dioxidothietan-3-yl)-2-(2-isopropylpyridin-3-yl)-8-(4-(1-methyl-4-(trifluoromethyl)-1H-imidazol-2-yl)benzyl)-7,9-dihydro-8H-purin-8-one

I-119

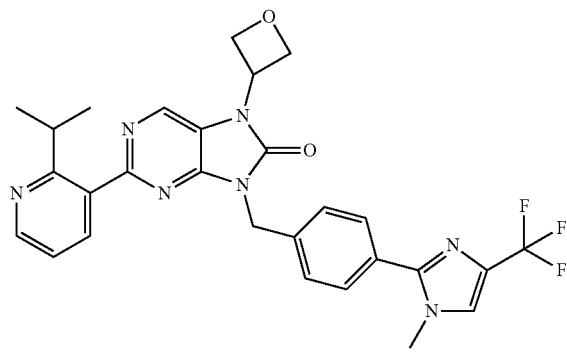

2-(2-isopropylpyridin-3-yl)-9-(4-(1-methyl-4-(trifluoromethyl)-1H-imidazol-2-yl)benzyl)-7-oxeten-3-yl)-7,9-dihydro-8H purin-8-one

I-122

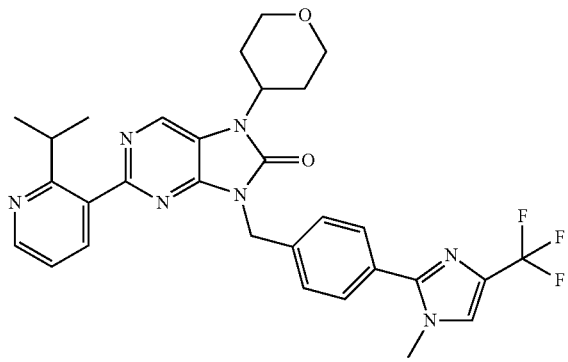

2-(2-isopropylpyridin-3-yl)-9-(4-(1-methyl-4-(trifluoromethyl)-1H-imidazol-2-yl)benzyl-7-(ieirahydro-2H-pyran-4-yl)-7,9-dihydro-8H-purin-8-one

I-120

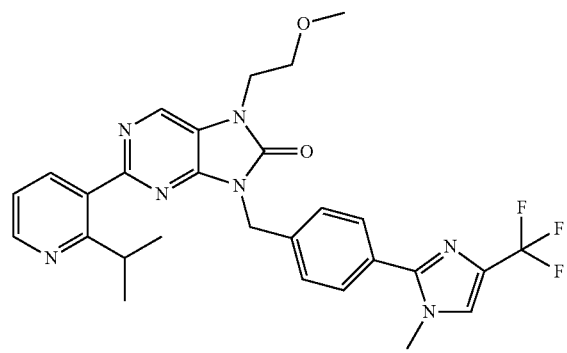

2-(2-isopropylpyridin-3-yl)-7-(2-methoxyethyl)-9-(4-(1-methyl-4-trifluoromethyl-1H-imidazol-2-yl)benzyl-7,9-dihydro-8H-purin-9-one

I-123

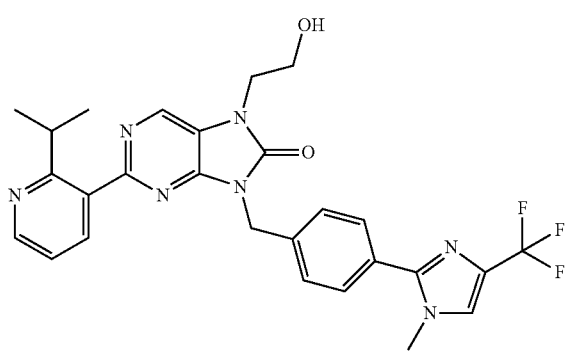

7-(2-hydroxyethyl)-2-(2-isopropylpyridin-3-yl)-3-(4-1-methyl-4-(trifluoromethyl)-1H-imidazol-2-yl)benzyl)-7,8-dihydro-8H-purin-8-one

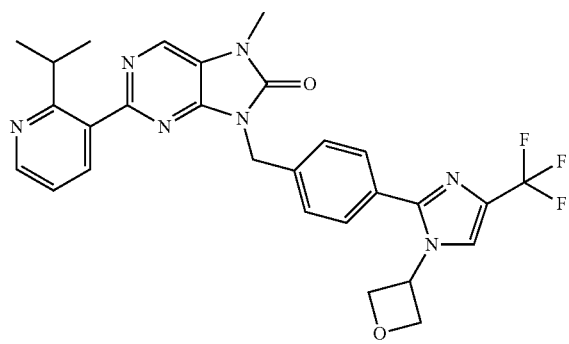

I-124

2-(2-isopropylpyridin-3-yl)-7-methyl-9-(4-(1-(oxetan-3-yl)-4-(trifluoromethyl)-1H-imidazol-2-yl)-benzyl)-7,9-dihydro-8H-purin-8-one

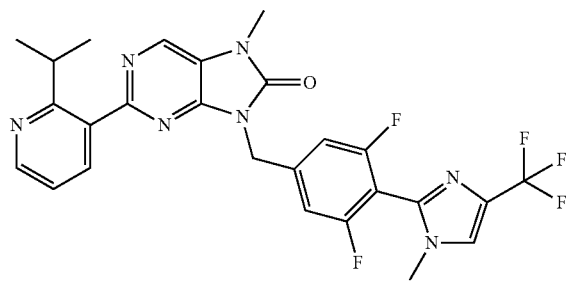

I-125

9-(3,5-difluoro-4-(1-methyl-4-(trifluoromethyl)-1H-imidazol-2-yl)benzyl)-2-(2-isopropylpyridin-3-yl)-7-methyl-7,9-dihydro-8H-purin-8-one

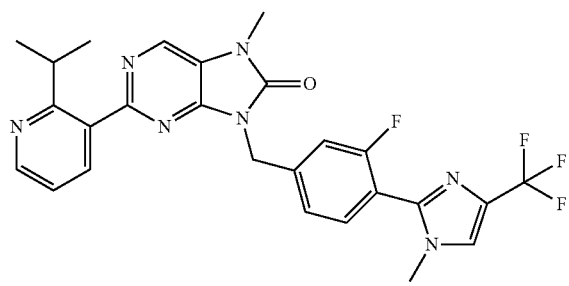

I-126

9-(3-fluoro-4-(1-methyl-4-(trifluoromethyl)-1H-imidazol-2-yl)benzyl)-2-(2-isopropylpyridin-3-yl)-7-methyl-7,9-dihydro-8H-purin-8-one

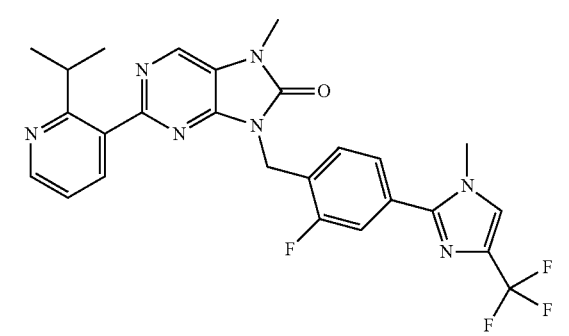

I-127

9-(2-fluoro-4-(1-methyl-4-(trifluoromethyl)-1H-imidazol-2-yl)benzyl)-2-(2-isopropylpyridin-3-yl)-7-methyl-7,9-dihydro-8H-purin-8-one

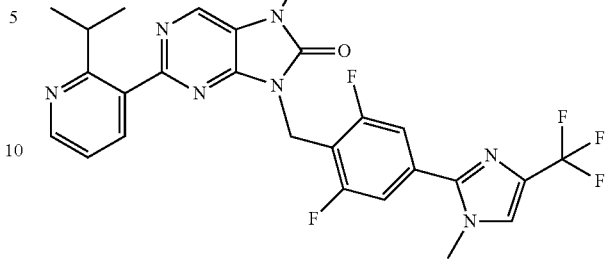

I-128

9-(2,8-difluoro-4-(1-methyl-4-(trifluoromethyl)-1H-imidazol-2-yl)benzyl)-2-(2-isopropylpyridin-3-yl)-7-methyl-7,9-dihydro-8H-purin-8-one

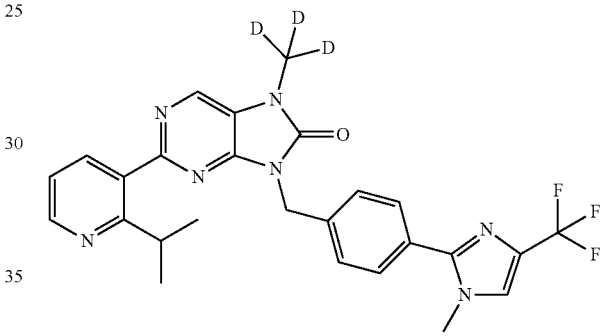

I-129

2-(2-isopropylpyridin-3-yl)-7-(methyl-d3)-9-(4-(1-methyl-4-(trifluoromethyl)-1H-imidazol-2-yl)benzyl)-7,9-dihydro-8H-purin-8-one

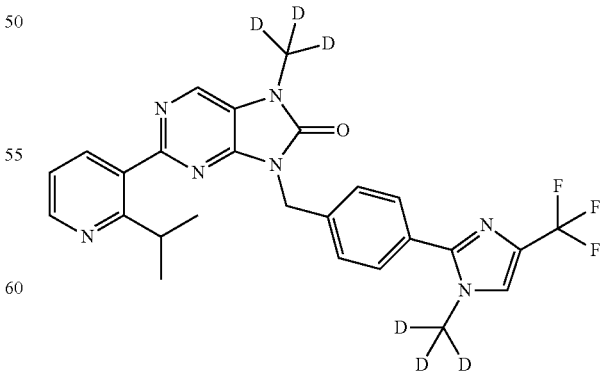

I-130

2-(2-isopyroylpyridin-3-yl)-7-(methyl-d3)-9-(-4-(1-(methyl-d3)-4-(trifluoromethyl)-1H-imidazol-2-yl)benzyl)-7,9-dihydro-8H-purin-8-one

I-131

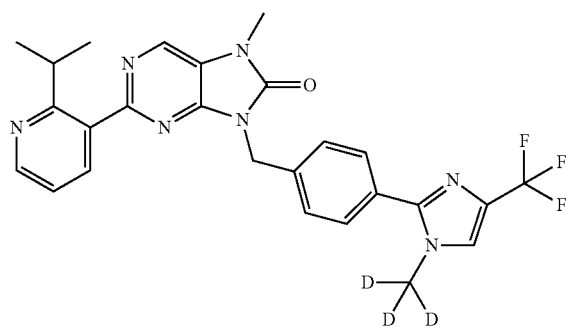

2-(2-isopropylpyridin-3-yl)-7-methyl-9-(4-(1-(methyl-d3)-4-(trifluoromethyl)-1H-imidazol-2-yl)benzyl)-7,9-dihydro-8H-purin-8-one

I-132

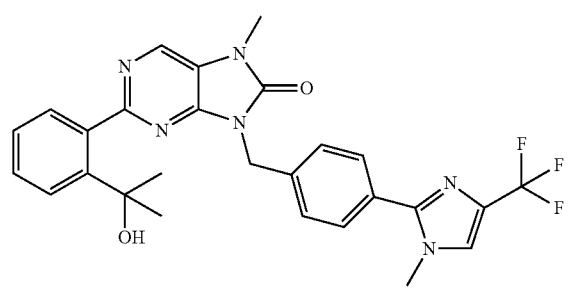

2-(2-(2-methyl)propan-2-yl)phenyl)-7-methyl-9-(4-(1-methyl-4-(trifluoromethl)-1H-imidazol-2-yl)benzyl)-7,9-dihydro-8H-purin-8-one

I-133

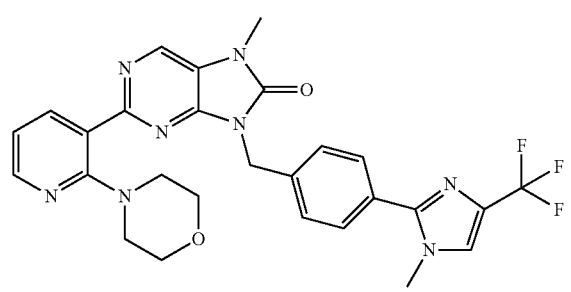

7-methyl-9-(4-(1-methyl-4-(trifluoromethyl)-1H-imidazol-2-yl)benzyl)-2-(2-morpholinopyridin-3-yl)-7,9-dihydro-8H-purin-8-one

I-134

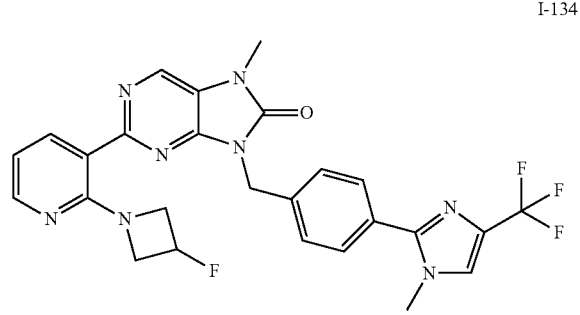

2-(2-(3-fluoroazetidin-1-yl)pyridin-3-yl)-7-methyl-9-(4-(trifluoromethyl)-1H-imidazol-1-yl)-7,9-dihydro-8H-purin-8-one

I-135

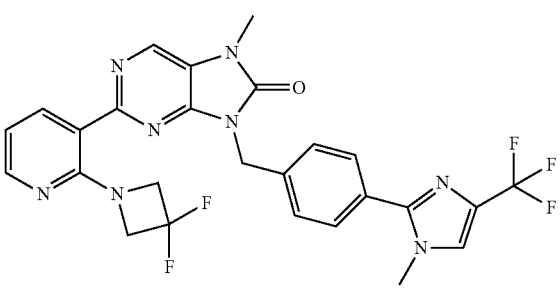

2-(2-(3-difluoroazetidin-1-yl)pyridin-3-yl)-7-methyl-9-(4-(trifluoromethyl)-1H-imidazol-1-yl)-7,9-dihydro-8H-purin-8-one

I-136

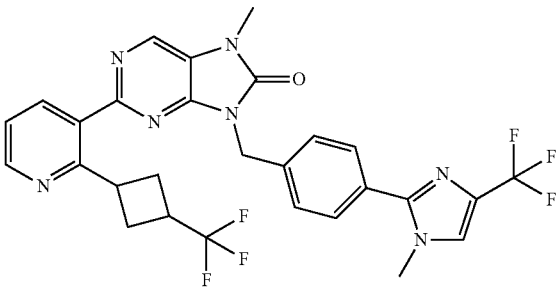

7-methyl-9-(4-(1-methyl-4-(trifluoromethyl)-1H-imidazol-2-yl)benzyl)-2-(2-(3-(trifluoromethyl)-azetidin-1-yl)pyridin-3-yl)-7,9-dihydro-8H-purin-8-one

I-137

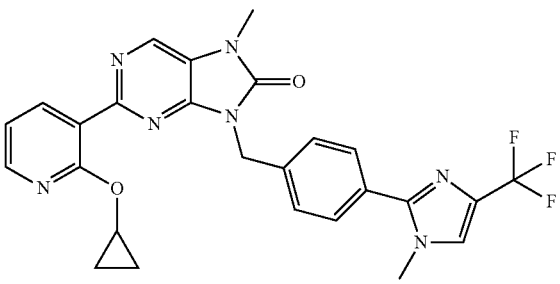

2-(2-cyclopropoxypyridin-3-yl)-7-(methyl-9-(4-(1-methyl-4-(trifluoromethyl)-1H-imidazol-2-yl)benzyl)-7,9-dihydro-8H-purin-8-one

I-138

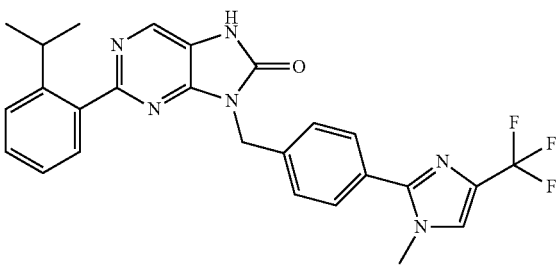

2-(2-isopropylpyridin-9-(4-(1-methyl-4-(trifluoromethyl)-1H-imidazol-2-yl)benzyl)-7,9-dihydro-8H-purin-8-one -continued

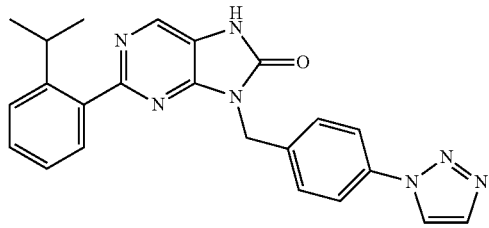

9-(4-1H-1,2,3-triazol-1-yl)benzyl)-2-(2-isopropylphenyl)-
7,9-dihydro-8H-purin-8-one

I-139

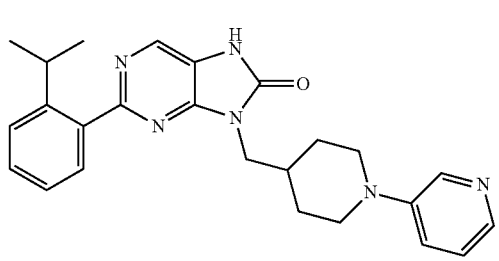

2-(2-isopropylphenyl)-8-((1-(pyridin-3-yl)-piperidin-4-yl)
methyl)-7,9-dihydro-8H-purin-8-one

I-143

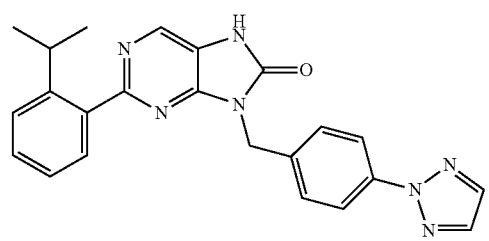

9-(4-(2H-1,2,3-triazol-2-yl)benzyl)-2-(2-isopropylphenyl)-
7,9-dihydro-8H-purin-8-one

I-140

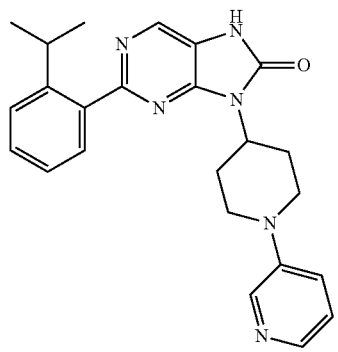

2-(2-isopropylphenyl)-8-(pyridin-3-yl)piperdin-
4-yl)-7,9-dihydro-8H-purin-8-one

I-144

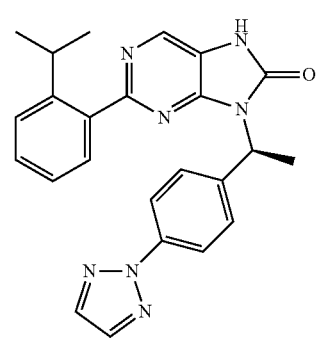

(S)-8-(1-(4-(2H-1,2,3-triazol-2-yl)-phenyl)
ethyl)-2-(2-isopropylphenyl)-7,9-dihydro-8H-
purin-8-one

I-141

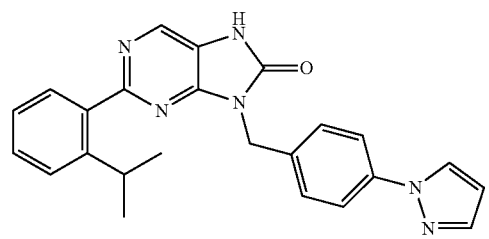

9-(4-(1H-pyrazol-1-yl)benzyl)-2-(2-isopropylphenyl)-
7,9-dihydro-8H-purin-8-one

I-145

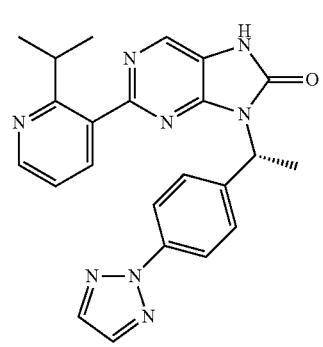

(R)-8-(1-(4-(2H-1,2,3-triazol-2-yl)phenyl)
ethyl)-2-(2-isopropylphenyl)-7,9-dihydro-
8H-purin-8-one

I-142

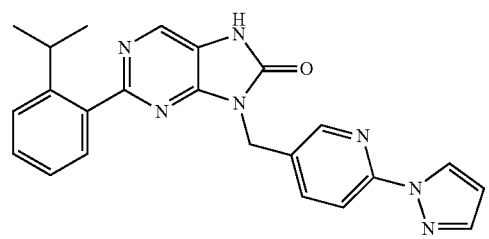

9-((8-(1H-pyrazol)-1-yl)pyridin-3-yl)methyl)-2-
(2-isopropylphenyl)-7,9-dihydro-8H-purin-8-one

I-146

I-147

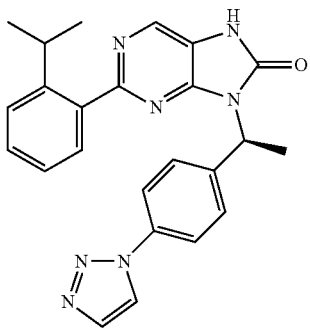

(S)-9-(1-(4-(1H-1,2,3-traizol-1-yl)
phenylethyl)-2-(2-isopropylphenyl)-
7,8-dihydro-8H-purin-8-one

I-148

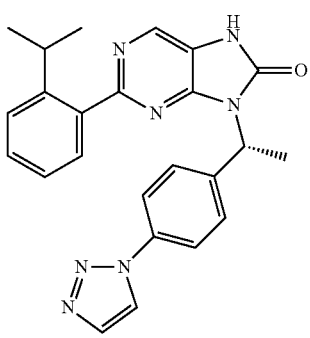

(R)-9-(1-(4-(1H-1,2,3-triazol-1-yl)phenyl)
ethyl)-2-(2-isopropylphenyl)-7,9-dihydro-
8H-purin-8-one

I-149

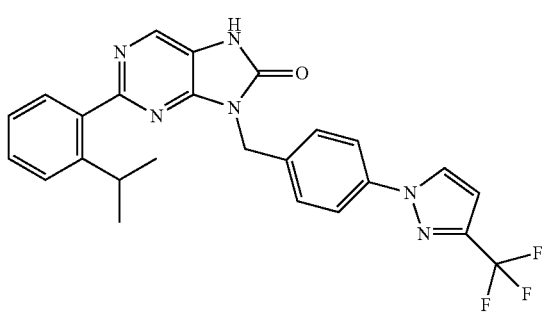

2-(2-isopropylphenyl)-9-(4-(3-(trifluoromethyl)-1H-
pyrazol-1-yl)benzyl)-7,9-dihydro-8H-purini-8-one

I-150

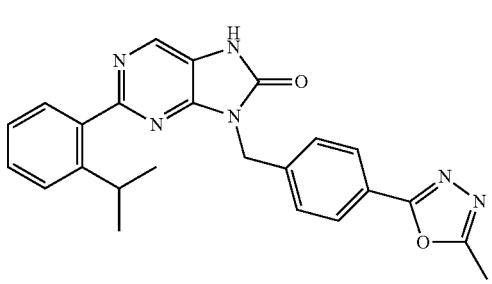

2-(2-isopropylphenyl)-9-(4-(5-methyl-1,3,4-oxadiazol-2-yl)
benzyl)-7,8-dihydro-8H-purin-8-one

I-151

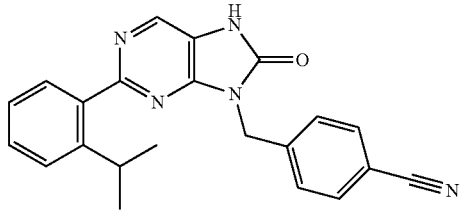

4-((2-(2-isopropylphenyl)-8-oxo-7,8-dihydro-8H-
purin-8-yl)methylbenzonitrile

I-152

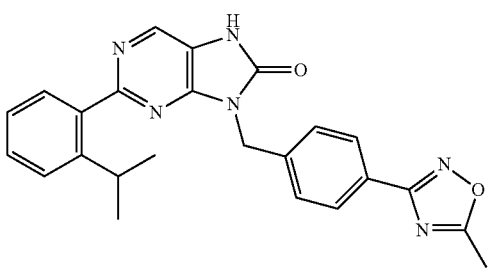

2-(2-isopropylphenyl)-9-(4-(5-methyl-1,2,4-oxadiazol-3-yl)
benzyl-7,8-dihydro-8H-purin-8-one

I-153

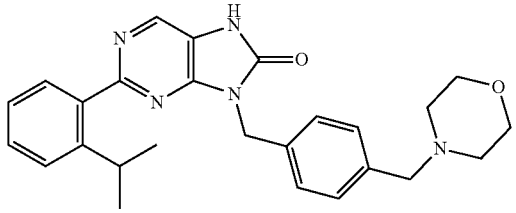

2-(2-isopropylphenyl)-8-(4-(morpholonomethl)benzyl)-
7,8-dihydro-8H-purin-8-one

I-154

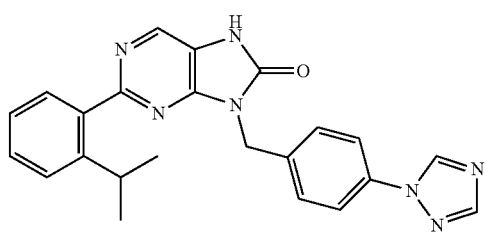

8-(4-(1H-1,2,4-triazol-1-yl)benzyl-2-(2-isopropylphenyl)-
7,9-dihydro-8H-purin-8-one

I-155

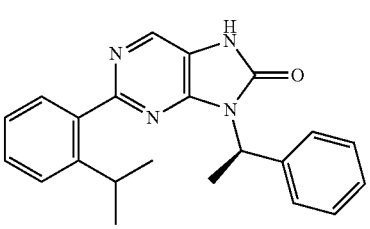

(R)-2-(2-isopropylphenyl)-8-(1-phenyethyl)-
7,9-dihydro-8H-purini-8-one

I-156

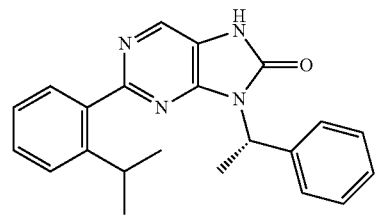

(S)-2-(2-isopropylphenyl)-8-(1-phenyethyl)-
7,9-dihydro-8H-purini-8-one

I-157

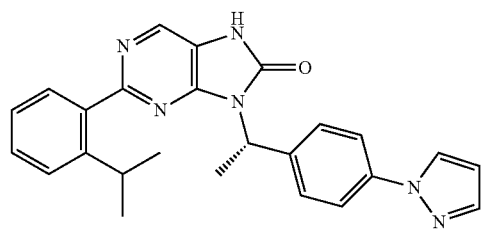

(S)-8-(1-(4-(1H-pyraol-1-yl)phenylethyl-2-(2-
isopropylphenyl)-7,9-dihydro-8H-purin-8-one

I-158

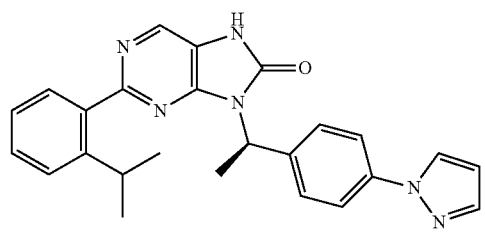

(R)-9-(1-(4-(1H-pyrazol-1-yl)phenylethyl-2-
(2-isopropylphenyl)-7,9-dihydro-8H-purin-8-one

I-159

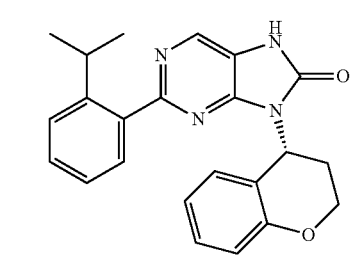

(R)-8-(chruman-4-yl)-2-(2-isopropylphenyl)-
7,9-dihydro-8H-purin-8-one

I-160

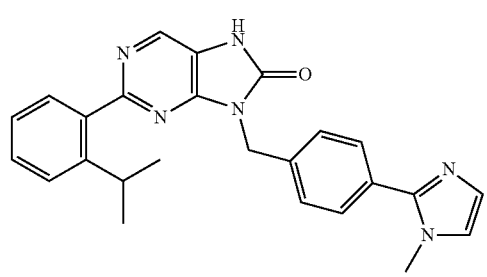

2-(2-isopropylphenyl)-9-(4-(1-methyl-1H-imidezol-2-yl
benzyl)-7,9-dihydro-8H-purin-8-one

I-161

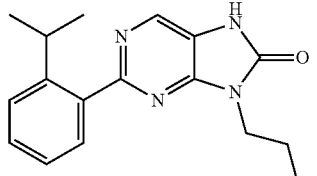

2-(2-isopropylphenyl)-9-(2-(1-(pyridin-3-yl)-piperidin-
4-yl)ethyl)-7,9-dihydro-8H-purin-8-one

I-162

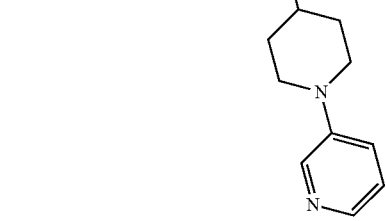

9-(2-chloro-4-(1H-pyraol-1-yl)benzyl)-2-(2-
isopropylbenzyl)-7,8-dihydro-8H-purini-8-one

I-163

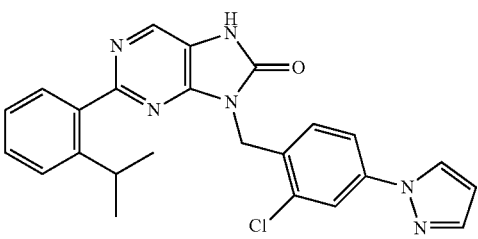

9-((1R,2S)-2-(4-(1H-pyrazol-1-yl)phenyl)cyclobutyl)-2-
(2-isopropylphenyl)-7,9-dihydro-8H-purin-8-one

I-164

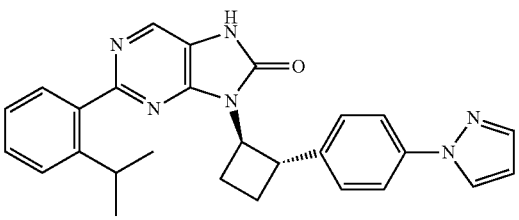

9-((1S,2R)-2-(4-(1H-pyrazol-1-yl)phenyl)cyclobutyl)-2-
(2-isopropylphenyl)-7,9-dihydro-8H-purin-8-one

I-165

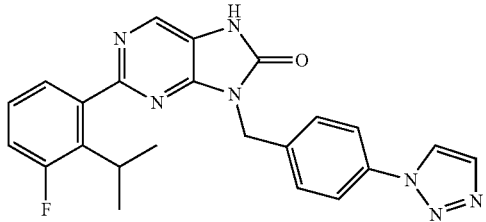

9-(4-(1H,1,2,3-triazol-2-yl)benzyl)-2-(3-fluoro-2-
isopropylphenyl)-7,9-dihydro-8H-purin-8-one

I-166

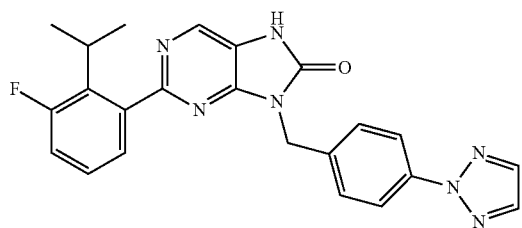

9-(4-(2H,1,2,3-triazol-2-yl)benzyl)-2-(3-fluoro-2-
isopropylphenyl)-7,9-dihydro-8H-purin-8-one

I-167

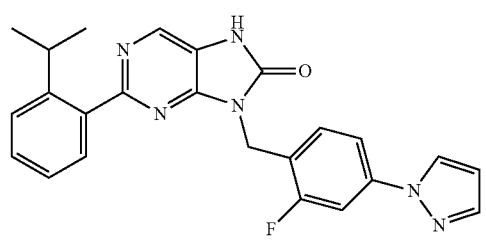

8-(2-fluoro-4-(1H-pyrazol-1-yl)benzyl)-2-(2-isopropylphenyl)-
7,9-dihydro-8H-purin-8-one

I-168

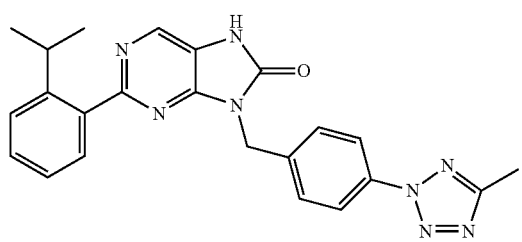

2-(2-isopropylphenyl)-8-(4-(5-methyl-2H-tetrazol-2-yl)
benzyl)-7,9-dihydro-8H-purin-8-one

I-169

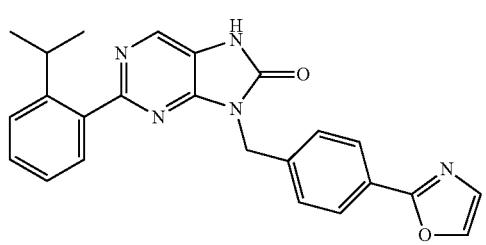

2-(2-isopropylphenyl)-9-(4-(oxazol-2-yl)benzyl)-
7,9-dihydro-8H-purin-8-one

I-170

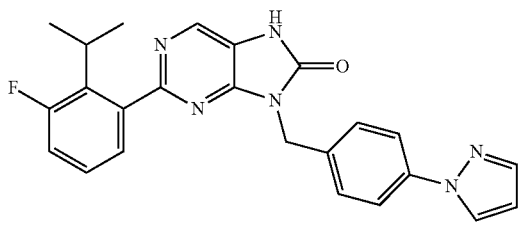

9-(4-(1H-pyrazol-1-yl)-benzyl)-2-(3-fluoro-2-isopropylphenyl)-
7,9-dihydro-8H-purin-8-one

I-171

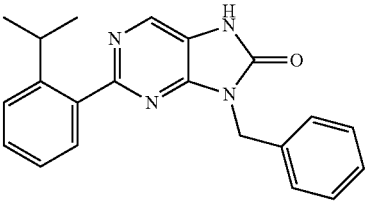

5-benzyl-2-(2-isopropylphenyl)-
7,9-dihydro-8H-purin-8-one

I-172

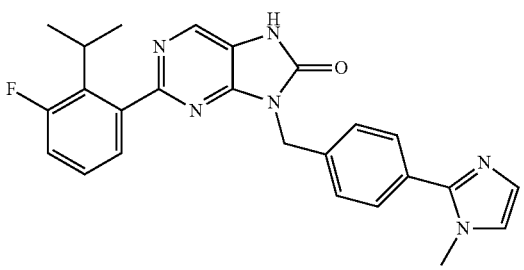

2-(3-fluoro-2-isopropylphenyl)-3-(4-(1-methyl-1H-
imidazol-2-yl)benzyl)-7,9-dihydro-8H-purin-8-one

I-173

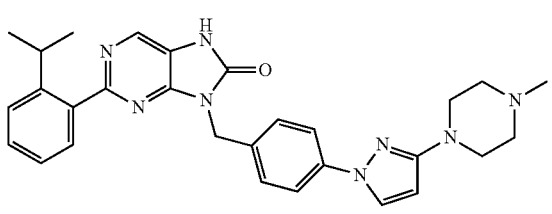

2-(2-isopropylphenyl)-8-(4-(3-(4-methylpiperatin-1-yl)-1H-
pyrazol-1-yl)benzyl)-7,9-dihydro-8H-purin-8-one

I-174

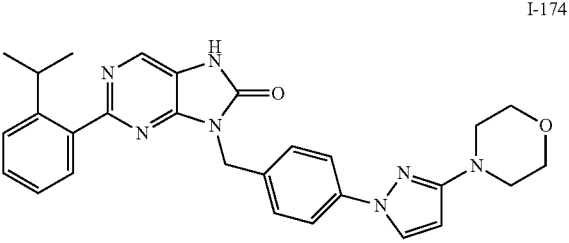

2-(2-isopropylphenyl)-8-(4-(3-morpholine-1H-pyroxol-1-yl)
benzyl)-7,9-dihydro-8H-purin-8-one

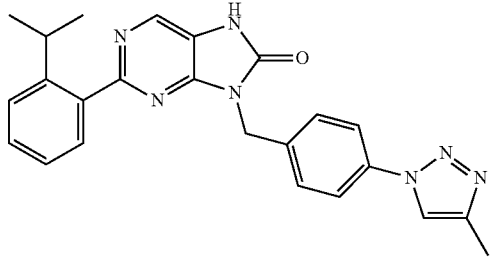

I-175

2-(2-isopropylphenyl)-9-(4-(4-methyl-1H-1,2,3-triazol-1-yl)benzyl)-7,9-dihydro-8H-purin-8-one

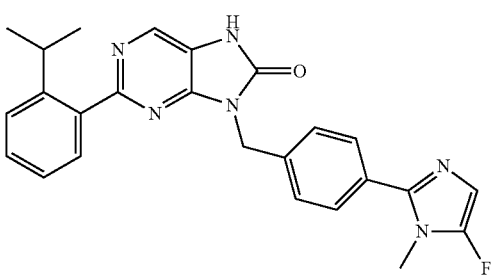

I-176

9-(4-(5-fluoro-1-methyl-1H-imidazol-2-yl)benzyl)-2-(2-isopropylphenyl)-7,8-dihydro-8H-purin-8-one

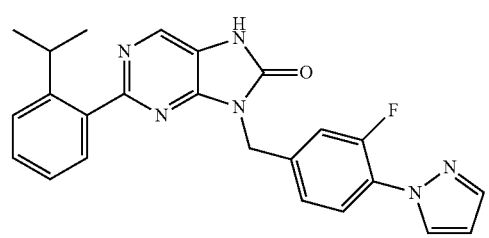

I-177

9-(3-fluoro-4-(1H-pyrazol-3-yl)benzyl)-2-(2-isopropylphenyl)-7,9-dihydro-8H-purin-8-one

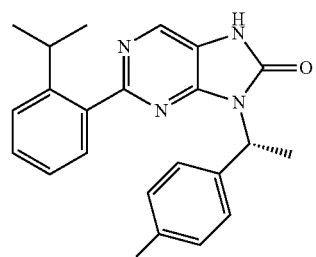

I-178

(R)-9-(1-(4-fluorophenyl)ethyl)-2-(2-isopropylphenyl)-7,8-dihydro-8H-purin-8-one

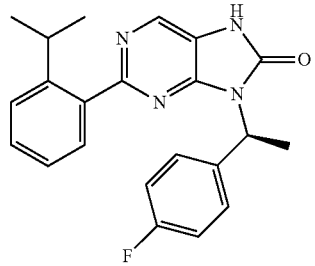

I-179

(S)-9-(1-(4-fluorophenyl)ethyl)-2-(2-isopropylphenyl)-7,8-dihydro-8H-purin-8-one

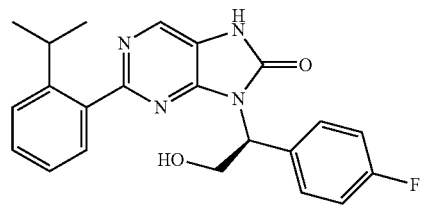

I-180

(S)-8-(1-(4-fluorophenyl)-2-hydroxyethyl)-2-(2-isopropylphenyl)-7,9-dihydro-8H-purin-8-one

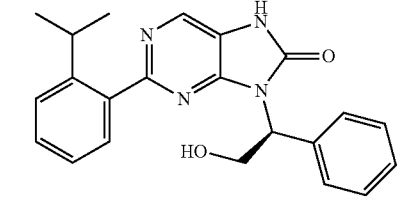

I-181

(S)-9-(2-hydroxy-1-phenyl)ethyl)-2-(2-isopropylphenyl)-7,8-dihydro-8H-purin-8-one

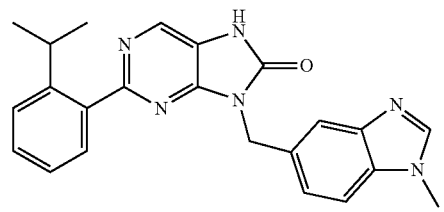

I-182

2-(2-isopropyl)phenyl)-8-((1-methyl-1H-benzo[d]imidazol-5-yl)methyl)-7,8-dihydro-8H-purin-8-one

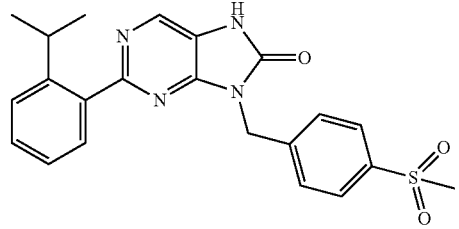

I-183

2-(2-isopropylphenyl)-9-(4-methylsulfonyl)benzyl)-7,9-dihydro-8H-purin-8-one

I-184

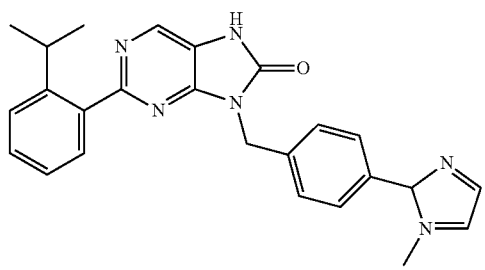

2-(2-isoproplphenyl)-9-(4-(5-methyl-1H-pyrazol-1-yl)
benzyl)-7,9-dihydro-8H-purin-8-one

I-185

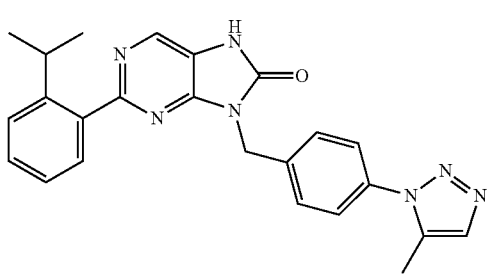

2-(2-isoproplphenyl)-9-(4-(5-methyl-1H-1,2,3-triazol-1-yl)
benzyl)-7,9-dihydro-8H-purin-8-one

I-186

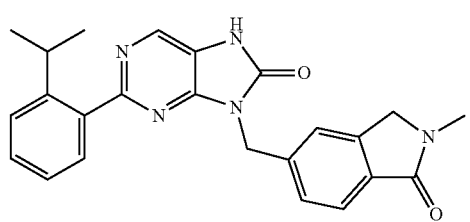

2-(2-isopropylphenyl)-8-((2-methyl-1-oxoisoindoxin-
5-yl)methyl)-7,9-dihydro-8H-purin-8-one

I-187

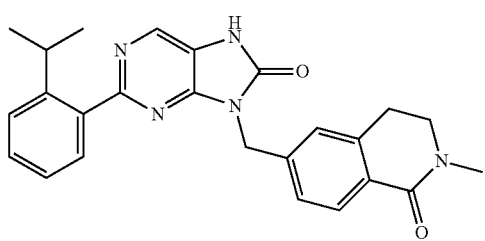

5-((2-(2-isopropylphenyl)-8-oxo-7,8-dihydro-
8H-purin-8-yl)methyl)-2-methyl-3,4-
dihydroquinolin-1(2H)-one

I-188

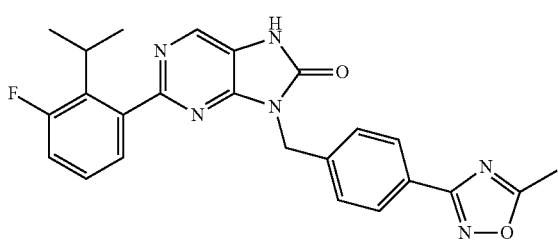

2-(3-fluoro-2-isopropylphenyl)-8-(4-(5-methyl-
1,2,4-oxadiazol-3-yl)benzyl)7,9-dihydro-8H-purin-8-one

I-189

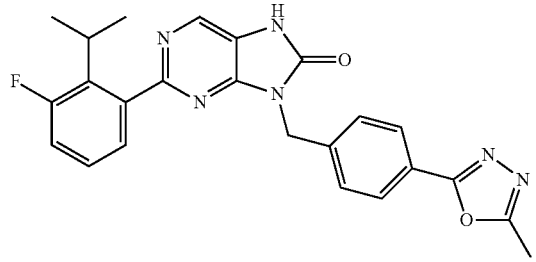

2-(3-fluoro-2-isopropylphenyl)-8-(4-(5-methyl-1,3,4-oxadiazol-
2-yl)benzyl)7,9-dihydro-8H-purin-8-one

I-190

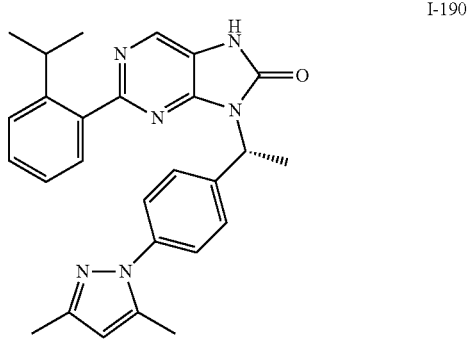

(R)-9-(1-(4-(3,5-dimethyl-1H-pyrazol-1yl)
phenyl)ethyl)-2-(2-isopropylphenyl)-
7,9-dihydro-8H-purin-8-one

I-191

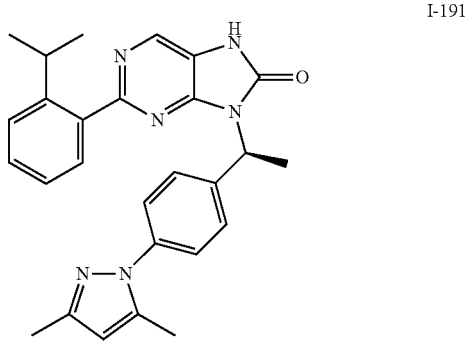

(S)-9-(1-(4-(3,5-dimethyl-1H-pyrazol-1yl)
phenyl)ethyl)-2-(2-isopropylphenyl)-
7,9-dihydro-8H-purin-8-one

I-192

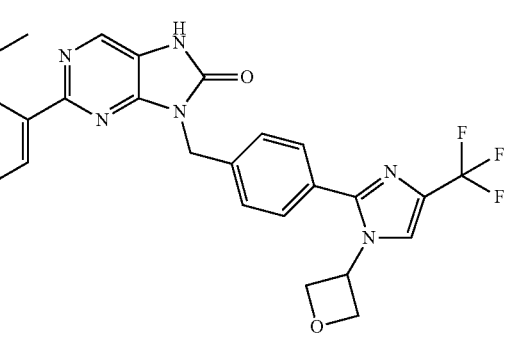

2-(2-isopropylphenyl)-8-(4-(1-(oxetan-3-yl)-4-(trifluoromethyl)-
1H-imidazol-2-yl)benzyl)-7,9-dihydro-8H-purin-8-one

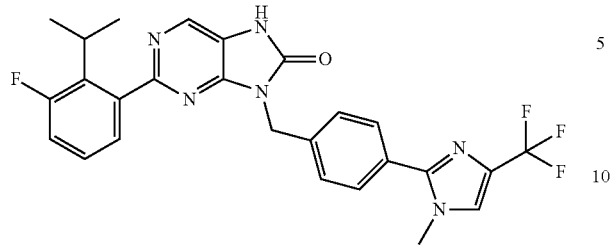

I-193

2-(3-fluoro-2-isopropylphenyl)-8-(4-(1-methyl-4-(trifluoromethyl)-1H-imidazol-2-yl)benzyl)-7,9-dihydro-8H-purin-8-one

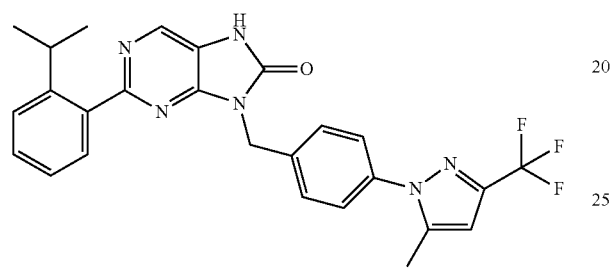

I-194

2-(2-isopropylphenyl)-9-(4-(5-methyl-3-(trifluoromethyl)-1H-pyrazol-1-yl)benzyl)-7,9-dihydro-8H-purin-8-one

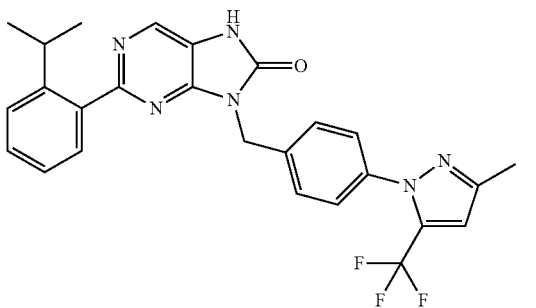

I-195

2-(2-isopropylphenyl)-3-(4-(3-methyl-5-(trifluoromethyl)-1H-pyrazol-1-yl)benzyl)-7,9-dihydro-8H-purin-8-one

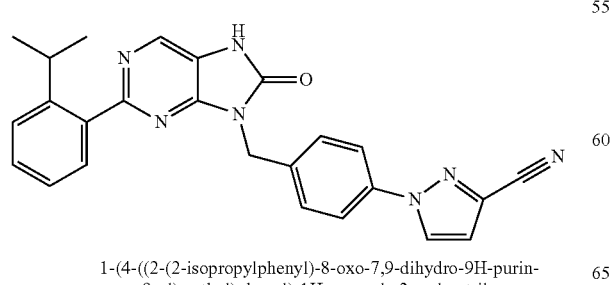

I-196

1-(4-((2-(2-isopropylphenyl)-8-oxo-7,9-dihydro-9H-purin-9-yl)methyl)phenyl)-1H-pyrazole-3-carbontrile

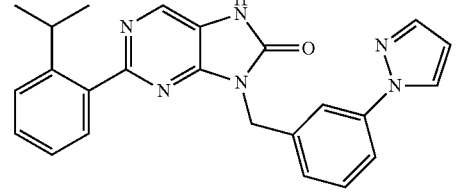

I-197

9-(3-(1H-pyrazol-1-yl)benzyl)-2-(2-isopropylphenyl)-7,9-dihydro-8H-purin-8-one

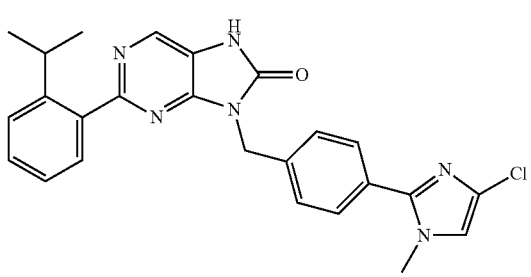

I-198

9-(4-(4-chloro-1-methyl-1H-imidazol-2-yl)benzyl)-2-(2-isopropyl)phenyl)-7,9-dihydro-8H-purin-8-one

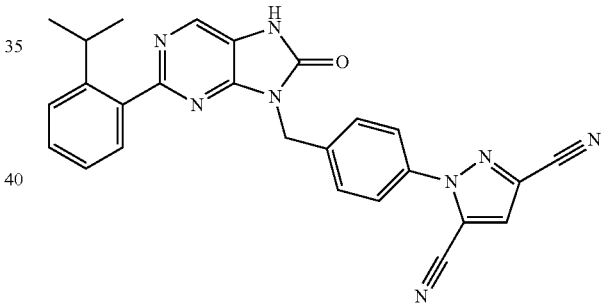

I-199

1-(4-((2-(2-ispropylphenyl)-8-oxo-7,8-dihydro-8H-purin-8-yl)methylphenyl)-1H-pyrazol-3,5-diozrobnitrile

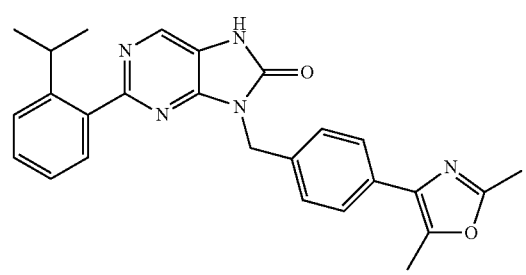

I-200

3-(4-(2,5-dimethyloxozol-4-yl)benzyl)-2-(2-isopropylphenyl)-7,9-dihydro-8H-purin-8-one

I-201

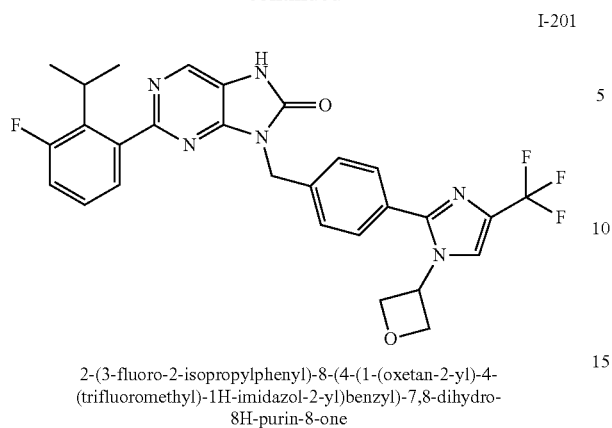

2-(3-fluoro-2-isopropylphenyl)-8-(4-(1-(oxetan-2-yl)-4-(trifluoromethyl)-1H-imidazol-2-yl)benzyl)-7,8-dihydro-8H-purin-8-one

I-202

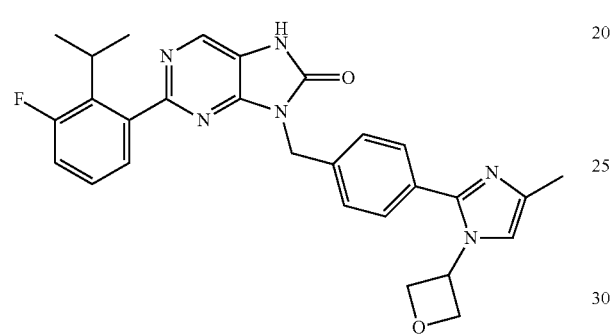

2-(3-fluoro-2-isopropylphenyl)-8-(4-(4-methyl-1-(oxetan-3-yl)-1H-imidazol-2-yl)tenzyl)-7,9-dihydro-8H-purin-8-one

I-203

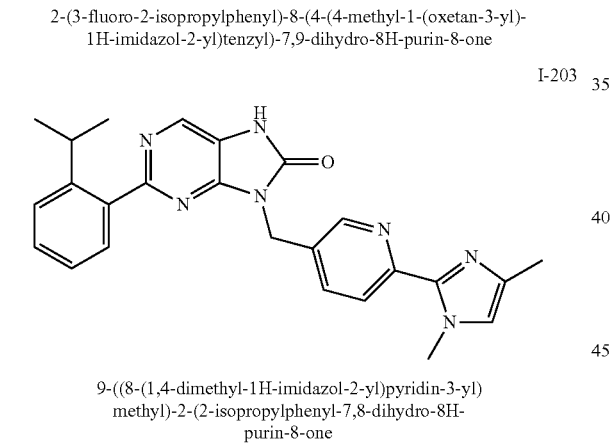

9-((8-(1,4-dimethyl-1H-imidazol-2-yl)pyridin-3-yl)methyl)-2-(2-isopropylphenyl)-7,8-dihydro-8H-purin-8-one

I-204

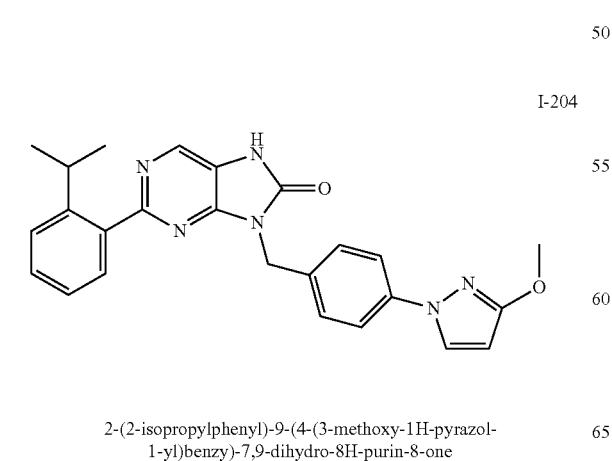

2-(2-isopropylphenyl)-9-(4-(3-methoxy-1H-pyrazol-1-yl)benzy)-7,9-dihydro-8H-purin-8-one

I-205

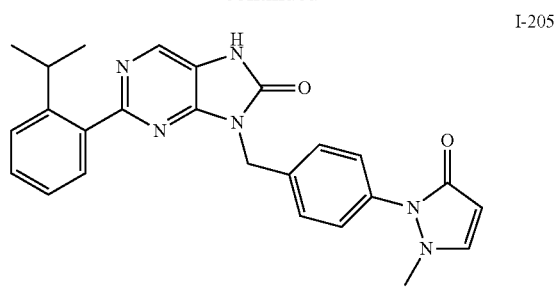

2-(2-isopropylphenyl)-6-(4-(2-methyl-5-oxo-2,5-dihydro-1H-pyrazol-1-yl)benzyl)-7,9-dihydro-8H-purin-8-one

I-206

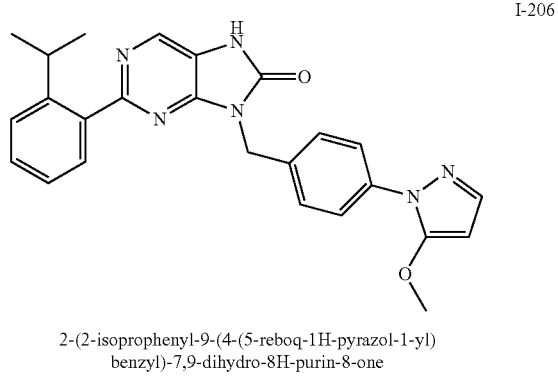

2-(2-isoprophenyl)-9-(4-(5-reboq-1H-pyrazol-1-yl)benzyl)-7,9-dihydro-8H-purin-8-one

I-207

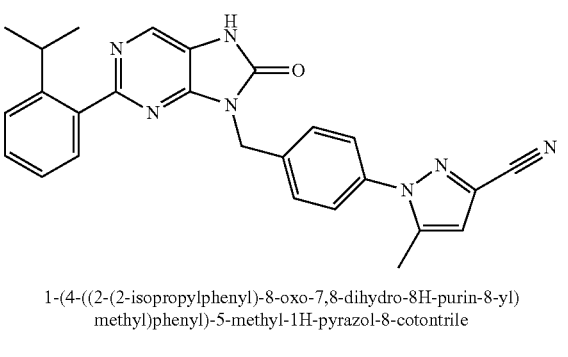

1-(4-((2-(2-isopropylphenyl)-8-oxo-7,8-dihydro-8H-purin-8-yl)methyl)phenyl)-5-methyl-1H-pyrazol-8-cotontrile

I-208

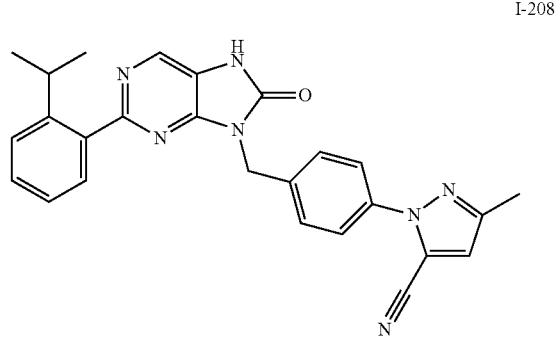

1-(4-((2-(2-isopropylphenyl)-8-oxo-7,8-dihydro-8H-purin-8-yl)methylphenyl)-3-methyl-1H-pyrazol-5-zarbonitrite

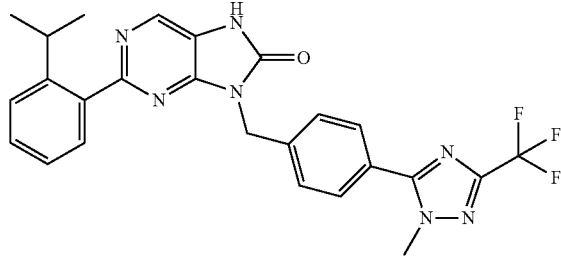

2-(2-isopropylphenyl)-9-(4-(1-methyl-3-(trifluoromethyl)-1H-1,2,4-triazol-5-yl)-benzyl)-7,9-dihydro-8H-purin-8-one

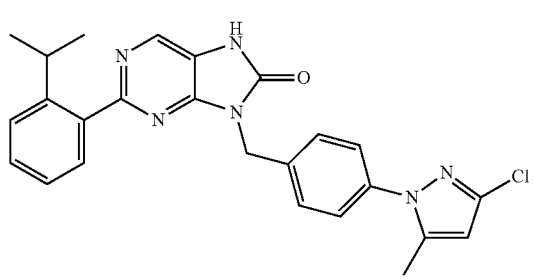

9-(4-(3-chloro-5-methyl-1H-pyrazol-1-yl)benzyl)-2-(2-isopropylphenyl)-7,9-dihydro-8H-purin-8-one

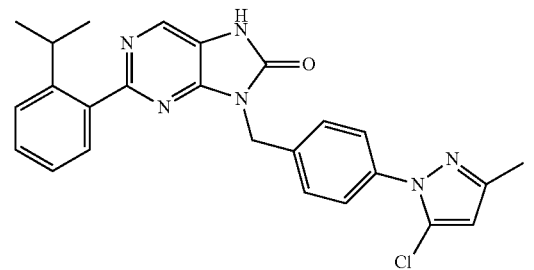

9-(4-(5-chloro-3-methyl-1H-pyrazol-1-yl)benzyl)-2-(2-isopropylphenyl)-7,9-dihydro-8H-purin-8-one

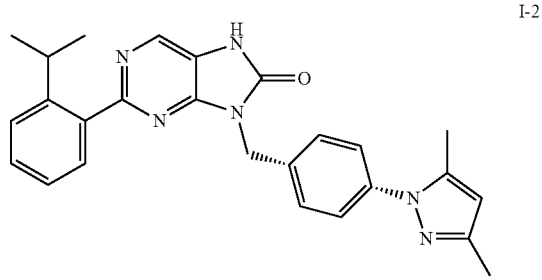

9-(((1s,4s)-4-(3,5-dimethyl-1H-pyrazol-1-yl)olyohexy)methyl)-2-(2-isopropyl)phenyl)-7,9-dihydro-8H-purin-8-one

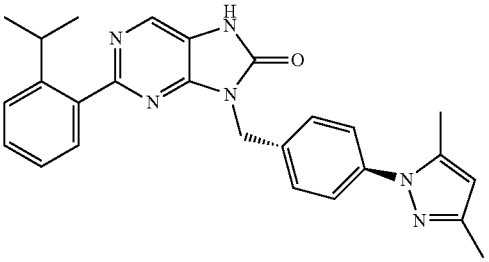

9-(((1r,4s)-4-(3,5-dimethyl-1H-pyrazol-1-yl)olyohexy)methyl)-2-(2-isopropyl)phenyl)-7,9-dihydro-8H-purin-8-one

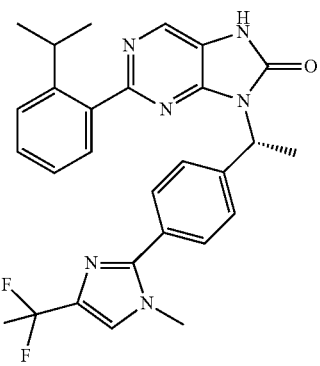

(R)-2-(2-isopropylphenyl)-8-(1-(4-(1-methyl-1-(trifluoromethyl-1H-imidazol-2-yl)phenyl)ethyl)-7,9-dihydro-8H-purin-8-one

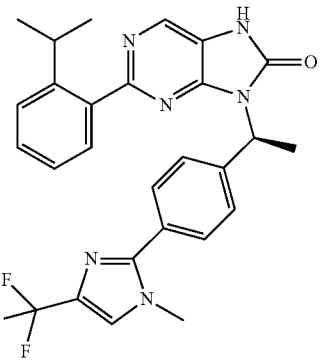

(S)-2-(2-isopropylphenyl)-8-(1-(4-(1-methyl-1-(trifluoromethyl-1H-imidazol-2-yl)phenyl)ethyl)-7,9-dihydro-8H-purin-8-one

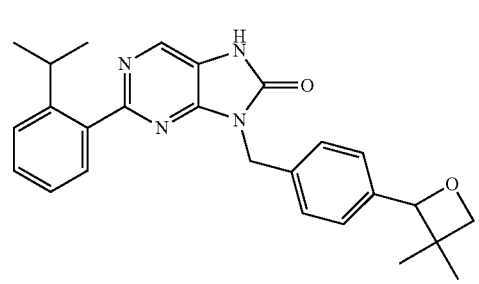

9-(4-(3,3-dimethyloxetan-2-yl)benzyl)-2-(2-isopropylphenyl)-7,9-dihydro-8H-purin-8-one

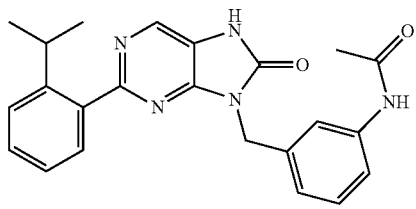

N-(1-((2-(2-isopropylphenyl)-8-oxo-7,8-dihydro-8H-purin-8-yl)methylphenyl)
acetemide

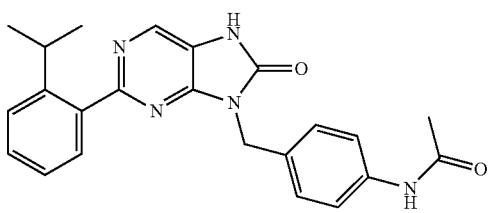

N-(4-((2-(2-isopropylphenyl)-8-oxo-7,8-dihydro-8H-purin-8-yl)(methyl)phenyl)
acetamide

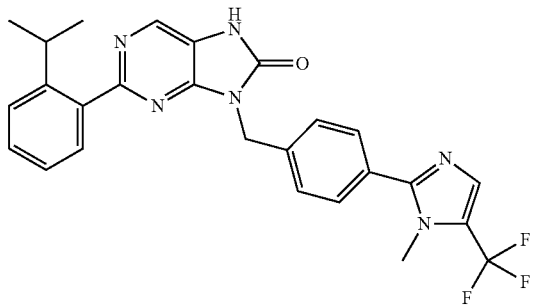

2-(2-isopropylphenyl)-9-(4-(1-methyl)-5-(trifluoromethyl)-1H-imidazol-2-yl)benzyl)7,9-dihydro-8H-purin-8-one

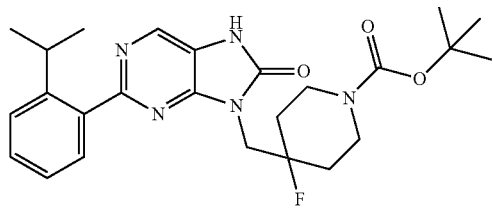

tert-butyl 4-fluoro-4-((2-(2-isopropylphenyl)-8-oxo-7,8-dihydro-8H-purin-8-yl)methyl)piperidine-1-cartoxyiate

I-217

I-218

I-219

I-220

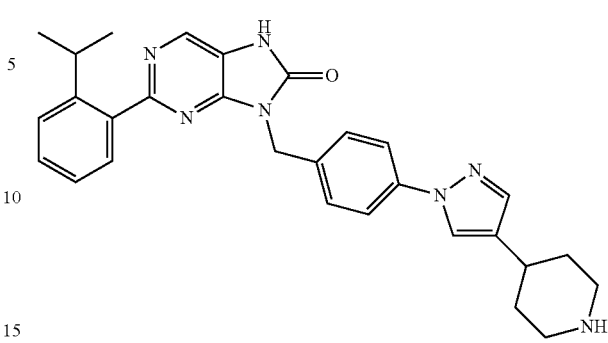

2-(2-isopropylphenyl)-9-(4-(4-(piperdine-4-yl)-1H-pyrazol-1-yl)benzyl)-7,9-dihydro-8H-purin-8-one

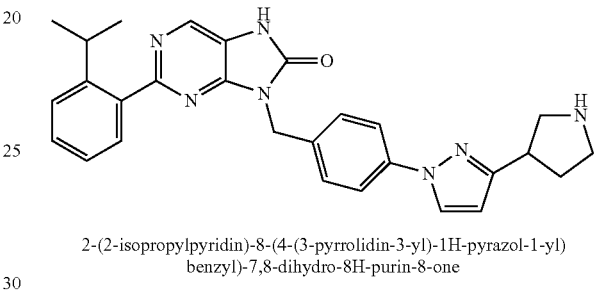

2-(2-isopropylpyridin)-8-(4-(3-pyrrolidin-3-yl)-1H-pyrazol-1-yl)benzyl)-7,8-dihydro-8H-purin-8-one

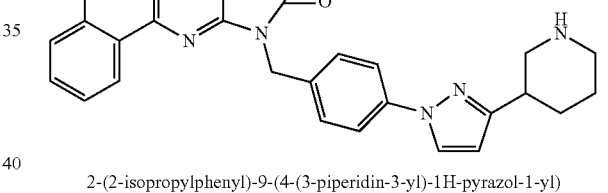

2-(2-isopropylphenyl)-9-(4-(3-piperidin-3-yl)-1H-pyrazol-1-yl)benzyl-7,9-dihydro-8H-purin-8-one

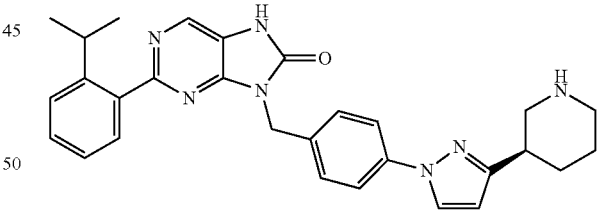

(R)-2-(2-isopropylphenyl)-9-(4-(3-(piperidin-3-yl)-1H-pyrazol-1-yl)-benzyl)-7,9-dihydro-9H-purin-8-one

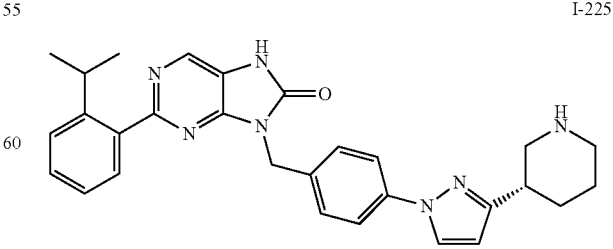

(S)-2-(2-isopropylphenyl)-9-(4-(3-(piperidin-3-yl)-1H-pyrazol-1-yl)-benzyl)-7,9-dihydro-9H-purin-8-one

I-221

I-222

I-223

I-224

I-225

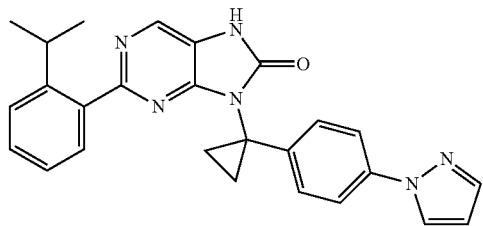

9-(1-(4-(1H-pyrazol-1-yl)-phenyl)cyclopropyl
2-(2-isopropylphenyl)-7,9-dihydro-1H-purin-8-one

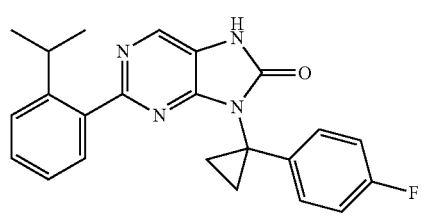

9-(1-(4-fluorophenyl)cyclopropyl)-2-(2-isopropylphenyl)-
7,9-dihydro-8H-purin-8-one

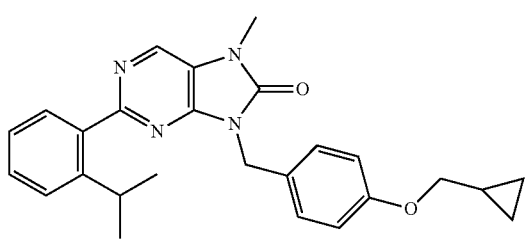

9-(4-(cyclopropyl)methoxy)benzyl)-2-(2-isoproply)phenyl)-
7-methyl-7,9-dihydro-8H-purin-8-one

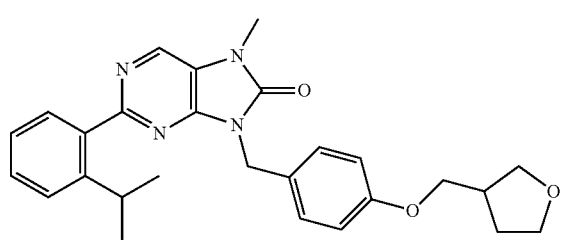

2-(2-isopropylphenyl)-7-methyl-9-(4-((tetrahydrofuran-3-yl)
methoxy)benzyl)-7,9-dihydro-8H-purin-8-one

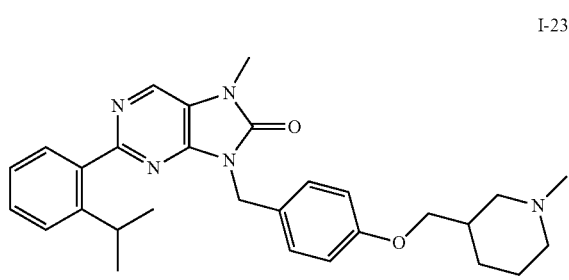

2-(2-isopropylphenyl)-7-methyl-8-(4-((1-methylpiperidin-3-yl)
methoxybenzyl)-7,9-dihydro-8H-purin-8-one

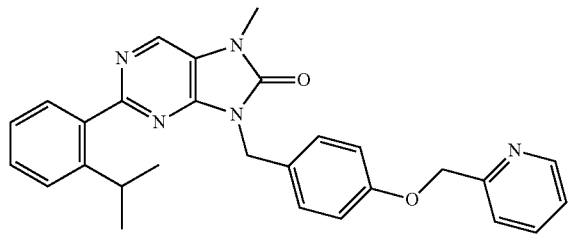

2-(2-isopropylphenyl)-7-methyl-9-(4-pyridin-2-yl
methoxy)benzyl)-7,9-dihydro-8H-purin-8-one

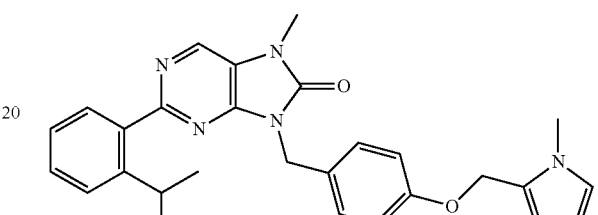

2-(2-isopropylphenyl)7-methyl-9-(4-((1-methyl-1H-imidazol-5-yl)
methoxy)benzyl)-7,9-dihydro-8H-purin-8-one

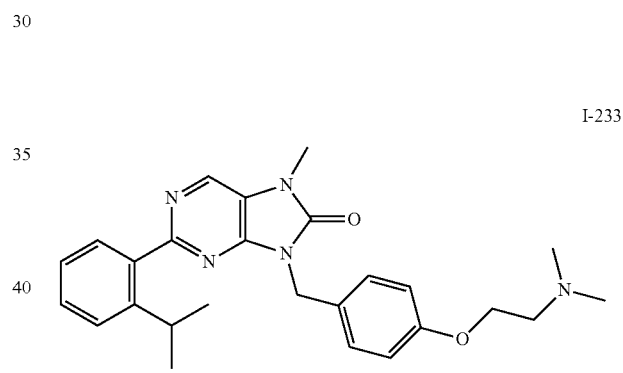

9-(4-(2-dimethylamino)ethoxy)benzyl)-2-(2-isopropylphenyl)-
7-methyl-7,9-dihydro-8H-purin-8-one

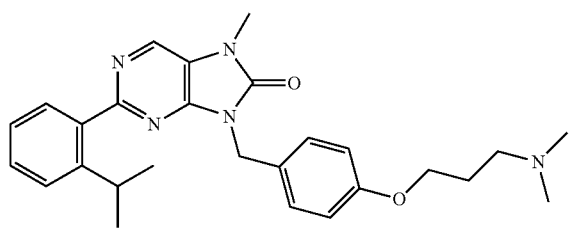

9-(4-(3-(dimethylamino)propyl(benzyl)-2-(2-
isopropylphenyl)-7-methyl-7,9-dihydro-8H-purin-8-one

I-235

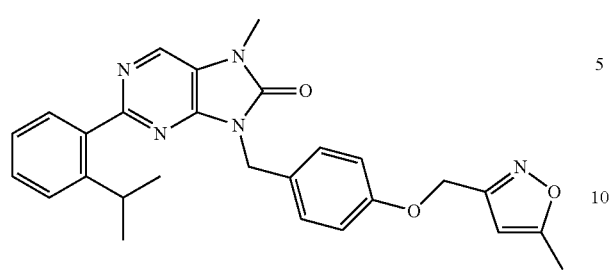

2-(2-isopropylphenyl)-7-methyl-8-(4-((5-methylisoxazi-3-yl)methox)benzyl)-7,9-dihydro-8H-purin-8-one

I-236

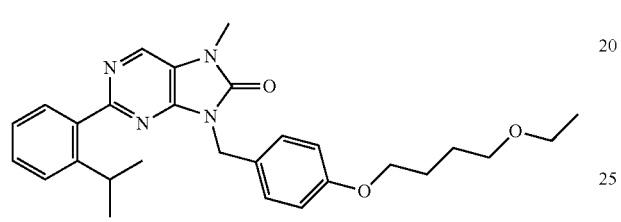

9-(4-(2-estro)ethoxy)benzyl)-2-(2-isopropyhenethyl)-7-methyl-7,9-dihydro-8H-purin-8-one

I-237

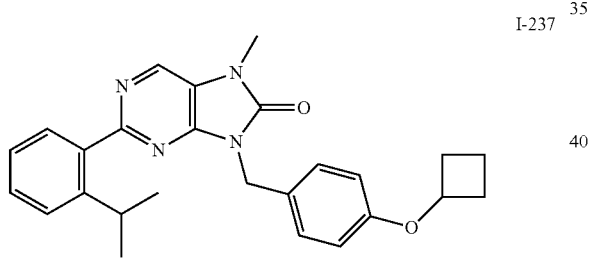

9-(4-cyclobutoxybenzyl)-2-(2-isopropylbenyl)-7-methyl-7,9-dihydro-8H-purin-8-one

I-238

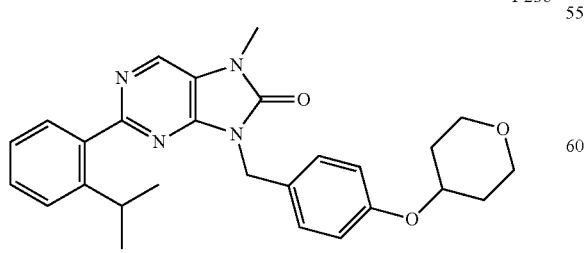

2-(2-isopropylphenyl)-7-methyl-9-(4-((tetrahydro-2H-pyran-4-yl)oxy)benzyl)-7,9-dihydro-8H-purin-8-one

I-239

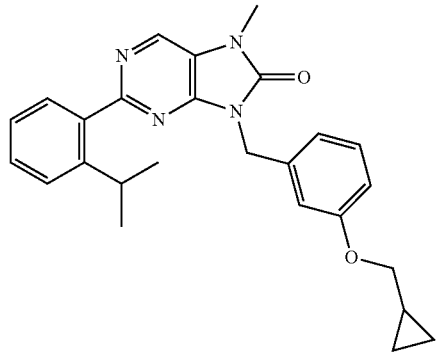

9-(3-(cyclobutoxybenzyl)-2-(2-isoproyl)phenyl)-7,9-dihydro-8H-purin-8-one

I-240

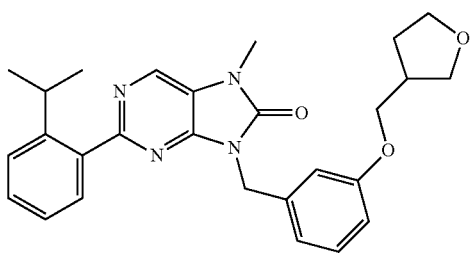

2-(2-isopropylphenyl)-7-methyl-9-(3-((tetraiydroduran-3-yl)methoxy)benzyl)-7,9-dihydro-8H-puirn-8-one

I-241

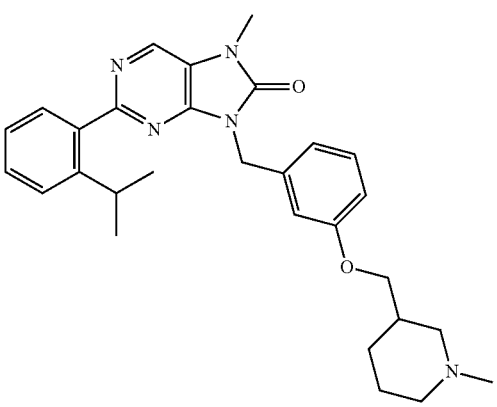

2-(2-isopropylphenyl)-7-methyl-8-(3-((t-methyl(piperidin-3-yl)methoxy)benzyl)-7,9-dihydro-8H-purin-8-one

I-242

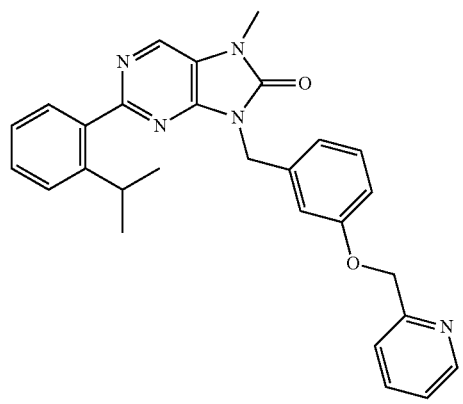

2-(2-isopropylphenyl)-7-methyl-8-(3-pyridin-2-yl methoxy)benzyl)-7,9-dihydro-8H-purin-8-one

I-243

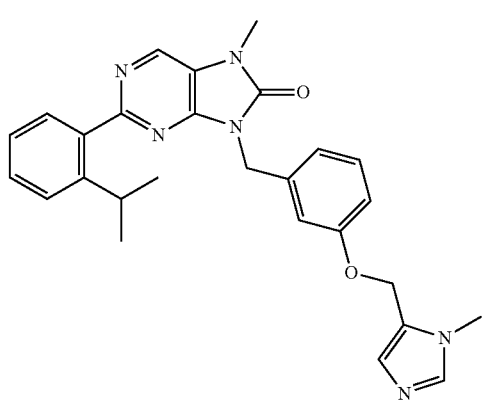

2-(2-isopropylphenyl)-7-methyl-9-(3-((1-methyl-1H-imidazol-5-yl)methoxy)benzyl)-7,9-dihydro-8H-purin-8-one

I-244

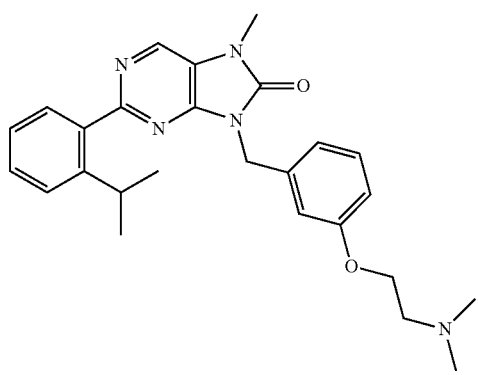

9-(3-(2-dimethylamino)ethoxy)tenzyl)-2-(2-isopropylphenyl)-7-methyl-7,9-dihydro-8H-purin-8-one

I-245

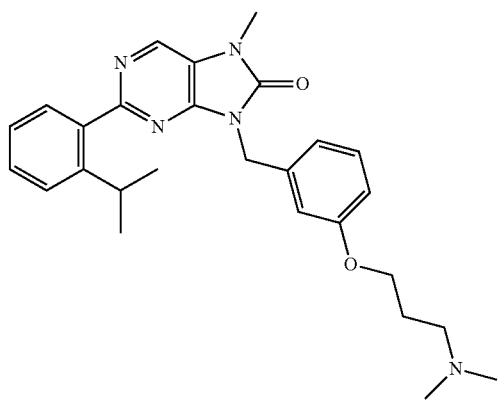

9-(3-(3-(dimethylamino)propyl)benzyl)-2-(2-isoproxy(phenyl)-7-methyl-7,9-dihydro-8H-purin-8-one

I-246

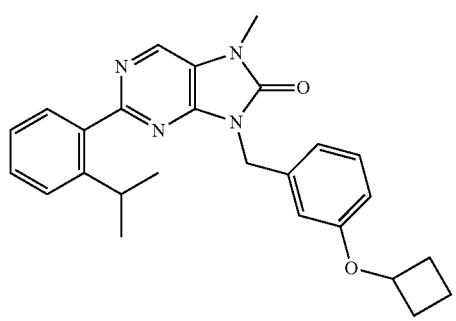

9-(3-cyclotoloxybenzyl)-2-(2-isopropylphenyl)-7-methyl-7,9-dihydro-8H-purin-8-one

I-247

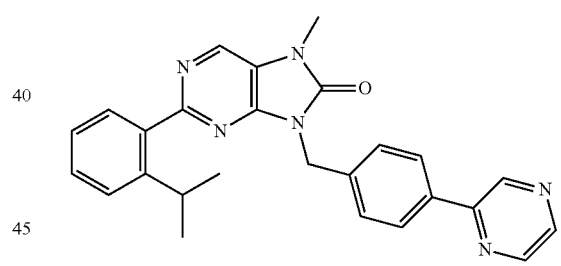

2-(2-isopropylphenyl)-8-(4-(pyrazin-2-yl)tenz yl)-7,9-dihydro-8H-purin-8-one

I-248

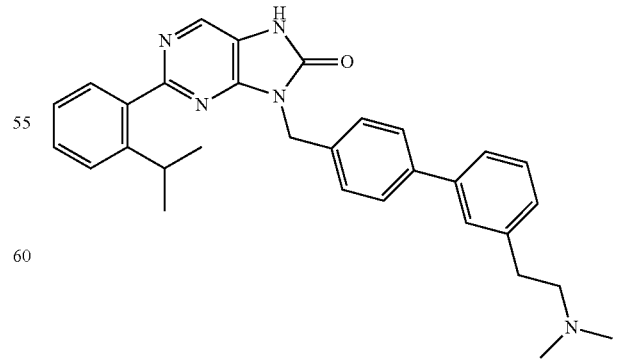

9-((3'-(2-(dimethylamino)ethyl)-1(1,1'-biphenyl-4-yl)methyl)-2-(2-isopropylphenyl)-7,9-dihydro-8H-purin-8-one

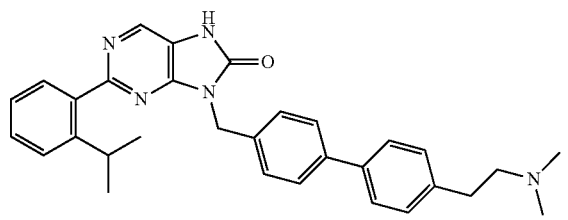

I-249

9-((4'-(2-(dimethlamino)ethyl)-(1,1'-bipheny)-4-yl)methyl)-2-(2-isopropylphenyl)-7,9-dihydro-8H-purin-8-one

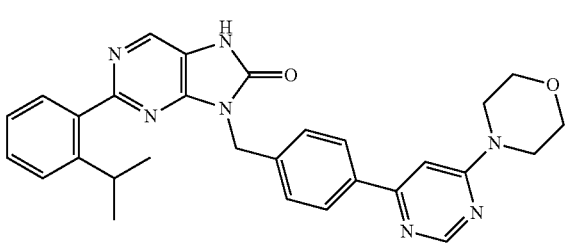

I-250

2-(2-isopropylphnyl)-9-(4-(8-morpholinopyrinidin-4-yl)benzyl)-7,9-dihydro-8H-purin-8-one

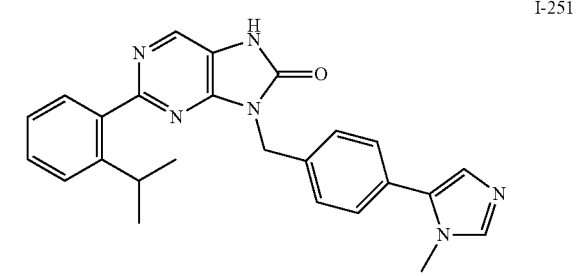

I-251

2-(2-isopropylphenyl-8-(4-(1-methyl-1H-imidazol-5-yl)benzyl)-7,9-dihydro-8H-purin-8-one

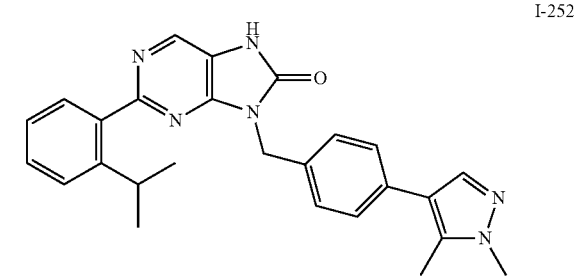

I-252

3-(4-(1,5-dimethyl-1H-pyrazol-4-yl)benzyl-2-(2-isopropylphenyl)-7,9-dihydro-8H-purin-8-one

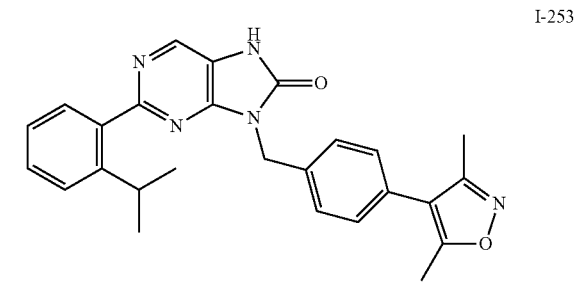

5-(4-(3,5-dimethylisoxazol-4-yl)benzyl)-2-(2-isopropylphenyl)-7,9-dihydro-8H-purin-8-one

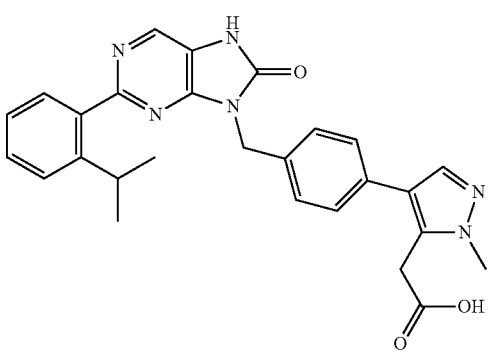

I-254

2-(4-(4-((2-(2-isoproproxy(mehtyl)-6-oxo-7,6-dihydro-9H-purin-9-yl)methyl)phenyl)-1-methyl-1H-pyrazol-5-yl)acetic acid

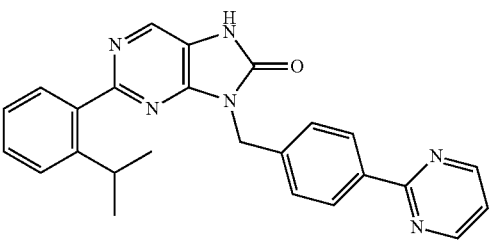

I-255

2-(2-isopropylphenyl)-8-(4-(pyrimidin-2-yl)benzyl)-7,9-dihydro-8H-purin-8-one

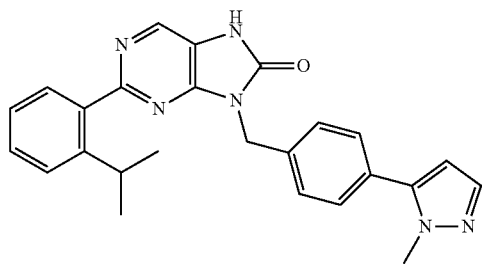

I-256

2-(2-isopropylphenyl)-9-(4-(1-methyl-1H-pyrazol-5-yl)benzyl0-7,9-dihydro-8H-purin-8-one

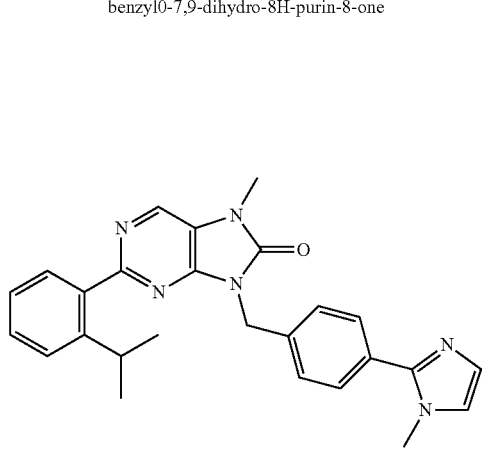

I-257

2-(2-isopropylphenyl)-7-methyl-8-(4-(1-methyl-1H-imidazol-2-yl)benzyl)-7,9-dihydro-8H-purin-8-one

I-258

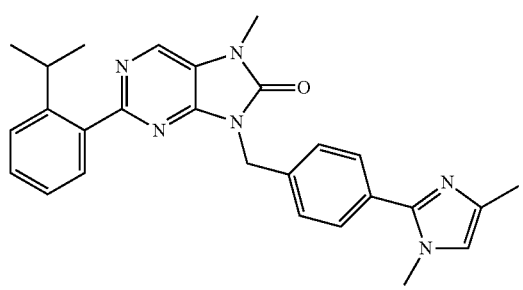

9-(4-(1,4-dimethyl-1H-imidazol-2-yl)benzyl)-2-
(2-isopropylphenyl-7-methyl-7,8-dihydro-8H-purin-8-one

I-259

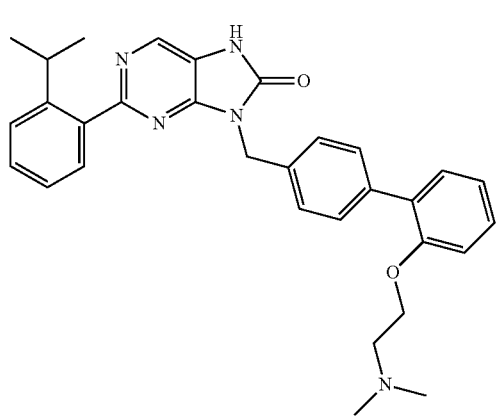

5-((2'-(2-[dimethylamino]ethoxy)-[1,1'-biphen yl]-4-yl)
methyl)-2-(2-isopropylphenyl)-7-methyl-7,9-dihydro-8H-
purin-8-one

I-260

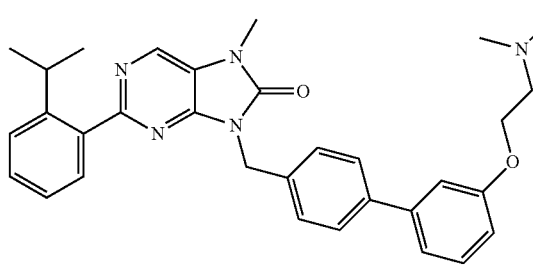

9-((3'-(2-dimethylamino)ethoxy)-[1-1'-biphen-yl]-4-yl)methyl)-2-
(2-isopropylphenyl)-7-methyl-7,9-dihydro-8H-purin-8-one

I-261

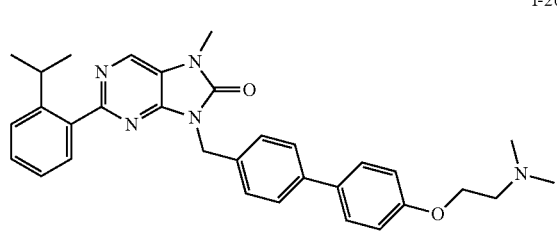

8-((4-(2-(dimethylamino)ethoxy)-(1,1-biphenyl)-4-yl)methyl)-2-
(2-isopropylphenyl)-7-methyl-7,9-dihydro-8H-purin-8-one

I-262

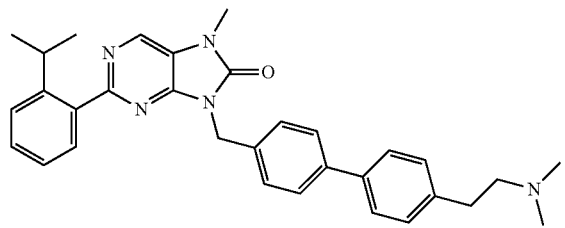

9-((4'-(2-(dimethylamino)ethyl)-[1,1'-biphenyl]-4-yl)methyl)-
2-(2-isopropylphenyl)-7-methyl-7,9-dihydro-8H-purin-8-one

I-263

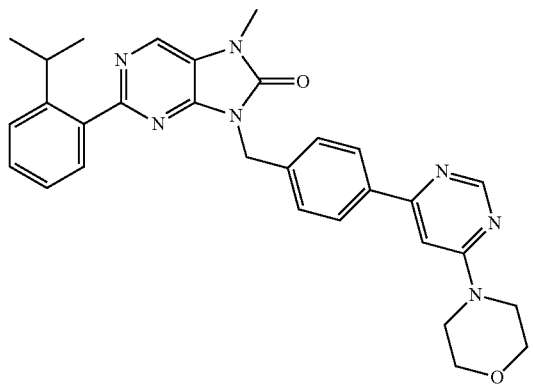

2-(2-isopropylphenyl)-7-methyl-9-(4-(8-morpholipyridin-4-yl)
benzyl)-7,9-dihydro-8H-purin-8-one

I-264

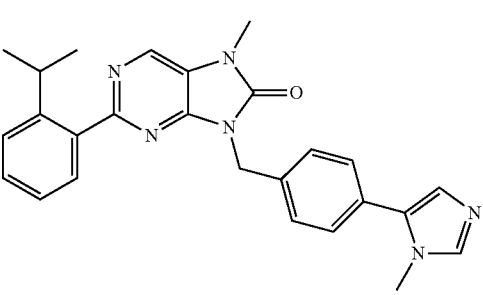

2-(2-isopropylphenyl)-7-methyl-8-(4-(1-methyl-1H-imidazol-
5-yl)benzyl)-7,8-dihydro-8H-purin-8-one

I-265

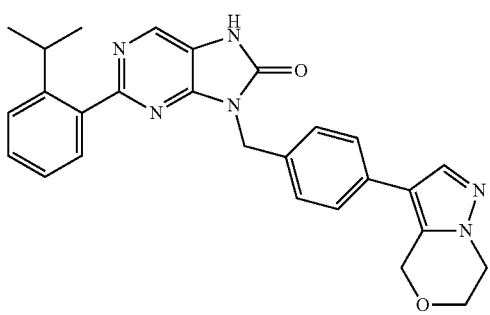

9-(4-(6,7-dihydro-4H-pyrazolo[5,1-o][1,4]oxazin-3-yl)(benzyl)-
2-(2-isopropylphenyl)-7-methyl-7,9-dihydro-8H-purin-8-one

I-266

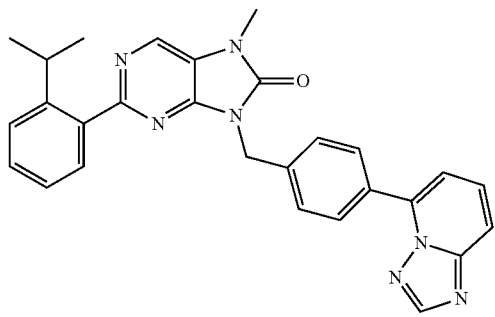

9-(4-([1,2,4]triazolo[1,5-a]pyridin-5-yl)benzyl)-2-(2-isopropyhenyl)-7-methyl-7,9-dihydro-8H-purin-8-one

I-267

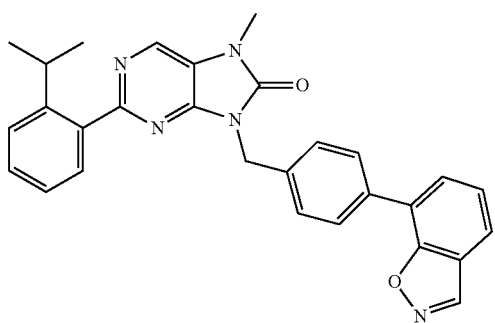

9-(4-(benzo(d)isoxazol-7-yl)benzyl)-2-(2-isopropyl)phenyl)-7-methyl-7,5-dihydro-8H-purin-8-one

I-268

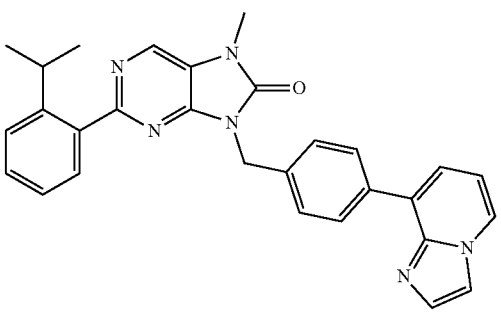

8-(4-(1H-imidazol-7-yl)benzyl)-2-(2-isoproylphenyl)-7-methyl-7,8-dihydro-8H-purin-8-one

I-269

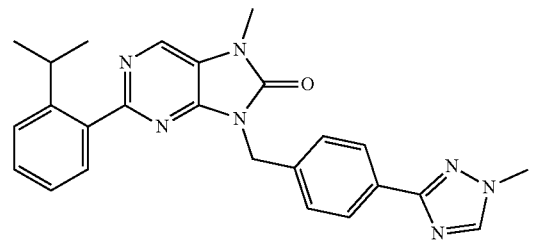

8-(4-(1H-imidazol-1,2-a)pyridin-8-yl)benzyl)-2-(2-isoproylphenyl)-7-methyl-7,8-dihydro-8H-purin-8-one

I-270

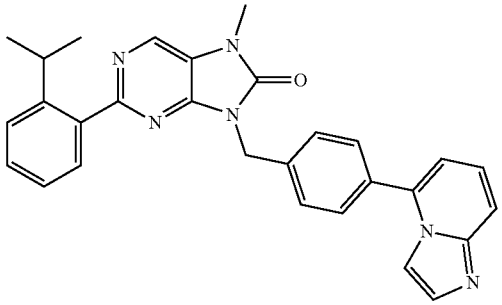

9-(4-[imidazol]1,2-a)pyridin-5-yl)benzyl)-2-(2-isoproylphenyl)-7-methyl-7,8-dihydro-8H-purin-8-one

I-271

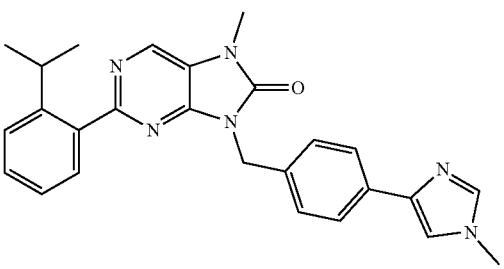

2-(2-isoproylphenyl)-7-methyl-8-(4-(1-methyl-1H-imidazol-4-yl)benzyl)-7,8-dihydro-8H-purin-8-one

I-272

2-(2-isoproylphenyl)-7-methyl-8-(4-(1-methyl-1H-1,2,4-triazol-3-yl)benzyl)-7,8-dihydro-8H-purin-8-one

I-273

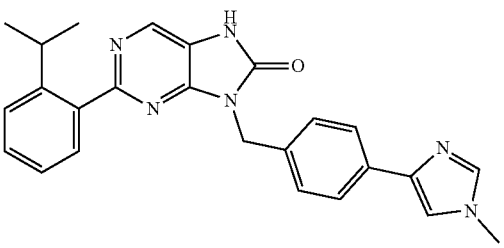

2-(2-isoproylphenyl)-8-(4-(1-methyl-1H-imidazol-4-yl)benzyl)-7,8-dihydro-8H-purin-8-one

I-274

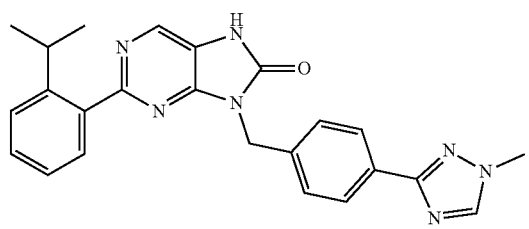

2-(2-isoproylphenyl)-9-(4-(1-methyl-1H-1,2,4-
triazol-3-yl)benzyl)-7,8-dihydro-8H-purin-8-one

I-275

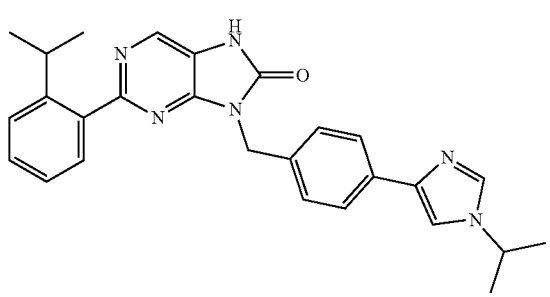

8-(4-(1-isoproylphenyl)-1H-imidazol-4-yl)benzyl)-2-
(2-iospropylphenyl)-7,8-dihydro-8H-purin-8-one

I-276

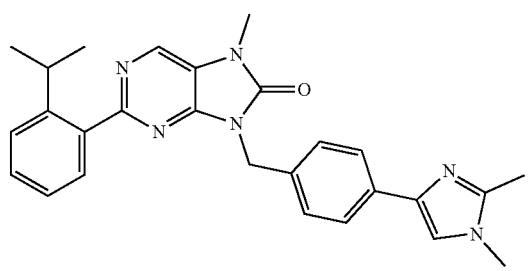

8-(4-(1-2-dimethyl-1H-imidazol-4-yl)benzyl)-2-
(2-iospropylphenyl)-7-methyl-7,8-dihydro-8H-purin-8-one

I-277

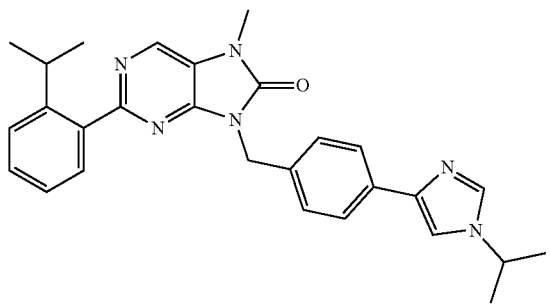

8-(4-(1-isopropyl-1H-imidazol-4-yl)benzyl)-2-
(2-isopropylphenyl)-7-methyl-7,8-dihydro-8H-purin-8-one

I-278

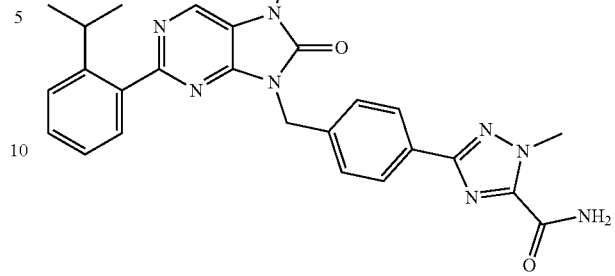

3-(4-((2-(2-isopropylphenyl)-7-methyl-8-oxo-7,8-
dihydro-8H-purin-8-yl)methyl)phenyl)-1-methyl-1H-
1,2,4-triazole-5-carboxamide

I-279

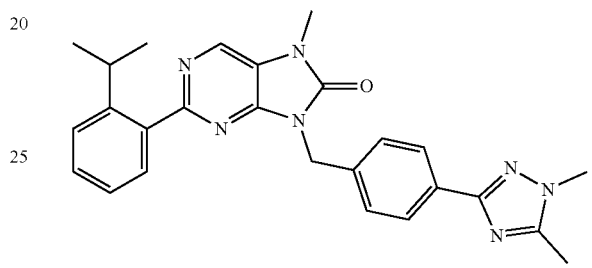

8-(4-(1,5-dimethyl-1H-1,2,4-triazol-3-yl)benzyl)-
2-(2-isopropylphenyl)-7-methyl-7,8-dihydro-8H-purin-8-one

I-280

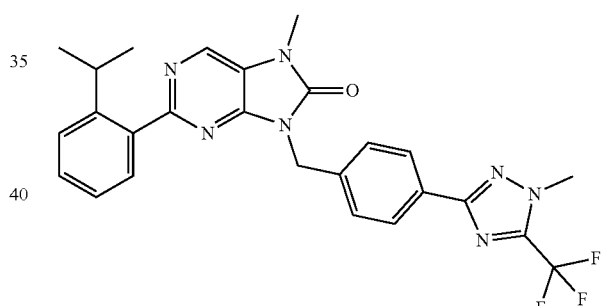

2-(2-isopropylphenyl)-7-methyl-8-(4-(1-methyl-
5-(trifluoromethyl)-1H-1,2,4-triazol-3-yl)benzyl)-
7,8-dihydro-8H-purin-8-one

I-281

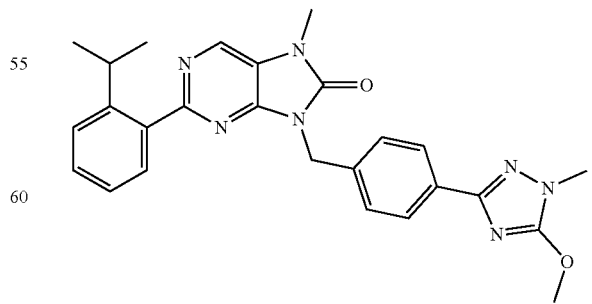

2-(2-isopropylphenyl)-9-(4-(5-methoxy-1-methyl-
1H-1,2,4-triazol-3-yl)benzyl)-7-methyl-7,8-dihydro-8H-purin-8-one

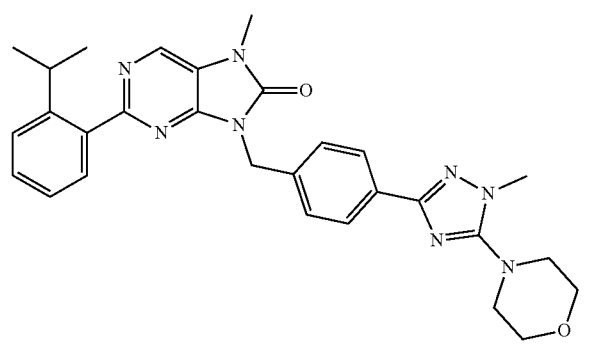

2-(2-isopropylphenyl)-7-methyl-3-(4-(5-methyl-5-morpholine-1H-1,2,4-triazol-3-yl)benzyl)-7,8-dihydro-8H-purin-8-one

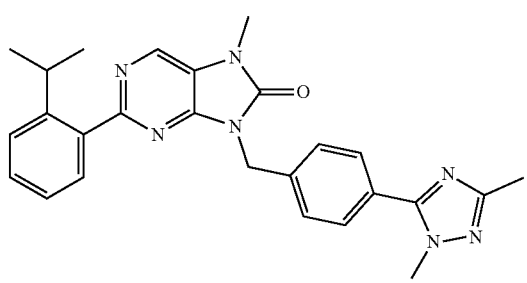

9-(4-(1,3-dimethyl-1H-1,2,4-triazol-5-yl)benzyl)-2-(2-isopropylphenyl)-7-methyl-7,9-dihydro-8H-purin-8-one

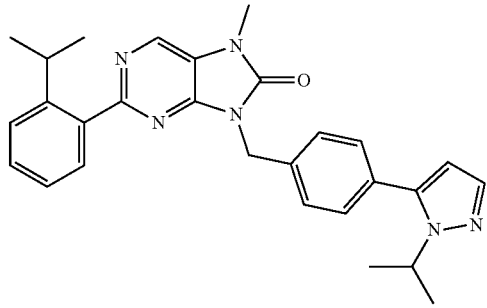

9-(4-(1-isopropyl-1H-pyrazol-5-yl)benzyl)-2-(2-isopropylphenyl)-7-methyl-7,9-dihydro-8H-purin-8-one

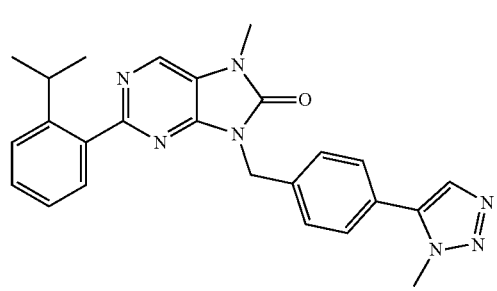

2-(2-isopropylphenyl)-7-methyl-8-(4-(1-methyl-1H-1,2,3-triazol-5-yl)benzyl)-7,9-dihydro-8H-purin-8-one

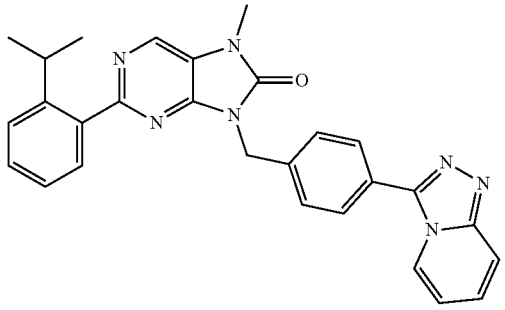

9-(4-([1,2,4]triazolo[4,3-a]pyridin-3-yl)benzyl)-2-(2-isopropylphenyl)-7-methyl-7,8-dihydro-8H-purin-8-one

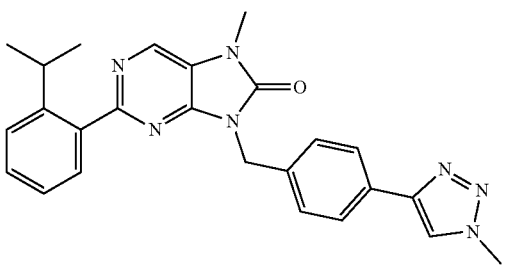

2-(2-isopropylphenyl)-7-methyl-8-(4-(1-methyl-1H-1,2,3-triazol-4-yl)benzyl)-7,8-dihydro-8H-purin-8-one

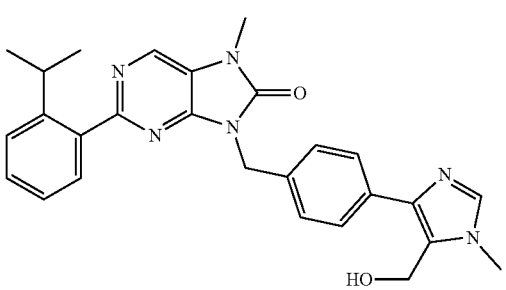

9-(4-(5-(hydroxymethyl)-1-methyl-1H-imidazol-4-yl)benzyl)-2-(2-isopropylphenyl)-7-methyl-7,9-dihydro-8H-purin-8-one

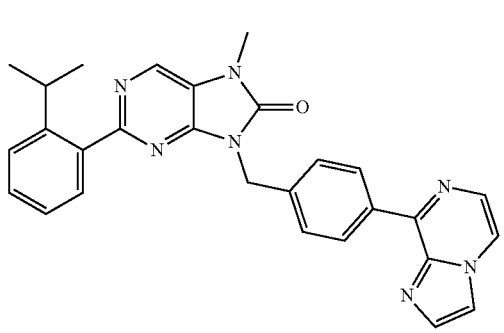

9-(4-(imidazo[1,2-a]pyrazin-8-yl)benzyl)-2-(2-isopropylphenyl)-7-methyl-7,9-dihydro-8H-purin-8-one

I-290

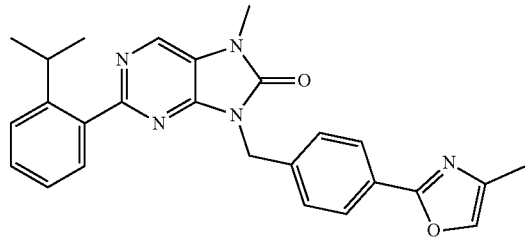

2-(2-isopropylphenyl]-7-methyl-8-(4-(4-methyl-
oxazol-2-yl)benzyl)-7,9-dihydro-8H-purin-8-one

I-291

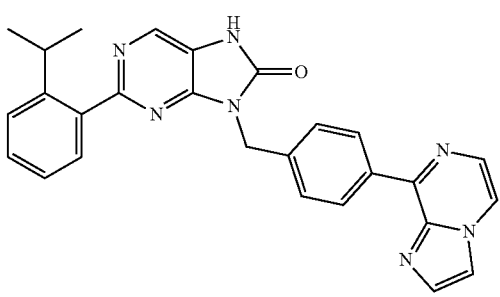

9-(4-(imidazo[1,2-a]pyrazin-8-yl)benzyl)-2-(2-
isopropylphenyl)-7,9-dihydro-8H-purin-8-one

I-292

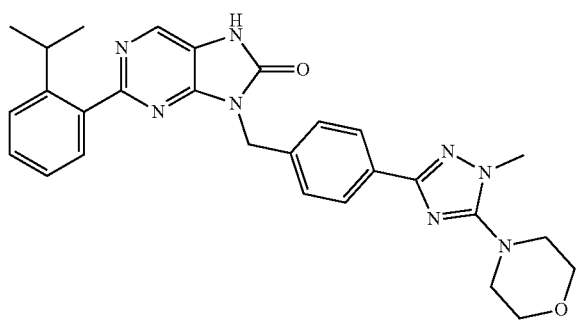

2-(2-isopropylphenyl)-8-(4-(1-methyl-5-morpholine-
1H-1,2,4-triazol-3-yl)benzyl)-7,9-dihydro-8H-purin-8-one

I-293

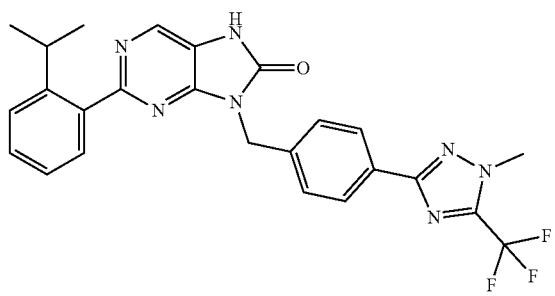

2-(2-isopropylphenyl)-8-(4-(1-methyl-5-
(trifluoromethyl)-1H-1,2,4-triazol-3-yl)benzyl)-7,9-
dihydro-8H-purin-8-one

I-294

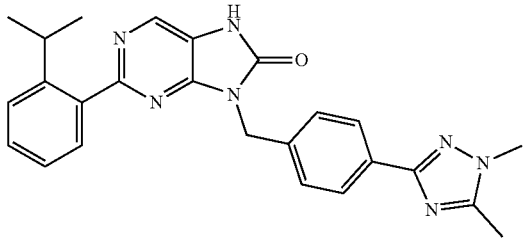

9-(4-(1,5-dimethyl-1H-1,2,4-triazol-3-yl)benzyl)-
2-(2-isopropylphenyl)-7,9-dihydro-8H-purin-8-one

I-295

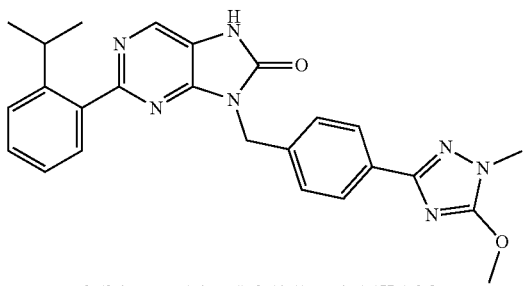

2-(2-isopropylphenyl)-9-(4-(1-methyl-1H-1,2,3-
triazol-3-yl)benzyl)-7,9-dihydro-8H-purin-8-one

I-296

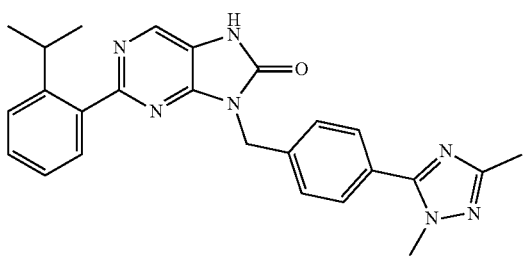

9-(4-(1,3-dimethyl-1H-1,2,4-triazol-5-yl)benzyl)-
2-(2-isopropylphenyl)-7,9-dihydro-8H-purin-8-one

I-297

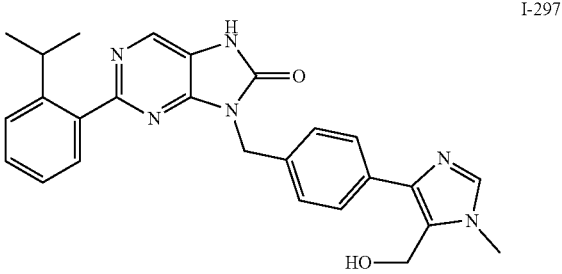

8-(4-(5-(hydroxymethyl)-1-methyl-1H-imidazol-
4-yl)benzyl)-2-(2-isopropylphenyl)-7,8-dihydro-8H-purin-8-one

I-298

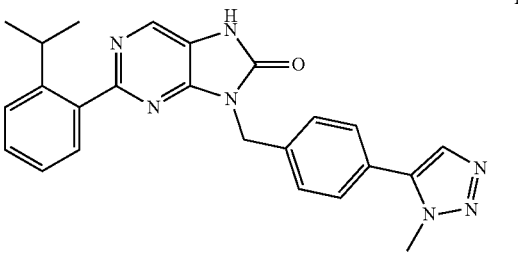

2-(2-isopropylphenyl)-8-(4-(1-methyl-1H-1,2,3-
triazol-5-ylbenzyl)-7,9-dihydro-8H-purin-8-one

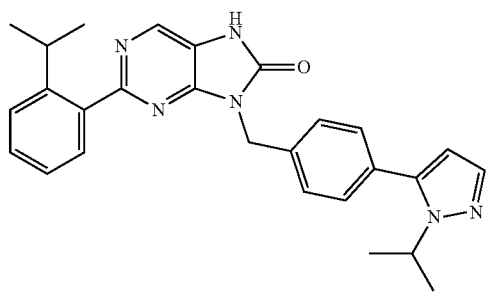

9-(4-(1-isopropyl-1H-pyrazol-5-yl)benzyl)-2-(2-isopropylphenyl)-7,8-dihydro-8H-purin-8-one

I-299

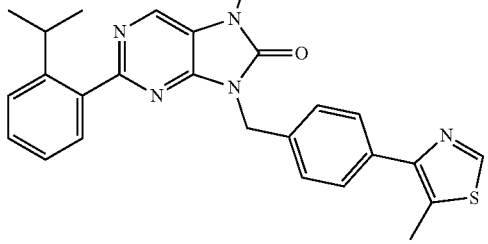

2-(2-isopropylphenyl)-7-methyl-9-(4-(5-methylthiazol-4-yl)benzyl)-7,8-dihydro-8H-purin-8-one

I-303

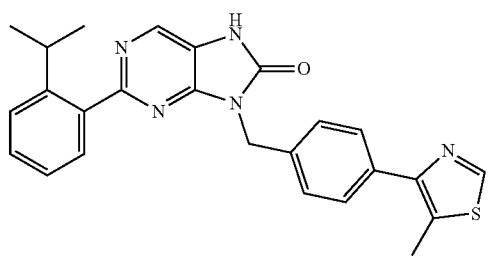

2-(2-isopropylphenyl)-9-(4-(5-methylthiazol-4-ylbenzyl)-7,9-dihydro-8H-purin-8-one

I-300

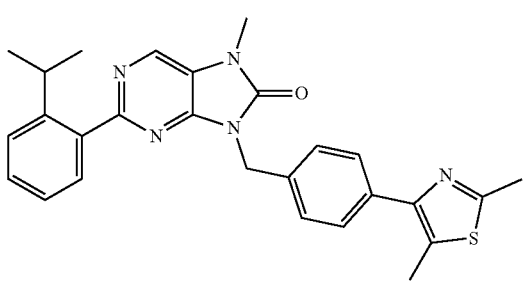

9-(4-(5-dimethylthiazol-4-yl)benzyl)-2-(2-isopropylphenyl)-7-methyl-7,9-dihydro-8H-purin-8-one

I-304

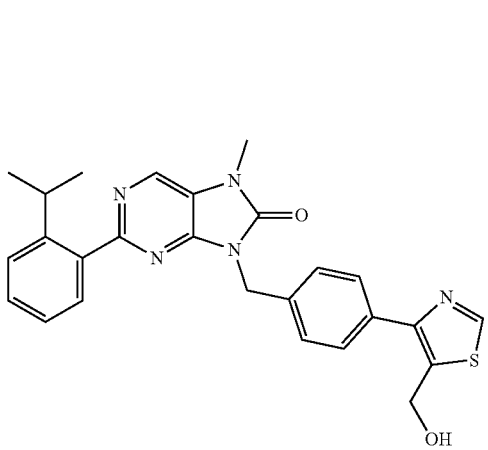

9-(4-(2,5-dimethylthiazol-4-yl)benzyl)-2-(2 sopropylphenyl)-7,9-dihydro-8H-purin-8-one

I-301

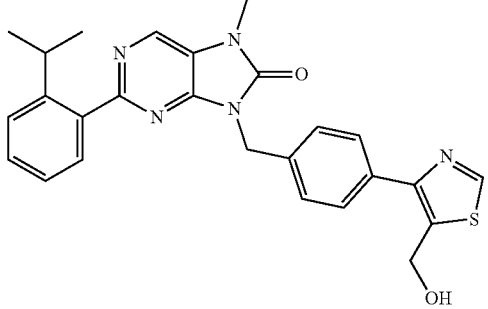

8-(4-(5-hydroxymethylthiazol-4-yl)benzyl)-2-(2-isopropylphenyl)-7-methyl-7,9-dihydro-8H-purin-8-one

I-305

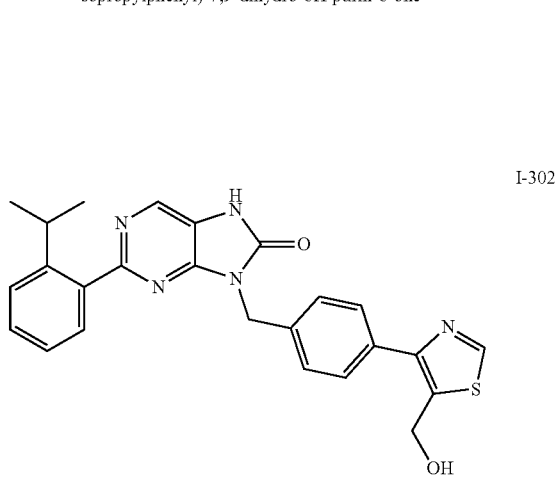

9-(4-(5-(hydroxymethyl)thiazol-4-yl)benzyl)-2-(2-isopropylphenyl)-7,9-dihydro-8H-purin-8-one

I-302

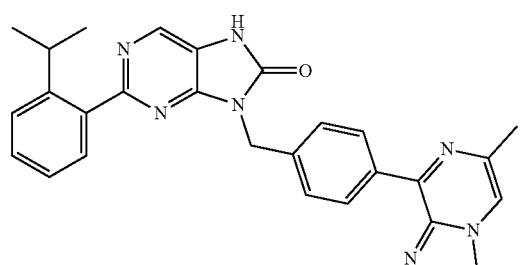

2-(2-isopropylphenyl)-8-(4-(6-methylimidazol[1.2-a]pyrazin-8-yl)benzyl)-7,9-dihydro-8H-purin-8-one

I-306

I-307

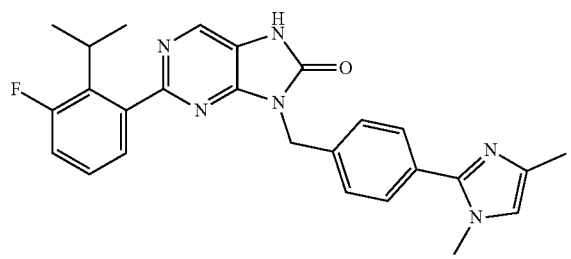

9-(4-(1,4-dimethyl-1H-imidazol-2-yl)benzyl)-2-
(3-fluoro-2-isopropylphenyl)-7,9-dihydro-8H-purin-8-one

I-308

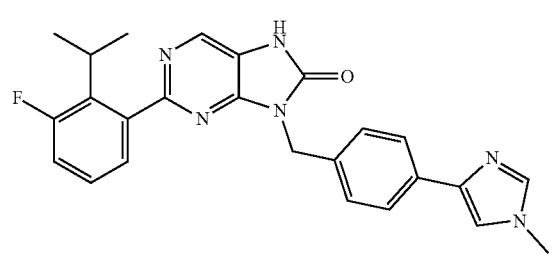

2-(3-fluoro-2-isopropylphenyl)-9-(4-(1-methyl-
1H-imidazol-4-yl)benzyl)-7,9-dihydro-8H-purin-8-one

I-309

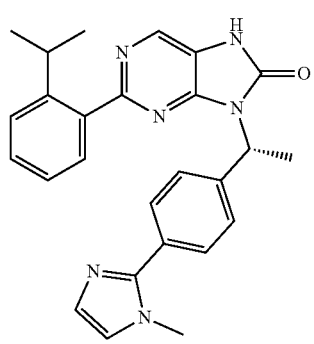

(R)-2-(2-isopropylphenyl)-8-(1-(4-(1-methyl-1H-
imidazol-2-yl)phenyl)ethyl)-7,9-dihydro-8H-purin-8-one

I-310

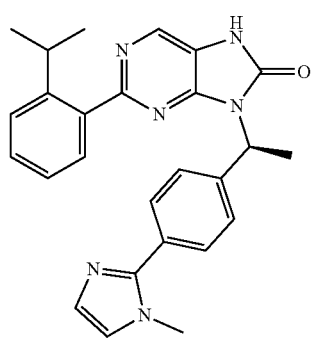

(S)-2-(2-isopropylphenyl)-8-(1-(4-(1-methyl-1H-
imidazol-2-yl)phenyl)ethyl)-7,9-dihydro-8H-purin-8-one

I-311

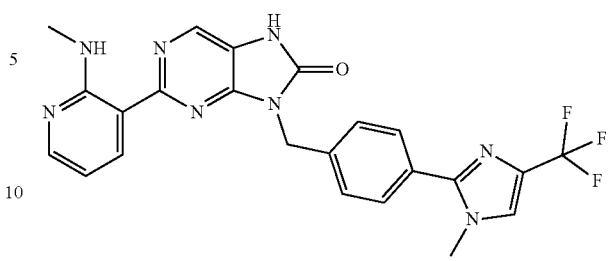

8-(4-(1-methyl-4-(trifluoromethyl)-1H-imidazol-
2-yl)benzyl)-2-(2-methylamino)pyridin-3-yl)-7,9-
dihydro-8H-purin-8-one

I-312

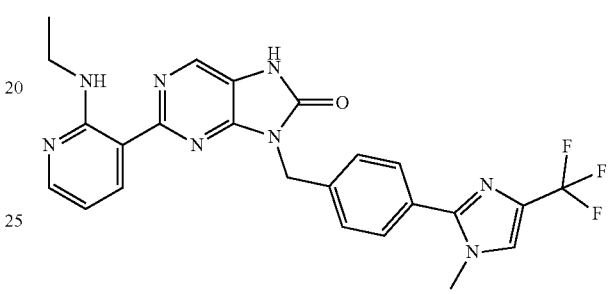

2-(2-ethylamino)pyridin-3-yl)-9-(4-(1-methyl-
4-(trifluoromethyl)-1H-imidazol-2-yl)benzyl)-7,9-
dihydro-8H-purin-8-one

I-313

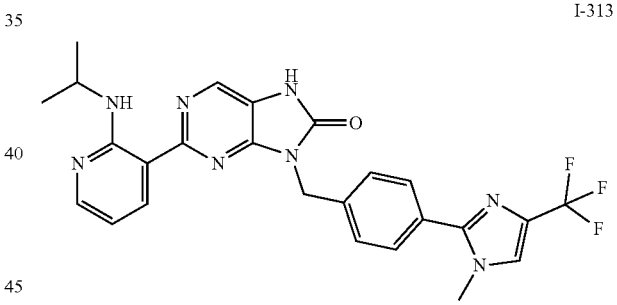

2-(2-isopropylamino)pyridin-3-yl)-8-yl)-8-(4-(1-methyl-
4-(trifluoromethyl)-1H-imidazol-2-yl)benzyl)-7,9-
dihydro-8H-purin-8-one

I-314

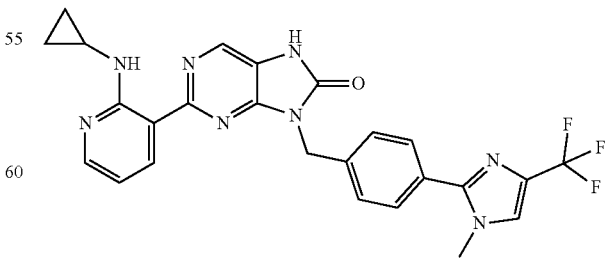

2-(2-cyclopropylamino)pyridin-3-yl)-8-(4-(1-
methyl-4-(trifluoromethyl)-1H-imidazol-2-yl)benzyl)-
7,9-dihydro-8H-purin-8-one -continued

I-315

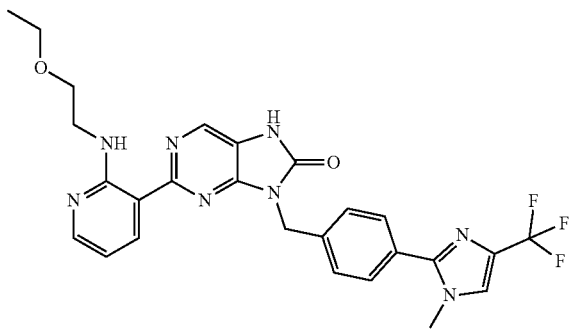

2-(2-((2-ethoxyethyl)aminopyridin-3-yl)-8-(4-
(1-methyl-4-(trifluoromethyl)-1H-imidazol-2-yl)benzyl)-
7,9-dihydro-8H-purin-8-one

I-316

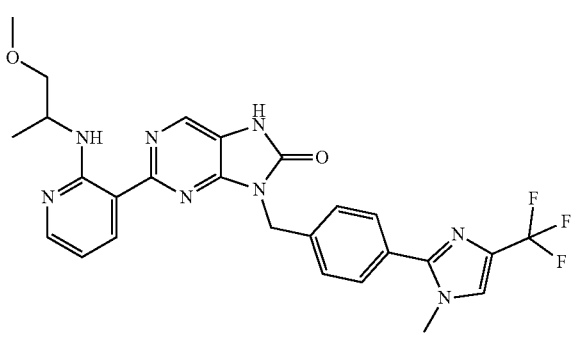

2-(2-cyclobutylamino)pyridin-3-yl)-8-(4-(1-
methyl-4-(trifluoromethyl)-1H-imidazol-2-yl)benzyl)-
7,9-dihydro-8H-purin-8-one

I-317

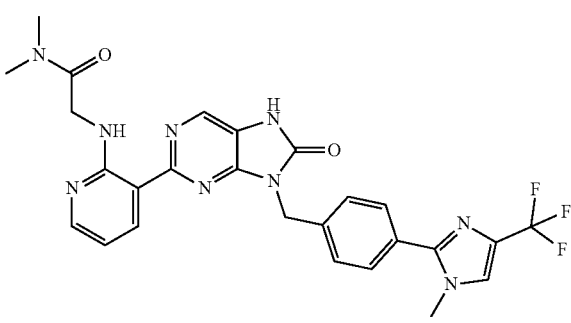

2-(2-((1-methoxypropan-2-yl)amino)pyridin-3-yl)-
8-(4-(1-methyl-4-(trifluoromethyl)-1H-imidazol-2-
yl)benzyl)-7,9-dihydro-8H-purin-8-one

I-318

N,N-dimethyl-2-((3-(9-(4-(1-methyl-4-(trifluoromethyl)-1H-
imidazol-2-yl)benzyl)-8-oxo-8,9-dihydro-7H-purin-
2-yl)pyridin-2-yl)amino)acetamide -continued

I-319

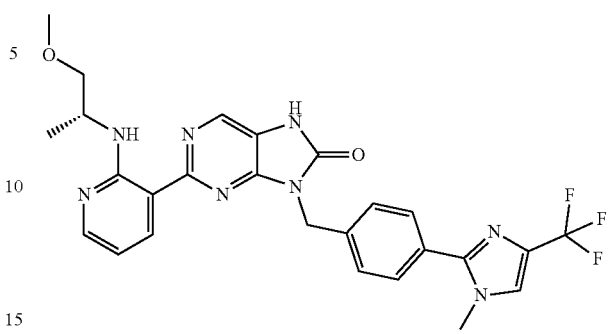

(R)-2-(2-((1-methoxypropan-2-yl)amino)pyridin-
3-yl)-8-(4-(1-methyl-4-(trifluoromethyl)-1H-imidazol-2-
yl)benzyl)-7,8-dihydro-8H-purin-8-one

I-320

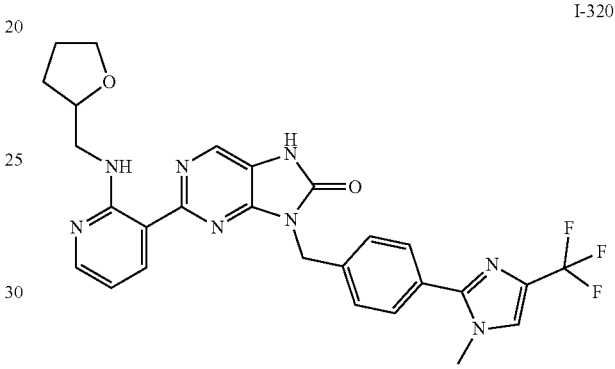

8-(4-(1-methyl-4-(trifluoromethyl)-1H-imidazol-2-
yl)benzyl)-2-(2-(((tetrahydrofuran-2-yl)methyl)amino)pyridin-
3-yl)-7,9-dihydro-8H-purin-8-one

I-321

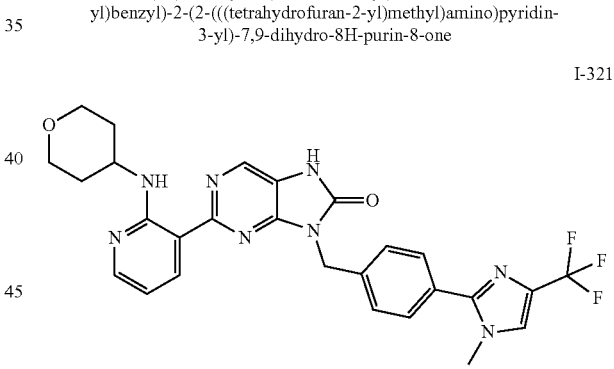

8-(4-(1-methyl-4-(trifluoromethyl)-1H-imidazol-2-
yl)benzyl)-2-(2-((tetrahydro-2H-pyran-4-yl)amino)pyridin-
3-yl)-7,8-dihydro-8H-purin-8-one

I-322

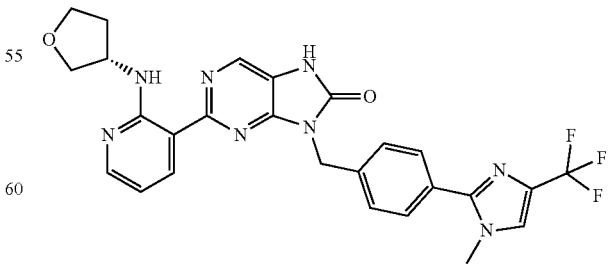

(S)-8-(4-(1-methyl-4-(trifluoromethyl)-1H-imidazol-2-
yl)benzyl)-2-(2-((tetrahydrofuran-3-yl)amino)pyridin-
3-yl)-7,9-dihydro-8H-purin-8-one

I-323

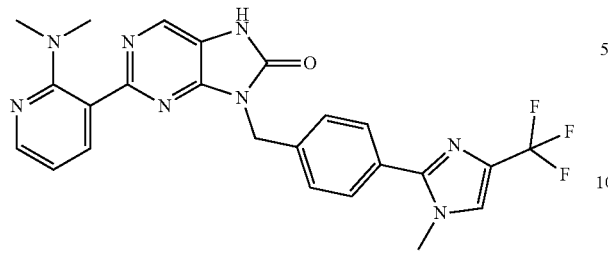

2-(2-dimethylaminopyridin-3-yl)-8-(4-(1-
methyl-4-(trifluoromethyl)-1H-imidazol-2-yl)benzyl)-
7,9-dihydro-8H-purin-8-one

I-324

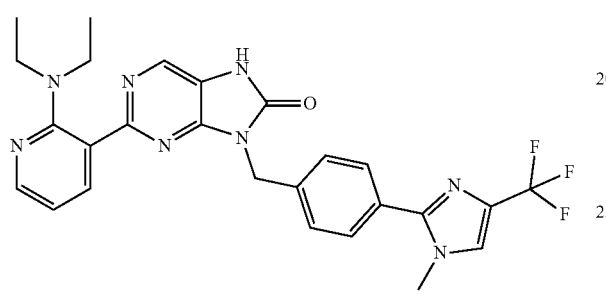

2-(2-diethylaminopyridin-3-yl)-8-(4-(1-
methyl-4-(trifluoromethyl)-1H-imidazol-2-yl)benzyl)-
7,9-dihydro-8H-purin-8-one

I-325

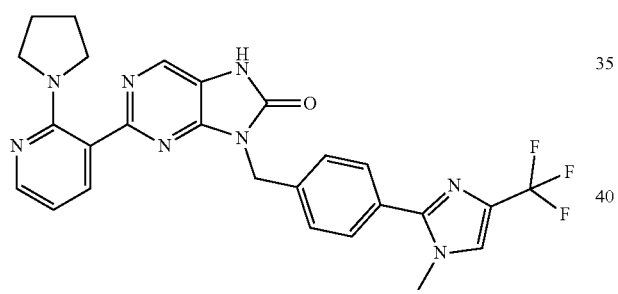

9-(4-(1-methyl-4-(trifluoromethyl)-1H-imidazol-
2-yl)benzyl)-2-(2-(pyrrolidin-1-yl)pyridin-3-yl)-
7,9-dihydro-8H-purin-8-one

I-326

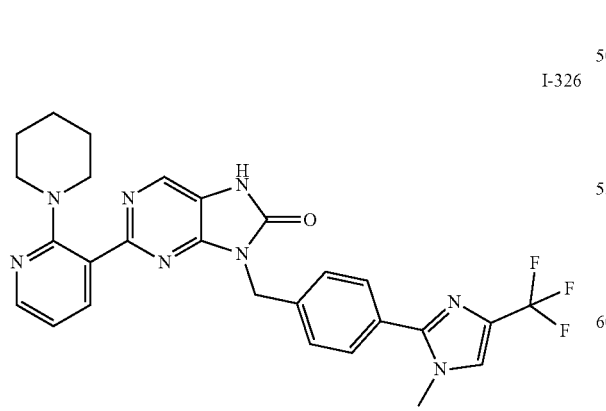

9-(4-(1-methyl-4-(trifluoromethyl)-1H-imidazol-
2-yl)benzyl)-2-(2-(piperidin-1-yl)pyridin-3-yl)-
7,9-dihydro-8H-purin-8-one

I-327

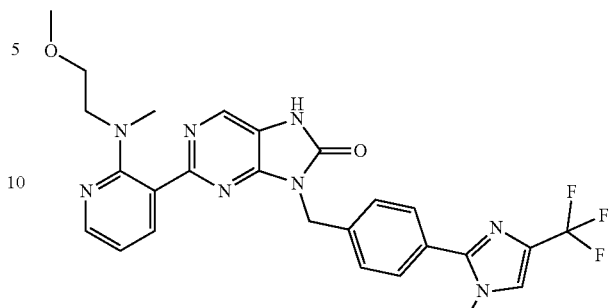

2-(2-(((2-methoxyethyl)(methylamino)pyridin-3-
yl)-9-(4-(1-methyl-4-(trifluoromethyl)-1H-imidazol-
2-yl)benzyl)-7,9-dihydro-8H-purin-8-one

I-328

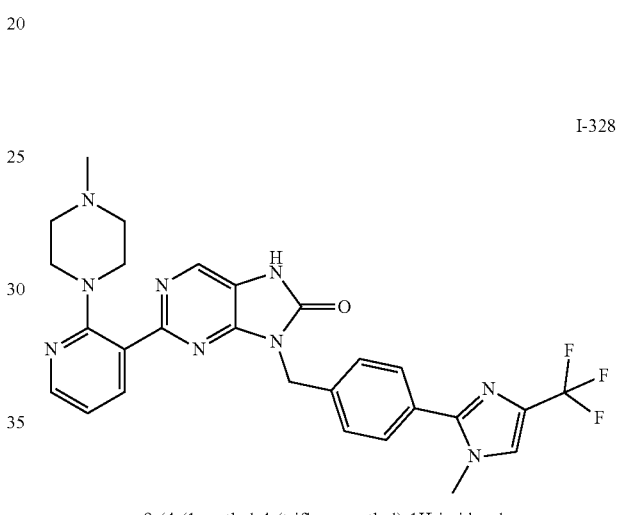

9-(4-(1-methyl-4-(trifluoromethyl)-1H-imidazol-
2-yl)benzyl)-2-(2-(4-methylpiperazin-1-yl)pyridin-
3-yl)-7,8-dihydro-8H-purin-8-one

I-329

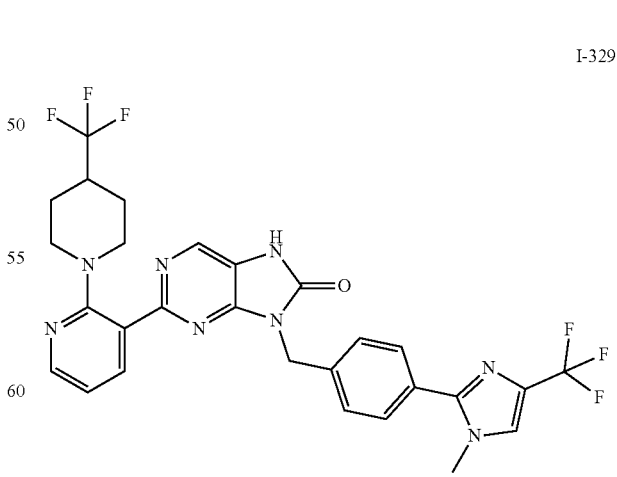

9-(4-(1-methyl-4-(trifluoromethyl)-1H-imidazol-
2-yl)benzyl)-2-(2-(4-(trifluoromethyl)piperadin-1-
yl)pyridin-3-yl)-7,8-dihydro-8H-purin-8-one

I-330

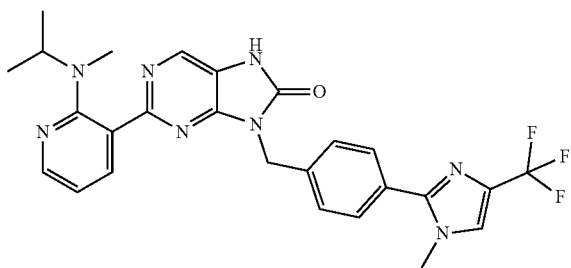

2-(2-(isopropyl)methylamino)pyridin-3-yl)-9-
(4-(1-methyl-4-trifluoromethyl)-1H-imidazol-2-yl)benzyl)-
7,9-dihydro-8H-purin-8-one

I-331

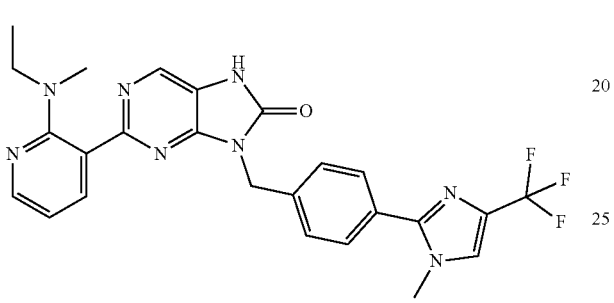

2-(2-(ethyl(methyl)amino)pyridin-3-yl)-9-(4-
(1-methyl-4-(trifluoromethyl)-1H-imidazol-2-yl)benzyl)-
7,9-dihydro-8H-purin-8-one

I-332

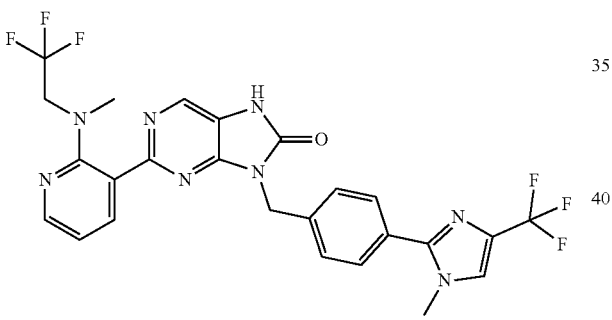

2-(2-(methyl(2,2,2-trifluoroethyl)amino)pyridin-
3-yl)-9-(4-(1-methyl-4-(trifluoromethyl)-1H-imidazol-
2-yl)benzyl)-7,9-dihydro-8H-purin-8-one

I-333

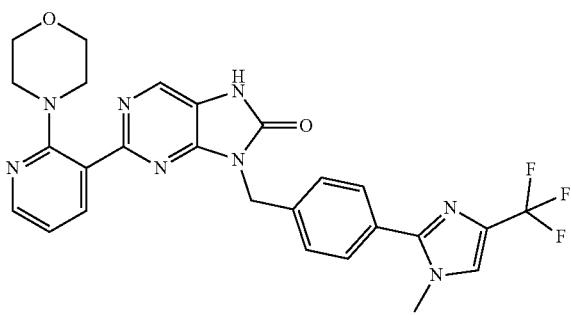

9-(4-(1-methyl-4-(trifluoromethyl)-1H-imidazol-2-yl)benzyl)-
2-(2-morpholinopyridin-3-yl)-7,9-dihydro-8H-purin-8-one

I-334

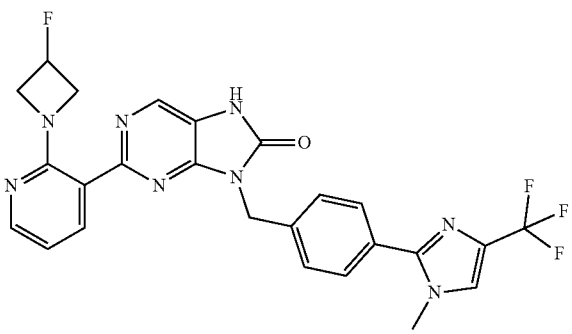

2-(2-(3-fluoroazetidin-1-yl)pyridin-3-yl)-9-
(4-(1-methyl-4-(trifluoromethyl)-1H-imidazol-2-yl)benzyl)-
7,9-dihydro-8H-purin-8-one

I-335

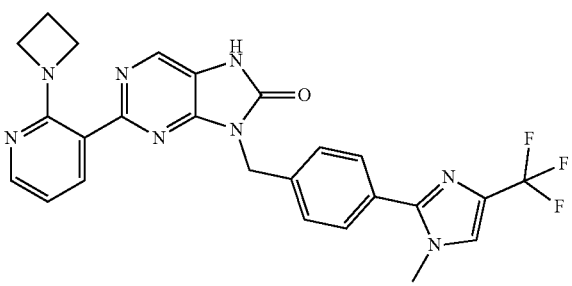

2-(2-(azetidin-1-yl)pyridin-3-yl)-9-(4-(1-
methyl-4-(trifluoromethyl)-1H-imidazol-2-yl)benzyl)-
7,9-dihydro-8H-purin-8-one

I-336

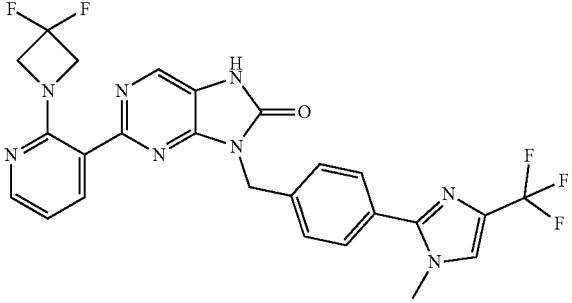

2-(2-(3,3-difluoroazetidin-1-yl)pyridin-3-yl)-9-
(4-(1-methyl-4-(trifluoromethyl)-1H-imidazol-2-yl)benzyl)-
7,9-dihydro-8H-purin-8-one

I-337

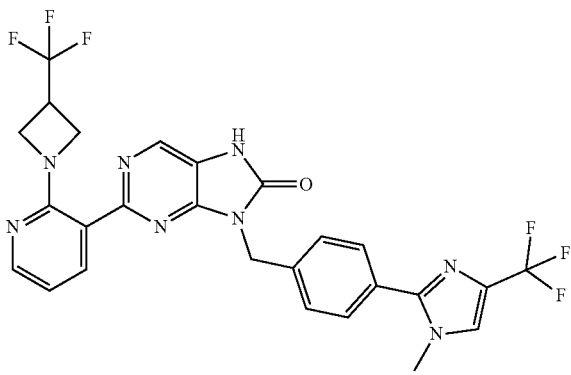

9-(4-(1-methyl-4-(trifluoromethyl)-1H-imidazol-
2-yl)benzyl)-2-(2-(3-(trifluoromethyl)azetidin-1-
yl)pyridin-3-yl)-7,9-dihydro-8H-purin-8-one

I-338

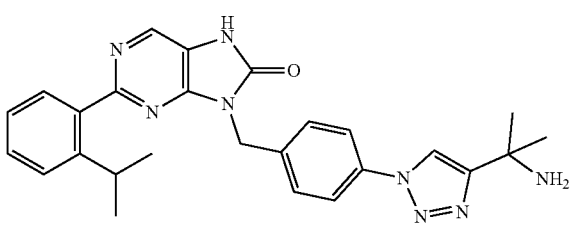

9-(4-(4-(2-aminopropan-2-yl)-1H-1,2,3-triazol-
1-yl)benzyl)-2-(2-isopropylphenyl)-7,9-dihydro-8H-purin-8-one

I-339

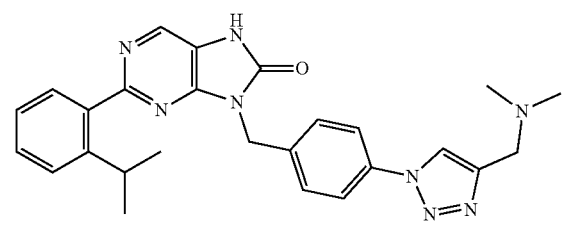

9-(4-(4-((dimethylamino)methyl)-1H-1,2,3-triazol-
1-yl)benzyl)-2-(2-isopropylphenyl)-7,9-dihydro-8H-purin-8-one

I-340

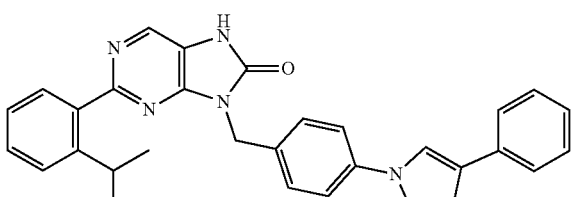

2-(2-isopropylphenyl)-9-(4-(4-phenyl-1H-1,2,3-triazol-
1-yl)benzyl)-7,9-dihydro-8H-purin-8-one

I-341

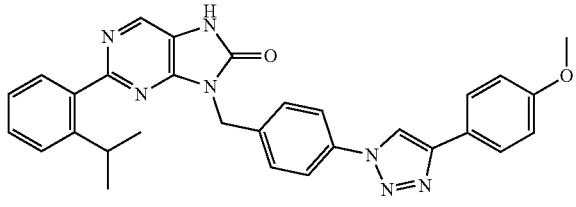

2-(2-isopropylphenyl)-9-(4-(4-(4-methoxyphenyl)-
1H-1,2,3-triazol-1-yl)benzyl)-7,9-dihydro-8H-purin-8-one

I-342

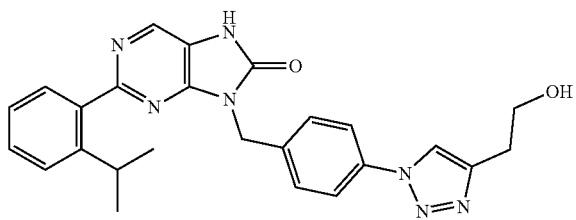

9-(4-(4-(2-hydroxyethyl)-1H-1,2,3-triazol-1-yl)benzyl)-2-
(2-isopropylphenyl)-7,9-dihydro-8H-purin-8-one

I-343

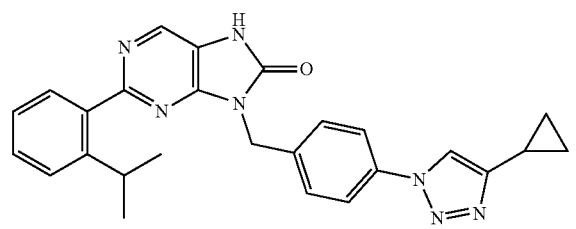

9-(4-(4-cyclopropyl)-1H-1,2,3-triazol-1-yl)benzyl)-2-
(2-isopropylphenyl)-7,8-dihydro-8H-purin-8-one

I-344

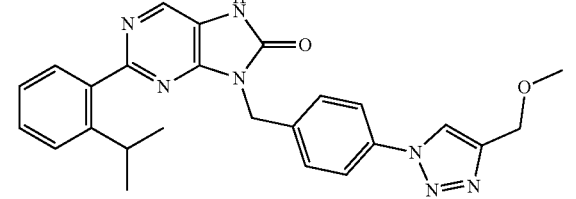

2-(2-isopropylphenyl)-8-(4-(4-(methoxymethyl)-
1H-1,2,3-triazol-1-yl)benzyl)-7,8-dihydro-8H-purin-8-one

I-345

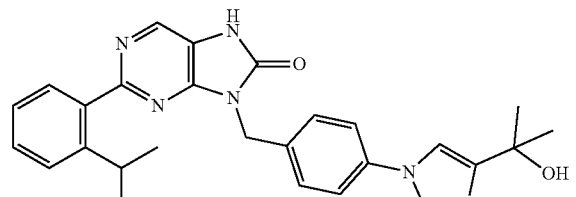

8-(4-(4-(2-hydroxypropan-2-yl)-1H-1,2,3-triazol-1-yl)benzyl)-2-
(2-isopropylphenyl)-7,8-dihydro-8H-purin-8-one

I-346

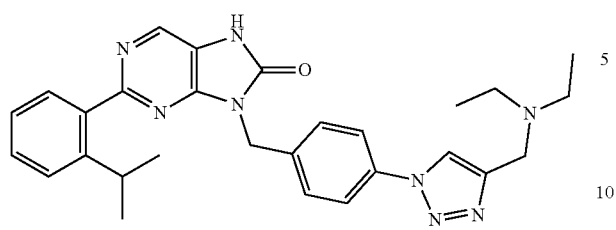

9-(4-(4-((diethylamino)methyl)-1H-1,2,3-triazol-1-yl)benzyl-2-(2-isopropylphenyl)-7,8-dihydro-8H-purin-8-one

I-347

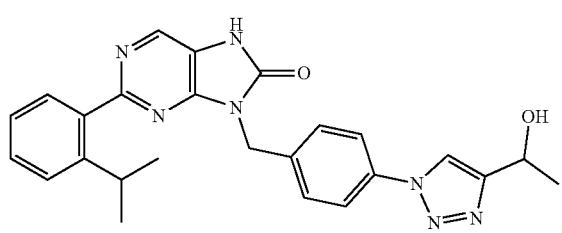

(R)-8-(4-(4-(1-hydroxyethyl)-1H-1,2,3-triazol-1-yl)benzyl)-2-(2-isopropylphenyl)-7,9-dihydro-8H-purin-8-one

I-348

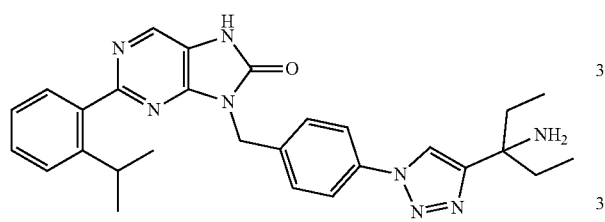

8-(4-(4-(3-aminopentan-3-yl)-1H-1,2,3-triazol-1-yl)benzyl)-2-(2-isopropylphenyl)-7,9-dihydro-8H-purin-8-one

I-349

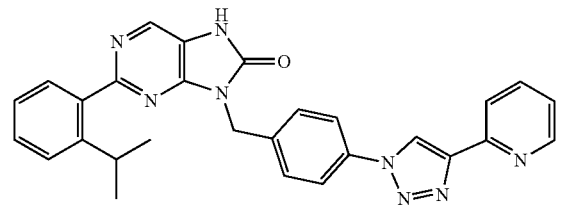

2-(2-isopropylphenyl)-9-(4-(4-(pyridin-2-yl)-1H-1,2,3-triazol-1-yl)benzyl)-7,9-dihydro-8H-purin-8-one

I-350

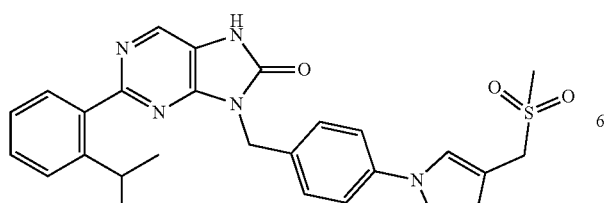

2-(2-isopropylphenyl)-9-(4-(4-((methylsulfonyl)methyl)-1H-1,2,3-triazol-1-yl)benzyl)-7,8-dihydro-8H-purin-8-one

I-351

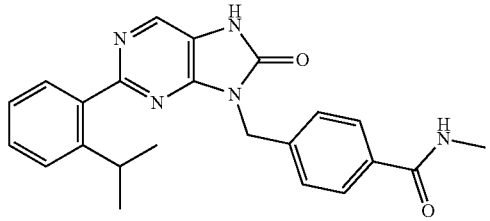

4-((2-(2-isopropylphenyl)-8-oxo-7,8-dihydro-9H-purin-8-yl)methyl)-N-methylbenzamide

I-352

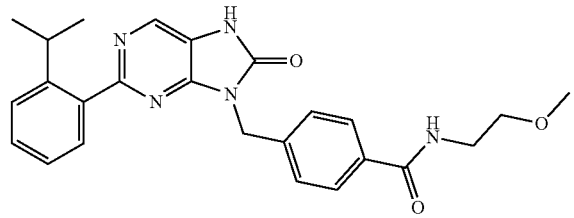

4-((2-(2-isopropylphenyl)-8-oxo-7,8-dihydro-9H-purin-8-yl)methyl)-N-(2-methylethyl)benzamide

I-353

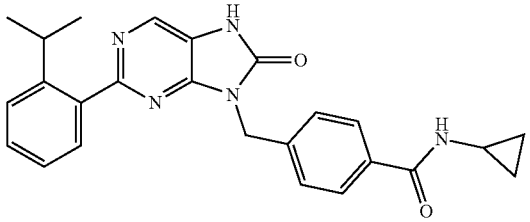

N-cyclopropyl-4-((2-(2-isopropylphenyl)-8-oxo-7,8-dihydro-9H-purin-8-yl)methyl)benzamide

I-354

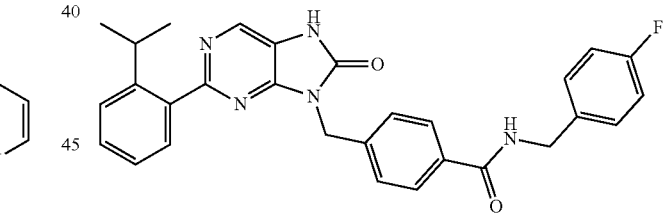

N-(4-fluorobenzyl)-4-((2-(2-isopropylphenyl)-8-oxo-7,8-dihydro-9H-purin-8-yl)methyl)benzamide

I-355

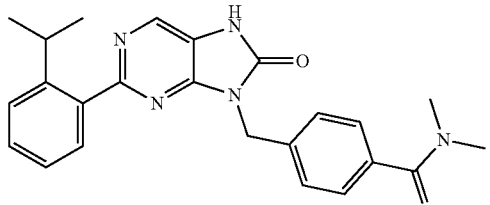

4-((2-(2-isopropylphenyl)-8-oxo-7,8-dihydro-8H-purin-8-yl)methyl)-N,N-dimethylbenzamide

I-356

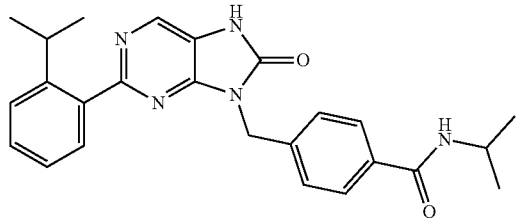

N-isopropyl-4-((2-(2-isopropylphenyl)-8-oxo-
7,8-dihydro-8H-purin-8-yl)methyl)benzamide

I-357

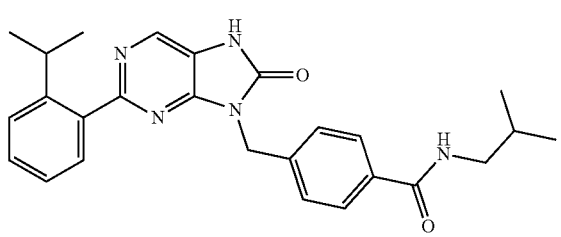

N-isopropyl-4-((2-(2-isopropylphenyl)-8-oxo-
7,8-dihydro-8H-purin-8-yl)methyl)benzamide

I-358

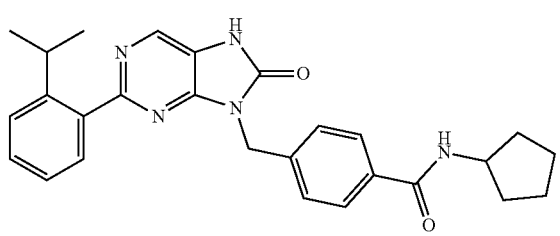

N-cyclopentyl-4-((2-(2-isopropylphenyl)-8-oxo-
7,8-dihydro-8H-purin-8-yl)methyl)benzamide

I-359

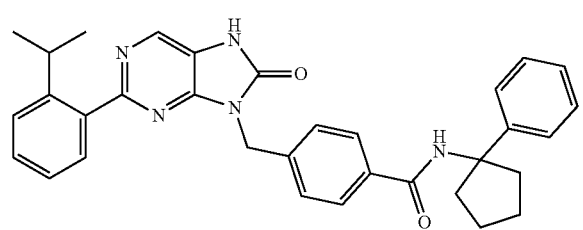

4-((2-(2-isopropylphenyl)-8-oxo-7,8-dihydro-9H-
purin-8-yl)methyl)-N-(1-phenylcyclopentyl)benzamide

I-360

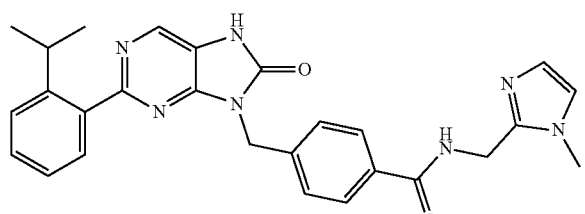

4-((2-(2-isopropylphenyl)-8-oxo-7,8-dihydro-8H-
purin-8-yl)methyl)-N-((1-methyl-1H-imidazol-2-yl)methyl)benzamide

I-361

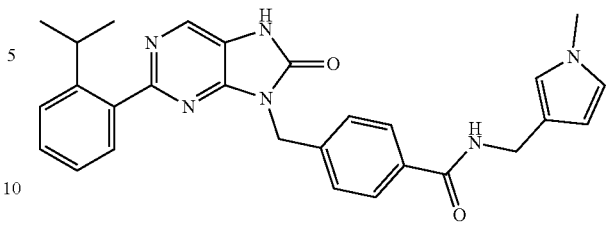

4-((2-(2-isopropylphenyl)-8-oxo-7,8-dihydro-8H-
purin-8-yl)methyl)-N-((1-methyl-1H-pyrazol-4-yl)
methyl)benzamide

I-362

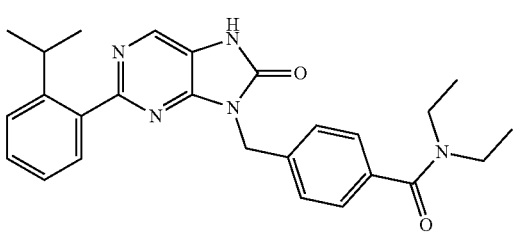

N,N-diethyl-4-((2-(2-isopropylphenyl)-8-oxo-
7,8-dihydro-8H-purin-8-yl)methyl))benzamide

I-363

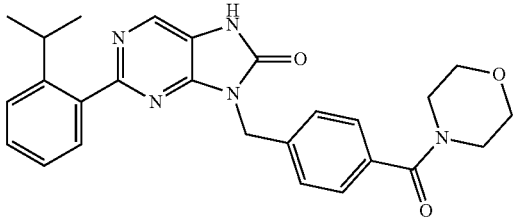

2-(2-isopropylphenyl)-8-(4-morpholine-4-carbomyl)benzyl)-
7,9-dihydro-8H-purin-8-one

I-364

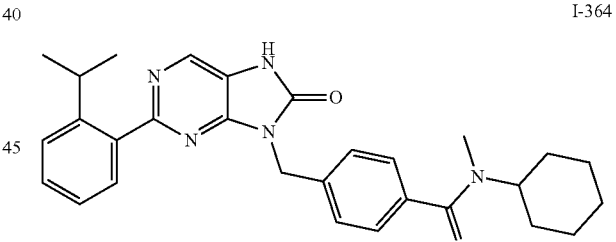

N-(4-fluorobenzyl)-4-((2-(2-isopropylphenyl)-
8-oxo-7,8-dihydro-8H-purin-9-yl)methyl)-N-methylbenzamide

I-365

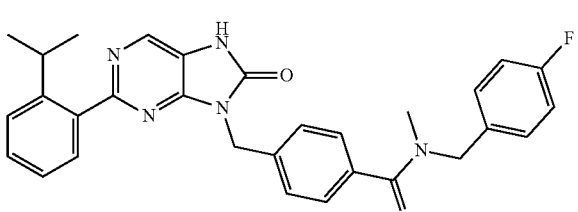

N-(4-fluorobenzyl)-4-((2-(2-isopropylphenyl)-
8-oxo-7,8-dihydro-8H-purin-9-yl)methyl)-N-methylbenzamide

I-366

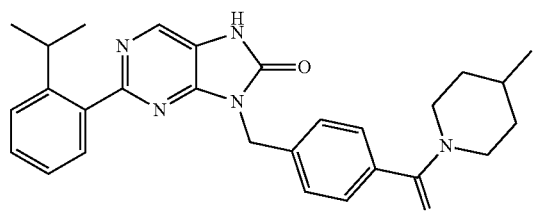

2-(2-isopropylphenyl)-8-(4-(4-methylpiperidine-1-carbonyl)benzyl)-7,9-dihydro-8H-purin-8-one

I-367

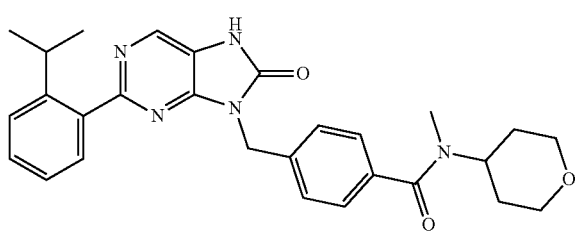

4-((2-(2-isopropylphenyl)-8-oxo-7,8-dihydro 9H-purin-9-yl)methyl)-N-(tetrahydro-2H-py 4-yl)benzamide

I-368

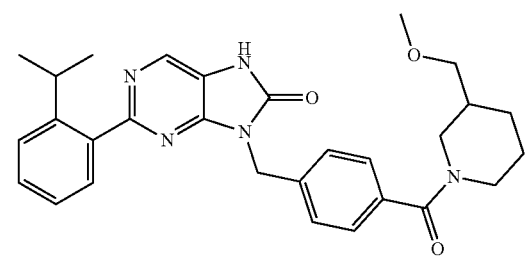

2-(2-isopropylphenyl)-8-(4-(3-(methoxymethylpiperidine-1-carbonyl)benzyl)-7,9-dihydro 8H-purin-8-one

I-369

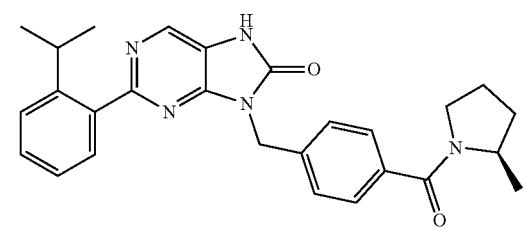

(R)-2-(2-isopropylphenyl)-8-(4-(2-methylpiperidine-1-carbonyl)benzyl)-7,9-dihydro 8H-purin-8-one

I-370

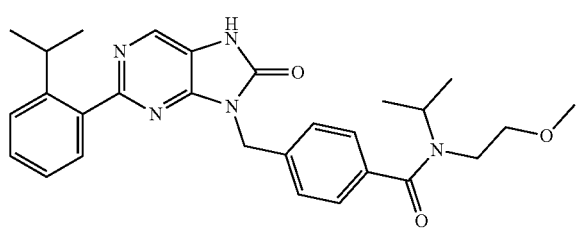

N-isopropyl-4-((2-(2-isopropylphenyl)-8-oxo-7,8-dihydro 8H-purin-8-yl)methyl)-N-(2-methoxyethy benzamide

I-371

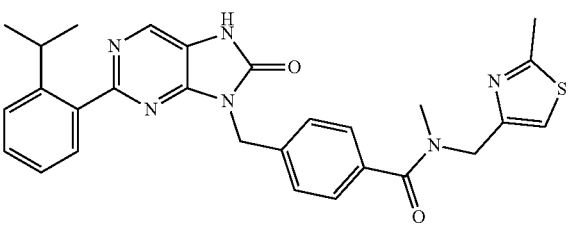

4-((2-(2-isopropylphenyl)-8-oxo-7,8-dihydro 9H-purin-9-yl)methyl)-N-methyl-N-((2-methylthiazol-4 yl)methyl)benzamide

I-372

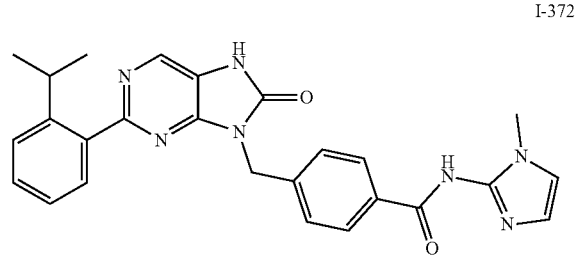

4-((2-(2-isopropylphenyl)-8-oxo-7,8-dihydro 8H-purin-8-yl)methyl)-N-(1-methyl-1H-imidazol-2-yl)benzamide

I-373

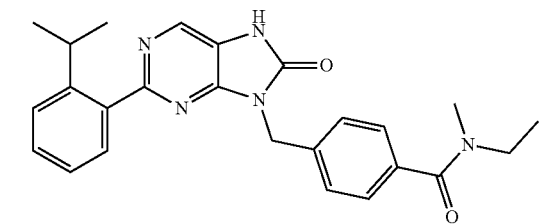

N-ethyl-4-((2-(2-isopropylphenyl)-8-oxo-7,8-dihydro-9H-purin-8-yl)methyl)-N-methylbenzamide

I-374

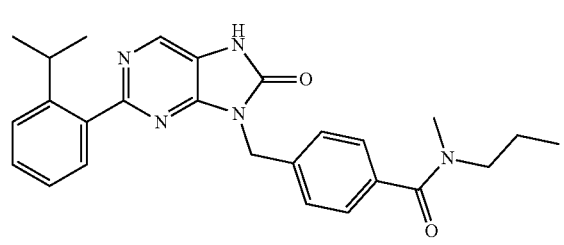

4-((2-(2-isopropylphenyl)-8-oxo-7,8-dihydro-9H-purin-8-yl)methyl)-N-methyl-N-propylbenzamide

I-375

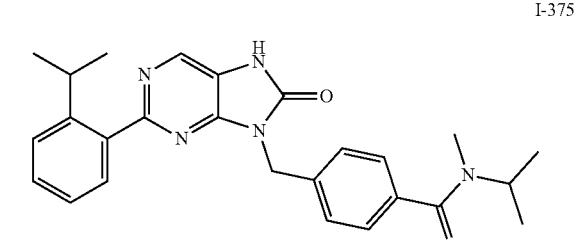

N-isopropyl-4-((2-(2-isopropylphenyl)-8-oxo-7,8-dihydro-9H-purin-8-yl)methyl)-N-methylbenzamide

I-376

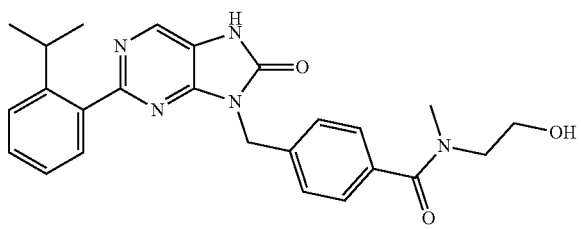

N-(2-hydroxyethyl)-4-((2-(2-isopropylphenyl)-8-oxo-7,8-dihydro-
8H-purin-8-yl)methyl)-N-methybenzamide

I-377

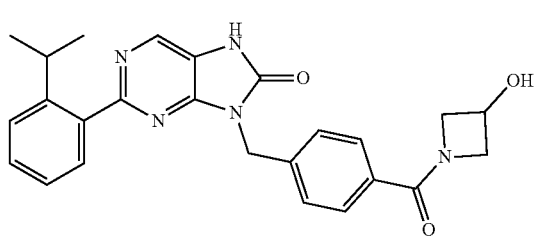

9-4-(3-hydroxyazetidine-1-carbonylbenzyl)-2-
(2-isopropylphenyl)-7,8-dihydro-8H-purin-8-one

I-378

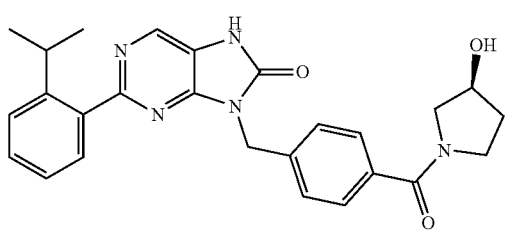

(S)-8-(4-(3-hydroxypyrrolidine-1-carbonylbenzyl)-2-
(2-isopropylphenyl)-7,8-dihydro-8H-purin-8-one

I-379

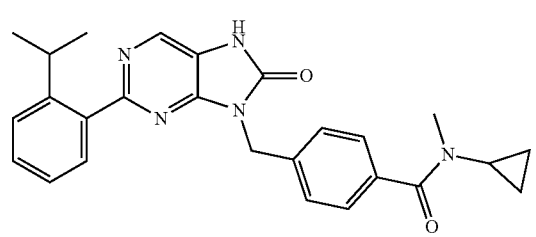

N-cyclopropyl-4-((2-(2-isopropylphenyl)-8-oxo-7,8-dihydro-
8H-purin-8-yl)methyl)-N-methylbenzamide

I-380

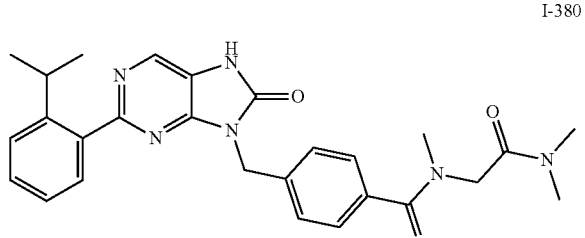

N-(2-(dimethylamino)-2-oxoethyl)-4-((2-(2-isopropylphenyl)-
8-oxo-7,8-dihydro-8H-purin-8-yl)methyl)-N-methylbenzamide

I-381

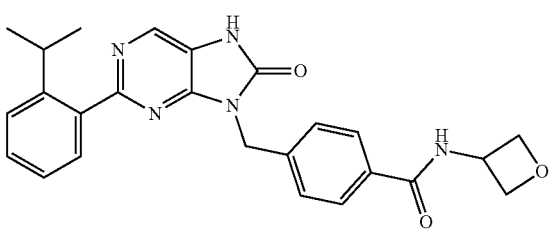

4-((2-(2-isopropylphenyl)-8-oxo-7,8-dihydro-
8H-purin-8-yl)methyl)-N-(oxetan-3-yl)benzamide

I-382

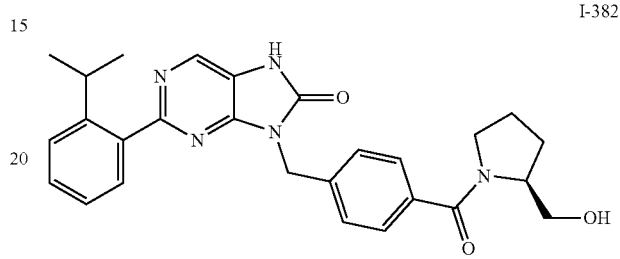

(S)-8-(4-(2-hydroxymethyl)pyrrolidine-1-carbonyl)benzyl)-2-
(2-isopropylphenyl)-7,8-dihydro-8H-purin-8-one

I-383

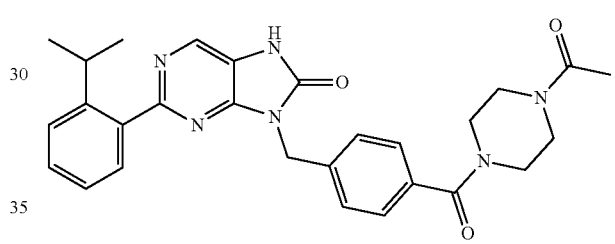

8-(4-(4-acetylpiperazine-1-carbonyl)benzyl)-2-
(2-isopropylphenyl)-7,8-dihydro-8H-purin-8-one

I-384

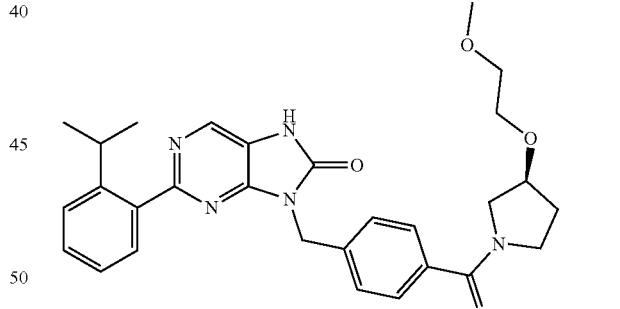

(S)-2-(2-isopropylphenyl)-9-(4-(3-(2-methoxyethoxy)pyrrolidine-
1-carbonyl)benzyl)-7,9-dihydro-8H-purin-8-one

I-385

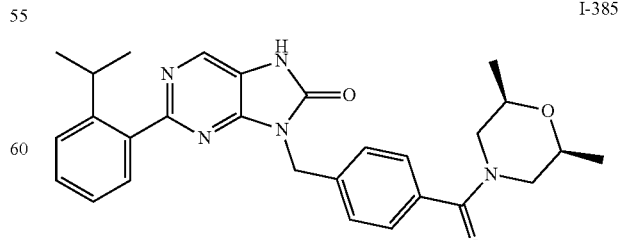

9-(4-((2R,6S), 2-5-dimethylmorphoine-4-carbonyl)benzyl)-2-
(2-isopropylphenyl)-7,8-dihydro-8H-purin-8-one

I-386

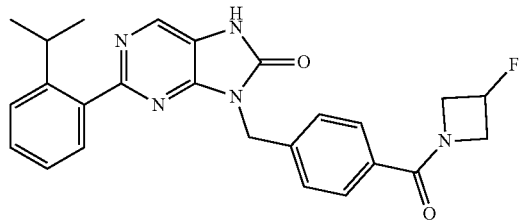

8-(4-(3-fluoroazetidine-1-carbonyl)benzyl)-2-
(2-isopropylphenyl)-7,8-dihydro-8H-purin-8-one

I-387

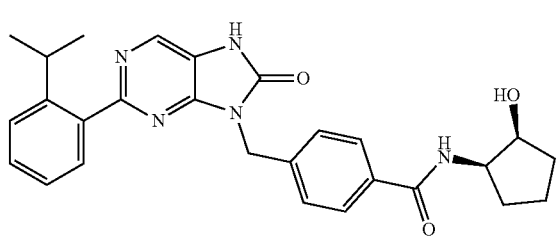

N-((1R,2S)-2-hydroxycyclopentyl)-4-((2-(2-isopropylphenyl)-
8-oxo-7,8-dihydro-8H-purin-8-yl)methyl)benzamide

I-388

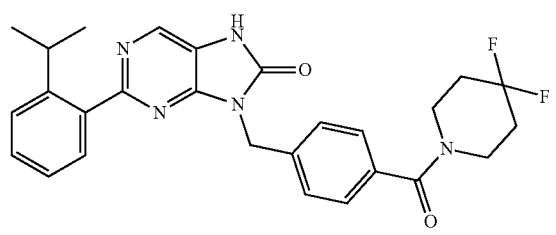

9-(4-(4,4-difluoropiperidine-1-carbonylbenzyl)-2-
(2-isopropylphenyl)-7,8-dihydro-8H-purin-8-one

I-389

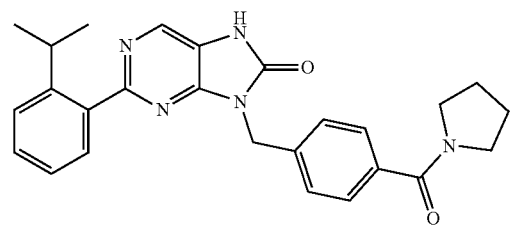

2-(2-isopropylphenyl)-8-(4-(pyrrolidine-1-carbonyl)benzyl)-
7,9-dihydro-8H-purin-8-one

I-390

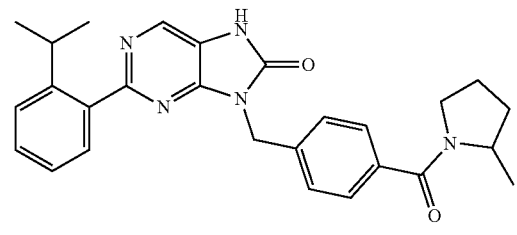

2-(2-isopropylphenyl)-8-(4-(2-methylpyrrolidine-1-carbonyl)benzyl)-
7,8-dihydro-8H-purin-8-one

I-391

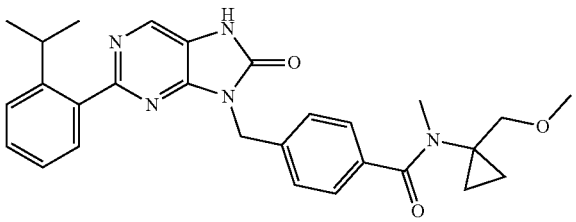

4-((2-(2-isopropylphenyl)-8-oxo-7,8-dihydro-9H-purin-9-yl)methyl-
N-(1-(methoxymethylcyclopropyl)-N-methylbenazmide

I-392

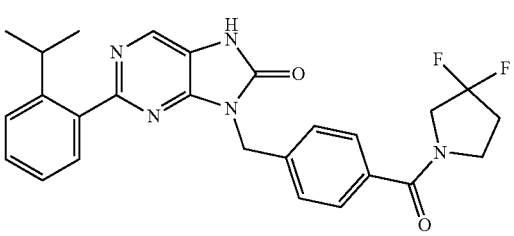

9-(4-(3,3-difluoropyrrolidine-1-carbonyl)benzyl)-
2-(2-isopropylphenyl)-7,9-dihydro-8H-purin-8-one

I-393

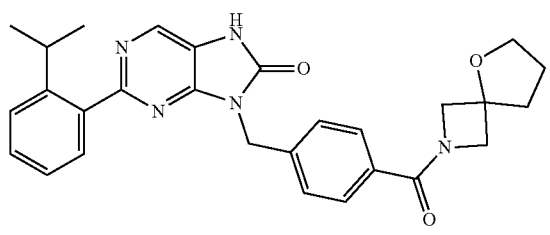

S-(4-(5-oxa-2-azaspiro[3,4]octane-2-carbonyl)benzyl)-
2-(2-isopropylphenyl)-7,9-dihydro-8H-purin-8-one

I-394

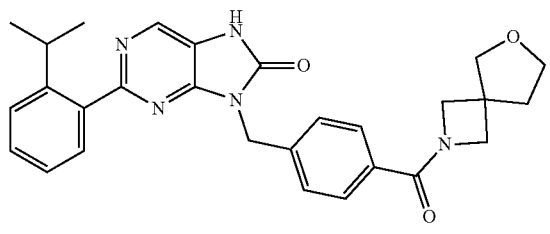

9-(4-(6-oxa-2-azaspiro[3,4]octane-2-carbonyl)benzyl)-
2-(2-isopropylphenyl)-7,9-dihydro-8H-purin-8-one

I-395

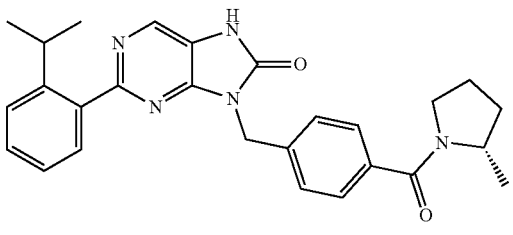

(S)-2-(2-isopropylphenyl)-8-(4-(2-methylpyrrolidine-
1-carbonyl)benzyl)-7,9-dihydro-8H-purin-8-one

I-396

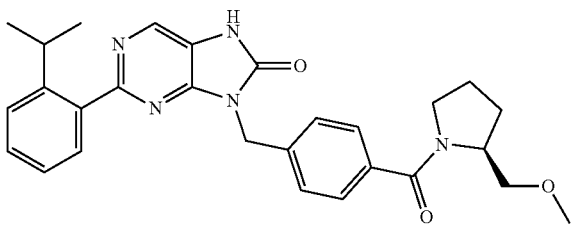

(S)-2-(2-isopropylphenyl)-8-(4-(2-methyl)pyrrolidine-
1-carbonyl)benzyl)-7,9-dihydro-8H-purin-8-one

I-397

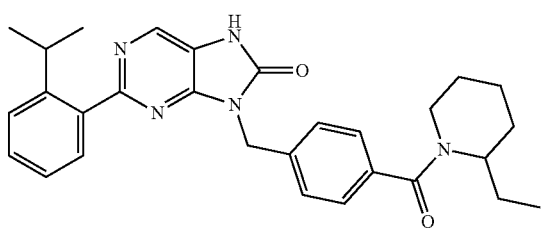

9-(4-(2-ethylpiperidine-1-carbonylbenzyl)-2-(2-isopropylphenyl)-
7,9-dihydro-8H-purin-8-one

I-398

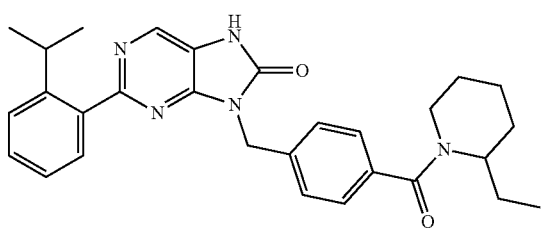

2-(2-isopropylphenyl)-9-(4-(2-methylpiperidine-1-
carbonyl)benzyl)-7,9-dihydro-8H-purin-8-one

I-399

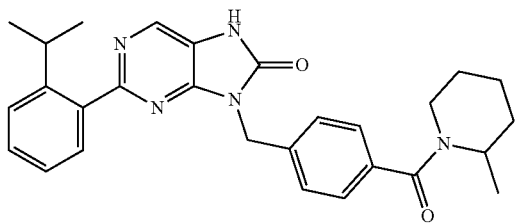

2-(2-isopropylphenyl)-9-(4-(3-methylpiperidine-1-
carbonyl)benzyl)-7,9-dihydro-8H-purin-8-one

I-400

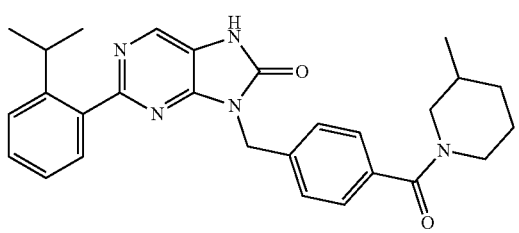

2-(2-isopropylphenyl)-9-(4-(2-methoxymethyl)piperidine-1-
carbonyl)benzyl)-7,8-dihydro-8H-purin-8-one

I-401

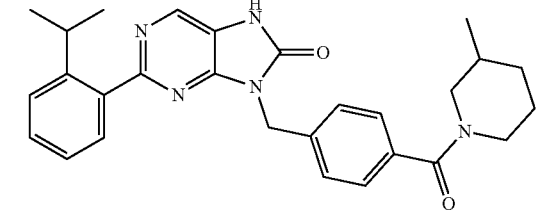

2-(2-isopropylphenyl)-8-(4-(3-methoxypiperidine-1-
carbonyl)benzyl)-7,8-dihydro-8H-purin-8-one

I-402

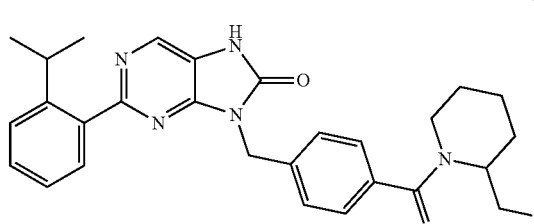

4-((2-(2-isopropylphenyl)-8-oxo-7,8-dihydro-9H-purin-8-yl)methyl)-N-
methyl-N-(tetrahydrofuran-3-yl)benzamide

I-403

(R)-2-(2-isopropylphenyl)-8-(4-(2-(methoxymethyl)pyrrolidine-
1-carbonyl)benzyl)-7,9-dihydro-8H-purin-8-one

I-404

(R)-2-(2-isopropylphenyl)-8-(4-(3-methylmorpholine-
4-carbonyl)benzyl)-7,8-dihydro-8H-purin-8-one

I-405

(S)-2-(2-isopropylphenyl)-8-(4-(3-methylmorpholine-
4-carbonyl)benzyl)-7,8-dihydro-8H-purin-8-one

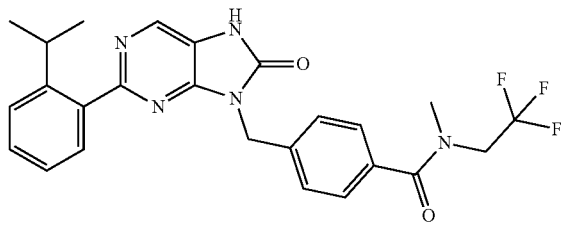

I-406

4-((2-(2-isopropylphenyl)-8-oxo-7,8-dihydro-8H-purin-8-yl)methyl)-N-methyl-N-(2,2,2-trifluoroethyl)benzamide

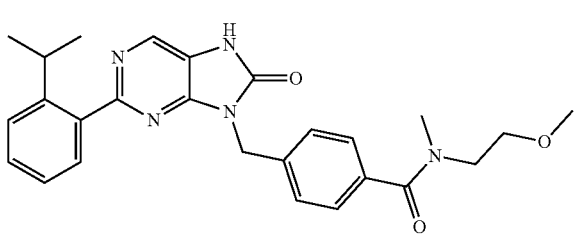

I-407

4-((2-(2-isopropylphenyl)-8-oxo-7,8-dihydro-8H-purin-8-yl)methyl)-N-(2-methoxyethyl)-N-methylbenzamide

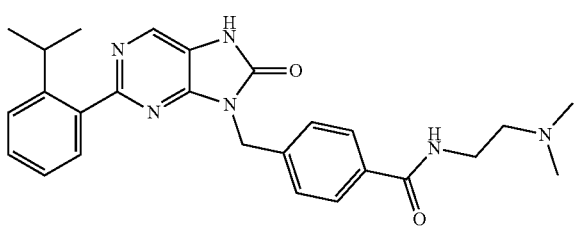

I-408

N-(2-(dimethylamino)ethyl)-4-((2-(2-isopropylphenyl)-8-oxo-7,8-dihydro-8H-purin-8-yl)methyl)benzamide

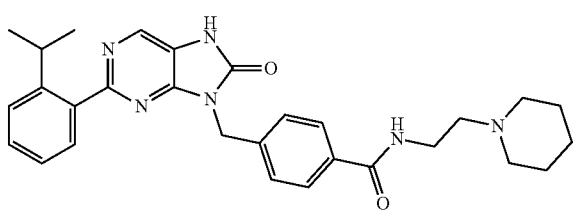

I-409

4-((2-(2-isopropylphenyl)-8-oxo-7,8-dihydro-8H-purin-8-yl)methyl)-N-(2-(piperidin-1-yl)ethyl)benzamide

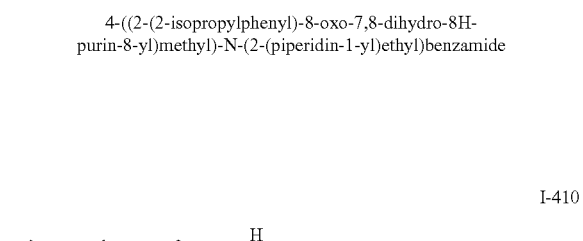

I-410

2-(2-isopropylphenyl)-8-(4-(4-methylpiperazine-1-carbonyl)benzyl)-7,8-dihydro-8H-purin-8-one

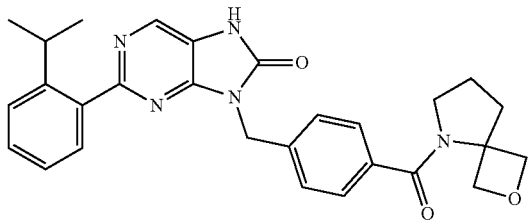

I-411

8-(4-(2-oxa-5-azaspiro[3,4]octane-5-carbonyl)benzyl)-2-(2-isopropylphenyl)-7,8-dihydro-8H-purin-8-one

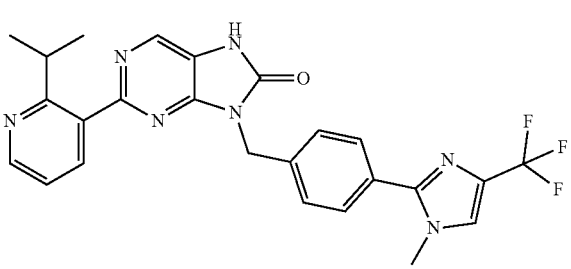

I-412

2-(2-methoxypyridin-3-yl)-8-(4-(1-methyl-4-(trifluoromethyl)-1H-imidazol-2-yl)benzyl)-7,8-dihydro-8H-purin-8-one

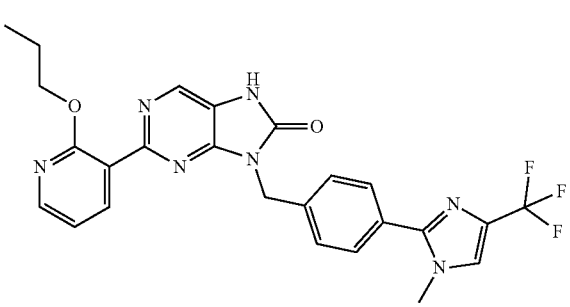

I-413

9-(4-(1-methyl-4-(trifluoromethyl)-1H-imidazol-2-yl)benzyl)-2-(2-propoxypyridin-3-yl)-7,8-dihydro-8H-purin-8-one

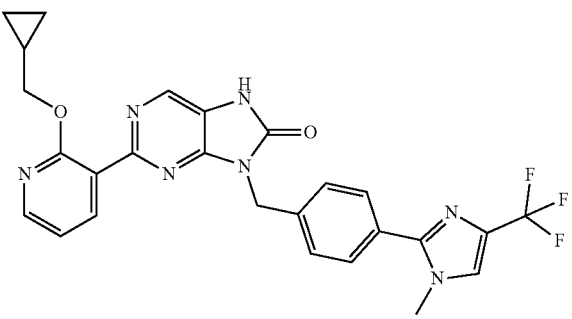

I-414

2-(2-cyclopropylmethoxypyridin-3-yl)-9-(4-(1-methyl-4-(trifluoromethyl)-1H-imidazol-2-yl)benzyl)-7,9-dihydro-8H-purin-8-one

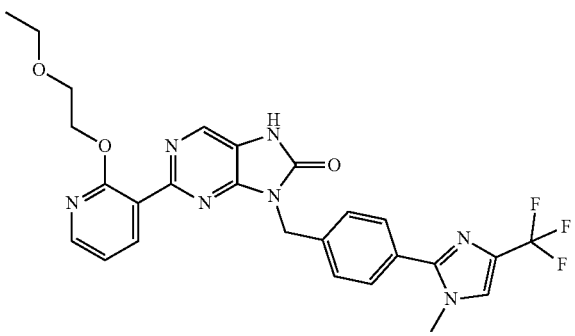

I-415

2-(2-(2-ethoxyethoxy)pyridin-3-yl)-9-(4-(1-methyl-4-
(trifluoromethyl)-1H-imidazol-2-yl)benzyl)-7,9-dihydro-8H-purin-8-one

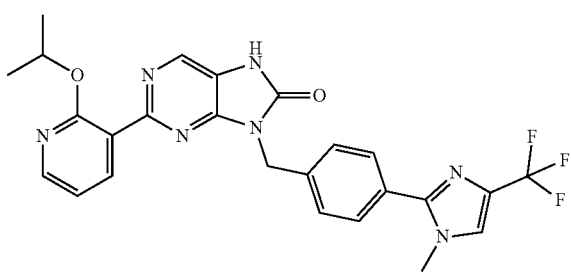

I-416

2-(2-isopropoxypyridin-3-yl)-8-(4-(1-methyl-4-(trifluoromethyl)-
1H-imidazol-2-yl)benzyl)-7,9-dihydro-8H-purin-8-one

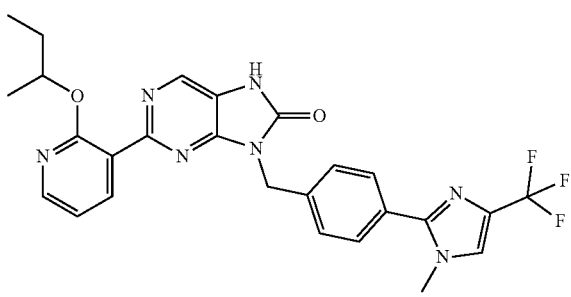

I-417

2-(2-azobutoxy)pyridin-3-yl)-8-(4-(1-methyl-4-(trifluoromethyl)-
1H-imidazol-2-yl)benzyl)-7,9-dihydro-8H-purin-8-one

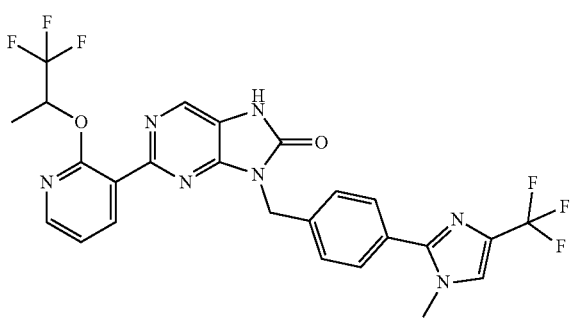

I-418

9-(4-(1-methyl-4-(trifluoromethyl)-1H-imidazol-2-yl)benzyl)-
2-(2-((1,1,1-trifluoropropan-2-yl)oxy)pyridin-
3-yl)-7,8-dihydro-8H-purin-8-one

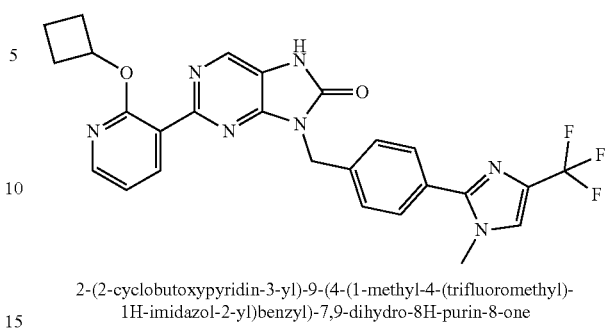

I-419

2-(2-cyclobutoxypyridin-3-yl)-9-(4-(1-methyl-4-(trifluoromethyl)-
1H-imidazol-2-yl)benzyl)-7,9-dihydro-8H-purin-8-one

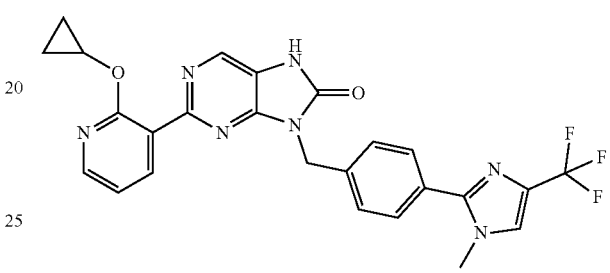

I-420

2-(2-cyclobutoxypyridin-3-yl)-9-(4-(1-methyl-4-(trifluoromethyl)-
1H-imidazol-2-yl)benzyl)-7,9-dihydro-8H-purin-8-one

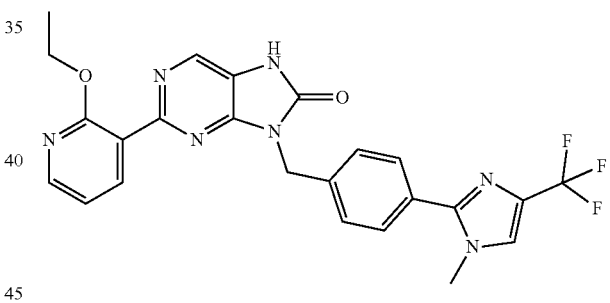

I-421

2-(2-ethoxypyridin-3-yl)-9-(4-(1-methyl-4-(trifluoromethyl)-
1H-imidazol-2-yl)benzyl)-7,9-dihydro-8H-purin-8-one

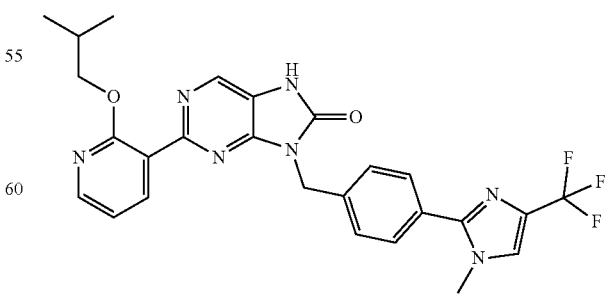

I-422

2-(2-isobutyoxypyridin-3-yl)-8-(4-(1-methyl-4-(trifluoromethyl)-
1H-imidazol-2-yl)benzyl)-7,8-dihydro-8H-purin-8-one

I-423

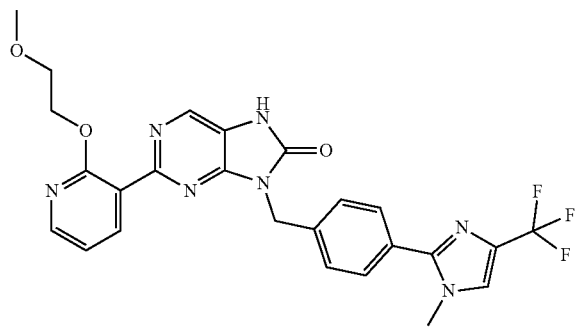

2-(2-(2-methoxyethoxy)pyridin-3-yl)-9-(4-(1-methyl-4-
(trifluoromethyl)-1H-imidazol-2-yl)benzyl)-
7,9-dihydro-8H-purin-8-one

I-424

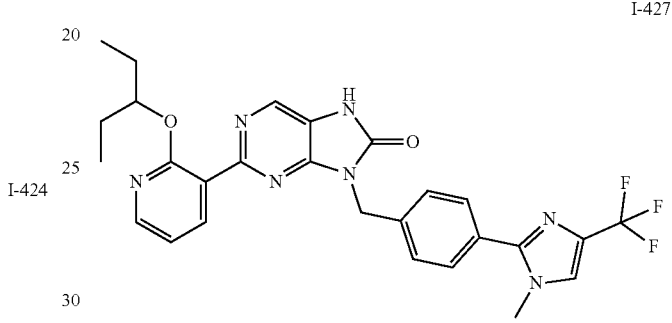

8-(4-(1-methyl-(4-(trifluoromethyl)-1H-imidazol-2-yl)benzyl)-
2-(2-((tetrahydrofuran-2-yl)methoxy)pyridin-3-yl)-
7,9-dihydro-8H-purin-8-one

I-425

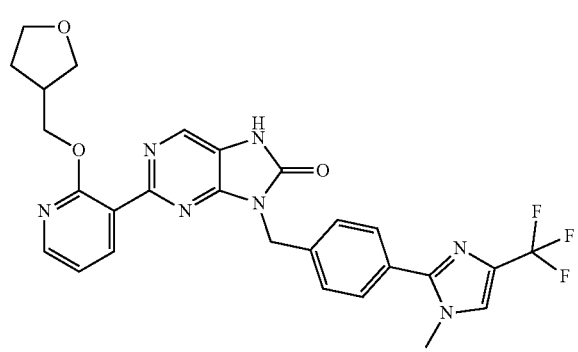

8-(4-(1-methyl-4-(trifluoromethyl)-1H-imidazol-2-yl)benzyl)-
2-(2-((tetrahydrofuran-3-yl)methoxy)pyridin-3-yl)-
7,9-dihydro-8H-purin-8-one

I-426

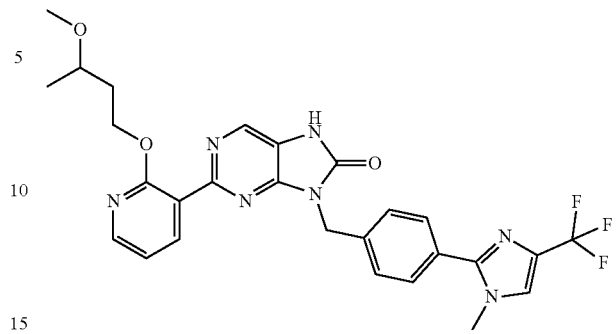

2-(2-(3-methoxybutoxy)pyridin-3-yl)-8-(4-(1-methyl-4-
(trifluoromethyl)-1H-imidazol-2-yl)benzyl)-
7,9-dihydro-8H-purin-8-one

I-427

8-(4-(1-methyl-4-(trifluoromethyl)-1H-imidazol-2-yl)benzyl)-
2-(2-pentan-3-yloxypyridin-3-yl)-7,8-dihydro-8H-purin-8-one

I-428

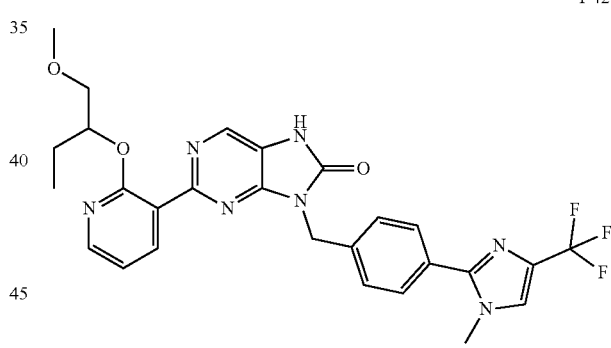

2-(2-((1-methoxybutan-2-yl)oxy)pyridin-3-yl)-8-(4-(1-methyl-4-
(trifluoromethyl)-1H-imidazol-2-yl)benzyl)-
7,9-dihydro-8H-purin-8-one

I-429

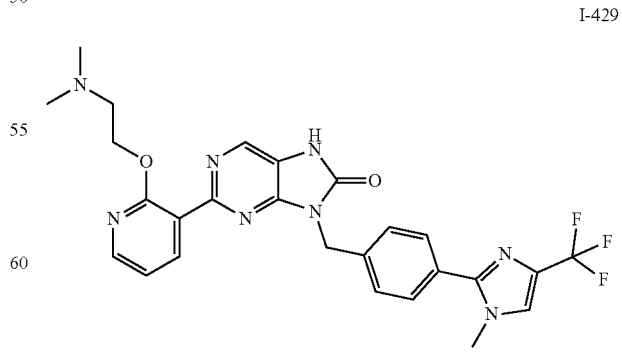

2-(2-(2-(dimethylamino)ethoxy)pyridin-3-yl)-8-(4-(1-methyl-4-
(trifluoromethyl)-1H-imidazol-2-yl)benzyl)-
7,9-dihydro-8H-purin-8-one

I-430

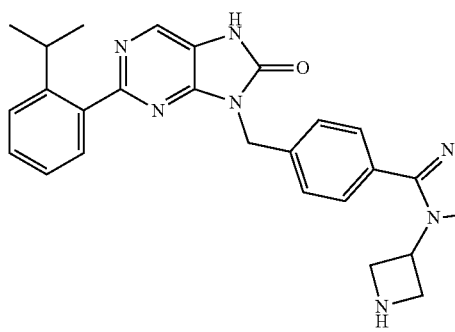

8-(4-(1-(azetidin-3-yl)-4-(trifluoromethyl)-1H-imidazol-2-yl)benzyl)-2-(2-isopropylphenyl)-7,9-dihydro-8H-purin-8-one

I-431

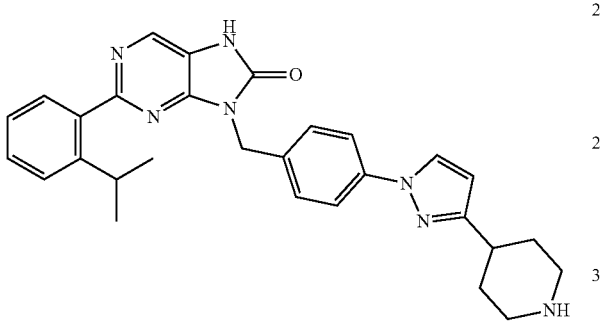

2-(2-isopropylphenyl)-9-(4-(3-(piperidin-4-yl)-1H-pyrazol-1-yl)benzyl)-7,9-dihydro-8H-purin-8-one

I-432

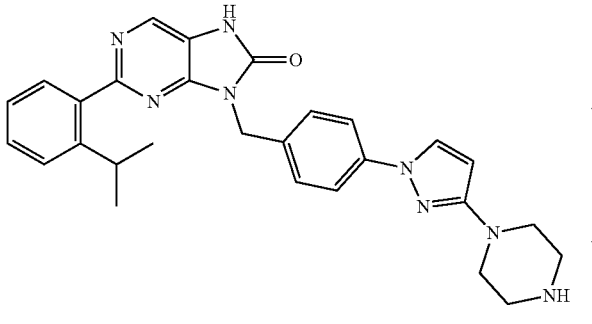

2-(2-isopropylphenyl)-8-(4-(3-(piperidin-1-yl)-1H-pyrazol-1-yl)benzyl)-7,9-dihydro-8H-purin-8-one

I-433

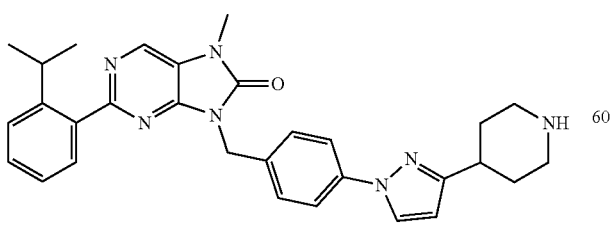

2-(2-isopropylphenyl)-7-methyl-8-(4-(3-(piperidin-4-yl)-1H-pyrazol-1-yl)benzyl)-7,9-dihydro-8H-purin-8-one

I-434

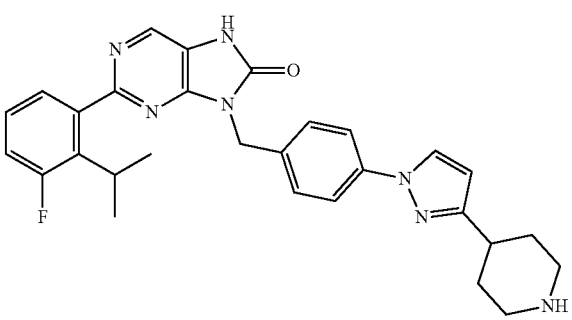

2-(3-fluoro-2-isopropylphenyl)-8-(4-(3-(piperidin-4-yl)-1H-pyrazol-1-yl)benzyl)-7,8-dihydro-8H-purin-8-one

I-435

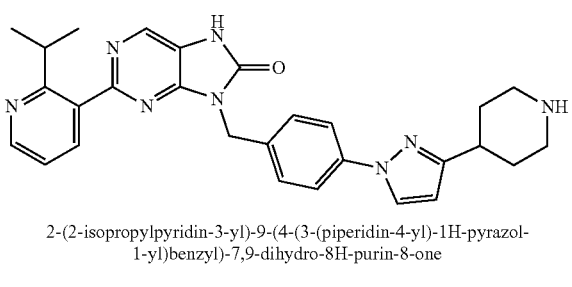

2-(2-isopropylpyridin-3-yl)-9-(4-(3-(piperidin-4-yl)-1H-pyrazol-1-yl)benzyl)-7,9-dihydro-8H-purin-8-one

I-436

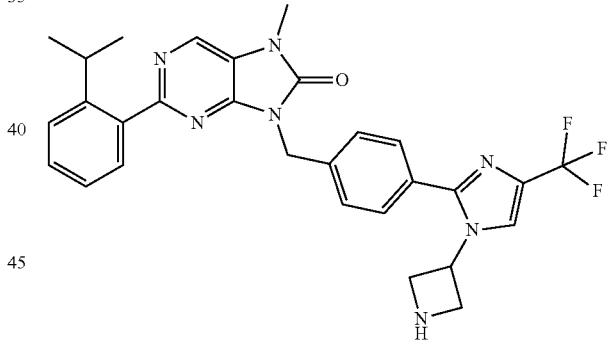

8-(4-(1-(azetidin-3-yl)-4-(trifluoromethyl)-1H-imidazol-2-yl)benzyl)-2-(2-isopropylphenyl)-7-methyl-7,9-dihydro-8H-purin-8-one

I-437

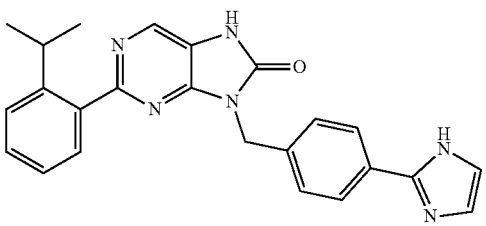

8-(4-(1H-imidazol-2-yl)benzyl)-2-(2-isopropylphenyl)-7,9-dihydro-8H-purin-8-one

I-438

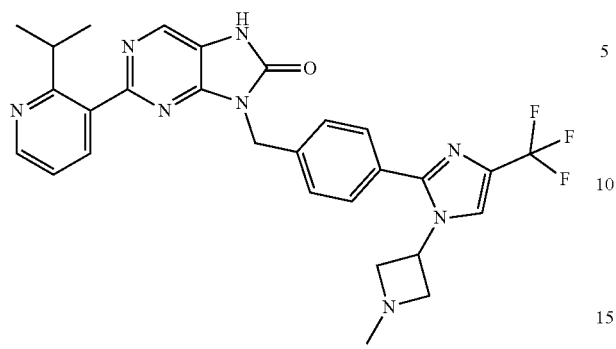

2-(2-isopropylpyridin-3-yl)-9-(4-(1-(1-methylazetidin-3-yl)-4-(trifluoromethyl)-1H-imidazol-2-yl)benzyl)-7,9-dihydro-8H-purin-8-one

I-439

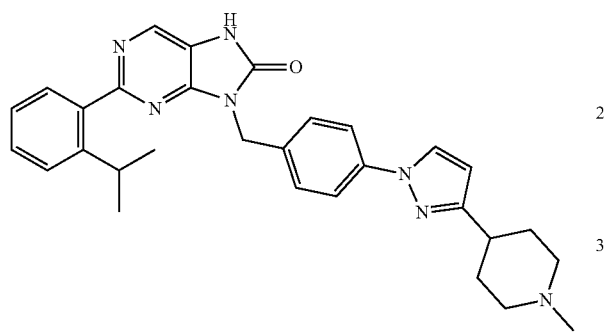

2-(2-isopropylphenyl)-8-(4-(3-(1-methyl)piperidin-4-yl)-1H-pyrazol-1-yl)benzyl)-7,9-dihydro-8H-purin-8-one

I-440

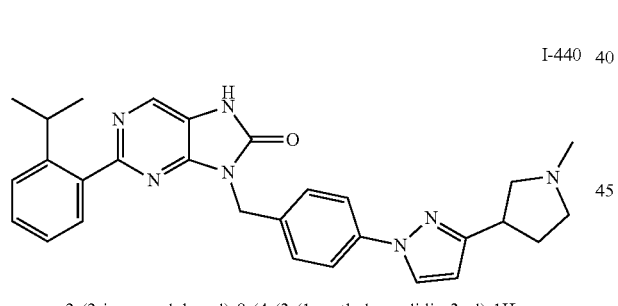

2-(2-isopropylphenyl)-8-(4-(3-(1-methylpyrrolidin-3-yl)-1H-pyrazol-1-yl)benzyl)-7,9-dihydro-8H-purin-8-one

I-441

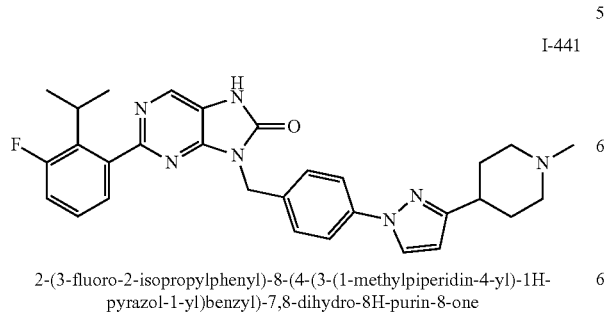

2-(3-fluoro-2-isopropylphenyl)-8-(4-(3-(1-methylpiperidin-4-yl)-1H-pyrazol-1-yl)benzyl)-7,8-dihydro-8H-purin-8-one

I-442

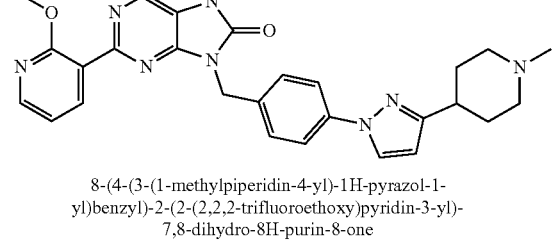

2-(2-isopropylpyridin-3-yl)-9-(4-(3-(1-methylpiperidin-4-yl)-1H-pyrazol-1-yl)benzyl)-7,8-dihydro-8H-purin-8-one

I-443

8-(4-(3-(1-methylpiperidin-4-yl)-1H-pyrazol-1-yl)benzyl)-2-(2-(2,2,2-trifluoroethoxy)pyridin-3-yl)-7,8-dihydro-8H-purin-8-one

I-444

2-(2-isopropylphenyl)-9-(4-(3-(1-methylpiperidin-3-yl)-1H-pyrazol-1-yl)benzyl)-7,9-dihydro-8H-purin-8-one

I-445

2-(2-isopropylphenyl)-9-(4-(1-methyl-4-(1-methylpiperidin-4-yl)-1H-imidazol-2-yl)benzyl)-7,9-dihydro-8H-purin-8-one

I-446

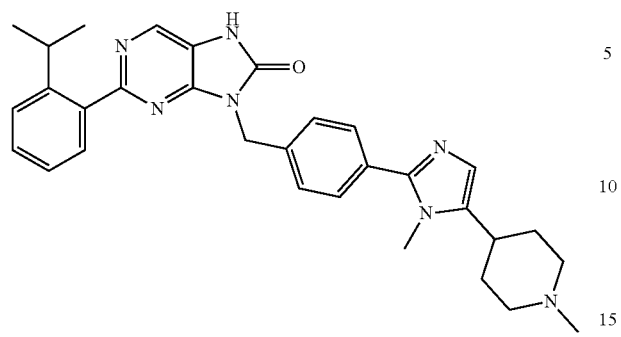

2-(2-isopropylphenyl)-9-(4-(1-methyl-5-(1-methylpiperidin-4-yl)-
1H-imidazol-2-yl)benzyl)-7,9-dihydro-8H-purin-8-one

I-447

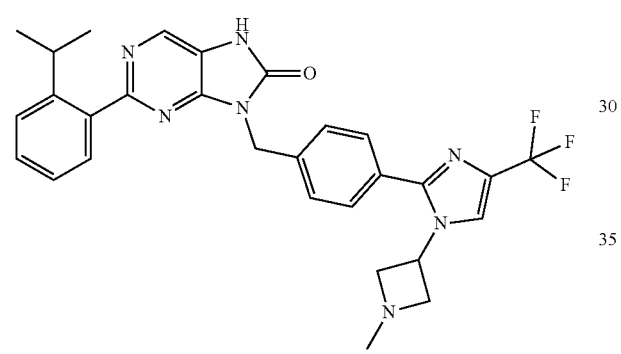

2-(2-isopropylphenyl)-9-(4-(1-(1-methylazetidin-3-yl)-4-
(trifluoromethyl)-1H-imidazol-2-yl)benzyl)-
7,8-dihydro-8H-purin-8-one

I-448

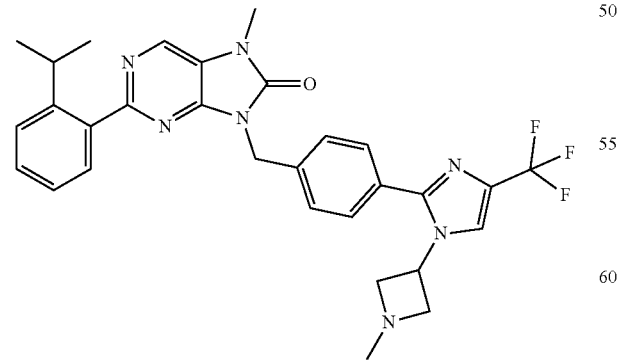

2-(2-isopropylphenyl)-7-methyl-8-(4-(1-(1-methylazetidin-3-yl)-4-
(trifluoromethyl)-1H-imidazol-2-yl)benzyl)-
7,9-dihydro-8H-purin-8-one

I-449

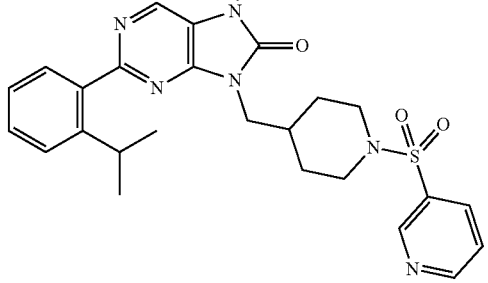

2-(2-isopropylphenyl)-7-methyl-8-((1-(pyridin-2-
ylsulfonyl)piperidin-4-yl)methyl)-7,9-dihydro-8H-purin-8-one

I-450

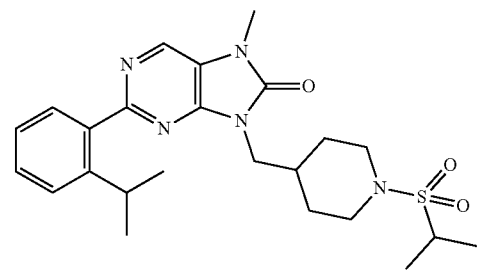

2-(2-isopropylphenyl)-8-((1-(isopropylsulfonyl)piperadin-
4-yl)methyl)-7-methyl-7,9-dihydro-8H-purin-8-one

I-451

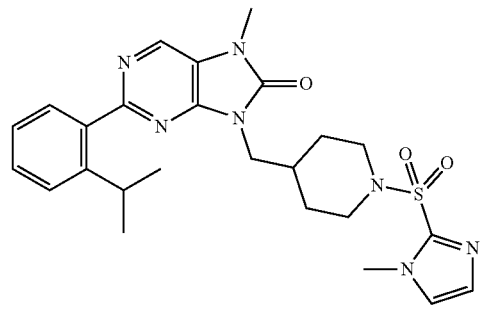

2-(2-isopropylphenyl)-7-methyl-8-((1-(((1-(methyl-1H-imidazol-2-
yl)sulfonyl)piperidin-4-yl)methyl)-7,9-dihydro-8H-purin-8-one

I-452

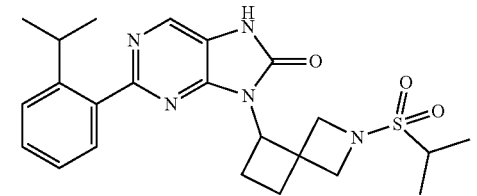

2-(2-isopropylphenyl)-9-(2-isopropylsulfonyl)-2-
azaspiro[3.3]heptan-5-yl)-7,9-dihydro-8H-purin-8-one

I-453

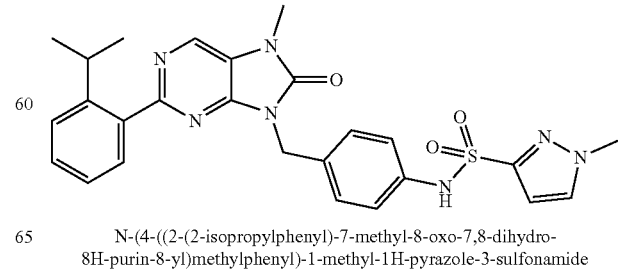

N-(4-((2-(2-isopropylphenyl)-7-methyl-8-oxo-7,8-dihydro-
8H-purin-8-yl)methylphenyl)-1-methyl-1H-pyrazole-3-sulfonamide

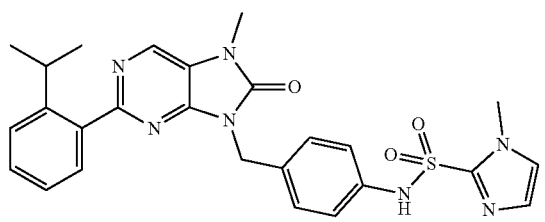

I-454

N-(4-((2-(2-isopropylphenyl)-7-methyl-8-oxo-7,8-dihydro-9H-purin-9-yl)methylphenyl)-1-methyl-1H-imidazole-2-sulfonamide

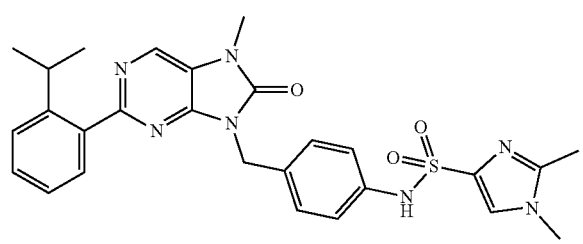

I-455

N-(4-((2-(2-isopropylphenyl)-7-methyl-8-oxo-7,8-dihydro-8H-purin-8-yl)methylphenyl)-1,2-dimethyl-1H-imidazole-4-sulfonamide

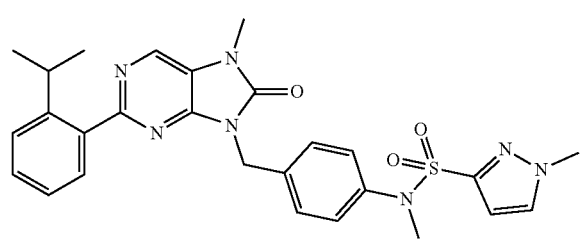

I-456

N-(4-((2-(2-isopropylphenyl)-7-methyl-8-oxo-7,8-dihydro-8H-purin-8-yl)methylphenyl)-N-1-dimethyl-1H-pyrazole-3-sulfonamide

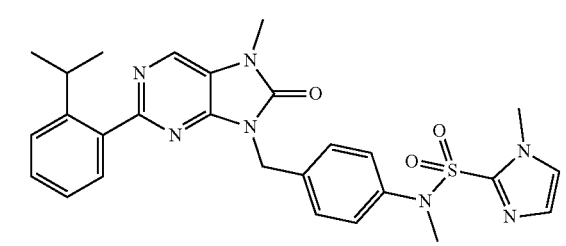

I-457

N-(4-((2-(2-isopropylphenyl)-7-methyl-8-oxo-7,8-dihydro-9H-purin-8-yl)methylphenyl)-N-1-dimethyl-1H-imidazole-sulfonamide

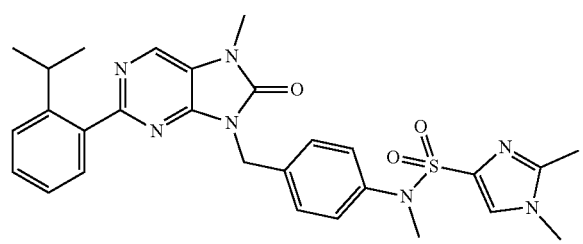

I-458

N-(4-((2-(2-isopropylphenyl)-7-methyl-8-oxo-7,8-dihydro-8H-purin-8-yl)methylphenyl)-N-1,2-trimethyl-1H-imidazole-4-sulfonamide

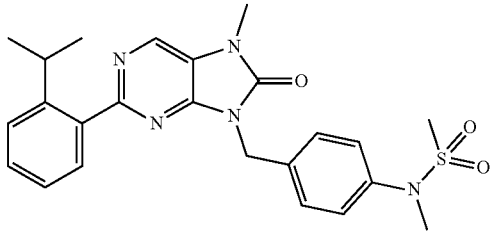

I-459

N-(4-((2-(2-isopropylphenyl)-7-methyl-8-oxo-7,8-dihydro-8H-purin-8-yl)methyl)phenyl)-N-methylmethanesulfonamide

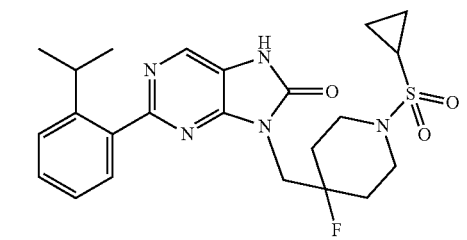

I-460

9-((1-(cyclopropylsulfonyl)-4-fluoropiperidin-4-yl)methyl)-2-(2-isopropylphenyl)-7,9-dihydro-8H-purin-8-one

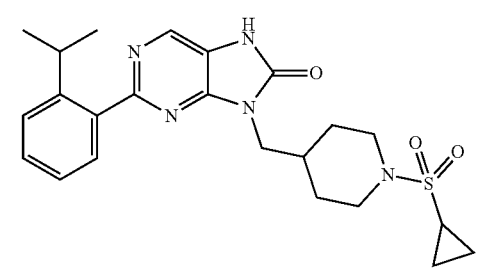

I-461

9-((1-(cyclopropylsulfonyl)piperidin-4-yl)methyl)-2-(2-isopropylphenyl)-7,8-dihydro-8H-purin-8-one

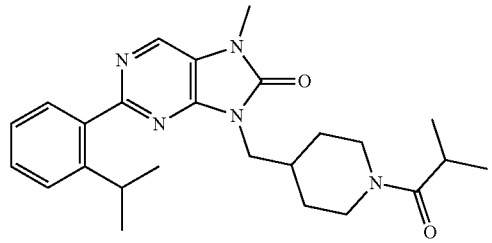

I-462

9-((1-(cyclopropylsulfonyl)piperidin-4-yl)methyl)-2-(2-isopropylphenyl)-7,8-dihydro-8H-purin-8-one

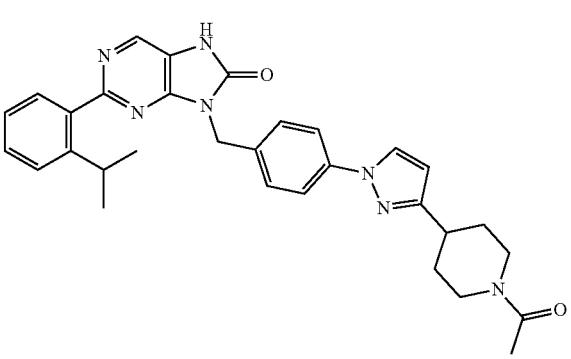

I-463

8-(4-(3-(1-acetylpiperidin-4-yl)-1H-pyrazol-1-yl)benzyl)-2-(2-isopropylphenyl)-7,9-dihydro-8H-purin-8-one

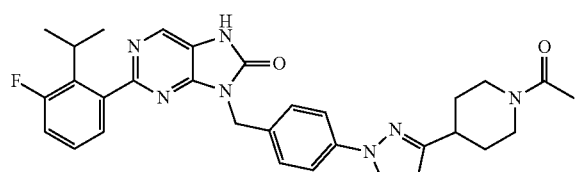

8-(4-(3-(1-acetylpiperidin-4-yl)-1H-pyrazol-1-yl)benzyl)-2-
(3-fluoro-2-isopropylphenyl)-7,8-dihydro-8H-purin-8-one

I-464

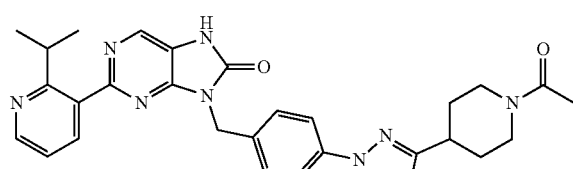

9-(4-(3-(1-acetylpiperidin-4-yl)-1H-pyrazol-1-yl)benzyl)-2-
(2-isopropylpyridin-3-yl)-7,9-dihydro-8H-purin-8-one

I-465

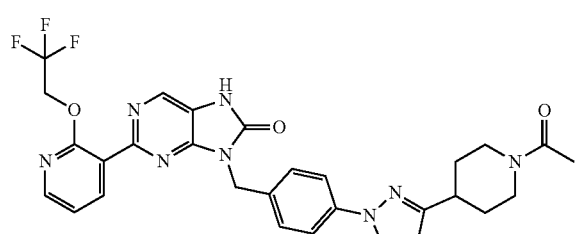

9-(4-(3-(1-acetylpiperidin-4-yl)-1H-pyrazol-1-yl)benzyl)-2-
(2-(2,2,2-trifluoroethoxy)pyridin-3-yl)-7,9-dihydro-8H-purin-8-one

I-466

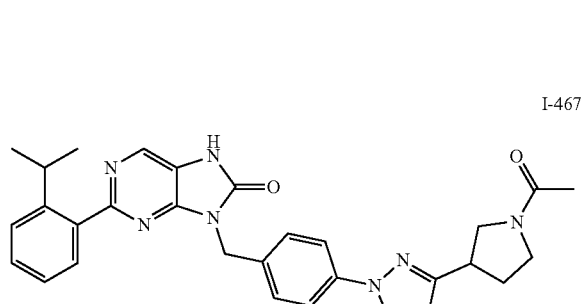

8-(4-(3-(1-acetylpyrrolidin-3-yl)-1H-pyrazol-1-yl)benzyl)-2-
(2-isopropylphenyl)-7,8-dihydro-8H-purin-8-one

I-467

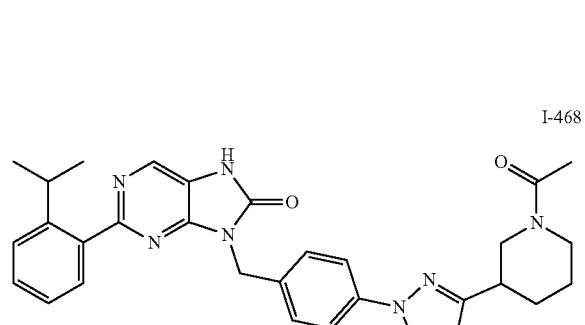

8-(4-(3-(1-acetylpiperidin-3-yl)-1H-pyrazol-1-yl)benzyl)-2-
(2-isopropylphenyl)-7,9-dihydro-8H-purin-8-one

I-468

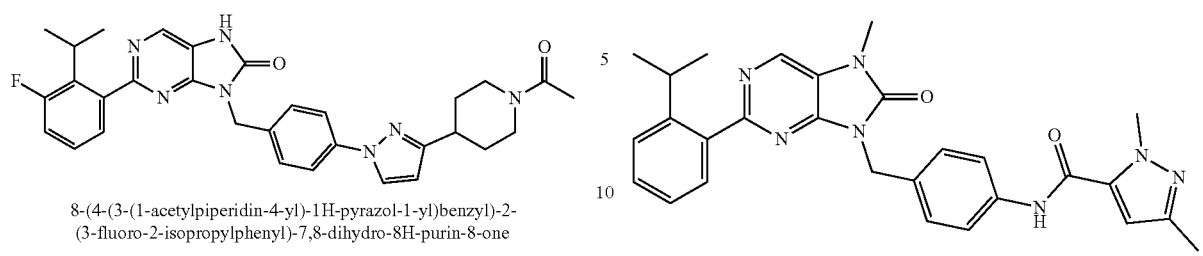

N-(4-((2-(2-isopropylphenyl)-7-methyl-8-oxo-7,8-dihydro-8H-purin-
8-yl)methyl)phenyl)-1,3-dimethyl-1H-pyrazole-5-carboxamide

I-469

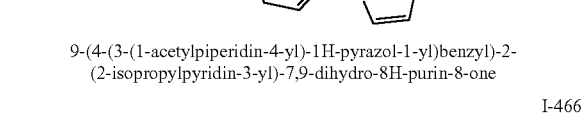

N-(4-((2-(2-isopropylphenyl)-7-methyl-8-oxo-7,8-dihydro-8H-purin-
9-yl)methyl)phenyl)-N-5-dimethyl-1H-pyrazole-3-carboxamide

I-470

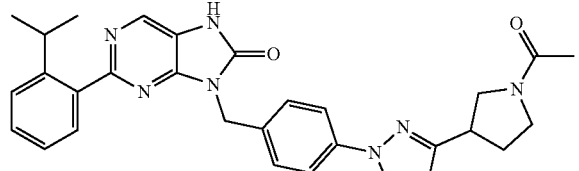

N-(4-((2-(2-isopropylphenyl)-7-methyl-8-oxo-7,8-dihydro-9H-purin-
8-yl)methyl)phenyl)-N-1,3-trimethyl-1H-pyrazole-5-carboxamide

I-471

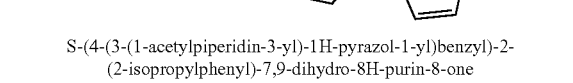

9-(4-(4-(1-acetylpiperidin-4-yl)-1-methyl-1H-imidazol-2-yl)benzyl)-
2-(2-isopropylphenyl)-7,9-dihydro-8H-purin-one

I-472

I-473

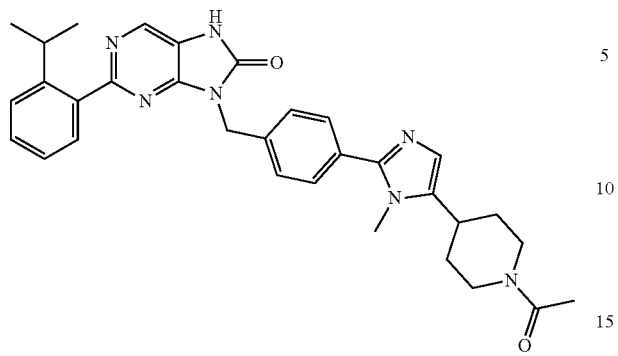

9-(4-(5-(1-acetylpiperidin-4-yl)-1-methyl-1H-imidazol-2-yl)benzyl)-2-(2-isopropylphenyl)-7,9-dihydro-8H-purin-8-one

I-474

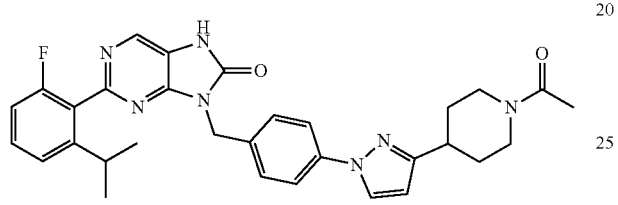

9-(4-(3-(1-acetylpiperidin-4-yl)-1H-pyrazol-1-yl)benzyl)-2-(2-fluoro-6-isopropylphenyl)-7,9-dihydro-8H-purin-8-one

I-475

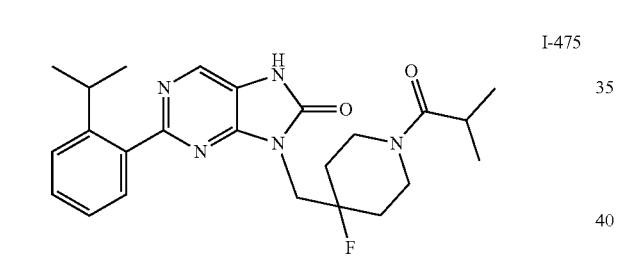

9-((4-fluoro-1-isobutyrylpiperidin-4-yl)methyl)-2-(2-isopropylphenyl)-7,9-dihydro-8H-purin-8-one

I-476

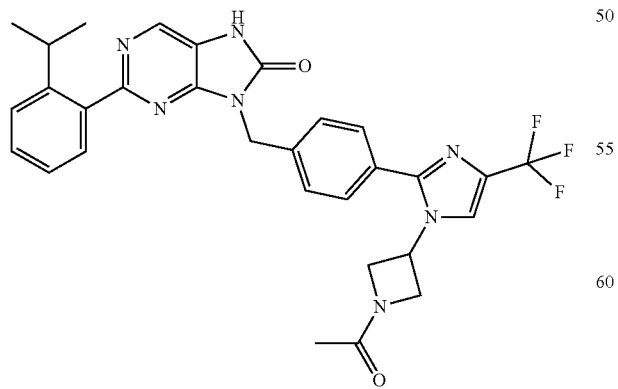

9-(4-(1-(1-acetylazetidin-3-yl)-4-(trifluoromethyl)-1H-imidazol-2-yl)benzyl)-2-(2-isopropylphenyl)-7,9-dihydro-8H-purin-8-one

I-477

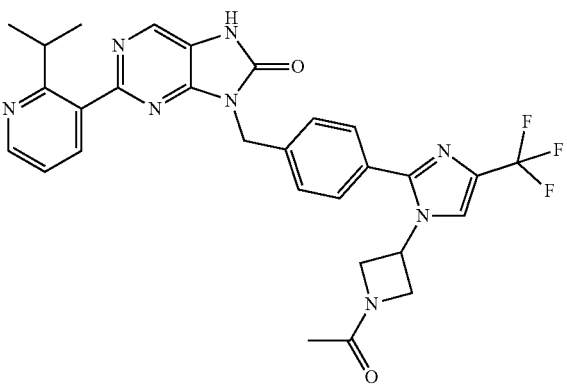

9-(4-(1-(1-acetylazetidin-3-yl)-4-(trifluoromethyl)-1H-imidazol-2-yl)benzyl)-2-(2-isopropylpyridin-3-yl)-7,9-dihydro-8H-purin-8-one

I-478

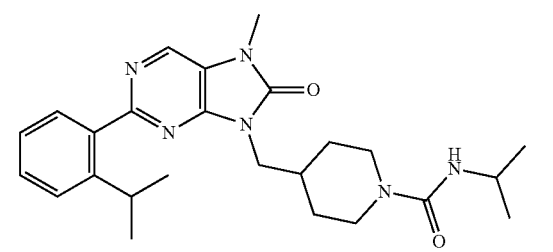

N-isopropyl-4-((2-(2-isopropylphenyl)-7-methyl-8-oxo-7,8-dihydro-8H-purin-8-yl)methyl)piperidine-1-carboxamide

I-479

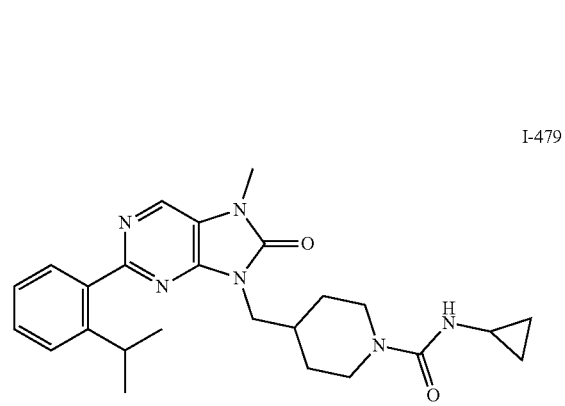

N-cyclopropyl-4-((2-(2-isopropylphenyl)-7-methyl-8-oxo-7,8-dihydro-8H-purin-8-yl)methyl)piperidine-1-carboxamide

I-480

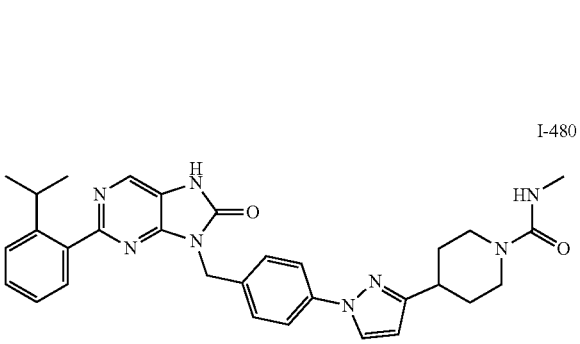

4-(1-(4-((2-(2-isopropylphenyl)-8-oxo-7,8-dihydro-8H-purin-9-yl)methyl)phenyl)-1H-pyrazzol-3-yl)-N-methylpiperidine-1-carboxamide

I-481

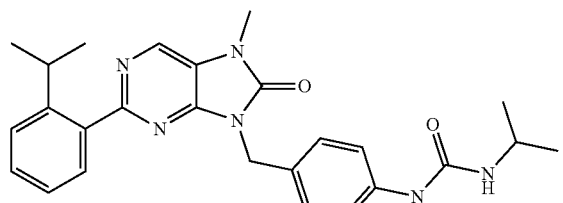

1-isopropyl-3-(4-((2-(2-isopropylphenyl)-7-methyl-8-oxo-7,8-dihydro-8H-purin-8-yl)methyl)phenyl)urea

I-482

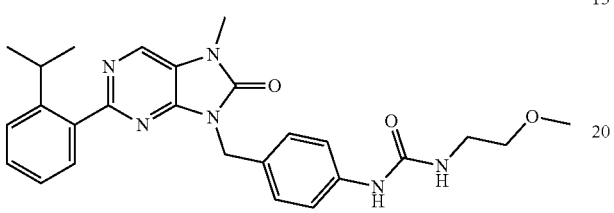

1-(4-((2-(2-isopropylphenyl)-7-methyl-8-oxo-7,8-dihydro-8H-purin-8-yl)methyl)phenyl)-3-(2-methoxyethyl)urea

I-483

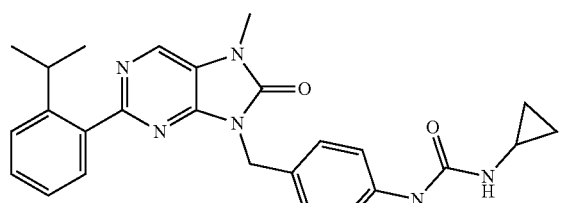

1-isopropyl-3-(4-((2-(2-isopropylphenyl)-7-methyl-8-oxo-7,8-dihydro-8H-purin-8-yl)methyl)phenyl)urea

I-484

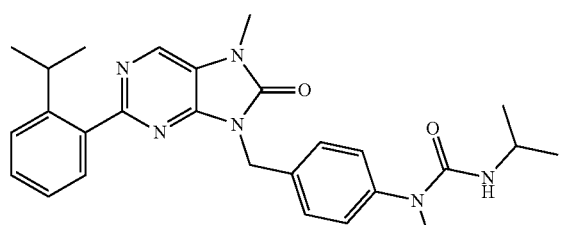

3-isopropyl-1-(4-((2-(2-isopropylphenyl)-7-methyl-8-oxo-7,8-dihydro-8H-purin-8-yl)methyl)phenyl)-1-methylurea

I-485

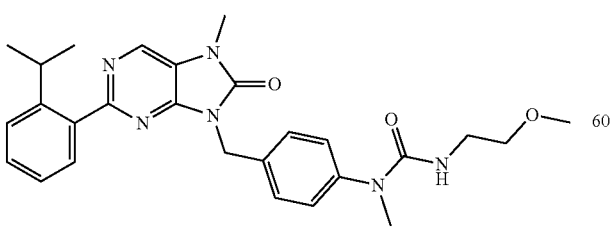

1-(4-((2-(2-isopropylphenyl)-7-methyl-8-oxo-7,8-dihydro-8H-purin-8-yl)methyl)phenyl)-3-(2-methoxyethyl)-1-methylurea

I-486

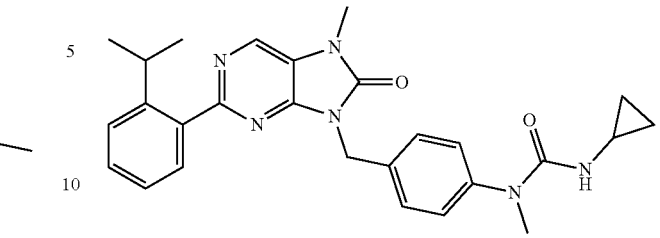

3-isopropyl-1-(4-((2-(2-isopropylphenyl-7-methyl-8-oxo-7,5-dihydro-8H-purin-9-yl)methoxyethyl)-1-methyl

I-487

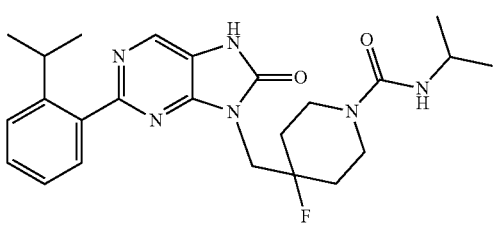

4-fluoro-N-isopropyl-4-((2-(2-isopropylphenyl)-8-oxo-7,8-dihydro-8H-purin-8-yl)methyl)piperidine-1-carboxamide

I-488

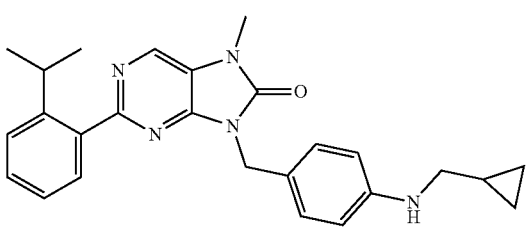

9-(4-isopropylphenyl(methyl)amino)benzyl)-2-(2-isopropyphenyl)-7-methyl-7,9-dihydro-8H-purin-8-one

I-489

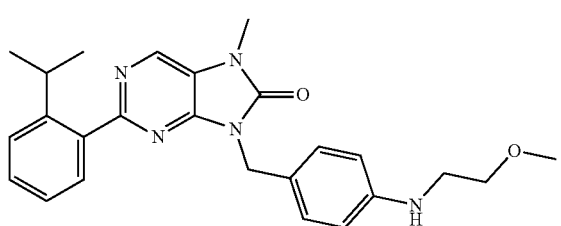

2-(2-isopropylphenyl)-8-(4-((2-methoxyethyl)amino)benzyl)-7-methyl-7,9-dihydro-8H-purin-8-one

I-490

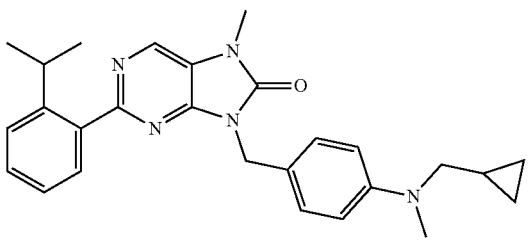

8-(4-((cyclopropylmethyl)(methyl)amino)benzyl)-2-(2-isopropylphenyl)-7-methyl-7,9-dihydro-8H-purin-8-one

I-491

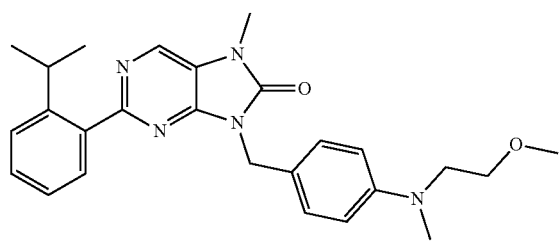

2-(2-isopropylphenyl)-8-(4-((2-methoxyethyl(methyl)amino)benzyl)-7-methyl-7,9-dihydro-8H-purin-8-one

I-492

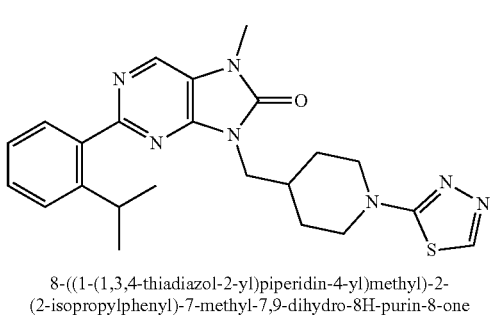

8-((1-(1,3,4-thiadiazol-2-yl)piperidin-4-yl)methyl)-2-(2-isopropylphenyl)-7-methyl-7,9-dihydro-8H-purin-8-one

I-493

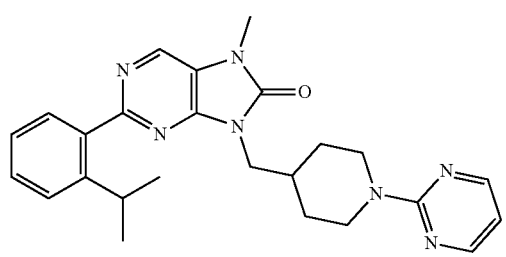

2-(2-isopropylphenyl)-7-methyl-9-((1-(pyrimidin-2-yl)piperidin-4-yl)methyl)-7,9-dihydro-8H-purin-8-one

I-494

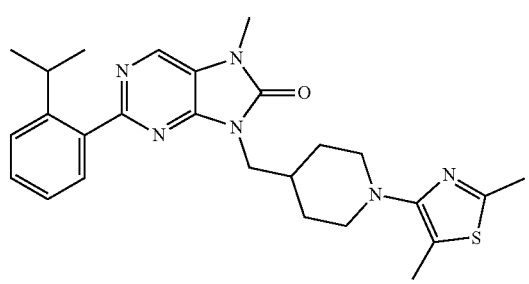

9-((1-(2,5-dimethylthiazol-4-yl)piperidin-4-yl)methyl)-2-(2-isopropylphenyl)-7-methyl-7,9-dihydro-8H-purin-8-one

I-495

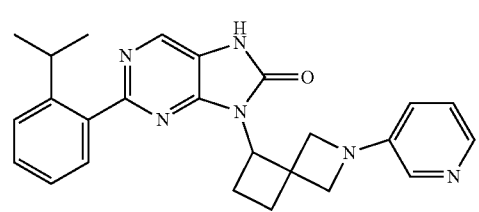

2-(2-isopropylphenyl)-8-(2-(pyridin-3-yl)-2-azaspiro[3.3]heptan-5-yl)-7,9-dihydro-8H-purin-8-one

I-496

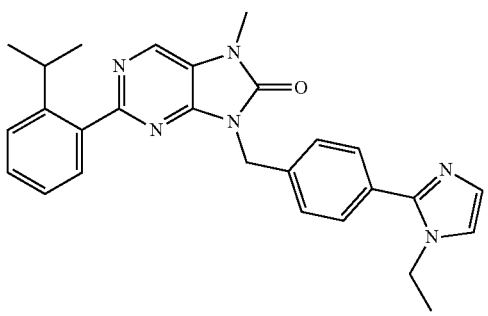

9-(4-(1-ethyl-1H-imidazole-2-yl(benzyl)-2-yl(benzyl)-2-(2-isopropylphenyl)-7-methyl-1,9dihydro-8H-purin-8-one

I-497

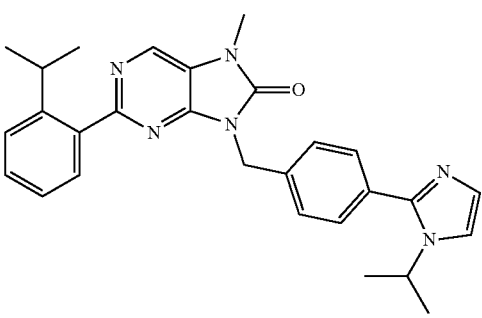

9-(4-(1-isopropyl-1H-imidazol-2-yl)benzyl)-2-(2-isopropylphenyl)-7-methyl-7,9-dihydro-8H-purin-8-one

I-498

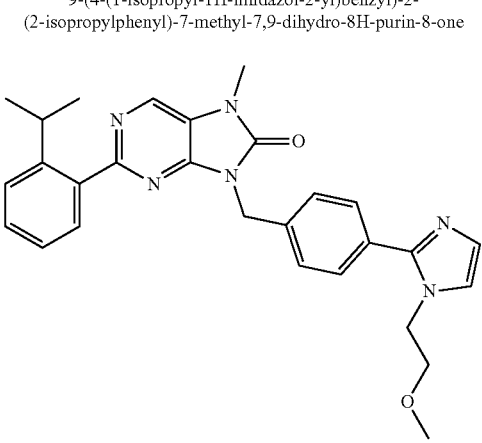

2-(2-isopropylphenyl)-9-(4-(1-(2-methoxyethyl)-1H-imidazol-2-yl)benzyl)-7-methyl-7,9-dihydro-8H-purin-8-one

I-499

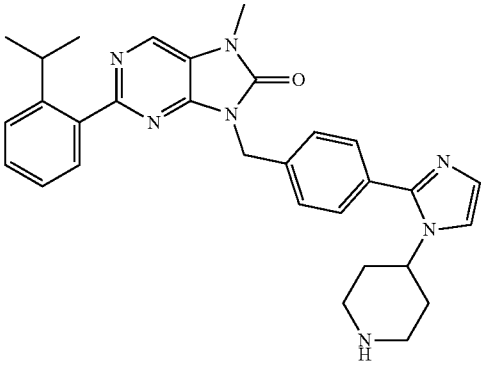

2-(2-isopropylphenyl)-7-methyl-8-(4-(1-(piperidin-4-yl)-1H-imidazol-2-yl)benzyl)-7,9-dihydro-8H-purin-8-one

I-500

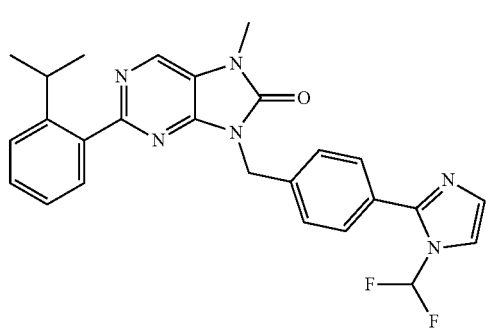

9-(4-(1-(difluoromethyl)-1H-imidazol-2-yl)benzyl)-2-
(2-isopropylphenyl)-7-methyl-7,9-dihydro-8H-purin-8-one

I-501

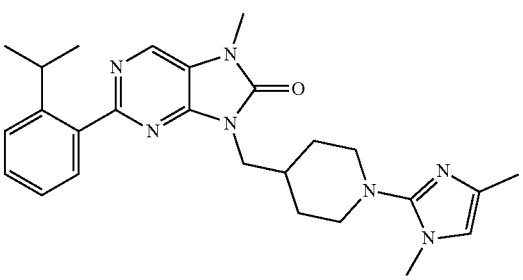

9-((1-(1,4-dimethyl-1H-imidazol-2-yl)piperidin-4-yl)methyl)-2-
(2-isopropylphenyl)-7-methyl-7,9-dihydro-8H-purin-8-one

I-502

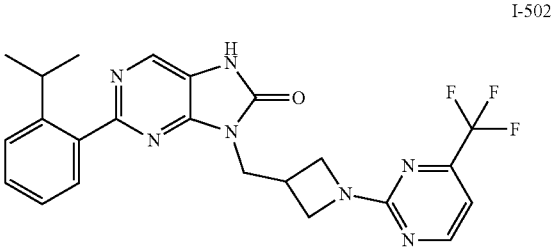

2-(2-isopropylphenyl)-9-((1-(4-(trifluoromethyl)pyrimidin-2-yl)azetidin-3-
yl)methyl)-7,9-dihydro-8H-purin-8-one

I-503

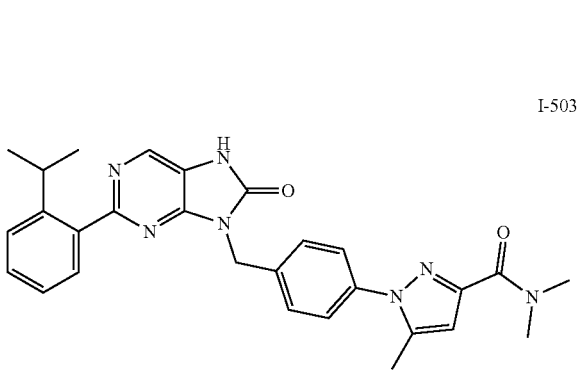

1-(4-((2-(2-isopropylphenyl)-8-oxo-7,8-dihydro-8H-purin-8-
yl)methyl)phenyl)-N,N,5-trimethyl-1H-pyrazole-3-carboxamide

I-504

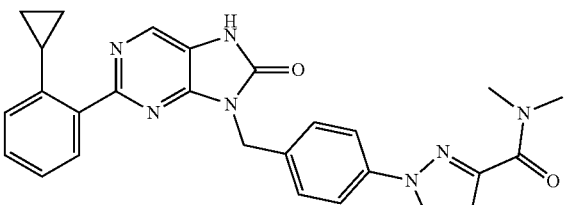

1-(4-((2-(2-cyclopropylphenyl)-8-oxo-7,8-dihydro-8H-purin-8-
yl)methyl)phenyl)-N,N,5-trimethyl-1H-pyrazole-3-carboxamide

I-505

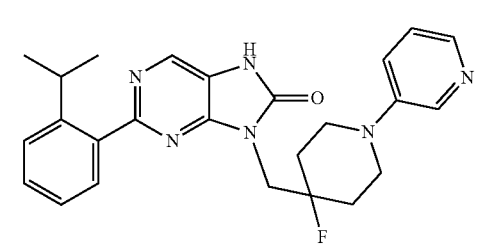

9-((4-fluoro-1-(pyridin-3-yl)piperidin-4-yl)methyl)-2-(2-
isopropylphenyl)-7,8-dihydro-8H-purin-8-one

I-506

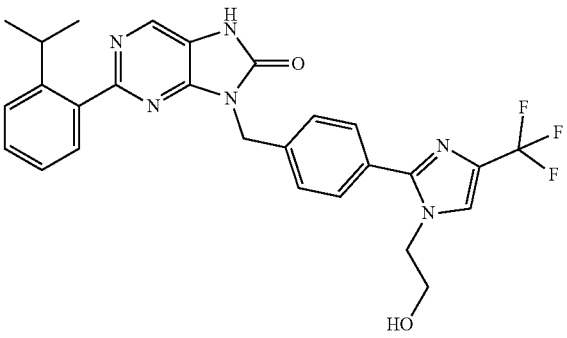

8-(4-(1-(2-hydroxyethyl)-4-(trifluoromethyl)-1H-imidazol-2-yl)benzyl)-
2-(2-isopropylphenyl)-7,9-dihydro-8H-purin-8-one

I-507

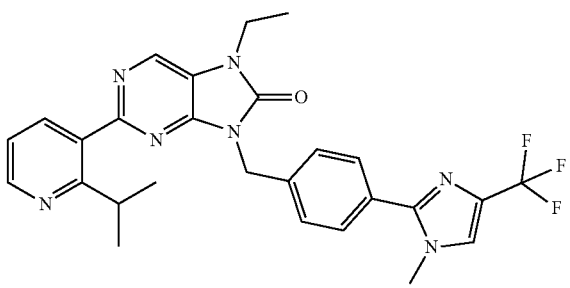

7-ethyl-2-(2-isopropylpyridin-3-yl)-9-(4-(1-methyl-4-(trifluoromethyl)-
1H-imidazol-2-yl)benzyl)-7,9-dihydro-8H-purin-8-one -continued

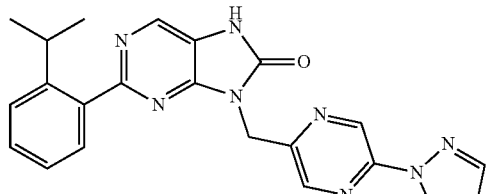

9-((5-(1H-pyrazol-1-yl)pyrazin-2-yl)methyl)-2-(2-isopropylphenyl)-7,9-dihydro-8H-purin-8-one

I-508

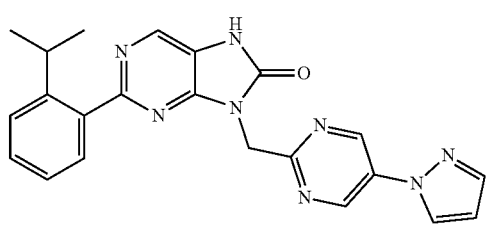

9-((5-(1H-pyrazol-1-yl)pyrimidin-2-yl)methyl)-2-(2-isopropylphenyl)-7,9-dihydro-8H-purin-8-one

I-509

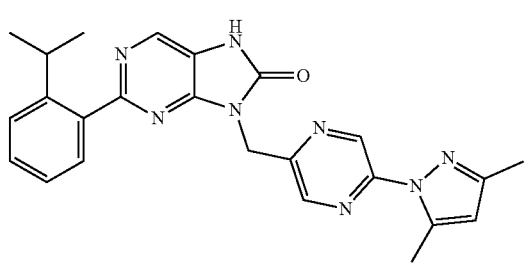

9-((5-(3,5-dimethyl-1H-pyrazol-1-yl)pyrazin-2-yl)methyl)-2-(2-isopropylphenyl)-7,9-dihydro-8H-purin-8-one

I-510

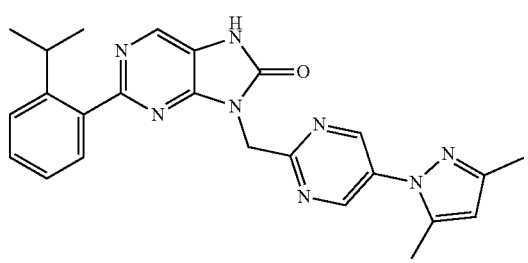

9-((5-(3,5-dimethyl-1H-pyrazol-1-yl)pyrimidin-2-yl)methyl)-2-(2-isopropylphenyl)-7,9-dihydro-8H-purin-8-one

I-511

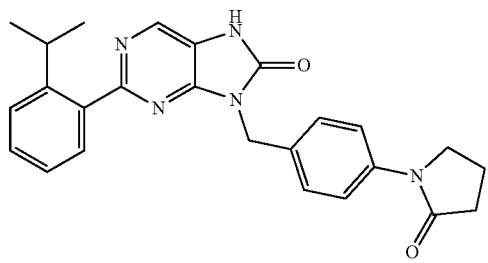

2-(2-isopropylphenyl)-9-(4-(2-oxopyrrolidin-1-yl)benzyl)-7,8-dihydro-8H-purin-8-one

I-512

-continued

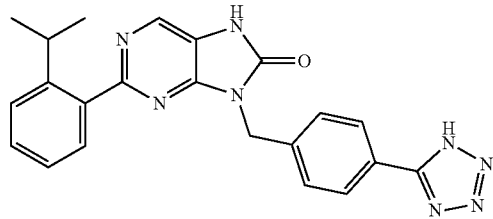

9-(4-(1H-tetrazol-5-yl)benzyl)-2-(2-isopropylphenyl)-7,9-dihydro-8H-purin-8-one

I-513

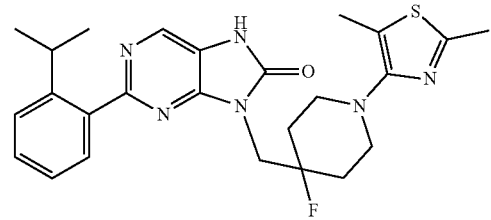

9-((1-(2,5-dimethylthiazol-4-yl)-4-fluoropiperidin-4-yl)methyl)-2-(2-isopropylphenyl)-7,9-dihydro-8H-purin-8-one

I-514

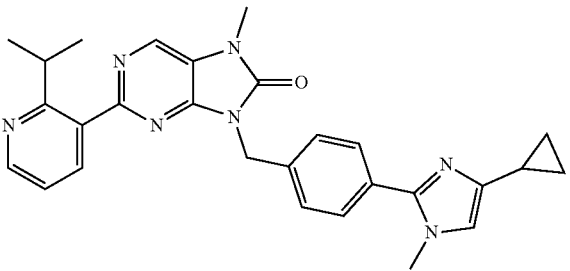

9-(4-(4-cyclopropyl-1-methyl-1H-imidazol-2-yl)benzyl)-2-(2-isopropylpyridin-3-yl)-7-methyl-7,9-dihydro-8H-purin-8-one

I-515

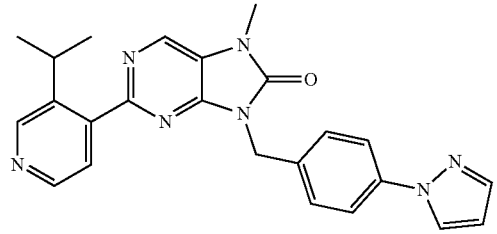

9-(4-(1H-pyrazol-1-yl)benzyl)-2-(3-isopropylpyridin-4-yl)-7-methyl-7,9-dihydro-8H-purin-8-one

I-516

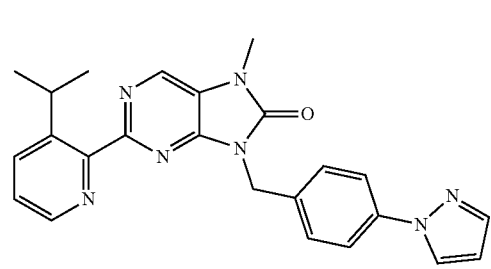

8-(4-(1H-pyrazol-1-yl)benzyl)-2-(3-isopropylpyridin-2-yl)-7-methyl-7,9-dihydro-8H-purin-8-one

I-517

-continued

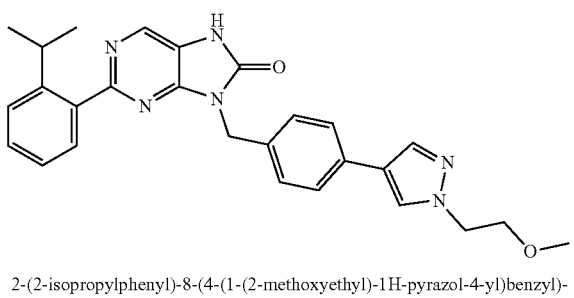

I-518

2-(2-isopropylphenyl)-8-(4-(1-(2-methoxyethyl)-1H-pyrazol-4-yl)benzyl)-7,9-dihydro-8H-purin-8-one

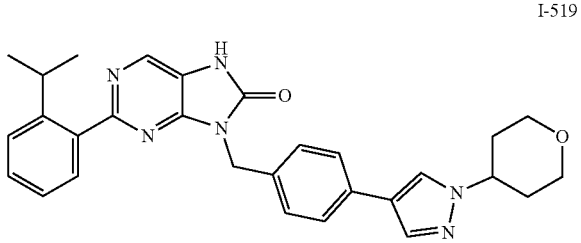

I-519

2-(2-isopropylphenyl)-8-(4-(1-tetrahydro-2H-pyran-4-yl)-1H-pyrazol-4-yl)benzyl)-7,9-dihydro-8H-purin-8-one

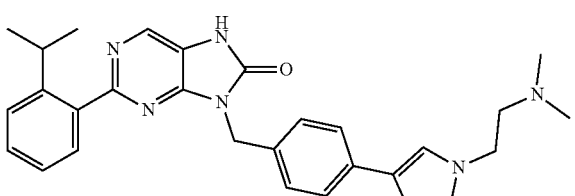

I-520

9-(4-(1-(2-(dimethylamino)ethyl)-1H-pyrazol-4-yl)benzyl)-2-(2-isopropylphenyl)-7,9-dihydro-8H-purin-8-one

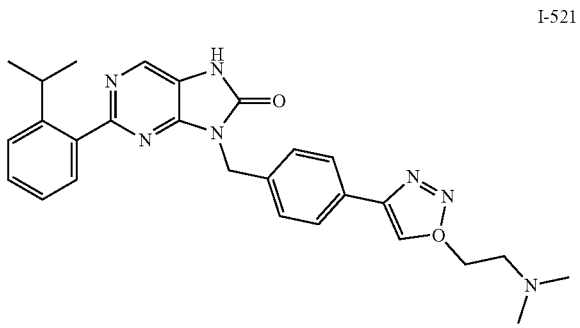

I-521

9-(4-(1-(2-(dimethylamino)ethyl)-1H-1,2,3-triazol-4-yl)benzyl)-2-(2-isopropylphenyl)-7,9-dihyrdo-8H-purin-8-one

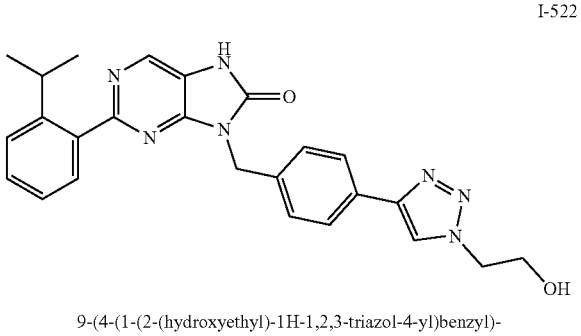

I-522

9-(4-(1-(2-(hydroxyethyl)-1H-1,2,3-triazol-4-yl)benzyl)-2-(2-isopropylphenyl)-7,9-dihydro-8H-purin-8-one -continued

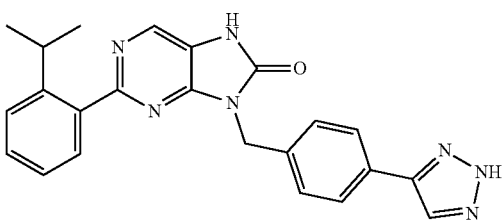

I-523

9-(4-(2H-1,2,3-triazol-4-yl)benzyl)-2-(2-isopropylphenyl)-7,9-dihydro-8H-purin-8-one

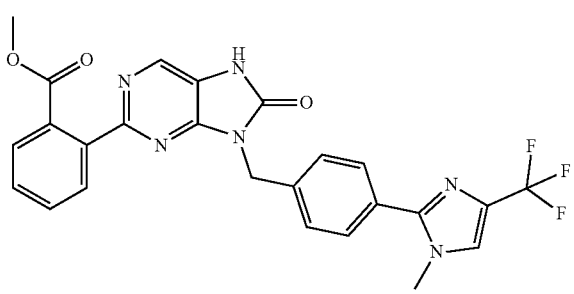

I-524 methyl 2-(9-(4-(1-methyl-4-(trifluoromethyl)-1H-imidazol-2-yl)benzyl)-8-oxo-8,9-dihydro-7H-purin-2-yl)benzoate

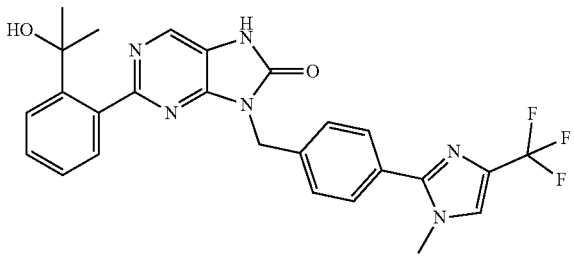

I-525

2-(2-(hydroxypropan-2-yl)phenyl)-9-(4-(1benzyl-4-trifluoromethyl)-1H-imidazol-2-yl)benzyl)-7-9-dihydro-8H-purin-8-one

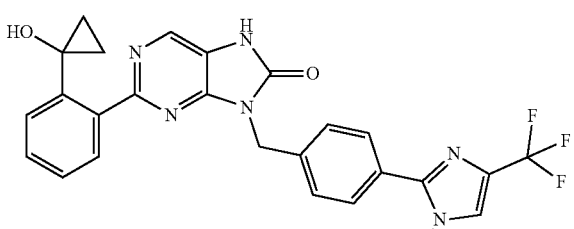

I-526

2-(2-(1-(hydroxypropanyl)phenyl)-9-(4-(1benzyl-4-trifluoromethyl)-1H-imidazol-2-yl)benzyl)-7-9-dihydro-8H-purin-8-one

I-527

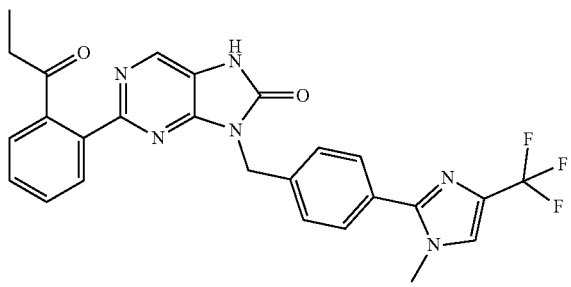

8-(4-(1-methyl-4-(trifluoromethyl)-1H-imidazol-2-yl)benzyl)-
2-(2-propionyl)phenyl)-7,9-dihydro-8H-purin-8-one

I-528

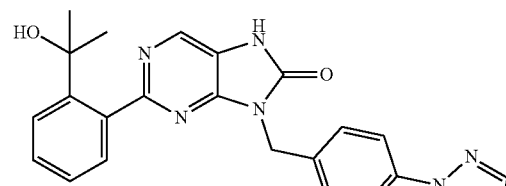

8-(4-(1H-pyrazol-1-yl)benzyl)-2-(2-(2-hydroxypropan-
2-yl)phenyl)-7,8-dihydro-8H-purin-8-one

I-529

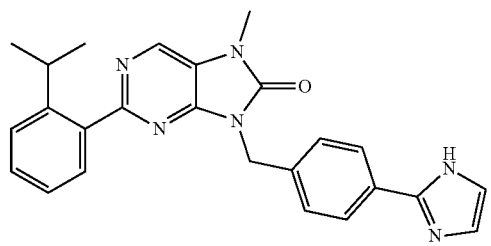

8-(4-(1H-imidazol-2-yl)benzyl)-2-(2-isopropylphenyl)-
7-methyl-7,9-dihydro-8H-purin-8-one

I-530

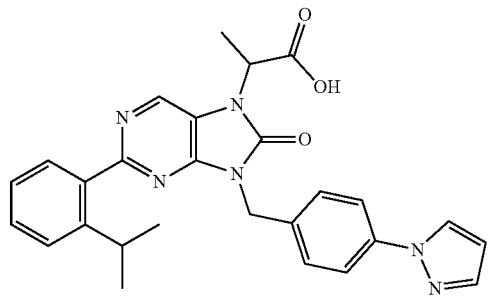

2-(9-(4-(1H-pyrazol-1-yl)benzyl)-2-(2-isopropylphenyl)-8-oxo-
8,9-dihydro-7H-purin-7-yl)propanoic acid

I-531

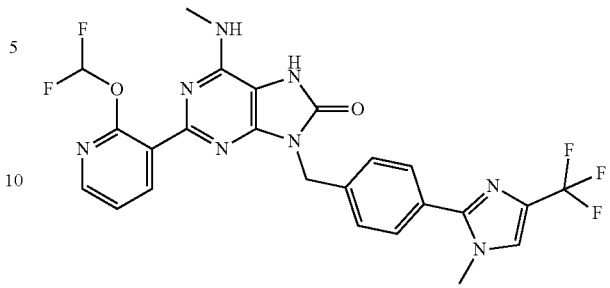

2-(2-(difluoromethoxy)pyridin-3-yl)-8-(4-(1-methyl)-4-
trifluoromethyl)-1H-imidazol-2-yl)benzyl)-8-
(methylamino)-7,9-dihydro-8H-purin-8-one

I-532

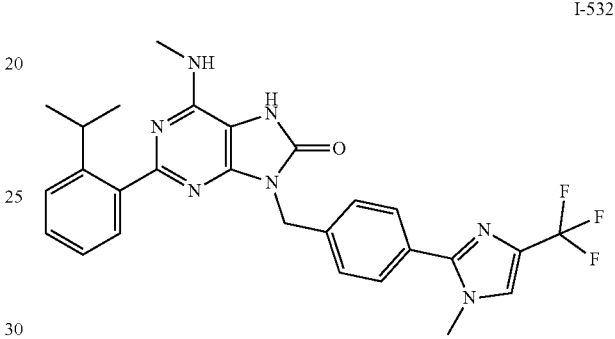

2-(2-(isopropylphenyl)-9-(4-(1-methyl)-4-(trifluoromethyl)-
1H-imidazol-2-yl)benzyl)-8-(methylamino)-
7,9-dihydro-8H-purin-8-one

I-533

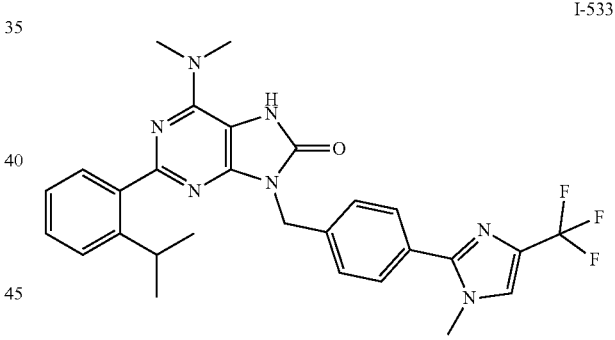

6-(dimethylamino)-2-(2-isopropylphenyl)-9-(4-(1-methyl)-4-
(trifluoromethyl)-1H-imidazol-2-yl)benzyl)-
7,9-dihydro-8H-purin-8-one

I-534

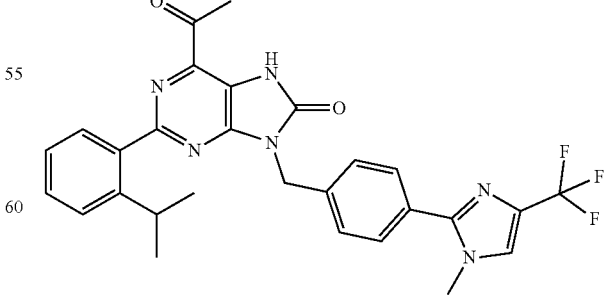

6-acetyl-2-(2-isopropylphenyl)-8-(4-(1-methyl-4-(trifluoromethyl)-1H-
imidazol-2-yl)benzyl)-7,9-dihydro-8H-purin-8-one

I-535

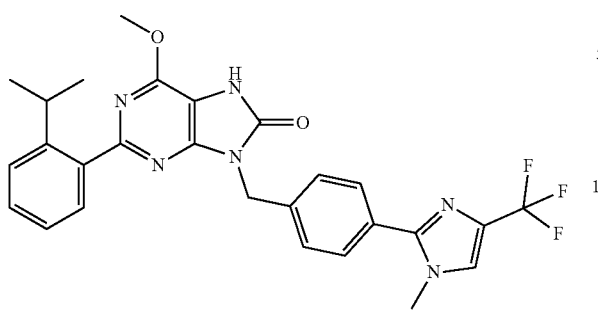

2-(2-isopropylphenyl-6-methoxy-9-(4-(1-methyl-4-(trifluoromethyl)-1H-imidazol-2-yl)benzyl)-7,9-dihydro-8H-purin-8-one

I-536

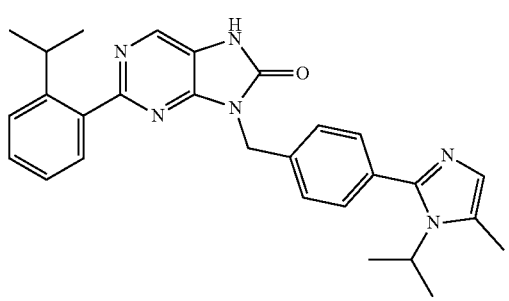

8-(4-(1-isopropyl-5-methyl-1H-imidazol-2-yl)benzyl)-2-(2-isopropylphenyl)-7,9-dihydro-8H-purin-8-one

I-537

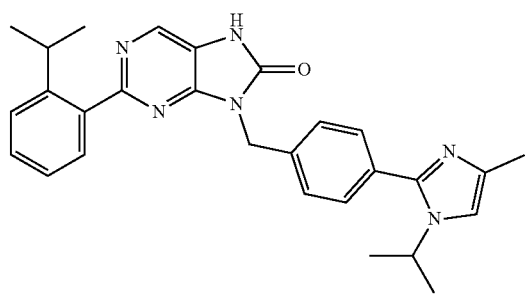

9-(4-(1-isopropyl-4-methyl-1H-imidazol-2-yl)benzyl)-2-(2-isopropylphenyl)-7,8-dihydro-8H-purin-8-one

I-538

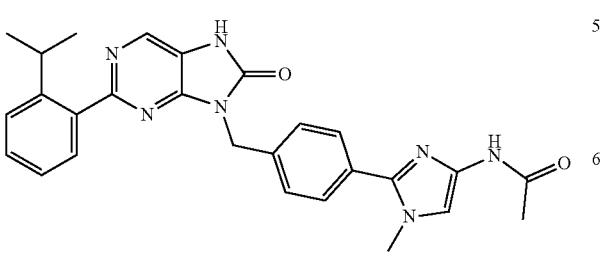

N-(2-(4-((2-(2-isopropylphenyl)-8-oxo-7,8-dihydro-8H-purin-9-yl)methyl)phenyl)-1-methyl-1H-imidazol-4-yl)acetamide

I-539

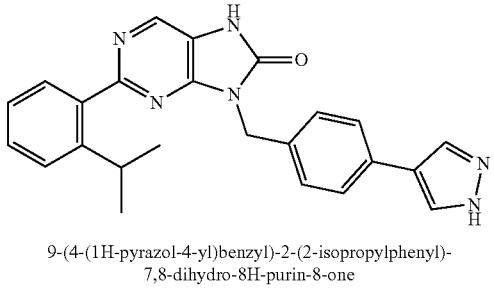

9-(4-(1H-pyrazol-4-yl)benzyl)-2-(2-isopropylphenyl)-7,8-dihydro-8H-purin-8-one

I-540

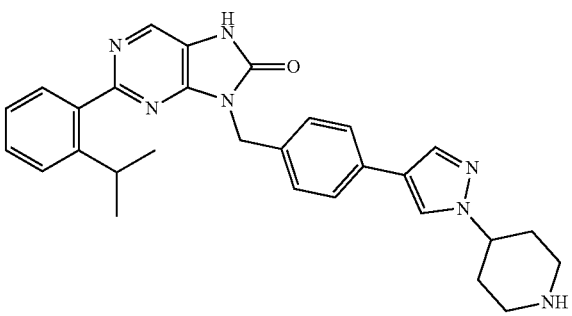

2-(2-isopropylphenyl)-9-(4-(1-piperidin-4-yl)-1H-pyrazol-4-yl)benzyl)-7,9-dihydro-8H-purin-8-one

I-541

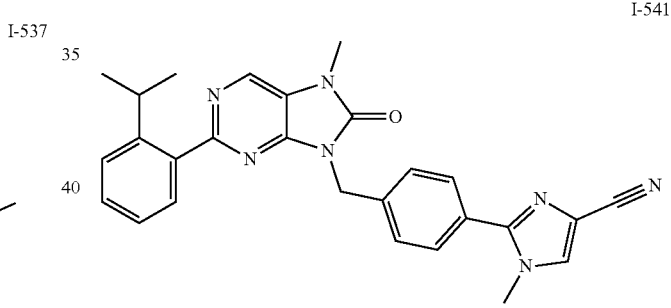

2-(4-((2-(2-isopropylphenyl)-7-methyl-8-oxo-7,8-dihydro-9H-purin-8-yl)methyl)phenyl)-1-methyl-1H-imidazole-4-carbonitrile

I-542

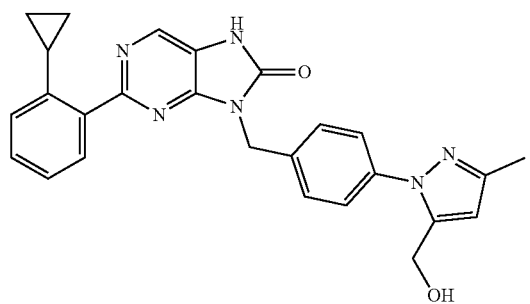

2-(2-isopropylphenyl)-9-(4-(3-hydroxyethyl)-3-methyl-1H-pyrazol-1-yl)benzyl)-7,9-dihydro-8H-purin-8-one -continued

I-543

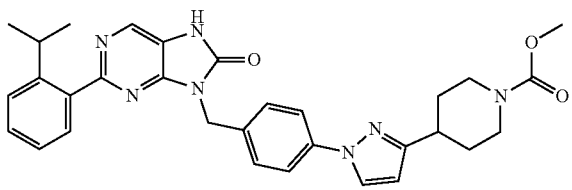

methyl 4-(1-(4-((2-(2-isopropylphenyl)-8-oxo-
7,8-dihydro-8H-purin-9-yl)methylphenyl)-1H-pyrazol-8-
yl)piperidin-1-carboxylate

I-544

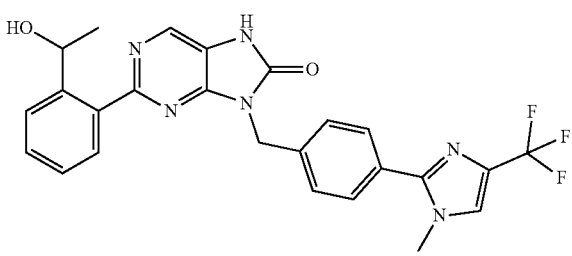

2-(2-(1-hydroxyethyl)phenyl)-9-(4-(1-methyl-4-
(trifluoromethyl)-1H-imidazol-2-yl)benzyl)-7,9-
dihydro-8H-purin-8-one In another embodiment of the application, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

It should be understood that all isomeric forms are included within the present application, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the application, and pharmaceutically acceptable salts, hydrates, solvates, stereoisomers and prodrugs thereof may exist in their tautomeric form (for example, as an amide or imino ether). All such tautomeric forms are contemplated herein as part of the present application.

The compounds of the application may contain asymmetric or chiral centers, and, therefore, exist in different stereoisomeric forms. It is intended that all stereoisomeric forms of the compounds of the application as well as mixtures thereof, including racemic mixtures, form part of the present application. In addition, the present application embraces all geometric and positional isomers. For example, if a compound of the application incorporates a double bond or a fused ring, both the cis- and trans-forms, as well as mixtures, are embraced within the scope of the application. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the application may be atropisomers (e.g., substituted biaryls) and are considered as part of this application. Enantiomers can also be separated by use of a chiral HPLC column.

It is also possible that the compounds of the application may exist in different tautomeric forms, and all such forms are embraced within the scope of the application. Also, for example, all keto-enol and imine-enamine forms of the compounds are included in the application.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this application, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the application. Also, for example, all keto-enol and imine-enamine forms of the compounds are included in the application.) Individual stereoisomers of the compounds of the application may, for example, be substantially free of other isomers, or may be admixed, for example, as racemates or with all other, or other selected, stereoisomers. The chiral centers of the present application can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this application. Reference to a compound of the Formula herein is understood to include reference to salts thereof, unless otherwise indicated.

The present application relates to compounds which are modulators of USP1. In one embodiment, the compounds of the present application are inhibitors of USP1.

In some embodiments, the compounds of the present application are selective over other USP enzymes including, but not limited to, USP2, USP4, USP5, USP6, USP7, USP8, USP9x, and USP12/46. As used herein "selective," "selective USP1 inhibitor," or "selective USP1 compound" refers to a compound, for example a compound of the application, that effectively inhibits USP1 to a greater extent than any other USP enzyme, (i.e., USP2, USP5, USP7, USP8, USP11, USP14, USP15, USP16, USP19, USP20, USP21, USP25, USP28, USP30, USP35, USP36, USP45, and USP12/46).

A "selective USP1 inhibitor," can be identified, for example, by comparing the ability of a compound to inhibit USP1 enzyme activity to its ability to inhibit the other USP enzymes. For example, a substance may be assayed for its ability to inhibit USP1, as well as for its ability to modulate (i.e., inhibit or activate) USP2, USP5, USP7, USP8, USP11, USP14, USP15, USP16, USP19, USP20, USP21, USP25, USP28, USP30, USP35, USP36, USP45, and USP12/46.

In certain embodiments, the compounds of the application exhibit at least 2-fold, 3-fold, 5-fold, 10-fold, 25-fold, 50-fold or 100-fold selectivity over one or more other USP enzymes (i.e., USP2, USP5, USP7, USP8, USP11, USP14, USP15, USP16, USP19, USP20, USP21, USP25, USP28, USP30, USP35, USP36, USP45, and USP12/46). In various embodiments, the compounds of the application exhibit up to 1000-fold selectivity over one or more other USP enzymes.

In certain embodiments, the compounds of the application exhibit at least 2-fold, 3-fold, 5-fold, 10-fold, 25-fold, 50-fold or 100-fold selectivity over other USP enzymes (i.e., USP2, USP5, USP7, USP8, USP11, USP14, USP15, USP16, USP19, USP20, USP21, USP25, USP28, USP30, USP35, USP36, USP45, and USP12/46). In various embodiments, the compounds of the application exhibit up to 1000-fold selectivity over other USP enzymes.

In certain embodiments, the compounds of the application exhibit at least 2-fold, 3-fold, 5-fold, 10-fold, 25-fold, 50-fold or 100-fold selectivity over USP2, USP5, USP7, USP8, USP11, USP14, USP15, USP16, USP19, USP20, USP21, USP25, USP28, USP30, USP35, USP36, USP45, and USP12/46. In various embodiments, the compounds of the application exhibit up to 1000-fold selectivity over USP2, USP5, USP7, USP8, USP11, USP14, USP15, USP16, USP19, USP20, USP21, USP25, USP28, USP30, USP35, USP36, USP45, and USP12/46.

The application is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method for Preparation of Compounds

The compounds of the present application may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below. Compounds of the present application can be synthesized by following the steps outlined in General Schemes 1-5 which comprise different sequences of assembling intermediates 2-a to 2-n. Starting materials are either commercially available or made by known procedures in the reported literature or as illustrated.

General Scheme 1

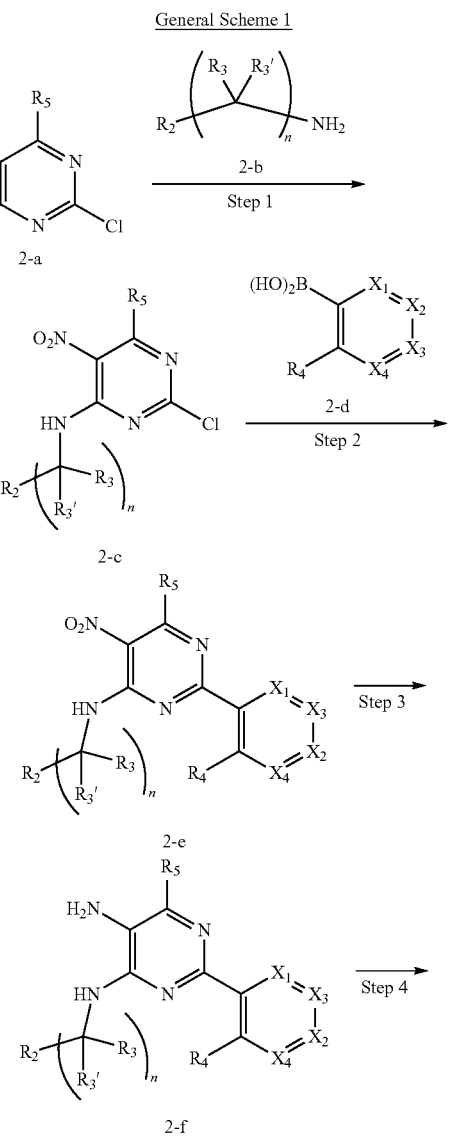

-continued

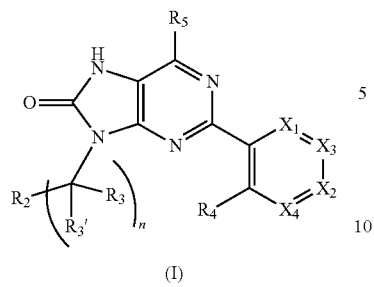

(I)

wherein n is 1 and $R_2$, $R_3$, $R_{3'}$, $R_4$, $R_5$, and $X_1$-$X_4$ are defined as in Formula (I).

The general way of preparing compounds of Formula (I) by using intermediates 2-a, 2-b, 2-c, 2-d, 2-e, and 2-f is outlined in General Scheme 1. Amination of 2-a with 2-b using a base, i.e., N,N-diisopropylethylamine (DIEA), in a solvent, i.e., acetonitrile (MeCN), yields 2-c. Coupling of 2-c with an arylboronic acid/ester or heteroarylboronic acid/ester 2-d using a catalytic amount of a palladium catalyst, i.e., [1,1'-Bis(diphenylphosphino) ferrocene]palladium(II) dichloride dichloromethane (Pd(dppf)Cl$_2$—CH$_2$C$_2$) and a base, i.e., potassium carbonate (K$_2$CO$_3$) or cesium carbonate (Cs$_2$CO$_3$), in a solvent, e.g., 1,4-dioxane, at elevated temperature provides 2-e. Reduction of intermediate 2-e using a metal (i.e., iron (Fe) powder) and ammonium chloride in a solvent, i.e., tetrahydrofuran (THF), ethanol (EtOH), and/or water, provides amine 2-f. Alternatively, amine 2-f can be obtained by reduction of intermediate 2-e with a metal catalyst and hydrogen (H$_2$) gas in a solvent, i.e., methanol (MeOH) or ethyl acetate (EtOAc). Cyclization of 2-f with carbonyldiimidazole (CDI) in a solvent, i.e., dichloromethane (DCM), provides the desired compound of Formula (I).

General Scheme 2

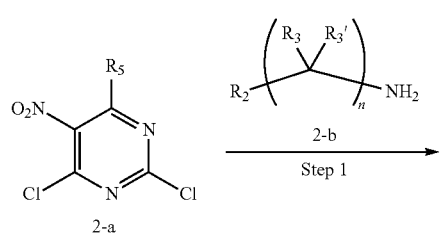

2-a

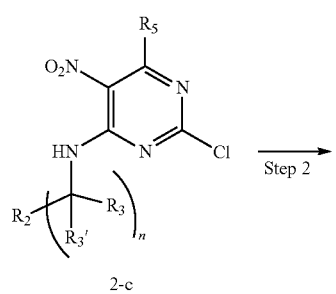

2-c

-continued

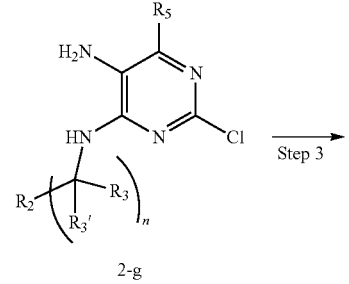

2-g

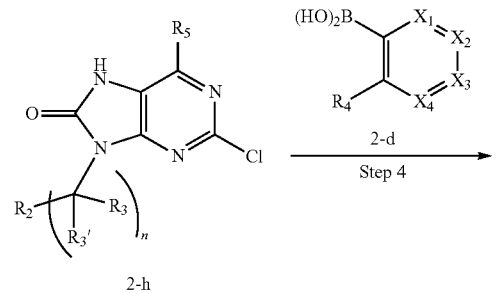

2-h

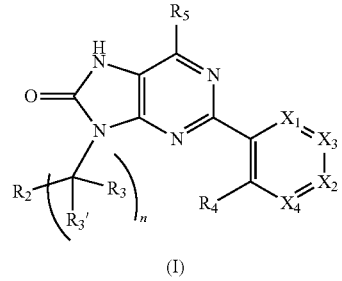

(I)

wherein n is 1 and $R_2$, $R_3$, $R_{3'}$, $R_4$, $R_5$, and $X_1$-$X_4$ are defined as in Formula (I).

Alternatively, compounds of Formula (I) can be prepared using intermediates 2-a, 2-b, 2-c, 2-d, 2-g, and 2-h as outlined in General Scheme 2. Amination of 2-a with 2-b using a base, i.e., N,N-diisopropylethylamine (DIEA), in a solvent, i.e., acetonitrile (MeCN), yields 2-c. Reduction of intermediate 2-c using a metal (i.e., iron (Fe) powder) and ammonium chloride in a solvent, i.e., tetrahydrofuran (THF), ethanol (EtOH), and/or waters provide amine 2-g. Alternatively, amine 2-g can be obtained by reduction of intermediate 2-c with a metal catalyst and hydrogen (H$_2$) gas in a solvent, i.e., methanol (MeOH) or ethyl acetate (EtOAc). Cyclization of 2-g with carbonyldiimidazole (CDI) in a solvent, i.e., dichloromethane (DCM), provides intermediate 2-h. Coupling of 2-h with an arylboronic acid/ester or heteroarylboronic acid/ester 2-d using a catalytic amount of a palladium catalyst, i.e., [1,1'-Bis (diphenylphosphino) ferrocene]palladium(II) dichloride dichloromethane (Pd(dppf)Cl$_2$.CH$_2$Cl$_2$) and a base, i.e., potassium carbonate (K$_2$CO$_3$) or cesium carbonate (Cs$_2$CO$_3$), in a solvent, e.g., 1,4-dioxane, at elevated temperature provides the desired compound of Formula (I).

General Scheme 3

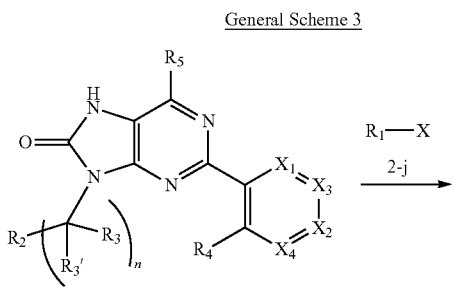

2-i

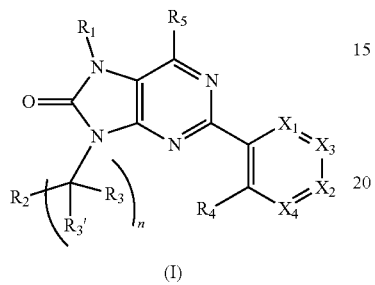

(I)

wherein $R_1$, $R_2$, $R_3$, $R_{3'}$, $R_4$, $R_5$, n, and $X_1$-$X_4$ are defined as in Formula (I).

Compounds of Formula (I) in General Scheme 3 can be prepared as outlined above. Alkylation of 2-i with intermediate 2-j wherein X is a halogen using a base, i.e., sodium hydride (NaH) or cesium carbonate ($Cs_2CO_3$) and in a solvent, i.e., dimethylformamide (DMF) provides the desired compounds of Formula (I). Alternatively, compounds of Formula (I) can be obtained by treating intermediates 2-i and 2-j wherein X is OH with diisopropyl azodicarboxylate (DIAD) and triphenyl phosphine in a solvent, i.e., tetrahydrofuran (THF).

General Scheme 4

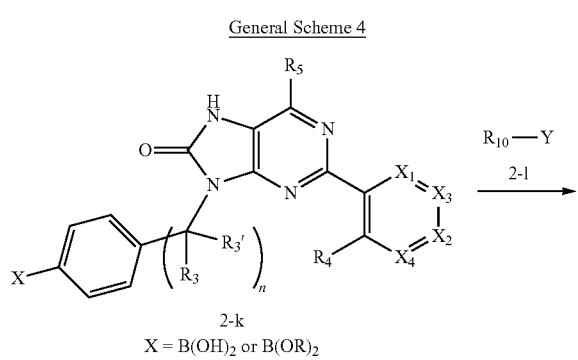

2-k
X = $B(OH)_2$ or $B(OR)_2$

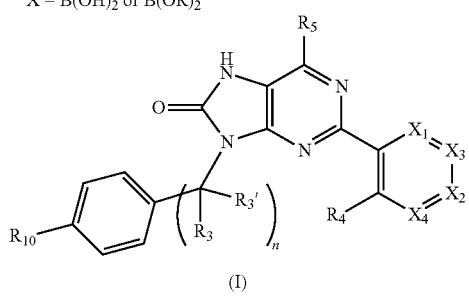

(I)

wherein $R_3$, $R_{3'}$, $R_4$, $R_5$, $R_{10}$, and $X_1$-$X_4$ are defined as in Formula (I).

Compounds of Formula (I) can be prepared using intermediates 2-k and 2-1 as outlined in General Scheme 4. Coupling of aryl boronic acid/ester 2-k with 2-1 (wherein Y is —Br or —O-triflate) using a catalytic amount of a palladium catalyst, i.e., [1,1'-Bis (diphenylphosphino) ferrocene]palladium(II) dichloride dichloromethane (Pd(dppf)$Cl_2.CH_2Cl_2$) and a base, i.e., potassium carbonate ($K_2CO_3$) or cesium carbonate ($Cs_2CO_3$), in a solvent, e.g., 1,4-dioxane, at elevated temperature provides the desired compound of Formula (I).

General Scheme 5

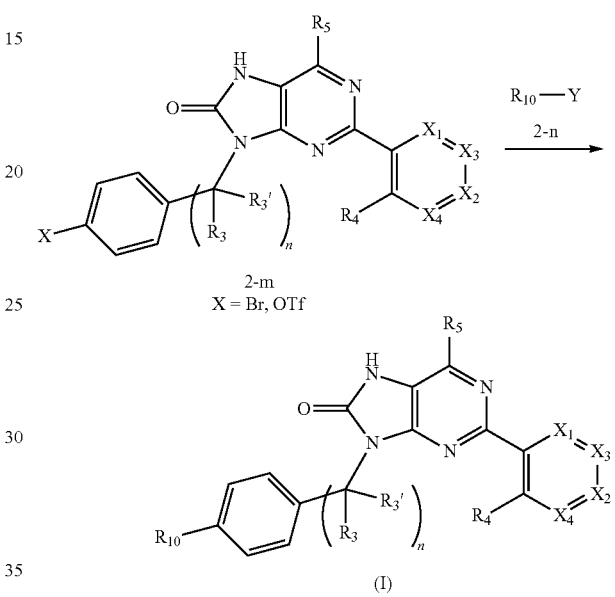

wherein $R_3$, $R_{3'}$, $R_4$, $R_5$, $R_{10}$, and $X_1$-$X_4$ are defined as in Formula (I).

Alternatively, compounds of Formula (I) can be prepared using intermediates 2-m and 2-n as outlined in General Scheme 5. Coupling of aryl bromide/triflate 2-m with 2-n (wherein Y is —$BF_3K$, —$B(OH)_2$ or —$(BOR)_2$, wherein R forms a boronate ester or MIDA boronate) using a catalytic amount of a palladium catalyst, i.e., [1,1'-Bis (diphenylphosphino) ferrocene]palladium(II) dichloride dichloromethane (Pd(dppf)$Cl_2.CH_2Cl_2$) and a base, i.e., potassium carbonate ($K_2CO_3$) or cesium carbonate ($Cs_2CO_3$), in a solvent, e.g., 1,4-dioxane, at elevated temperature provides the desired compound of Formula (I).

A mixture of enantiomers, diastereomers, cis/trans isomers resulting from the process described above can be separated into their single components by chiral salt technique, chromatography using normal phase, reverse phase or chiral column, depending on the nature of the separation.

It should be understood that in the description and formula shown above, the various groups $R_1$, $R_2$, $R_4$, $R_5$, and $X_1$-$X_4$ and other variables are as defined above, except where otherwise indicated. Furthermore, for synthetic purposes, the compounds of General Schemes 1-5 are mere representative with elected radicals to illustrate the general synthetic methodology of the compounds of Formula (I) as defined herein.

Methods of Using the Compounds

Another aspect of the application relates to a method of treating or preventing a disease or disorder associated with modulation of ubiquitin specific protease 1 (USP1). The method comprises administering to a patient in need of a treatment for diseases or disorders associated with modulation of USP1 an effective amount the compositions and compounds of Formula (I), or a pharmaceutically acceptable salt, hydrate, solvate, prodrug, stereoisomer, or tautomer thereof.

In another aspect, the present application relates to a method of treating, preventing, inhibiting or eliminating a disease or disorder in a patient associated with the inhibition of ubiquitin specific protease 1 (USP1), the method comprising administering to a patient in need thereof an effective amount of a compound of Formula (I), or a pharmaceutically acceptable salt, hydrate, solvate, prodrug, stereoisomer, or tautomer thereof. In one embodiment, the disease or disorder is cancer.

Another aspect of the application relates to a method of inhibiting ubiquitin specific protease 1 (USP1). The method involves administering to a patient in need thereof an effective amount of a compound of Formula (I), or a pharmaceutically acceptable salt, hydrate, solvate, prodrug, stereoisomer, or tautomer thereof.

In another aspect, the present application relates to a method of treating or preventing cancer. The method comprises administering to a patient in need of a treatment for cancer an effective amount of a compound of Formula (I), or a pharmaceutically acceptable salt, hydrate, solvate, prodrug, stereoisomer, or tautomer thereof.

Another aspect of the application relates to a method of treating or preventing a disease or disorder associated with DNA damage. The method comprises administering to a patient in need of a treatment for diseases or disorders associated with DNA damage an effective amount of a compound of Formula (I), or a pharmaceutically acceptable salt, hydrate, solvate, prodrug, stereoisomer, or tautomer thereof. In one embodiment, the disease or disorder is cancer.

In another aspect, the present application relates to a method of inhibiting or reducing DNA repair activity modulated by ubiquitin specific protease 1 (USP1). The method comprises administering to a patient in need thereof an effective amount of a compound of Formula (I), or a pharmaceutically acceptable salt, hydrate, solvate, prodrug, stereoisomer, or tautomer thereof.

Another aspect of the present application relates to a compound of Formula (I), or a pharmaceutically acceptable salt, hydrate, solvate, prodrug, stereoisomer, or tautomer thereof, for use in a method of treating or preventing a disease associated with inhibiting USP1. In one embodiment, the disease or disorder is cancer.

In another aspect, the present application relates to a compound of Formula (I), or a pharmaceutically acceptable salt, hydrate, solvate, prodrug, stereoisomer, or tautomer thereof, for use in a method for treating or preventing cancer.

Another aspect of the present application relates to a compound of Formula (I), or a pharmaceutically acceptable salt, hydrate, solvate, prodrug, stereoisomer, or tautomer thereof, for use in a method of treating or preventing a disease or disorder associated with DNA damage. In one embodiment, the disease or disorder is cancer.

In another aspect, the present application relates to a compound of Formula (I), or a pharmaceutically acceptable salt, hydrate, solvate, prodrug, stereoisomer, or tautomer thereof, for use in a method of inhibiting or reducing DNA repair activity modulated by ubiquitin specific protease 1 (USP1).

Another aspect of the present application relates to the use of a compound of Formula (I), or a pharmaceutically acceptable salt, hydrate, solvate, prodrug, stereoisomer, or tautomer thereof, in the manufacture of a medicament for treating or preventing a disease associated with inhibiting USP1. In one embodiment, the disease or disorder is cancer.

In another aspect, the present application relates to the use of a compound of Formula (I), or a pharmaceutically acceptable salt, hydrate, solvate, prodrug, stereoisomer, or tautomer thereof, in the manufacture of a medicament for treating or preventing cancer.

Another aspect of the present application relates to the use of a compound of Formula (I), or a pharmaceutically acceptable salt, hydrate, solvate, prodrug, stereoisomer, or tautomer thereof, in the manufacture of a medicament for treating or preventing a disease or disorder associated with DNA damage. In one embodiment, the disease or disorder is cancer.

In another aspect, the present application relates to the use of a compound of Formula (I), or a pharmaceutically acceptable salt, hydrate, solvate, prodrug, stereoisomer, or tautomer thereof, in the manufacture of a medicament for treating a disease or disorder associated with DNA damage. In one embodiment, the disease or disorder is cancer.

Another aspect of the present application relates to the use of a compound of Formula (I), or a pharmaceutically acceptable salt, hydrate, solvate, prodrug, stereoisomer, or tautomer thereof, in the manufacture of a medicament for inhibiting or reducing DNA repair activity modulated by ubiquitin specific protease 1 (USP1).

In other embodiments, the present application relates to the use of an inhibitor of USP1 for the preparation of a medicament used in treatment, prevention, inhibition or elimination of a disease or disorder associated with cancer.

The present application also relates to the use of an inhibitor of USP1 for the preparation of a medicament used in the treatment, prevention, inhibition or elimination of a disease or condition mediated by USP1, wherein the medicament comprises a compound of Formula (I).

In another aspect, the present application relates to a method for the manufacture of a medicament for treating, preventing, inhibiting, or eliminating a disease or condition mediated by USP1, wherein the medicament comprises a compound of Formula (I).

In other embodiments, the present application relates to the use of an inhibitor of USP1 for the preparation of a medicament used in treatment, prevention, inhibition or elimination of a disease or disorder associated with cancer.

In another embodiment, the present application relates to a compound of Formula (I) or a pharmaceutical composition comprising a compound of the present application and a pharmaceutically acceptable carrier used for the treatment of cancers.

In some embodiments of the methods described herein, the cancer is selected from adrenocortical carcinoma, AIDS-related lymphoma, AIDS-related malignancies, anal cancer, cerebellar astrocytoma, extrahepatic bile duct cancer, bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell-lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, liver cancer, non-small cell lung cancer, small cell lung cancer, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (e.g., renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodennal and pineal tumors, cutaneous t-celllymphoma, testicular cancer, malignant thymoma, thyroid cancer, gestational trophoblastic tumor, urethral cancer, uterine sarcoma, vaginal cancer, vulvar cancer, and Wilms' tumor. In other embodiments, the cancer is a non-small cell lung cancer. In other embodiments of the methods described herein, the cancer is a dedifferentiated ID-driven cancer. In yet other embodiments, the cancer is a hematologic cancer. In other embodiments, the cancer is a cancer that is sensitive to USP-1 inhibiton. In yet other embodiments, the cancer is a cancer that is sensitive to USP-1 inhibiton due to a dysfunctional DNA-repair pathway.

In any of the embodiments of the application, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

In other embodiments, the cancer is selected from liposarcoma, neuroblastoma, glioblastoma, bladder cancer, adrenocortical cancer, multiple myeloma, colorectal cancer, non-small cell lung cancer, Human Papilloma Virus-associated cervical, oropharyngeal, penis, anal, thyroid or vaginal cancer or Epstein-Barr Virus-associated nasopharyngeal carcinoma, gastric cancer, rectal cancer, thyroid cancer, Hodgkin lymphoma and diffuse large B-cell lymphoma.

Another aspect of the application is directed to pharmaceutical compositions comprising a compound of Formula (I), or a pharmaceutically acceptable salt, hydrate, solvate, prodrug, stereoisomer, or tautomer thereof, and a pharmaceutically acceptable carrier. The pharmaceutical acceptable carrier may further include an excipient, diluent, or surfactant.

In one embodiment, methods of treating a disease or disorder associated with modulation of ubiquitin specific protease 1 (USP1) including, cancer, comprise administering to a patient suffering from at least one of said diseases or disorder a compound of Formula (I).

One therapeutic use of the compounds or compositions of the present application which inhibit ubiquitin specific protease 1 (USP1) is to provide treatment to patients or subjects suffering from cancer.

The disclosed compounds of the application can be administered in effective amounts to treat or prevent a disorder and/or prevent the development thereof in subjects.

Compounds of the application can be administered in therapeutically effective amounts in a combinational therapy with one or more therapeutic agents (pharmaceutical combinations) or modalities, e.g., non-drug therapies. For example, synergistic effects can occur with other anti-proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy includes the administration of the subject compounds in further combination with other biologically active ingredients (such as, but not limited to, a second and different antineoplastic agent or a second agent that targets a USP-1 independent mechanism of DNA repair) and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Application and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, and PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the application is directed to pharmaceutical compositions comprising a compound of Formula (I) and a pharmaceutically acceptable carrier. The pharmaceutical acceptable carrier may further include an excipient, diluent, or surfactant.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. Proton nuclear magnetic resonance (NMR) spectra were obtained on either Bruker or Varian spectrometers at 300 or 400 MHz. Spectra are given in ppm ($\delta$) and coupling constants, J, are reported in Hertz. Tetramethylsilane (TMS) was used as an internal standard. Mass spectra were collected using a Waters ZQ Single Quad Mass Spectrometer (ion trap ESI). Purity and low resolution mass spectral data were measured using Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, ELSD and ESI. Column: Acquity UPLC BEH C18 1.7 µm 2.1×50 mm; Flow rate 0.6 mL/min; Solvent A (95/5/0.1 10 mM ammonium formate/acetonitrile/formic acid), Solvent B (95/5/0.09 acetonitrile/water/formic acid); gradient: 5-100% B from 0 to 2 min, hold 100% B to 2.2 min, then 5% B at 2.21 min. Preparatory HPLC purifications were conducted on a Waters SunFire C18 OBD Prep Column, 100 Å, 5 µm, 19 mm×50 mm, Waters XBridge BEH C18 OBD Prep Column, 130 Å, 5 µm, 19 mm×50 mm with UV detection (Waters 2489 UV/998 PDA), Waters SunFire C18 OBD Prep Column, 100 Å, 5 µm, 19 mm×150 mm, Waters XBridge BEH Shield RP18 OBD Prep Column, 130 Å, 5 µm, 19 mm×150 mm, or Waters XSelect CSH C18 OBD Prep Column, 130 Å, 5 µm, 19 mm×150 mm at 254 nm or 220 nm using a standard solvent gradient program (see HPLC Methods 1-8 designated below). Preparatory chiral HPLC purifications were conducted using either a Phenomenex Lux 5u Cellulose-4 column, AXIA Packed 250 mm×21.2 mm, 5 µm or a Daicel CHIRALPAK® IC 20×250 mm, 5 m column. Technical specifications used for the analytical characterization of compounds are detailed in LCMS Method 1 (preparation of intermediates) or LCMS Method 2.

Preparative HPLC Aqueous Method 1 (ESI, 6 Min Method): Instruments: HPLC: Waters 2545 Binary Gradient Module. MS: Waters 3100/ZQ Mass Detector. UV: Waters 2489 UV/998 PDA.

Conditions: Mobile phase A: water with 0.1% formic acid; Mobile phase B: acetonitrile with 0.1% formic acid Column: Waters SunFire C18 OBD Prep Column, 100 Å, 5 µm, 19 mm×50 mm. Column temperature: Ambient LC gradient: Hold 0% B for 0.9 min, then 0% to 5% in 0.01 min; then 5% to 35% in 3.84 min; then 35% to 100% in 0.01 min; hold at 100% for 0.74 min, then 100% to 0% in 0.01 min; hold at 0% for 0.49 min.

LC Flow rate: 23 mL/min binary pump, 2 mL/min acetonitrile at column dilution

UV wavelength: 220 nm and 254 nm

Ionization Mode: ESI positive/negative

Preparative HPLC Aqueous Method 2 (ESI, 6 min method): Instruments: HPLC: Waters 2545 Binary Gradient Module. MS: Waters 3100/ZQ Mass Detector. UV: Waters 2489 UV/998 PDA.

Conditions: Mobile phase A: water with 0.1% ammonium hydroxide; Mobile phase B: acetonitrile with 0.1% ammonium hydroxide
Column: Waters XBridge BEH C18 OBD Prep Column, 130 Å, 5 μm, 19 mm×50 mm Column temperature: Ambient
LC gradient: Hold 0% B for 0.9 min, then 0% to 5% in 0.01 min; then 5% to 35% in 3.84 min; then 35% to 100% in 0.01 min; hold at 100% for 0.74 min, then 100% to 0% in 0.01 min; hold at 0% for 0.49 min.
LC Flow rate: 23 mL/min binary pump, 2 mL/min acetonitrile at column dilution
UV wavelength: 220 nm and 254 nm
Ionization Mode: ESI positive/negative
Preparative HPLC Polar Method 3 (ESI, 6 Main Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% formic acid; Mobile phase B: acetonitrile with 0.1% formic acid
Column: Waters SunFire C18 OBD Prep Column, 100 Å, 5 μm, 19 mm×50 mm
Column temperature: Ambient
LC gradient: 15% for 0.9 min, then 15% to 25% in 0.01 min, then 25% to 65% in 3.84 min; and 65% to 100% in 0.01 min; hold at 100% for 0.74 min, then 100% to 0% in 0.01 min; hold at 0% for 0.49 min.
LC Flow rate: 23 mL/min binary pump, 2 mL/min acetonitrile at column dilution
UV wavelength: 220 nm and 254 nm
Ionization Mode: ESI positive/negative
Preparative HPLC Polar Method 4 (ESI, 6 Main Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% ammonium hydroxide; Mobile phase B: acetonitrile with 0.1% ammonium hydroxide
Column: Waters XBridge BEH C18 OBD Prep Column, 130 Å, 5 μm, 19 mm×50 mm Column temperature: Ambient
LC gradient: Hold 15% B for 0.9 min, then 15% to 25% in 0.01 min; then 25% to 65% in 3.84 min; then 65 to 100% to 100% in 0.01 min; hold at 100% for 0.74 min, then 100% to 0% in 0.01 min; hold at 0% for 0.49 min.
LC Flow rate: 23 mL/min binary pump, 2 mL/min acetonitrile at column dilution UV wavelength: 220 nm and 254 nm
Ionization Mode: ESI positive/negative
Preparative HPLC Generic Method 5 (ESI, 6 Min Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% formic acid; Mobile phase B: acetonitrile with 0.1% formic acid
Column: Waters SunFire C18 OBD Prep Column, 100 Å, 5 μm, 19 mm×50 mm
Column temperature: Ambient
LC gradient: Hold 35% B for 0.9 min, then 35% to 45% in 0.01 min; then 45% to 85% in 3.84 min; then 85 to 100% to 100% in 0.01 min; hold at 100% for 0.74 min, then 100% to 0% in 0.01 min; hold at 0% for 0.49 min.
LC Flow rate: 23 mL/min binary pump, 2 mL/min acetonitrile at column dilution
UV wavelength: 220 nm and 254 nm
Ionization Mode: ESI positive/negative
Preparative HPLC Generic Method 6 (ESI, 6 Min Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% ammonium hydroxide; Mobile phase B: acetonitrile with 0.1% ammonium hydroxide
Column: Waters XBridge BEH C18 OBD Prep Column, 130 Å, 5 μm, 19 mm×50 mm
Column temperature: Ambient
LC gradient: Hold 35% B for 0.9 min, then 35% to 45% in 0.01 min; then 45% to 85% in 3.84 min; then 85 to 100% to 100% in 0.01 min; hold at 100% for 0.74 min, then 100% to 0% in 0.01 min; hold at 0% for 0.49 min.
LC Flow rate: 23 mL/min binary pump, 2 mL/min acetonitrile at column dilution
UV wavelength: 220 nm and 254 nm
Ionization Mode: ESI positive/negative
Preparative HPLC Non-Polar Method 7 (ESI, 6 Min Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% formic acid; Mobile phase B: acetonitrile with 0.1% formic acid
Column: Waters SunFire C18 OBD Prep Column, 100 Å, 5 μm, 19 mm×50 mm
Column temperature: Ambient
LC gradient: Hold 50% B for 0.9 min, then 50% to 60% in 0.01 min; then 60% to 100% in 3.84 min; then hold at 100% for 0.75 min, then 100% to 0% in 0.01 min; hold at 0% for 0.49 min.
LC Flow rate: 23 mL/min binary pump, 2 mL/min acetonitrile at column dilution
UV wavelength: 220 nm and 254 nm
Ionization Mode: ESI positive/negative
Preparative HPLC Non-Polar Method 8 (ESI, 6 Min Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% ammonium hydroxide; Mobile phase B: acetonitrile with 0.1% ammonium hydroxide
Column: Waters XBridge BEH C18 OBD Prep Column, 130 Å, 5 μm, 19 mm×50 mm
Column temperature: Ambient
LC gradient: Hold 50% B for 0.9 min, then 50% to 60% in 0.01 min; then 60% to 100% in 3.84 min; then hold at 100% for 0.75 min, then 100% to 0% in 0.01 min; hold at 0% for 0.49 min.
LC Flow rate: 23 mL/min binary pump, 2 mL/min acetonitrile at column dilution
UV wavelength: 220 nm and 254 nm
Ionization Mode: ESI positive/negative
LCMS Method 1 (ESI, 2.5 Min Method):
Instruments: MS: Waters ZQ Mass Detector, HPLC: Waters Acquity Binary Solvent Manager; UV: Waters Acquity PDA; LSD: Waters Acquity ELSD
Conditions: Mobile phase A: 95% water/5% acetonitrile with 0.1% formic acid in 10 mM ammonium formate; Mobile phase B: 95% acetonitrile/5% water with 0.09% formic acid
Column: Waters Acquity UPLC BEH C18, 1.7 um, 2.1×50 mm
Column Temperature: 35° C.
LC gradient: 5-100% B over 2.0 min, hold 100% B to 2.2 min
LC Flow Rate: 0.6 mL/min
UV Wavelength: 220 nm
Ionization Mode: ESI positive/negative LCMS Method 2 (ESI, 2.5 Min Method):
Instruments: MS: Waters ZQ Mass Detector; HPLC: Waters Acquity Binary Solvent Manager; UV: Waters Acquity PDA; ELSD: Waters Acquity ELSD
Conditions: Mobile phase A: 95% water/5% acetonitrile with 0.1% formic acid; Mobile phase B: 95% acetonitrile/5% water with 0.085% formic acid
Column: Waters Acquity UPLC CSH C18, 1.7 um, 2.1×50 mm
Column Temperature: 35° C.
LC Gradient: 5-100% B over 2.0 min, hold 100% B to 2.2 min
LC Flow Rate: 0.6 mL/min
UV Wavelength: 220 nm
Ionization Mode: ESI positive/negative
Abbreviations used in the following examples and elsewhere herein are:
CDI 1,1'-carbonyldiimidazole
DCE 1,2-dichloroethane
DCM dichloromethane
DIEA N,N-diisopropylethylamine
DMF N,N-dimethylformamide
DMSO dimethylsulfoxide
dppf bis(diphenylphosphino)ferrocene
ESI electrospray ionization
EtOAc ethyl acetate
EtOH ethanol
h hours
HATU 1-[Bis(dimethylamino)methylene]-1H-1,2,3-triazolo[4,5-b]pyridinium 3-oxid hexafluorophosphate
HBTU N,N,N',N'-Tetramethyl-O-(1H-benzotriazol-1-yl)uronium hexafluorophosphate
HCl hydrogen chloride
HPLC high performance liquid chromatography
i-PrOH isopropyl alcohol
LCMS liquid chromatography-mass spectrometry
Me4tButylXPhos 2-Di-tert-butylphosphino-3,4,5,6-tetramethyl-2',4',6'-triisopropyl-1,1'-biphenyl
MeOH methanol
min minutes
MS mass spectrometry
NaOH sodium hydroxide
PdAMPHOS Dichlorobis{[4-(N,N-dimethylamino)phenyl]di-t-butylphosphino}palladium(II)
$Pd_2(dba)_3$ tris(dibenzylideneacetone)dipalladium
$Pd(dppf)Cl_2 \cdot CH_2Cl_2$ [1,1'-Bis(diphenylphosphino)ferrocene]dichloropalladium(II), complex with dichloromethane
PE Petroleum ether $R_f$ retention factor
Rt retention time
RuPhos 2-Dicyclohexylphosphino-2',6'-diisopropoxybiphenyl
RuPhos precatalyst Chloro-(2-dicyclohexylphosphino-2',6'-diisopropoxy-1,1'-biphenyl)[2-(2-aminoethyl)phenyl]palladium(II)-methyl-t-butyl ether adduct
RuPhos Pd G3 (2-Dicyclohexylphosphino-2',6'-diisopropoxy-1,1'-biphenyl)[2-(2'-amino-1,1'-biphenyl)]palladium(II) methanesulfonate
tBuXPhos Pd G3 [(2-Di-tert-butylphosphino-2',4',6'-triisopropyl-1,1'-biphenyl)-2-(2'-amino-1,1'-biphenyl)]palladium(II) methanesulfonate
tBuXPhos 2-Di-tert-butylphosphino-2',4',6'-triisopropylbiphenyl
THF tetrahydrofuran
TFA trifluoroacetic acid
Xantphos 4,5-Bis(diphenylphosphino)-9,9-dimethylxanthene
XPhos 2-dicyclohexylphosphino-2',4',6'-triisopropylbiphenyl
XPhos Pd G1 (2-Dicyclohexylphosphino-2',4',6'-triisopropyl-1,1'-biphenyl)[2-(2-aminoethyl)phenyl)]palladium(II) chloride
XPhos Pd G2 Chloro(2-dicyclohexylphosphino-2',4',6'-triisopropyl-1,1'-biphenyl)[2-(2'-amino-1,1'-biphenyl)]palladium(II)

Example 1: Intermediate B-1. 2-(3-Fluoro-2-isopropylphenyl)-4,4,5,5-tetramethyl-1,3,2-dioxaborolane

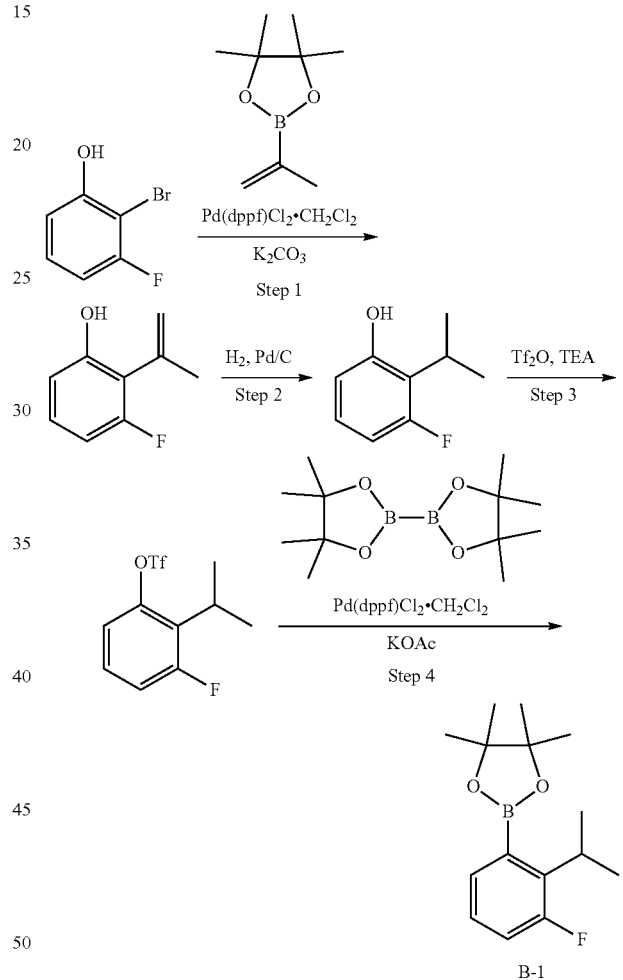

Step 1. 3-Fluoro-2-(prop-1-en-2-yl)phenol

A mixture of 2-bromo-3-fluorophenol (2 g, 10.47 mmol), 4,4,5,5-tetramethyl-2-(prop-1-en-2-yl)-1,3,2-dioxaborolane (1.95 g, 11.60 mmol), $Pd(dppf)Cl_2 \cdot CH_2Cl_2$ (858 mg, 1.05 mmol), potassium carbonate (2.90 g, 21.00 mmol), water (4 mL) and 1,4-dioxane (20 mL) was stirred for 16 h at 60° C. under an atmosphere of nitrogen. After cooling to ambient temperature, the reaction mixture was concentrated under vacuum and the residue was purified by silica gel chromatography eluting with EtOAc/PE (1:2) to afford 500 mg (31%) of 3-fluoro-2-(prop-1-en-2-yl)phenol as light brown oil. MS (ESI) m/z 153 [M+H]$^+$.

Step 2. 3-Fluoro-2-isopropylphenol

A flask containing 3-fluoro-2-(prop-1-en-2-yl)phenol (500 mg, 3.29 mmol) and palladium on carbon (10 wt. %, 500 mg) in MeOH (20 mL) was evacuated and back-filled with hydrogen three times and then charged with hydrogen. The resulting mixture was stirred for 16 h at ambient temperature, then was filtered and concentrated under vacuum resulting in 500 mg (99%) of 3-fluoro-2-isopropylphenol. MS (ESI) m/z 155 [M+H]$^+$.

Step 3. 3-Fluoro-2-isopropylphenyl trifluoromethanesulfonate

A solution of 3-fluoro-2-(propan-2-yl)phenol (500 mg, 3.24 mmol) and triethylamine (394 mg, 3.89 mmol) in DCM (8 mL) at 0° C. was treated dropwise with trifluoromethanesulfonic anhydride (1 g, 3.55 mmol). The resulting solution was stirred for 2 h at 0° C., whereupon the reaction mixture was poured into water (10 mL), and extracted with DCM (2×20 mL). The organic layers were combined, washed with brine (10 mL), dried over anhydrous sodium sulfate, filtered and concentrated under vacuum. The residue was purified by silica gel chromatography (eluting with a gradient of 1-10% EtOAc/PE) resulting in 570 mg (61%) of 3-fluoro-2-isopropylphenyl trifluoromethanesulfonate. $^1$H NMR (300 MHz, DMSO-d$_6$) δ 7.52-7.43 (m, 1H), 7.40-7.33 (m, 1H), 7.25 (d, J=8.4 Hz, 1H), 3.29-3.17 (m, 1H), 1.32 (d, J=6.90 Hz, 3H), 1.31 (d, J=6.9 Hz, 3H).

Step 4. 2-(3-Fluoro-2-isopropylphenyl)-4,4,5,5-tetramethyl-1,3,2-dioxaborolane A mixture of 3-fluoro-2-(propan-2-yl)phenyl trifluoromethanesulfonate (550 mg, 1.92 mmol), 4,4,5,5-tetramethyl-2-(tetramethyl-1,3,2-dioxaborolan-2-yl)-1,3,2-dioxaborolane (977 mg, 3.85 mmol), Pd(dppf)Cl$_2$.CH$_2$Cl$_2$ (155 mg, 0.19 mmol), potassium acetate (377 mg, 3.84 mmol) and 1,4-dioxane (20 mL) was stirred for 16 h at 80° C. under an atmosphere of nitrogen. The mixture was cooled to ambient temperature, concentrated under vacuum, and was purified by silica gel chromatography eluting with EtOAc/PE (1/100-1/10) to afford 400 mg (79%) of 2-(3-fluoro-2-isopropylphenyl)-4,4,5,5-tetramethyl-1,3,2-dioxaborolane. MS (ESI) m/z 265 [M+H]$^+$.

Intermediate B-2. 2-Isopropyl-3-(4,4,5,5-tetramethyl-1,3,2-dioxaborolan-2-yl)pyridine

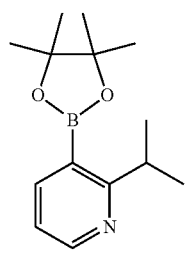

B-2

2-Isopropyl-3-(4,4,5,5-tetramethyl-1,3,2-dioxaborolan-2-yl)pyridine was synthesized according to Example 1, substituting 2-bromopyridin-3-ol for 2-bromo-3-fluorophenol. MS (ESI) m/z 248 [M+H]$^+$.

Intermediate B-3. 2-(2-Fluoro-6-isopropylphenyl)-4,4,5,5-tetramethyl-1,3,2-dioxaborolane

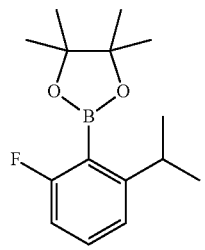

B-3

2-(2-Fluoro-6-isopropylphenyl)-4,4,5,5-tetramethyl-1,3,2-dioxaborolane was synthesized from 2-bromo-6-fluorophenol according to the procedure outlined for Example 1. MS (ESI) m/z 264 [M+H]$^+$

Intermediate B-4. 2-(2-(Difluoromethyl)phenyl)-4,4,5,5-tetramethyl-1,3,2-dioxaborolane

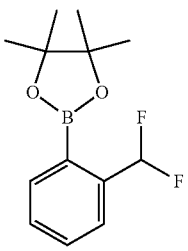

B-4

2-(2-(Difluoromethyl)phenyl)-4,4,5,5-tetramethyl-1,3,2-dioxaborolane was prepared from 1-bromo-2-(difluoromethyl)benzene according to Step 4 of Example 1. Purification by prep-TLC (eluting with 2% EtOAc/PE) afforded the title compound. MS (ESI) m/z 254.1 [M+H]$^+$

Intermediate B-5. 1-Methyl-7-(4,4,5,5-tetramethyl-1,3,2-dioxaborolan-2-yl)indoline

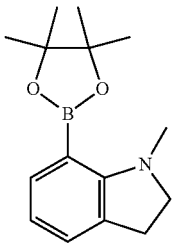

B-5

1-Methyl-7-(4,4,5,5-tetramethyl-1,3,2-dioxaborolan-2-yl)indoline was synthesized from 7-bromoindoline following Step 4 of Example 1. MS (ESI) m/z 259.1 [M+H]$^+$

Intermediate B-6. 1-(2-(4,4,5,5-Tetramethyl-1,3,2-dioxaborolan-2-yl)phenyl)ethan-1-one

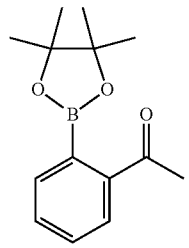

B-6

1-(2-(4,4,5,5-Tetramethyl-1,3,2-dioxaborolan-2-yl)phenyl)ethan-1-one was synthesized from 1-(2-bromophenyl)ethan-1-one following Step 4 of Example 1. MS (ESI) m/z 246.8 [M+H]$^+$

Intermediate B-7. 2-(2-(1-Methoxyethyl)phenyl)-4,4,5,5-tetramethyl-1,3,2-dioxaborolane

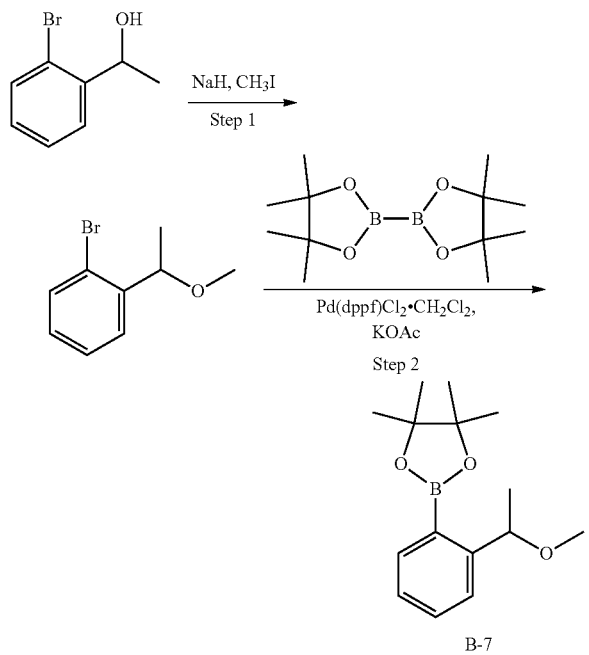

B-7

Step 1. 1-Bromo-2-(1-methoxyethyl)benzene

1-Bromo-2-(1-methoxyethyl)benzene was prepared from 1-(2-bromophenyl)ethan-1-ol following the conditions in Example 9. MS (ESI) m/z 214.0, 215.9 [M+H]$^+$.

Step 2. 2-(2-(1-Methoxyethyl)phenyl)-4,4,5,5-tetramethyl-1,3,2-dioxaborolane 2-(2-(1-Methoxyethyl)phenyl)-4,4,5,5-tetramethyl-1,3,2-dioxaborolane was prepared from 1-bromo-2-(1-methoxyethyl)benzene following Step 4 of Example 1. MS (ESI) m/z 262.1 [M+H]$^+$.

Intermediate B-8. 2-(2-Cyclopropylphenyl)-4,4,5,5-tetramethyl-1,3,2-dioxaborolane

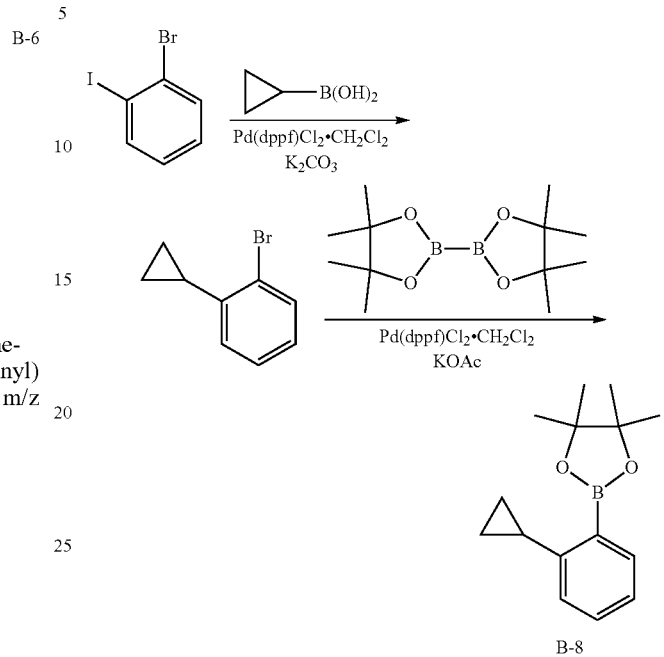

B-8

Step 1. 1-Bromo-2-cyclopropylbenzene

1-Bromo-2-cyclopropylbenzene was synthesized according to Step 1 of Example 1, employing 1-bromo-2-iodobenzene and cyclopropylboronic acid. $^1$H NMR (400 MHz, CD$_3$OD) δ 7.53-7.49 (m, 1H), 7.24-7.19 (m, 1H), 7.06-6.93 (m, 2H), 2.18-2.10 (m, 1H), 1.01-0.96 (m, 2H), 0.68-0.53 (m, 2H).

Step 2. 2-(2-Cyclopropylphenyl)-4,4,5,5-tetramethyl-1,3,2-dioxaborolane

A mixture of 1-bromo-2-cyclopropylbenzene (11.00 g, 55.82 mmol), Pd(dppf)Cl$_2$.CH$_2$Cl$_2$ (4.56 g, 5.58 mmol), potassium acetate (16.43 g, 167.45 mmol), 4,4,5,5-tetramethyl-2-(tetramethyl-1,3,2-dioxaborolan-2-yl)-1,3,2-dioxaborolane (17.01 g, 66.98 mmol) and 1,4-dioxane (500 mL) was stirred for 16 h at 90° C. under an atmosphere of nitrogen. After cooling to ambient temperature, the reaction mixture was poured into water (200 mL) and was extracted with EtOAc (3×200 mL). The organic layers were combined, dried over anhydrous sodium sulfate, filtered and concentrated under vacuum. The residue was purified by silica gel chromatography (eluting with 0% to 0.1% EtOAc/PE), the product was further purified by C18-reversed phase silica gel chromatography (eluting 5% to 100% acetonitrile/aqueous Sodium hydride CO$_3$ solution (10 mmol)). This resulted in 6.1 g (44%) of 2-(2-cyclopropylphenyl)-4,4,5,5-tetramethyl-1,3,2-dioxaborolane as a yellow oil. $^1$H NMR (400 MHz, CD$_3$OD) δ 7.70-7.63 (m, 1H), 7.37-7.19 (m, 1H), 7.18-7.06 (m, 1H), 6.91-6.81 (m, 1H), 2.74-2.62 (m, 1H), 1.38-1.35 (m, 12H), 1.00-0.89 (m, 2H), 0.72-0.60 (m, 2H). MS (ESI) m/z 244.9 [M+H]$^+$.

Intermediate B-9. 2-Cyclopropyl-3-(4,4,5,5-tetramethyl-1,3,2-dioxaborolan-2-yl)pyridine

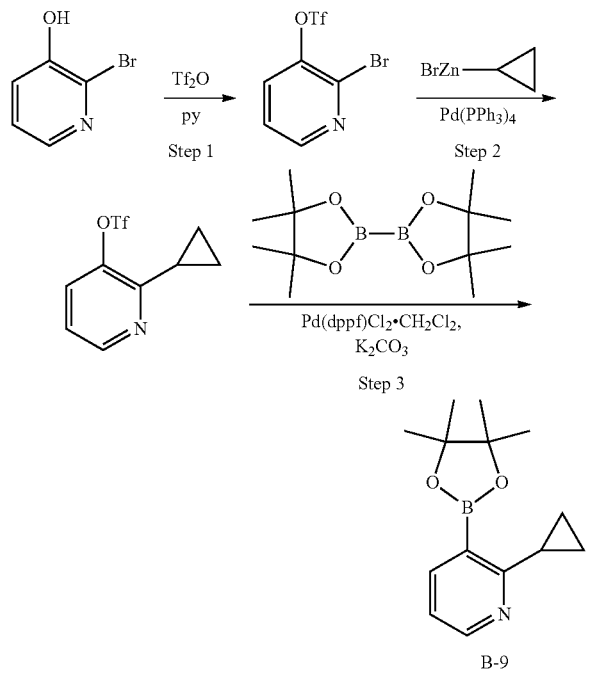

B-9

Step 1. 2-Bromopyridin-3-yl trifluoromethanesulfonate

A mixture of 2-bromopyridin-3-ol (25 g, 143.68 mmol) and pyridine (145 mL) at 0° C. was treated by dropwise addition of trifluoromethanesulfonic anhydride (24.2 mL, 143.24 mmol) and the resulting solution was stirred overnight at ambient temperature. The reaction mixture was poured into saturated sodium bicarbonate solution (500 mL) and was then extracted with DCM (200 mL). The organic layers were combined, dried over anhydrous sodium sulfate, filtered and concentrated under vacuum. The residue was purified by vacuum distillation under reduced pressure (−0.2 MPa). The fraction collected at 130° C. afforded 25 g (57%) of 2-bromopyridin-3-yl trifluoromethanesulfonate as a colorless oil. MS (ESI) m/z 304.9, 306.9 [M]$^+$.

Step 2. 2-Cyclopropylpyridin-3-yl trifluoromethanesulfonate

Under nitrogen, a mixture of 2-bromopyridin-3-yl trifluoromethanesulfonate (5.0 g, 16.34 mmol) and tetrakis(triphenylphosphine)palladium(0) (944 mg, 0.82 mmol) in THF (25 mL) was treated with bromo(cyclopropyl)zinc (43 mL of a 0.5 M solution in THF, 21.3 mmol) at ambient temperature. The resulting solution was stirred for 16 h at 70° C. After cooling to ambient temperature, the reaction mixture was poured into saturated sodium bicarbonate solution (100 mL) and was extracted with EtOAc (3×100 mL). The organic layers were combined, dried over anhydrous sodium sulfate, filtered and concentrated under vacuum. The residue was purified by silica gel chromatography (eluting with 5% EtOAc/PE) to afford 1.9 g (44%) of 2-cyclopropylpyridin-3-yl trifluoromethanesulfonate as a colorless oil. MS (ESI) m/z 267.0 [M+H]$^+$.

Step 3. 2-Cyclopropyl-3-(4,4,5,5-tetramethyl-1,3,2-dioxaborolan-2-yl)pyridine Under nitrogen, a mixture of 2-cyclopropylpyridin-3-yl trifluoromethanesulfonate (5 g, 18.71 mmol), 4,4,5,5-tetramethyl-2-(tetramethyl-1,3,2-dioxaborolan-2-yl)-1,3,2-dioxaborolane (5.71 g, 22.49 mmol), potassium carbonate (5.25 g, 37.99 mmol) and Pd(dppf)Cl$_2$·CH$_2$Cl$_2$ (1.56 g, 1.91 mmol) in 1,4-dioxane (80 mL) was stirred for 20 h at 100° C. After cooling to ambient temperature, the reaction mixture was poured into EtOAc (250 mL), washed with brine (100 mL), dried over anhydrous sodium sulfate, filtered and concentrated under vacuum. The residue was initially purified by silica gel chromatography (eluting with a gradient of 0-15% EtOAc/PE), then was further purified by C18-reversed phase silica gel chromatography (eluting with 0% to 35% acetonitrile/10 mmol aqueous NH$_4$HCO$_3$ solution) resulting in 3 g (65%) of 2-cyclopropyl-3-(tetramethyl-1,3,2-dioxaborolan-2-yl)pyridine as a brown oil. $^1$H NMR (400 MHz, CDCl$_3$) δ 8.46-8.44 (m, 1H), 7.98-7.96 (m, 1H), 7.00-6.97 (m, 1H), 2.84-2.89 (m, 1H), 1.36 (s, 12H), 1.11-1.07 (m, 2H), 0.98-0.95 (m, 2H). MS (ESI) m/z 164.2 [M+H-C$_6$H$_{10}$]$^+$.

Example 2: Intermediate B-10. 4-(1H-1,2,3-triazol-1-yl)benzonitrile and Intermediate B-11. 4-(2H-1,2,3-triazol-2-yl)benzonitrile

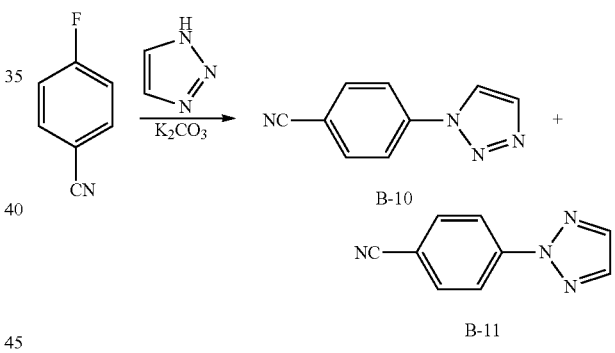

A mixture of 4-fluorobenzonitrile (20 g, 165.14 mmol), 1H-1,2,3-triazole (13 g, 188.23 mmol) and potassium carbonate (46 g, 332.83 mmol) in DMF (50 mL) was stirred for 18 h at 80° C. After cooling to ambient temperature, the reaction mixture was poured into water (200 mL) and was then extracted with EtOAc (3×50 mL). The organic layers were combined, dried over anhydrous sodium sulfate, filtered and concentrated under vacuum. The residue was purified by silica gel chromatography (eluting with 3:1 EtOAc/PE) to afford 10 g (36%) of 4-(1H-1,2,3-triazol-1-yl)benzonitrile as a white solid, and 9 g (32%) of 4-(2H-1,2,3-triazol-2-yl)benzonitrile as a white solid.

Intermediate B-10, 4-(1H-1,2,3-triazol-1-yl)benzonitrile (R$_f$=0.2 in 50% EtOAc/PE): $^1$H NMR (300 MHz, DMSO-d$_6$) δ 8.24 (s, 2H), 8.22-8.16 (m, 2H), 8.09-8.00 (m, 2H). MS (ESI) m/z 171 [M+H]$^+$.

Intermediate B-11, 4-(2H-1,2,3-triazol-2-yl)benzonitrile ($R_f$=0.8 in 50% EtOAc/PE): $^1$H NMR (300 MHz, DMSO-$d_6$) δ 9.00 (d, J=1.2 Hz, 1H), 8.25-8.05 (m, 4H), 8.04 (d, J=1.2 Hz, 1H). MS (ESI) m/z 171 [M+H]$^+$.

Example 3: Intermediate B-12. (4-(1H-1,2,3-Triazol-1-yl)phenyl)methanamine

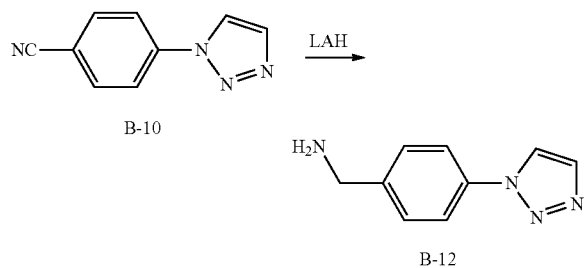

A solution of Intermediate B-10 (8 g, 47.01 mmol) in THF (20 mL) at 0° C. was treated batchwise with lithium aluminum hydride (5.7 g, 150.20 mmol). Once addition was complete, the resulting solution was stirred for 2 h at 0° C. then was quenched by addition of sodium sulfate decahydrate. The resulting mixture was filtered, concentrated under vacuum and was purified by silica gel chromatography (eluting with 10:1 DCM/MeOH) to afford [4-(1H-1,2,3-triazol-1-yl)phenyl]methanamine (7.5 g, white solid, 92%). MS (ESI) m/z 175 [M+H]$^+$.

Intermediate B-13. (4-(2H-1,2,3-Triazol-2-yl)phenyl)methanamine

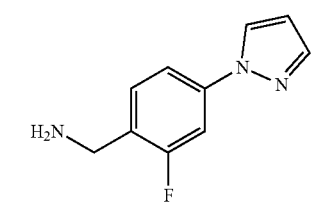

(4-(2H-1,2,3-Triazol-2-yl)phenyl)methanamine was synthesized from 4-(2H-1,2,3-triazol-2-yl)benzonitrile following Example 3. MS (ESI) m/z 175 [M+H]$^+$.

Example 4: Intermediate B-14. (2-Chloro-4-(1H-pyrazol-1-yl)phenyl)methanamine

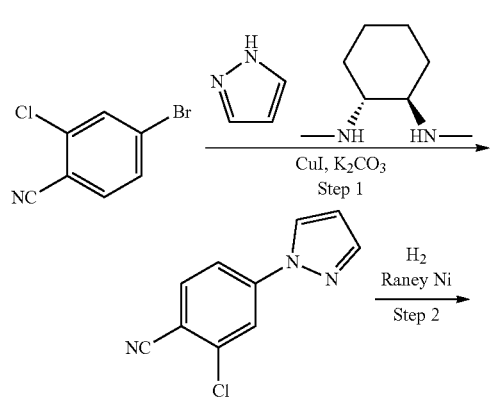

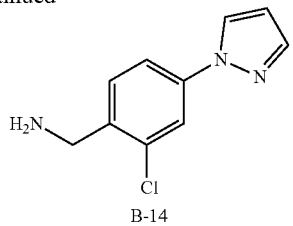

Step 1. 2-Chloro-4-(1H-pyrazol-1-yl)benzonitrile

Under an atmosphere of nitrogen was placed 4-bromo-2-chlorobenzonitrile (4.3 g, 19.86 mmol), 1H-pyrazole (2 g, 29.38 mmol), copper(I) iodide (760 mg, 3.99 mmol), trans-N,N'-dimethylcyclohexane-1,2-diamine (1.2 g, 8.44 mmol), potassium carbonate (5.5 g, 39.79 mmol) and 1,4-dioxane (30 mL). The resulting mixture was stirred for 16 h at 110° C. After cooling to ambient temperature, the reaction mixture was filtered and concentrated under vacuum. The residue was purified by silica gel chromatography (eluting with 1:1 EtOAc/PE) to afford 3 g (74%) of 2-chloro-4-(1H-pyrazol-1-yl)benzonitrile as a yellow solid. MS (ESI) m/z 204 [M+H]$^+$.

Step 2. (2-Chloro-4-(1H-pyrazol-1-yl)phenyl)methanamine

A mixture of 2-chloro-4-(1H-pyrazol-1-yl)benzonitrile (3 g, 14.73 mmol), Raney nickel (3 g) and MeOH (40 mL) was evacuated and backfilled with hydrogen several times and was then charged with hydrogen. The resulting mixture was stirred for 2 h at ambient temperature, then was filtered and concentrated under vacuum to afford 1 g (33%) of [2-chloro-4-(1H-pyrazol-1-yl)phenyl]methanamine as a green solid. MS (ESI) m/z 208 [M+H]$^+$.

Intermediate B-15. (2-Fluoro-4-(1H-pyrazol-1-yl)phenyl)methanamine (2-Fluoro-4-(1H-pyrazol-1-yl)phenyl)methanamine was synthesized from 4-bromo-2-fluorobenzonitrile according to Example 4. MS (ESI) m/z 192 [M+H]$^+$.

Example 5: Intermediate B-16. 1-(4-(1H-Pyrazol-1-yl)phenyl)ethan-1-amine

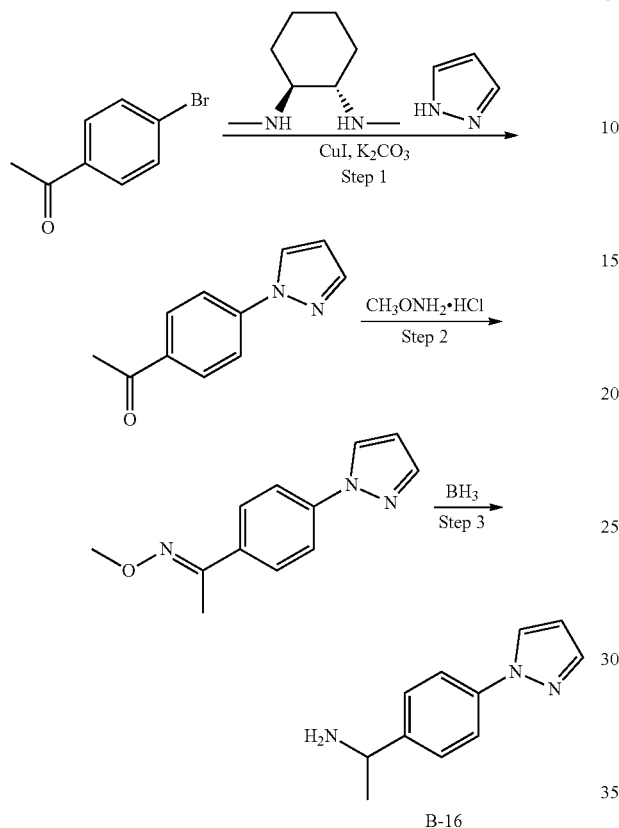

B-16

Step 1. 1-(4-(1H-Pyrazol-1-yl)phenyl)ethan-1-one 1-(4-(1H-Pyrazol-1-yl)phenyl)ethan-1-one was prepared from 1-(4-bromophenyl)ethan-1-one according to Step 1 of Example 4. MS (ESI) m/z 187 [M+H]$^+$.

Step 2. 1-(4-(1H-Pyrazol-1-yl)phenyl)ethan-1-one O-methyl oxime

A mixture of 1-(4-(1H-pyrazol-1-yl)phenyl)ethan-1-one (3.2 g, 17.30 mmol), O-methylhydroxylamine hydrochloride (2.14 g, 25.62 mmol), acetic acid (6 mL) and EtOH (60 mL) was stirred for 16 h at ambient temperature. The reaction mixture was concentrated under vacuum, then was purified by silica gel chromatography (eluting with 1:1 EtOAc/PE) to afford 3.0 g (81%) of 1-(4-(1H-pyrazol-1-yl)phenyl)ethan-1-one O-methyl oxime as a white solid. MS (ESI) m/z 216 [M+H]$^+$.

Step 3. 1-(4-(1H-Pyrazol-1-yl)phenyl)ethan-1-amine

A mixture of 1-(4-(1H-pyrazol-1-yl)phenyl)ethan-1-one O-methyl oxime (3.0 g, 13.98 mmol) was treated with a solution of borane in THF (1 M, 40 mL, 40 mmol) and the resulting solution was stirred for 16 h at 80° C. After cooling to ambient temperature, MeOH (20 mL) was added and the resulting solution was stirred for additional 3 h. The mixture was concentrated under vacuum and purified by silica gel chromatography (eluting with 10:1 DCM/MeOH) to afford 2.0 g (77%) of 1-(4-(1H-pyrazol-1-yl)phenyl)ethan-1-amine as a colorless oil. MS (ESI) m/z 188 [M+H]$^+$.

Example 6: Intermediate B-17. (4-(1H-Pyrazol-1-yl)phenyl)methanamine

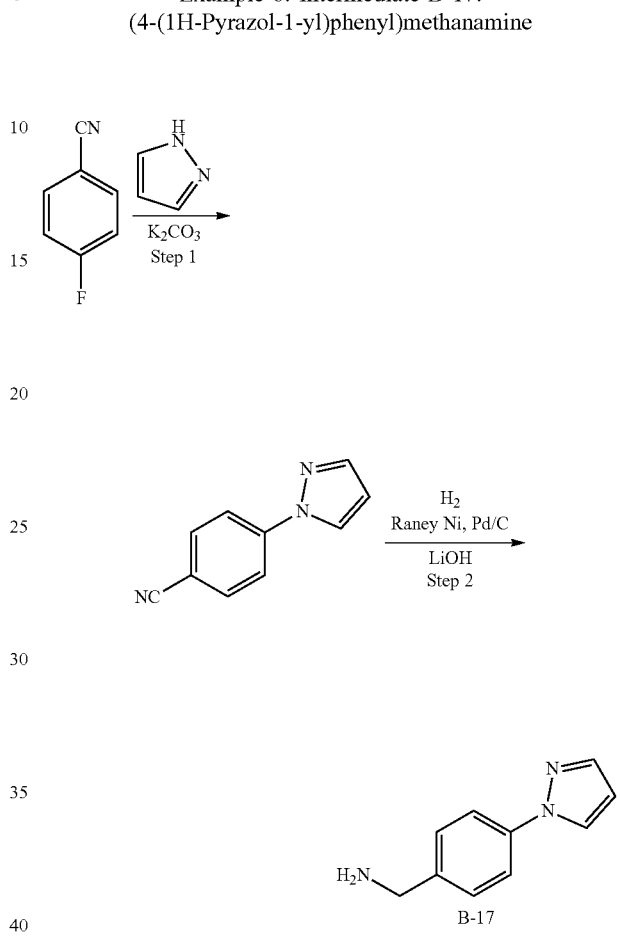

B-17

Step 1. 4-(1H-Pyrazol-1-yl)benzonitrile

A mixture of 1H-pyrazole (15 g, 220.34 mmol), 4-fluorobenzonitrile (27 g, 222.93 mmol), potassium carbonate (60.7 g, 439.19 mmol) in DMF (200 mL) was stirred for 16 h at 110° C. After cooling to ambient temperature, the reaction mixture was poured into water (500 mL) and the resulting solids were collected by filtration and dried under vacuum, resulting in 30 g (80%) of 4-(1H-pyrazol-1-yl)benzonitrile. MS (ESI) m/z 170 [M+H]$^+$.

Step 2. (4-(1H-Pyrazol-1-yl)phenyl)methanamine

A mixture of 4-(1H-pyrazol-1-yl)benzonitrile (15 g, 88.66 mmol), Raney nickel (10 g), palladium on carbon (10 wt. %, 1 g) and lithium hydroxide (1 g, 41.75 mmol) in EtOAc (200 mL) was evacuated and back-filled with hydrogen several times and then charged with hydrogen. The resulting mixture was stirred for 16 h at ambient temperature, then was filtered and concentrated under vacuum. The residue was purified by silica gel chromatography (eluting with a gradient of 1-10% DCM/MeOH) resulting in 8 g (52%) of (4-(1H-pyrazol-1-yl)phenyl)methanamine. MS (ESI) m/z 174 [M+H]$^+$.

Example 7: Intermediate B-18. tert-Butyl 4-(1-(4-(aminomethyl)phenyl)-1H-pyrazol-4-yl)piperidine-1-carboxylate

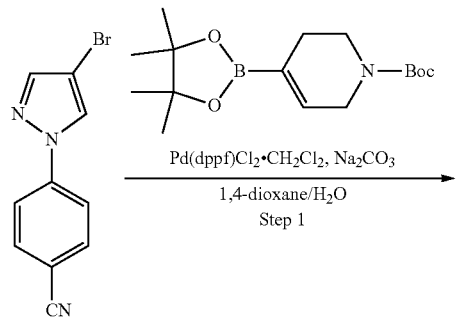

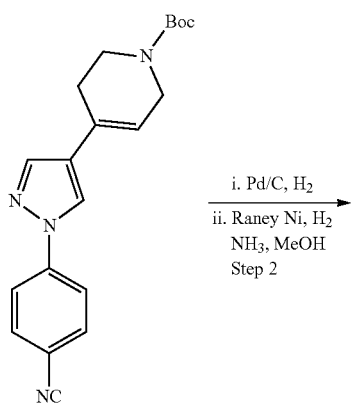

Step 1. tert-Butyl 4-(1-(4-cyanophenyl)-1H-pyrazol-4-yl)-3,6-dihydropyridine-1 (2H)-carboxylate In a 250 mL round-bottom flask purged and maintained with an inert atmosphere of nitrogen, a mixture of 4-(4-bromo-1H-pyrazol-1-yl)benzonitrile (prepared from 4-bromo-1H-pyrazole following Step 1 of Example 6) (2.4 g, 9.67 mmol), tert-butyl 4-(4,4,5,5-tetramethyl-1,3,2-dioxaborolan-2-yl)-3,6-dihydropyridine-1(2H)-carboxylate (3.59 g, 11.61 mmol), Pd(dppf)Cl$_2$·CH$_2$Cl$_2$ (1.19 g, 1.46 mmol), potassium carbonate (4 g, 28.94 mmol), 1,4-dioxane (70 mL) and water (16 mL) was stirred at 80° C. for 16 h. After cooling to room temperature, the reaction mixture was poured into water (50 mL) and was extracted with ethyl acetate (3×50 mL). The organic layers were combined, dried over anhydrous sodium sulfate, filtered and concentrated under vacuum. The residue was purified by silica gel chromatography (eluting with 1/2 ethyl acetate/petroleum ether) to afford 3.3 g (97%) of tert-butyl 4-(1-(4-cyanophenyl)-1H-pyrazol-4-yl)-3,6-dihydropyridine-1(2H)-carboxylate as a brown solid. MS (ESI) m/z 351.0 [M+H]$^+$.

Step 2. tert-Butyl 4-(1-(4-(aminomethyl)phenyl)-1H-pyrazol-4-yl)piperidine-1-carboxylate A mixture of tert-butyl 4-(1-(4-cyanophenyl)-1H-pyrazol-4-yl)-3,6-dihydropyridine-1(2H)-carboxylate (1 g, 2.85 mmol), methanol (100 mL) and palladium on carbon (10 wt. % loading, 500 mg) was placed under an atmosphere of hydrogen and was stirred for 30 min at ambient temperature. The reaction mixture was filtered and concentrated under vacuum. The residue was treated with a solution of ammonia in methanol (7 M, 20 mL) and Raney Ni (500 mg), placed under an atmosphere of hydrogen, and stirred for 1 h at ambient temperature. The reaction mixture was filtered and concentrated under vacuum to afford 0.8 g (79%) of tert-butyl 4-(1-(4-(aminomethyl)phenyl)-1H-pyrazol-4-yl)piperidine-1-carboxylate as a colorless oil. MS (ESI) m/z 357.2 [M+H]$^+$.

Example 8: Intermediate B-19. 2-(4-(1H-Pyrazol-1-yl)phenyl)cyclobutan-1-amine

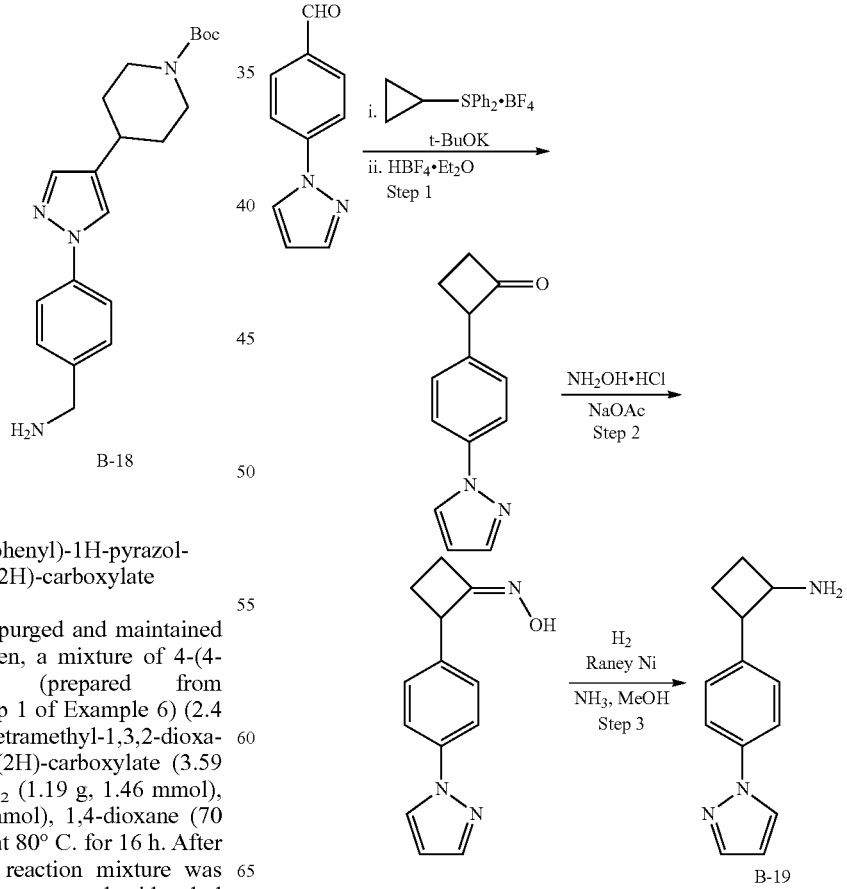

Step 1. 2-(4-(1H-Pyrazol-1-yl)phenyl)cyclobutan-1-one

A solution of 4-(1H-pyrazol-1-yl)benzaldehyde (prepared from 4-fluorobenzaldehyde following Step 1 of Example 6) (1.5 g, 8.71 mmol) and cyclopropyldiphenylsulfonium tetrafluoroborate (2.74 g, 8.72 mmol) in THF (90 mL) was treated with dropwise addition of a solution of potassium tert-butoxide (1 M in THF, 13 mL, 13 mmol) with stirring at 0° C. After stirring for 1 h at 0° C., tetrafluoroboric acid diethyl ether complex (50-55% w/w, 15 mL) was added and the resulting mixture was stirred for 16 h at ambient temperature. The reaction mixture was poured into diethyl ether (300 mL), washed with saturated aqueous sodium carbonate (3×300 mL), dried over anhydrous sodium sulfate, filtered and concentrated under vacuum. The residue was purified by silica gel chromatography (eluting with a gradient of 1-40% EtOAc/PE) to afford 1.4 g (76%) of 2-(4-(1H-pyrazol-1-yl)phenyl)cyclobutan-1-one as a yellow solid. MS (ESI) m/z 213 [M+H]$^+$.

Step 2. 2-(4-(1H-Pyrazol-1-yl)phenyl)cyclobutan-1-one oxime

A solution of 2-(4-(1H-pyrazol-1-yl)phenyl)cyclobutan-1-one (900 mg, 4.24 mmol), sodium acetate (522 mg, 6.37 mmol) and hydroxylammonium chloride (440 mg, 6.38 mmol) in MeOH (10 mL) was stirred for 30 min at ambient temperature. Then the reaction mixture was poured into methyl tertiary butyl ether (50 mL) and was washed with water (2×50 mL) and brine (2×50 mL), dried over anhydrous sodium sulfate, filtered and concentrated under vacuum. The residue was purified by silica gel chromatography (eluting with a gradient of 1-30% EtOAc/PE) to afford 320 mg (33%) of 2-(4-(1H-pyrazol-1-yl)phenyl)cyclobutan-1-one oxime as a light yellow solid. MS (ESI) m/z 228 [M+H]$^+$.

Step 3. 2-(4-(1H-Pyrazol-1-yl)phenyl)cyclobutan-1-amine

A flask containing a mixture of 2-(4-(1H-pyrazol-1-yl)phenyl)cyclobutan-1-one oxime (820 mg, 3.61 mmol), Raney nickel (800 mg) and a solution of ammonia in MeOH (7M, 40 mL, 28 mmol) was placed under an atmosphere of hydrogen gas and was stirred for 1 h at ambient temperature. The reaction mixture was filtered and concentrated under vacuum to afford 750 mg (97%) of 2-(4-(1H-pyrazol-1-yl)phenyl)cyclobutan-1-amine as a greenish oil. MS (ESI) m/z 214 [M+H]$^+$.

Intermediate B-20. 4-(5-(Trifluoromethyl)-1H-imidazol-2-yl)benzonitrile

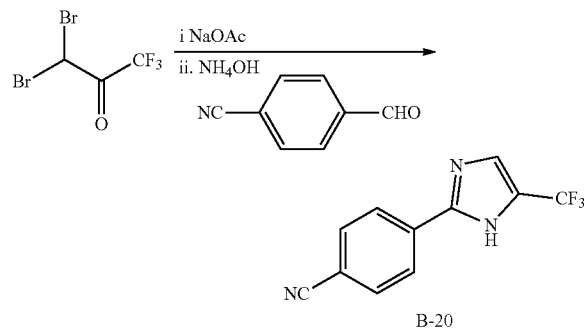

B-20

A mixture of 3,3-dibromo-1,1,1-trifluoropropan-2-one (6.13 g, 22.72 mmol), sodium acetate (1.88 g, 22.93 mmol) and water (6 mL) was stirred for 45 min at 100° C. After cooling to ambient temperature, the mixture was added to a solution of 4-formylbenzonitrile (3 g, 22.88 mmol) and ammonium hydroxide (20 mL) in MeOH (100 mL) and the resulting mixture was stirred for 40 min at ambient temperature, then 1 h at 100° C. After cooling to ambient temperature, the reaction mixture was concentrated under vacuum and was then extracted with EtOAc (3×30 mL). The organic layers were combined, dried over anhydrous sodium sulfate, filtered and concentrated under vacuum. The residue was purified by silica gel chromatography (eluting with a gradient of 1-50% EtOAc/PE) to afford 5 g (92%) of 4-(5-(trifluoromethyl)-1H-imidazol-2-yl)benzonitrile as a yellow solid. MS (ESI) m/z 238 [M+H]$^+$.

Example 9: Intermediate B-21, 4-(1-methyl-4-(trifluoromethyl)-1H-imidazol-2-yl)benzonitrile and Intermediate B-22, 4-(1-methyl-5-(trifluoromethyl)-1H-imidazol-2-yl)benzonitrile

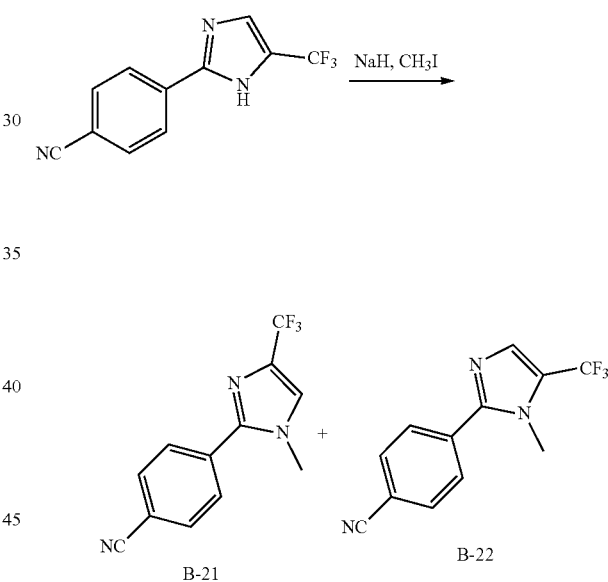

A solution of Intermediate B-20 (5.0 g, 21.08 mmol) in THF (100 mL) at 0° C. was treated portionwise with sodium hydride (60% dispersion in mineral oil, 844 mg, 21.10 mmol). After stirring for 1 h at 0° C., iodomethane (2.99 g, 21.07 mmol) was added dropwise and resulting mixture was stirred for 2 h at 0° C. The reaction mixture was poured into water (25 mL) and was then extracted with EtOAc (3×100 mL). The organic layers were combined, dried over anhydrous sodium sulfate, filtered and concentrated under vacuum to afford 4.8 g (91%) of a ~15:1 mixture of 4-(1-methyl-4-(trifluoromethyl)-1H-imidazol-2-yl)benzonitrile and 4-(1-methyl-5-(trifluoromethyl)-1H-imidazol-2-yl)benzonitrile as a yellow oil. MS (ESI) m/z 251.9 [M+H]$^+$.

Note: if desired, the minor isomer, 4-(1-methyl-5-(trifluoromethyl)-1H-imidazol-2-yl)benzonitrile, can be separated from the major isomer, 4-(1-methyl-4-(trifluoromethyl)-1H-imidazol-2-yl)benzonitrile, by silica gel chromatography (eluting with a gradient of 0-15% EtOAc/PE).

Example 10: Intermediate B-23. (4-(1-Methyl-4-(trifluoromethyl)-1H-imidazol-2-yl)phenyl)methanamine

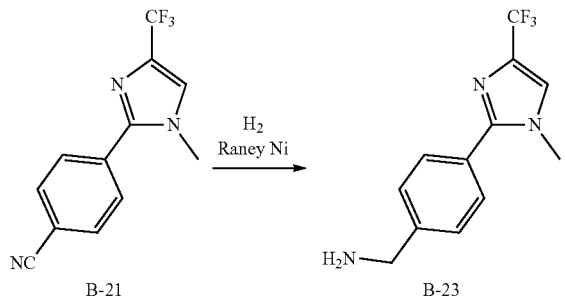

A mixture of Intermediate B-21 (1.5 g, 5.97 mmol) and Raney nickel (1.0 g) in EtOAc (20 mL) was evacuated and backfilled with hydrogen several times and was then charged with hydrogen. The resulting mixture was stirred for 2 h at ambient temperature, then was filtered and concentrated under vacuum to afford 1.5 g (98%) of (4-(1-methyl-4-(trifluoromethyl)-1H-imidazol-2-yl)phenyl)methanamine as a yellow oil. MS (ESI) m/z 256.0 [M+H]$^+$.

Intermediate B-24. (4-(1-(Methyl-d₃)-4-(trifluoromethyl)-1H-imidazol-2-yl)phenyl) methanamine

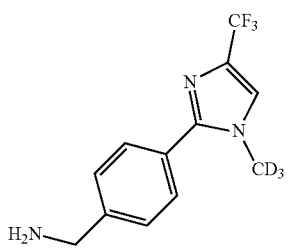

(4-(1-(Methyl-d$_3$)-4-(trifluoromethyl)-1H-imidazol-2-yl)phenyl)methanamine was prepared in analogous fashion to Intermediate B-23, substituting iodomethane-d$_3$ for iodomethane. MS (ESI) m/z 259.0 [M+H]$^+$.

Intermediate B-25. (4-(1-Methyl-5-(trifluoromethyl)-1H-imidazol-2-yl)phenyl) methanamine

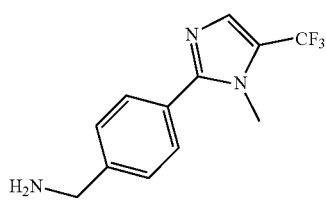

(4-(1-methyl-5-(trifluoromethyl)-1H-imidazol-2-yl)phenyl)methanamine was prepared from Intermediate B-22 following Example 10.

Intermediate B-26. (6-(1H-Pyrazol-1-yl)pyridin-3-yl)methanamine

(6-(1H-Pyrazol-1-yl)pyridin-3-yl)methanamine was prepared as a yellow oil according to Example 6. MS (ESI) m/z 175.2 [M+H]$^+$.

Example 11: Intermediate B-27. tert-Butyl 3-(1-(4-(aminomethyl)phenyl)-1H-pyrazol-3-yl)pyrrolidine-1-carboxylate

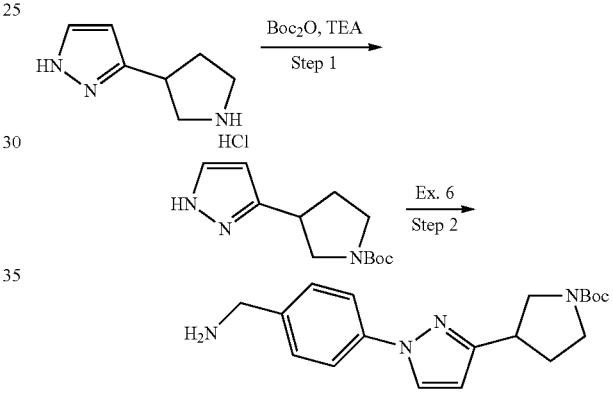

Step 1. tert-Butyl 3-(1H-pyrazol-3-yl)pyrrolidine-1-carboxylate

A mixture of 3-(pyrrolidin-3-yl)-1H-pyrazole hydrochloride (500 mg, 2.88 mmol), triethyl amine (873 mg, 8.64 mmol) and di-tert-butyl dicarbonate (753 mg, 3.46 mmol) in DCM (10 mL) was stirred for 1 h at ambient temperature. The reaction mixture was diluted with DCM (30 mL), washed with water (3×30 mL) and brine (50 mL), dried over anhydrous sodium sulfate, filtered and concentrated under vacuum to afford 680 mg (99%) of tert-butyl 3-(1H-pyrazol-3-yl)pyrrolidine-1-carboxylate as a colorless oil. MS (ESI) m/z 238 [M+H]$^+$.

Step 2. tert-butyl 3-(1-(4-(aminomethyl)phenyl)-1H-pyrazol-3-yl)pyrrolidine-1-carboxylate tert-Butyl 3-(1-(4-(aminomethyl)phenyl)-1H-pyrazol-3-yl)pyrrolidine-1-carboxylate was synthesized from tert-butyl 3-(1H-pyrazol-3-yl)pyrrolidine-1-carboxylate following Example 6. MS (ESI) m/z 343 [M+H]$^+$.

Intermediate B-28. (4-(4-Methyl-1H-1,2,3-triazol-1-yl)phenyl)methanamine

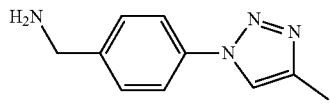
B-28

(4-(4-Methyl-1H-1,2,3-triazol-1-yl)phenyl)methanamine was prepared according to conditions outlined in Example 6. MS (ESI) m/z 188.9 [M+H]+.

Intermediate B-29. (4-(3-(4-Methylpiperazin-1-yl)-1H-pyrazol-1-yl)phenyl)methanamine

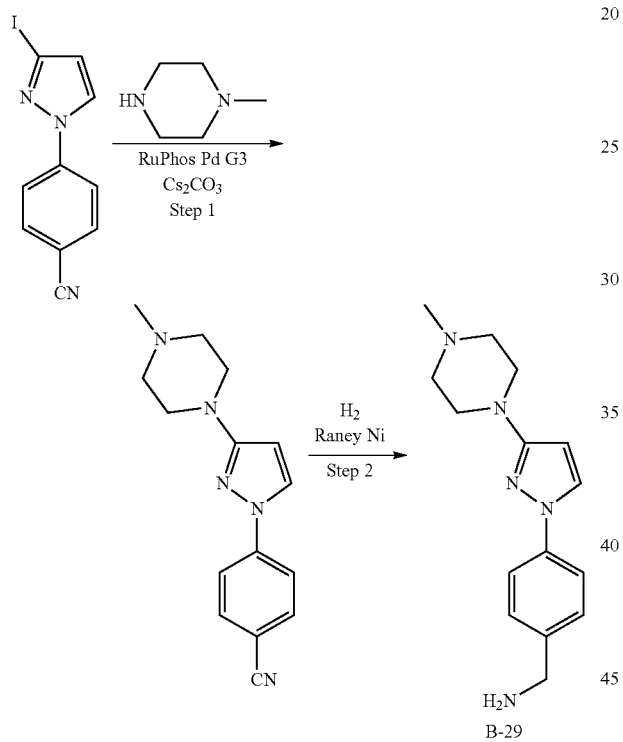

Step 1. 4-(3-(4-Methylpiperazin-1-yl)-1H-pyrazol-1-yl)benzonitrile

Under nitrogen, a mixture of 4-(3-iodo-1H-pyrazol-1-yl)benzonitrile (prepared from 3-iodo-1H-pyrazole following Step 1 of Example 6) (2.95 g, 10.00 mmol), 1-methylpiperazine (1.2 g, 12.00 mmol), RuPhos Pd G3 (836 mg, 1.00 mmol) and cesium carbonate (6.52 g, 20.00 mmol) in 1,4-dioxane (100 mL) was stirred for 18 h at 100° C. After cooling to ambient temperature, the reaction mixture was poured into water (100 mL) and was then extracted with EtOAc (3×100 mL). The organic layers were combined, dried over anhydrous sodium sulfate, filtered and concentrated under vacuum. The residue was purified by silica gel chromatography (eluting with a gradient of 1-5% DCM/MeOH) to afford 700 mg (25%) of 4-(3-(4-methylpiperazin-1-yl)-1H-pyrazol-1-yl)benzonitrile as a white solid. MS (ESI) m/z 268.1 [M+H]+.

Step 2. (4-(3-(4-Methylpiperazin-1-yl)-1H-pyrazol-1-yl)phenyl)methanamine (4-(3-(4-methylpiperazin-1-yl)-1H-pyrazol-1-yl)phenyl)methanamine was synthesized from 4-(3-(4-methylpiperazin-1-yl)-1H-pyrazol-1-yl)benzonitrile following Step 2 of Example 4. MS (ESI) m/z 272.1 [M+H]+.

Example 12: Intermediate B-30. (4-(1-Methyl-1H-imidazol-2-yl)phenyl)methanamine

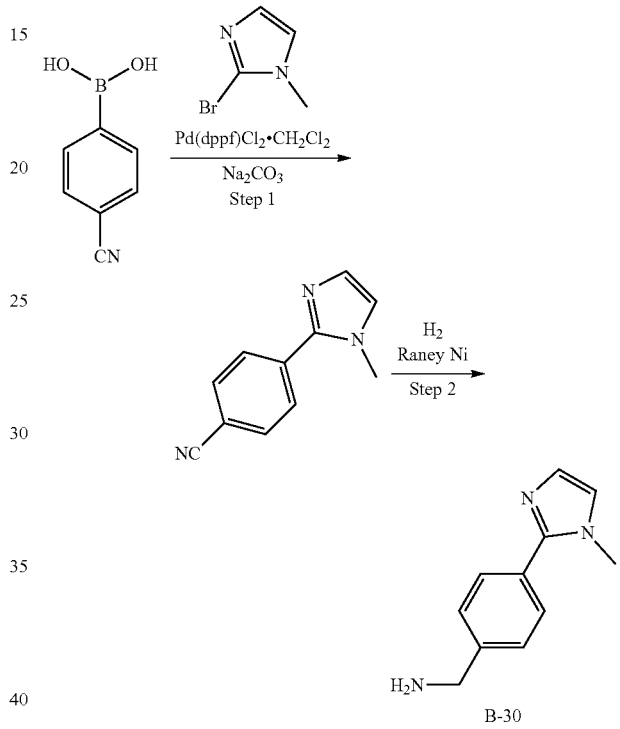
B-30

Step 1. 4-(1-Methyl-1H-imidazol-2-yl)benzonitrile

A mixture of 2-bromo-1-methyl-1H-imidazole (12 g, 74.53 mmol), (4-cyanophenyl)boronic acid (13.15 g, 89.44 mmol), Pd(dppf)Cl₂·CH₂Cl₂ (6.09 g, 7.45 mmol), sodium carbonate (15.8 g, 149.06 mmol), 1,4-dioxane (300 mL) and water (60 mL) was stirred for 18 h at 80° C. under an atmosphere of nitrogen. After cooling to ambient temperature, the reaction mixture was poured into EtOAc (200 mL) and was then washed with water (2×100 mL), dried over anhydrous sodium sulfate, filtered and concentrated under vacuum. The residue was purified by silica gel chromatography (eluting with a gradient of 1-5% MeOH/DCM) to afford 7.8 g (46%) of 4-(1-methyl-1H-imidazol-2-yl)benzonitrile as a light yellow oil. MS (ESI) m/z 184 [M+H]+.

Step 2. (4-(1-Methyl-1H-imidazol-2-yl)phenyl)methanamine (4-(1-methyl-1H-imidazol-2-yl)phenyl)methanamine was synthesized from 4-(1-methyl-1H-imidazol-2-yl)benzonitrile according to Step 2 of Example 4. MS (ESI) m/z 188 [M+H]+.

Intermediate B-31. (4-(1-((2-(Trimethylsilyl)ethoxy) methyl)-1H-imidazol-2-yl)phenyl) methanamine

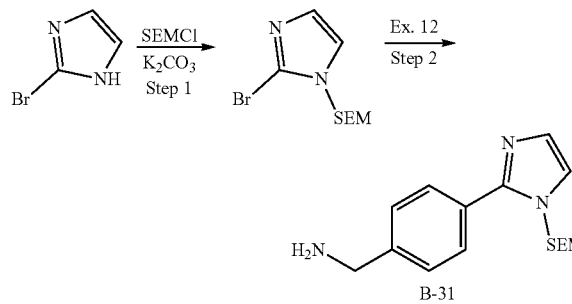

Step 1. 2-Bromo-1-((2-(trimethylsilyl)ethoxy) methyl)-1H-imidazole

A mixture of 2-bromo-1H-imidazole (20 g, 136.99 mmol) and potassium carbonate (56.71 g, 410.97 mmol) in acetone (200 mL) was treated by the dropwise addition of (2-(chloromethoxy)ethyl)trimethylsilane (27.29 g, 164.39 mmol) and the resulting mixture was stirred for 3 h at ambient temperature. The reaction mixture was filtered, concentrated under vacuum and the residue was purified by silica gel chromatography (eluting with a gradient of 1-10% EtOAc/PE) to afford 30 g (80%) of 2-bromo-1-((2-(trimethylsilyl)ethoxy)methyl)-1H-imidazole as a colorless oil. MS (ESI) m/z 277 [M+H]$^+$.

Step 2. (4-(1-((2-(trimethylsilyl)ethoxy)methyl)-1H-imidazol-2-yl)phenyl)methanamine (4-(1-((2-(Trimethylsilyl)ethoxy)methyl)-1H-imidazol-2-yl)phenyl)methanamine was synthesized from 2-bromo-1-((2-(trimethylsilyl)ethoxy)methyl)-1H-imidazole according to Example 12. MS (ESI) m/z 304 [M+H]$^+$.

Example 13: Intermediate B-32. Ethyl 1-(4-(aminomethyl)phenyl)-5-methyl-1H-pyrazole-3-carboxylate

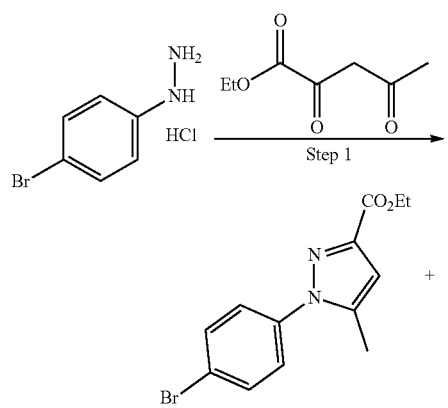

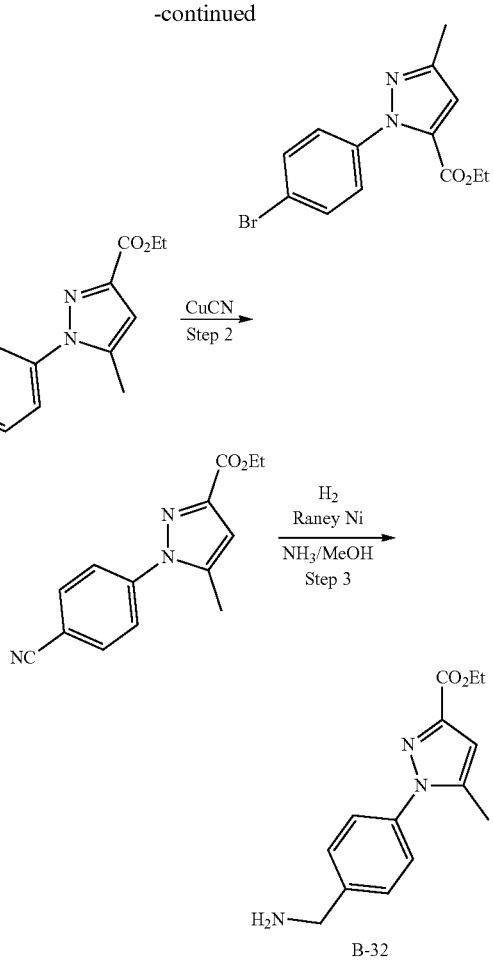

Step 1. Ethyl 1-(4-bromophenyl)-5-methyl-1H-pyrazole-3-carboxylate and ethyl 1-(4-bromophenyl)-3-methyl-1H-pyrazole-5-carboxylate A solution of (4-bromophenyl)hydrazine hydrochloride (10 g, 44.74 mmol) and ethyl 2,4-dioxopentanoate (8.5 g, 53.75 mmol) in EtOH (500 mL) was stirred for 2 h at 80° C., then was concentrated under vacuum. The residue was purified by silica gel chromatography (eluting with 1:10 EtOAc/PE) to afford 8.27 g (61%) of ethyl 1-(4-bromophenyl)-5-methyl-1H-pyrazole-3-carboxylate and 1.5 g (11%) of ethyl 1-(4-bromophenyl)-3-methyl-1H-pyrazole-5-carboxylate.

Ethyl 1-(4-bromophenyl)-5-methyl-1H-pyrazole-3-carboxylate (brown oil, $R_f$=0.2 in 50% EtOAc/PE): $^1$H NMR (400 MHz, CD$_3$OD) δ 7.83-7.63 (m, 2H), 7.54-7.37 (m, 2H), 6.76 (s, 1H), 4.38 (q, J=7.1 Hz, 2H), 2.36 (s, 3H), 1.39 (t, J=7.1 Hz, 3H). MS (ESI) m/z 309, 311 [M+H]$^+$.

Ethyl 1-(4-bromophenyl)-3-methyl-1H-pyrazole-5-carboxylate (light yellow solid, $R_f$=0.35 in 50% EtOAc/PE): $^1$H NMR (400 MHz, CD$_3$OD) δ 7.74-7.59 (m, 2H), 7.43-7.26 (m, 2H), 6.89 (s, 1H), 4.24 (q, J=7.1 Hz, 2H), 2.34 (s, 3H), 1.24 (t, J=7.1 Hz, 3H). MS (ESI) m/z 309, 311 [M+H]⁺

Step 2. Ethyl 1-(4-cyanophenyl)-5-methyl-1H-pyrazole-3-carboxylate

A mixture of ethyl 1-(4-bromophenyl)-5-methyl-1H-pyrazole-3-carboxylate (8.27 g, 26.75 mmol), copper(I) cyanide (2.7 g, 30.15 mmol) and DMF (20 mL) was stirred for 18 h at 140° C. After cooling to ambient temperature, the reaction mixture was poured into concentrated ammonium hydroxide (150 mL) and was then extracted with EtOAc (2×500 mL). The organic layers were combined, dried over anhydrous sodium sulfate, filtered and concentrated under vacuum. The residue was purified by silica gel chromatography (eluting with 1:5 EtOAc/PE) to afford 1.5 g (22%) of ethyl 1-(4-cyanophenyl)-5-methyl-1H-pyrazole-3-carboxylate as a white solid. MS (ESI) m/z 256 [M+H]⁺.

Step 3. Ethyl 1-(4-(aminomethyl)phenyl)-5-methyl-1H-pyrazole-3-carboxylate

Ethyl 1-(4-(aminomethyl)phenyl)-5-methyl-1H-pyrazole-3-carboxylate was synthesized from ethyl 1-(4-cyanophenyl)-5-methyl-1H-pyrazole-3-carboxylate according to Step 3 of Example 8. MS (ESI) m/z 260 [M+H]⁺

Intermediate B-33. Ethyl 1-(4-(aminomethyl)phenyl)-3-methyl-1H-pyrazole-5-carboxylate

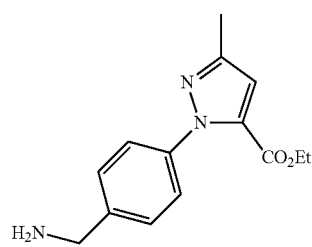

B-33

Ethyl 1-(4-bromophenyl)-3-methyl-1H-pyrazole-5-carboxylate (synthesized in Step 1 of Example 13) was converted to ethyl 1-(4-(aminomethyl)phenyl)-3-methyl-1H-pyrazole-5-carboxylate following Steps 2-3 of Example 13. MS (ESI) m/z 260.2 [M+H]⁺.

Example 14: Intermediate B-34. (4-(1-(2-(Benzyloxy)ethyl)-4-(trifluoromethyl)-1H-imidazol-2-yl)phenyl)methanamine

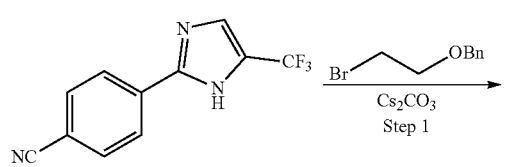

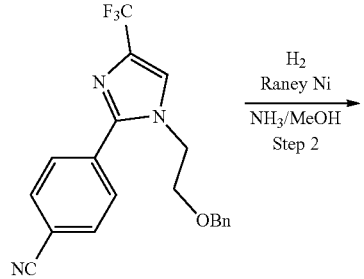

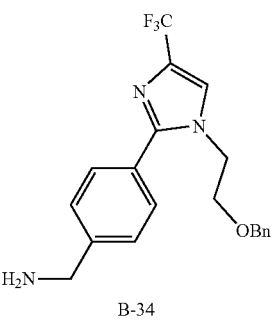

B-34

Step 1. 4-(1-(2-(Benzyloxy)ethyl)-4-(trifluoromethyl)-1H-imidazol-2-yl)benzonitrile A mixture of Intermediate B-20 (1 g, 4.22 mmol), ((2-bromoethoxy)methyl)benzene (1.09 g, 5.07 mmol) and cesium carbonate (2.75 g, 8.44 mmol) in DMF (15 mL) was stirred for 18 h at 110° C. After cooling to ambient temperature, the reaction mixture was poured into water (100 mL) and was then extracted with EtOAc (2×100 mL). The organic layers were combined, dried over anhydrous sodium sulfate, filtered and concentrated under vacuum to afford 1.5 g (96%) of 4-(1-(2-(benzyloxy)ethyl)-4-(trifluoromethyl)-1H-imidazol-2-yl)benzonitrile as a colorless oil. MS (ESI) m/z 371.8 [M+H]⁺.

Step 2. (4-(1-(2-(Benzyloxy)ethyl)-4-(trifluoromethyl)-1H-imidazol-2-yl)phenyl) methanamine (4-[1-[2-(Benzyloxy)ethyl]-4-(trifluoromethyl)-1H-imidazol-2-yl]phenyl)methanamine was synthesized from 4-(1-(2-(benzyloxy)ethyl)-4-(trifluoromethyl)-1H-imidazol-2-yl)benzonitrile according to Step 3 of Example 8. MS (ESI) m/z 376.0 [M+H]⁺.

Intermediate B-35. (4-(1-(Oxetan-3-yl)-4-(trifluoromethyl)-1H-imidazol-2-yl)phenyl) methanamine

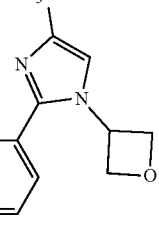

B-35

(4-(1-(Oxetan-3-yl)-4-(trifluoromethyl)-1H-imidazol-2-yl)phenyl)methanamine was synthesized from Intermediate B-20 according to Example 14, substituting 3-iodooxetane for ((2-bromoethoxy)methyl)benzene. MS (ESI) m/z 297.95 [M+H]+.

Intermediate B-36. tert-Butyl 3-(2-(4-(aminomethyl)phenyl)-4-(trifluoromethyl)-1H-imidazol-1-yl)azetidine-1-carboxylate

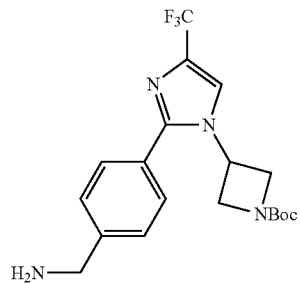

B-36 tert-Butyl 3-(2-(4-(aminomethyl)phenyl)-4-(trifluoromethyl)-1H-imidazol-1-yl) azetidine-1-carboxylate was synthesized from Intermediate B-20 according to Example 14, substituting tert-butyl 3-iodoazetidine-1-carboxylate for ((2-bromoethoxy)methyl)benzene. MS (ESI) m/z 397.2 [M+H]+.

Intermediate B-37. (4-(4-Chloro-1-methyl-1H-imidazol-2-yl)phenyl)methanamine

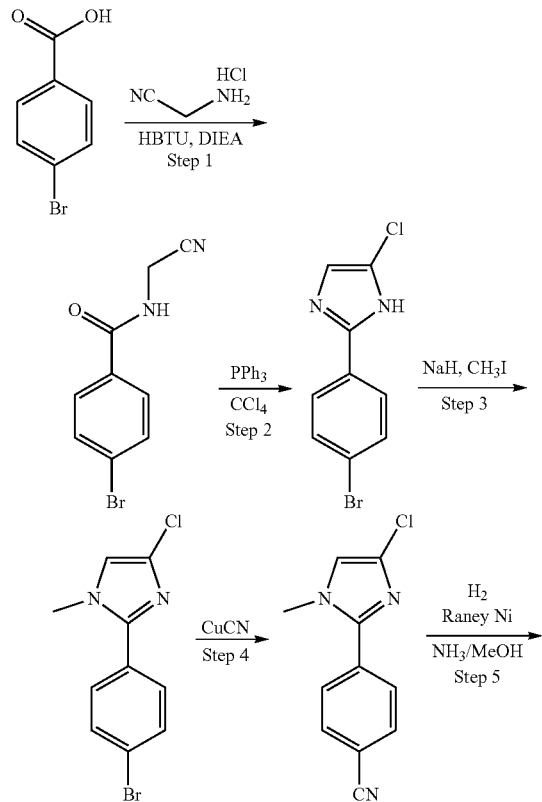

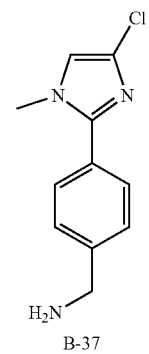

B-37

Step 1. 4-Bromo-N-(cyanomethyl)benzamide

A solution of 4-bromobenzoic acid (5 g, 24.87 mmol), 2-aminoacetonitrile hydrochloride (3.47 g, 37.50 mmol), HBTU (14 g, 36.92 mmol) and DIEA (6.42 g, 49.67 mmol) in DMF (100 mL) was stirred for 16 h at ambient temperature, then was poured into water (300 mL) and was extracted with EtOAc (3×100 mL). The organic layers were combined, dried over anhydrous sodium sulfate, filtered and concentrated under vacuum. The residue was purified by silica gel chromatography (eluting with a gradient of 0-100% EtOAc/PE) to afford 4 g (67%) of 4-bromo-N-(cyanomethyl)benzamide as a white solid. $^1$H NMR (400 MHz, CD$_3$OD) δ 7.82-7.72 (m, 2H), 7.75-7.63 (m, 2H), 4.34 (s, 2H).

Step 2. 2-(4-Bromophenyl)-5-chloro-1H-imidazole

A solution of 4-bromo-N-(cyanomethyl)benzamide (2.5 g, 10.46 mmol), triphenylphosphine (6.86 g, 26.14 mmol) and carbon tetrachloride (4.02 g, 26.14 mmol) in acetonitrile (100 mL) was stirred for 16 h at 50° C. After cooling to ambient temperature, the reaction mixture was concentrated under vacuum, diluted with saturated aqueous sodium bicarbonate solution (20 mL) and extracted with EtOAc (2×20 mL). The organic layers were combined, dried over anhydrous sodium sulfate, filtered and concentrated under vacuum. The residue was purified by silica gel chromatography (eluting with a gradient of 1:100 to 25:75 EtOAc/PE) to afford 800 mg (30%) of 2-(4-bromophenyl)-5-chloro-1H-imidazole as a yellow solid. MS (ESI) m/z 258.8 [M+H]+.

Step 3. 2-(4-Bromophenyl)-4-chloro-1-methyl-1H-imidazole

A solution of 2-(4-bromophenyl)-5-chloro-1H-imidazole (800 mg, 3.11 mmol) in DMF (30 mL) at 0° C. was treated portionwise with sodium hydride (60% dispersion in mineral oil, 186 mg, 4.66 mmol). The resulting mixture was stirred for 30 min at 0° C., then was treated with iodomethane (661 mg, 4.66 mmol) at 0° C. The resulting solution was stirred for 1 h at 0° C., then the reaction mixture was poured into water (100 mL) and extracted with EtOAc (2×100 mL). The organic layers were combined, dried over anhydrous sodium sulfate, filtered and concentrated under vacuum to afford 600 mg (71%) of 2-(4-bromophenyl)-4-chloro-1-methyl-1H-imidazole as yellow oil. MS (ESI) m/z 272.8 [M+H]+.

Step 4. 4-(4-Chloro-1-methyl-1H-imidazol-2-yl)benzonitrile

A solution of 2-(4-bromophenyl)-4-chloro-1-methyl-1H-imidazole (600 mg, 2.21 mmol) and copper(I) cyanide (297 mg, 3.32 mmol) in DMF (7 mL) was stirred for 24 h at 130° C. After cooling to ambient temperature, the reaction mixture was poured into concentrated ammonium hydroxide (100 mL) and was extracted with EtOAc (2×100 mL). The organic layers were combined, dried over anhydrous sodium sulfate, filtered and concentrated under vacuum. The residue was purified by silica gel chromatography (eluting with a gradient of 1-25% EtOAc/PE) to afford 250 mg (52%) of 4-(4-chloro-1-methyl-1H-imidazol-2-yl)benzonitrile as a yellow solid. MS (ESI) m/z 218.0 [M+H]+.

Step 5. (4-(4-Chloro-1-methyl-1H-imidazol-2-yl)phenyl)methanamine (4-(4-Chloro-1-methyl-1H-imidazol-2-yl)phenyl)methanamine was synthesized from 4-(4-chloro-1-methyl-1H-imidazol-2-yl)benzonitrile according to Step 3 of Example 8. MS (ESI) m/z 222.0 [M+H]+.

Example 15: Intermediate B-38. 1-(4-(Aminomethyl)phenyl)-1H-pyrazole-3-carbonitrile

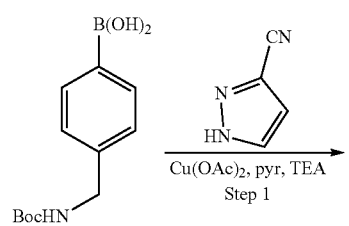

Step 1. tert-Butyl (4-(3-cyano-1H-pyrazol-1-yl)benzyl)carbamate

A mixture of 1H-pyrazole-3-carbonitrile (320 mg, 3.44 mmol), [4-([[(tert-butoxy)carbonyl]amino]methyl)phenyl]boronic acid (1.03 g, 4.10 mmol), triethylamine (521 mg, 5.15 mmol), pyridine (815 mg, 10.30 mmol) and copper(II) acetate (840 mg, 4.62 mmol) in DCM (20 mL) was stirred for 18 h at 40° C. The reaction mixture was filtered and concentrated under vacuum, and the residue was purified by silica gel chromatography (eluting with 1:3 EtOAc/PE) to afford 0.4 g (39%) of tert-butyl (4-(3-cyano-1H-pyrazol-1-yl)benzyl)carbamate as a white solid. MS (ESI) m/z 299 [M+H]+.

Step 2. 1-(4-(Aminomethyl)phenyl)-1H-pyrazole-3-carbonitrile

A solution of tert-butyl (4-(3-cyano-1H-pyrazol-1-yl)benzyl)carbamate (400 mg, 1.34 mmol) in DCM (15 mL) and TFA (5 mL) was stirred for 0.5 h at ambient temperature, then was concentrated under vacuum to afford 0.43 g (crude) of 1-(4-(aminomethyl)phenyl)-1H-pyrazole-3-carbonitrile as a colorless oil. MS (ESI) m/z 199 [M+H]+.

Intermediate B-39. (4-(5-Methyl-1H-pyrazol-1-yl)phenyl)methanamine

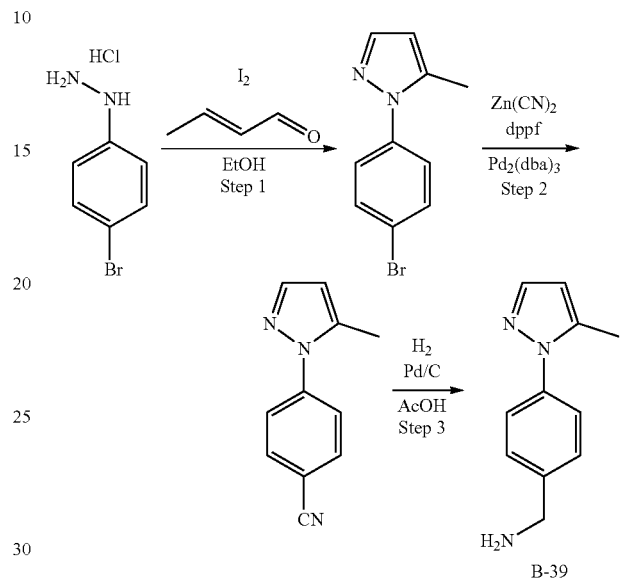

Step 1. 1-(4-Bromophenyl)-5-methyl-1H-pyrazole

A mixture of (4-bromophenyl)hydrazine hydrochloride (3.36 g, 15.03 mmol) and (E)-but-2-enal (1.054 g, 15.03 mmol) in EtOH (40 ml) was treated with iodine (3.82 g, 15.03 mmol) and the resulting mixture was heated to 80° C. for 16 h. The mixture was cooled to ambient temperature, the solvent was removed, and the residue partitioned between EtOAc and 5% aqueous sodium thiosulfate (100 mL). The organic layer was separated, dried over sodium sulfate, filtered and concentrated. The residue was purified by silica gel chromatography (eluting with a gradient of 0-40% EtOAc/hexanes) to afford 477 mg (13%) of 1-(4-bromophenyl)-5-methyl-1H-pyrazole. $^1$H NMR (300 MHz, CDCl$_3$) δ 7.76 (d, J=2.6 Hz, 1H), 7.52 (s, 4H), 6.24 (d, J=2.4 Hz, 1H), 2.35 (s, 3H). MS (ESI) m/z 237.02, 239.01 [M+H]+.

Step 2. 4-(5-Methyl-1H-pyrazol-1-yl)benzonitrile

A mixture of zinc cyanide (260 mg, 2.213 mmol), dppf (112 mg, 0.20 mmol), Pd$_2$(dba)$_3$ (92 mg, 0.10 mmol), and 1-(4-bromophenyl)-5-methyl-1H-pyrazole (477 mg, 2.012 mmol) in DMF (20 ml) was heated to 140° C. for 16 h. Additional zinc cyanide (300 mg) was added and the mixture was heated to 140° C. for another 16 h. The mixture was cooled, EtOAc was added and the organic layer was washed successively with water (2×) and brine. The mixture was dried over sodium sulfate, filtered, concentrated, and purified by silica gel chromatography (eluting with a gradient of 0-60% EtOAc/hexanes) to afford 360 mg (98%) of 4-(5-methyl-1H-pyrazol-1-yl)benzonitrile. $^1$H NMR (300 MHz, CDCl$_3$) δ 7.86 (d, J=2.4 Hz, 1H), 7.83-7.64 (m, 4H), 6.30 (d, J=2.4 Hz, 1H), 2.36 (s, 3H). MS (ESI) m/z 184.07 [M+H]+.

Step 3. (4-(5-Methyl-1H-pyrazol-1-yl)phenyl)methanamine

A solution of 4-(5-methyl-1H-pyrazol-1-yl)benzonitrile (360 mg, 1.965 mmol) in MeOH (30 ml) and acetic acid (3 ml) was degassed with nitrogen for 5 min, then was treated with palladium on carbon (10 wt. %, 100 mg). The reaction mixture was evacuated and back-filled with hydrogen three times and charged with hydrogen to 40 psi. The mixture was stirred for 16 h, then was filtered and dried to afford 360 mg (98%) of (4-(5-methyl-1H-pyrazol-1-yl)phenyl)methanamine. $^1$H NMR (300 MHz, DMSO-$d_6$) δ 8.51 (d, J=2.4 Hz, 1H), 8.02-7.85 (m, 4H), 6.39 (d, J=2.4 Hz, 1H), 5.62-5.41 (m, 2H), 2.58-2.41 (m, 2H), 2.24 (s, 3H). MS (ESI) m/z 188.08 [M+H]$^+$.

Intermediate B-40. (4-(3-(Difluoromethyl)-5-methyl-1H-pyrazol-1-yl)phenyl)methanamine

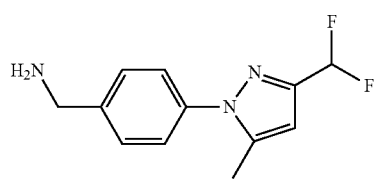

B-40

(4-(3-(Difluoromethyl)-5-methyl-1H-pyrazol-1-yl)phenyl)methanamine was prepared according to Example 6. MS (ESI) m/z 233.9 [M+H]$^+$.

Intermediate B-41. (4-(5-Fluoro-1-methyl-1H-imidazol-2-yl)phenyl)methanamine hydrochloride

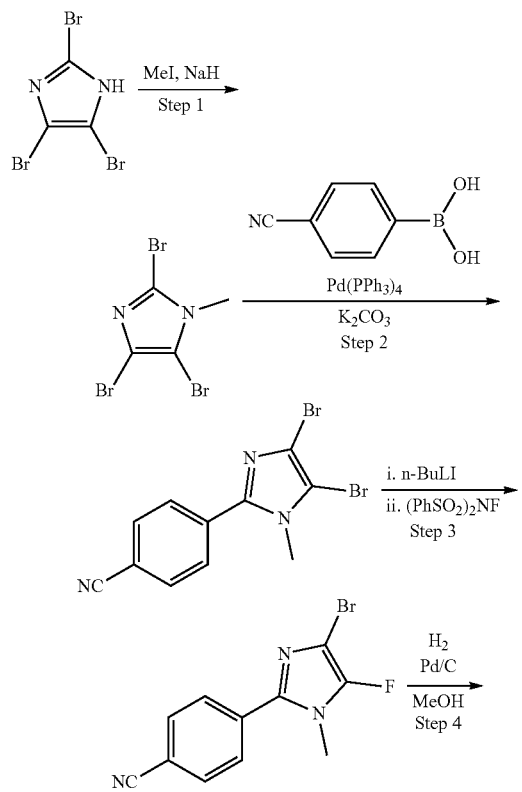

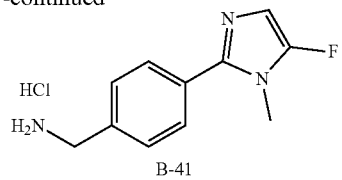

B-41

Step 1. 2,4,5-Tribromo-1-methyl-1H-imidazole

To a suspension of sodium hydride (0.787 g, 19.69 mmol) in DMF (15 mL) was added 2, 4, 5-tribromo-1H-imidazole (5 g, 16.41 mmol) in DMF (10 mL) at ambient temperature. The mixture was stirred at 50° C. for 1 h, cooled to 0° C., and treated with methyl iodide (1.128 ml, 18.05 mmol). The mixture was warmed to 50° C. and stirred 16 h, the DMF was removed under reduced pressure and EtOAc was added. The mixture was washed with water, dried over sodium sulfate, filtered and concentrated. Purification by silica gel chromatography (eluting with a gradient of 10-80% EtOAc/hexanes) afforded 4.87 g (94%) of 2,4,5-tribromo-1-methyl-1H-imidazole. $^1$H NMR (300 MHz, CDCl$_3$) δ 3.62 (s, 3H). MS (ESI) m/z 316.77 [M+H]$^+$.

Step 2. 4-(4,5-Dibromo-1-methyl-1H-imidazol-2-yl)benzonitrile

To a solution of 2,4,5-tribromo-1-methyl-1H-imidazole (3.94 g, 12.36 mmol), (4-cyanophenyl)boronic acid (1.816 g, 12.36 mmol) and potassium carbonate (3.42 g, 24.72 mmol) in dioxane (40 mL) and water (4 mL) was added tetrakis(triphenylphosphine)palladium(0) (0.714 g, 0.618 mmol). The mixture was degassed with nitrogen for 10 min, then heated to 90° C. for 16 h. After cooling to ambient temperature, EtOAc was added, the mixture washed with brine, dried over sodium sulfate, filtered and concentrated. Purification by silica gel chromatography (eluting with a gradient of 5-70% EtOAc/hexanes) afforded 2.5 g (59%) of 4-(4,5-dibromo-1-methyl-1H-imidazol-2-yl)benzonitrile. $^1$H NMR (300 MHz, CDCl$_3$) δ 7.74 (m, 4H), 3.75 (s, 3H). MS (ESI) m/z 342.00 [M+H]$^+$.

Step 3. 4-(4-Bromo-5-fluoro-1-methyl-1H-imidazol-2-yl)benzonitrile

To a solution of 4-(4,5-dibromo-1-methyl-1H-imidazol-2-yl)benzonitrile (380 mg, 1.114 mmol) in THF (10 ml) at −78° C. was added n-butyllithium (0.766 ml, 1.226 mmol). The mixture was stirred at −78° C. for 1 h, then a solution of N-fluoro-N-(phenylsulfonyl) benzenesulfonamide (422 mg, 1.337 mmol) in THF (1 mL) was added, and the reaction slowly warmed to room temperature over 1 h. After 16 h, EtOAc was added, the mixture washed with brine, dried over sodium sulfate, filtered and concentrated. Purification by silica gel chromatography (eluting with a gradient of 7-60% EtOAc/hexanes) afforded 210 mg (67%) of 4-(4-bromo-5-fluoro-1-methyl-1H-imidazol-2-yl)benzonitrile. $^1$H NMR (300 MHz, CDCl$_3$) δ 7.72 (m, 4H), 3.69 (s, 3H). MS (ESI) m/z 279.96, 281.95 [M+H]$^+$

Step 4. (4-(5-Fluoro-1-methyl-1H-imidazol-2-yl)phenyl)methanamine hydrochloride A solution of 4-(4-bromo-5-fluoro-1-methyl-1H-imidazol-2-yl)benzonitrile (277 mg, 0.989 mmol) in MeOH (30 mL) was treated with 1N aqueous HCl (10 mL, 10.00 mmol), degassed with nitrogen for 5 min, and palladium on carbon (10 wt. %, 100 mg, 0.940 mmol) was added. The mixture was evacuated and backfilled with hydrogen (3×), and shaken under 40 psi hydrogen for 16 h. The reaction mixture was filtered, dried over sodium sulfate, filtered and concentrated to afford 239 mg (100%) of (4-(5-fluoro-1-methyl-1H-imidazol-2-yl)phenyl)methanamine hydrochloride. $^1$H NMR (300 MHz, DMSO-$d_6$) δ 7.94-7.61 (m, 4H), 7.46 (m, 1H), 4.22-4.03 (m, 2H), 3.65 (s, 3H).

Intermediate B-42, (4-(5-methyl-3-(trifluoromethyl)-1H-pyrazol-1-yl)phenyl)methanamine and Intermediate B-43, (4-(3-methyl-5-(trifluoromethyl)-1H-pyrazol-1-yl)phenyl) methanamine

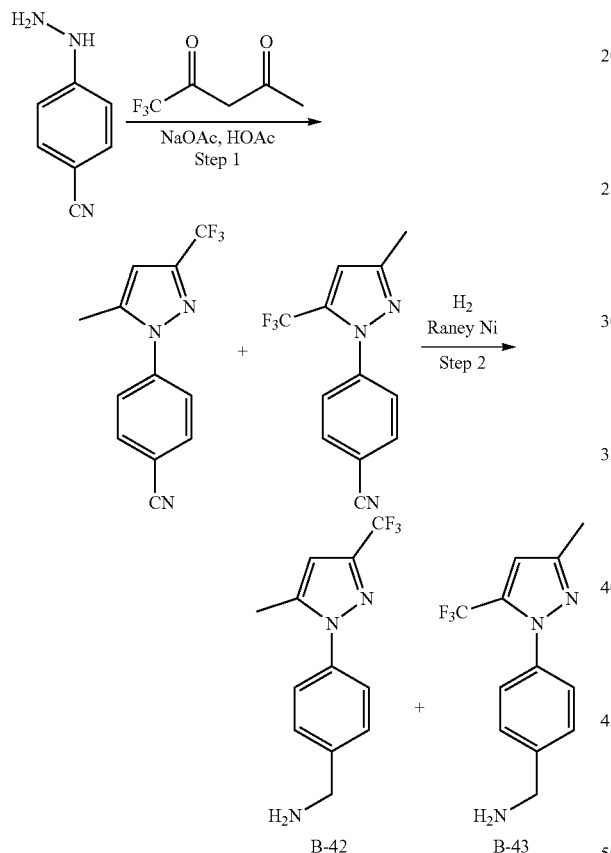

Step 1. 4-(5-Methyl-3-(trifluoromethyl)-1H-pyrazol-1-yl)benzonitrile and 4-(3-methyl-5-(trifluoromethyl)-1H-pyrazol-1-yl)benzonitrile A mixture of 4-hydrazinylbenzonitrile (2 g, 15.02 mmol), 1,1,1-trifluoropentane-2,4-dione (3.1 g, 20.12 mmol), sodium acetate (2.5 g, 30.48 mmol) and acetic acid (10 mL) was stirred for 1 h at 120° C. After cooling to ambient temperature, the reaction mixture was concentrated under vacuum and purified by silica gel chromatography (eluting with a gradient of 10-30% EtOAc/PE to afford 2 g (53%) of a ~2:1 mixture of 4-(5-methyl-3-(trifluoromethyl)-1H-pyrazol-1-yl)benzonitrile and 4-(3-methyl-5-(trifluoromethyl)-1H-pyrazol-1-yl)benzonitrile as a yellow solid. MS (ESI) m/z 252.0 [M+H]$^+$ Step 2. (4-(5-Methyl-3-(trifluoromethyl)-1H-pyrazol-1-yl)phenyl)methanamine and (4-(3-methyl-5-(trifluoromethyl)-1H-pyrazol-1-yl)phenyl)methanamine A ~2:1 mixture of (4-(5-methyl-3-(trifluoromethyl)-1H-pyrazol-1-yl)phenyl)methanamine and (4-(3-methyl-5-(trifluoromethyl)-1H-pyrazol-1-yl)phenyl)methanamine was synthesized from a ~2:1 mixture of 4-(5-methyl-3-(trifluoromethyl)-1H-pyrazol-1-yl)benzonitrile and 4-(3-methyl-5-(trifluoromethyl)-1H-pyrazol-1-yl)benzonitrile according to Step 2 of Example 4. MS (ESI) m/z 256.0 [M+H]$^+$.

Example 16: Intermediate B-44. tert-Butyl 4-(1-(4-(aminomethyl)phenyl)-1H-pyrazol-3-yl)piperazine-1-carboxylate

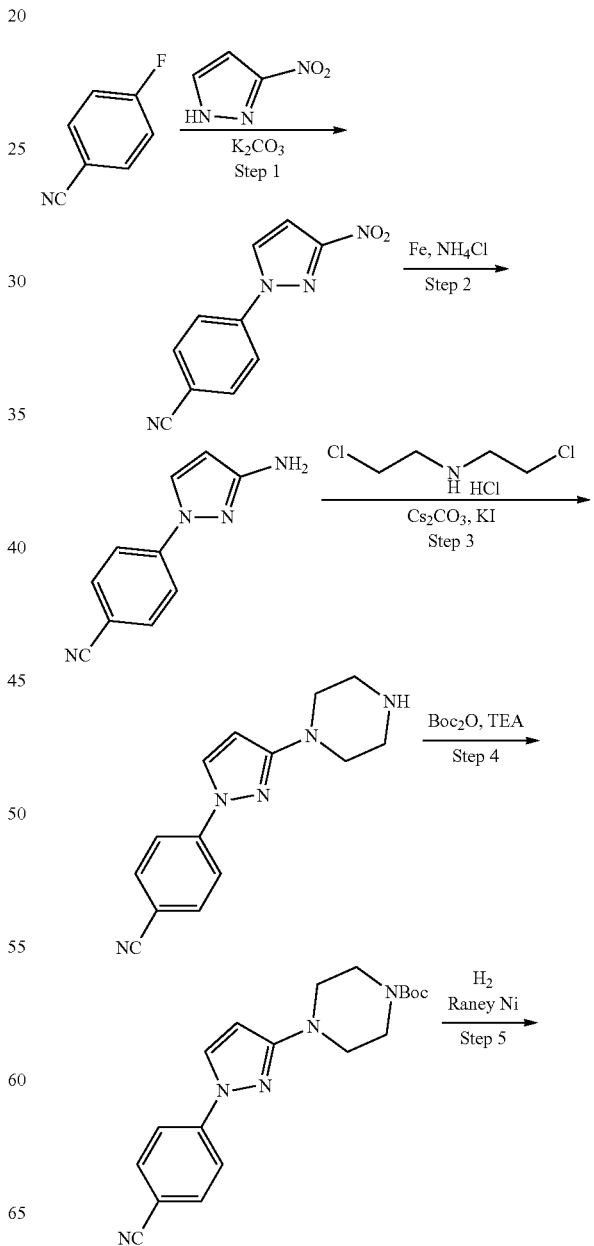

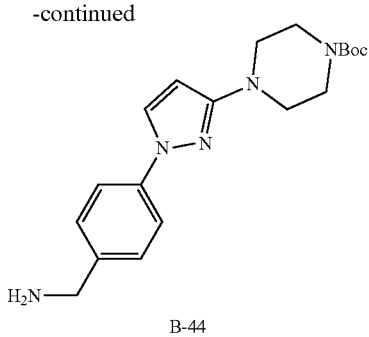

B-44

Step 1. 4-(3-Nitro-1H-pyrazol-1-yl)benzonitrile 4-(3-nitro-1H-pyrazol-1-yl)benzonitrile was synthesized from 3-nitro-1H-pyrazole according to Step 1 of Example 6. MS (ESI) m/z 215 [M+H]$^+$.

Step 2. 4-(3-Amino-1H-pyrazol-1-yl)benzonitrile 4-(3-amino-1H-pyrazol-1-yl)benzonitrile was synthesized from 4-(3-nitro-1H-pyrazol-1-yl)benzonitrile according to Step 2 of Example 18. MS (ESI) m/z 185 [M+H]$^+$.

Step 3. 4-(3-(Piperazin-1-yl)-1H-pyrazol-1-yl)benzonitrile

A mixture of 4-(3-amino-1H-pyrazol-1-yl)benzonitrile (3 g, 16.29 mmol), bis(2-chloroethyl)amine (5.7 g, 40.13 mmol), cesium carbonate (16 g, 49.11 mmol) and potassium iodide (13.3 g) in acetonitrile (100 mL) was stirred for 6 days at 80° C. After cooling to ambient temperature, the resulting mixture was filtered and concentrated under vacuum. The residue was purified by silica gel chromatography (eluting with 10:1 DCM/MeOH) to afford 3 g (73%) of 4-(3-(piperazin-1-yl)-1H-pyrazol-1-yl)benzonitrile as a yellow solid. MS (ESI) m/z 254 [M+H]$^+$.

Step 4. tert-Butyl 4-(1-(4-cyanophenyl)-1H-pyrazol-3-yl)piperazine-1-carboxylate tert-Butyl 4-(1-(4-cyanophenyl)-1H-pyrazol-3-yl)piperazine-1-carboxylate was synthesized from 4-(3-(piperazin-1-yl)-1H-pyrazol-1-yl)benzonitrile according to Step 1 of Example 11. MS (ESI) m/z 354 [M+H]$^+$.

Step 5. tert-Butyl 4-(1-(4-(aminomethyl)phenyl)-1H-pyrazol-3-yl)piperazine-1-carboxylate tert-Butyl 4-(1-(4-(aminomethyl)phenyl)-1H-pyrazol-3-yl)piperazine-1-carboxylate was synthesized from tert-butyl 4-(1-(4-cyanophenyl)-1H-pyrazol-3-yl)piperazine-1-carboxylate according to Example 10. MS (ESI) m/z 358 [M+H]$^+$.

Example 17: Intermediate B-45. (4-(3-Methoxy-1H-pyrazol-1-yl)phenyl)methanamine

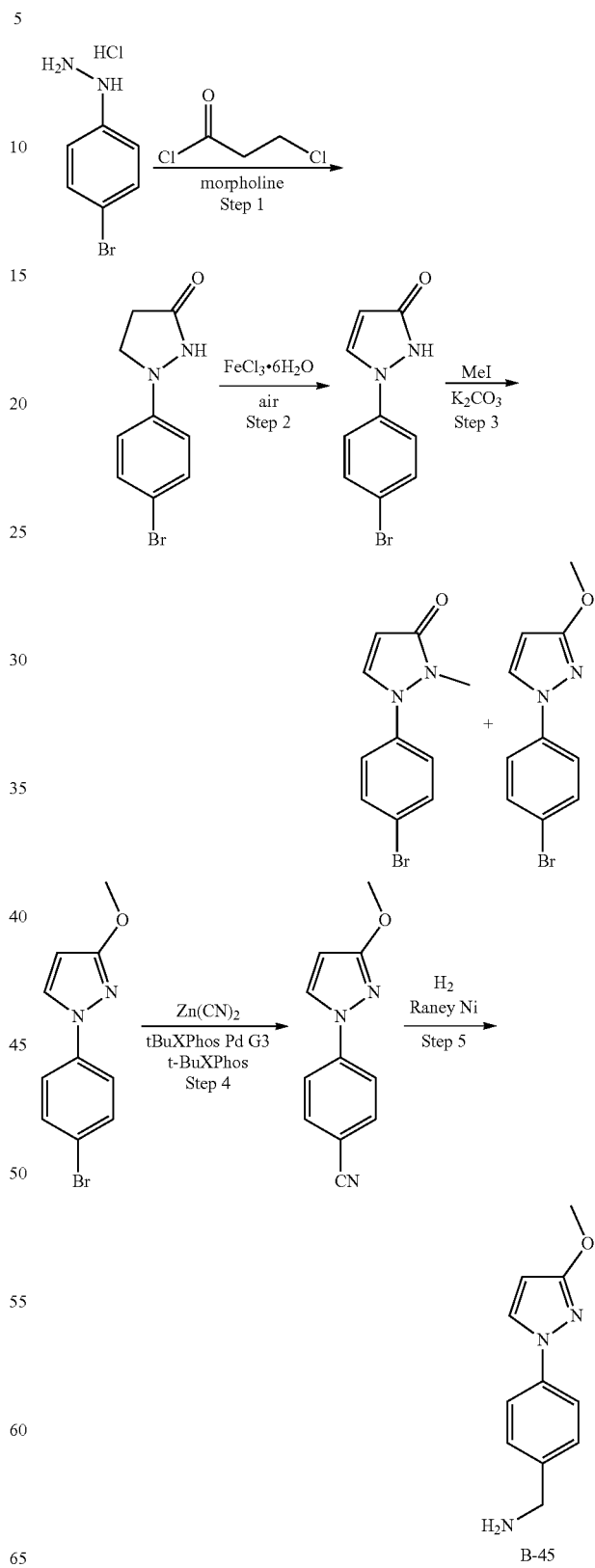

B-45

Step 1. 1-(4-Bromophenyl)pyrazolidin-3-one

A mixture of (4-bromophenyl)hydrazine hydrochloride (5 g, 22.37 mmol) and morpholine (9.57 g, 109.85 mmol) in DCM (100 mL) at 0° C. was treated by dropwise addition of 3-chloropropanoyl chloride (2.85 g, 22.45 mmol). The resulting solution was stirred 16 h at ambient temperature, then was washed with water (3×20 mL), dried over anhydrous sodium sulfate, filtered and concentrated under vacuum. The residue was purified by silica gel chromatography (eluting with 50% EtOAc/PE) to afford 2 g (35%) of 1-(4-bromophenyl)pyrazolidin-3-one as a yellow oil. MS (ESI) m/z 241.0, 243.0 [M+H]$^+$.

Step 2. 1-(4-Bromophenyl)-1,2-dihydro-3H-pyrazol-3-one

A mixture of 1-(4-bromophenyl)pyrazolidin-3-one (2 g, 8.30 mmol) and iron(III) chloride hexahydrate (2.24 g, 8.30 mmol) in DMF (25 mL) was stirred for 16 h at 80° C. After cooling to ambient temperature, the reaction mixture was poured into EtOAc (100 mL), washed with water (2×25 mL) and then concentrated under vacuum. The residue was purified by silica gel chromatography (eluting with 25% EtOAc/PE) to afford 1.9 g (91%) of 1-(4-bromophenyl)-1,2-dihydro-3H-pyrazol-3-one as a yellow solid. MS (ESI) m/z 239.0, 241.0 [M+H]$^+$.

Step 3. 1-(4-Bromophenyl)-2-methyl-1,2-dihydro-3H-pyrazol-3-one and 1-(4-bromophenyl)-3-methoxy-1H-pyrazole A mixture of 1-(4-bromophenyl)-1,2-dihydro-3H-pyrazol-3-one (1.8 g, 7.53 mmol) and potassium carbonate (5.20 g, 37.63 mmol) in water (48 mL) and Tween 20 (2 mL) was treated by the dropwise addition of iodomethane (5.35 g, 37.69 mmol) with stirring at ambient temperature. The resulting mixture was stirred 16 h, then was extracted with EtOAc (5×50 mL). The organic layers were combined, dried over anhydrous sodium sulfate, filtered and concentrated under vacuum. The residue was purified by silica gel chromatography (eluting with a gradient of 0-100% EtOAc/PE) to afford 900 mg (45%) of 1-(4-bromophenyl)-3-methoxy-1H-pyrazole as an off-white solid and 800 mg (40%) of 1-(4-bromophenyl)-2-methyl-1,2-dihydro-3H-pyrazol-3-one as a yellow oil.

1-(4-Bromophenyl)-2-methyl-1,2-dihydro-3H-pyrazol-3-one ($R_f$=0.1 in 75% EtOAc/PE): $^1$H NMR (400 MHz, CD$_3$OD) δ 7.84 (d, J=4.0 Hz, 1H), 7.73-7.71 (m, 2H), 7.34-7.31 (m, 2H), 5.64 (d, J=4.0 Hz, 1H), 3.32 (s, 3H). $^{13}$C NMR (400 MHz, CD$_3$OD) δ 167.8, 141.7, 135.9, 132.9, 125.6, 121.7, 96.2, 29.3. MS (ESI) m/z 253.0, 255.0 [M+H]$^+$.

1-(4-Bromophenyl)-3-methoxy-1H-pyrazole ($R_f$=0.8 in 75% EtOAc/PE): $^1$H NMR (400 MHz, CD$_3$OD) δ 8.01 (d, J=4.0 Hz, 1H), 7.58-7.56 (m, 4H), 5.95 (d, J=4.0 Hz, 1H), 3.94 (s, 3H). $^{13}$C NMR (400 MHz, CD$_3$OD) δ 166.5, 139.3, 131.9, 128.5, 118.9, 117.7, 93.4, 56.5. MS (ESI) m/z 253.0, 255.0 [M+H]$^+$.

Step 4. 4-(3-Methoxy-1H-pyrazol-1-yl)benzonitrile

Under an atmosphere of nitrogen, a mixture of 1-(4-bromophenyl)-3-methoxy-1H-pyrazole (900 mg, 3.56 mmol), zinc cyanide (416 mg, 3.54 mmol), tBuXPhos (76 mg, 0.18 mmol) and tBuXPhos Pd G3 (141 mg, 0.18 mmol) in THF (4 mL) and water (20 mL) was stirred vigorously for 18 h at 40° C. The reaction mixture was poured into saturated potassium carbonate solution (10 mL) and was then extracted with EtOAc (3×50 mL). The organic layers were combined, dried over anhydrous sodium sulfate, filtered and concentrated under vacuum. The residue was purified by silica gel chromatography (eluting with 6% EtOAc/PE) to afford 500 mg (67%) of 4-(3-methoxy-1H-pyrazol-1-yl)benzonitrile as an off-white solid. MS (ESI) m/z 200.1 [M+H]$^+$.

Step 5. (4-(3-Methoxy-1H-pyrazol-1-yl)phenyl)methanamine (4-(3-Methoxy-1H-pyrazol-1-yl)phenyl)methanamine was prepared from 4-(3-methoxy-1H-pyrazol-1-yl)benzonitrile according to Step 2 of Example 4. MS (ESI) m/z 203.7 [M+H]$^+$.

Intermediate B-46. 1-(4-(aminomethyl)phenyl)-1H-pyrazole-3,5-dicarbonitrile

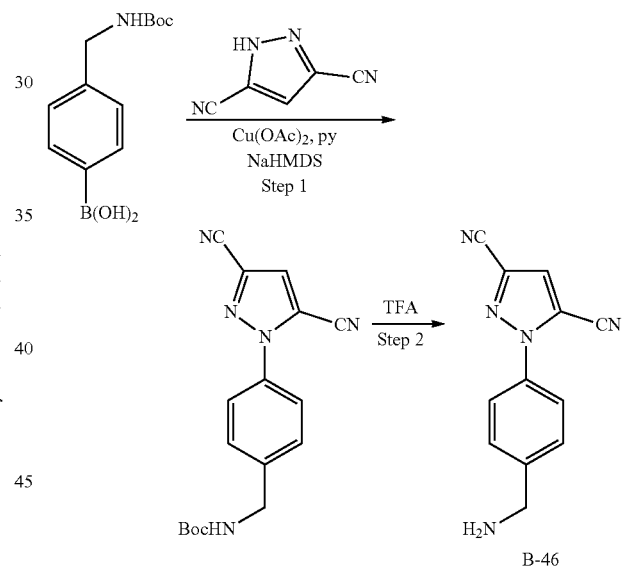

Step 1. tert-Butyl (4-(3,5-dicyano-1H-pyrazol-1-yl)benzyl)carbamate

A mixture of 1H-pyrazole-3,5-dicarbonitrile (1.00 g, 8.47 mmol), (4-(((tert-butoxycarbonyl)amino)methyl)phenyl)boronic acid (4.25 g, 16.93 mmol), copper(II) acetate (1.54 g, 8.47 mmol), sodium bis(trimethylsilyl)amide (10.2 mL of a 1M solution in THF, 10.20 mL, 10.20 mmol), pyridine (Py, 3.35 g, 42.34 mmol) and 4 Å molecular sieves (1 g) in toluene (100 mL) was stirred overnight at 120° C. After cooling to ambient temperature, the reaction mixture was filtered and concentrated under vacuum. The residue was purified by silica gel chromatography (eluting with a gradient of 1-25% EtOAc/PE) to afford 300 mg (11%) of tert-butyl (4-(3,5-dicyano-1H-pyrazol-1-yl)benzyl)carbamate as a colorless oil. MS (ESI) m/z 324.0 [M+H]$^+$.

Step 2. 1-(4-(Aminomethyl)phenyl)-1H-pyrazole-3,5-dicarbonitrile

A solution of tert-butyl (4-(3,5-dicyano-1H-pyrazol-1-yl)benzyl)carbamate (300 mg, 0.93 mmol) in DCM (10 mL) and TFA (3 mL) was stirred for 1 h at ambient temperature. The reaction mixture was concentrated under vacuum, dispersed in water (20 mL), neutralized with saturated sodium bicarbonate solution, and the resulting mixture extracted with DCM (2×20 mL). The organic layers were combined, dried over anhydrous sodium sulfate, filtered and concentrated under vacuum to afford 100 mg (48%) of 1-(4-(aminomethyl)phenyl)-1H-pyrazole-3,5-dicarbonitrile as a yellow solid. MS (ESI) m/z 223.7 [M+H]$^+$.

Intermediate B-47. (4-(4-Methyl-1-(oxetan-3-yl)-1H-imidazol-2-yl)phenyl)methanamine

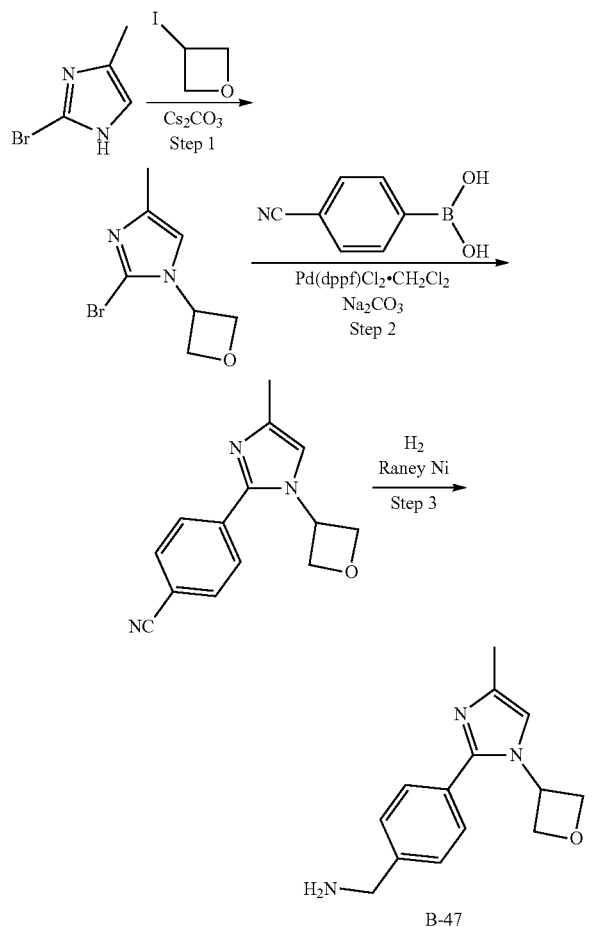

Step 1. 2-Bromo-4-methyl-1-(oxetan-3-yl)-1H-imidazole

2-Bromo-4-methyl-1-(oxetan-3-yl)-1H-imidazole was prepared from 2-bromo-4-methyl-1H-imidazole following Step 1 of Example 14. MS (ESI) m/z 216.9, 218.9 [M+H]$^+$.

Step 2. 4-(4-Methyl-1-(oxetan-3-yl)-1H-imidazol-2-yl)benzonitrile 4-(4-Methyl-1-(oxetan-3-yl)-1H-imidazol-2-yl)benzonitrile was prepared from 2-bromo-4-methyl-1-(oxetan-3-yl)-1H-imidazole following Step 1 of Example 12. MS (ESI) m/z 239.7 [M+H]$^+$.

Step 3. (4-(4-Methyl-1-(oxetan-3-yl)-1H-imidazol-2-yl)phenyl)methanamine (4-(4-Methyl-1-(oxetan-3-yl)-1H-imidazol-2-yl)phenyl)methanamine was prepared from 4-(4-methyl-1-(oxetan-3-yl)-1H-imidazol-2-yl)benzonitrile following Step 3 of Example 8. MS (ESI) m/z 244.1 [M+H]$^+$.

Intermediate B-48. 1-(4-(1-methyl-4-(trifluoromethyl)-1H-imidazol-2-yl)phenyl) cyclopropan-1-amine

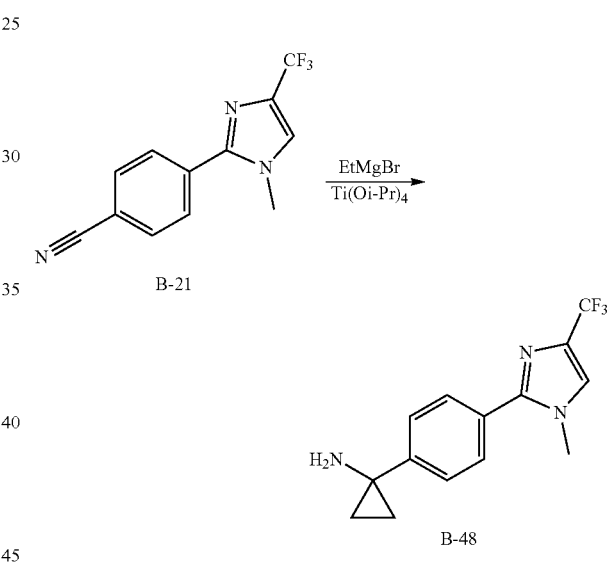

To a solution of Intermediate B-21 (500 mg, 1.99 mmol) and titanium(IV) isopropoxide (0.642 ml, 2.19 mmol) in diethyl ether (10 ml) was added ethyl magnesium bromide (1.460 ml, 4.38 mmol) at −70° C. The mixture was diluted with THF (3 ml) and was stirred at −70° C. for 10 min, then slowly warmed up to ambient temperature over 1 h. The mixture was then treated with boron trifluoride etherate (0.504 ml, 3.98 mmol) and was stirred for 2 h. The reaction was quenched by addition of 1N HCl (6 mL), diethyl ether (30 mL) was added and the mixture was basified with 10% NaOH (20 mL) to achieve a pH 11-12. The mixture was extracted twice with diethyl ether and the combined organic extracts were dried over sodium sulfate, filtered and concentrated to a residue which was purified by silica gel chromatography to afford 1-(4-(1-methyl-4-(trifluoromethyl)-1H-imidazol-2-yl)phenyl) cyclopropan-1-amine (62 mg, 11%). $^1$H NMR (300 MHz, CDCl$_3$) δ: 7.58 (d, J=9.0 Hz, 2H), 7.38 (d, J=8.4 Hz, 2H), 7.30 (d, J=0.9 Hz, 1H), 3.76 (s, 3H), 1.19-1.12 (m, 2H), 1.07-1.00 (m, 2H). MS (ESI) m/z 282.15 [M+H]$^+$.

Example 18: Intermediate B-49. 2-Chloro-9-(4-(1-methyl-4-(trifluoromethyl)-1H-imidazol-2-yl)benzyl)-7,9-dihydro-8H-purin-8-one

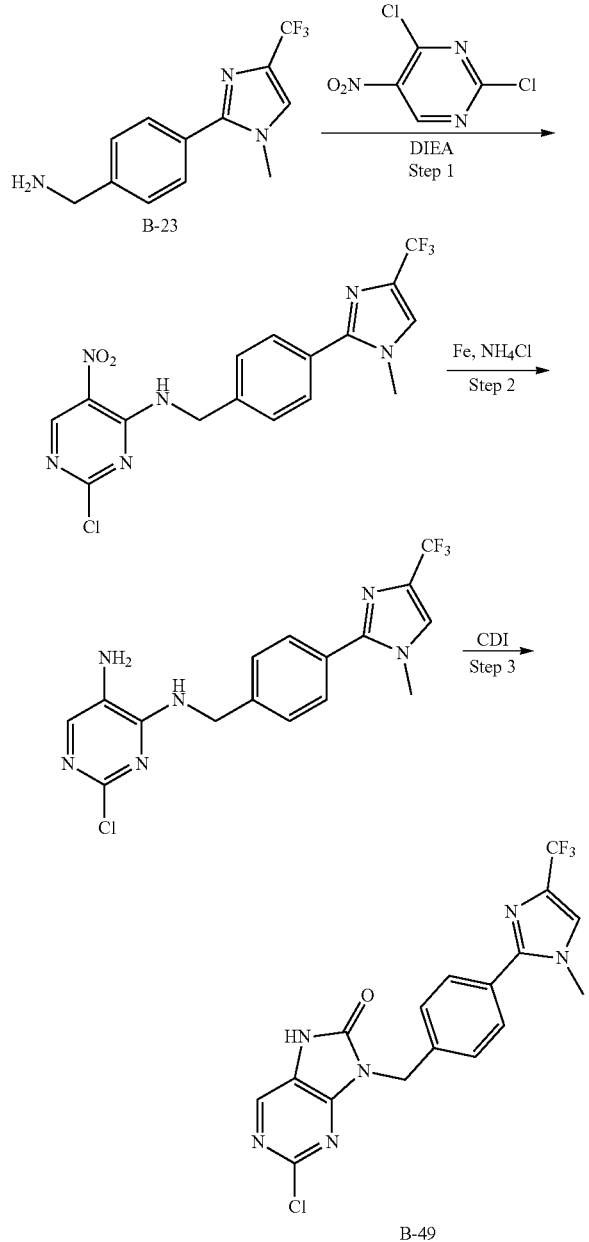

B-49

Step 1. 2-Chloro-N-(4-(1-methyl-4-(trifluoromethyl)-1H-imidazol-2-yl)benzyl)-5-nitropyrimidin-4-amine A mixture of 2,4-dichloro-5-nitropyrimidine (730 mg, 3.76 mmol) and DIEA (1.22 g, 9.40 mmol) in THF (20 mL) was treated with dropwise addition of a solution of Intermediate B-23 (800 mg, 3.13 mmol) in THF (10 mL) at −78° C. The solution was stirred for 2 h at −78° C. and allowed to warm to ambient temperature gradually over 1 h before being concentrated under vacuum. The residue was purified by silica gel chromatography (eluting with 0-50% EtOAc/PE) to afford 1.1 g (85%) of 2-chloro-N-(4-(1-methyl-4-(trifluoromethyl)-1H-imidazol-2-yl)benzyl)-5-nitropyrimidin-4-amine as a yellow oil. MS (ESI) m/z 413.1 [M+H]$^+$.

Step 2. 2-Chloro-N$^4$-(4-(1-methyl-4-(trifluoromethyl)-1H-imidazol-2-yl)benzyl)pyrimidine-4,5-diamine A mixture of 2-chloro-N-(4-(1-methyl-4-(trifluoromethyl)-1H-imidazol-2-yl)benzyl)-5-nitropyrimidin-4-amine (1.100 g, 2.67 mmol), iron powder (744 mg, 13.32 mmol) and ammonium chloride (285 mg, 5.33 mmol) in 3:3:1 THF/EtOH/water (21 mL) was stirred for 1 h at 80° C. After cooling to ambient temperature, the reaction mixture was filtered and concentrated under vacuum. The residue was purified by silica gel chromatography (eluting with a gradient of 0-100% EtOAc/PE) to afford 0.9 g (88%) of 2-chloro-N$^4$-(4-(1-methyl-4-(trifluoromethyl)-1H-imidazol-2-yl)benzyl)pyrimidine-4,5-diamine as a yellow solid. MS (ESI) m/z 383.1 [M+H]$^+$.

Step 3. 2-Chloro-9-(4-(1-methyl-4-(trifluoromethyl)-1H-imidazol-2-yl)benzyl)-7,9-dihydro-8H-purin-8-one A mixture of 2-chloro-N$^4$-(4-(1-methyl-4-(trifluoromethyl)-1H-imidazol-2-yl)benzyl)pyrimidine-4,5-diamine (900 mg, 2.35 mmol) and CDI (1.525 g, 9.40 mmol) in DCM (20 mL) was stirred for 2 h at 40° C. The reaction mixture was concentrated under vacuum and dissolved in EtOAc (100 mL). The resulting solution was washed with water (3×100 mL), dried over anhydrous sodium sulfate, filtered and concentrated under vacuum. The residue was purified by silica gel chromatography (eluting with a gradient of 0-100% EtOAc/PE) to afford 0.7 g (73%) of 2-chloro-9-(4-(1-methyl-4-(trifluoromethyl)-1H-imidazol-2-yl)benzyl)-7,9-dihydro-8H-purin-8-one as a yellow solid. MS (ESI) m/z 408.9 [M+H]$^+$.

Intermediate B-50: 2-(Dimethylamino)ethyl methanesulfonate

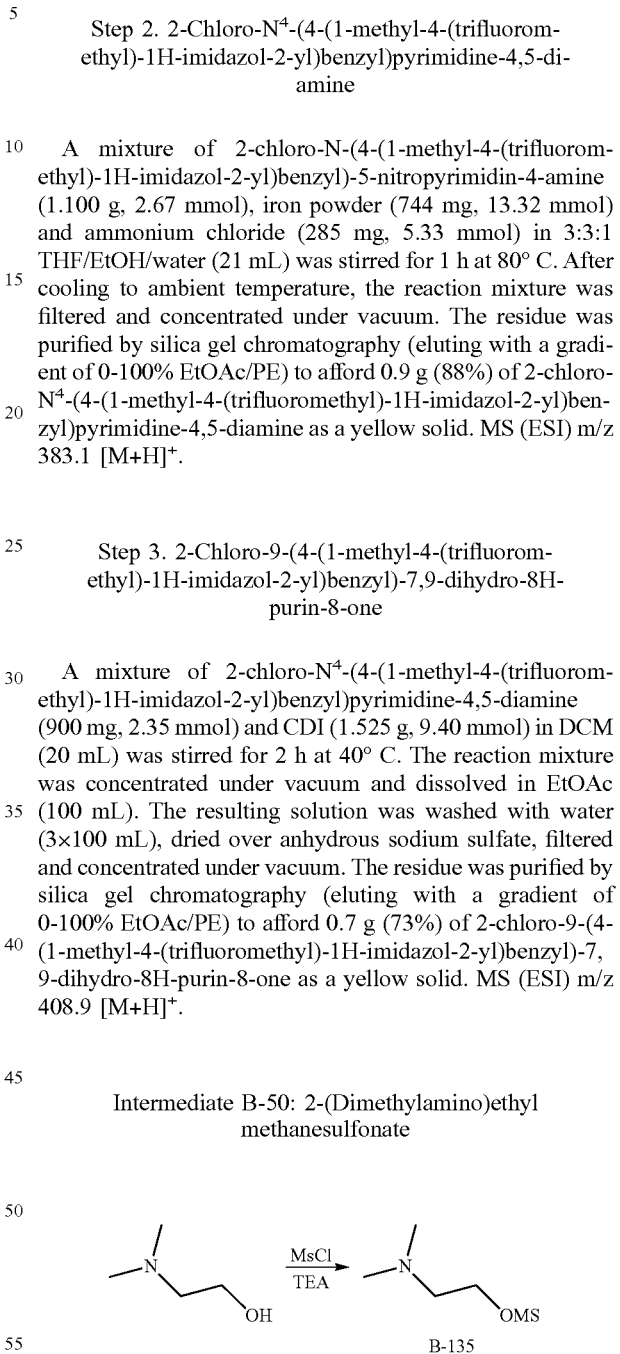

B-135

A mixture of 2-(dimethylamino)ethan-1-ol (890 mg, 9.98 mmol), triethyl amine (3.03 g, 29.94 mmol) and DCM (50 mL) was treated with methanesulfonyl chloride (1.725 g, 17.25 mmol) at 0° C. and the resulting solution was stirred for 1 h at 0° C. The reaction mixture was poured into water (50 mL) and extracted with EtOAc (20 mL×3). The organic layers were combined, dried over anhydrous sodium sulfate, filtered and concentrated under vacuum to afford 500 mg (crude) of 2-(dimethylamino)ethyl methanesulfonate as a light yellow solid. MS (ESI) m/z 168 [M+H]$^+$.

Example 19. Intermediate B-51: 5-(aminomethyl)-2-methylisoindolin-1-one

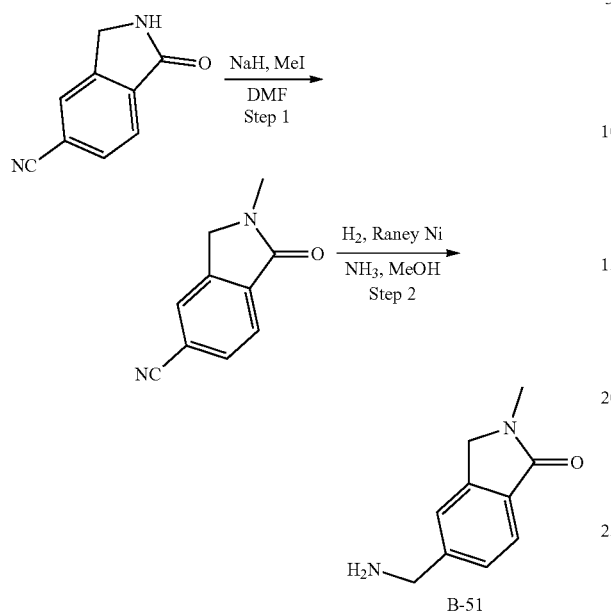

Step 1. 2-Methyl-1-oxoisoindoline-5-carbonitrile

A mixture of 1-oxoisoindoline-5-carbonitrile (500 mg, 3.16 mmol) and DMF (10 mL) was treated with sodium hydride (60% dispersion in mineral oil, 190 mg, 4.75 mmol) at 0° C. and the resulting mixture was stirred for 0.5 h at room temperature. Iodomethane (539 mg, 3.80 mmol) was added and the resulting solution was stirred for 1 h at 0° C. The reaction mixture was poured into ice/water (50 mL) and then extracted with EtOAc (3×100 mL). The organic layers were combined, dried over anhydrous sodium sulfate, filtered and concentrated under vacuum to afford 150 mg (28%) of 2-methyl-1-oxoisoindoline-5-carbonitrile as a yellow solid. MS (ESI) m/z 173.1 [M+H]$^+$.

Step 2. 5-(Aminomethyl)-2-methylisoindolin-1-one 5-(Aminomethyl)-2-methylisoindolin-1-one was obtained as a white solid from 2-Methyl-1-oxoisoindoline-5-carbonitrile following Step 3 of Example 8. MS (ESI) m/z 176.8 [M+H]$^+$.

Intermediate B-52. (4-(3-Fluoro-1H-pyrazol-1-yl)phenyl)methanamine

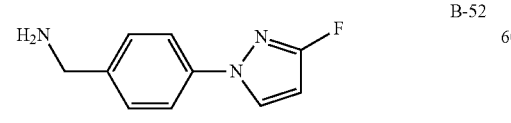

(4-(3-Fluoro-1H-pyrazol-1-yl)phenyl)methanamine was prepared according to Example 6. MS (ESI) m/z 191.8 [M+H]$^+$.

Intermediate B-53. (4-(2-Methyl-1H-pyrrol-1-yl)phenyl)methanamine

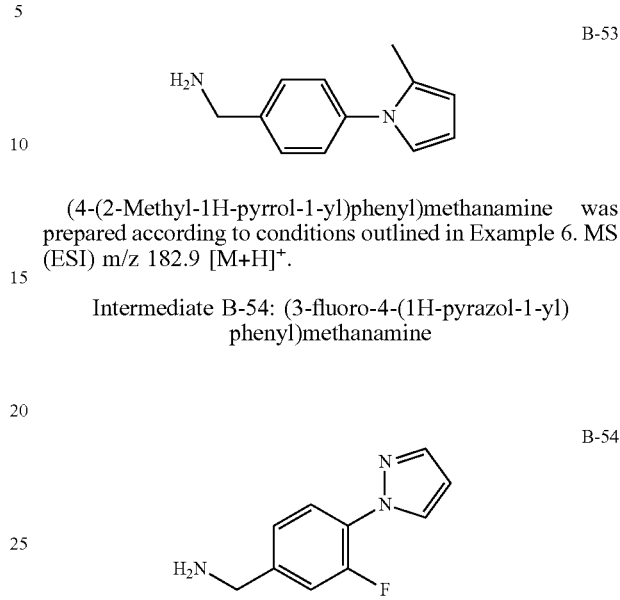

(4-(2-Methyl-1H-pyrrol-1-yl)phenyl)methanamine was prepared according to conditions outlined in Example 6. MS (ESI) m/z 182.9 [M+H]$^+$.

Intermediate B-54: (3-fluoro-4-(1H-pyrazol-1-yl)phenyl)methanamine (3-Fluoro-4-(1H-pyrazol-1-yl)phenyl)methanamine was prepared from 3,4-difluorobenzonitrile following Example 6.

Intermediate B-55. 2-(2-(Difluoromethyl)phenyl)-4,4,5,5-tetramethyl-1,3,2-dioxaborolane

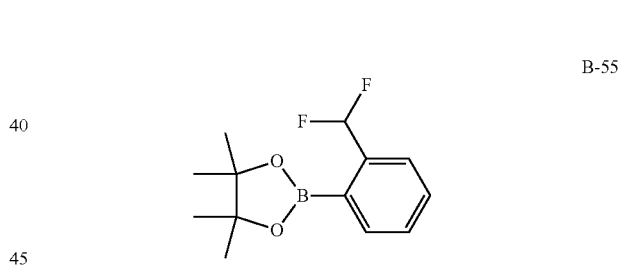

2-(2-(Difluoromethyl)phenyl)-4,4,5,5-tetramethyl-1,3,2-dioxaborolane was obtained as a colorless oil from 1-bromo-2-(difluoromethyl)benzene following Step 4 of Example 1. GC-MS (EI) m/z 254.1 [M]$^+$.

Intermediate B-56. 1-(2-(4,4,5,5-tetramethyl-1,3,2-dioxaborolan-2-yl)phenyl)ethan-1-one

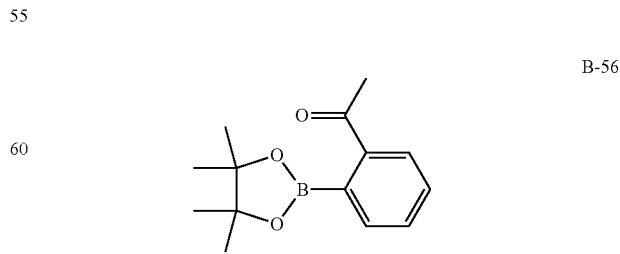

1-(2-(4,4,5,5-tetramethyl-1,3,2-dioxaborolan-2-yl)phenyl)ethan-1-one was obtained as a brown solid from 1-(2- bromophenyl)ethan-1-one following Step 4 of Example 1. MS (ESI) m/z 246.8 [M+H]⁺.

Intermediate B-57. 2-(4-Fluoro-2-isopropylphenyl)-4,4,5,5-tetramethyl-1,3,2-dioxaborolane

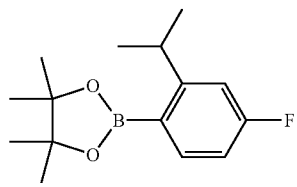

B-57

2-(4-Fluoro-2-isopropylphenyl)-4,4,5,5-tetramethyl-1,3,2-dioxaborolane was synthesized as a yellow oil from 2-bromo-4-fluorophenol following Example 1. $^1$H NMR (300 MHz, DMSO-$d_6$) δ 7.42-7.37 (m, 2H), 7.25-7.14 (m, 1H), 3.18-3.06 (m, 1H), 1.29 (d, J=6.80 Hz, 6H), 1.18-1.06 (m, 12H).

Intermediate B-58. 2-(5-Fluoro-2-isopropylphenyl)-4,4,5,5-tetramethyl-1,3,2-dioxaborolane

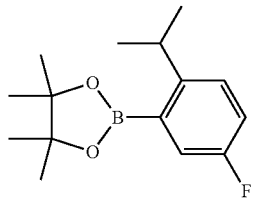

B-58

2-(5-Fluoro-2-isopropylphenyl)-4,4,5,5-tetramethyl-1,3,2-dioxaborolane was synthesized from 2-bromo-5-fluorophenol following Example 1. MS (ESI) m/z 265 [M+H]⁺.

Intermediate B-59. 5-fluoro-2-isopropyl-3-(4,4,5,5-tetramethyl-1,3,2-dioxaborolan-2-yl)pyridine

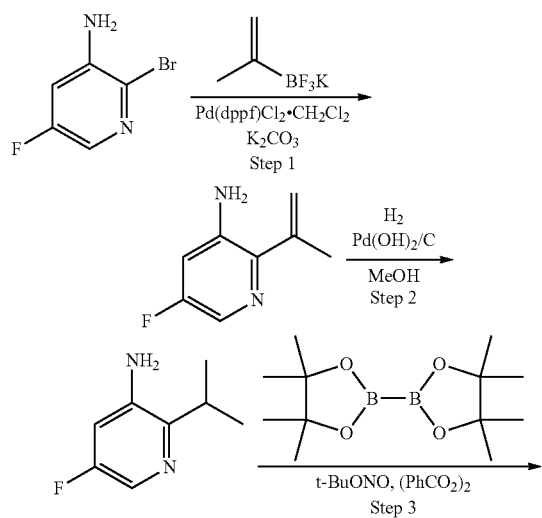

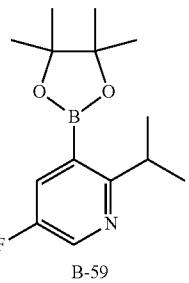

B-59

Step 1. 5-Fluoro-2-(prop-1-en-2-yl)pyridin-3-amine

In a 100 mL flask purged and maintained with an inert atmosphere of nitrogen, a mixture of 2-bromo-5-fluoropyridin-3-amine (1 g, 5.24 mmol), potassium isopropenyltrifluoroborate (852 mg, 5.76 mmol), Pd(dppf)Cl₂·CH₂Cl₂ (427 mg, 0.52 mmol), potassium carbonate (1.445 g, 10.46 mmol), 1,4-dioxane (40 mL) and water (5 mL) was stirred for 6 h at 105° C. After cooling to ambient temperature, the reaction mixture was diluted with water (50 mL) and was extracted with EtOAc (3×50 mL). The organic layers were combined, dried over anhydrous sodium sulfate, filtered and concentrated under vacuum. The residue was purified by silica gel chromatography (eluting with 1/100 to 1/3 EtOAc/PE) to afford 700 mg (88%) of 5-fluoro-2-(prop-1-en-2-yl)pyridin-3-amine as an off-white solid. MS (ESI) m/z 152.9 [M+H]⁺.

Step 2. 5-Fluoro-2-isopropylpyridin-3-amine

A mixture of 5-fluoro-2-(prop-1-en-2-yl)pyridin-3-amine (700 mg, 4.60 mmol), MeOH (20 mL) and palladium hydroxide on carbon (≥75% Pd, 500 mg) was placed under an atmosphere of hydrogen and stirred for 2 h at ambient temperature. The reaction mixture was filtered and concentrated under vacuum to afford 500 mg (70%) of 5-fluoro-2-(propan-2-yl)pyridin-3-amine as a light yellow solid. MS (ESI) m/z 155.2 [M+H]⁺.

Step 3. 5-Fluoro-2-isopropyl-3-(4,4,5,5-tetramethyl-1,3,2-dioxaborolan-2-yl)pyridine A mixture of 5-fluoro-2-(propan-2-yl)pyridin-3-amine (500 mg, 3.24 mmol), acetonitrile (3 mL), 4,4,5,5-tetramethyl-2-(tetramethyl-1,3,2-dioxaborolan-2-yl)-1,3,2-dioxaborolane (907 mg, 3.57 mmol) and benzoyl peroxide (78 mg, 0.30 mmol) was treated with tert-butyl nitrite (501 mg, 4.86 mmol) with stirring at ambient temperature. The resulting solution was stirred for 16 h, then was concentrated under vacuum. The residue was purified by silica gel chromatography (eluting with 1/100 to 1/10 EtOAc/PE) to afford 140 mg (16%) of 5-fluoro-2-(propan-2-yl)-3-(tetramethyl-1,3,2-dioxaborolan-2-yl)pyridine as a red solid. MS (ESI) m/z 266.1 [M+H]⁺.

Example 20: Intermediate B-60. 3-Isopropyl-4-(tributylstannyl)pyridine

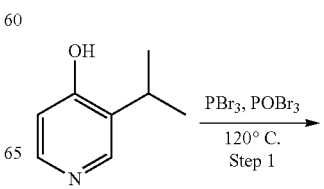

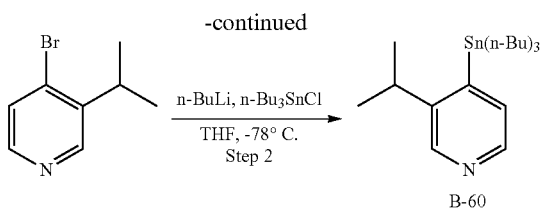

Step 1. 4-Bromo-3-isopropylpyridine

A mixture of 3-(propan-2-yl)pyridin-4-ol (synthesized from 3-bromopyridin-4-ol following Steps 1-2 of Example 1) (1 g, 7.29 mmol), phosphorous tribromide (2.13 g, 7.87 mmol) and phosphoryl bromide (2.14 g, 7.46 mmol) was stirred for 3 h at 120° C. After cooling to room temperature, the reaction mixture was poured into ice/water (20 mL) and the pH value was adjusted to 8 with 2N NaOH. The resulting solution was extracted with DCM (2×100 mL) and the organic layers were combined, dried over anhydrous sodium sulfate, filtered and concentrated under vacuum. The residue was purified by silica gel chromatography (eluting with 1/99 to 25/75 EtOAc/PE) to afford 500 mg (34%) of 4-bromo-3-(propan-2-yl)pyridine as a yellow oil. MS (ESI) m/z 199.9, 201.9 [M+H]$^+$.

Step 2. 3-Isopropyl-4-(tributylstannyl)pyridine

In a flask purged and maintained with an inert atmosphere of nitrogen, a solution of 4-bromo-3-(propan-2-yl)pyridine (600 mg, 3.00 mmol) in THF (8 mL) at −78° C. was treated dropwise with n-butyllithium (2.5 M in hexane, 1.2 mL, 3.00 mmol) and the resulting solution was stirred for 0.5 h at −78° C. Tributylchlorostannane (1.04 g, 3.18 mmol) was added and the resulting mixture was stirred for 2 h at −78° C. The reaction was quenched by the addition of saturated ammonium chloride solution (10 mL), and the resulting solution was extracted with EtOAc (2×10 mL). The organic layers were combined, dried over anhydrous sodium sulfate, filtered and concentrated under vacuum. The residue was purified by silica gel chromatography (eluting with 1/99 to 25/75 EtOAc/PE) to afford 180 mg (15%) of 3-isopropyl-4-(tributylstannyl)pyridine as colorless oil. $^1$H NMR (300 MHz, CDCl$_3$) δ 8.49 (s, 1H), 8.31 (d, J=4.80 Hz, 1H), 7.27 (d, J=5.40 Hz, 1H), 2.71-2.66 (m, 1H), 1.65-1.49 (m, 6H), 1.41-1.22 (m, 18H), 0.99-0.84 (m, 9H).

Intermediate B-61. 3-Isopropyl-2-(tributylstannyl)pyridine

3-Isopropylpyridin-2-ol (prepared from 3-bromopyridin-2-ol following Steps 1 and 2 of Example 1) was used to prepare 3-isopropyl-2-(tributylstannyl)pyridine as a colorless oil following Example 20. $^1$H NMR (300 MHz, CDCl$_3$) δ 8.58 (br s, 1H), 7.46-7.44 (m, 1H), 7.15-7.07 (m, 1H), 2.88-2.85 (m, 1H), 1.65-1.17 (m, 24H), 0.91-0.75 (m, 9H).

Intermediate B-62. 9-(4-Bromobenzyl)-2-chloro-7,9-dihydro-8H-purin-8-one

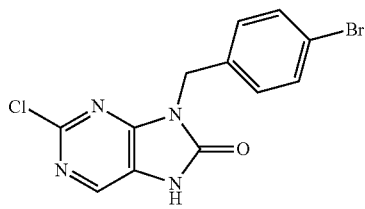

9-(4-Bromobenzyl)-2-chloro-7,9-dihydro-8H-purin-8-one was synthesized from (4-bromophenyl)methanamine according to Example 18. MS (ESI) m/z 341 [M+H]$^+$.

Intermediate B-63. (4-(5-Methyl-1H-1,2,3-triazol-1-yl)phenyl)methanamine

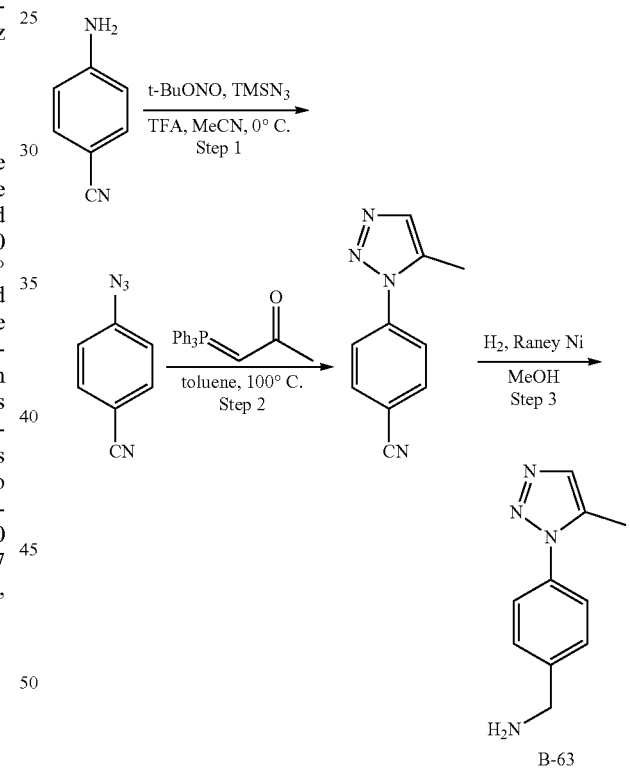

Step 1. 4-Azidobenzonitrile

A mixture of 4-aminobenzonitrile (5 g, 42.32 mmol) in TFA (3.25 mL) and acetonitrile (100 mL) was treated with dropwise addition of tert-butyl nitrite (7.55 g, 73.22 mmol) and azidotrimethylsilane (6.75 mL) with stirring at 0° C. The resulting solution was stirred for 1 h at 0° C. then was poured into water (50 mL) and was extracted with EtOAc (3×100 mL). The organic layers were combined, dried over anhydrous sodium sulfate, filtered and concentrated under vacuum. The residue was purified by silica gel chromatography (eluting with 1/3 EtOAc/PE) to afford 3.8 g (62%) of 4-azidobenzonitrile as a yellow solid. MS (ESI) m/z 145.1 [M+H]⁺.

Step 2.
4-(5-Methyl-1H-1,2,3-triazol-1-yl)benzonitrile

In a 100 mL round-bottom flask purged and maintained with an inert atmosphere, a mixture of 4-azidobenzonitrile (2 g, 13.88 mmol), 1-(triphenyl-λ⁵-phosphaneylidene)propan-2-one (4.4 g, 13.82 mmol) and toluene (25 mL) was stirred for 18 h at 100° C. After cooling to ambient temperature, the reaction mixture was concentrated under vacuum and the resulting residue was purified by silica gel chromatography (eluting with 1:1 EtOAc/PE) to afford 2.1 g (82%) of 4-(5-methyl-1H-1,2,3-triazol-1-yl)benzonitrile as a light yellow solid. MS (ESI) m/z 185.1 [M+H]⁺.

Step 3. (4-(5-Methyl-1H-1,2,3-triazol-1-yl)phenyl)
methanamine (4-(5-Methyl-1H-1,2,3-triazol-1-yl)phenyl)methanamine was obtained from 4-(5-methyl-1H-1,2,3-triazol-1-yl)benzonitrile as a light yellow solid following Example 10. MS (ESI) m/z 189.0 [M+H]⁺.

Intermediate B-64. 6-(aminomethyl)-2-methyl-3,4-dihydroisoquinolin-1(2H)-one

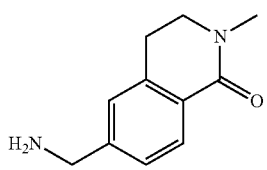

B-64

6-(Aminomethyl)-2-methyl-3,4-dihydroisoquinolin-1 (2H)-one was prepared according to Example 19. MS (ESI) m/z 191.0 [M+H]⁺.

Intermediate B-65. 1-(4-(Aminomethyl)phenyl)-1H-pyrazole-3-carbonitrile

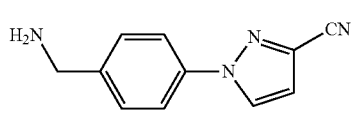

B-65

1-(4-(Aminomethyl)phenyl)-1H-pyrazole-3-carbonitrile was prepared as a colorless oil from 1H-pyrazole-3-carbonitrile according to Example 15. MS (ESI) m/z 199.0 [M+H]⁺.

Intermediate B-66.
(4-(2,5-Dimethyloxazol-4-yl)phenyl)methanamine

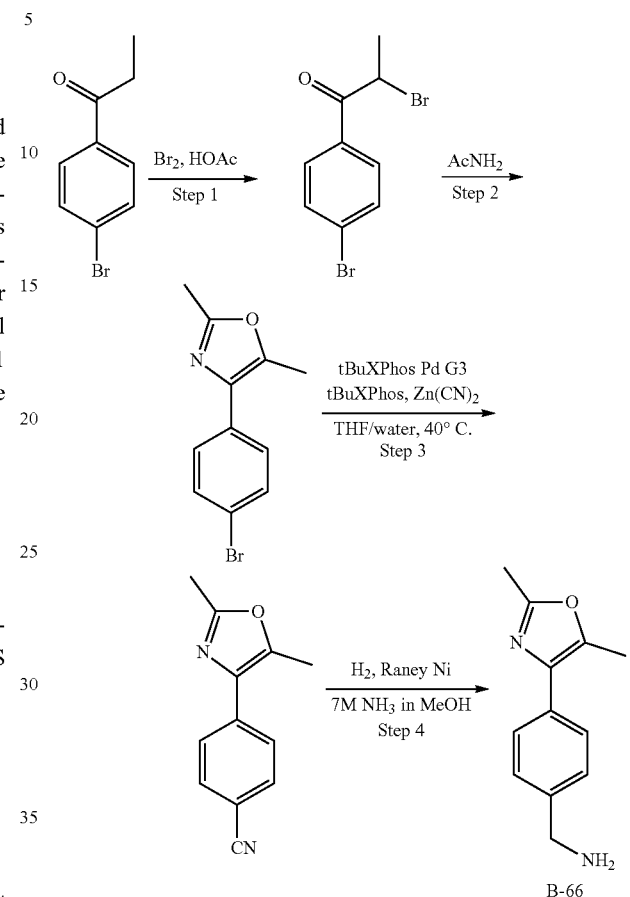

Step 1. 2-Bromo-1-(4-bromophenyl)propan-1-one

A mixture of 1-(4-bromophenyl)propan-1-one (10 g, 46.93 mmol) and acetic acid (20 mL) was treated with dropwise addition of bromine (8.2 g, 51.31 mmol) and the resulting solution was stirred for 2 h at 25° C. The reaction mixture was poured into water (100 mL) and was extracted with EtOAc (3×100 mL). The organic layers were combined, dried over anhydrous sodium sulfate, filtered and concentrated under vacuum. The residue was purified by silica gel chromatography (eluting with 1/10 EtOAc/PE) to afford 5.0 g (36%) of 2-bromo-1-(4-bromophenyl)propan-1-one as a yellow solid (R$_f$=0.4 in 25% EtOAc/PE). ¹H NMR (400 MHz, CDCl₃) δ 7.96-7.77 (m, 2H), 7.72-7.54 (m, 2H), 5.21 (q, J=6.60 Hz, 1H), 1.89 (d, J=6.60 Hz, 3H).

Step 2. 4-(4-Bromophenyl)-2,5-dimethyloxazole

A mixture of 2-bromo-1-(4-bromophenyl)propan-1-one (4.0 g, 13.70 mmol) and acetamide (814 mg, 13.78 mmol) was stirred for 1 h at 135° C. After cooling to room temperature, the reaction mixture was poured into saturated sodium bicarbonate solution (100 mL) and was then extracted with EtOAc (2×150 mL). The organic layers were combined, dried over anhydrous sodium sulfate, filtered and concentrated under vacuum. The residue was purified by silica gel chromatography (eluting with 1/10 EtOAc/PE) to

245 afford 2.3 g (67%) of 4-(4-bromophenyl)-2,5-dimethyloxazole as a light yellow solid. MS (ESI) m/z 251.6, 253.6 [M+H]$^+$.

Step 3. 4-(2,5-Dimethyloxazol-4-yl)benzonitrile 4-(2,5-Dimethyloxazol-4-yl)benzonitrile was prepared from 4-(4-bromophenyl)-2,5-dimethyloxazole following Step 4 of Example 17. MS (ESI) m/z 199.0 [M+H]$^+$ Step 4. (4-(2,5-Dimethyloxazol-4-yl)phenyl)methanamine (4-(2,5-Dimethyloxazol-4-yl)phenyl)methanamine was obtained from 4-(2,5-dimethyloxazol-4-yl)benzonitrile as a colorless oil following Step 3 of Example 8. MS (ESI) m/z 203.2 [M+H]$^+$ Intermediate B-67, 1-(4-(Aminomethyl)phenyl)-5-methyl-1H-pyrazole-3-carbonitrile and Intermediate B-68, 1-(4-(aminomethyl)phenyl)-3-methyl-1H-pyrazole-5-carbonitrile

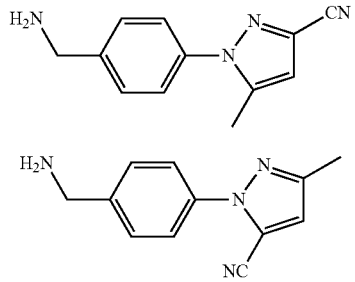

B-67

B-68

A mixture (~1:1) of 1-(4-(aminomethyl)phenyl)-5-methyl-1H-pyrazole-3-carbonitrile and 1-(4-(aminomethyl)phenyl)-3-methyl-1H-pyrazole-5-carbonitrile was prepared from 5-methyl-1H-pyrazole-3-carbonitrile following Example 15. MS (ESI) m/z 212.9 [M+H]$^+$.

Intermediate B-69: (4-(1-Methyl-1H-pyrazol-3-yl)phenyl)methanamine

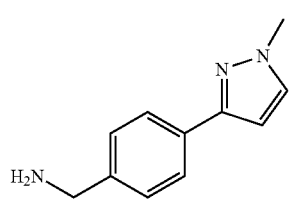

B-69 tert-Butyl (4-(1-methyl-1H-pyrazol-3-yl)benzyl)carbamate (formed from reaction of 3-bromo-1-methyl-1H-pyrazole and (4-(((tert-butoxycarbonyl)amino)methyl)phenyl)boronic acid following Step 1 of Example 7) was used in the preparation of the title compound following Step 2 of Example 15. MS (ESI) m/z 188.1 [M+H]$^+$.

246

Intermediate B-70. 9-(4-(1H-Pyrazol-1-yl)benzyl)-2-chloro-7-methyl-7,9-dihydro-8H-purin-8-one

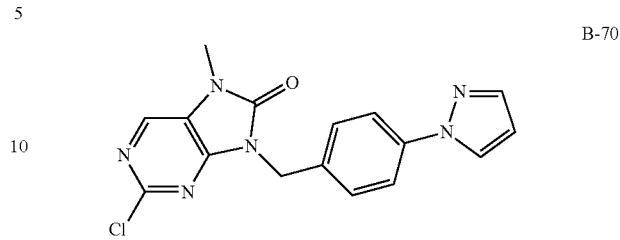

B-70

9-(4-(1H-pyrazol-1-yl)benzyl)-2-chloro-7,9-dihydro-8H-purin-8-one (prepared from Intermediate B-17 following Example 18) was used in the preparation of 9-(4-(1H-pyrazol-1-yl)benzyl)-2-chloro-7-methyl-7,9-dihydro-8H-purin-8-one following Example 33. MS (ESI) m/z 341 [M+H]$^+$.

Example 21: Intermediate B-71. 4-Chloro-2-(2-isopropylphenyl)-5-nitropyrimidine

Step 1. 2-Chloro-4-methoxy-5-nitropyrimidine

A solution of 2,4-dichloro-5-nitropyrimidine (50 g, 257.76 mmol) in MeOH (1 L) at −30° C. was treated with dropwise addition of a solution of sodium methanolate (13.9 g, 257 mmol) in MeOH (500 mL) and the resulting mixture was stirred for 2 h at 0° C. The reaction mixture was warmed to ambient temperature, concentrated under vacuum and purified by silica gel chromatography (eluting with a gradient of 1-10% EtOAc/PE) to afford 10 g (20%) of 2-chloro-4-methoxy-5-nitropyrimidine as a white solid. MS (ESI) m/z 190 [M+H]$^+$.

Step 2. 2-(2-Isopropylphenyl)-4-methoxy-5-nitropyrimidine

A mixture of 2-chloro-4-methoxy-5-nitropyrimidine (11 g, 58 mmol), (2-isopropylphenyl)boronic acid (9.52 g, 58 mmol), Pd(dppf)Cl$_2$·CH$_2$Cl$_2$ (4.73 g, 5.80 mmol) and potassium carbonate (16.02 g, 116 mmol) in 1,4-dioxane (200 mL) and water (50 mL) was stirred for 16 h at 80° C. After cooling to ambient temperature, the reaction mixture was poured into water (50 mL) and was extracted with EtOAc (3×100 mL). The organic layers were combined, dried over anhydrous sodium sulfate, filtered, concentrated under vacuum and purified by silica gel chromatography (eluting with a gradient of 1-10% EtOAc/PE) to afford 10 g (63%) of 2-(2-isopropylphenyl)-4-methoxy-5-nitropyrimidine as a yellow oil. MS (ESI) m/z 274 [M+H]$^+$.

Step 3. 2-(2-Isopropylphenyl)-5-nitropyrimidin-4-ol

A mixture of 2-(2-isopropylphenyl)-4-methoxy-5-nitropyrimidine (6 g, 22 mmol) and 33% hydrogen bromide in acetic acid (100 mL) was stirred for 1 h at 100° C. After cooling to ambient temperature, the reaction mixture was poured into water/ice (300 mL) and extracted with DCM (2×200 mL). The organic layers were combined, dried over anhydrous sodium sulfate, filtered and concentrated under vacuum to afford 5 g (88%) of 2-(2-isopropylphenyl)-5-nitropyrimidin-4-ol as a yellow oil. MS (ESI) m/z 260 [M+H]$^+$.

Step 4. 4-Chloro-2-(2-isopropylphenyl)-5-nitropyrimidine

A mixture of 2-(2-isopropylphenyl)-5-nitropyrimidin-4-ol (5 g, 19.3 mmol) and phosphorus(V) oxychloride (100 mL) was stirred for 2 h at 90° C. After cooling to ambient temperature, the reaction mixture was concentrated under vacuum and was purified by silica gel chromatography (eluting with a gradient of 1-10% EtOAc/PE) to afford 2.7 g (50%) of 4-chloro-2-(2-isopropylphenyl)-5-nitropyrimidine as a yellow oil. $^1$H NMR (300 MHz, CDCl$_3$) δ 9.35 (s, 1H), 7.89-7.79 (m, 1H), 7.64-7.48 (m, 2H), 7.37-7.30 (m, 1H), 3.68-3.59 (m, 1H), 1.30 (d, J=6.8 Hz, 6H). MS (ESI) m/z 278.1 [M+H]$^+$.

Intermediate B-72: (4-(1,4-Dimethyl-1H-pyrazol-3-yl)phenyl)methanamine

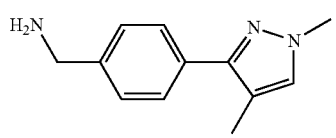

B-72

Using an analogous sequence as in the preparation of Intermediate B-69, (4-(1,4-dimethyl-1H-pyrazol-3-yl)phenyl)methanamine was synthesized from 3-bromo-1,4-dimethyl-1H-pyrazole (obtained from 3-bromo-4-methyl-1H-pyrazole using conditions in Example 9). MS (ESI) m/z 202.0 [M+H]$^+$.

Intermediate B-73: (4-(5-Morpholino-3-(trifluoromethyl)-1H-pyrazol-1-yl)phenyl)methanamine

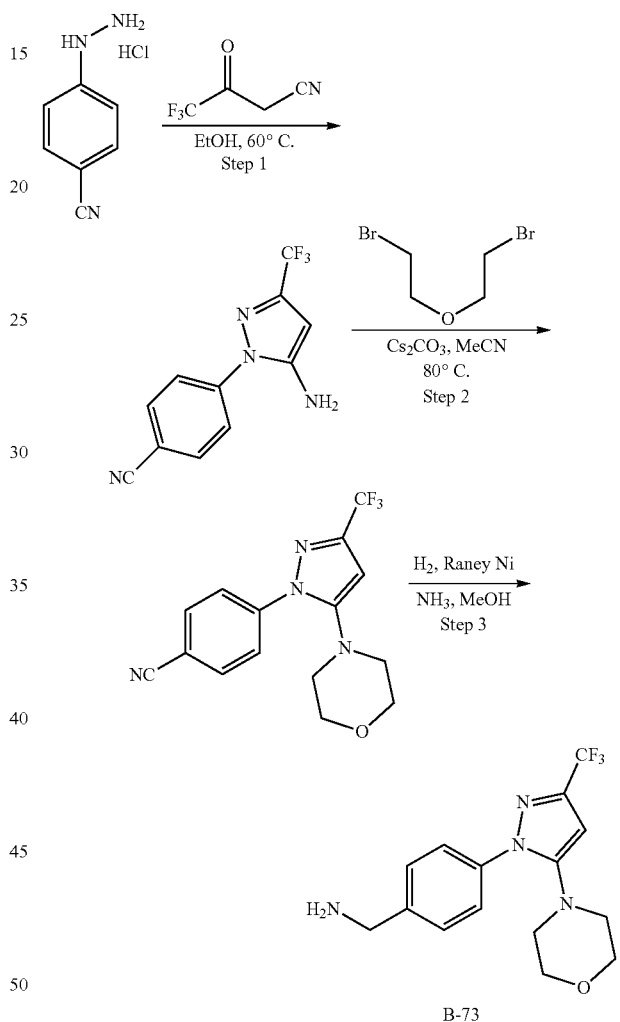

B-73

Step 1. 4-(5-Amino-3-(trifluoromethyl)-1H-pyrazol-1-yl)benzonitrile

A mixture of 4-hydrazinylbenzonitrile hydrochloride (742 mg, 4.37 mmol), 4,4,4-trifluoro-3-oxobutanenitrile (500 mg, 3.65 mmol) and EtOH (10 mL) was stirred for 16 h at 60° C. After cooling to room temperature, the reaction mixture was concentrated under vacuum and the residue was purified by silica gel chromatography (eluting with 3/7 EtOAc/PE) to afford 181 mg (20%) of 4-(5-Amino-3-(trifluoromethyl)-1H-pyrazol-1-yl)benzonitrile as a yellow solid. MS (ESI) m/z 253.0 [M+H]$^+$.

Step 2. 4-(5-Morpholino-3-(trifluoromethyl)-1H-pyrazol-1-yl)benzonitrile

In a sealed tube, a mixture of 4-(5-amino-3-(trifluoromethyl)-1H-pyrazol-1-yl)benzonitrile (130 mg, 0.52 mmol), 1-bromo-2-(2-bromoethoxy)ethane (1.052 g, 4.54 mmol), cesium carbonate (503 mg, 1.54 mmol) and acetonitrile (5 mL) was stirred for 16 h at 80° C. After cooling to room temperature, the reaction mixture was filtered and concentrated under vacuum and the residue was purified by prep-TLC (eluting with 1:3 EtOAc/PE) to afford 120 mg (72%) of 4-(5-morpholino-3-(trifluoromethyl)-1H-pyrazol-1-yl)benzonitrile as a yellow solid. MS (ESI) m/z 323.1 [M+H]$^+$.

Step 3. (4-(5-Morpholino-3-(trifluoromethyl)-1H-pyrazol-1-yl)phenyl)methanamine (4-(5-Morpholino-3-(trifluoromethyl)-1H-pyrazol-1-yl)phenyl)methanamine was obtained as a yellow solid from 4-(5-morpholino-3-(trifluoromethyl)-1H-pyrazol-1-yl)benzonitrile following Step 3 of Example 8. MS (ESI) m/z 327.1 [M+H]$^+$.

Intermediate B-74: (4-(3-Methoxy-5-methyl-1H-pyrazol-1-yl)phenyl)methanamine

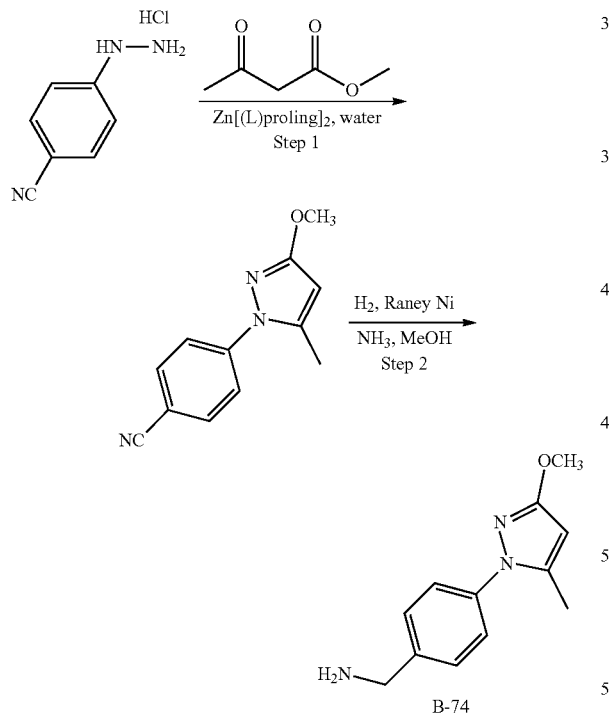

Step 1. 4-(3-Methoxy-5-methyl-1H-pyrazol-1-yl)benzonitrile

A mixture of (L)-proline (1.0 g, 8.69 mmol), MeOH (20 mL), triethylamine (1.2 mL) and zinc acetate (796 mg, 4.34 mmol) was stirred for 1.5 h at ambient temperature and the precipitate was collected by filtration and dried under vacuum to afford 1.4 g (crude) of Zn[(L)proline]2 as a white solid.

A solution of 4-hydrazinylbenzonitrile hydrochloride (1.69 g, 9.96 mmol), methyl 3-oxobutanoate (1.16 g, 9.96 mmol), water (10 mL) and Zn[(L)proline]2 (293 mg, 0.99 mmol) was stirred for 16 h at ambient temperature, then the reaction mixture was diluted with water (20 mL) and extracted with EtOAc (3×50 mL). The organic layers were combined, dried over anhydrous sodium sulfate, filtered and concentrated under vacuum. The residue was purified by silica gel chromatography (eluting with 1/9 EtOAc/PE) to afford 120 mg (6%) of 4-(3-methoxy-5-methyl-1H-pyrazol-1-yl)benzonitrile as a yellow solid. MS (ESI) m/z 213.9 [M+H]$^+$.

Step 2. (4-(3-Methoxy-5-methyl-1H-pyrazol-1-yl)phenyl)methanamine (4-(3-Methoxy-5-methyl-1H-pyrazol-1-yl)phenyl)methanamine was obtained as a yellow solid from 4-(3-methoxy-5-methyl-1H-pyrazol-1-yl)benzonitrile following Step 3 of Example 8. MS (ESI) m/z 218.2 [M+H]$^+$.

Intermediate B-75. 4-Chloro-2-(3-fluoro-2-isopropylphenyl)-5-nitropyrimidine

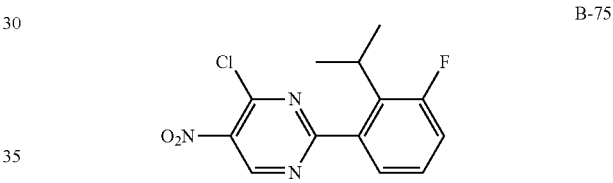

4-Chloro-2-(3-fluoro-2-isopropylphenyl)-5-nitropyrimidine was prepared from 2-(3-fluoro-2-isopropylphenyl)-4,4,5,5-tetramethyl-1,3,2-dioxaborolane according to Example 21. $^1$H NMR (400 MHz, CDCl$_3$) δ 9.34 (s, 1H), 7.54-7.45 (m, 1H), 7.35-7.25 (m, 1H), 7.26-7.13 (m, 1H), 3.45-3.29 (m, 1H), 1.42-1.27 (m, 6H). MS (ESI) m/z 295.9 [M+H]$^+$.

Intermediate B-76: (3,5-Difluoro-4-(1-methyl-4-(trifluoromethyl)-1H-imidazol-2-yl)phenyl)methanamine

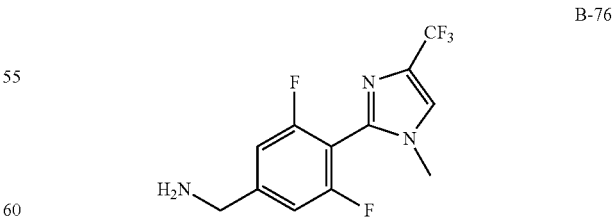

In an analogous fashion to the preparation of Intermediate B-23, (3,5-difluoro-4-(1-methyl-4-(trifluoromethyl)-1H-imidazol-2-yl)phenyl)methanamine was prepared as a green oil starting from 3,5-difluoro-4-formylbenzonitrile. MS (ESI) m/z 291.9 [M+H]$^+$.

Intermediate B-77: (2-Fluoro-4-(1-methyl-4-(trifluoromethyl)-1H-imidazol-2-yl)phenyl)methanamine

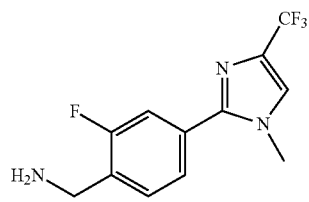

B-77

In an analogous fashion to the preparation of Intermediate B-23, (2-fluoro-4-(1-methyl-4-(trifluoromethyl)-1H-imidazol-2-yl)phenyl)methanamine was prepared from 2-fluoro-4-formylbenzonitrile.

Intermediate B-78. 4-((2-(2-Isopropylphenyl)-8-oxo-7,8-dihydro-9H-purin-9-yl)methyl)phenyl trifluoromethanesulfonate

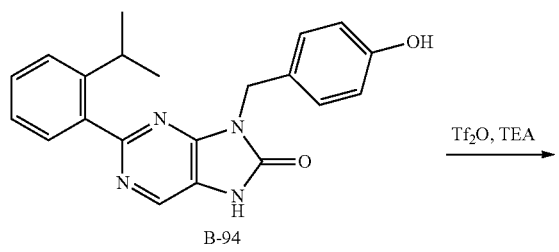

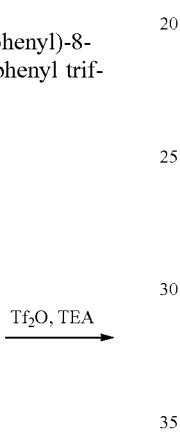

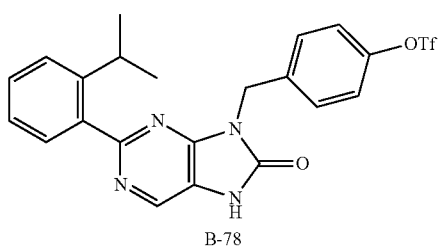

B-78

A mixture of Intermediate B-94 (5 g, 13.87 mmol), triethylamine (6.20 mL, 44.69 mmol) and DCM (100 mL) at −25° C. was treated with dropwise addition of a solution of trifluoromethanesulfonic anhydride (4.30 g, 15.23 mmol) in DCM (100 mL) and the resulting solution was stirred for 1 h at −25° C. The reaction mixture was then poured into water (200 mL) and was extracted with DCM (3×200 mL). The organic layers were combined, dried over anhydrous sodium sulfate, filtered, and concentrated under vacuum. Initial purification by silica gel chromatography (eluting first with a gradient of 0-100% EtOAc/PE, then with a gradient of 0-10% MeOH/DCM) afforded the crude product ($R_f$=0.1 in 100% EtOAc), and a second purification using $C_{18}$-reversed phase silica gel chromatography (eluting with a gradient of 5-95% acetonitrile/NH$_4$HCO$_3$ solution (0.05%)) afforded pure 4-((2-(2-isopropylphenyl)-8-oxo-7,8-dihydro-9H-purin-9-yl)methyl)phenyl trifluoromethanesulfonate (1.02 g, 14.9%) of as an off-white solid. $^1$H NMR (300 MHz, DMSO-d$_6$) δ 11.60 (br s, 1H), 8.40 (s, 1H), 7.52-7.44 (m, 5H), 7.42-7.34 (m, 2H), 7.25-7.19 (m, 1H), 5.08 (s, 2H), 3.40-3.31 (m, 1H), 1.04 (d, J=6.90 Hz, 6H). MS (ESI) m/z 493 [M+H]$^+$.

Example 22: Intermediate B-79. 2-(2-Isopropylphenyl)-9-(4-(4,4,5,5-tetramethyl-1,3,2-dioxaborolan-2-yl)benzyl)-7,9-dihydro-8H-purin-8-one

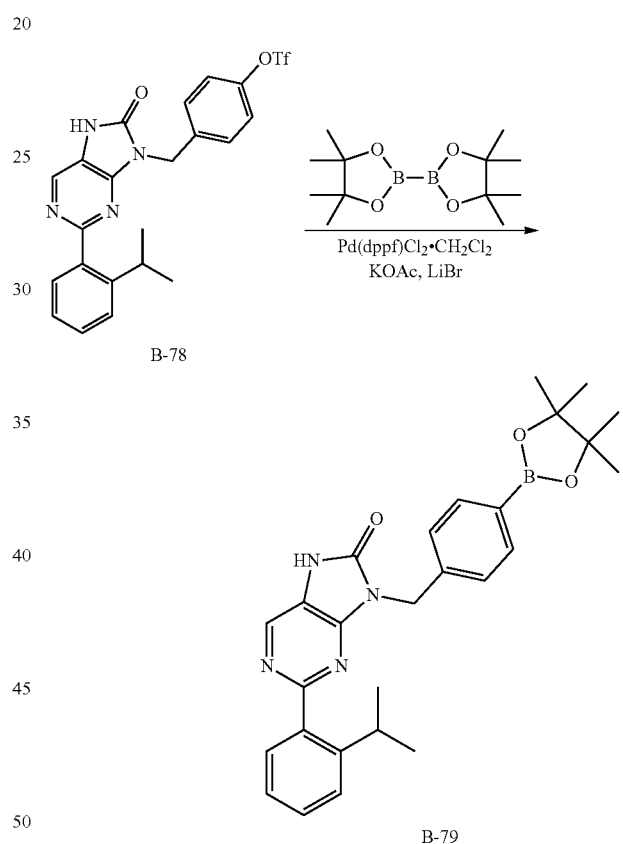

Under an atmosphere of nitrogen, a mixture of Intermediate B-78 (~80% pure, 300 mg, 0.49 mmol), 4,4,5,5-tetramethyl-2-(tetramethyl-1,3,2-dioxaborolan-2-yl)-1,3,2-dioxaborolane (774.4 mg, 3.05 mmol), Pd(dppf)Cl$_2$.CH$_2$Cl$_2$ (49.76 mg, 0.06 mmol), potassium acetate (515.8 mg, 5.26 mmol) and lithium bromide (106.1 mg, 1.23 mmol) in 1,4-dioxane (30 mL) was stirred for 16 h at 100° C. After cooling to ambient temperature, the reaction mixture was filtered, concentrated under vacuum and purified by prep-TLC (eluting with 1:20 MeOH/DCM) to afford 110 mg of 2-(2-isopropylphenyl)-9-(4-(4,4,5,5-tetramethyl-1,3,2-dioxaborolan-2-yl)benzyl)-7,9-dihydro-8H-purin-8-one (~69% pure by HPLC, contaminated with bis(diphenylphosphino)ferrocene dioxide). MS (ESI) m/z 471 [M+H]$^+$.

Example 23: Intermediate B-80. 2-(2-Isopropylphenyl)-7-methyl-9-(piperidin-4-ylmethyl)-7,9-dihydro-8H-purin-8-one

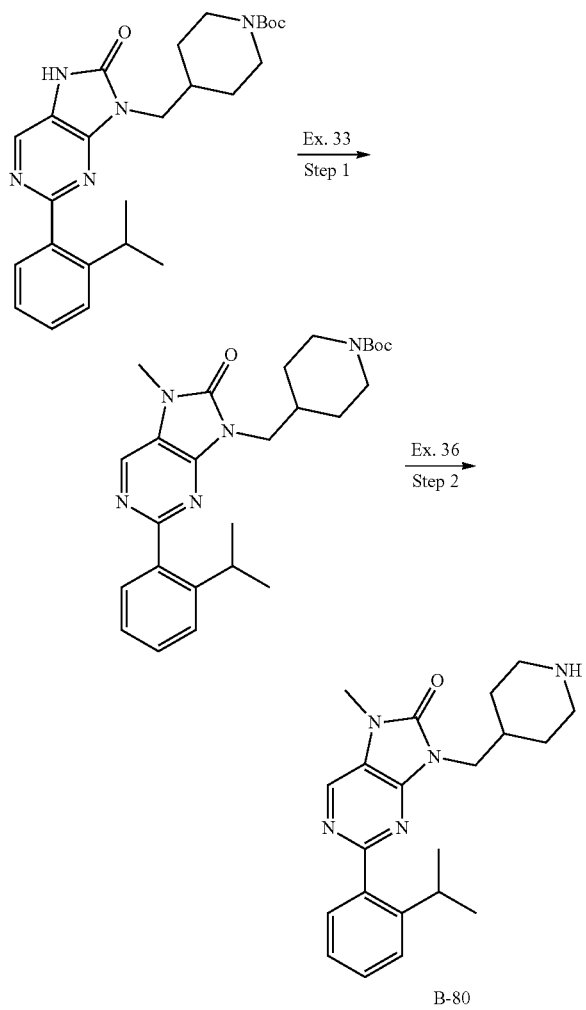

B-80

Step 1. tert-Butyl 4-((2-(2-isopropylphenyl)-7-methyl-8-oxo-7,8-dihydro-9H-purin-9-yl)methyl)piperidine-1-carboxylate tert-Butyl 4-((2-(2-isopropylphenyl)-8-oxo-7,8-dihydro-9H-purin-9-yl)methyl)piperidine-1-carboxylate (obtained from tert-butyl 4-(aminomethyl)piperidine-1-carboxylate following Example 31) was used to prepare tert-butyl 4-((2-(2-isopropylphenyl)-7-methyl-8-oxo-7,8-dihydro-9H-purin-9-yl)methyl)piperidine-1-carboxylate following Example 33. MS (ESI) m/z 466.2 [M+H]$^+$.

Step 2. 2-(2-Isopropylphenyl)-7-methyl-9-(piperidin-4-ylmethyl)-7,9-dihydro-8H-purin-8-one 2-(2-Isopropylphenyl)-7-methyl-9-(piperidin-4-ylmethyl)-7,9-dihydro-8H-purin-8-one was synthesized as a light yellow solid from tert-butyl 4-((2-(2-isopropylphenyl)-7-methyl-8-oxo-7,8-dihydro-9H-purin-9-yl)methyl)piperidine-1-carboxylate following Example 36. $^1$H NMR (300 MHz, DMSO-d$_6$) δ 8.55 (s, 1H), 7.55-7.35 (m, 3H), 7.30- 7.15 (m, 1H), 3.75-3.65 (m, 2H), 3.60-3.40 (m, 1H), 3.42 (s, 3H), 2.99-2.82 (m, 2H), 2.43-2.34 (m, 2H), 2.01-1.85 (m, 1H), 1.55-1.45 (m, 2H), 1.30-1.01 (m, 8H). MS (ESI) m/z 366.2 [M+H]$^+$.

Intermediate B-81. (4-(3,3-Dimethyloxetan-2-yl)phenyl)methanamine

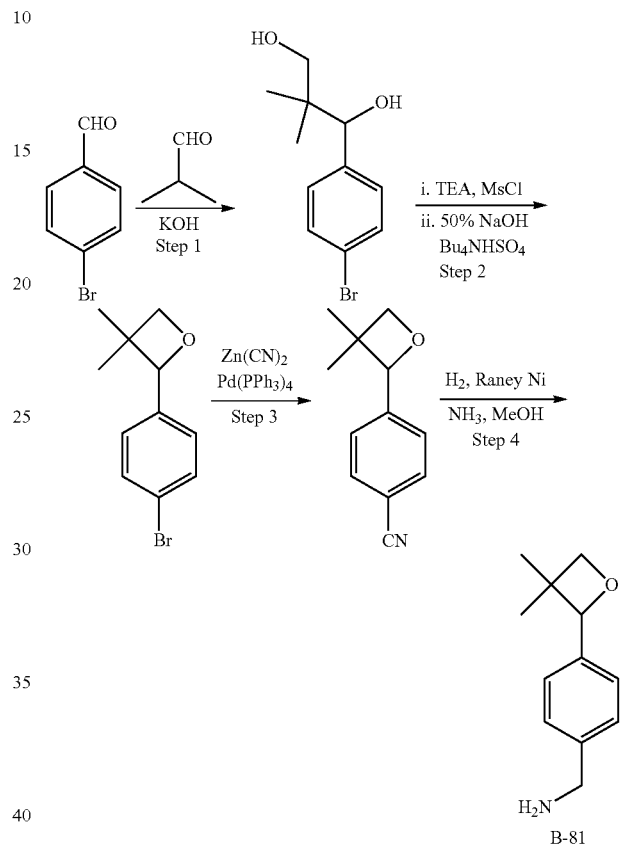

B-81

Step 1. 1-(4-Bromophenyl)-2,2-dimethylpropane-1,3-diol

A mixture of 4-bromobenzaldehyde (21.6 g, 116.75 mmol), 2-methylpropanal (18 g, 249.63 mmol) and MeOH (200 mL) was treated with slow addition of a solution of 2 N aqueous potassium hydroxide solution (125 ml) at 0° C. The resulting solution was stirred for 16 h at 67° C. and was then cooled to ambient temperature. The reaction mixture was concentrated to remove MeOH and was treated with water (100 mL). The resulting solution was extracted with EtOAc (3×100 mL), the organic layers were then combined, dried over anhydrous sodium sulfate, filtered and concentrated under vacuum. The residue was triturated with DCM, filtered and concentrated to afford 18 g (59%) of 1-(4-bromophenyl)-2,2-dimethylpropane-1,3-diol as a white solid. MS (ESI) m/z 241.2, 243.2 [M+H-H$_2$O]$^+$.

Step 2. 2-(4-Bromophenyl)-3,3-dimethyloxetane

A mixture of 1-(4-bromophenyl)-2,2-dimethylpropane-1,3-diol (8 g, 30.87 mmol), DCM (100 mL) and triethylamine (3.12 g, 30.83 mmol) was treated with slow addition of methanesulfonyl chloride (3.90 g, 34.05 mmol) at 0° C. and the resulting solution was stirred for 2 h at ambient temperature. The resulting mixture was washed with water (2×100 mL) and was poured into 50% aqueous NaOH solution (15.5 mL). Tetrabutylammonium hydrogen sulfate (0.23 g, 6.77 mmol) was then added and the resulting mixture was stirred for 4 h at ambient temperature. The reaction mixture was poured into water (100 mL) and was extracted with DCM (2×100 mL). The organic layers were combined, dried over anhydrous sodium sulfate, filtered and concentrated under vacuum. The residue was purified by silica gel chromatography (eluting with 1/20 EtOAc/PE) to afford 3.3 g (44%) of 2-(4-bromophenyl)-3,3-dimethyloxetane as a yellow oil. $^1$H NMR (400 MHz, CDCl$_3$) δ 7.58-7.41 (m, 2H), 7.21-7.08 (m, 2H), 5.45 (s, 1H), 4.52 (d, J=5.60 Hz, 1H), 4.24 (d, J=5.60 Hz, 1H), 1.39 (s, 3H), 0.78 (s, 3H).

Step 3. 4-(3,3-Dimethyloxetan-2-yl)benzonitrile 4-(3,3-Dimethyloxetan-2-yl)benzonitrile was prepared as a yellow oil following Step 5 of Example 25. $^1$H NMR (400 MHz, CDCl$_3$) δ 7.71-7.63 (m, 2H), 7.44-7.35 (m, 2H), 5.52 (s, 1H), 4.55 (d, J=5.60 Hz, 1H), 4.26 (d, J=5.60 Hz, 1H), 1.43 (s, 3H), 0.77 (s, 3H).

Step 4. (4-(3,3-Dimethyloxetan-2-yl)phenyl)methanamine

[4-(3,3-Dimethyloxetan-2-yl)phenyl]methanamine was prepared as a yellow oil following Step 3 of Example 8. MS (ESI) m/z 192.2 [M+H]$^+$.

Intermediate B-82. 9-(4-Azidobenzyl)-2-(2-isopropylphenyl)-7,9-dihydro-8H-purin-8-one

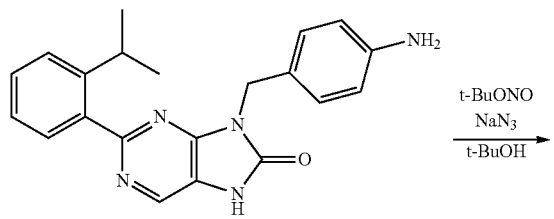

A solution of sodium azide (490 mg, 7.54 mmol) in t-butanol (10 mL) and water (0.5 mL) was treated by the addition of Intermediate B-134 (950 mg, 2.64 mmol) and t-butylnitrite (3.3 g, 32.04 mmol). The resulting solution was stirred for 4 h at ambient temperature, then was poured into brine (30 mL) and then extracted with EtOAc (3×50 mL). The organic layers were combined, dried over anhydrous sodium sulfate, filtered and concentrated under vacuum. The residue was purified by silica gel chromatography (eluting with 2:1 EtOAc/PE) to afford 303.4 mg (30%) of 9-(4-azidobenzyl)-2-(2-isopropylphenyl)-7,9-dihydro-8H-purin-8-one as a yellow solid. $^1$H NMR (400 MHz, CD$_3$OD) δ 8.30 (s, 1H), 7.38-7.45 (m, 5H), 7.27-7.22 (m, 1H), 7.04-7.00 (m, 2H), 5.12 (s, 2H), 3.32-3.30 (m, 1H), 1.16-1.11 (m, 6H). MS (ESI) m/z 386.1 [M+H]$^+$.

Intermediate B-83. 2-(2-Isopropylphenyl)-9-(1-(4-(4,4,5,5-tetramethyl-1,3,2-dioxaborolan-2-yl)phenyl)ethyl)-7,9-dihydro-8H-purin-8-one

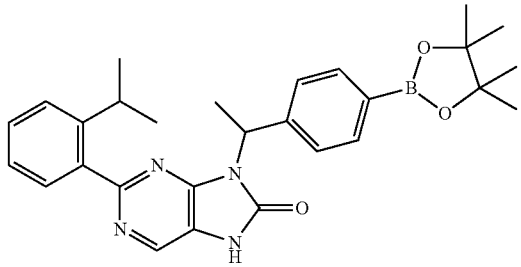

2-(2-Isopropylphenyl)-9-(1-(4-(4,4,5,5-tetramethyl-1,3,2-dioxaborolan-2-yl)phenyl)ethyl)-7,9-dihydro-8H-purin-8-one was prepared in an analogous fashion to Intermediate B-79, starting from 1-(4-bromophenyl)ethan-1-amine. $^1$H NMR (400 MHz, DMSO-d$_6$) δ 11.58 (s, 1H), 8.39 (s, 1H), 7.64-7.62 (m, 2H), 7.50-7.47 (m, 1H), 7.40-7.36 (m, 4H), 7.25-7.23 (m, 1H), 5.72-5.70 (m, 1H), 3.45-3.35 (m, 1H), 1.95 (d, J=7.2 Hz, 3H), 1.27 (s, 12H), 1.03-1.00 (m, 6H). MS (ESI) m/z 485.2 [M+H]$^+$.

Intermediate B-84, tert-Butyl 4-(2-iodo-1-methyl-1H-imidazol-4-yl)piperidine-1-carboxylate and tert-butyl 4-(2-iodo-1-methyl-1H-imidazol-5-yl)piperidine-1-carboxylate

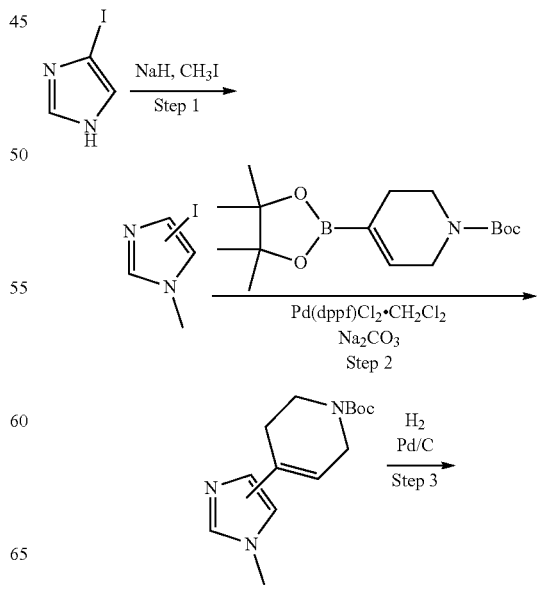

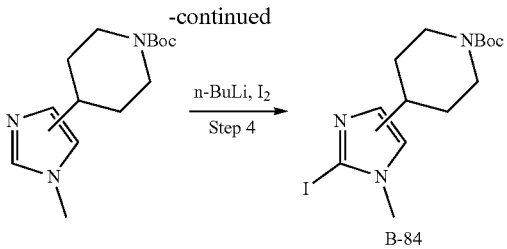

B-84

Step 1. 4-Iodo-1-methyl-1H-imidazole and 5-iodo-1-methyl-1H-imidazole

Under an atmosphere of nitrogen at 0° C., a solution of 4-iodo-1H-imidazole (5.82 g, 30.00 mmol) in THF (50 mL) was treated with portionwise addition of sodium hydride (60% dispersion in mineral oil, 1.44 g, 36.00 mmol). After stirring for 30 min at 0° C., iodomethane was added (2.8 mL, 45.00 mmol) and the mixture was stirred for 1 h at 0° C. The reaction mixture was poured into water (100 mL) and was extracted with EtOAc (2×100 mL). The organic layers were combined, dried over anhydrous sodium sulfate, filtered and concentrated under vacuum to afford 6.24 g (90%) of a ~3:1 mixture of 4-iodo-1-methyl-1H-imidazole and 5-iodo-1-methyl-1H-imidazole as a light yellow solid. MS (ESI) m/z 209 [M+H]$^+$.

Step 2. tert-Butyl 4-(1-methyl-1H-imidazol-4-yl)-3,6-dihydropyridine-1(2H)-carboxylate and tert-butyl 4-(1-methyl-1H-imidazol-5-yl)-3,6-dihydropyridine-1(2H)-carboxylate A ~3:1 mixture of 4-iodo-1-methyl-1H-imidazole and 5-iodo-1-methyl-1H-imidazole (6.24 g, 30.00 mmol), tert-butyl 4-(4,4,5,5-tetramethyl-1,3,2-dioxaborolan-2-yl)-5,6-dihydropyridine-1(2H)-carboxylate (11.1 g, 36.00 mmol), Pd(dppf)Cl$_2$·CH$_2$Cl$_2$ (2.45 g, 3.00 mmol) and sodium carbonate (6.36 g, 60.00 mmol) in water (60 mL) and 1,4-dioxane (300 mL) was stirred under an atmosphere of nitrogen for 3 h at 80° C. After cooling to ambient temperature, the reaction mixture was poured into EtOAc (100 mL) and was washed with water (2×100 mL), dried over anhydrous sodium sulfate, filtered and concentrated under vacuum. The residue was purified by silica gel chromatography (eluting with a gradient of 1-5% DCM/MeOH) to afford 5 g (57%) of a ~3:1 mixture of tert-butyl 4-(1-methyl-1H-imidazol-4-yl)-3,6-dihydropyridine-1(2H)-carboxylate and tert-butyl 4-(1-methyl-1H-imidazol-5-yl)-3,6-dihydropyridine-1(2H)-carboxylate as a yellow oil. MS (ESI) m/z 264 [M+H]$^+$.

Step 3. tert-Butyl 4-(1-methyl-1H-imidazol-4-yl)piperidine-1-carboxylate and tert-butyl 4-(1-methyl-1H-imidazol-5-yl)piperidine-1-carboxylate A ~3:1 mixture of tert-butyl 4-(1-methyl-1H-imidazol-4-yl)-3,6-dihydropyridine-1(2H)-carboxylate and tert-butyl 4-(1-methyl-1H-imidazol-5-yl)-3,6-dihydropyridine-1(2H)-carboxylate (5 g, 19.01 mmol) and palladium on carbon (10 wt. %, 5 g) in MeOH (100 mL) was evacuated and backfilled with hydrogen several times and was then charged with hydrogen. The resulting mixture was stirred for 1 h at ambient temperature before being filtered and concentrated under vacuum, resulting in 1.7 g (34%) of a ~3:1 mixture of tert-butyl 4-(1-methyl-1H-imidazol-4-yl)piperidine-1-carboxylate and tert-butyl 4-(1-methyl-1H-imidazol-5-yl)piperidine-1-carboxylate as a yellow oil. MS (ESI) m/z 266 [M+H]$^+$.

Step 4. tert-Butyl 4-(2-iodo-1-methyl-1H-imidazol-4-yl)piperidine-1-carboxylate and tert-butyl 4-(2-iodo-1-methyl-1H-imidazol-5-yl)piperidine-1-carboxylate A ~3:1 mixture of tert-butyl 4-(1-methyl-1H-imidazol-4-yl)piperidine-1-carboxylate and tert-butyl 4-(1-methyl-1H-imidazol-5-yl)piperidine-1-carboxylate (1.67 g, 6.30 mmol) in THF (15 mL) at −78° C. was treated by dropwise addition of n-butyllithium (2.5 M in THF, 3 mL, 7.56 mmol). After the mixture was stirred for 45 min at −78° C., a solution of I2 (4.79 g, 18.87 mmol) in THF (15 mL) was added and the resulting mixture was stirred for 3 h at −78° C. The reaction mixture was poured into saturated ammonium chloride solution (100 mL) and was then extracted with EtOAc (3×30 mL). The organic layers were combined, dried over anhydrous sodium sulfate, filtered and concentrated under vacuum. The residue was purified by silica gel chromatography (eluting with a gradient of 1-50% EtOAc/PE) to afford 1.16 g (47%) of a ~3:1 mixture of tert-butyl 4-(2-iodo-1-methyl-1H-imidazol-4-yl)piperidine-1-carboxylate and tert-butyl 4-(2-iodo-1-methyl-1H-imidazol-5-yl)piperidine-1-carboxylate as a light yellow oil. MS (ESI) m/z 392 [M+H]$^+$.

Intermediate B-85, 2-Bromo-1-isopropyl-4-methyl-1H-imidazole and 2-bromo-1-isopropyl-5-methyl-1H-imidazole

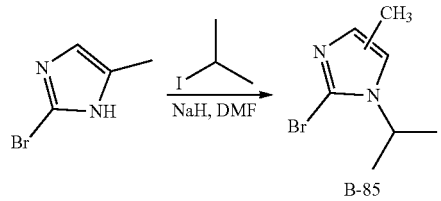

B-85

A mixture of 2-bromo-5-methyl-1H-imidazole (500 mg, 3.13 mmol) and DMF (10 mL) was treated with portionwise addition of NaH (60% dispersion in mineral oil, 250 mg, 5.22 mmol) at 0° C. After stirring for 30 min at 0° C., 2-iodopropane (639 mg, 3.76 mmol) was added and the resulting mixture was stirred for 1 h at ambient temperature. The reaction mixture was poured into saturated ammonium chloride solution (10 mL) and was extracted with EtOAc (10 mL×2). The organic layers were combined, washed with water (20 mL), dried over anhydrous sodium sulfate, filtered and concentrated under vacuum. The residue was purified by silica gel chromatography (eluting with 1% to 3% EtOAc/PE) to afford 400 mg (64%) of a ~8:1 mixture of 2-bromo-1-isopropyl-4-methyl-1H-imidazole and 2-bromo-1-isopropyl-5-methyl-1H-imidazole as a yellow solid. MS (ESI) m/z 203, 205 [M+H]$^+$.

Intermediate B-86. 2-(2-Isopropylphenyl)-7-methyl-9-(4-(4,4,5,5-tetramethyl-1,3,2-dioxaborolan-2-yl)benzyl)-7,9-dihydro-8H-purin-8-one

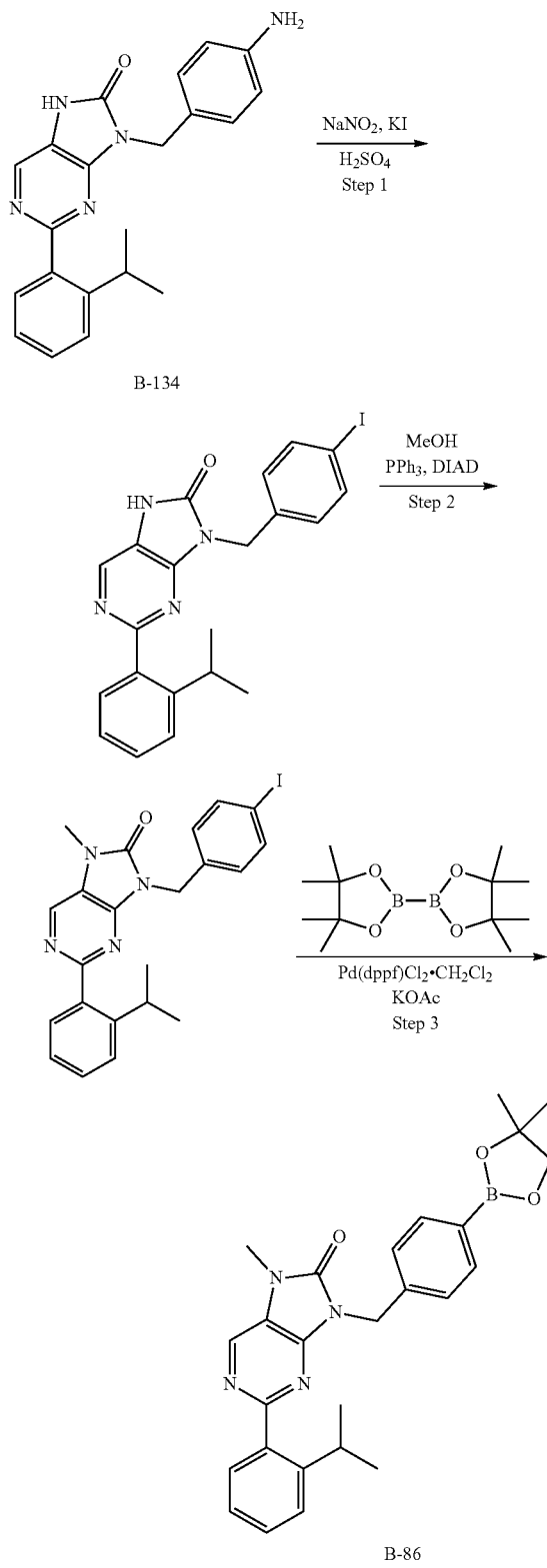

Step 1. 9-(4-Iodobenzyl)-2-(2-isopropylphenyl)-7,9-dihydro-8H-purin-8-one

A mixture of Intermediate B-134 (4.8 g, 13.35 mmol) and DMSO (13 mL) at 0° C. was treated by the slow addition of sulfuric acid (16 mL). After stirring for 1 h, a solution of sodium nitrite (1.29 g, 18.70 mmol) in water (4 mL) was added and the resulting mixture was stirred for 1 h at 0° C., followed by dropwise addition of a solution of potassium iodide (6.2 g, 37.34 mmol) in water (20 mL) at 0° C. The resulting mixture was stirred for 16 h at ambient temperature, then was poured into water (50 mL) and then extracted with DCM (3×50 mL). The organic layers were combined, dried over anhydrous sodium sulfate, filtered and concentrated under vacuum. The residue was purified by silica gel chromatography (eluting with 50-50% EtOAc/PE) to afford 5 g (80%) of 9-(4-iodobenzyl)-2-(2-isopropylphenyl)-7,9-dihydro-8H-purin-8-one as a red solid. MS (ESI) m/z 471.1 [M+H]$^+$.

Step 2. 9-(4-Iodobenzyl)-2-(2-isopropylphenyl)-7-methyl-7,9-dihydro-8H-purin-8-one 9-(4-Iodobenzyl)-2-(2-isopropylphenyl)-7-methyl-7,9-dihydro-8H-purin-8-one was prepared as a yellow solid according to Example 34. MS (ESI) m/z 485.1 [M+H]$^+$.

Step 3. 2-(2-Isopropylphenyl)-7-methyl-9-(4-(4,4,5,5-tetramethyl-1,3,2-dioxaborolan-2-yl)benzyl)-7,9-dihydro-8H-purin-8-one 2-(2-Isopropylphenyl)-7-methyl-9-(4-(4,4,5,5-tetramethyl-1,3,2-dioxaborolan-2-yl)benzyl)-7,9-dihydro-8H-purin-8-one was synthesized following Example 22. $^1$H NMR (300 MHz, CD$_3$OD) δ 8.59 (s, 1H), 7.64-7.55 (m, 2H), 7.50-45 (m, 1H), 7.42-7.38 (m, 2H), 7.26-7.22 (m, 2H), 7.21-7.15 (m, 1H), 5.09 (s, 2H), 3.45 (s, 3H), 3.39-3.32 (m, 1H), 1.27 (s, 12H), 1.05 (d, J=6.9 Hz, 6H). MS (ESI) m/z 485.3 [M+H]$^+$.

Intermediate B-87. (4-(3-(Azetidin-1-yl)-5-methyl-1H-pyrazol-1-yl)phenyl)methanamine

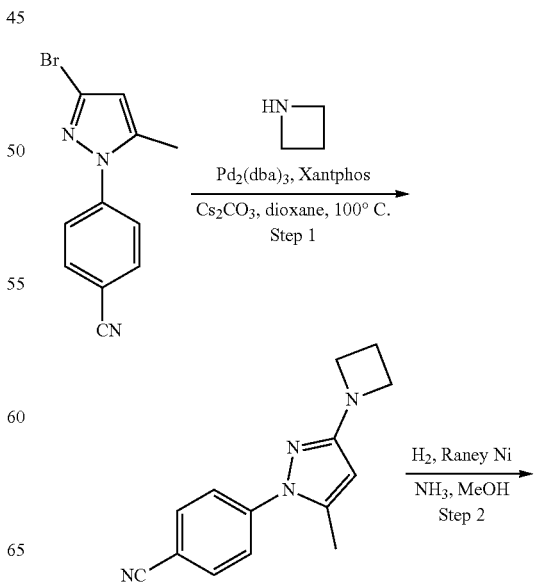

-continued

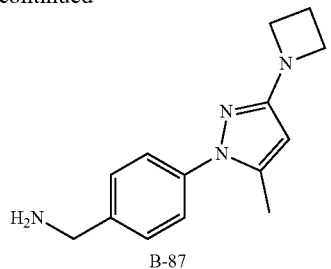

B-87

Step 1. 4-(3-(Azetidin-1-yl)-5-methyl-1H-pyrazol-1-yl)benzonitrile

In a 100 mL round-bottom flask purged and maintained with an inert atmosphere of nitrogen, a mixture of 4-(3-bromo-5-methyl-1H-pyrazol-1-yl)benzonitrile (prepared from 3-bromo-5-methyl-1H-pyrazole following Example 6) (1.0 g, 3.82 mmol), azetidine (218 mg, 3.82 mmol), Xantphos (221 mg, 0.38 mmol), Pd$_2$(dba)$_3$ (87 mg, 0.10 mmol), cesium carbonate (3.108 g, 9.54 mmol) and 1,4-dioxane (10 mL) was stirred for 16 h at 100° C. After cooling to room temperature, the reaction mixture was poured into water (20 mL) and was extracted with DCM (3×10 mL). The organic layers were combined, dried over anhydrous sodium sulfate, filtered and concentrated under vacuum. The residue was purified by silica gel chromatography (eluting with 3/7 EtOAc/PE) to afford 200 mg (22%) of 4-[3-(azetidin-1-yl)-5-methyl-1H-pyrazol-1-yl]benzonitrile as a yellow solid. MS (ESI) m/z 239.1 [M+H]$^+$.

Step 2. (4-(3-(Azetidin-1-yl)-5-methyl-1H-pyrazol-1-yl)phenyl)methanamine (4-(3-(Azetidin-1-yl)-5-methyl-1H-pyrazol-1-yl)phenyl)methanamine was obtained as a green oil from 4-(3-(azetidin-1-yl)-5-methyl-1H-pyrazol-1-yl)benzonitrile following Step 3 of Example 8. MS (ESI) m/z 243.2 [M+H]$^+$.

Example 24. Intermediate B-88. (1-(Pyridin-3-yl)piperidin-4-yl)methanamine

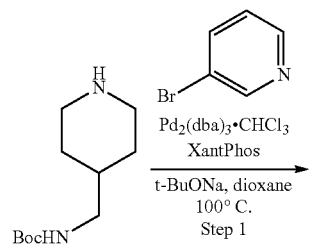

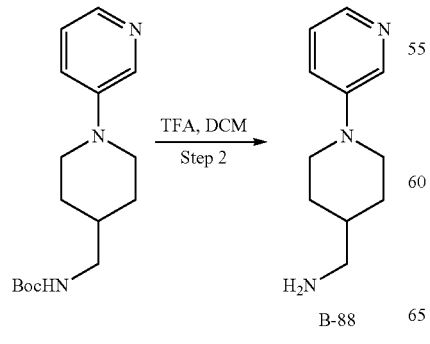

B-88

Step 1. tert-Butyl ((1-(pyridin-3-yl)piperidin-4-yl)methyl)carbamate

In a flask purged and maintained under an inert atmosphere of nitrogen, a mixture of 3-bromopyridine (2 g, 12.66 mmol), tert-butyl (piperidin-4-ylmethyl)carbamate (8.13 g, 37.94 mmol), sodium tert-butoxide (3.65 g, 37.98 mmol), Pd$_2$(dba)$_3$·CHCl$_3$ (1.32 g, 1.28 mmol), Xantphos (734 mg, 1.27 mmol) and 1,4-dioxane (40 mL) was stirred for 18 h at 100° C. After cooling to room temperature, the reaction mixture was poured into water (20 mL) and extracted with EtOAc (3×40 mL). The organic layers were combined, dried over anhydrous sodium sulfate, filtered and concentrated under vacuum. The residue was purified by flash chromatography eluting with EtOAc/PE (1/4) to give tert-butyl ((1-(pyridin-3-yl)piperidin-4-yl)methyl)carbamate (3 g, 81%). MS (ESI) m/z 292 [M+H]$^+$.

Step 2. (1-(Pyridin-3-yl)piperidin-4-yl)methanamine (1-(Pyridin-3-yl)piperidin-4-yl)methanamine was obtained from tert-butyl ((1-(pyridin-3-yl)piperidin-4-yl)methyl)carbamate following Example 36. MS (ESI) m/z 192 [M+H]$^+$.

Intermediate B-89. 2-(1-(pyridin-3-yl)piperidin-4-yl)ethan-1-amine

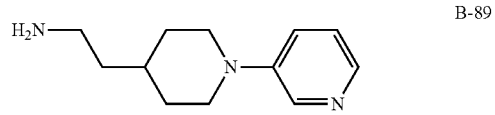 [SMILES: NCCC1CCN(c2cccnc2)CC1]

B-89

2-(1-(Pyridin-3-yl)piperidin-4-yl)ethan-1-amine was prepared as a yellow solid from tert-butyl (2-(piperidin-4-yl)ethyl)carbamate following Example 24. MS (ESI) m/z 206 [M+H]$^+$.

Intermediate B-90. 1-(Pyridin-3-yl)piperidin-4-amine

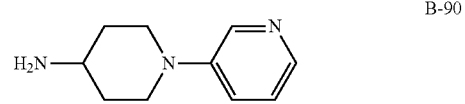

B-90

1-(Pyridin-3-yl)piperidin-4-amine was prepared as a yellow oil from tert-butyl piperidin-4-ylcarbamate following Example 24. MS (ESI) m/z 178.0 [M+H]$^+$.

Intermediate B-91. 1-(4-(1H-Pyrazol-1-yl)phenyl)cyclopropan-1-amine hydrochloride

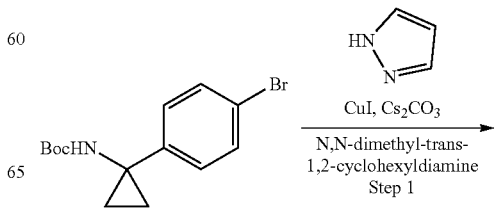

-continued

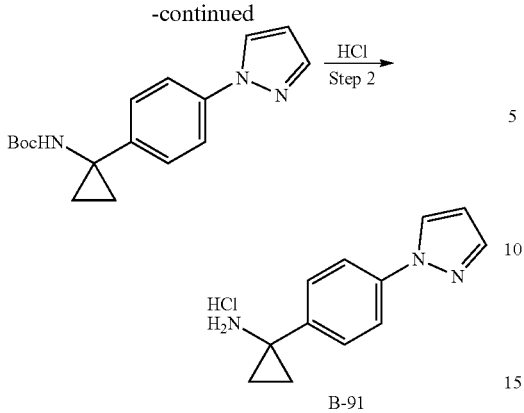

B-91

Step 1. tert-Butyl (1-(4-(1H-pyrazol-1-yl)phenyl)cyclopropyl)carbamate tert-butyl (1-(4-(1H-pyrazol-1-yl)phenyl)cyclopropyl) carbamate was synthesized as a yellow solid following Step 1 of Example 4. $^1$H NMR (300 MHz, CDCl$_3$) δ 7.88 (br s, 1H), 7.70 (s, 1H), 7.60 (br d, J=8.2 Hz, 2H), 7.35-7.26 (m, 2H), 6.44 (br s, 1H), 5.35 (br s, 1H), 1.44 (br s, 9H), 1.26 (br d, J=15.5 Hz, 4H). MS (ESI) m/z 300.13 [M+H]$^+$.

Step 2. 1-(4-(1H-Pyrazol-1-yl)phenyl)cyclopropan-1-amine hydrochloride

To a solution of tert-butyl (1-(4-(1H-pyrazol-1-yl)phenyl)cyclopropyl)carbamate (0.4 g, 1.336 mmol) in 1,4-dioxane (3 mL) was added HCl (4N in 1,4-dioxane, 3 mL, 12 mmol) at ambient temperature. The reaction mixture was heated to 50° C. for 1 h, then was cooled to ambient temperature. The resulting white solids were collected by vacuum filtration, washed with ether and dried under reduced pressure to afford 1-(4-(1H-pyrazol-1-yl)phenyl)cyclopropan-1-amine hydrochloride (289 mg, 92%). MS (ESI) m/z 200.12 [M+H]$^+$.

Intermediate B-92. (4-(3-Morpholino-1H-pyrazol-1-yl)phenyl)methanamine

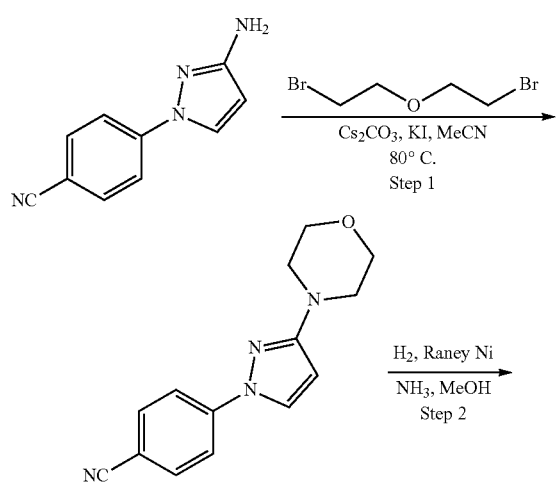

-continued

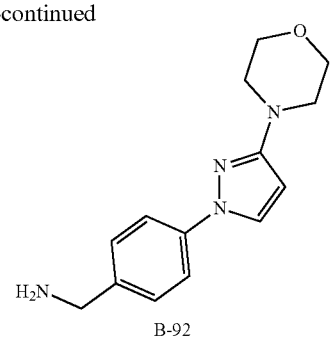

B-92

Step 1. 4-(3-Morpholino-1H-pyrazol-1-yl)benzonitrile

A mixture of 4-(3-amino-1H-pyrazol-1-yl)benzonitrile (prepared in Example 16) (3 g, 16.29 mmol), 1-bromo-2-(2-bromoethoxy)ethane (7.56 g, 32.60 mmol), potassium iodide (13.53 g, 81.50 mmol), cesium carbonate (15.94 g, 48.92 mmol) and acetonitrile (40 mL) was stirred for 18 h at 80° C. After cooling to room temperature, the reaction mixture was poured into water (200 mL) and was extracted with EtOAc (3×50 mL). The organic layers were combined, dried over anhydrous sodium sulfate, filtered and concentrated under vacuum. The residue was purified by silica gel chromatography (eluting with 0/100 to 50/50 EtOAc/PE) to afford 2 g (24%) of 4-(3-morpholino-1H-pyrazol-1-yl)benzonitrile as a yellow solid. MS (ESI) m/z 254.9 [M+H]$^+$.

Step 2. (4-(3-morpholino-1H-pyrazol-1-yl)phenyl)methanamine (4-(3-Morpholino-1H-pyrazol-1-yl)phenyl)methanamine was obtained as a yellow oil from 4-(3-morpholino-1H-pyrazol-1-yl)benzonitrile following Step 3 of Example 8. MS (ESI) m/z 259.1 [M+H]$^+$ Example 25. Intermediate B-93. (4-(4-(Difluoromethyl)-1-methyl-1H-imidazol-2-yl)phenyl)methanamine

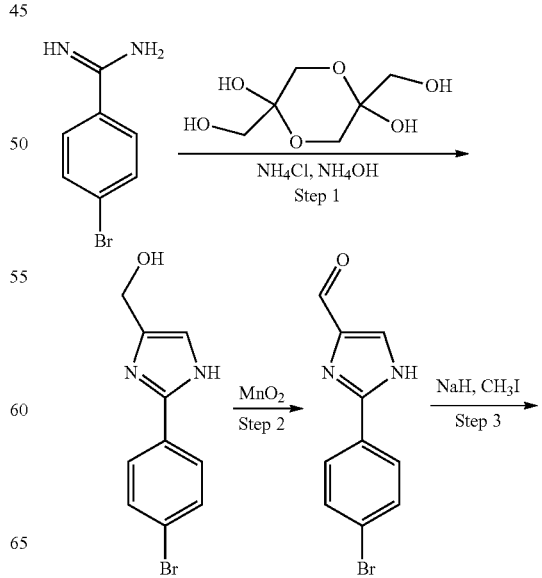

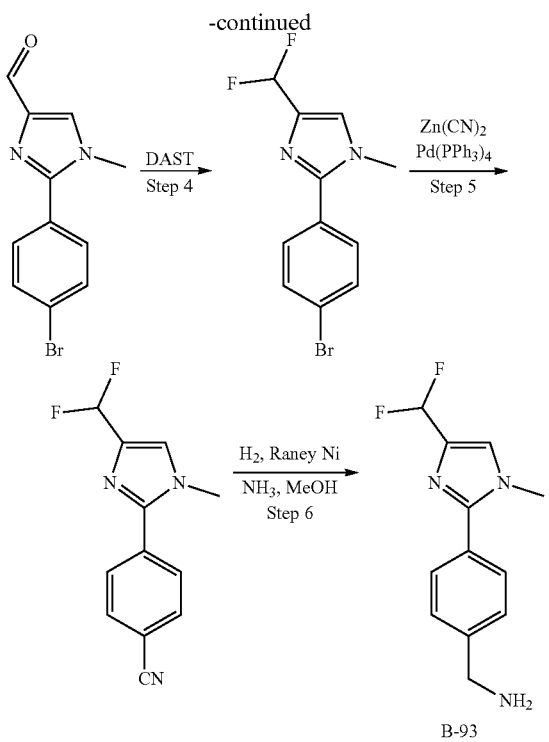

Step 1. (2-(4-Bromophenyl)-1H-imidazol-4-yl)methanol

A mixture of 4-bromobenzene-1-carboximidamide (15 g, 75.36 mmol), concentrated ammonium hydroxide (500 mL), 2,5-bis(hydroxymethyl)-1,4-dioxane-2,5-diol (15 g, 83.26 mmol) and ammonium chloride (20 g, 373.52 mmol) was stirred for 1.5 h at 80° C. After cooling to ambient temperature, the resulting precipitate was collected by filtration and dried under vacuum to afford 12 g (60%) of [2-(4-bromophenyl)-1H-imidazol-4-yl]methanol as a brown solid. MS (ESI) m/z 252.6, 254.6 [M+H]$^+$.

Step 2. 2-(4-Bromophenyl)-1H-imidazole-4-carbaldehyde

A mixture of [2-(4-bromophenyl)-1H-imidazol-4-yl]methanol (4.5 g, 17.07 mmol), THF (80 mL) and MnO$_2$ (15.6 g, 179.44 mmol) was stirred for 18 h at 60° C. After cooling to ambient temperature, the reaction mixture was filtered and concentrated under vacuum to afford 3.3 g (77%) of 2-(4-bromophenyl)-1H-imidazole-4-carbaldehyde as a yellow solid. MS (ESI) m/z 250.8, 252.8 [M+H]$^+$.

Step 3. 2-(4-Bromophenyl)-1-methyl-1H-imidazole-4-carbaldehyde 2-(4-bromophenyl)-1-methyl-1H-imidazole-4-carbaldehyde was prepared as a yellow solid following Example 9. MS (ESI) m/z 264.8, 266.8 [M+H]$^+$.

Step 4. 2-(4-Bromophenyl)-4-(difluoromethyl)-1-methyl-1H-imidazole

Into a 100 mL 3-necked round-bottom flask purged and maintained with an inert atmosphere of nitrogen a mixture of 2-(4-bromophenyl)-1-methyl-1H-imidazole-4-carbaldehyde (630 mg, 2.31 mmol) and DCM (20 mL) was treated by the dropwise addition of diethylaminosulfur trifluoride (2.86 mL, 23.05 mmol) with stirring at 0° C. The resulting solution was stirred for 18 h at ambient temperature then was poured into saturated sodium bicarbonate solution (200 mL) and was extracted with DCM (4×100 mL). The organic layers were combined, dried over anhydrous sodium sulfate, filtered and concentrated under vacuum. The residue was purified by silica gel chromatography (eluting with 0/100 to 70/30 EtOAc/PE) to afford 678 mg (56%) of 2-(4-bromophenyl)-4-(difluoromethyl)-1-methyl-1H-imidazole as a yellow oil. MS (ESI) m/z 286.9, 288.9 [M+H]$^+$.

Step 5. 4-(4-(Difluoromethyl)-1-methyl-1H-imidazol-2-yl)benzonitrile

Into a 25 mL round-bottom flask purged and maintained with an inert atmosphere of nitrogen, a mixture of 2-(4-bromophenyl)-4-(difluoromethyl)-1-methyl-1H-imidazole (578 mg, 1.93 mmol), DMF (5 mL), tetrakis(triphenylphosphine)palladium(0) (233 mg, 0.20 mmol) and zinc cyanide (236 mg, 2.01 mmol) was stirred for 18 h at 120° C. After cooling to ambient temperature, the reaction mixture was poured into water (10 mL) and was extracted with EtOAc (4×10 mL). The organic layers were combined, dried over anhydrous sodium sulfate, filtered and concentrated under vacuum. The residue was purified by prep-TLC (eluting with 1/1 EtOAc/PE) to afford 150 mg (30%) of 4-[4-(difluoromethyl)-1-methyl-1H-imidazol-2-yl]benzonitrile as a yellow solid. MS (ESI) m/z 234.2 [M+H]$^+$.

Step 6. (4-(4-(Difluoromethyl)-1-methyl-1H-imidazol-2-yl)phenyl)methanamine

[4-[4-(Difluoromethyl)-1-methyl-1H-imidazol-2-yl]phenyl]methanamine was obtained as a yellow solid following Step 3 of Example 8. MS (ESI) m/z 237.9 [M+H]$^+$.

Example 26: Intermediate B-94. 9-(4-Hydroxybenzyl)-2-(2-isopropylphenyl)-7,9-dihydro-8H-purin-8-one

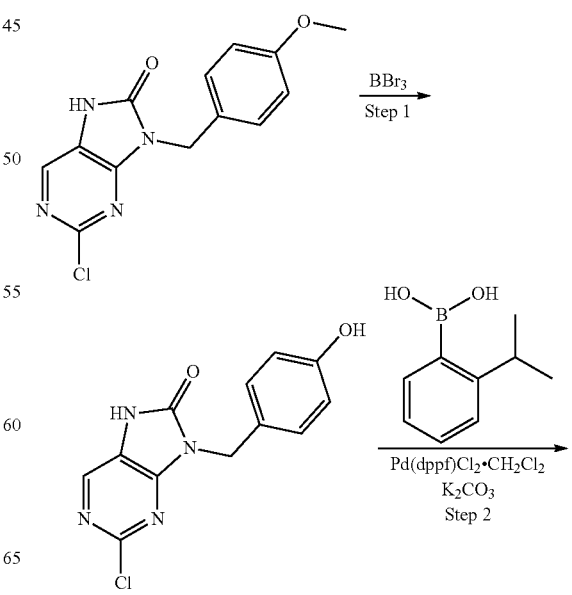

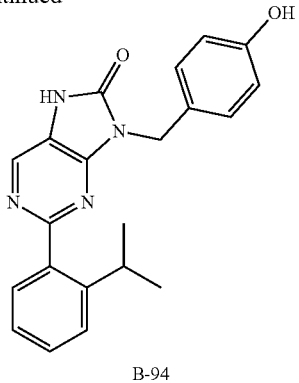

B-94

Step 1. 2-Chloro-9-(4-hydroxybenzyl)-7,9-dihydro-8H-purin-8-one

A mixture of 2-chloro-9-(4-methoxybenzyl)-7,9-dihydro-8H-purin-8-one (prepared from (4-methoxyphenyl)methanamine according to Example 18) (7 g, 24.08 mmol) and DCM (200 mL) under a nitrogen atmosphere at 0° C. was treated with dropwise addition of boron tribromide (1M in DCM, 121 mL, 121 mmol). The resulting solution was stirred for 4 h at 0° C., then was poured into water/ice (500 mL). The solids were collected by vacuum filtration and dried under vacuum to afford 4 g (60%) of 2-chloro-9-(4-hydroxybenzyl)-7,9-dihydro-8H-purin-8-one as a light yellow solid. MS (ESI) m/z 277 $[M+H]^+$.

Step 2. 9-(4-Hydroxybenzyl)-2-(2-isopropylphenyl)-7,9-dihydro-8H-purin-8-one 9-(4-Hydroxybenzyl)-2-(2-isopropylphenyl)-7,9-dihydro-8H-purin-8-one was synthesized according to Step 1 of Example 1. $^1$H-NMR (300 MHz, DMSO-d$_6$) δ 11.46 (br s, 1H), 9.39 (br s, 1H), 8.35 (s, 1H), 7.51-7.35 (m, 3H), 7.26-7.15 (m, 3H), 6.69 (d, J=8.1 Hz, 2H), 4.89 (s, 2H), 3.43-3.50 (m, 1H), 1.12 (d, J=6.6 Hz, 6H). MS (ESI) m/z 361 $[M+H]^+$.

Example 27: Intermediate B-95. 4-((2-(2-Isopropylphenyl)-8-oxo-7,8-dihydro-9H-purin-9-yl)methyl)benzoic acid

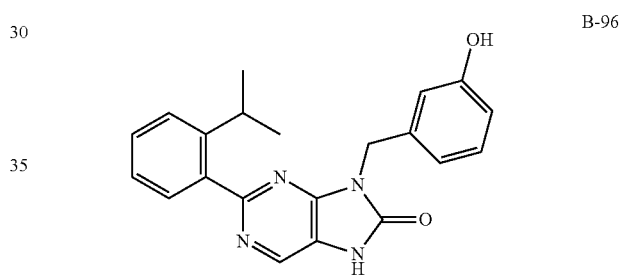

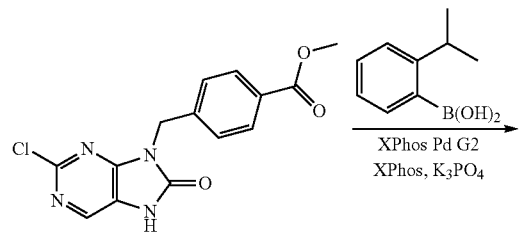

B-95

Under an atmosphere of nitrogen, a mixture of methyl 4-((2-chloro-8-oxo-7,8-dihydro-9H-purin-9-yl)methyl)benzoate (prepared from methyl 4-(aminomethyl)benzoate hydrochloride following Example 18) (200 mg, 0.628 mmol), (2-isopropylphenyl)boronic acid (154 mg, 0.941 mmol), 1M potassium phosphate (1255 µL, 1.255 mmol), XPhos Pd G2 (9.87 mg, 0.013 mmol) and XPhos (8.97 mg, 0.019 mmol) was heated at 110° C. for 18 h. The reaction mixture was cooled to ambient temperature, recharged with (2-isopropylphenyl)boronic acid (154 mg, 0.941 mmol), 1M potassium phosphate (1255 µL, 1.255 mmol), XPhos Pd G2 (9.87 mg, 0.013 mmol) and XPhos (8.97 mg, 0.019 mmol) and heated to 110° C. for 18 h. The reaction mixture was cooled to ambient temperature and was washed with EtOAc. The aqueous layer was carefully acidified with concentrated HCl to pH 2 and extracted with EtOAc (2×). The combined acidic extracts were washed with brine, dried over sodium sulfate, filtered, and concentrated to afford 257 mg (100% yield) of 4-((2-(2-isopropylphenyl)-8-oxo-7,8-dihydro-9H-purin-9-yl)methyl)benzoic acid as a white solid. MS (ESI) m/z 389 $[M+H]^+$.

Intermediate B-96. 9-(3-Hydroxybenzyl)-2-(2-isopropylphenyl)-7,9-dihydro-8H-purin-8-one

B-96

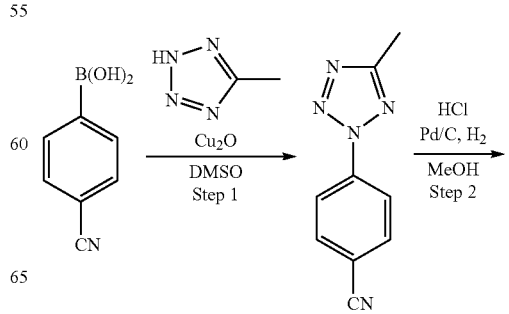

9-(3-Hydroxybenzyl)-2-(2-isopropylphenyl)-7,9-dihydro-8H-purin-8-one was prepared as a light yellow solid following an analogous sequence to Example 26. $^1$H NMR (300 MHz, DMSO-d$_6$) δ 11.54 (br s, 1H), 9.39 (s, 1H), 8.39 (s, 1H), 7.52-7.49 (m, 1H), 7.43-7.02 (m, 2H), 7.26-7.21 (m, 1H), 7.10-7.07 (m, 1H), 6.75-6.51 (m, 3H), 4.93 (s, 2H), 3.49-3.40 (m, 1H), 1.09 (d, J=6.90 Hz, 6H). MS (ESI) m/z 361.2 $[M+H]^+$.

Intermediate B-97. (4-(5-Methyl-2H-tetrazol-2-yl)phenyl)methanamine hydrochloride

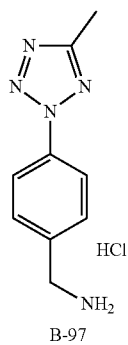

B-97

Step 1. 4-(5-Methyl-2H-tetrazol-2-yl)benzonitrile

A mixture of copper(I) oxide (0.170 g, 1.189 mmol), 5-methyl-2H-tetrazole (Ig, 11.89 mmol), (4-cyanophenyl)boronic acid (3.50 g, 23.79 mmol) and DMSO (20 mL) was stirred open to atmosphere for 16 h at 100° C. The mixture was cooled to ambient temperature, filtered, diluted with DCM and MeOH and re-filtered. The filtrate was washed with water (2×50 mL), brine (50 mL), dried over sodium sulfate, filtered, and concentrated. Purification by silica gel chromatography (0 to 5% MeOH/DCM gradient) afforded 190 mg (9%) of 4-(5-methyl-2H-tetrazol-2-yl)benzonitrile. $^1$H NMR (300 MHz, CDCl$_3$) δ 2.60 (s, 3H) 7.80 (d, J=8.50 Hz, 2H) 8.2 (d, J=8.50 Hz, 2H). MS (ESI) m/z 186.03 [M+H]$^+$

Step 2. (4-(5-Methyl-2H-tetrazol-2-yl)phenyl)methanamine hydrochloride

A solution of 4-(5-methyl-2H-tetrazol-2-yl)benzonitrile (190 mg, 1.026 mmol) and 1N HCl (10 mL, 10.00 mmol) in MeOH (30 ml) was degassed with nitrogen for 5 min, treated with 10% Pd—C (100 mg), and shaken under a 40 psi hydrogen atmosphere for 16 h. The mixture was filtered and the filtrate dried to afford 176 mg of (4-(5-methyl-2H-tetrazol-2-yl)phenyl)methanamine hydrochloride (76%). $^1$H NMR (300 MHz, DMSO-d$_6$) δ ppm 3.33 (s, 3H) 4.02-4.27 (m, 2H) 7.74 (d, J=8.79 Hz, 2H) 8.09 (d, J=8.79 Hz, 2H) 8.33-8.68 (br, 2H). MS (ESI) m/z 190.06 [M+H]$^+$.

Intermediate B-98. 2-Chloro-7-cyclopropyl-9-(4-(1-methyl-4-(trifluoromethyl)-1H-imidazol-2-yl)benzyl)-7,9-dihydro-8H-purin-8-one

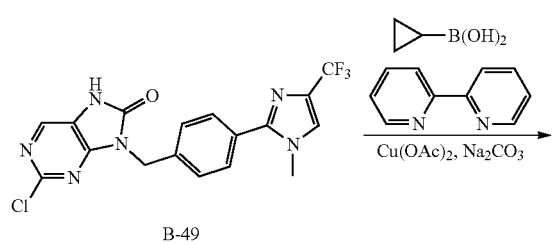

B-49

B-98

A mixture of cyclopropylboronic acid (84 mg, 0.979 mmol), Intermediate B-49 (200 mg, 0.489 mmol) and sodium carbonate (104 mg, 0.979 mmol) in DCE/DMF (2:1, 3 mL) was treated with a suspension of copper(II) acetate (89 mg, 0.489 mmol) and 2,2'-bipyridine (76 mg, 0.489 mmol) in hot DCE (1 mL) and was heated to 70° C. for 18 hours. The mixture was cooled to room temperature and was treated with saturated aqueous ammonium chloride. The organic layer was separated and the aqueous layer was extracted with DCM (3×10 mL). The combined organic layers were washed with brine, dried over sodium sulfate and concentrated to a residue that was purified by silica gel chromatography (eluting with 0-6% MeOH/DCM) to yield 2-chloro-7-cyclopropyl-9-(4-(1-methyl-4-(trifluoromethyl)-1H-imidazol-2-yl)benzyl)-7,9-dihydro-8H-purin-8-one (0.185 g, 58% yield). $^1$H NMR (300 MHz, CDCl$_3$) δ: 8.16-8.12 (m, 1H), 7.60 (m, 4H), 7.26 (s, 1H), 5.10 (s, 2H), 3.74 (s, 3H), 2.98-2.93 (m, 1H), 1.15 (br d, J=6.4 Hz, 2H), 1.05-0.98 (m, 2H). MS (ESI) m/z 449.00 [M+H]$^+$.

Intermediate B-99, tert-Butyl 2-(4-(aminomethyl)phenyl)-2,6-dihydropyrrolo[3,4-c]pyrazole-5(4H)-carboxylate and Intermediate B-100, tert-butyl 1-(4-(aminomethyl)phenyl)-4,6-dihydropyrrolo[3,4-c]pyrazole-5(1H)-carboxylate

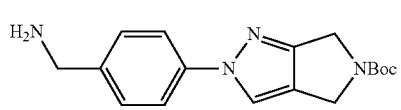

B-99

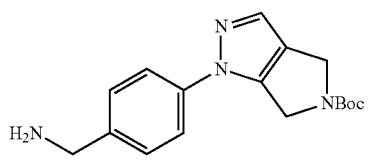

B-100 tert-Butyl 2-(4-(aminomethyl)phenyl A mixture of)-2,6-dihydropyrrolo[3,4-c]pyrazole-5(4H)-carboxylate and tert-butyl 1-(4-(aminomethyl)phenyl)-4,6-dihydropyrrolo[3,4-c]pyrazole-5(1H)-carboxylate was prepared from tert-butyl 2,6-dihydropyrrolo[3,4-c]pyrazole-5(4H)-carboxylate following Example 6. MS (ESI) m/z 315 [M+H]$^+$.

Example 28: Intermediate B-101. 2-(3-Fluoro-2-isopropylphenyl)-9-(4-(4,4,5,5-tetramethyl-1,3,2-dioxaborolan-2-yl)benzyl)-7,9-dihydro-8H-purin-8-one

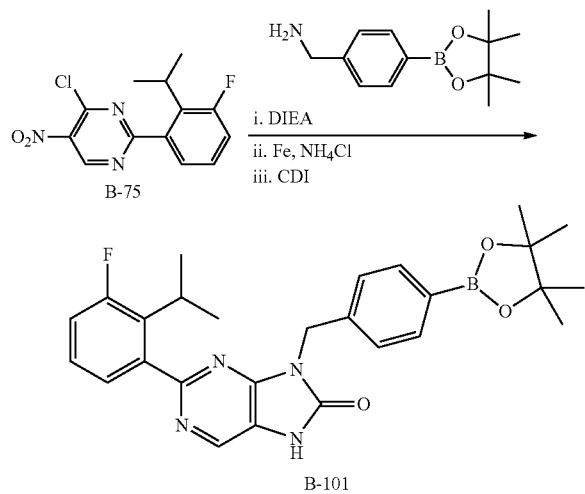

A solution of Intermediate B-75 (0.2M in i-PrOH, 1.69 mL, 0.338 mmol), (4-(4,4,5,5-tetramethyl-1,3,2-dioxaborolan-2-yl)phenyl)methanamine (0.2M in i-PrOH, 1.86 mL, 0.372 mmol), and DIEA (300 µL, 1.72 mmol) was heated at 50° C. for 2 h, then was concentrated under reduced pressure. The residue was taken up in MeOH (1 mL), THF (1 mL) and water (1 mL) and was treated with iron (55 mg, 1 mmol) and ammonium chloride (100 mg, 2 mmol). The reaction was heated at 80° C. for 3 h. The reaction mixture was cooled to ambient temperature, filtered through a plug of cotton and concentrated under a stream of nitrogen. The residue was treated with 1N NaOH (2 mL), extracted with EtOAc (2×2 mL) and the combined extracts concentrated under reduced pressure. The residue was taken up in dioxane (2 mL), treated with CDI (150 mg, 900 mol) and heated to 80° C. for 3 h. The solution was concentrated under a stream of nitrogen and was treated with 1N NaOH (2 mL), extracted with EtOAc (2×2 mL) and the combined extracts concentrated under reduced pressure. Purification using a Biotage Isolera (25 g column, eluting with a gradient of 10-80% EtOAc/hexanes) afforded 101 mg (61% yield) of 2-(3-fluoro-2-isopropylphenyl)-9-(4-(4,4,5,5-tetramethyl-1,3,2-dioxaborolan-2-yl)benzyl)-7,9-dihydro-8H-purin-8-one. MS (ESI) m/z 489.2 [M+H]⁺.

Intermediate B-102: (6-(1H-Pyrazol-1-yl)pyridin-3-yl)methanamine

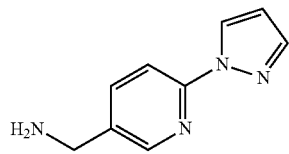

(6-(1H-Pyrazol-1-yl)pyridin-3-yl)methanamine was prepared as a yellow oil from 6-chloronicotinonitrile following Example 6. MS (ESI) m/z 175.2 [M+H]⁺.

Intermediate B-103. tert-Butyl 3-(1-(4-(aminomethyl)phenyl)-1H-pyrazol-3-yl)piperidine-1-carboxylate

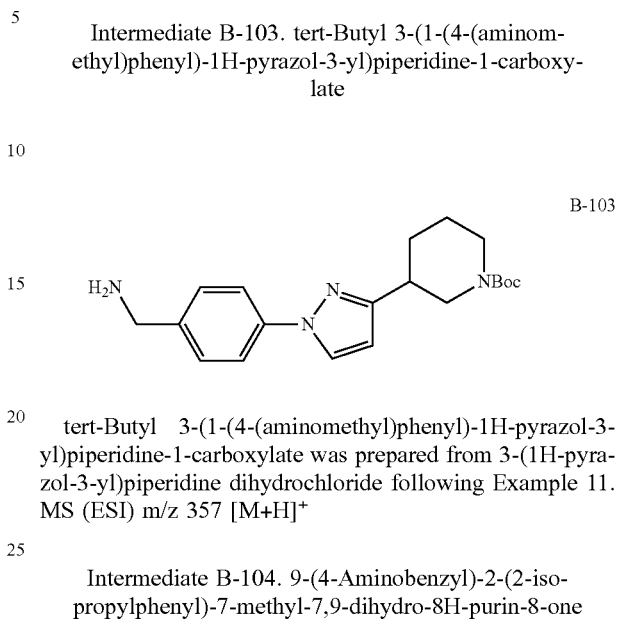

tert-Butyl 3-(1-(4-(aminomethyl)phenyl)-1H-pyrazol-3-yl)piperidine-1-carboxylate was prepared from 3-(1H-pyrazol-3-yl)piperidine dihydrochloride following Example 11. MS (ESI) m/z 357 [M+H]⁺

Intermediate B-104. 9-(4-Aminobenzyl)-2-(2-isopropylphenyl)-7-methyl-7,9-dihydro-8H-purin-8-one

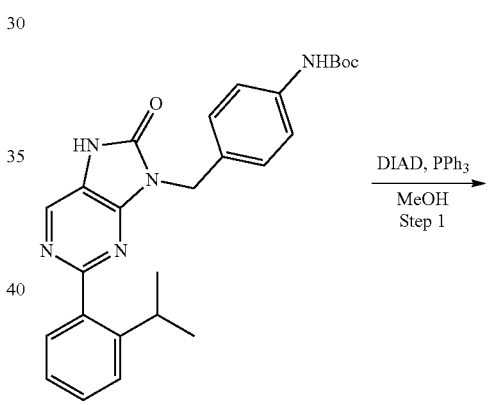

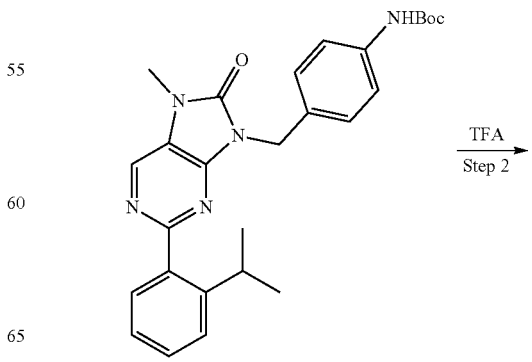

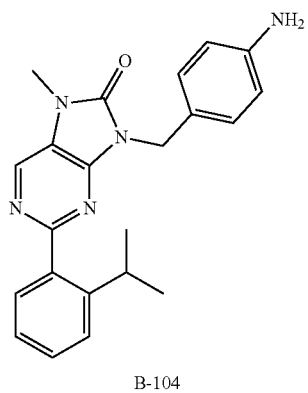

B-104

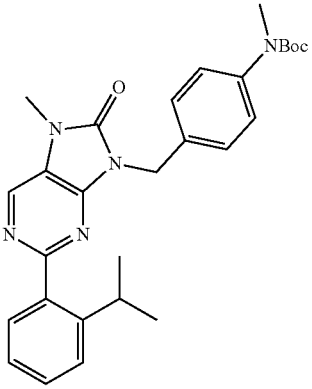

TFA
Step 2

Step 1. tert-Butyl (4-((2-(2-isopropylphenyl)-7-methyl-8-oxo-7,8-dihydro-9H-purin-9-yl)methyl)phenyl)carbamate tert-Butyl (4-((2-(2-isopropylphenyl)-8-oxo-7,8-dihydro-9H-purin-9-yl)methyl)phenyl)carbamate (described in Example 30) was used to synthesize tert-butyl (4-((2-(2-isopropylphenyl)-7-methyl-8-oxo-7,8-dihydro-9H-purin-9-yl)methyl)phenyl)carbamate as a yellow solid following Example 34. MS (ESI) m/z 474.2 [M+H]$^+$.

Step 2. 9-(4-Aminobenzyl)-2-(2-isopropylphenyl)-7-methyl-7,9-dihydro-8H-purin-8-one 9-(4-Aminobenzyl)-2-(2-isopropylphenyl)-7-methyl-7,9-dihydro-8H-purin-8-one was obtained a light yellow solid following Example 36. $^1$H NMR (300 MHz, DMSO-d$_6$) δ 8.54 (s, 1H), 7.63-7.35 (m, 3H), 7.30-7.25 (m, 1H), 7.05 (d, J=8.1 Hz, 2H), 6.48 (d, J=8.1 Hz, 2H), 5.07 (br s, 2H), 4.86 (s, 2H), 3.56-3.42 (m, 1H), 3.42 (s, 3H), 1.15 (d, J=6.9 Hz, 6H). MS (ESI) m/z 374.2 [M+H]$^+$.

Intermediate B-105. 2-(2-Isopropylphenyl)-7-methyl-9-(4-(methylamino)benzyl)-7,9-dihydro-8H-purin-8-one

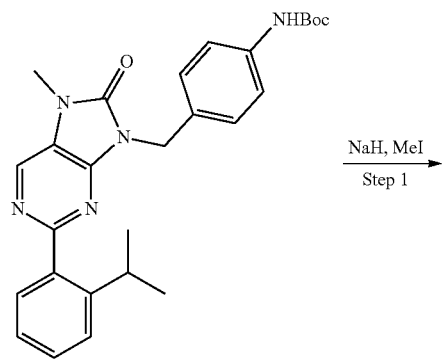

NaH, MeI
Step 1

B-105

Step 1. tert-Butyl (4-((2-(2-isopropylphenyl)-7-methyl-8-oxo-7,8-dihydro-9H-purin-9-yl)methyl)phenyl)(methyl)carbamate tert-Butyl (4-((2-(2-isopropylphenyl)-7-methyl-8-oxo-7,8-dihydro-9H-purin-9-yl)methyl)phenyl)(methyl)carbamate was prepared from tert-butyl (4-((2-(2-isopropylphenyl)-7-methyl-8-oxo-7,8-dihydro-9H-purin-9-yl)methyl)phenyl)carbamate using conditions described in Example 9. MS (ESI) m/z 488.3 [M+H]$^+$.

Step 2. 2-(2-Isopropylphenyl)-7-methyl-9-(4-(methylamino)benzyl)-7,9-dihydro-8H-purin-8-one 2-(2-Isopropylphenyl)-7-methyl-9-(4-(methylamino)benzyl)-7,9-dihydro-8H-purin-8-one was prepared from tert-butyl (4-((2-(2-isopropylphenyl)-7-methyl-8-oxo-7,8-dihydro-9H-purin-9-yl)methyl)phenyl)(methyl)carbamate following Example 36. $^1$H NMR (300 MHz, DMSO-d$_6$) δ 8.54 (s, 1H), 7.54-7.38 (m, 3H), 7.29-7.24 (m, 1H), 7.13 (d, J=8.4 Hz, 2H), 6.45 (d, J=8.7 Hz, 2H), 5.64 (q, J=5.1 Hz, 1H), 4.88 (s, 2H), 3.55-3.46 (m, 1H), 3.42 (s, 3H), 2.62 (d, J=5.1 Hz, 3H), 1.15 (d, J=6.6 Hz, 6H). MS (ESI) m/z 388.2 [M+H]$^+$.

Intermediate B-106. (2,6-difluoro-4-(1-methyl-4-(trifluoromethyl)-1H-imidazol-2-yl)phenyl)methanamine

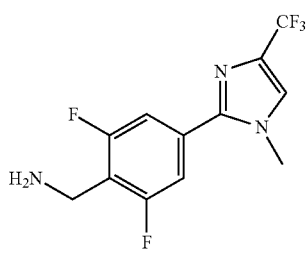

B-106

In an analogous fashion to the preparation of Intermediate B-23, (2,6-difluoro-4-(1-methyl-4-(trifluoromethyl)-1H-imidazol-2-yl)phenyl)methanamine was prepared from 2,6-difluoro-4-formylbenzonitrile.

Intermediate B-107. (3-Fluoro-4-(1-methyl-4-(trifluoromethyl)-1H-imidazol-2-yl)phenyl)methanamine

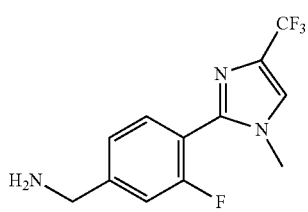

B-107

In an analogous fashion to the preparation of Intermediate B-23, (3-fluoro-4-(1-methyl-4-(trifluoromethyl)-1H-imidazol-2-yl)phenyl)methanamine was prepared as a yellow solid from 3-fluoro-4-formylbenzonitrile. MS (ESI) m/z 273.6 [M+H]⁺.

Intermediate B-108. 2-(2-Fluoropyridin-3-yl)-9-(4-(1-methyl-4-(trifluoromethyl)-1H-imidazol-2-yl)benzyl)-7,9-dihydro-8H-purin-8-one

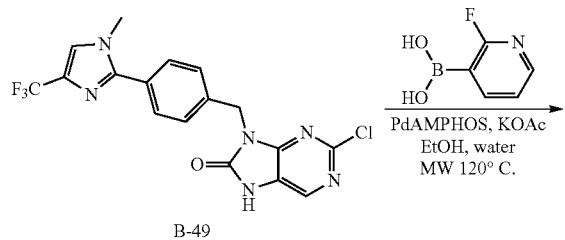

B-49

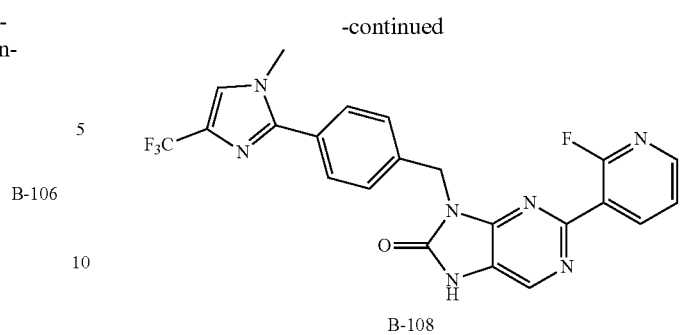

B-108

Into a 30 mL microwave tube purged and maintained with an inert atmosphere of nitrogen was placed Intermediate B-49 (1.5 g, 3.67 mmol), (2-fluoropyridin-3-yl)boronic acid (2.585 g, 18.35 mmol), potassium acetate (792 mg, 8.07 mmol), EtOH (15 mL), water (3 mL) and PdAMPHOS (260 mg, 0.37 mmol). The resulting mixture was heated with microwave irradiation for 4 h at 120° C. After cooling to ambient temperature, the reaction mixture was concentrated under vacuum. The residue was purified by silica gel chromatography (eluting with 1/10 MeOH/DCM) and the product was further purified by C18-reversed phase silica gel chromatography (eluting with 30% to 60% acetonitrile/water (10 mmol NH₄HCO₃)) resulting in 564 mg (33%) of 2-(2-fluoropyridin-3-yl)-9-([4-[1-methyl-)-1H-imidazol-2-yl]phenyl]methyl)-8,9-dihydro-7H-purin-8-one as a white solid. ¹H NMR (400 MHz, DMSO-d₆) δ 11.70 (s, 1H), 8.56-8.53 (m, 1H), 8.45 (s, 1H), 8.33 (d, J=8.00 Hz, 1H), 7.91 (s, 1H), 7.70 (d, J=8.40 Hz, 2H), 7.56-7.49 (m, 3H), 5.14 (s, 2H), 3.76 (s, 3H). MS (ESI) m/z 470.2 [M+H]⁺.

Intermediate B-109. (4-(2,5-dimethyloxazol-4-yl)phenyl)methanamine

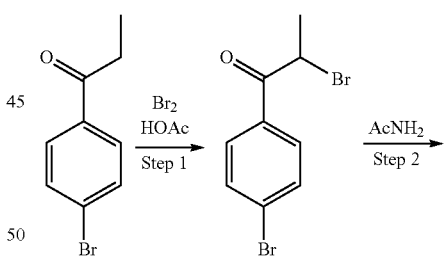

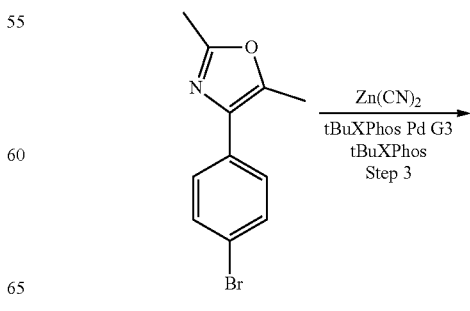

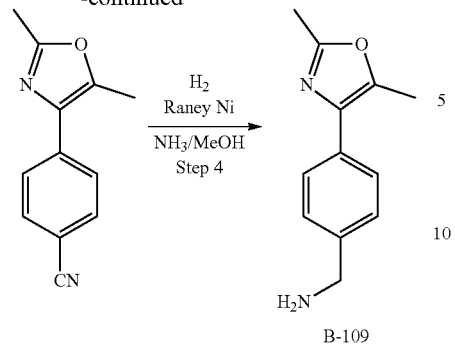

Step 1. 2-Bromo-1-(4-bromophenyl)propan-1-one

A mixture of 1-(4-bromophenyl)propan-1-one (10 g, 46.9 mmol) and acetic acid (20 mL) was treated with dropwise addition of bromine (8.2 g, 51.3 mmol) and the resulting solution was stirred for 2 h at 25° C. The reaction mixture was poured into water (100 mL) and was extracted with EtOAc (3×100 mL). The organic layers were combined, dried over anhydrous sodium sulfate, filtered, concentrated under vacuum and purified by silica gel chromatography (eluting with 1:10 EtOAc/PE) to afford 5.0 g (36%) of 2-bromo-1-(4-bromophenyl)propan-1-one as a yellow solid. $^1$H NMR (400 MHz, CDCl$_3$) δ 7.96-7.77 (m, 2H), 7.72-7.54 (m, 2H), 5.21 (q, J=6.6 Hz, 1H), 1.89 (d, J=6.6 Hz, 3H).

Step 2. 4-(4-Bromophenyl)-2,5-dimethyloxazole

A mixture of 2-bromo-1-(4-bromophenyl)propan-1-one (4.0 g, 13.7 mmol) and acetamide (814 mg, 13.8 mmol) was heated at 135° C. for 1 h. After cooling to ambient temperature, the reaction mixture was poured into saturated sodium bicarbonate solution (100 mL) and was extracted with EtOAc (2×150 mL). The organic layers were combined, dried over anhydrous sodium sulfate, filtered, concentrated under vacuum and purified by silica gel chromatography (eluting with 1:10 EtOAc/PE) to afford 2.3 g (67%) of 4-(4-bromophenyl)-2,5-dimethyloxazole as a light yellow solid. MS (ESI) m/z 251.6, 253.6 [M+H]$^+$.

Step 3. 4-(2,5-Dimethyloxazol-4-yl)benzonitrile 4-(2,5-Dimethyloxazol-4-yl)benzonitrile was prepared from 4-(4-bromophenyl)-2,5-dimethyloxazole following Step 4 of Example 17. MS (ESI) m/z 199.0 [M+H]$^+$.

Step 4. (4-(2,5-Dimethyloxazol-4-yl)phenyl)methanamine (4-(2,5-Dimethyloxazol-4-yl)phenyl)methanamine was prepared from 4-(2,5-dimethyloxazol-4-yl)benzonitrile following Step 3 of Example 8. MS (ESI) m/z 203.2 [M+H]$^+$

Intermediate B-110. 1-(3-(2-(4-(Aminomethyl)phenyl)-4-(trifluoromethyl)-1H-imidazol-1-yl)azetidin-1-yl)ethan-1-one

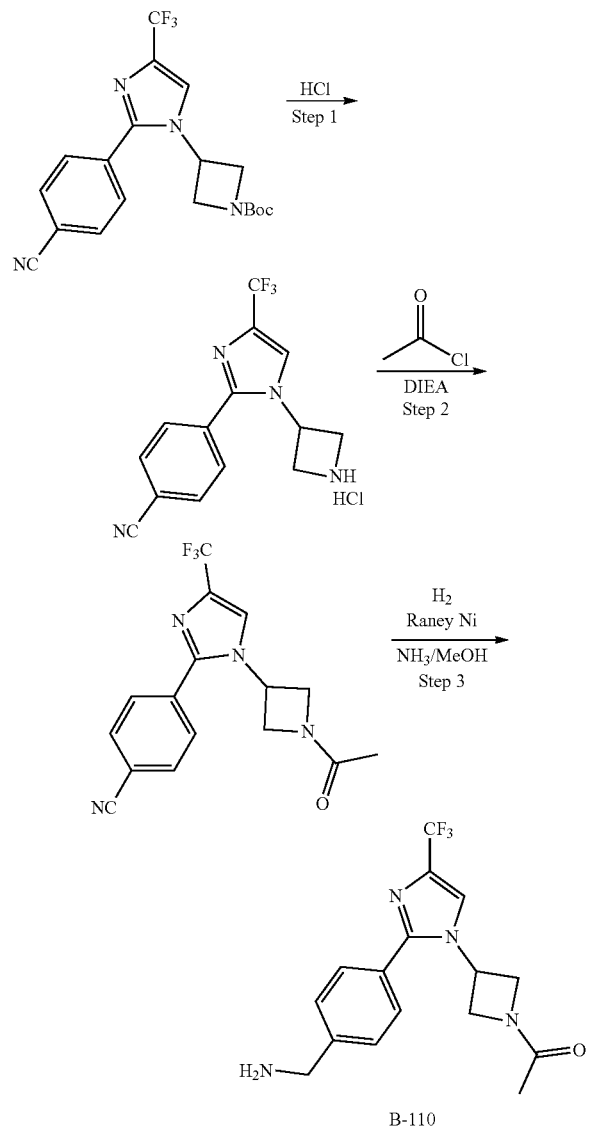

Step 1. 4-(1-(Azetidin-3-yl)-4-(trifluoromethyl)-1H-imidazol-2-yl)benzonitrile hydrochloride A mixture of tert-butyl 3-(2-(4-cyanophenyl)-4-(trifluoromethyl)-1H-imidazol-1-yl)azetidine-1-carboxylate (1.0 g, 2.54 mmol) and HCl (4M in dioxane, 10 mL) was stirred for 2 h at ambient temperature. The resulting mixture was concentrated under vacuum to afford 0.9 g (crude) of 4-(1-(azetidin-3-yl)-4-(trifluoromethyl)-1H-imidazol-2-yl)benzonitrile hydrochloride as a brown oil. MS (ESI) m/z 292.9 [M+H]$^+$.

Step 2. 4-(1-(1-Acetylazetidin-3-yl)-4-(trifluoromethyl)-1H-imidazol-2-yl)benzonitrile 4-(1-(1-acetylazetidin-3-yl)-4-(trifluoromethyl)-1H-imidazol-2-yl)benzonitrile was prepared from 4-(1-(azetidin-3- yl)-4-(trifluoromethyl)-1H-imidazol-2-yl)benzonitrile hydrochloride following Step 2 of Example 51. MS (ESI) m/z 335.0 [M+H]⁺.

Step 3. 1-(3-(2-(4-(Aminomethyl)phenyl)-4-(trifluoromethyl)-1H-imidazol-1-yl)azetidin-1-yl)ethan-1-one 1-(3-(2-(4-(Aminomethyl)phenyl)-4-(trifluoromethyl)-1H-imidazol-1-yl)azetidin-1-yl)ethan-1-one was synthesized from 4-(1-(1-acetylazetidin-3-yl)-4-(trifluoromethyl)-1H-imidazol-2-yl)benzonitrile following Step 3 of Example 8. MS (ESI) m/z 339.0 [M+H]⁺.

Intermediate B-111, 1-(4-(aminomethyl)phenyl)-5-methyl-1H-pyrazole-3-carbonitrile and Intermediate B-112, 1-(4-(aminomethyl)phenyl)-3-methyl-1H-pyrazole-5-carbonitrile

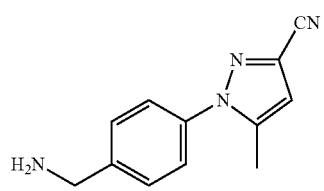

B-111

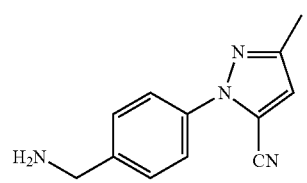

B-112

A ~1:1 mixture of 1-(4-(aminomethyl)phenyl)-5-methyl-1H-pyrazole-3-carbonitrile and 1-(4-(aminomethyl)phenyl)-3-methyl-1H-pyrazole-5-carbonitrile was prepared following Example 15, using 5-methyl-1H-pyrazole-3-carbonitrile in place of 1H-pyrazole-3-carbonitrile. MS (ESI) m/z 212.9 [M+H]⁺.

Intermediate B-113. 4-Chloro-2-(2-isopropylpyridin-3-yl)-5-nitropyrimidine

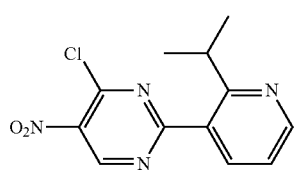

B-113

4-Chloro-2-(2-isopropylpyridin-3-yl)-5-nitropyrimidine was prepared from Intermediate B-2 according to Example 21. MS (ESI) m/z 279.0 [M+H]⁺.

Intermediate B-114, 2-(4-Bromophenyl)-1-methyl-1,2-dihydro-3H-pyrazol-3-one and Intermediate B-115, 1-(4-bromophenyl)-5-methoxy-1H-pyrazole

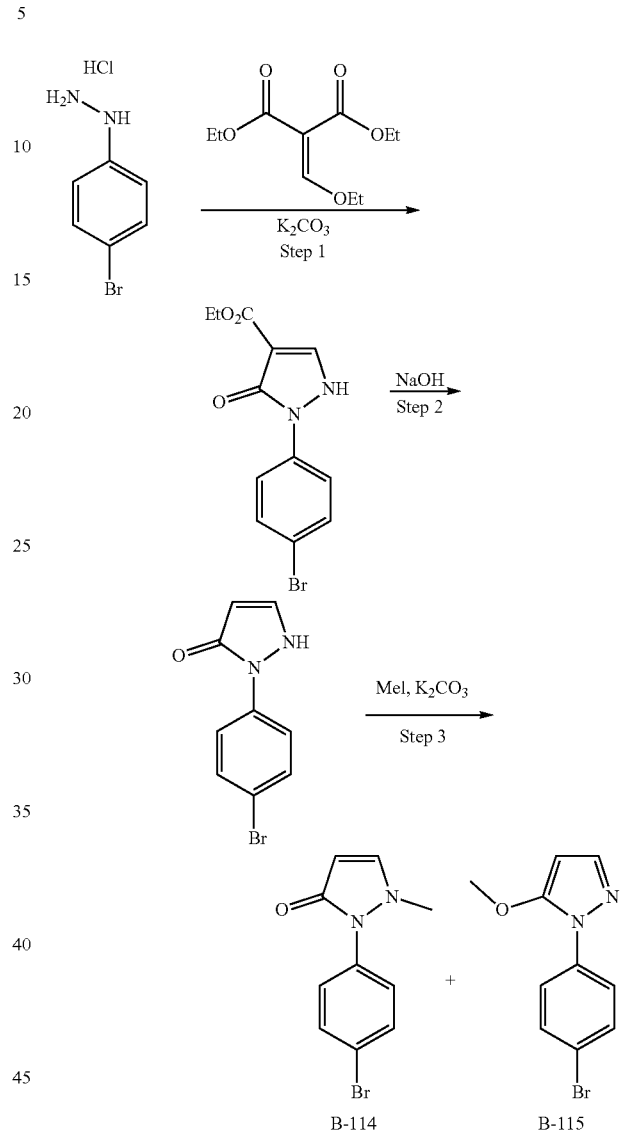

Step 1. Ethyl 2-(4-bromophenyl)-3-oxo-2,3-dihydro-1H-pyrazole-4-carboxylate

A mixture of (4-bromophenyl)hydrazine hydrochloride (10 g, 44.74 mmol), EtOH (500 mL), potassium carbonate (31 g, 224.30 mmol) and diethyl 2-(ethoxymethylene)malonate (10.2 g, 47.17 mmol) was stirred for 18 h at 80° C. After cooling to ambient temperature, the mixture was concentrated under vacuum, dispersed in water (200 mL) and the pH adjusted to 4 by slow addition of 2N HCl. The resulting solution was extracted with EtOAc (3×200 mL), the organic layers were combined, dried over anhydrous sodium sulfate, filtered and concentrated under vacuum to afford 18 g (crude) of ethyl 2-(4-bromophenyl)-3-oxo-2,3-dihydro-1H-pyrazole-4-carboxylate as a dark red solid. MS (ESI) m/z 311.0, 313.0 [M+H]⁺.

Step 2. 2-(4-Bromophenyl)-1,2-dihydro-3H-pyrazol-3-one

A mixture of ethyl 2-(4-bromophenyl)-3-oxo-2,3-dihydro-1H-pyrazole-4-carboxylate (8 g, 25.71 mmol), NaOH (6.24 g, 156.01 mmol) and water (156 mL) was stirred for 4 h at 125° C. After cooling to ambient temperature, the pH value of the solution was adjusted to 3.5 with concentrated HCl and the resulting mixture was extracted with EtOAc (3×500 mL). The organic layers were combined, dried over anhydrous sodium sulfate, filtered and concentrated under vacuum. The residue was purified by silica gel chromatography (eluting with 30% EtOAc/PE) to afford 4.5 g (70%) of 2-(4-bromophenyl)-1,2-dihydro-3H-pyrazol-3-one as a light yellow solid. MS (ESI) m/z 239.0, 240.9 [M+H]$^+$.

Step 3. 2-(4-Bromophenyl)-1-methyl-1,2-dihydro-3H-pyrazol-3-one and 1-(4-bromophenyl)-5-methoxy-1H-pyrazole A mixture of 2-(4-bromophenyl)-1,2-dihydro-3H-pyrazol-3-one (4 g, 16.73 mmol), potassium carbonate (11.54 g, 83.50 mmol), water (96 mL) and tween-20 (4 mL) at ambient temperature was treated with dropwise addition of iodomethane (11.88 g, 83.70 mmol) and the resulting mixture was stirred for 2 h. The reaction mixture was extracted with EtOAc (4×50 mL), the organic layers were combined, dried over anhydrous sodium sulfate, filtered and concentrated under vacuum. The residue was purified by silica gel chromatography (eluting with a gradient of 9-100% EtOAc/PE) to afford 1.8 g (43%) of 2-(4-bromophenyl)-1-methyl-1,2-dihydro-3H-pyrazol-3-one as an off-white solid and 1.5 g (35%) of 1-(4-bromophenyl)-5-methoxy-1H-pyrazole as a yellow oil.

2-(4-Bromophenyl)-1-methyl-1,2-dihydro-3H-pyrazol-3-one (R$_f$=0.1 in 50% EtOAc/PE): $^1$H NMR (300 MHz, CD$_3$OD) δ 7.81 (d, J=3.5 Hz, 1H), 7.77-7.68 (m, 2H), 7.38-7.27 (m, 2H), 5.52 (d, J=3.5 Hz, 1H), 3.30 (s, 3H). $^{13}$C NMR (300 MHz, CD$_3$OD) δ 167.8, 146.4, 133.8, 133.7, 129.2, 123.2, 96.2, 37.5. MS (ESI) m/z 253.0, 255.0 [M+H]$^+$.

1-(4-Bromophenyl)-5-methoxy-1H-pyrazole (R$_f$=0.7 in 50% EtOAc/PE): $^1$H NMR (400 MHz, CD$_3$OD) δ 7.57 (d, J=1.4 Hz, 4H), 7.50 (d, J=2.0 Hz, 1H), 5.83 (d, J=2.0 Hz, 1H), 3.96 (s, 3H). $^{13}$C NMR (400 MHz, CD$_3$OD) δ 156.9, 140.0, 137.4, 131.7, 123.6, 119.5, 85.9, 58.4. MS (ESI) m/z 253.0, 255.0 [M+H]$^+$.

Example 29. Intermediate B-116. 2-(4-(Aminomethyl)phenyl)-1-methyl-1,2-dihydro-3H-pyrazol-3-one

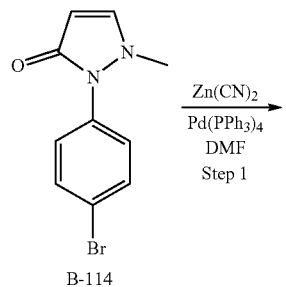

B-114

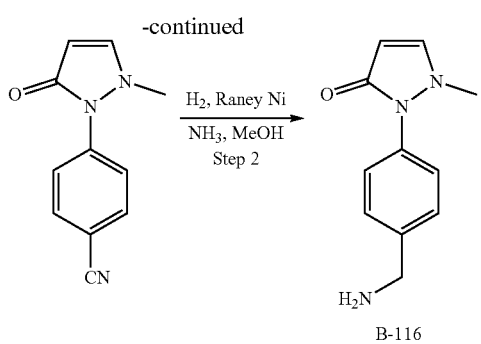

B-116

Step 1. 4-(2-Methyl-5-oxo-2,5-dihydro-1H-pyrazol-1-yl)benzonitrile 4-(2-Methyl-5-oxo-2,5-dihydro-1H-pyrazol-1-yl)benzonitrile was synthesized from Intermediate B-114 as an off-white solid following Step 5 of Example 25. MS (ESI) m/z 200.1 [M+H]$^+$.

Step 2. 2-(4-(Aminomethyl)phenyl)-1-methyl-1,2-dihydro-3H-pyrazol-3-one 2-(4-(Aminomethyl)phenyl)-1-methyl-1,2-dihydro-3H-pyrazol-3-one was obtained as a yellow oil from 4-(2-methyl-5-oxo-2,5-dihydro-1H-pyrazol-1-yl)benzonitrile following Step 3 of Example 8. MS (ESI) m/z 203.7 [M+H]$^+$.

Intermediate B-117: (4-(5-Methoxy-1H-pyrazol-1-yl)phenyl)methanamine

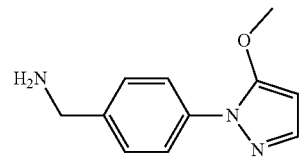

(4-(5-Methoxy-1H-pyrazol-1-yl)phenyl)methanamine was prepared from Intermediate B-115 following Example 29. MS (ESI) m/z 203.7 [M+H]$^+$.

Intermediate B-118, 1-(4-(1H-1,2,3-Triazol-1-yl)phenyl)ethan-1-one and Intermediate B-119, 1-(4-(2H-1,2,3-triazol-2-yl)phenyl)ethan-1-one

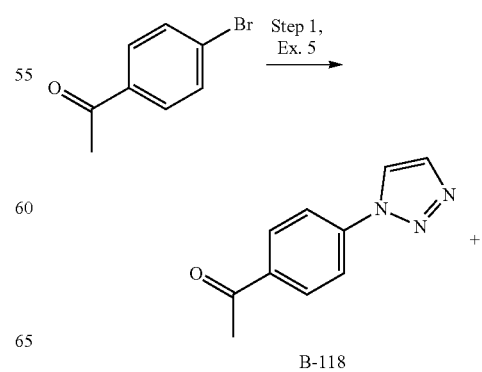

B-118

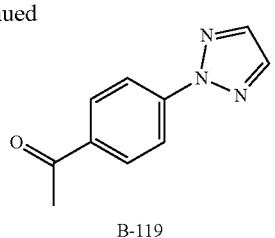

B-119

1-(4-(1H-1,2,3-triazol-1-yl)phenyl)ethan-1-one and 1-(4-(2H-1,2,3-triazol-2-yl)phenyl)ethan-1-one were prepared according to Step 1 of Example 5 and separated by prep-TLC (eluting with 1% to 50% EtOAc/PE).

1-(4-(1H-1,2,3-Triazol-1-yl)phenyl)ethan-1-one ($R_f$=0.2, EtOAc/PE=1/1): $^1$H NMR (400 MHz, CD$_3$OD) δ 8.66 (d, J=1.20 Hz, 1H), 8.22-8.19 (m, 2H), 8.06-8.02 (m, 2H), 7.93 (d, J=1.20 Hz, 1H), 2.66 (s, 3H). MS (ESI) m/z 188 [M+H]$^+$.

1-(4-(2H-1,2,3-Triazol-2-yl)phenyl)ethan-1-one ($R_f$=0.7, EtOAc/PE=1/1): $^1$H NMR (400 MHz, CD$_3$OD) δ 8.23-8.20 (m, 2H), 8.17-8.14 (m, 2H), 7.99 (s, 2H), 2.65 (s, 3H). MS (ESI) m/z 188 [M+H]$^+$.

Intermediate B-120: 1-(4-(1H-1,2,3-Triazol-1-yl)phenyl)ethan-1-amine

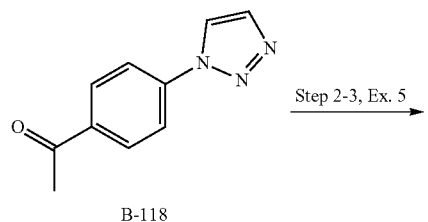

1-(4-(1H-1,2,3-Triazol-1-yl)phenyl)ethan-1-amine was prepared as an off-white solid from Intermediate B-118 following Steps 2-3 of Example 5. MS (ESI) m/z 189 [M+H]$^+$.

Intermediate B-121: 1-(4-(2H-1,2,3-Triazol-2-yl)phenyl)ethan-1-amine

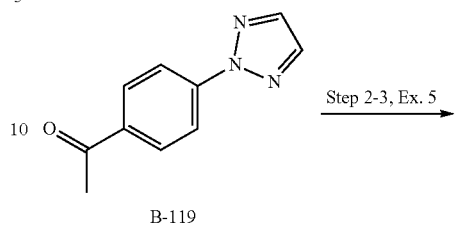

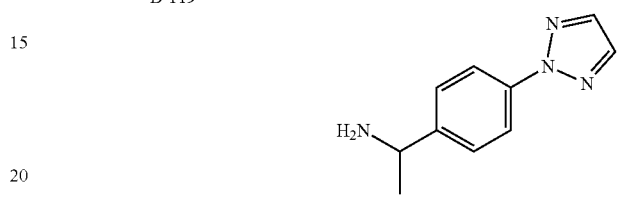

B-121

1-(4-(2H-1,2,3-Triazol-2-yl)phenyl)ethan-1-amine was prepared from Intermediate B-119 following Steps 2-3 of Example 5. MS (ESI) m/z 189 [M+H]$^+$ Intermediate B-122. 2-Bromo-1-methyl-4-nitro-1H-imidazole

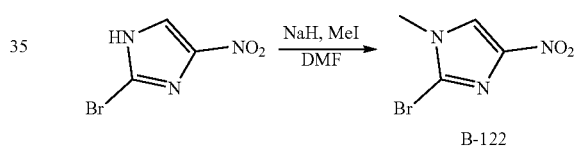

A mixture of 2-bromo-4-nitro-1H-imidazole (10 g, 52.09 mmol) in DMF (100 mL) was treated with portionwise addition of sodium hydride (60% dispersion in mineral oil, 2.53 g, 62.83 mmol) at 0° C. The mixture was stirred for 30 min at room temperature, iodomethane (8.93 g, 62.89 mmol) was added and the resulting solution was stirred 16 h at room temperature. The reaction mixture was poured into ice/water (400 mL) and the resulting precipitate was collected by filtration and dried under vacuum to afford 8.8 g (82%) of 2-bromo-1-methyl-4-nitro-1H-imidazole as a white solid. MS (ESI) m/z 205.7, 207.7 [M+H]$^+$.

Intermediate B-123. tert-Butyl 4-(1-(4-(aminomethyl)phenyl)-1H-pyrazol-3-yl)piperidine-1-carboxylate

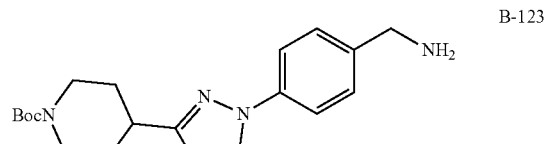

tert-Butyl 4-(1-(4-(aminomethyl)phenyl)-1H-pyrazol-3-yl)piperidine-1-carboxylate was prepared from 3-bromo-1H-pyrazole as a gray oil following Example 7. MS (ESI) m/z 357 [M+H]⁺.

Intermediate B-124. [4-[5-methoxy-3-(trifluoromethyl)-1H-pyrazol-1-yl]phenyl]methanamine

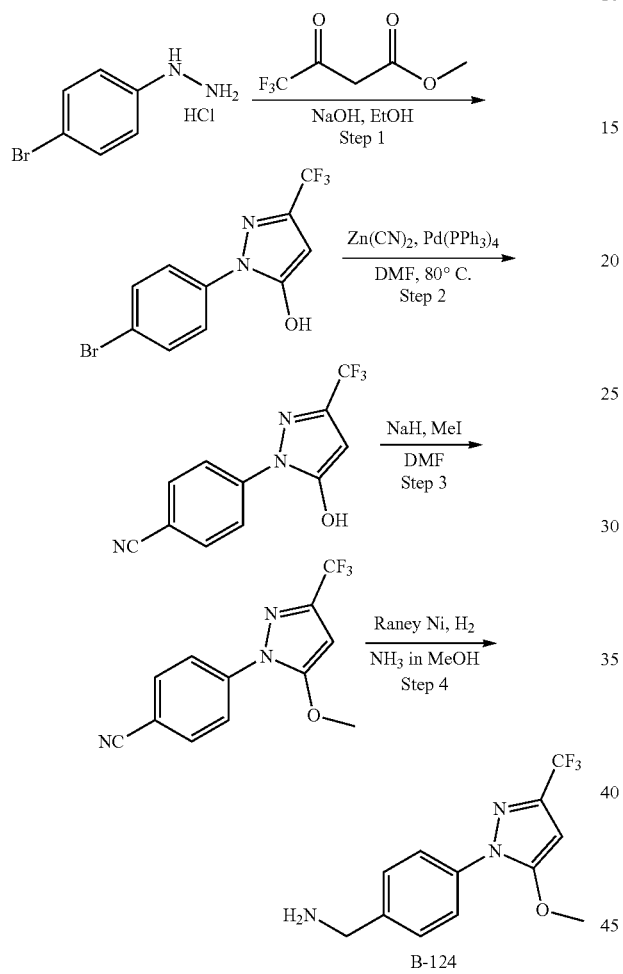

B-124

Step 1. 1-(4-Bromophenyl)-3-(trifluoromethyl)-1H-pyrazol-5-ol

A mixture of (4-bromophenyl)hydrazine hydrochloride (7.4 g, 33.11 mmol), EtOH (200 mL) and NaOH (1.35 g, 33.76 mmol) was stirred for 30 min at ambient temperature. Methyl 4,4,4-trifluoro-3-oxobutanoate (6.89 g, 40.51 mmol) was added and the resulting solution was stirred for 16 h at 90° C. After cooling to ambient temperature, another batch of NaOH (2.70 g, 67.52 mmol) was added and the resulting mixture was stirred for additional 1 h at 90° C. After cooling to ambient temperature, water (200 mL) was added and the pH was carefully adjusted to 4-5 by the addition of 1M hydrochloric acid. The resulting solution was extracted with EtOAc (3×500 mL) and the organic layers were combined, dried over anhydrous sodium sulfate, filtered and concentrated under vacuum. The residue was purified by silica gel chromatography (eluting with 1:7 EtOAc/PE) to afford 4.1 g (40%) of 1-(4-bromophenyl)-3-(trifluoromethyl)-1H-pyrazol-5-ol as a yellow solid. MS (ESI) m/z 306.6, 308.6 [M+H]⁺.

Step 2. 4-(5-Hydroxy-3-(trifluoromethyl)-1H-pyrazol-1-yl)benzonitrile 4-(5-Hydroxy-3-(trifluoromethyl)-1H-pyrazol-1-yl)benzonitrile was prepared from 1-(4-bromophenyl)-3-(trifluoromethyl)-1H-pyrazol-5-ol as a light red oil following Step 5 of Example 25. MS (ESI) m/z 253.6 [M+H]⁺.

Step 3. 4-[5-Methoxy-3-(trifluoromethyl)-1H-pyrazol-1-yl]benzonitrile

Following conditions described in Example 9, 4-[5-methoxy-3-(trifluoromethyl)-1H-pyrazol-1-yl]benzonitrile was obtained in 95% yield as a white solid. MS (ESI) m/z 268.1 [M+H]⁺.

Step 4. [4-[5-Methoxy-3-(trifluoromethyl)-1H-pyrazol-1-yl]phenyl]methanamine

Following Step 3 of Example 8, [4-[5-methoxy-3-(trifluoromethyl)-1H-pyrazol-1-yl]phenyl]methanamine was obtained as a yellow oil. MS (ESI) m/z 255.1 [M+H-NH₃]⁺.

Intermediate B-125, [4-(3-Chloro-5-methyl-1H-pyrazol-1-yl)phenyl]methanamine and Intermediate B-126, [4-(5-chloro-3-methyl-1H-pyrazol-1-yl)phenyl]methanamine

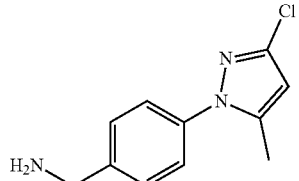

B-125

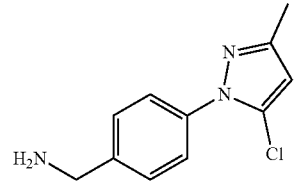

B-126

Starting from 3-chloro-5-methyl-1H-pyrazole, a ~1:2 mixture of [4-(3-chloro-5-methyl-1H-pyrazol-1-yl)phenyl]methanamine and [4-(5-chloro-3-methyl-1H-pyrazol-1-yl)phenyl]methanamine was obtained as a yellow oil following Example 15. MS (ESI) m/z 221.9 [M+H]⁺.

Intermediate B-127. [4-(3,5-Dimethyl-1H-pyrazol-1-yl)cyclohexyl]methanamine

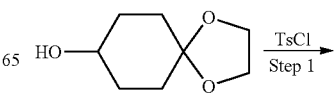

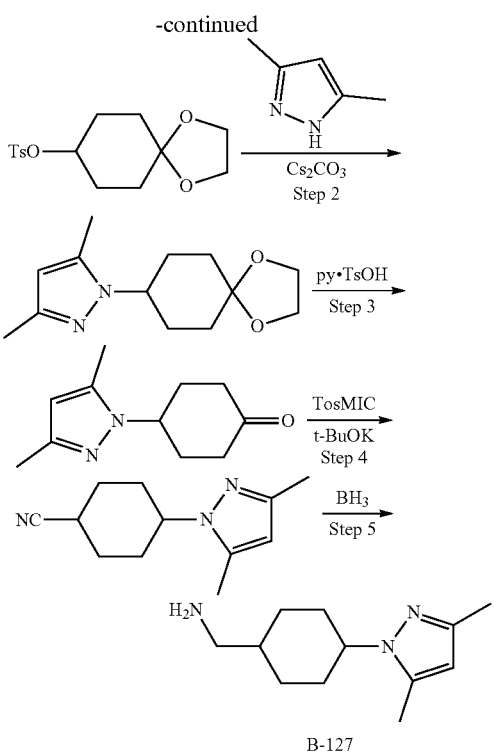

B-127

Step 1. 1,4-Dioxaspiro[4.5]decan-8-yl 4-methylbenzene-1-sulfonate

A mixture of 1,4-dioxaspiro[4.5]decan-8-ol (10 g, 63.21 mmol) and pyridine (150 mL) was treated dropwise with 4-methylbenzene-1-sulfonyl chloride (14.6 g, 76.58 mmol) at ambient temperature and the resulting solution was stirred for 16 h. The reaction mixture was poured into water (200 mL) and was extracted with EtOAc (3×100 mL). The organic layers were combined, washed successively with 0.5 M hydrochloric acid (3×100 mL), 1M sodium bicarbonate solution (100 mL) and brine (100 mL), then were dried over anhydrous sodium sulfate, filtered and concentrated under vacuum. The residue was purified by silica gel chromatography (eluting with 1/3 EtOAc/PE) to afford 14 g (71%) of 1,4-dioxaspiro[4.5]decan-8-yl 4-methylbenzene-1-sulfonate as an off-white solid. MS (ESI) m/z 141.0 [M+H-TsOH]$^+$.

Step 2. 1-[1,4-Dioxaspiro[4.5]decan-8-yl]-3,5-dimethyl-1H-pyrazole

A mixture of 1,4-dioxaspiro[4.5]decan-8-yl 4-methylbenzene-1-sulfonate (8 g, 25.61 mmol), 3,5-dimethyl-1H-pyrazole (9.75 g, 101.42 mmol), DMF (150 mL) and cesium carbonate (17 g, 52.18 mmol) was stirred for 4 h at 100° C. After cooling to ambient temperature, the reaction mixture was diluted with water (300 mL) and was extracted with EtOAc (3×200 mL). The organic layers were combined, dried over anhydrous sodium sulfate, filtered and concentrated under vacuum. The residue was purified by silica gel chromatography (eluting with 1/2 EtOAc/PE) to afford 2.5 g (41%) of 1-[1,4-dioxaspiro[4.5]decan-8-yl]-3,5-dimethyl-1H-pyrazole as a yellow oil. MS (ESI) m/z 237.0 [M+H]$^+$.

Step 3. 4-(3,5-Dimethyl-1H-pyrazol-1-yl)cyclohexan-1-one

A mixture of 1-[1,4-dioxaspiro[4.5]decan-8-yl]-3,5-dimethyl-1H-pyrazole (2.36 g, 0.01 mol), acetone (30 mL), water (30 mL) and pyridinium p-toluenesulfonate (5.02 g, 0.02 mol) was stirred overnight at 65° C. After cooling to ambient temperature, the reaction mixture was poured into water (50 mL) and was extracted with EtOAc (3×100 mL). The organic layers were combined, dried over anhydrous sodium sulfate, filtered and concentrated under vacuum. The residue was purified by silica gel chromatography (eluting with 0 to 40% EtOAc/PE) to afford 1.1 g (57%) of 4-(3,5-dimethyl-1H-pyrazol-1-yl)cyclohexan-1-one as a yellow oil. MS (ESI) m/z 193.2 [M+H]$^+$.

Step 4. 4-(3,5-Dimethyl-1H-pyrazol-1-yl)cyclohexane-1-carbonitrile

A mixture of 4-(3,5-dimethyl-1H-pyrazol-1-yl)cyclohexan-1-one (1 g, 5.20 mmol), ethylene glycol dimethyl ether (30 mL) and p-toluenesulfonyl isocyanide (1.32 g, 6.76 mmol) was treated with portionwise addition of potassium tert-butoxide (1.34 g, 11.94 mmol) at 0° C. and was allowed to warm to ambient temperature. After 3 h the solution was poured into water (150 mL) and was extracted with EtOAc (3×80 mL). The organic layers were combined, dried over anhydrous sodium sulfate, filtered and concentrated under vacuum. The residue was purified by silica gel chromatography (eluting with 1/2 EtOAc/PE) to afford 600 mg (57%, yellow oil) of 4-(3,5-dimethyl-1H-pyrazol-1-yl)cyclohexane-1-carbonitrile as a mixture of cis and trans isomers. MS (ESI) m/z 204.2 [M+H]$^+$.

Step 5. [4-(3,5-Dimethyl-1H-pyrazol-1-yl)cyclohexyl]methanamine

Into a 100 mL round-bottom flask under nitrogen atmosphere 4-(3,5-dimethyl-1H-pyrazol-1-yl)cyclohexane-1-carbonitrile (500 mg, 2.46 mmol) was treated with a solution of borane in THF (1 M, 8 mL, 8.00 mmol) and the resulting solution was stirred at ambient temperature. After 3 h, the reaction mixture was quenched by the addition of MeOH (20 mL) and the resulting mixture was stirred for 30 min at ambient temperature and then was concentrated under vacuum. The residue was purified by silica gel chromatography (eluting with 1/10 MeOH/DCM) to afford 320 mg (63%, yellow oil) of [4-(3,5-dimethyl-1H-pyrazol-1-yl)cyclohexyl]methanamine as a mixture of cis and trans isomers. MS (ESI) m/z 208.2 [M+H]$^+$.

Intermediate B-128. 1-(4-(1-Methyl-4-(trifluoromethyl)-1H-imidazol-2-yl)phenyl)ethan-1-amine

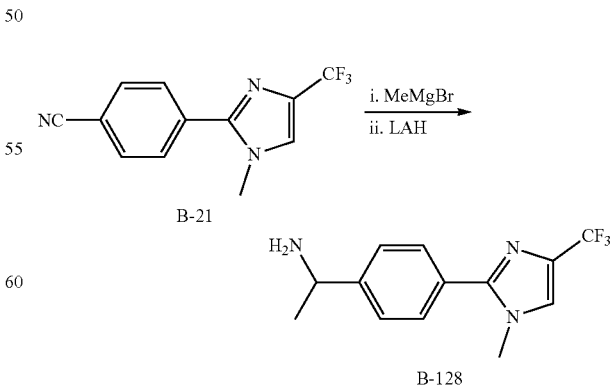

Under nitrogen, a solution of Intermediate B-21 (500 mg, 1.99 mmol) and THF (5 mL) was treated with dropwise addition of a 1M solution of methyl magnesium bromide in THF (4 mL, 4.00 mmol) at 0° C. After addition was complete, the resulting mixture was stirred for 1 h at 0° C. and 1 h at 60° C. After cooling to 0° C., a 1M solution of lithium aluminum hydride in THF (4 mL, 4.00 mmol) was added and the resulting mixture was allowed to warm to ambient temperature gradually and then stirred for 1 h at 60° C. After cooling to ambient temperature, the reaction was quenched by the addition of $Na_2SO_4.10\ H_2O$ (1 g) and the resulting mixture was filtered and concentrated under vacuum. The residue was purified by $C_{18}$-reversed phase silica gel chromatography (eluting with 5% to 40% acetonitrile/water (0.05% TFA)) to afford 348 mg (65%) of 1-[4-[1-methyl-4-(trifluoromethyl)-1H-imidazol-2-yl]phenyl]ethan-1-amine as a yellow solid. MS (ESI) m/z 270.1 [M+H]$^+$.

Intermediate B-129. [4-[1-Cyclopropyl-4-(trifluoromethyl)-1H-imidazol-2-yl]phenyl]methanamine

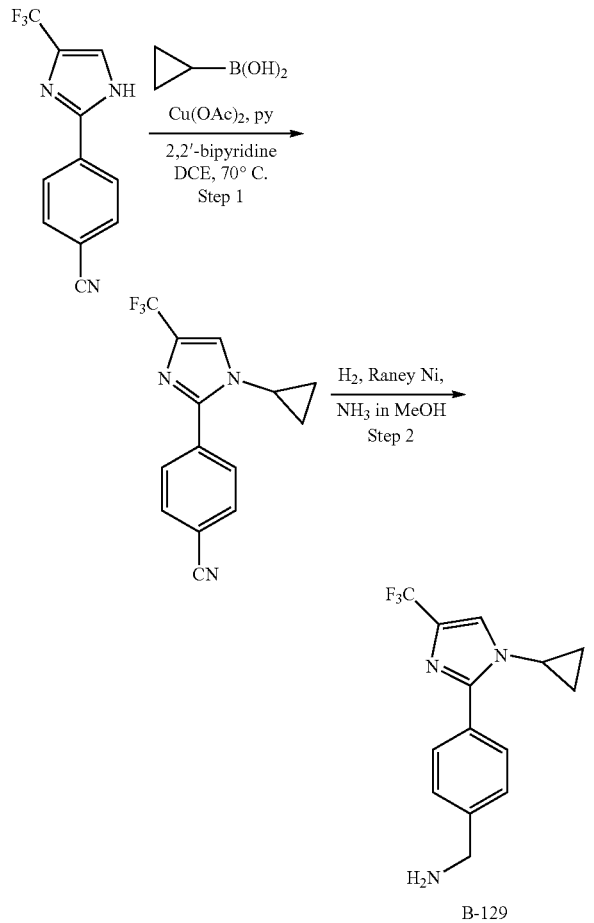

B-129

Step 1. 4-[1-Cyclopropyl-4-(trifluoromethyl)-1H-imidazol-2-yl]benzonitrile

In a 500 mL round-bottom flask a mixture of 4 Å molecular sieves (3 g), Intermediate B-20 (1 g, 4.22 mmol), copper(II) acetate (2.3 g, 12.66 mmol), DCE (200 mL), cyclopropylboronic acid (1.1 g, 12.81 mmol), pyridine (1.33 g, 16.81 mmol) and 2,2'-bipyridine (1.3 g, 8.32 mmol) was stirred for 16 h at 70° C. After cooling to ambient temperature, the reaction mixture was diluted with DCM (200 mL), filtered and concentrated under vacuum. The residue was purified by silica gel chromatography (eluting with 0 to 30% EtOAc/PE) to afford 356 mg (30%) of 4-[1-cyclopropyl-4-(trifluoromethyl)-1H-imidazol-2-yl]benzonitrile as a yellow solid. MS (ESI) m/z 278.1 [M+H]$^+$.

Step 2. [4-[1-Cyclopropyl-4-(trifluoromethyl)-1H-imidazol-2-yl]phenyl]methanamine

[4-[1-Cyclopropyl-4-(trifluoromethyl)-1H-imidazol-2-yl]phenyl]methanamine was obtained as a yellow solid following Step 3 of Example 8. MS (ESI) m/z 282.3 [M+H]$^+$ Intermediate B-130. 2-[2-[4-(Aminomethyl)phenyl]-4-(trifluoromethyl)-1H-imidazol-1-yl]ethan-1-ol

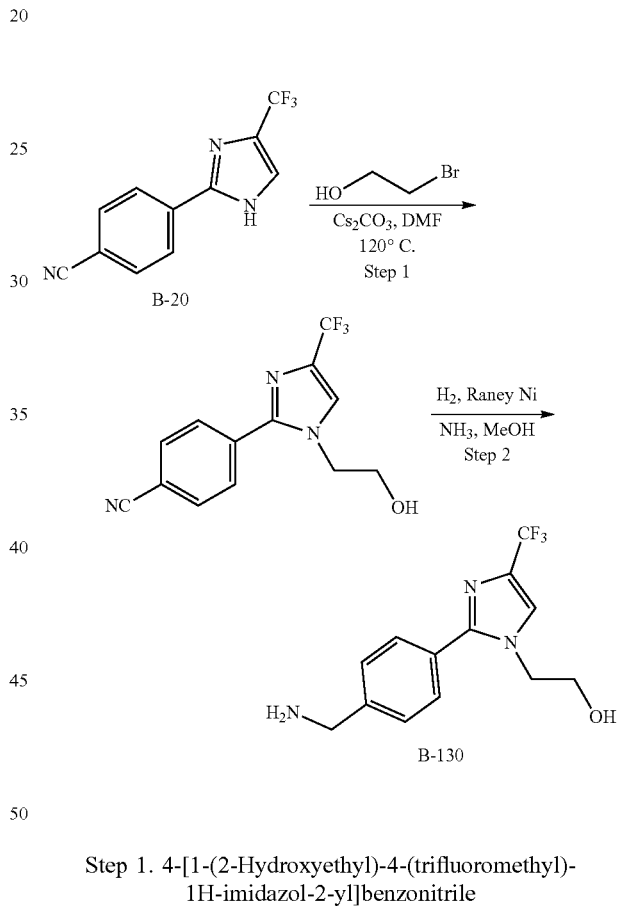

B-130

Step 1. 4-[1-(2-Hydroxyethyl)-4-(trifluoromethyl)-1H-imidazol-2-yl]benzonitrile

In a 100 mL round-bottom flask a mixture of Intermediate B-20 (400 mg, 1.69 mmol), DMF (5 mL), cesium carbonate (1.1 g, 3.38 mmol) and 2-bromoethan-1-ol (232 mg, 1.86 mmol) was stirred for 16 h at 120° C. After cooling to ambient temperature, the reaction mixture was poured into water (10 mL) and then extracted with EtOAc (3×10 mL). The organic layers were combined, dried over anhydrous sodium sulfate, filtered and concentrated under vacuum. The residue was purified by prep-TLC (eluting with 3:2 acetate/PE) to afford 150 mg (32%) of 4-[1-(2-hydroxyethyl)-4-(trifluoromethyl)-1H-imidazol-2-yl]benzonitrile as a yellow solid. MS (ESI) m/z 282.1 [M+H]$^+$.

Step 2. 2-[2-[4-(Aminomethyl)phenyl]-4-(trifluoromethyl)-1H-imidazol-1-yl]ethan-1-ol 2-[2-[4-(aminomethyl)phenyl]-4-(trifluoromethyl)-1H-imidazol-1-yl]ethan-1-ol was obtained as a yellow solid following Step 3 of Example 8. MS (ESI) m/z 286.0 [M+H]$^+$.

Intermediate B-131: 2-Chloro-7-methyl-9-(4-(1-methyl-4-(trifluoromethyl)-1H-imidazol-2-yl)benzyl)-7,9-dihydro-8H-purin-8-one

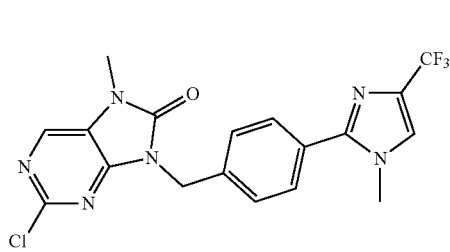

B-131

2-Chloro-7-methyl-9-(4-(1-methyl-4-(trifluoromethyl)-1H-imidazol-2-yl)benzyl)-7,9-dihydro-8H-purin-8-one was synthesized as a white solid from Intermediate B-49 according to Example 33. $^1$H NMR (300 MHz, CD$_3$OD) δ 8.25 (s, 1H), 7.70-7.59 (m, 5H), 5.20 (s, 2H), 3.78 (s, 3H), 3.49 (s, 3H). MS (ESI) m/z 422.9 [M+H]$^+$.

Intermediate B-132: (4-(1-Methyl-3-(trifluoromethyl)-1H-1,2,4-triazol-5-yl)phenyl)methanamine hydrochloride

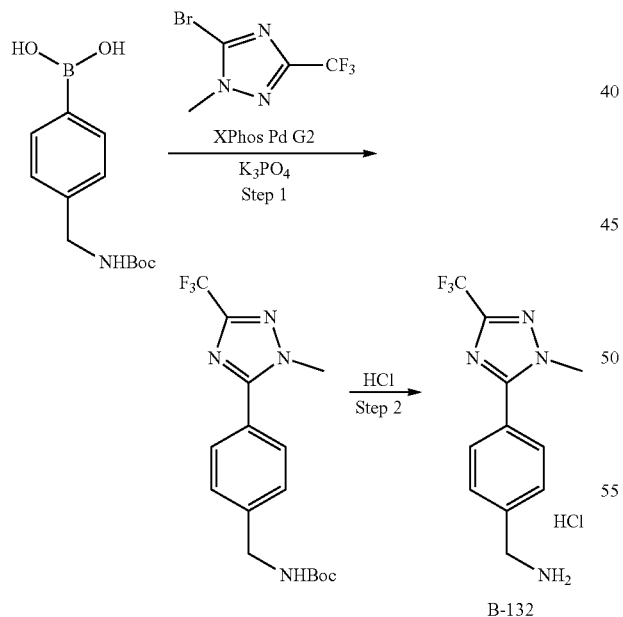

B-132

Step 1. tert-Butyl (4-(1-methyl-3-(trifluoromethyl)-1H-1,2,4-triazol-5-yl)benzyl)carbamate In a reaction vial under nitrogen, a mixture of 5-bromo-1-methyl-3-(trifluoromethyl)-1H-1,2,4-triazole (0.2 M in dioxane, 150 μL, 30 μmol), (4-(((tert-butoxycarbonyl)amino)methyl)phenyl)boronic acid (0.2 M in dioxane, 225 μl, 45 μmol), potassium phosphate (0.2 M in water, 150 μL, 150 μmol), XPhos Pd G2 (0.02 M in dioxane, 60.0 μL, 1.2 μmol) and XPhos (0.02 M in dioxane, 90 μl, 1.800 μmol) was heated at 100° C. for 45 min. After cooling to ambient temperature, the mixture was concentrated under a stream of nitrogen and was partitioned between saturated sodium bicarbonate (600 uL) and EtOAc (600 uL). The organic layer was separated and combined with a second extract of EtOAc (600 uL) and the combined extracts were dried under a stream of nitrogen to afford tert-butyl (4-(1-methyl-3-(trifluoromethyl)-1H-1,2,4-triazol-5-yl)benzyl)carbamate.

Step 2: (4-(1-Methyl-3-(trifluoromethyl)-1H-1,2,4-triazol-5-yl)phenyl)methanamine hydrochloride A mixture of tert-butyl (4-(1-methyl-3-(trifluoromethyl)-1H-1,2,4-triazol-5-yl)benzyl)carbamate, dioxane (200 uL), MeOH (100 uL) and 4 M HCl/dioxane (75 uL) was heated at 50° C. for 45 min, then was concentrated under a stream of nitrogen to afford crude (4-(1-methyl-3-(trifluoromethyl)-1H-1,2,4-triazol-5-yl)phenyl)methanamine hydrochloride.

Intermediate B-133. 2,6-dichloro-9-(4-(1-methyl-4-(trifluoromethyl)-1H-imidazol-2-yl)benzyl)-7,9-dihydro-8H-purin-8-one

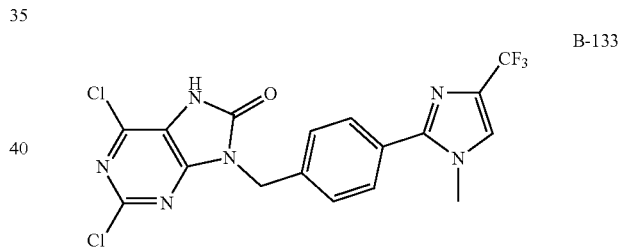

B-133

2,6-Dichloro-9-(4-(1-methyl-4-(trifluoromethyl)-1H-imidazol-2-yl)benzyl)-7,9-dihydro-8H-purin-8-one was prepared from Intermediate B-49 and 2,4,6-trichloro-5-nitropyrimidine according to Example 18.

Example 30. Intermediate B-134. 9-(4-Aminobenzyl)-2-(2-isopropylphenyl)-7,9-dihydro-8H-purin-8-one

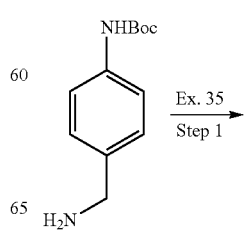

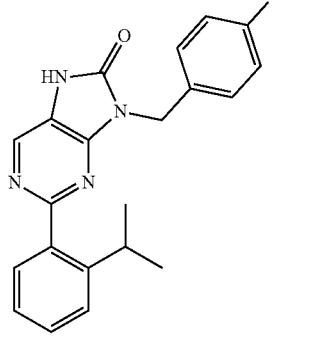

B-134

Step 1. tert-butyl (4-((2-(2-Isopropylphenyl)-8-oxo-7,8-dihydro-9H-purin-9-yl)methyl)phenyl)carbamate tert-Butyl (4-((2-(2-isopropylphenyl)-8-oxo-7,8-dihydro-9H-purin-9-yl)methyl)phenyl)carbamate was synthesized from tert-butyl (4-(aminomethyl)phenyl)carbamate following Example 35. MS (ESI) m/z 460.2 [M+H]⁺.

Step 2. 9-(4-Aminobenzyl)-2-(2-isopropylphenyl)-7,9-dihydro-8H-purin-8-one 9-(4-Aminobenzyl)-2-(2-isopropylphenyl)-7,9-dihydro-8H-purin-8-one was synthesized from tert-butyl (4-((2-(2-isopropylphenyl)-8-oxo-7,8-dihydro-9H-purin-9-yl)methyl) phenyl)carbamate following Example 36. MS (ESI) m/z 360.2 [M+H]⁺.

Intermediate B-135. 9-(4-(1H-1,2,3-Triazol-5-yl) benzyl)-2-(2-isopropylphenyl)-7,9-dihydro-8H-purin-8-one

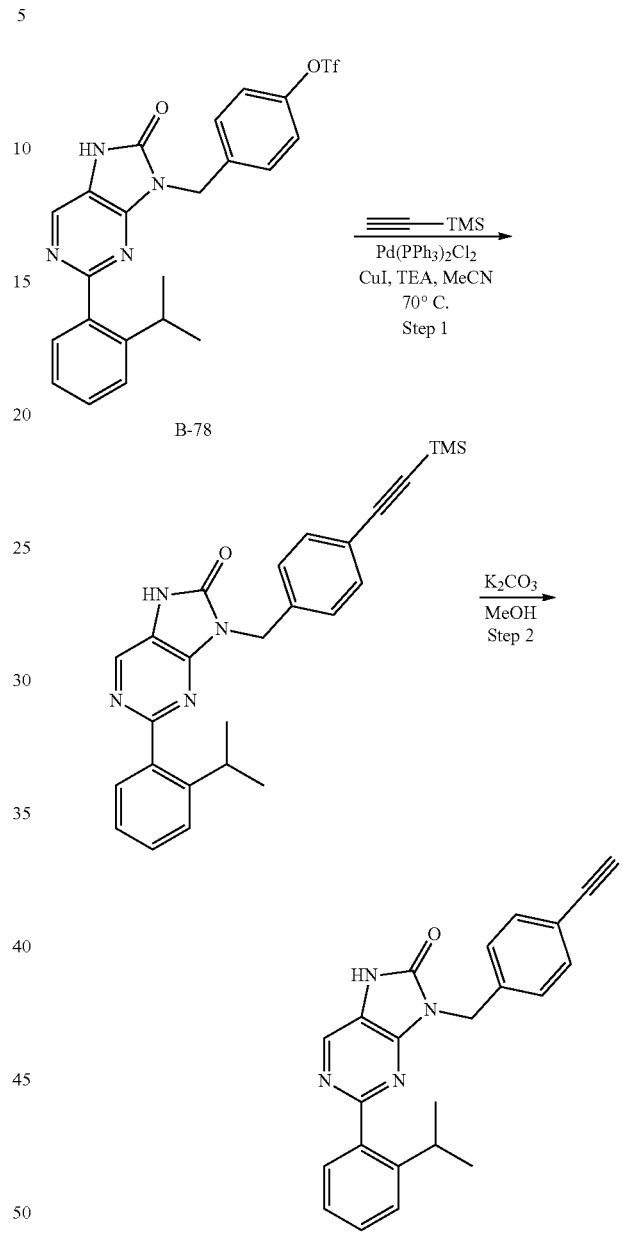

Step 1. 2-(2-Isopropylphenyl)-9-(4-((trimethylsilyl) ethynyl)benzyl)-7,9-dihydro-8H-purin-8-one In a flask purged and maintained under an inert atmosphere of nitrogen, a solution of Intermediate B-78 (2 g, 4.06 mmol) in acetonitrile (80 mL), ethynyltrimethylsilane (1.99 g, 20.28 mmol), copper(I) iodide (773 mg, 4.06 mmol), triethylamine (2.05 g, 20.26 mmol) and Pd(PPh₃)₂Cl₂ (285 mg, 0.41 mmol) was stirred for 16 h at 70° C. After cooling to room temperature, the reaction mixture was concentrated under vacuum and the residue was purified by silica gel chromatography (eluting with 60/40 to 90/10 EtOAc/PE) to afford 150 mg (8.3%) of 2-(2-isopropylphenyl)-9-(4-((trimethylsilyl)ethynyl)benzyl)-7,9-dihydro-8H-purin-8-one as a yellow solid. MS (ESI) m/z 441.2 [M+H]$^+$ Step 2. 9-(4-Ethynylbenzyl)-2-(2-isopropylphenyl)-7,9-dihydro-8H-purin-8-one A solution of 2-(2-isopropylphenyl)-9-(4-((trimethylsilyl)ethynyl)benzyl)-7,9-dihydro-8H-purin-8-one (50 mg, 0.11 mmol) in MeOH (5 mL) and potassium carbonate (32 mg, 0.23 mmol) was stirred for 2 h at room temperature, then was concentrated under vacuum. The residue was purified by prep-TLC (eluting with 1/20 MeOH/DCM) to afford 40 mg (91%) of 9-(4-ethynylbenzyl)-2-(2-isopropylphenyl)-7,9-dihydro-8H-purin-8-one as a white solid. MS (ESI) m/z 369.2 [M+H]$^+$ Example 31: 9-(4-(3,5-Dimethyl-1H-pyrazol-1-yl)benzyl)-2-(2-isopropylphenyl)-7,9-dihydro-8H-purin-8-one (I-1)

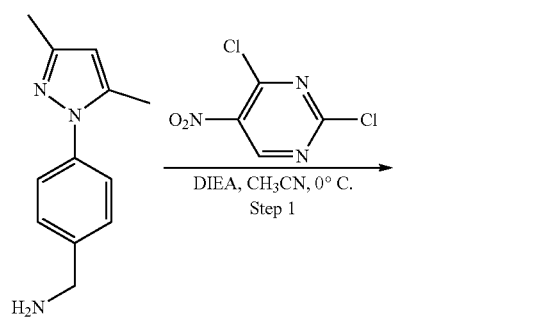

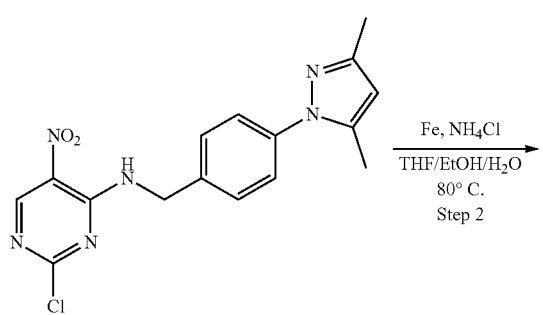

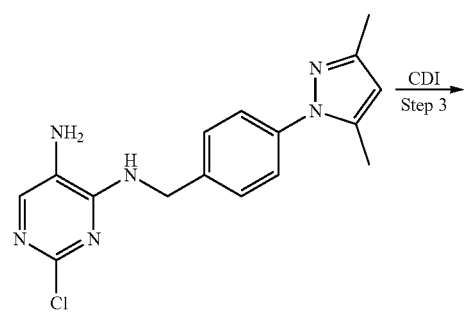

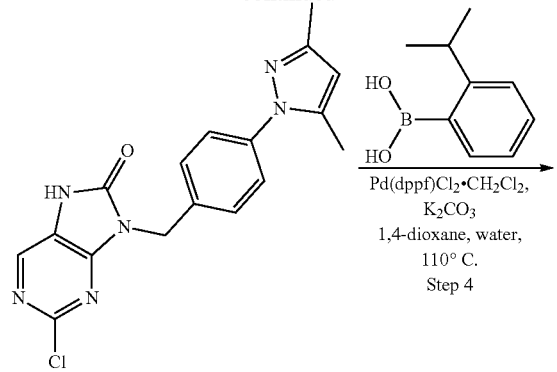

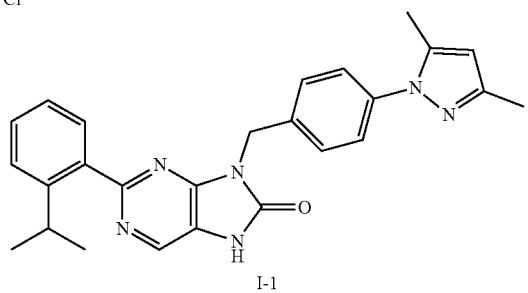

I-1

Step 1. 2-Chloro-N-(4-(3,5-dimethyl-1H-pyrazol-1-yl)benzyl)-5-nitropyrimidin-4-amine A solution of (4-(3,5-dimethyl-1H-pyrazol-1-yl)phenyl)methanamine (300 mg, 1.49 mmol), 2,4-dichloro-5-nitropyrimidine (346 mg, 1.78 mmol), acetonitrile (10 mL) and DIEA (384 mg, 2.97 mmol) was stirred for 1 h at 0° C. The reaction mixture was concentrated under reduced pressure and the residue was purified by silica gel chromatography (eluting with 1:1 EtOAc/PE) to afford 500 mg (93%) of 2-chloro-N-(4-(3,5-dimethyl-1H-pyrazol-1-yl)benzyl)-5-nitropyrimidin-4-amine as a brown oil. MS (ESI) m/z 359 [M+H]$^+$.

Step 2. 2-Chloro-N$^4$-(4-(3,5-dimethyl-1H-pyrazol-1-yl)benzyl)pyrimidine-4,5-diamine A mixture of 2-chloro-N-(4-(3,5-dimethyl-1H-pyrazol-1-yl)benzyl)-5-nitropyrimidin-4-amine (500 mg, 1.39 mmol), iron powder (391 mg, 6.98 mmol), ammonium chloride (223 mg, 4.17 mmol) and a 3:3:1 mixture of THF/EtOH/water (21 mL) was stirred for 1 h at 80° C. After cooling to ambient temperature, the reaction mixture was filtered and concentrated under vacuum to afford 400 mg (87%) of 2-chloro-N$^4$-(4-(3,5-dimethyl-1H-pyrazol-1-yl)benzyl)pyrimidine-4,5-diamine as a brown solid. MS (ESI) m/z 329 [M+H]$^+$.

Step 3. 2-Chloro-9-(4-(3,5-dimethyl-1H-pyrazol-1-yl)benzyl)-7,9-dihydro-8H-purin-8-one A solution of 2-chloro-N$^4$-(4-(3,5-dimethyl-1H-pyrazol-1-yl)benzyl)pyrimidine-4,5-diamine (400 mg, 1.22 mmol), CDI (790 mg, 4.87 mmol) and DCM (15 mL) was stirred for 16 h at ambient temperature. The reaction mixture was concentrated under vacuum and the residue was purified by C18-reversed phase silica gel chromatography (eluting with 1:1 acetonitrile/water) to afford 400 mg (93%) of 2-chloro-9-(4-(3,5-dimethyl-1H-pyrazol-1-yl)benzyl)-7,9-dihydro-8H-purin-8-one as a yellow oil. MS (ESI) m/z 355 [M+H]$^+$.

Step 4. 9-(4-(3,5-Dimethyl-1H-pyrazol-1-yl)benzyl)-2-(2-isopropylphenyl)-7,9-dihydro-8H-purin-8-one (I-1)

In a 50 mL round-bottom flask purged and maintained with an inert atmosphere of nitrogen, a mixture of 2-chloro-9-(4-(3,5-dimethyl-1H-pyrazol-1-yl)benzyl)-7,9-dihydro-8H-purin-8-one (100 mg, 0.28 mmol), (2-isopropylphenyl)boronic acid (56 mg, 0.34 mmol), Pd(dppf)Cl$_2$.CH$_2$Cl$_2$ (23 mg, 0.028 mmol), potassium carbonate (78 mg, 0.56 mmol), 1,4-dioxane (10 mL) and water (3 mL) was stirred at 110° C. for 3 h. After cooling to ambient temperature, the mixture was concentrated under reduced pressure and purified by prep-TLC (eluting with 1:1 EtOAc/petroleum). Additional purification by prep-HPLC to afforded 27.6 mg (22%) of 9-(4-(3,5-dimethyl-1H-pyrazol-1-yl)benzyl)-2-(2-isopropylphenyl)-7,9-dihydro-8H-purin-8-one (I-1).

Example 32: 2-(2-Isopropylpyridin-3-yl)-9-(4-(1-methyl-4-(trifluoromethyl)-1H-imidazol-2-yl)benzyl)-7,9-dihydro-8H-purin-8-one (I-2)

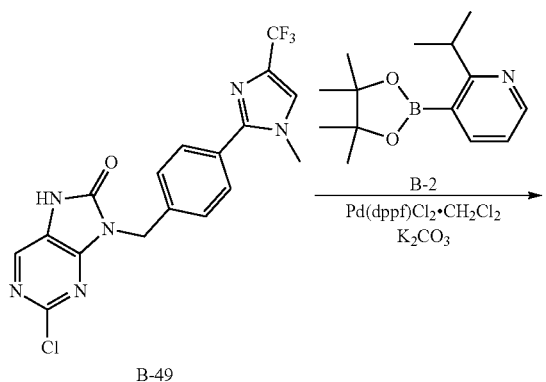

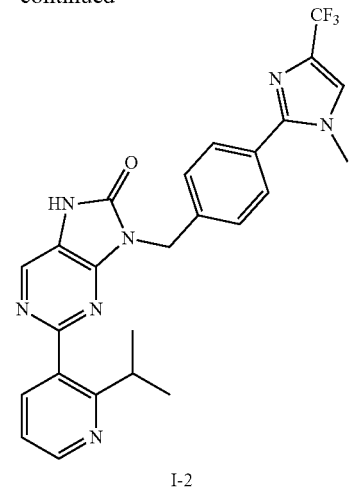

I-2

In a flask purged and maintained with an inert atmosphere of nitrogen, a mixture of Intermediate B-49 (100 mg, 0.24 mmol), Pd(dppf)Cl$_2$.CH$_2$Cl$_2$ (19.9 mg, 0.02 mmol), potassium carbonate (101.4 mg, 0.73 mmol), water (1 mL), Intermediate B-2 (72.5 mg, 0.29 mmol) and 1,4-dioxane (10 mL) was stirred at 100° C. for 16 h. After cooling to ambient temperature, the reaction mixture was concentrated under vacuum and the residue was purified by silica gel chromatography (eluting with 0-100% EtOAc/PE). Additional purification by prep-HPLC afforded 19.1 mg (16%) of 2-(2-isopropylpyridin-3-yl)-9-(4-(1-methyl-4-(trifluoromethyl)-1H-imidazol-2-yl)benzyl)-7,9-dihydro-8H-purin-8-one (I-2) as a white solid.

Table 2 (General Procedure A). The compounds listed in Table 2 were synthesized according to either Example 31 or Example 32 using the appropriate commercially-available reagents and/or Intermediates described herein. Enantiomers, when generated, were separated by chiral HPLC and absolute stereochemistries were arbitrarily assigned.

TABLE 2

| Cmpd no. | LCMS | $^1$H NMR (300 MHz) δ ppm | Chemical Name |
|---|---|---|---|
| I-1 | m/z: 439.18 [M + H]$^+$ Rt (min): 1.59 | $^1$H NMR (400 MHz, CD$_3$OD) δ 8.32 (s, 1H), 7.59-7.56 (m, 2H), 7.46-7.39 (m, 5H), 7.28-7.24 (m, 1H), 6.05 (s, 1H), 5.20 (s, 2H), 3.35-3.32 (m, 1H), 2.22 (d, J = 6.80 Hz, 6H), 1.16 (d, J = 6.80 Hz, 6H). | 9-(4-(3,5-dimethyl-1H-pyrazol-1-yl)benzyl)-2-(2-isopropylphenyl)-7,9-dihydro-8H-purin-8-one |
| I-2 | m/z: 494.3928 [M + H]$^+$ Rt (min): 0.8967 | $^1$H NMR (400 MHz, CD$_3$OD) δ 8.60-8.53 (m, 1H), 8.39 (s, 1H), 8.03-7.96 (m, 1H), 7.71-7.56 (m, 5H), 7.38-7.30 (m, 1H), 5.23 (s, 2H), 3.76 (s, 3H), 3.64-3.51 (m, 1H), 1.23 (d, J = 6.8 Hz, 6H). | 2-(2-isopropylpyridin-3-yl)-9-(4-(1-methyl-4-(trifluoromethyl)-1H-imidazol-2-yl)benzyl)-7,9-dihydro-8H-purin-8-one |
| I-3 | m/z: 413.2378 [M + H]$^+$ Rt (min): 1.08 | | 9-(4-(2H-1,2,3-triazol-2-yl)benzyl)-2-(2-isopropylpyridin-3-yl)-7,9-dihydro-8H-purin-8-one |
| I-4 | m/z: 437.1739 [M + H]$^+$ Rt (min): 1.32 | | 9-(4-(2H-1,2,3-triazol-2-yl)benzyl)-2-(2-(difluoromethoxy)pyridin-3-yl)-7,9-dihydro-8H-purin-8-one |
| I-5 | m/z: 443.3482 [M + H]$^+$ | | 9-(4-(2H-1,2,3-triazol-2-yl)benzyl)-2-(2-isobutoxypyridin-3-yl)-7,9- |

TABLE 2-continued

| Cmpd no. | LCMS | $^{1}$H NMR (300 MHz) δ ppm | Chemical Name |
|---|---|---|---|
| | Rt (min): 1.46 | | dihydro-8H-purin-8-one |
| I-6 | m/z: 425.2801 [M + H]$^{+}$ Rt (min): 1.65 | $^{1}$H-NMR (400 MHz, DMSO-d$_6$) δ 8.60 (s, 1H), 8.46 (d, J = 2.8 Hz, 1H), 7.81-7.79 (m, 2H), 7.73-7.72 (m, 1H), 7.52-7.38 (m, 5H), 7.28-7.24 (m, 1H), 6.53 (t, J = 2.0 Hz, 1H), 5.11 (s, 2H), 3.46-3.39 (m, 4H), 1.09 (d, J = 7.2 Hz, 6H). | 9-(4-(1H-pyrazol-1-yl)benzyl)-2-(2-isopropylphenyl)-7-methyl-7,9-dihydro-8H-purin-8-one |
| I-7 | m/z: 426.255 [M + H]$^{+}$ Rt (min): 1.16 | $^{1}$H NMR (400 MHz, DMSO-d$_6$) δ 8.63-8.59 (m, 2H), 8.46 (d, J = 2.40 Hz, 1H), 7.96 (d, J = 7.60 Hz, 1H), 7.81 (d, J = 8.40 Hz, 2H), 7.72 (s, 1H), 7.47 (d, J = 8.40 Hz, 2H), 7.33-7.30 (m, 1H), 6.53 (s, 1H), 5.12 (s, 2H), 3.65-3.58 (m, 1H), 3.46 (s, 3H), 1.12 (d, J = 6.80 Hz, 6H). | 9-(4-(1H-pyrazol-1-yl)benzyl)-2-(2-isopropylpyridin-3-yl)-7-methyl-7,9-dihydro-8H-purin-8-one |
| I-8 | m/z: 443.2182 [M + H]$^{+}$ Rt (min): 1.69 | $^{1}$H-NMR (400 MHz, DMSO-d$_6$) δ 8.60 (s, 1H), 8.45 (d, J = 2.4 Hz, 1H), 7.81-7.78 (m, 2H), 7.72-7.72 (m, 1H), 7.47-7.44 (m, 2H), 7.31-7.29 (m, 2H), 7.24-7.18 (m, 1H), 6.53-6.52 (m, 1H), 5.10 (s, 2H), 3.46 (s, 3H), 3.32-3.24 (m, 1H), 1.22-1.19 (m, 6H). | 9-(4-(1H-pyrazol-1-yl)benzyl)-2-(3-fluoro-2-isopropylphenyl)-7-methyl-7,9-dihydro-8H-purin-8-one |
| I-9 | m/z: 443.2182 [M + H]$^{+}$ Rt (min): 1.71 | $^{1}$H NMR (400 M Hz, DMSO-d$_6$) δ 8.61 (s, 1H), 8.56-8.56 (d, J = 2.4 Hz, 1H), 7.79-7.81 (m, 2H), 7.72 (s, 1H), 7.45-7.48 (m, 3H), 7.30-7.33 (m, 1H), 7.23-7.24 (m, 1H), 6.52-6.53 (m, 1H), 5.11 (s, 2H), 3.43-3.46 (s, 4H), 1.07-1.09 (m, 6H). | 9-(4-(1H-pyrazol-1-yl)benzyl)-2-(5-fluoro-2-isopropylphenyl)-7-methyl-7,9-dihydro-8H-purin-8-one |
| I-10 | m/z: 443.2832 [M + H]$^{+}$ Rt (min): 1.69 | $^{1}$H NMR (300 MHz, CD$_3$OD) δ 8.42 (s, 1H), 8.17-8.16 (m, 1H), 7.69-7.66 (m, 3H), 7.53-7.48 (m, 3H), 7.14-7.09 (m, 1H), 6.99-6.93 (m, 1H), 6.48-6.47 (m, 1H), 5.17 (s, 2H), 3.50 (s, 3H), 3.41-3.32 (m, 1H), 1.12-1.08 (m, 6H). | 9-(4-(1H-pyrazol-1-yl)benzyl)-2-(4-fluoro-2-isopropylphenyl)-7-methyl-7,9-dihydro-8H-purin-8-one |
| I-11 | m/z: 443.242 [M + H]$^{+}$ Rt (min): 1.59 | $^{1}$H NMR (400 MHz, CD$_3$OD) δ 8.49 (s, 1H), 8.20 (d, J = 2.4 Hz, 1H), 7.72-7.68 (m, 3H), 7.64-7.56 (m, 2H), 7.48-7.42 (m, 1H), 7.27-7.25 (d, J = 4.0 Hz, 1H), 7.07-7.02 (m, 1H), 6.53 (t, J = 2.0 Hz, 1H), 5.21 (s, 2H), 3.56 (s, 3H), 2.74-2.67 (m, 1H), 1.14-1.10 (m, 6H). | 9-(4-(1H-pyrazol-1-yl)benzyl)-2-(2-fluoro-6-isopropylphenyl)-7-methyl-7,9-dihydro-8H-purin-8-one |
| I-12 | m/z: 412.2168 [M + H]$^{+}$ Rt (min): 1.02 | $^{1}$H NMR (300 MHz, DMSO-d$_6$) δ 11.63 (s, 1H), 8.59-8.57 (m, 1H), 8.45-8.42 (m, 2H), 7.97-7.94 (m, 1H), 7.87-7.78 (m, 2H), 7.72-7.71 (m, 1H), 7.47-7.44 (m, 2H), 7.32-7.28 (m, 1H), 6.52-6.52 (m, 1H), 5.07 (s, 2H), 3.67-3.59 (m, 1H), 1.13-1.11 (m, 6H). | 9-(4-(1H-pyrazol-1-yl)benzyl)-2-(2-isopropylpyridin-3-yl)-7,9-dihydro-8H-purin-8-one |
| I-13 | m/z: 426.255 [M + H]$^{+}$ Rt (min): 1.11 | $^{1}$H NMR (400 MHz, CD$_3$OD) δ 8.55-8.53 (m, 1H), 8.37 (s, 1H), 8.20 (s, 1H), 7.97-7.95 (m, 1H), 7.74-7.70 (m, 3H), 7.60 (d, J = 8.80 Hz, 2H), 7.35-7.30 (m, 1H), 6.51 (t, J = 2.00 Hz, 1H), 5.89-5.83 (m, 1H), 3.59-3.52 (m, 1H), 2.08 (d, J = 7.20 Hz, 3H), 1.19-1.12 (m, 6H). | (S)-9-(1-(4-(1H-pyrazol-1-yl)phenyl)ethyl)-2-(2-isopropylpyridin-3-yl)-7,9-dihydro-8H-purin-8-one |
| I-14 | m/z: 426.255 [M + H]$^{+}$ Rt (min): 1.11 | $^{1}$H NMR (400 MHz, CD$_3$OD) δ 8.55 (t, J = 2.80 Hz, 1H), 8.36 (s, 1H), 8.19-8.18 (m, 1H), 7.97-7.94 (m, 1H), 7.72-7.69 (m, 3H), 7.60 (d, J = 8.40 Hz, 2H), 7.35-7.32 (m, 1H), 6.50 (s, 1H), 5.89-5.84 (m, 1H), 3.59-3.52 (m, 1H), 2.07 (d, J = 7.20 Hz, 3H), 1.17 (d, J = 6.80 Hz, 3H), 1.16 (d, J = 6.80 Hz, 3H). | (R)-9-(1-(4-(1H-pyrazol-1-yl)phenyl)ethyl)-2-(2-isopropylpyridin-3-yl)-7,9-dihydro-8H-purin-8-one |

TABLE 2-continued

| Cmpd no. | LCMS | ¹H NMR (300 MHz) δ ppm | Chemical Name |
|---|---|---|---|
| I-15 | m/z: 446.0951 [M + H]⁺ Rt (min): 1.46 | | 9-(4-(2H-1,2,3-triazol-2-yl)benzyl)-2-(4-fluoro-2-isopropoxyphenyl)-7,9-dihydro-8H-purin-8-one |
| I-16 | m/z: 418.131 [M + H]⁺ Rt (min): 1.37 | | 9-(4-(2H-1,2,3-triazol-2-yl)benzyl)-2-(3-fluoro-2-methoxyphenyl)-7,9-dihydro-8H-purin-8-one |
| I-17 | m/z: 426.2275 [M + H]⁺ Rt (min): 1.14 | | 9-(4-(1H-pyrazol-1-yl)benzyl)-2-(4-isopropylpyridin-3-yl)-7-methyl-7,9-dihydro-8H-purin-8-one |
| I-18 | m/z: 468.0558 [M + H]⁺ Rt (min): 1.36 | ¹H NMR (400 MHz, DMSO-d₆) δ 11.56 (br s, 1H), 8.44-8.41 (m, 2H), 8.31-8.29 (m, 1H), 8.22-8.20 (m, 1H), 7.80-7.78 (m, 2H), 7.72-7.72 (m, 1H), 7.49-7.47 (m, 2H), 7.27-7.24 (m, 1H), 6.53-6.52 (m, 1H), 5.10-5.03 (m, 4H). | 9-(4-(1H-pyrazol-1-yl)benzyl)-2-(2-(2,2,2-trifluoroethoxy)pyridin-3-yl)-7,9-dihydro-8H-purin-8-one |
| I-19 | m/z: 414.0512 [M + H]⁺ Rt (min): 1.16 | ¹H NMR (400 MHz, DMSO-d₆) δ 11.56 (s, 1H), 8.46 (s, 1H), 8.39 (s, 1H), 8.24-8.23 (m, 1H), 8.02-8.00 (m, 1H), 7.82-7.80 (m, 2H), 7.73 (s, 1H), 7.52-7.50 (m, 2H), 7.10-7.07 (m, 1H), 6.54-6.52 (m, 1H), 5.07 (s, 2H), 4.39-4.34 (m, 2H), 1.24-1.20 (m, 3H). | 9-(4-(1H-pyrazol-1-yl)benzyl)-2-(2-ethoxypyridin-3-yl)-7,9-dihydro-8H-purin-8-one |
| I-20 | m/z: 443.0969 [M + H]⁺ Rt (min): 1.02 | | 9-(4-(1H-pyrazol-1-yl)benzyl)-2-(2-(2-methoxyethoxy)phenyl)-7,9-dihydro-8H-purin-8-one |
| I-21 | m/z: 427.1365 [M + H]⁺ Rt (min): 1.24 | | 9-(4-(1H-pyrazol-1-yl)benzyl)-2-(2-propoxyphenyl)-7,9-dihydro-8H-purin-8-one |
| I-22 | m/z: 467.1015 [M + H]⁺ Rt (min): 1.36 | | 9-(4-(1H-pyrazol-1-yl)benzyl)-2-(2-(2,2,2-trifluoroethoxy)phenyl)-7,9-dihydro-8H-purin-8-one |
| I-23 | m/z: 439.1226 [M + H]⁺ Rt (min): 1.23 | | 9-(4-(1H-pyrazol-1-yl)benzyl)-2-(2-(cyclopropylmethoxy)phenyl)-7,9-dihydro-8H-purin-8-one |
| I-24 | m/z: 508.1895 [M + H]⁺ Rt (min): 1.62 | | 9-((1R,2S)-2-(4-(1H-pyrazol-1-yl)phenyl)cyclobutyl)-2-(2-(2,2,2-trifluoroethoxy)pyridin-3-yl)-7,9-dihydro-8H-purin-8-one |
| I-25 | m/z: 449.2674 [M + H]⁺ Rt (min): 1.5976 | | 9-(4-(1H-pyrazol-1-yl)benzyl)-2-(2,2-difluorobenzo[d][1,3]dioxol-4-yl)-7,9-dihydro-8H-purin-8-one |
| I-26 | m/z: 550.43 [M + H]⁺ Rt (min): 1.4417 | ¹H NMR (400 MHz, CD₃OD) δ 8.35 (s, 1H), 8.30-8.24 (m, 1H), 8.20-8.13 (m, 1H), 7.70-7.57 (m, 5H), 7.24-7.16 (m, 1H), 5.24 (s, 2H), 5.01-4.89 (m, 2H), 3.75 (s, 3H). | 9-(4-(1-methyl-4-(trifluoromethyl)-1H-imidazol-2-yl)benzyl)-2-(2-(2,2,2-trifluoroethoxy)pyridin-3-yl)-7,9-dihydro-8H-purin-8-one |
| I-27 | m/z: 397.321 [M + H]⁺ Rt (min): 1.45 | | 9-(4-(1H-pyrazol-1-yl)benzyl)-2-(2-ethylphenyl)-7,9-dihydro-8H-purin-8-one |
| I-28 | m/z: 413.3782 [M + H]⁺ Rt (min): 1.165 | | 9-(4-(1H-pyrazol-1-yl)benzyl)-2-(4-isopropylpyrimidin-5-yl)-7,9-dihydro-8H-purin-8-one |

TABLE 2-continued

| Cmpd no. | LCMS | ¹H NMR (300 MHz) δ ppm | Chemical Name |
|---|---|---|---|
| I-29 | m/z: 422.3512 [M + H]⁺ Rt (min): 1.3417 | | 9-(4-(1H-pyrazol-1-yl)benzyl)-2-(1-methyl-1H-indol-7-yl)-7,9-dihydro-8H-purin-8-one |
| I-30 | m/z: 492.4 [M + H]⁺ Rt (min): 0.99 | ¹H NMR (400 MHz, DMSO-d₆) δ 11.67 (ds, 1H), 8.46-8.45 (m, 2H), 8.03-7.98 (m, 1H), 7.92(s, 1H), 7.68 (d, J = 8.4 Hz, 2H), 7.48 (d, J = 8.0 Hz, 2H), 7.24-7.20 (m, 1H), 5.13 (s, 2H), 3.75 (s, 3H), 2.79-2.76 (m, 1H), 0.98-0.95 (m, 2H), 0.81-0.73 (m, 2H). | 2-(2-cyclopropylpyridin-3-yl)-9-(4-(1-methyl-4-(trifluoromethyl)-1H-imidazol-2-yl)benzyl)-7,9-dihydro-8H-purin-8-one |
| I-31 | m/z: 501.4 [M + H]⁺ Rt (min): 1.51 | ¹H NMR (400 MHz, DMSO-d₆) δ 8.36 (s, 1H), 8.07 (d, J = 8.4 Hz, 1H), 7.91 (s, 1H), 7.87-7.56 (m, 6H), 7.51-7.49 (m, 2H), 5.13 (s, 2H), 3.75 (s, 3H). | 2-(2-(difluoromethyl)phenyl)-9-(4-(1-methyl-4-(trifluoromethyl)-1H-imidazol-2-yl)benzyl)-7,9-dihydro-8H-purin-8-one |
| I-32 | m/z: 536.4523 [M + H]⁺ Rt (min): 0.8827 | ¹H NMR (400 MHz, CD₃OD) δ 8.59-8.58 (m, 1H), 8.40 (s, 1H), 8.30 (s, 1H), 8.02-7.99 (m, 1H), 7.61 (d, J = 8.0 Hz, 2H), 7.49 (d, J = 8.0 Hz, 2H), 7.38-7.34 (m, 1H), 5.53-5.48 (m, 1H), 5.27 (s, 2H), 4.98-4.89 (m, 2H), 4.89-4.81 (m, 2H), 3.64-3.53 (m, 1H), 1.26 (d, J = 6.8 Hz, 6H). | 2-(2-isopropylpyridin-3-yl)-9-(4-(1-(oxetan-3-yl)-4-(trifluoromethyl)-1H-imidazol-2-yl)benzyl)-7,9-dihydro-8H-purin-8-one |
| I-33 | m/z: 534.4369 [M + H]⁺ Rt (min): 0.9483 | ¹H NMR (400 MHz, CD₃OD) δ 8.45-8.44 (m, 1H), 8.43 (s, 1H), 8.36 (s, 1H), 7.99-7.96 (m, 1H), 7.60 (d, J = 8.4 Hz, 2H), 7.46 (d, J = 8.4 Hz, 2H), 7.25-7.23 (m, 1H), 5.53-5.45 (m, 1H), 5.24 (s, 2H), 4.98-4.93 (m, 2H), 4.83-4.79 (m, 2H), 2.64-2.53 (m, 1H), 1.05-1.02 (m, 2H), 0.86-0.82 (m, 2H). | 2-(2-cyclopropylpyridin-3-yl)-9-(4-(1-(oxetan-3-yl)-4-(trifluoromethyl)-1H-imidazol-2-yl)benzyl)-7,9-dihydro-8H-purin-8-one |
| I-34 | m/z: 506.4 [M + H]⁺ Rt (min): 0.85 | ¹H NMR (400 MHz, CD₃OD) δ 8.26 (s, 1H), 7.64-7.61 (m, 5H), 7.26 (d, J = 7.8 Hz, 1H), 7.12 (d, J = 6.6 Hz, 1H), 6.74 (t, J = 7.8 Hz, 1H), 5.21 (s, 2H), 3.73 (s, 3H), 3.39-3.31 (m, 2H), 3.04-2.92 (m, 2H), 2.30 (s, 3H). | 9-(4-(1-methyl-4-(trifluoromethyl)-1H-imidazol-2-yl)benzyl)-2-(1-methylindolin-7-yl)-7,9-dihydro-8H-purin-8-one |
| I-35 | m/z: 518.38 [M + H]⁺ Rt (min): | | 2-(2-(difluoromethoxy)pyridin-3-yl)-9-(4-(1-methyl-4-(trifluoromethyl)-1H-imidazol-2-yl)benzyl)-7,9-dihydro-8H-purin-8-one |
| I-36 | m/z: 531.3816 [M + H]⁺ Rt (min): 1.6125 | | 2-(2,2-difluorobenzo[d][1,3]dioxol-4-yl)-9-(4-(1-methyl-4-(trifluoromethyl)-1H-imidazol-2-yl)benzyl)-7,9-dihydro-8H-purin-8-one |
| I-37 | m/z: 535.41 [M + H]⁺ Rt (min): | | 9-(4-(1-methyl-4-(trifluoromethyl)-1H-imidazol-2-yl)benzyl)-2-(2-(trifluoromethoxy)phenyl)-7,9-dihydro-8H-purin-8-one |
| I-38 | m/z: 493.4 [M + H]⁺ Rt (min): 0.96 | ¹H NMR (300 MHz, DMSO-d₆) δ 11.62 (br s, 1H), 8.38 (s, 1H), 8.14-8.11 (m, 1H), 7.93 (s, 1H), 7.72 (d, J = 8.4 Hz, 2H), 7.61-7.43 (m, 4H), 7.40-7.37 (m, 1H), 5.11 (s, 2H), 3.77 (s, 3H), 2.25 (s, 3H). | 2-(2-acetylphenyl)-9-(4-(1-methyl-4-(trifluoromethyl)-1H-imidazol-2-yl)benzyl)-7,9-dihydro-8H-purin-8-one |
| I-39 | m/z: 494.4388 [M + H]⁺ Rt (min): 1.12 | ¹H NMR (400 MHz, DMSO-d₆) δ 11.70 (br s, 1H), 8.58-8.55 (m, 1H), 8.44 (s, 1H), 7.94-7.91 (m, 1H), 7.49-7.41 (m, 4H), 7.29-7.24 (m, 1H), 6.91 (d, J = 2.0 Hz, 1H), 5.14 (s, 2H), 3.63-3.55 (m, 1H), 2.25 (s, 3H), 1.09 (d, J = 6.8 Hz, 6H). | 2-(2-isopropylpyridin-3-yl)-9-(4-(3-methyl-5-(trifluoromethyl)-1H-pyrazol-1-yl)benzyl)-7,9-dihydro-8H-purin-8-one |
| I-40 | m/z: 494.3945 | ¹H NMR (400 MHz, DMSO-d₆) δ 11.67 (br s, 1H), 8.58-8.56 (m, | 2-(2-isopropylpyridin-3-yl)-9-(4-(5-methyl-3- |

TABLE 2-continued

| Cmpd no. | LCMS | ¹H NMR (300 MHz) δ ppm | Chemical Name |
|---|---|---|---|
| | [M + H]⁺ Rt (min): 1.1567 | 1H), 8.43 (d, J = 5.2 Hz, 1H), 7.96-7.92 (m, 1H), 7.56-7.49 (m, 4H), 7.29-7.26 (m, 1H), 6.73 (s, 1H), 5.13 (s, 2H), 3.65-3.58 (m, 1H), 2.30 (s, 3H), 1.11 (d, J = 6.80 Hz, 6H). | (trifluoromethyl)-1H-pyrazol-1-yl)benzyl)-7,9-dihydro-8H-purin-8-one |
| I-41 | m/z: 550.4655 [M + H]⁺ Rt (min): 1.6683 | ¹H NMR (400 MHz, DMSO-d₆) δ 11.69 (br s, 1H), 8.40 (s, 1H), 8.32-8.23 (m, 1H), 8.21-8.14 (m, 1H), 7.55-7.47 (m, 2H), 7.43-7.40 (m, 2H), 7.26-7.18 (m, 1H), 6.90 (s, 1H), 5.11 (s, 2H), 5.07-4.96 (m, 2H), 2.25 (s, 3H). | 9-(4-(3-methyl-5-(trifluoromethyl)-1H-pyrazol-1-yl)benzyl)-2-(2-(2,2,2-trifluoroethoxy)pyridin-3-yl)-7,9-dihydro-8H-purin-8-one |
| I-42 | m/z: 550.4572 [M + H]⁺ Rt (min): 1.6917 | ¹H NMR (400 MHz, DMSO-d₆) δ 11.64 (br s, 1H), 8.41 (s, 1H), 8.31-8.24 (m, 1H), 8.24-8.15 (m, 1H), 7.55-7.50 (m, 4H), 7.27-7.19 (m, 1H), 6.72 (s, 1H), 5.12 (s, 2H), 5.09-4.97 (m, 2H), 2.29 (s, 3H). | 9-(4-(5-methyl-3-(trifluoromethyl)-1H-pyrazol-1-yl)benzyl)-2-(2-(2,2,2-trifluoroethoxy)pyridin-3-yl)-7,9-dihydro-8H-purin-8-one |
| I-43 | m/z: 538.5 [M + H]⁺ Rt (min): 0.9717 | | 2-(2-isopropylpyridin-3-yl)-9-(4-(1-(2-methoxyethyl)-4-(trifluoromethyl)-1H-imidazol-2-yl)benzyl)-7,9-dihydro-8H-purin-8-one |
| I-44 | m/z: 505.3749 [M + H]⁺ Rt (min): 1.3008 | | 2-(1-methyl-1H-indazol-7-yl)-9-(4-(1-methyl-4-(trifluoromethyl)-1H-imidazol-2-yl)benzyl)-7,9-dihydro-8H-purin-8-one |
| I-45 | m/z: 504.3 [M + H]⁺ Rt (min): 1.4459 | | 2-(1-methyl-1H-indol-7-yl)-9-(4-(1-methyl-4-(trifluoromethyl)-1H-imidazol-2-yl)benzyl)-7,9-dihydro-8H-purin-8-one |
| I-46 | m/z: 426.3239 [M + H]⁺ Rt (min): 0.8 | | 2-(2-isopropylpyridin-3-yl)-9-(4-(1-methyl-1H-pyrazol-3-yl)benzyl)-7,9-dihydro-8H-purin-8-one |
| I-47 | m/z: 440.4 [M + H]⁺ Rt (min): 0.8692 | ¹H NMR (300 MHz, CD₃OD) δ 8.57-8.50 (m, 1H), 8.33 (s, 1H), 7.97-7.93 (m, 1H), 7.55 (d, J = 8.40 Hz, 2H), 7.44 (d, J = 8.10 Hz, 2H), 7.37 (s, 1H), 7.33-7.28 (m, 1H), 5.15 (s, 2H), 3.81 (s, 3H), 3.57-3.48 (m, 1H), 2.13 (s, 3H), 1.17 (d, J = 6.90 Hz, 6H). | 9-(4-(1,4-dimethyl-1H-pyrazol-3-yl)benzyl)-2-(2-isopropylpyridin-3-yl)-7,9-dihydro-8H-purin-8-one |
| I-48 | m/z: 532.4562 [M + H]⁺ Rt (min): 1.4734 | | 2-(2-(difluoromethoxy)pyridin-3-yl)-7-methyl-9-(4-(1-methyl-4-(trifluoromethyl)-1H-imidazol-2-yl)benzyl)-7,9-dihydro-8H-purin-8-one |
| I-49 | m/z: 549.39 [M + H]⁺ Rt (min): 1.6917 | | 7-methyl-9-(4-(1-methyl-4-(trifluoromethyl)-1H-imidazol-2-yl)benzyl)-2-(2-(trifluoromethoxy)phenyl)-7,9-dihydro-8H-purin-8-one |
| I-50 | m/z: 564.4 [M + H]⁺ Rt (min): 1.5976 | | 7-methyl-9-(4-(1-methyl-4-(trifluoromethyl)-1H-imidazol-2-yl)benzyl)-2-(2-(2,2,2-trifluoroethoxy)pyridin-3-yl)-7,9-dihydro-8H-purin-8-one |
| I-51 | m/z: 520.459 [M + H]⁺ Rt (min): 0.9636 | ¹H NMR (300 MHz, CDCl₃) δ 11.43 (br s, 1H), 8.57 (d, J = 4.7 Hz, 1H), 8.23 (s, 1H), 7.89 (d, J = 7.6 Hz, 1H), 7.62 (d, J = 8.5 Hz, 2H), 7.33-7.23 (m, 3H), 7.17-7.12 (m, 1H), 3.70 (s, 3H), 3.66-3.61 (m, 1H), 3.61-3.51 (m, 1H), 1.75 (br s, 2H), 1.61 (br s, 2H), 1.19 (d, J = 6.4 Hz, 6H) | 2-(2-isopropylpyridin-3-yl)-9-(1-(4-(1-methyl-4-(trifluoromethyl)-1H-imidazol-2-yl)phenyl)cyclopropyl)-7,9-dihydro-8H-purin-8-one |
| I-52 | m/z: 460.3201 [M + H]⁺ | ¹H NMR (400 MHz, DMSO-d₆) δ 11.65 (s, 1H), 8.58-8.57 (m,1H), 8.42 (s, 1H), 7.95-7.93 (m, 1H), | 9-(4-(3-chloro-5-methyl-1H-pyrazol-1-yl)benzyl)-2-(2-isopropylpyridin-3-yl)-7,9- |

TABLE 2-continued

| Cmpd no. | LCMS | ¹H NMR (300 MHz) δ ppm | Chemical Name |
|---|---|---|---|
| | Rt (min): 1.031 | 7.50-7.45 (m, 4H), 7.30-7.27 (m, 1H), 6.35 (s, 1H), 5.10 (s, 2H), 3.64-3.58 (m, 1H), 2.31-2.26 (m, 3H), 1.11 (d, J = 6.80 Hz, 6H). | dihydro-8H-purin-8-one |
| I-53 | m/z: 460.3201 [M + H]⁺ Rt (min): 1.0175 | ¹H NMR (400 MHz, CD₃OD) δ 8.58-8.54 (m, 1H), 8.38 (s, 1H), 8.01-7.97 (m, 1H), 7.63-7.55 (m, 2H), 7.53-7.46 (m, 2H), 7.36-7.31 (m, 1H), 6.32 (s, 1H), 5.22 (s, 2H), 3.60-3.51 (m, 1H), 2.26 (s, 3H), 1.21 (d, J = 6.80 Hz, 6H). | 9-(4-(5-chloro-3-methyl-1H-pyrazol-1-yl)benzyl)-2-(2-isopropylpyridin-3-yl)-7,9-dihydro-8H-purin-8-one |
| I-54 | m/z: 425.3419 [M + H]⁺ Rt (min): 1.1255 | | 2-(2-isopropylpyridin-3-yl)-9-(4-(2-methyl-1H-pyrrol-1-yl)benzyl)-7,9-dihydro-8H-purin-8-one |
| I-55 | m/z: 509.4 [M + H]⁺ Rt (min): 1.4357 | ¹H NMR (400 MHz, DMSO-d₆) δ 8.39 (s, 1H), 7.60-7.50 (m, 4H), 7.48-7.41 (m, 3H), 7.39-7.36 (m, 1H), 7.28-7.22 (m, 1H), 5.27 (s, 2H), 4.86-4.84 (m, 1H), 3.78 (s, 3H), 3.05 (s, 3H), 1.40 (d, J = 6.30 Hz, 3H). | (R)-2-(2-(1-methoxyethyl)phenyl)-9-(4-(1-methyl-4-(trifluoromethyl)-1H-imidazol-2-yl)benzyl)-7,9-dihydro-8H-purin-8-one |
| I-56 | m/z: 509.4 [M + H]⁺ Rt (min): 1.4434 | ¹H NMR (400 MHz, DMSO-d₆) δ 8.39 (s, 1H), 7.60-7.50 (m, 4H), 7.48-7.41 (m, 3H), 7.39-7.36 (m, 1H), 7.28-7.22 (m, 1H), 5.27 (s, 2H), 4.86-4.84 (m, 1H), 3.78 (s, 3H), 3.05 (s, 3H), 1.40 (d, J = 6.30 Hz, 3H). | (S)-2-(2-(1-methoxyethyl)phenyl)-9-(4-(1-methyl-4-(trifluoromethyl)-1H-imidazol-2-yl)benzyl)-7,9-dihydro-8H-purin-8-one |
| I-57 | m/z: 470.3325 [M + H]⁺ Rt (min): 1.2469 | ¹H NMR (400 MHz, DMSO-d₆) δ 11.70 (s, 1H), 8.56-8.53 (m, 1H), 8.45 (s, 1H), 8.33 (d, J = 8.00 Hz, 1H), 7.91 (s, 1H), 7.70 (d, J = 8.40 Hz, 2H), 7.56-7.49 (m, 3H), 5.14 (s, 2H), 3.76 (s, 3H). | 2-(2-fluoropyridin-3-yl)-9-(4-(1-methyl-4-(trifluoromethyl)-1H-imidazol-2-yl)benzyl)-7,9-dihydro-8H-purin-8-one |
| I-58 | m/z: 476.3789 [M + H]⁺ Rt (min): 1.0417 | | 9-(4-(3-(difluoromethyl)-5-methyl-1H-pyrazol-1-yl)benzyl)-2-(2-isopropylpyridin-3-yl)-7,9-dihydro-8H-purin-8-one |
| I-59 | m/z: 430.3479 [M + H]⁺ Rt (min): 0.9717 | ¹H NMR (300 MHz, CD₃OD) δ 8.62-8.53 (m, 1H), 8.39 (s, 1H), 8.16-8.08 (m, 1H), 8.05-7.95 (m, 1H), 7.67 (d, J = 8.70 Hz, 2H), 7.55 (d, J = 8.70 Hz, 2H), 7.41-7.30 (m, 1H), 6.17-6.08 (m, 1H), 5.19 (s, 2H), 3.65-3.49 (m, 1H), 1.22 (d, J = 6.60 Hz, 6H). | 9-(4-(3-fluoro-1H-pyrazol-1-yl)benzyl)-2-(2-isopropylpyridin-3-yl)-7,9-dihydro-8H-purin-8-one |
| I-60 | m/z: 510.3818 [M + H]⁺ Rt (min): 1.1794 | ¹H NMR (300 MHz, DMSO-d₆) δ 8.61-8.59 (m, 1H), 8.44 (s, 1H), 7.98-7.95 (m, 1H), 7.64-7.61 (m, 2H), 7.51-7.48 (m, 2H), 7.33-7.29 (m, 1H), 6.47 (s, 1H), 5.11 (s, 2H), 3.98 (s, 3H), 3.68-3.59 (m, 1H), 1.13 (d, J = 6.60 Hz, 6H). | 2-(2-isopropylpyridin-3-yl)-9-(4-(5-methoxy-3-(trifluoromethyl)-1H-pyrazol-1-yl)benzyl)-7,9-dihydro-8H-purin-8-one |
| I-61 | m/z: 494.3882 [M + H]⁺ Rt (min): 0.8692 | | 2-(2-ethylpyridin-3-yl)-7-methyl-9-(4-(1-methyl-4-(trifluoromethyl)-1H-imidazol-2-yl)benzyl)-7,9-dihydro-8H-purin-8-one |
| I-62 | m/z: 480.3448 [M + H]⁺ Rt (min): 0.8018 | | 7-methyl-9-(4-(1-methyl-4-(trifluoromethyl)-1H-imidazol-2-yl)benzyl)-2-(2-methylpyridin-3-yl)-7,9-dihydro-8H-purin-8-one |
| I-63 | m/z: 507.4219 [M + H]⁺ Rt (min): 1.692 | | 2-(2-isopropylphenyl)-7-methyl-9-(4-(1-methyl-4-(trifluoromethyl)-1H-imidazol-2-yl)benzyl)-7,9-dihydro-8H-purin-8-one |
| I-64 | m/z: 502.3257 [M + H]⁺ Rt (min): 1.2467 | | 2-(2-(difluoromethyl)pyridin-3-yl)-9-(4-(1-methyl-4-(trifluoromethyl)-1H-imidazol-2-yl)benzyl)-7,9-dihydro-8H-purin-8-one |

TABLE 2-continued

| Cmpd no. | LCMS | ¹H NMR (300 MHz) δ ppm | Chemical Name |
|---|---|---|---|
| I-65 | m/z: 525.4348 [M + H]⁺ Rt (min): 1.7325 | | 2-(3-fluoro-2-isopropylphenyl)-7-methyl-9-(4-(1-methyl-4-(trifluoromethyl)-1H-imidazol-2-yl)benzyl)-7,9-dihydro-8H-purin-8-one |
| I-66 | m/z: 498.3541 [M + H]⁺ Rt (min): 1.4357 | | 2-(6-fluoro-2-methylpyridin-3-yl)-7-methyl-9-(4-(1-methyl-4-(trifluoromethyl)-1H-imidazol-2-yl)benzyl)-7,9-dihydro-8H-purin-8-one |
| I-67 | m/z: 512.3322 [M + H]⁺ Rt (min): 1.4762 | ¹H NMR (300 MHz, CD₃OD) δ 8.50-8.49 (m, 1H), 8.42 (s, 1H), 7.85-7.81 (m, 1H), 7.70-7.60 (m, 5H), 5.26 (s, 2H), 3.78 (s, 3H), 3.73-3.64 (m, 1H), 1.23 (d, J = 6.60 Hz, 6H). | 2-(5-fluoro-2-isopropylpyridin-3-yl)-9-(4-(1-methyl-4-(trifluoromethyl)-1H-imidazol-2-yl)benzyl)-7,9-dihydro-8H-purin-8-one |
| I-68 | m/z: 481.4 [M + H]⁺ Rt (min): 0.8422 | ¹H NMR (300 MHz, DMSO-d₆) δ 11.65 (br s, 1H), 8.61-8.59 (m, 1H), 8.44 (s, 1H), 7.98-7.95 (m, 1H), 7.43 (s, 4H), 7.33-7.29 (m, 1H), 5.57 (s, 1H), 5.08 (s, 2H), 3.78-3.73 (m, 4H), 3.70-3.54 (m, 1H), 2.28-2.21 (m, 5H), 1.21-1.16 (m, 6H). | 9-(4-(3-(azetidin-1-yl)-5-methyl-1H-pyrazol-1-yl)benzyl)-2-(2-isopropylpyridin-3-yl)-7,9-dihydro-8H-purin-8-one |
| I-69 | m/z: 526.3755 [M + H]⁺ Rt (min): 1.5976 | ¹H NMR (300 MHz, CD₃OD) δ 8.54 (s, 1H), 8.50-8.49 (m, 1H), 7.86-7.81 (m, 1H), 7.70-7.60 (m, 5H), 5.28 (s, 2H), 3.77 (s, 3H), 3.71-3.66 (m, 1H), 3.57 (s, 3H), 1.22 (d, J = 6.60 Hz, 6H). | 2-(5-fluoro-2-isopropylpyridin-3-yl)-7-methyl-9-(4-(1-methyl-4-(trifluoromethyl)-1H-imidazol-2-yl)benzyl)-7,9-dihydro-8H-purin-8-one |
| I-70 | m/z: 505.4407 [M + H]⁺ Rt (min): 1.6111 | | 2-(2-cyclopropylphenyl)-7-methyl-9-(4-(1-methyl-4-(trifluoromethyl)-1H-imidazol-2-yl)benzyl)-7,9-dihydro-8H-purin-8-one |
| I-71 | m/z: 506.447 [M + H]⁺ Rt (min): 1.0983 | ¹H NMR (300 MHz, CD₃OD) δ 8.53 (s, 1H), 8.46-8.44 (m, 1H), 8.03-8.00 (m, 1H), 7.70 (s, 1H), 7.67-7.61 (m, 4H), 7.28-7.24 (m, 1H), 5.29 (s, 2H), 3.77 (s, 3H), 3.57 (s, 3H), 2.68-2.59 (m, 1H), 1.08-1.03 (m, 2H), 0.88-0.84 (m, 2H). | 2-(2-cyclopropylpyridin-3-yl)-7-methyl-9-(4-(1-methyl-4-(trifluoromethyl)-1H-imidazol-2-yl)benzyl)-7,9-dihydro-8H-purin-8-one |
| I-72 | m/z: 516.3631 [M + H]⁺ Rt (min): 1.3359 | | 2-(2-(difluoromethyl)pyridin-3-yl)-7-methyl-9-(4-(1-methyl-4-(trifluoromethyl)-1H-imidazol-2-yl)benzyl)-7,9-dihydro-8H-purin-8-one |
| I-73 | m/z: 496.4 [M + H]⁺ Rt (min): 1.3412 | | 2-(6-methoxy-2-methylpyridin-3-yl)-9-(4-(1-methyl-4-(trifluoromethyl)-1H-imidazol-2-yl)benzyl)-7,9-dihydro-8H-purin-8-one |
| I-74 | m/z: 528.5 [M + H]⁺ Rt (min): 1.6245 | | 2-(2-fluoro-6-isopropoxypyridin-3-yl)-9-(4-(1-methyl-4-(trifluoromethyl)-1H-imidazol-2-yl)benzyl)-7,9-dihydro-8H-purin-8-one |
| I-75 | m/z: 500.4 [M + H]⁺ Rt (min): 1.4117 | | 2-(2-fluoro-6-methoxypyridin-3-yl)-9-(4-(1-methyl-4-(trifluoromethyl)-1H-imidazol-2-yl)benzyl)-7,9-dihydro-8H-purin-8-one |
| I-76 | m/z: 520.394 [M + H]⁺ Rt (min): 1.07 | ¹H NMR (400 MHz, CD₃OD) δ 8.59-8.52 (m, 1H), 8.39 (s, 1H), 8.03-7.95 (m, 1H), 7.84-7.76 (m, 2H), 7.74-7.68 (m, 1H), 7.61-7.54 (m, 2H), 7.37-7.29 (m, 1H), 5.23 (s, 2H), 3.68-3.53 (m, 2H), 1.23 (d, J = 6.80 Hz, 6H), 1.05-0.93 (m, 2H), 0.89-0.80 (m, 2H). | 9-(4-(1-cyclopropyl-4-(trifluoromethyl)-1H-imidazol-2-yl)benzyl)-2-(2-isopropylpyridin-3-yl)-7,9-dihydro-8H-purin-8-one |
| I-77 | m/z: 565.5124 [M + H]⁺ | ¹H NMR (400 MHz, DMSO-d₆) δ 9.04 (br s, 1H), 8.57-8.55 (m, 1H), 8.42 (s, 1H), 7.94-7.92 (m, | 2-(2-isopropylpyridin-3-yl)-9-(4-(5-morpholino-3-(trifluoromethyl)-1H-pyrazol- |

TABLE 2-continued

| Cmpd no. | LCMS | ¹H NMR (300 MHz) δ ppm | Chemical Name |
|---|---|---|---|
| | Rt (min): 1.166 | 1H), 7.76-7.68 (m, 2H), 7.52-7.45 (m, 2H), 7.28-7.26 (m, 1H), 6.50 (s, 1H), 5.10 (s, 2H), 3.68-3.52 (m, 5H), 2.87-2.76 (m, 4H), 1.11 (d, J = 6.80 Hz, 6H). | 1-yl)benzyl)-7,9-dihydro-8H-purin-8-one |
| I-78 | m/z: 456.3 [M + H]⁺ Rt (min): 0.8827 | ¹H NMR (300 MHz, DMSO-d₆) δ 8.61-8.59 (m, 1H), 8.42 (s, 1H), 7.98-7.95 (m, 1H), 7.59 (d, J = 8.40 Hz, 2H), 7.41 (d, J = 8.40 Hz, 2H), 7.33-7.29 (m, 1H), 5.71 (s, 1H), 5.06 (s, 2H), 3.88 (s, 3H), 3.67-3.36 (m, 1H), 2.15 (s, 3H), 1.14 (d, J = 6.60 Hz, 6H). | 2-(2-isopropylpyridin-3-yl)-9-(4-(3-methoxy-5-methyl-1H-pyrazol-1-yl)benzyl)-7,9-dihydro-8H-purin-8-one |
| I-79 | m/z: 508.3033 [M + H]⁺ Rt (min): 0.9906 | ¹H NMR (300 MHz, CD₃OD) δ 8.54-8.52 (m, 1H), 8.34 (s, 1H), 7.99-7.89 (m, 1H), 7.69-7.55 (m, 5H), 7.36-7.25 (m, 1H), 5.93-5.79 (m, 1H), 3.72 (s, 3H), 3.66-3.51 (m, 1H), 2.08 (d, J = 7.50 Hz, 3H), 1.25-1.12 (m, 6H). | (R)-2-(2-isopropylpyridin-3-yl)-9-(1-(4-(1-methyl-4-(trifluoromethyl)-1H-imidazol-2-yl)phenyl)ethyl)-7,9-dihydro-8H-purin-8-one |
| I-80 | m/z: 508.3517 [M + H]⁺ Rt (min): 0.9906 | ¹H NMR (300 MHz, CD₃OD) δ 8.62-8.53 (m, 1H), 8.39 (s, 1H), 8.04-7.94 (m, 1H), 7.74-7.61 (m, 5H), 7.41-7.30 (m, 1H), 5.99-5.85 (m, 1H), 3.77 (s, 3H), 3.72-3.56 (m, 1H), 2.13 (d, J = 7.50 Hz, 3H), 1.30-1.17 (m, 6H). | (S)-2-(2-isopropylpyridin-3-yl)-9-(1-(4-(1-methyl-4-(trifluoromethyl)-1H-imidazol-2-yl)phenyl)ethyl)-7,9-dihydro-8H-purin-8-one |
| I-81 | m/z: 497.1921 [M + H]⁺ Rt (min): 0.9096 | ¹H NMR (400 MHz, CD₃OD) δ 8.57-8.54 (m, 1H), 8.38 (s, 1H), 8.01-7.97 (m, 1H), 7.68-7.57 (m, 5H), 7.35-7.32 (m, 1H), 5.23 (s, 2H), 3.61-3.54 (m, 1H), 1.23 (d, J = 6.80 Hz, 6H). | 2-(2-isopropylpyridin-3-yl)-9-(4-(1-(methyl-d3)-4-(trifluoromethyl)-1H-imidazol-2-yl)benzyl)-7,9-dihydro-8H-purin-8-one |
| I-82 | m/z: 530.2242 [M + H]⁺ Rt (min): 0.977 | ¹H NMR (400 MHz, CD₃OD) δ 8.57-8.55 (m, 1H), 8.40 (s, 1H), 8.03-7.98 (m, 1H), 7.82 (d, J = 4.80 Hz, 1H), 7.36-7.26 (m, 3H), 5.24 (s, 2H), 3.64-3.52 (m, 4H), 1.24 (d, J = 6.80 Hz, 6H). | 9-(3,5-difluoro-4-(1-methyl-4-(trifluoromethyl)-1H-imidazol-2-yl)benzyl)-2-(2-isopropylpyridin-3-yl)-7,9-dihydro-8H-purin-8-one |
| I-83 | m/z: 512.1745 [M + H]⁺ Rt (min): 0.9475 | ¹H NMR (300 MHz, DMSO-d6) δ 11.65 (s, 1H), 8.60-8.57 (m, 1H), 8.44 (s, 1H), 7.99-7.93 (m, 2H), 7.58 (t, J = 7.80 Hz, 1H), 7.41-7.37 (m, 1H), 7.32-7.27 (m, 2H), 5.15 (s, 2H), 3.65-3.57 (m, 4H), 1.13 (d, J = 6.60 Hz, 6H). | 9-(3-fluoro-4-(1-methyl-4-(trifluoromethyl)-1H-imidazol-2-yl)benzyl)-2-(2-isopropylpyridin-3-yl)-7,9-dihydro-8H-purin-8-one |
| I-84 | m/z: 512.2395 [M + H]⁺ Rt (min): 0.9636 | ¹H NMR (400 MHz, CD₃OD) δ 8.58-8.55 (m, 1H), 8.42 (s, 1H), 8.02-7.99 (m, 1H), 7.72-7.70 (m, 1H), 7.54-7.46 (m, 3H), 7.36-7.32 (m, 1H), 5.30 (s, 2H), 3.80 (s, 3H), 3.63-3.55 (m, 1H), 1.21 (d, J = 6.80 Hz, 6H). | 9-(2-fluoro-4-(1-methyl-4-(trifluoromethyl)-1H-imidazol-2-yl)benzyl)-2-(2-isopropylpyridin-3-yl)-7,9-dihydro-8H-purin-8-one |
| I-85 | m/z: 530.246 [M + H]⁺ Rt (min): 0.99 | ¹H NMR (300 MHz, DMSO-d₆) δ 8.54-8.50 (m, 1H), 8.12-8.10 (m, 1H), 7.98 (s, 1H), 7.89-7.86 (m, 1H), 7.45-7.41 (m, 2H), 7.25-7.21 (m, 1H), 5.09 (s, 2H), 3.89-3.75 (m, 1H), 3.80 (s, 3H), 1.12 (d, J = 6.60 Hz, 6H). | 9-(2,6-difluoro-4-(1-methyl-4-(trifluoromethyl)-1H-imidazol-2-yl)benzyl)-2-(2-isopropylpyridin-3-yl)-7,9-dihydro-8H-purin-8-one |
| I-86 | m/z: 513.2146 [M + H]⁺ Rt (min): 1.1783 | | 9-(4-(1-methyl-4-(trifluoromethyl)-1H-imidazol-2-yl)benzyl)-2-(2-(methylsulfinyl)phenyl)-7,9-dihydro-8H-purin-8-one |
| I-87 | m/z: 476.2 [M + H]⁺ Rt (min): 0.7208 | | 9-(4-(4-(difluoromethyl)-1-methyl-1H-imidazol-2-yl)benzyl)-2-(2-isopropylpyridin-3-yl)-7,9-dihydro-8H-purin-8-one |
| I-88 | m/z: 454.125 [M + H]⁺ Rt (min): 1.4342 | | 2-(2-(difluoromethoxy)pyridin-3-yl)-9-(4-(3-fluoro-1H-pyrazol-1-yl)benzyl)-7,9-dihydro-8H-purin-8-one |
| I-89 | m/z: 453.15 | | 2-(2-(difluoromethoxy)phenyl)-9- |

TABLE 2-continued

| Cmpd no. | LCMS | ¹H NMR (300 MHz) δ ppm | Chemical Name |
|---|---|---|---|
| | [M + H]⁺ Rt (min): 1.5166 | | (4-(3-fluoro-1H-pyrazol-1-yl)benzyl)-7,9-dihydro-8H-purin-8-one |
| I-90 | m/z: 494.4512 [M + H]⁺ Rt (min): 0.8287 | ¹H NMR (300 MHz, CD₃OD) δ 8.31 (s, 1H), 7.65 (s,5H), 7.51-7.30 (m, 2H), 7.17-7.07 (m, 1H), 7.02-6.96 (m, 1H), 5.23 (s, 2H), 3.76 (s, 3H), 2.57 (s, 6H). | 2-(2-(dimethylamino)phenyl)-9-(4-(1-methyl-4-(trifluoromethyl)-1H-imidazol-2-yl)benzyl)-7,9-dihydro-8H-purin-8-one |
| I-91 | m/z: 425.1473 [M + H]⁺ Rt (min): 1.51 | ¹H NMR (400 MHz, CD₃OD) δ 8.29 (s, 1H), 8.19 (s, 1H), 7.71-7.68 (m, 3H), 7.54-7.51 (m, 2H), 7.23-7.20 (m, 1H), 7.16-7.09 (m, 2H), 6.51-6.50 (m, 1H), 5.16 (s, 2H), 3.19-3.11 (m, 1H), 2.46 (s, 3H), 1.11-1.09 (m, 6H). | 9-(4-(1H-pyrazol-1-yl)benzyl)-2-(2-isopropyl-3-methylphenyl)-7,9-dihydro-8H-purin-8-one |
| I-92 | m/z: 441.1345 [M + H]⁺ Rt (min): 1.5 | | 9-(4-(1H-pyrazol-1-yl)benzyl)-2-(2-isopropyl-3-methoxyphenyl)-7,9-dihydro-8H-purin-8-one |
| I-93 | m/z: 445.0988 [M + H]⁺ Rt (min): 1.66 | ¹H NMR (300 MHz, DMSO-d₆) δ 11.63 (s, 1H), 8.44 (d, J = 2.4 Hz, 1H), 8.39 (s, 1H), 7.80-7.77 (m, 2H), 7.72 (s, 1H), 7.53-7.41 (m, 3H), 7.33-7.24 (m, 2H), 6.53-6.52 (m, 1H), 5.06 (s, 2H), 3.42-3.32 (m, 1H), 1.30-1.15 (m, 6H). | 9-(4-(1H-pyrazol-1-yl)benzyl)-2-(3-chloro-2-isopropylphenyl)-7,9-dihydro-8H-purin-8-one |
| I-94 | m/z: 409.3484 [M + H]⁺ Rt (min): 1.4233 | | 9-(4-(1H-pyrazol-1-yl)benzyl)-2-(2-cyclopropylphenyl)-7,9-dihydro-8H-purin-8-one |
| I-95 | m/z: 443.286 [M + H]⁺ Rt (min): 1.6417 | | 9-(4-(1H-pyrazol-1-yl)benzyl)-2-(5-chloro-2-cyclopropylphenyl)-7,9-dihydro-8H-purin-8-one |
| I-96 | m/z: 429.308 [M + H]⁺ Rt (min): 1.4897 | ¹H NMR (400 MHz, CD₃OD) δ 8.33 (s, 1H), 8.19 (d, J = 2.8 Hz, 1H), 7.73-7.65 (m, 3H), 7.59-7.50 (m, 2H), 7.43 (m, 1H), 7.25-7.22 (m, 1H), 7.02-6.99 (m, 1H), 6.50-6.49 (m, 1H), 5.17 (s, 2H), 2.68 (m, 1H), 1.09 (d, J = 6.8 Hz, 6H). | 9-(4-(1H-pyrazol-1-yl)benzyl)-2-(2-fluoro-6-isopropylphenyl)-7,9-dihydro-8H-purin-8-one |
| I-97 | m/z: 477.3542 [M + H]⁺ Rt (min): 1.6867 | | 9-(4-(1H-pyrazol-1-yl)benzyl)-2-(2-cyclopropyl-5-(trifluoromethyl)phenyl)-7,9-dihydro-8H-purin-8-one |
| I-98 | m/z: 491.4 [M + H]⁺ Rt (min): 1.485 | ¹H NMR (400 MHz, CD₃OD) δ 8.36 (s, 1H), 7.73-7.51 (m, 6H), 7.41-7.32 (m, 1H), 7.31-7.23 (m, 1H), 7.15-7.08 (m, 1H), 5.25 (s, 2H), 3.77 (s, 3H), 2.33-2.21 (m, 1H), 0.71-0.61 (m, 2H), 0.59-0.47 (m, 2H). | 2-(2-cyclopropylphenyl)-9-(4-(1-methyl-4-(trifluoromethyl)-1H-imidazol-2-yl)benzyl)-7,9-dihydro-8H-purin-8-one |
| I-99 | m/z: 495.4426 [M + H]⁺ Rt (min): 1.63 | ¹H NMR (300 MHz, CDCl₃) δ 9.31 (br s, 1H), 8.38 (s, 1H), 7.67-7.62 (m, 3H), 7.39-7.23 (m, 4H), 7.09-7.06 (m, 1H), 6.80 (s, 1H), 5.22 (s, 2H), 4.24-4.17 (m, 2H), 2.52-2.44 (m, 1H), 2.34 (s, 3H), 1.24-1.20 (m, 3H), 0.82-0.75 (m, 2H), 0.69-0.57 (m, 2H). | ethyl 1-(4-((2-(2-cyclopropylphenyl)-8-oxo-7,8-dihydro-9H-purin-9-yl)methyl)phenyl)-3-methyl-1H-pyrazole-5-carboxylate |
| I-100 | m/z: 531.5 [M + H]⁺ Rt (min): 1.7046 | ¹H NMR (300 MHz, CDCl₃) δ 8.39 (s, 1H), 7.61-7.47 (m, 4H), 7.32-7.19 (m, 4H), 7.00 (s, 1H), 5.10 (s, 2H), 3.67 (s, 3H), 2.94 (td, J = 3.3, 6.9 Hz, 1H), 2.47-2.33 (m, 1H), 1.11 (br d, J = 6.4 Hz, 2H), 1.06-0.97 (m, 2H), 0.72-0.61 (m, 2H), 0.57-0.47 (m, 2H) | 7-cyclopropyl-2-(2-cyclopropylphenyl)-9-(4-(1-methyl-4-(trifluoromethyl)-1H-imidazol-2-yl)benzyl)-7,9-dihydro-8H-purin-8-one |
| I-101 | m/z: 532.4481 [M + H]⁺ | ¹H NMR (300 MHz, CDCl₃) δ 8.52 (dd, J = 1.8, 4.7 Hz, 1H), 8.48 (s, 1H), 7.98 (dd, J = 1.8, | 7-cyclopropyl-2-(2-cyclopropylpyridin-3-yl)-9-(4-(1-methyl-4-(trifluoromethyl)- |

TABLE 2-continued

| Cmpd no. | LCMS | ¹H NMR (300 MHz) δ ppm | Chemical Name |
|---|---|---|---|
| | Rt (min): 1.2469 | 4.7 Hz, 1H), 7.62 (m, 4H), 7.31 (s, 1H), 7.19-7.13 (m, 1H), 5.19 (s, 2H), 3.75 (s, 3H), 3.05-2.98 (m, 1H), 2.82-2.72 (m, 1H), 1.23-1.15 (m, 4H), 1.09 (br d, J = 2.1 Hz, 2H), 0.95-0.87 (m, 2H) | 1H-imidazol-2-yl)benzyl)-7,9-dihydro-8H-purin-8-one |
| I-102 | m/z: 452.2523 [M + H]⁺ Rt (min): 0.99 | ¹H NMR (400 MHz, CD₃OD, ppm) δ 8.34(s, 1H), 7.55(d, J = 8.00 Hz, 4H), 7.48-7.41(m, 4H), 7.30-7.26 (m, 1H), 5.19(s, 2H), 4.29(s, 2H), 4.07(s, 2H), 3.33-3.27(m, 1H), 1.16-1.12(m, 6H). | 9-(4-(5,6-dihydropyrrolo[3,4-c]pyrazol-1(4H)-yl)benzyl)-2-(2-isopropylphenyl)-7,9-dihydro-8H-purin-8-one |
| I-103 | m/z: 470.0799 [M + H]⁺ Rt (min): 1.03 | ¹H NMR (300 MHz, DMSO-d₆) δ 8.40 (s, 1H), 7.56-7.53 (m, 2H), 7.44-7.41 (m, 3H), 7.30-7.16 (m, 3H), 5.06 (s, 2H), 4.20 (s, 2H), 3.85 (s, 2H), 3.32-3.24 (m, 2H), 1.21-1.20 (m, 6H). | 9-(4-(5,6-dihydropyrrolo[3,4-c]pyrazol-1(4H)-yl)benzyl)-2-(3-fluoro-2-isopropylphenyl)-7,9-dihydro-8H-purin-8-one |
| I-104 | m/z: 470.0811 [M + H]⁺ Rt (min): 1.03 | ¹H NMR (300 MHz, DMSO-d₆) δ 8.40 (s, 1H), 8.28 (s, 1H), 7.74-7.71 (m, 2H), 7.42-7.40 (m, 2H), 7.30-7.17 (m, 3H), 5.04-5.00 (m, 2H), 3.89-3.88 (m, 4H), 3.32-3.26 (m, 2H), 1.29-1.20 (m, 6H). | 9-(4-(5,6-dihydropyrrolo[3,4-c]pyrazol-2(4H)-yl)benzyl)-2-(3-fluoro-2-isopropylphenyl)-7,9-dihydro-8H-purin-8-one |

Example 33: 2-(2-Isopropylpyridin-3-yl)-7-methyl-9-(4-(1-methyl-4-(trifluoromethyl)-1H-imidazol-2-yl)benzyl)-7,9-dihydro-8H-purin-8-one (I-105)

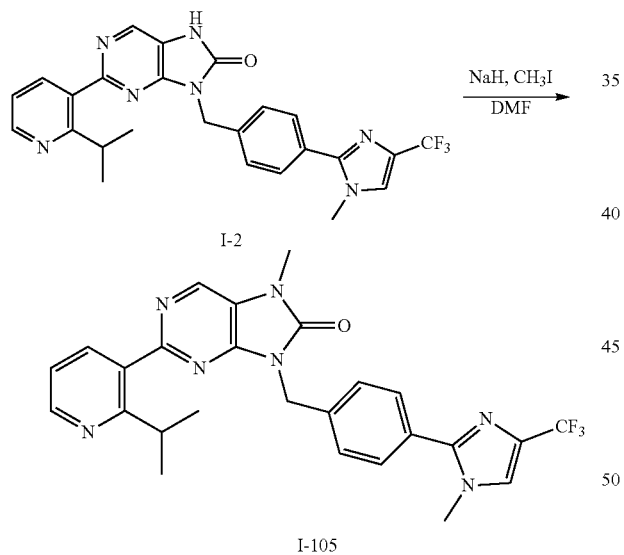

A mixture of 2-(2-isopropylpyridin-3-yl)-9-(4-(1-methyl-4-(trifluoromethyl)-1H-imidazol-2-yl)benzyl)-7,9-dihydro-8H-purin-8-one (I-2) (100 mg, 0.20 mmol) and DMF (1 mL) was cooled to 0° C. and sodium hydride (60% dispersion in mineral oil, 10.5 mg, 0.26 mmol) was added portionwise at 0° C. After stirring 0.5 h at 0° C., iodomethane (43.2 mg, 0.30 mmol) was added and the resulting mixture was stirred for 5 h at ambient temperature. Water (2 mL) was added and the mixture was extracted with EtOAc (3×2 mL). The organic layers were combined, dried over anhydrous sodium sulfate, filtered and concentrated under vacuum. The residue was purified by reverse phase prep-HPLC to afford 34.7 mg (34%) of 2-(2-isopropylpyridin-3-yl)-7-methyl-9-(4-(1-methyl-4-(trifluoromethyl)-1H-imidazol-2-yl)benzyl)-7,9-dihydro-8H-purin-8-one (I-105) as a white solid.

Example 34. 9-(4-(1-(2-Hydroxyethyl)-4-(trifluoromethyl)-1H-imidazol-2-yl)benzyl)-2-(2-isopropylphenyl)-7-methyl-7,9-dihydro-8H-purin-8-one (I-106)

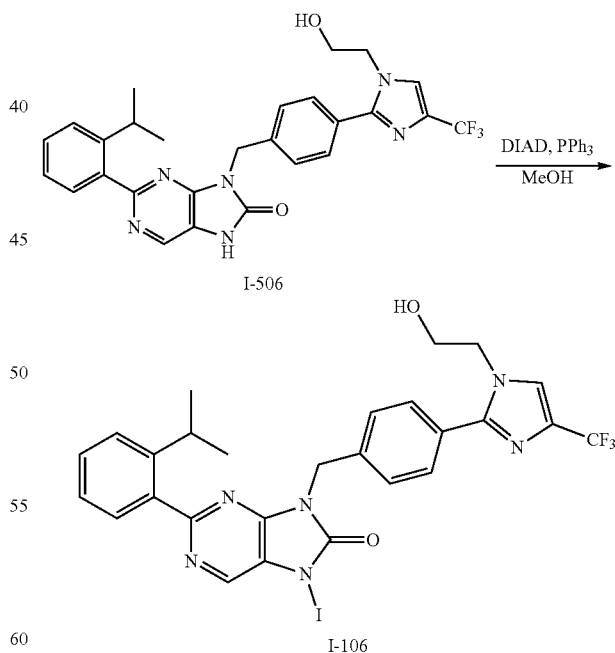

Under nitrogen atmosphere at 0° C., a mixture of 9-(4-(1-(2-hydroxyethyl)-4-(trifluoromethyl)-1H-imidazol-2-yl)benzyl)-2-(2-isopropylphenyl)-7,9-dihydro-8H-purin-8-one (I-506) (140 mg, 0.27 mmol), tetrahydrofuran (3 mL), triphenylphosphine (127 mg, 0.48 mmol) and methanol (26 mg, 0.82 mmol) was treated by dropwise addition of diisopropyl azodicarboxylate (DIAD, 109 mg, 0.84 mmol). The resulting solution was heated at 50° C. for 16 h, cooled to room temperature and concentrated under vacuum. The residue was purified by silica gel chromatography (eluting with 1:1 EtOAc/PE), then purified by prep-HPLC to afford 24.4 mg (17%) of 9-(4-(1-(2-hydroxyethyl)-4-(trifluoromethyl)-1H-imidazol-2-yl)benzyl)-2-(2-isopropylphenyl)-7-methyl-7,9-dihydro-8H-purin-8-one (I-106) as a white solid.

Table 3 (General Procedure B). The compounds listed in Table 3 were synthesized according to either Example 33 or Example 34 using the appropriate commercially-available reagents and/or Intermediates described herein. Enantiomers, when generated, were separated by chiral HPLC and absolute stereochemistries were arbitrarily assigned.

TABLE 3

| Cmpd no. | LCMS | $^1$H NMR (300 MHz) δ ppm | Chemical Name |
|---|---|---|---|
| I-105 | m/z: 508.3043 [M + H]$^+$ Rt (min): 1.0175 | $^1$H NMR (300 MHz, CD$_3$OD) δ 8.60-8.58 (m, 1H), 8.53 (s, 1H), 8.07-8.04 (m, 1H), 7.70-7.59 (m, 5H), 7.41-7.37 (m, 1H), 5.28 (s, 2H), 3.77 (s, 3H), 3.68-3.58 (m, 1H), 3.57 (s, 3H), 1.26 (d, J = 6.60 Hz, 6H). | 2-(2-isopropylpyridin-3-yl)-7-methyl-9-(4-(1-methyl-4-(trifluoromethyl)-1H-imidazol-2-yl)benzyl)-7,9-dihydro-8H-purin-8-one |
| I-106 | m/z: 537.4 [M + H]$^+$ Rt (min): 1.5166 | $^1$H NMR (400 MHz, DMSO-d$_6$) δ 8.61 (s, 1H), 7.97 (s, 1H), 7.71-7.64 (m, 2H), 7.55-7.39 (m, 5H), 7.31-7.22 (m, 1H), 5.15 (s, 2H), 5.12-5.04 (m, 1H), 4.06 (t, J = 5.20 Hz, 2H), 3.68 (t, J = 5.20 Hz, 2H), 3.46 (s, 3H), 3.451-3.27 (m, 1H), 1.10 (d, J = 6.80 Hz, 6H). | 9-(4-(1-(2-hydroxyethyl)-4-(trifluoromethyl)-1H-imidazol-2-yl)benzyl)-2-(2-isopropylphenyl)-7-methyl-7,9-dihydro-8H-purin-8-one |
| I-107 | m/z: 482.2349 [M + H]$^+$ Rt (min): 1.23 | $^1$H NMR (400 MHz, CDCl$_3$) δ 8.40 (s, 1H), 7.88 (s, 1H), 7.70 (s, 1H), 7.66-7.58 (m, 5H), 7.46-7.39 (m, 2H), 7.30-7.26 (m, 1H), 6.44 (s, 1H), 5.17 (s, 2H), 4.08-4.05 (m, 2H), 3.56-3.49 (m, 1H), 2.76-2.73 (m, 2H), 2.36 (s, 6H), 1.24-1.23 (m, 6H). | 9-(4-(1H-pyrazol-1-yl)benzyl)-7-(2-(dimethylamino)ethyl)-2-(2-isopropylphenyl)-7,9-dihydro-8H-purin-8-one |
| I-108 | m/z: 534.5019 [M + H]$^+$ Rt (min): 1.0708 | $^1$H NMR (300 MHz, CDCl$_3$) δ 8.64-8.57 (m, 1H), 8.23 (s, 1H), 7.95 (br d, J = 7.3 Hz, 1H), 7.53-7.43 (m, 4H), 7.23-7.17 (m, 2H), 3.73-3.66 (m, 1H), 3.64 (s, 3H), 3.42 (s, 3H), 1.68-1.54 (m, 4H), 1.26 (d, J = 6.7 Hz, 6H) | 2-(2-isopropylpyridin-3-yl)-7-methyl-9-(1-(4-(1-methyl-4-(trifluoromethyl)-1H-imidazol-2-yl)phenyl)cyclopropyl)-7,9-dihydro-8H-purin-8-one |
| I-109 | m/z: 495.4 [M + H]$^+$ Rt (min): 0.9096 | $^1$H NMR (300 MHz, CD$_3$OD) δ 8.57-8.55 (m, 1H), 8.49 (s, 1H), 8.01-7.98 (m, 1H), 7.53-7.52 (m, 2H), 7.39-7.36 (m, 3H), 5.58 (s, 1H), 5.22 (s, 2H), 3.85 (t, J = 7.20 Hz, 4H), 3.56-3.54 (m, 4H), 2.37-2.28(m, 2H), 2.20 (s, 3H), 1.22 (d, J = 6.90 Hz, 6H). | 9-(4-(3-(azetidin-1-yl)-5-methyl-1H-pyrazol-1-yl)benzyl)-2-(2-isopropylpyridin-3-yl)-7-methyl-7,9-dihydro-8H-purin-8-one |
| I-110 | m/z: 549.4547 [M + H]$^+$ Rt (min): 1.638 | $^1$H NMR (400 MHz, CD$_3$OD) δ 8.46 (s, 1H), 8.28 (d, J = 1.20 Hz, 1H), 7.63-7.56 (m, 2H), 7.50-7.37 (m, 5H), 7.30-7.21 (m, 1H), 5.55-5.43 (m, 1H), 5.24 (s, 2H), 4.99-4.90 (m, 2H), 4.86-4.77 (m, 2H), 3.54 (s, 3H), 3.36-3.32 (m, 1H), 1.17 (d, J = 6.80 Hz, 6H). | 2-(2-isopropylphenyl)-7-methyl-9-(4-(1-(oxetan-3-yl)-4-(trifluoromethyl)-1H-imidazol-2-yl)benzyl)-7,9-dihydro-8H-purin-8-one |
| I-111 | m/z: 459.4 [M + H]$^+$ Rt (min): 1.6516 | $^1$H NMR (400 MHz, DMSO-d$_6$) δ 8.54 (s, 1H), 7.55-7.48 (m, 1H), 7.48-7.43 (m, 1H), 7.43-7.35 (m, 1H), 7.30-7.21 (m, 1H), 5.70 (s, 1H), 3.98-3.88 (m, 1H), 3.75 (d, J = 7.20 Hz, 2H), 3.56-3.44 (m, 1H), 3.41 (s, 3H), 2.15 (s, 3H), 2.03 (s, 3H), 1.92-1.83 (m, 1H), 1.78-1.66 (m, 6H), 1.31-1.05 (m, 8H). | 9-(((1s,4s)-4-(3,5-dimethyl-1H-pyrazol-1-yl)cyclohexyl)methyl)-2-(2-isopropylphenyl)-7-methyl-7,9-dihydro-8H-purin-8-one |
| I-112 | m/z: 459.4 [M + H]$^+$ Rt (min): 1.719 | $^1$H NMR (400 MHz, DMSO-d$_6$) δ 8.54 (s, 1H), 7.55-7.47 (m, 1H), 7.47-7.34 (m, 2H), 7.22-7.20 (m, 1H), 5.73-5.72 (m, 1H), 4.01-3.93 (m, 3H), 3.54-3.46 (m, 1H), 3.41 (s, 3H), 2.31-2.29 (m, 3H), 2.15 (s, 3H), 2.12-1.98 (m, 5H), 1.72-1.51 (m, 6H), 1.15 (d, J = 6.80 Hz, 6H). | 9-(((1r,4r)-4-(3,5-dimethyl-1H-pyrazol-1-yl)cyclohexyl)methyl)-2-(2-isopropylphenyl)-7-methyl-7,9-dihydro-8H-purin-8-one |
| I-113 | m/z: 508.3694 [M + H]$^+$ | $^1$H NMR (300 MHz, CD$_3$OD) δ 8.60-8.58 (m, 1H), 8.53 (2, 1H), 8.04-8.01 (m, 1H), 7.66-7.63 (m, 2H), 7.52-7.49 | 2-(2-isopropylpyridin-3-yl)-7-methyl-9-(4-(5-methyl-3- |

TABLE 3-continued

| Cmpd no. | LCMS | ¹H NMR (300 MHz) δ ppm | Chemical Name |
|---|---|---|---|
|  | Rt (min): 1.2874 | (m, 2H), 6.59 (s, 1H), 5.29 (s, 2H), 3.62-3.57 (m, 4H), 2.34 (s, 3H), 1.24 (d, J = 6.40 Hz, 6H). | (trifluoromethyl)-1H-pyrazol-1-yl)benzyl)-7,9-dihydro-8H-purin-8-one |
| I-114 | m/z: 534.4369 [M + H]⁺ Rt (min): 1.1783 | ¹H NMR (400 MHz, CD₃OD) δ 8.59-8.47 (m, 2H), 8.03-7.95 (m, 1H), 7.83-7.75 (m, 2H), 7.74-7.68 (m, 1H), 7.64-7.54 (m, 2H), 7.38-7.29 (m, 1H), 5.25 (s, 2H), 3.67-3.52 (m, 5H), 1.22 (d, J = 6.80 Hz, 6H), 1.04-0.94 (m, 2H), 0.88-0.79 (m, 2H). | 9-(4-(1-cyclopropyl-4-(trifluoromethyl)-1H-imidazol-2-yl)benzyl)-2-(2-isopropylpyridin-3-yl)-7-methyl-7,9-dihydro-8H-purin-8-one |
| I-115 | m/z: 522.4608 [M + H]⁺ Rt (min): 1.097 | ¹H NMR (400 MHz, CD₃OD) δ 8.59-8.57 (m, 1H), 8.52 (s, 1H), 8.01-7.98 (m, 1H), 7.70-7.63 (m, 5H), 7.37-7.34 (m, 1H), 5.97-5.91 (m, 1H), 3.77 (s, 3H), 3.68-3.58 (m, 1H), 3.55 (s, 3H), 2.12 (d, J = 7.20 Hz, 3H), 1.27-1.20 (m, 6H). | (R)-2-(2-isopropylpyridin-3-yl)-7-methyl-9-(1-(4-(1-methyl-4-(trifluoromethyl)-1H-imidazol-2-yl)phenyl)ethyl)-7,9-dihydro-8H-purin-8-one |
| I-116 | m/z: 522.4681 [M + H]⁺ Rt (min): 1.0984 | ¹H NMR (400 MHz, CD₃OD) δ 8.59-8.57 (m, 1H), 8.52 (s, 1H), 8.01-7.98 (m, 1H), 7.70-7.64 (m, 5H), 7.37-7.34 (m, 1H), 5.96-5.91 (m, 1H), 3.77 (s, 3H), 3.68-3.60 (m, 1H), 3.55 (s, 3H), 2.12 (d, J = 7.60 Hz, 3H), 1.27-1.21 (m, 6H). | (S)-2-(2-isopropylpyridin-3-yl)-7-methyl-9-(1-(4-(1-methyl-4-(trifluoromethyl)-1H-imidazol-2-yl)phenyl)ethyl)-7,9-dihydro-8H-purin-8-one |
| I-117 | m/z: 579.5543 [M + H]⁺ Rt (min): 1.2874 | ¹H NMR (400 MHz, DMSO-d₆) δ 8.63 (s, 1H), 8.61-8.54 (m, 1H), 7.95-7.92 (m, 1H), 7.74-7.70 (m, 2H), 7.51-7.48 (m, 2H), 7.31-7.27 (m, 1H), 6.50 (s, 1H), 5.14 (s, 2H), 3.63-3.54 (m, 5H), 3.46 (s, 3H), 2.81-2.78 (m, 4H), 1.11 (d, J = 6.80 Hz, 6H). | 2-(2-isopropylpyridin-3-yl)-7-methyl-9-(4-(5-morpholino-3-(trifluoromethyl)-1H-pyrazol-1-yl)benzyl)-7,9-dihydro-8H-purin-8-one |
| I-118 | m/z: 470.3 [M + H]⁺ Rt (min): 0.9883 | ¹H NMR (300 MHz, DMSO-d₆) δ 8.63-8.60 (m, 2H), 7.99-7.96 (m, 1H), 7.59 (d, J = 8.40 Hz, 2H), 7.42 (d, J = 8.40 Hz, 2H), 7.34-7.30 (m, 1H), 5.71 (s, 1H), 5.10 (s, 2H), 3.88 (s, 3H), 3.67-3.58 (m, 1H), 3.47 (s, 3H), 2.15 (s, 3H), 1.14 (d, J = 6.90 Hz, 6H). | 2-(2-isopropylpyridin-3-yl)-9-(4-(3-methoxy-5-methyl-1H-pyrazol-1-yl)benzyl)-7-methyl-7,9-dihydro-8H-purin-8-one |
| I-119 | m/z: 550.4299 [M + H]⁺ Rt (min): 1.0446 | ¹H NMR (400 MHz, DMSO-d₆) δ 8.82 (s, 1H), 8.60-8.59 (m, 1H), 7.98-7.60 (m, 1H), 7.91 (d, J = 2.40 Hz, 1H), 7.72-7.67 (m, 2H), 7.48 (d, J = 8.40 Hz, 2H), 7.33-7.29 (m, 1H), 5.61-5.54 (m, 1H), 5.15-5.08 (m, 4H), 5.00-4.96 (m, 2H), 3.73 (s, 3H), 3.61-3.31 (m, 1H), 1.16-1.12 (m, 6H). | 2-(2-isopropylpyridin-3-yl)-9-(4-(1-methyl-4-(trifluoromethyl)-1H-imidazol-2-yl)benzyl)-7-(oxetan-3-yl)-7,9-dihydro-8H-purin-8-one |
| I-120 | m/z: 552.4071 [M + H]⁺ Rt (min): 1.085 | ¹H NMR (400 MHz, DMSO-d₆) δ 8.64 (s, 1H), 8.59-8.57 (m, 1H), 7.96-7.94 (m, 1H), 7.92-7.90 (m, 1H), 7.70-7.67 (m, 2H), 7.48-7.45 (m, 2H), 7.31-7.28 (m, 1H), 5.15 (s, 2H), 4.12 (t, J = 5.20 Hz, 2H), 3.74 (s, 3H), 3.68 (t, J = 5.20 Hz, 2H), 3.63-3.59 (m, 1H), 3.26 (s, 3H), 1.12 (d, J = 6.40 Hz, 6H). | 2-(2-isopropylpyridin-3-yl)-7-(2-methoxyethyl)-9-(4-(1-methyl-4-(trifluoromethyl)-1H-imidazol-2-yl)benzyl)-7,9-dihydro-8H-purin-8-one |
| I-121 | m/z: 598.4064 [M + H]⁺ Rt (min): 1.085 |  | 7-(1,1-dioxidothietan-3-yl)-2-(2-isopropylpyridin-3-yl)-9-(4-(1-methyl-4-(trifluoromethyl)-1H-imidazol-2-yl)benzyl)-7,9-dihydro-8H-purin-8-one |
| I-122 | m/z: 578.4492 [M + H]⁺ Rt (min): 1.112 |  | 2-(2-isopropylpyridin-3-yl)-9-(4-(1-methyl-4-(trifluoromethyl)-1H-imidazol-2-yl)benzyl)-7-(tetrahydro-2H-pyran-4-yl)-7,9-dihydro-8H-purin-8-one |
| I-123 | m/z: 538.3385 [M + H]⁺ |  | 7-(2-hydroxyethyl)-2-(2-isopropylpyridin-3-yl)-9-(4-(1-methyl-4- |

TABLE 3-continued

| Cmpd no. | LCMS | ¹H NMR (300 MHz) δ ppm | Chemical Name |
|---|---|---|---|
| | Rt (min): 0.9097 | | (trifluoromethyl)-1H-imidazol-2-yl)benzyl)-7,9-dihydro-8H-purin-8-one |
| I-124 | m/z: 550.2679 [M + H]⁺ Rt (min): 0.9767 | | 2-(2-isopropylpyridin-3-yl)-7-methyl-9-(4-(1-(oxetan-3-yl)-4-(trifluoromethyl)-1H-imidazol-2-yl)benzyl)-7,9-dihydro-8H-purin-8-one |
| I-125 | m/z: 544.2222 [M + H]⁺ Rt (min): 1.0715 | | 9-(3,5-difluoro-4-(1-methyl-4-(trifluoromethyl)-1H-imidazol-2-yl)benzyl)-2-(2-isopropylpyridin-3-yl)-7-methyl-7,9-dihydro-8H-purin-8-one |
| I-126 | m/z: 526.2587 [M + H]⁺ Rt (min): 1.0446 | ¹H NMR (300 MHz, DMSO-d₆) δ 8.65 (s, 1H), 8.61-8.58 (m, 1H), 7.99-7.93 (m, 2H), 7.58 (t, J = 7.80 Hz, 1H), 7.42-7.38 (m, 1H), 7.34--7.28 (m, 2H), 5.19 (s, 2H), 3.62-3.55 (m, 4H), 3.47 (s, 3H), 1.12 (d, J = 6.90 Hz, 6H). | 9-(3-fluoro-4-(1-methyl-4-(trifluoromethyl)-1H-imidazol-2-yl)benzyl)-2-(2-isopropylpyridin-3-yl)-7-methyl-7,9-dihydro-8H-purin-8-one |
| I-127 | m/z: 526.2157 [M + H]⁺ Rt (min): 1.058 | ¹H NMR (400 MHz, CD₃OD) δ 8.68 (d, J = 4.40 Hz, 1H), 8.59 (s, 1H), 8.50-8.46 (m, 1H), 7.72-7.67 (m, 2H), 7.56-7.46(m, 3H), 5.35 (s, 2H), 3.98-3.90 (m, 1H), 3.80 (s, 3H) 3.58 (s, 3H), 1.30 (d, J = 6.80 Hz, 6H). | 9-(2-fluoro-4-(1-methyl-4-(trifluoromethyl)-1H-imidazol-2-yl)benzyl)-2-(2-isopropylpyridin-3-yl)-7-methyl-7,9-dihydro-8H-purin-8-one |
| I-128 | m/z: 544.2872 [M + H]⁺ Rt (min): 1.0984 | ¹H NMR (300 MHz, CD₃OD) δ 8.56-8.54 (m, 1H), 8.49 (s, 1H), 7.97-7.94 (m, 1H), 7.72 (s, 1H), 7.37-7.31 (m, 3H), 5.34 (s, 2H), 3.80 (s, 3H), 3.63-3.50 (m, 1H), 3.51 (s, 3H), 1.25 (d, J = 6.90 Hz, 6H). | 9-(2,6-difluoro-4-(1-methyl-4-(trifluoromethyl)-1H-imidazol-2-yl)benzyl)-2-(2-isopropylpyridin-3-yl)-7-methyl-7,9-dihydro-8H-purin-8-one |
| I-129 | m/z: 511.2647 [M + H]⁺ Rt (min): 1.015 | ¹H NMR (400 MHz, CD₃OD) δ 8.59-8.48 (m, 2H), 8.03-7.96 (m, 1H), 7.70-7.56 (m, 5H), 7.38-7.30 (m, 1H), 5.25 (s, 2H), 3.75 (s, 3H), 3.64-3.52 (m, 1H), 1.23 (d, J = 6.80 Hz, 6H). | 2-(2-isopropylpyridin-3-yl)-7-(methyl-d3)-9-(4-(1-methyl-4-(trifluoromethyl)-1H-imidazol-2-yl)benzyl)-7,9-dihydro-8H-purin-8-one |
| I-130 | m/z: 514.2547 [M + H]⁺ Rt (min): 1.0041 | ¹H NMR (400 MHz, CD₃OD) δ 8.57-8.52 (m, 1H), 8.51 (s, 1H), 8.01-7.97 (m, 1H), 7.71-7.56 (m, 5H), 7.36-7.32 (m, 1H), 5.25 (s, 2H), 3.62-3.54 (m, 1H), 1.23 (d, J = 6.80 Hz, 6H). | 2-(2-isopropylpyridin-3-yl)-7-(methyl-d3)-9-(4-(1-(methyl-d3)-4-(trifluoromethyl)-1H-imidazol-2-yl)benzyl)-7,9-dihydro-8H-purin-8-one |
| I-131 | m/z: 511.2382 [M + H]⁺ Rt (min): 1.0175 | ¹H NMR (400 MHz, CD₃OD) δ 8.57-8.54 (m, 1H), 8.49 (s, 1H), 8.00-7.95 (m, 1H), 7.67-7.57 (m, 5H), 7.33-7.30 (m, 1H), 5.24 (s, 2H), 3.62-3.52 (m, 4H), 1.22 (d, J = 6.80 Hz, 6H). | 2-(2-isopropylpyridin-3-yl)-7-methyl-9-(4-(1-(methyl-d3)-4-(trifluoromethyl)-1H-imidazol-2-yl)benzyl)-7,9-dihydro-8H-purin-8-one |
| I-132 | m/z: 523.4 [M + H]⁺ Rt (min): 1.3917 | | 2-(2-(2-hydroxypropan-2-yl)phenyl)-7-methyl-9-(4-(1-methyl-4-(trifluoromethyl)-1H-imidazol-2-yl)benzyl)-7,9-dihydro-8H-purin-8-one |
| I-133 | m/z: 551.405 [M + H]⁺ Rt (min): 1.0041 | | 7-methyl-9-(4-(1-methyl-4-(trifluoromethyl)-1H-imidazol-2-yl)benzyl)-2-(2-morpholinopyridin-3-yl)-7,9-dihydro-8H-purin-8-one |
| I-134 | m/z: 539.3129 [M + H]⁺ Rt (min): | | 2-(2-(3-fluoroazetidin-1-yl)pyridin-3-yl)-7-methyl-9-(4-(1-methyl-4-(trifluoromethyl)-1H- |

TABLE 3-continued

| Cmpd no. | LCMS | ¹H NMR (300 MHz) δ ppm | Chemical Name |
|---|---|---|---|
| | 0.955 | | imidazol-2-yl)benzyl)-7,9-dihydro-8H-purin-8-one |
| I-135 | m/z: 557.3753 [M + H]⁺ Rt (min): 1.3412 | | 2-(2-(3,3-difluoroazetidin-1-yl)pyridin-3-yl)-7-methyl-9-(4-(1-methyl-4-(trifluoromethyl)-1H-imidazol-2-yl)benzyl)-7,9-dihydro-8H-purin-8-one |
| I-136 | m/z: 589.4218 [M + H]⁺ Rt (min): 1.2383 | | 7-methyl-9-(4-(1-methyl-4-(trifluoromethyl)-1H-imidazol-2-yl)benzyl)-2-(2-(3-(trifluoromethyl)azetidin-1-yl)pyridin-3-yl)-7,9-dihydro-8H-purin-8-one |
| I-137 | m/z: 522.4094 [M + H]⁺ Rt (min): 1.3412 | | 2-(2-cyclopropoxypyridin-3-yl)-7-methyl-9-(4-(1-methyl-4-(trifluoromethyl)-1H-imidazol-2-yl)benzyl)-7,9-dihydro-8H-purin-8-one |

Example 35: 2-(2-Isopropylphenyl)-9-(4-(1-methyl-4-(trifluoromethyl)-1H-imidazol-2-yl)benzyl)-7,9-dihydro-8H-purin-8-one (I-138)

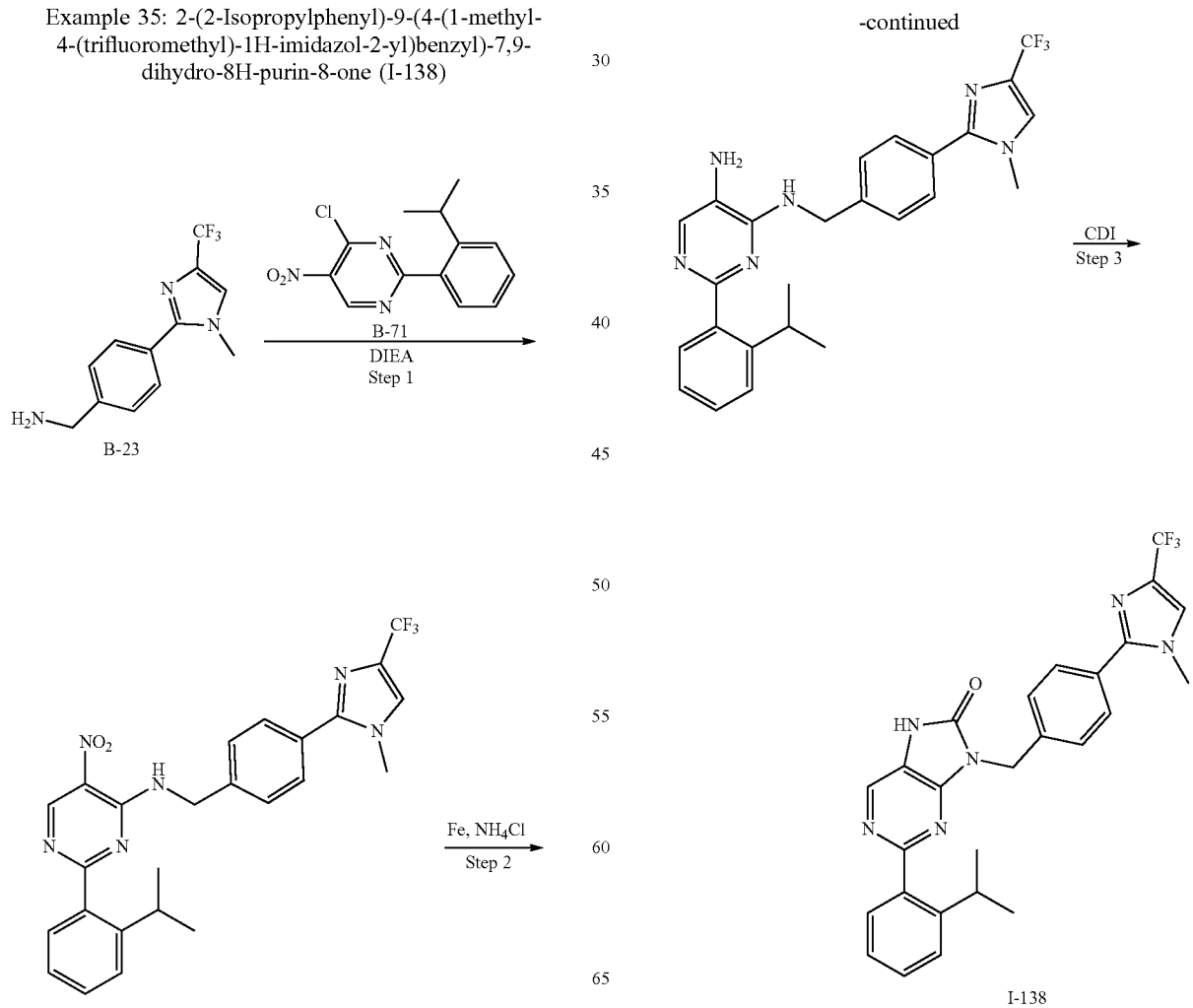

Step 1. 2-(2-Isopropylphenyl)-N-(4-(1-methyl-4-(trifluoromethyl)-1H-imidazol-2-yl)benzyl)-5-nitropyrimidin-4-amine A mixture of Intermediate B-71 (4.03 g, 14.51 mmol) and DIEA (5.66 g, 43.79 mmol) in THF (280 mL) at −78° C. was treated with dropwise addition of a solution of Intermediate B-23 (3.73 g, 14.61 mmol) in THF (20 mL) and the resulting solution was stirred for 2 h at −78° C. The reaction was allowed to warm to ambient temperature gradually over 1 h whereupon the reaction mixture was concentrated under vacuum and the residue was purified by silica gel chromatography (eluting with 33% EtOAc/PE) to afford 4.8 g (66%) of 2-(2-isopropylphenyl)-N-(4-(1-methyl-4-(trifluoromethyl)-1H-imidazol-2-yl)benzyl)-5-nitropyrimidin-4-amine as a yellow solid. MS (ESI) m/z 497.1 [M+H]$^+$

Step 2. 2-(2-Isopropylphenyl)-N$^4$-(4-(1-methyl-4-(trifluoromethyl)-1H-imidazol-2-yl)benzyl)pyrimidine-4,5-diamine A mixture of 2-(2-isopropylphenyl)-N-(4-(1-methyl-4-(trifluoromethyl)-1H-imidazol-2-yl)benzyl)-5-nitropyrimidin-4-amine (4.1 g, 8.26 mmol), iron powder (2.31 g, 41.36 mmol), and ammonium chloride (1.31 g, 24.49 mmol), in 3:3:1 EtOH/THF/water (42 mL) was stirred for 1 h at 80° C. The reaction mixture was filtered and concentrated under vacuum to afford 5.3 g (crude) of 2-(2-isopropylphenyl)-N$^4$-(4-(1-methyl-4-(trifluoromethyl)-1H-imidazol-2-yl)benzyl)pyrimidine-4,5-diamine as a brown solid. MS (ESI) m/z 467.2 [M+H]$^+$

Step 3. 2-(2-Isopropylphenyl)-9-(4-(1-methyl-4-(trifluoromethyl)-1H-imidazol-2-yl)benzyl)-7,9-dihydro-8H-purin-8-one A mixture of 2-(2-isopropylphenyl)-N$^4$-(4-(1-methyl-4-(trifluoromethyl)-1H-imidazol-2-yl)benzyl)pyrimidine-4,5-diamine (3.0 g, 6.43 mmol) and CDI (3.12 g, 19.24 mmol) in DCM (30 mL) was stirred for 2 h at 40° C., then was concentrated under vacuum, dispersed in water (100 mL) and extracted with EtOAc (2×150 mL). The combined organic extracts were dried over anhydrous sodium sulfate, filtered and concentrated under vacuum. The residue was purified initially by silica gel chromatography (eluting with 50% EtOAc/PE), then was further purified by prep-HPLC resulting in 1.005 g (40%) of 2-(2-isopropylphenyl)-9-(4-(1-methyl-4-(trifluoromethyl)-1H-imidazol-2-yl)benzyl)-7,9-dihydro-8H-purin-8-one (I-138) as a white solid.

Table 4 (General Procedure C). The compounds listed in Table 4 were synthesized according to Example 35 using the appropriate commercially-available reagents and/or Intermediates described herein. Enantiomers, when generated, were separated by chiral HPLC and absolute stereochemistries were arbitrarily assigned.

TABLE 4

| Cmpd no. | LCMS | $^1$H NMR (300 MHz) δ ppm | Chemical Name |
| --- | --- | --- | --- |
| I-138 | m/z: 493.18 [M + H]$^+$ Rt (min): 1.58 | $^1$H NMR (400 MHz, CD$_3$OD) δ 8.30 (s, 1H), 7.67-7.62 (m, 5H), 7.46-7.38 (m, 3H), 7.27-7.23 (m, 1H), 5.22 (s, 2H), 3.75 (s, 3H), 3.35-3.28 (m, 1H), 1.20-1.14 (m, 6H). | 2-(2-isopropylphenyl)-9-(4-(1-methyl-4-(trifluoromethyl)-1H-imidazol-2-yl)benzyl)-7,9-dihydro-8H-purin-8-one |
| I-139 | m/z: 412.2818 [M + H]$^+$ Rt (min): 1.32 | $^1$H NMR (300 MHz, CD$_3$OD) δ 8.52 (s, 1H), 8.34 (s, 1H), 7.95-7.78 (m, 3H), 7.65 (d, J = 6.20 Hz, 2H), 7.50-7.35 (m, 3H), 7.30-7.21 (m, 1H), 5.23 (s, 2H), 3.30-3.15 (m, 1H), 1.13 (d, J = 6.90 Hz, 6H). | 9-(4-(1H-1,2,3-triazol-1-yl)benzyl)-2-(2-isopropylphenyl)-7,9-dihydro-8H-purin-8-one |
| I-140 | m/z: 412.2818 [M + H]$^+$ Rt (min): 1.59 | $^1$H-NMR (300 MHz, DMSO-d$_6$) δ 8.40 (s, 1H), 8.12 (s, 2H), 7.99 (d, J = 8.40 Hz, 2H), 7.56-7.45 (m, 3H), 7.45-7.32 (m, 2H), 7.30-7.18 (m, 1H), 5.12 (s, 2H), 3.52-3.31 (m, 1H), 1.06 (d, J = 6.60 Hz, 6H). | 9-(4-(2H-1,2,3-triazol-2-yl)benzyl)-2-(2-isopropylphenyl)-7,9-dihydro-8H-purin-8-one |
| I-141 | m/z: 426.2854 [M + H]$^+$ Rt (min): 1.67 | $^1$H NMR (300 MHz, DMSO-d$_6$) δ 11.57 (s, 1H), 8.39 (s, 1H), 8.09 (s, 2H), 7.97(d, J = 8.40 Hz, 2H), 7.55(d, J = 8.40 Hz, 2H), 7.49(d, J = 7.50 Hz, 1H), 7.45-7.30 (m, 2H), 7.29-7.15 (m, 1H), 5.76(q, J = 7.50 Hz, 1H), 3.49-3.35 (m, 1H), 1.96 (d, J = 7.50 Hz, 3H), 1.04-0.95(m, 6H). | (S)-9-(1-(4-(2H-1,2,3-triazol-2-yl)phenyl)ethyl)-2-(2-isopropylphenyl)-7,9-dihydro-8H-purin-8-one |
| I-142 | m/z: 426.32 [M + H]$^+$ Rt (min): 1.67 | $^1$H NMR (300 MHz, DMSO-d$_6$, ppm) δ 11.47 (br s, 1H), 8.39 (s, 1H), 8.09 (s, 2H), 7.98(d, J = 8.70 Hz, 2H), 7.56(d, J = 8.40 Hz, 2H), 7.49 (d, J = 7.20 Hz, 1H), 7.40-7.27 (m, 2H), 7.27-7.10 (m, 1H), 5.79(q, J = 7.20 Hz, 1H), 3.49-3.35 (m, 1H), 1.97 (d, J = 7.50 Hz, 3H), 1.05-0.95(m, 6H). | (R)-9-(1-(4-(2H-1,2,3-triazol-2-yl)phenyl)ethyl)-2-(2-isopropylphenyl)-7,9-dihydro-8H-purin-8-one |
| I-143 | m/z: 429.3747 [M + H]$^+$ | $^1$H NMR (400 MHz, CDCl$_3$) δ 10.0 (br s, 1H), 8.32 (s, 1H), 8.31 (s, 1H), 8.08 (s, 1H), 7.60 (d, J = 7.60 | 2-(2-isopropylphenyl)-9-((1-(pyridin-3-yl)piperidin-4-yl)methyl)-7,9-dihydro- |

TABLE 4-continued

| Cmpd no. | LCMS | ¹H NMR (300 MHz) δ ppm | Chemical Name |
|---|---|---|---|
| | Rt (min): 1.03 | Hz, 1H), 7.55-7.38 (m, 2H), 7.29-7.21 (m, 1H), 7.20-7.11 (m, 2H), 3.95 (d, J = 7.20 Hz, 2H), 3.75-3.65 (m, 2H), 3.55-3.40 (m, 1H), 2.80-2.68 (m, 2H), 2.30-2.10 (m, 1H), 1.85-1.75 (m, 2H), 1.60-1.45 (m, 2H), 1.25 (d, J = 7.20 Hz, 6H). | 8H-purin-8-one |
| I-144 | m/z: 415.3364 [M + H]⁺ Rt (min): 0.96 | ¹H NMR (300 MHz, CD₃OD) δ 8.30 (s, 1H), 8.25 (d, J = 3.00 Hz, 1H), 7.94 (d, J = 3.90 Hz, 1H), 7.47-7.36 (m, 4H), 7.27-7.21 (m, 2H), 4.65-4.53 (m, 1H), 3.97-3.93 (m, 2H), 3.44-3.37 (m, 1H), 3.01-2.77 (m, 4H), 1.91-1.85 (m, 2H), 1.18 (d, J = 6.90 Hz, 6H). | 2-(2-isopropylphenyl)-9-(1-(pyridin-3-yl)piperidin-4-yl)-7,9-dihydro-8H-purin-8-one |
| I-145 | m/z: 411.2225 [M + H]⁺ Rt (min): 1.51 | | 9-(4-(1H-pyrazol-1-yl)benzyl)-2-(2-isopropylphenyl)-7,9-dihydro-8H-purin-8-one |
| I-146 | m/z: 412.2818 [M + H]⁺ Rt (min): 1.5 | | 9-((6-(1H-pyrazol-1-yl)pyridin-3-yl)methyl)-2-(2-isopropylphenyl)-7,9-dihydro-8H-purin-8-one |
| I-147 | m/z: 426.1938 [M + H]⁺ Rt (min): 1.39 | ¹H NMR (400 MHz, CD₃OD) δ 8.53 (s, 1H), 8.34 (m, 1H), 7.90-7.85 (m, 3H), 7.74-7.72 (m, 2H), 7.53-7.46 (m, 3H), 7.33-7.31 (m, 1H), 5.98-5.93 (m,1H), 3.33-3.28 (m, 1H), 2.11 (d, J = 7.20 Hz, 3H), 1.14-1.01 (m, 6H). | (S)-9-(1-(4-(1H-1,2,3-triazol-1-yl)phenyl)ethyl)-2-(2-isopropylphenyl)-7,9-dihydro-8H-purin-8-one |
| I-148 | m/z: 426.2366 [M + H]⁺ Rt (min): 1.39 | ¹H NMR (400 MHz, CD₃OD) δ 8.54 (s, 1H), 8.41 (m, 1H), 7.90-7.86 (m, 3H), 7.74-7.72 (m, 2H), 7.46-7.40 (m, 3H), 7.28-7.25 (m, 1H), 5.95-5.83 (m, 1H), 3.33-3.21 (m, 1H), 2.11 (d, J = 7.60 Hz, 3H), 1.14-1.02 (m, 6H). | (R)-9-(1-(4-(1H-1,2,3-triazol-1-yl)phenyl)ethyl)-2-(2-isopropylphenyl)-7,9-dihydro-8H-purin-8-one |
| I-149 | m/z: 479.2247 [M + H]⁺ Rt (min): 1.79 | | 2-(2-isopropylphenyl)-9-(4-(3-(trifluoromethyl)-1H-pyrazol-1-yl)benzyl)-7,9-dihydro-8H-purin-8-one |
| I-150 | m/z: 427.0969 [M + H]⁺ Rt (min): 1.34 | | 2-(2-isopropylphenyl)-9-(4-(5-methyl-1,3,4-oxadiazol-2-yl)benzyl)-7,9-dihydro-8H-purin-8-one |
| I-151 | m/z: 370.1039 [M + H]⁺ Rt (min): 1.47 | | 4-((2-(2-isopropylphenyl)-8-oxo-7,8-dihydro-9H-purin-9-yl)methyl)benzonitrile |
| I-152 | m/z: 427.3232 [M + H]⁺ Rt (min): 1.5436 | | 2-(2-isopropylphenyl)-9-(4-(5-methyl-1,2,4-oxadiazol-3-yl)benzyl)-7,9-dihydro-8H-purin-8-one |
| I-153 | m/z: 444.14 [M + H]⁺ Rt (min): | | 2-(2-isopropylphenyl)-9-(4-(morpholinomethyl)benzyl)-7,9-dihydro-8H-purin-8-one |
| I-154 | m/z: 412.0846 [M + H]⁺ Rt (min): 1.29 | | 9-(4-(1H-1,2,4-triazol-1-yl)benzyl)-2-(2-isopropylphenyl)-7,9-dihydro-8H-purin-8-one |
| I-155 | m/z: 359.122 [M + H]⁺ Rt (min): 1.69 | | (R)-2-(2-isopropylphenyl)-9-(1-phenylethyl)-7,9-dihydro-8H-purin-8-one |
| I-156 | m/z: 359.1219 [M + H]⁺ | | (S)-2-(2-isopropylphenyl)-9-(1-phenylethyl)-7,9-dihydro-8H-purin-8-one |

TABLE 4-continued

| Cmpd no. | LCMS | ¹H NMR (300 MHz) δ ppm | Chemical Name |
|---|---|---|---|
| | Rt (min): 1.69 | | |
| I-157 | m/z: 425.2752 [M + H]⁺ Rt (min): 1.59 | ¹H NMR (400 MHz, CD₃OD) δ 8.31 (s, 1H), 8.18 (d, J = 2.4 Hz, 1H), 7.71-7.68 (m, 3H), 7.61 (d, J = 8.8 Hz, 2H), 7.44-7.39 (m, 3H), 7.26-7.22 (m, 1H), 6.50 (t, J = 2.4 Hz, 1H), 5.88-5.82 (m, 1H), 3.34-3.28 (m, 1H), 2.07 (d, J = 7.2 Hz, 3H), 1.11 (d, J = 7.20 Hz, 3H), 1.09 (d, J = 7.2 Hz, 3H). | (S)-9-(1-(4-(1H-pyrazol-1-yl)phenyl)ethyl)-2-(2-isopropylphenyl)-7,9-dihydro-8H-purin-8-one |
| I-158 | m/z: 425.2802 [M + H]⁺ Rt (min): 1.59 | ¹H NMR (400 MHz, CD₃OD) δ 8.31 (s, 1H), 8.18 (d, J = 2.4 Hz, 1H), 7.71-7.68 (m, 3H), 7.61 (d, J = 8.8 Hz, 2H), 7.44-7.39 (m, 3H), 7.26-7.22 (m, 1H), 6.50 (t, J = 2.4 Hz, 1H), 5.88-5.82 (m, 1H), 3.34-3.28 (m, 1H), 2.07 (d, J = 7.2 Hz, 3H), 1.11 (d, J = 7.20 Hz, 3H), 1.09 (d, J = 7.2 Hz, 3H). | (R)-9-(1-(4-(1H-pyrazol-1-yl)phenyl)ethyl)-2-(2-isopropylphenyl)-7,9-dihydro-8H-purin-8-one |
| I-159 | m/z: 387.2 [M + H]⁺ Rt (min): 1.58 | ¹H NMR (400 MHz, CD₃OD) δ 8.35 (s, 1H), 7.40-7.30 (m, 3H), 7.25-7.09 (m, 2H), 6.89-6.71 (m, 3H), 5.90-5.85 (m, 1H), 4.60-4.50 (m, 1H), 7.45-7.18 (m, 1H), 3.21-3.01 (m, 2H), 2.31-2.12 (m, 1H), 1.03 (d, J = 6.80 Hz, 3H), 0.95 (d, J = 6.80 Hz, 3H) | (R)-9-(chroman-4-yl)-2-(2-isopropylphenyl)-7,9-dihydro-8H-purin-8-one |
| I-160 | m/z: 425.1005 [M + H]⁺ Rt (min): 0.98 | ¹H NMR (400 MHz, CDCl₃) δ 11.23 (s, 1H), 8.25 (s, 1H), 7.67-7.66 (m, 2H), 7.60-7.58 (m, 1H), 7.55-7.54 (m, 1H), 7.43-7.39 (m, 2H), 7.26-7.24 (m, 1H), 7.24-7.22 (m, 1H), 7.03-7.00 (m, 1H), 5.17 (s, 2H), 3.76 (s, 3H), 3.50-3.43 (m, 1H), 1.21-1.19 (m, 6H). | 2-(2-isopropylphenyl)-9-(4-(1-methyl-1H-imidazol-2-yl)benzyl)-7,9-dihydro-8H-purin-8-one |
| I-161 | m/z: 443.2182 [M + H]⁺ Rt (min): 1.1 | ¹H NMR (400 MHz, CD₃OD) δ 8.30 (s, 1H), 8.18 (s, 1H), 7.92-7.90 (m, 1H), 7.49-7.41 (m, 3H), 7.38-7.35 (m, 1H), 7.29-7.22 (m, 2H), 4.08 (t, J = 6.80 Hz, 2H), 3.72-3.69 (m, 2H), 3.48-3.41 (m, 1H), 2.70-2.69 (m, 2H), 1.99-1.89 (m, 2H), 1.84-1.80 (m, 2H), 1.55-1.48 (m, 1H), 1.44-1.35 (m, 2H), 1.25-1.18 (m, 6H). | 2-(2-isopropylphenyl)-9-(2-(1-(pyridin-3-yl)piperidin-4-yl)ethyl)-7,9-dihydro-8H-purin-8-one |
| I-162 | m/z: 445.1508 [M + H]⁺ Rt (min): 1.66 | ¹H NMR (300 MHz, CDCl₃) δ 9.52 (br s, 1H), 8.49 (s, 1H), 7.90-7.83 (m, 2H), 7.73-7.72 (m, 1H), 7.60-7.52 (m, 2H), 7.43-7.38 (m, 3H), 7.27 (s, 1H), 6.48 (s, 1H), 5.34 (s, 2H), 3.43-3.36 (m, 1H), 1.16-1.13 (m, 6H). | 9-(2-chloro-4-(1H-pyrazol-1-yl)benzyl)-2-(2-isopropylphenyl)-7,9-dihydro-8H-purin-8-one |
| I-163 | m/z: 451.0999 [M + H]⁺ Rt (min): 1.75 | ¹H NMR (400 MHz, CDCl₃) δ 9.87 (s, 1H), 8.40 (s, 1H), 7.89 (d, J = 2.0 Hz, 1H), 7.72 (s, 1H), 7.65-7.55 (m, 3H), 7.54-7.45 (m, 2H), 7.35-7.32 (m, 3H), 6.46 (s, 1H), 5.20-5.13 (m, 1H), 4.86-4.78 (m, 1H), 3.60-3.57 (m, 1H), 3.33-3.12 (m, 1H), 2.49-2.42 (m, 1H), 2.37-2.31 (m, 1H), 1.99-1.89 (m, 1H), 1.32-1.13 (m, 6H). | 9-((1R,2S)-2-(4-(1H-pyrazol-1-yl)phenyl)cyclobutyl)-2-(2-isopropylphenyl)-7,9-dihydro-8H-purin-8-one |
| I-164 | m/z: 451.1105 [M + H]⁺ Rt (min): 1.75 | ¹H NMR (400 MHz, CDCl₃) δ 9.87 (s, 1H), 8.40 (s, 1H), 7.89 (d, J = 2.0 Hz, 1H), 7.72 (s, 1H), 7.65-7.55 (m, 3H), 7.54-7.45 (m, 2H), 7.35-7.32 (m, 3H), 6.46 (s, 1H), 5.20-5.13 (m, 1H), 4.86-4.78 (m, 1H), 3.60-3.57 (m, 1H), 3.33-3.12 (m, 1H), 2.49-2.42 (m, 1H), 2.37-2.31 (m, 1H), 1.99-1.89 (m, 1H), 1.32-1.13 (m, 6H). | 9-((1S,2R)-2-(4-(1H-pyrazol-1-yl)phenyl)cyclobutyl)-2-(2-isopropylphenyl)-7,9-dihydro-8H-purin-8-one |
| I-165 | m/z: 430.0399 [M + H]⁺ Rt (min): | ¹H NMR (400 MHz, CD₃OD) δ 8.51 (s, 1H), 8.34 (s, 1H), 7.88-7.83 (m, 3H), 7.65-7.61 (m, 2H), 7.29-7.25 (m, 2H), 7.14-7.10 (m, | 9-(4-(1H-1,2,3-triazol-1-yl)benzyl)-2-(3-fluoro-2-isopropylphenyl)-7,9-dihydro-8H-purin-8-one |

TABLE 4-continued

| Cmpd no. | LCMS | ¹H NMR (300 MHz) δ ppm | Chemical Name |
|---|---|---|---|
| | 1.35 | 1H), 5.21 (s, 2H), 3.14-3.10 (m, 1H), 1.29-1.23 (m, 6H). | |
| I-166 | m/z: 430.0403 [M + H]⁺ Rt (min): 1.62 | ¹H NMR (400 MHz, CDCl₃) δ 8.33 (s, 1H), 8.06-8.02 (m, 2H), 7.90 (s, 2H), 7.59-7.55 (m, 2H), 7.30-7.24 (m, 2H), 7.14-7.10 (m, 1H), 5.20 (s, 2H), 3.14-3.08 (m, 1H), 1.26-1.24 (m, 6H). | 9-(4-(2H-1,2,3-triazol-2-yl)benzyl)-2-(3-fluoro-2-isopropylphenyl)-7,9-dihydro-8H-purin-8-one |
| I-167 | m/z: 429.1469 [M + H]⁺ Rt (min): 1.58 | ¹H NMR (300 MHz, DMSO-d₆) δ 11.56 (s, 1H), 8.52-8.39 (m, 1H), 7.75-7.64 (m, 3H), 7.48-7.22 (m, 5H), 6.54 (s, 1H), 5.09 (s, 2H), 3.61-3.57 (m, 1H), 1.22-0.91 (m, 6H). | 9-(2-fluoro-4-(1H-pyrazol-1-yl)benzyl)-2-(2-isopropylphenyl)-7,9-dihydro-8H-purin-8-one |
| I-168 | m/z: 427.0969 [M + H]⁺ Rt (min): 1.57 | | 2-(2-isopropylphenyl)-9-(4-(5-methyl-2H-tetrazol-2-yl)benzyl)-7,9-dihydro-8H-purin-8-one |
| I-169 | m/z: 412.0846 [M + H]⁺ Rt (min): 1.49 | | 2-(2-isopropylphenyl)-9-(4-(oxazol-2-yl)benzyl)-7,9-dihydro-8H-purin-8-one |
| I-170 | m/z: 429.1115 [M + H]⁺ Rt (min): 1.58 | ¹H NMR (400 MHz, DMSO-d₆) δ 11.62 (s, 1H), 8.46-8.40 (m, 2H), 7.81-7.79 (m, 3H), 7.46-744 (m, 2H), 7.32-7.26 (m, 2H), 7.21-7.17 (m, 1H), 6.53-6.52 (m, 1H), 5.06 (s, 2H), 3.32-3.27 (m, 1H), 1.21 (d, J = 6.4 Hz, 6H). | 9-(4-(1H-pyrazol-1-yl)benzyl)-2-(3-fluoro-2-isopropylphenyl)-7,9-dihydro-8H-purin-8-one |
| I-171 | m/z: 345.1513 [M + H]⁺ Rt (min): 1.59 | ¹H NMR (300 MHz, DMSO-d₆) δ 8.36 (s, 1H), 7.54-7.18 (m, 9H), 5.02 (s, 2H), 3.49-3.40 (m, 1H), 1.09 (d, J = 6.90 Hz, 6H). | 9-benzyl-2-(2-isopropylphenyl)-7,9-dihydro-8H-purin-8-one |
| I-172 | m/z: 443.15 [M + H]⁺ Rt (min): 0.83 | ¹H NMR (400 MHz, CD₃OD) δ 8.33 (s, 1H), 7.58-7.54 (m, 4H), 7.33-7.22 (m, 2H), 7.21-7.07 (m, 2H), 7.01 (s, 1H), 5.20 (s, 2H), 3.72 (s, 3H), 3.18-3.11 (m, 1H), 1.18-1.16 (m, 6H). | 2-(3-fluoro-2-isopropylphenyl)-9-(4-(1-methyl-1H-imidazol-2-yl)benzyl)-7,9-dihydro-8H-purin-8-one |
| I-173 | m/z: 509.47 [M + H]⁺ Rt (min): 0.8961 | ¹H NMR (400 MHz, CD₃OD) δ 8.31-8.30 (m, 1H), 8.00-7.97 (m, 1H), 7.60-7.58 (m, 2H), 7.48-7.7.38 (m, 5H), 7.27-7.23 (m, 1H), 6.02-6.00 (m, 1H), 5.12 (s, 2H), 3.32-3.22 (m, 5H), 2.60-2.52 (m, 4H), 2.33 (s, 3H), 1.13 (d, J = 6.8 Hz, 6H). | 2-(2-isopropylphenyl)-9-(4-(3-(4-methylpiperazin-1-yl)-1H-pyrazol-1-yl)benzyl)-7,9-dihydro-8H-purin-8-one |
| I-174 | m/z: 496.4 [M + H]⁺ Rt (min): 1.5706 | ¹H NMR (400 MHz, CD₃OD) δ 8.32 (s, 1H), 8.01 (d, J = 2.40 Hz, 1H), 7.66-7.58 (m, 2H), 7.52-7.37 (m, 5H), 7.26-7.23 (m, 1H), 6.03 (d, J = 2.80 Hz, 1H), 5.14 (s, 2H), 3.84-3.77 (m, 4H), 3.31-3.20 (m, 5H), 1.14 (d, J = 6.90 Hz, 6H). | 2-(2-isopropylphenyl)-9-(4-(3-morpholino-1H-pyrazol-1-yl)benzyl)-7,9-dihydro-8H-purin-8-one |
| I-175 | m/z: 426.3171 [M + H]⁺ Rt (min): 1.3817 | | 2-(2-isopropylphenyl)-9-(4-(4-methyl-1H-1,2,3-triazol-1-yl)benzyl)-7,9-dihydro-8H-purin-8-one |
| I-176 | m/z: 443.3 [M + H]⁺ Rt (min): 0.977 | ¹H NMR (300 MHz, CDCl₃) δ 11.35 (br s, 1H), 8.12 (s, 1H), 7.58 (d, J = 2.1 Hz, 3H), 7.55-7.44 (m, 2H), 7.42-7.31 (m, 2H), 7.29-7.06 (m, 1H), 6.65 (d, J = 7.6 Hz, 1H), 5.16 (s, 2H), 3.58 (s, 3H), 3.52-3.31 (m, 1H), 1.17 (d, J = 7.0 Hz, 6H). | 9-(4-(5-fluoro-1-methyl-1H-imidazol-2-yl)benzyl)-2-(2-isopropylphenyl)-7,9-dihydro-8H-purin-8-one |
| I-177 | m/z: 429.2857 [M + H]⁺ Rt (min): 1.5706 | | 9-(3-fluoro-4-(1H-pyrazol-1-yl)benzyl)-2-(2-isopropylphenyl)-7,9-dihydro-8H-purin-8-one |
| I-178 | m/z: 377.2326 | | (R)-9-(1-(4-fluorophenyl)ethyl)-2-(2- |

TABLE 4-continued

| Cmpd no. | LCMS | ¹H NMR (300 MHz) δ ppm | Chemical Name |
|---|---|---|---|
| | [M + H]⁺ Rt (min): 1.7055 | | isopropylphenyl)-7,9-dihydro-8H-purin-8-one |
| I-179 | m/z: 377.2653 [M + H]⁺ Rt (min): 1.7055 | | (S)-9-(1-(4-fluorophenyl)ethyl)-2-(2-isopropylphenyl)-7,9-dihydro-8H-purin-8-one |
| I-180 | m/z: 393.2704 [M + H]⁺ Rt (min): 1.4357 | | (S)-9-(1-(4-fluorophenyl)-2-hydroxyethyl)-2-(2-isopropylphenyl)-7,9-dihydro-8H-purin-8-one |
| I-181 | m/z: 375.2513 [M + H]⁺ Rt (min): 1.3952 | | (S)-9-(2-hydroxy-1-phenylethyl)-2-(2-isopropylphenyl)-7,9-dihydro-8H-purin-8-one |
| I-182 | m/z: 399.31 [M + H]⁺ Rt (min): 0.7567 | | 2-(2-isopropylphenyl)-9-((1-methyl-1H-benzo[d]imidazol-5-yl)methyl)-7,9-dihydro-8H-purin-8-one |
| I-183 | m/z: 423.2614 [M + H]⁺ Rt (min): 1.2975 | | 2-(2-isopropylphenyl)-9-(4-(methylsulfonyl)benzyl)-7,9-dihydro-8H-purin-8-one |
| I-184 | m/z: 425.3161 [M + H]⁺ Rt (min): 1.5976 | ¹H NMR (300 MHz, CDCl₃) δ 9.92 (b, s, 1H), 8.25 (s, 1H), 7.78 (s, 1H), 7.59 (m, 5H), 7.41 (m, 2H), 7.28 (m, 1H), 6.21(s, 1H), 5.16 (m, 2H), 3.44 (m, 1H), 2.35 (s, 3H), 1.23 (d, J = 6.7 Hz, 6H). | 2-(2-isopropylphenyl)-9-(4-(5-methyl-1H-pyrazol-1-yl)benzyl)-7,9-dihydro-8H-purin-8-one |
| I-185 | m/z: 426.3171 [M + H]⁺ Rt (min): 1.3409 | ¹H NMR (400 MHz, CD₃OD) δ 8.36 (s, 1H), 7.70-7.60 (m, 3H), 7.57-7.53 (m, 2H) 7.49-7.41 (m, 3H), 7.30-7.21 (m, 1H), 5.27 (s, 2H), 3.31-3.23 (m, 1H), 2.36 (s, 3H), 1.14 (d, J = 6.80 Hz, 6H). | 2-(2-isopropylphenyl)-9-(4-(5-methyl-1H-1,2,3-triazol-1-yl)benzyl)-7,9-dihydro-8H-purin-8-one |
| I-186 | m/z: 414.3545 [M + H]⁺ Rt (min): 1.1933 | ¹H NMR (300 MHz, CD₃OD) δ 8.33 (s, 1H), 7.72 (d, J = 7.50 Hz, 1H), 7.62-7.50 (m, 2H), 7.48-7.35 (m, 3H), 7.27-7.22 (m, 1H), 5.25 (s, 2H), 4.45 (s, 2H), 3.32-3.14 (m, 4H), 1.11 (d, J = 6.90 Hz, 6H). | 2-(2-isopropylphenyl)-9-((2-methyl-1-oxoisoindolin-5-yl)methyl)-7,9-dihydro-8H-purin-8-one |
| I-187 | m/z: 428.3976 [M + H]⁺ Rt (min): 1.275 | | 6-((2-(2-isopropylphenyl)-8-oxo-7,8-dihydro-9H-purin-9-yl)methyl)-2-methyl-3,4-dihydroisoquinolin-1(2H)-one |
| I-188 | m/z: 445.3015 [M + H]⁺ Rt (min): 1.405 | | 2-(3-fluoro-2-isopropylphenyl)-9-(4-(5-methyl-1,2,4-oxadiazol-3-yl)benzyl)-7,9-dihydro-8H-purin-8-one |
| I-189 | m/z: 445.3235 [M + H]⁺ Rt (min): 1.405 | | 2-(3-fluoro-2-isopropylphenyl)-9-(4-(5-methyl-1,3,4-oxadiazol-2-yl)benzyl)-7,9-dihydro-8H-purin-8-one |
| I-190 | m/z: 453.36 [M + H]⁺ Rt (min): 1.6733 | | (R)-9-(1-(4-(3,5-dimethyl-1H-pyrazol-1-yl)phenyl)ethyl)-2-(2-isopropylphenyl)-7,9-dihydro-8H-purin-8-one |
| I-191 | m/z: 453.36 [M + H]⁺ Rt (min): 1.6733 | | (S)-9-(1-(4-(3,5-dimethyl-1H-pyrazol-1-yl)phenyl)ethyl)-2-(2-isopropylphenyl)-7,9-dihydro-8H-purin-8-one |
| I-192 | m/z: 535.4166 [M + H]⁺ Rt (min): | ¹H NMR (300 MHz, CD₃OD) δ 8.37-8.25 (m, 2H), 7.65-7.56 (m, 2H), 7.53-7.35 (m, 5H), 7.34-7.19 (m, 1H), 5.58-5.42 (m, 1H), 5.01- | 2-(2-isopropylphenyl)-9-(4-(1-(oxetan-3-yl)-4-(trifluoromethyl)-1H-imidazol-2-yl)benzyl)-7,9- |

TABLE 4-continued

| Cmpd no. | LCMS | ¹H NMR (300 MHz) δ ppm | Chemical Name |
|---|---|---|---|
| | 1.5183 | 4.77 (m, 7H), 3.42-3.24 (m, 1H), 1.13 (d, J = 6.9 Hz, 6H). | dihydro-8H-purin-8-one |
| I-193 | m/z: 511.42 [M + H]⁺ Rt (min): 1.6133 | ¹H NMR (400 MHz, CD₃OD) δ 8.33 (s, 1H), 7.70-7.53 (m, 5H), 7.31-7.21 (m, 2H), 7.16-7.06 (m, 1H), 5.21 (s, 2H), 3.74 (s, 3H), 3.21-3.09 (m, 1H), 1.28-1.25 (m, 6H). | 2-(3-fluoro-2-isopropylphenyl)-9-(4-(1-methyl-4-(trifluoromethyl)-1H-imidazol-2-yl)benzyl)-7,9-dihydro-8H-purin-8-one |
| I-194 | m/z: 493.413 [M + H]⁺ Rt (min): 1.815 | ¹H NMR (300 MHz, DMSO-d₆) δ 11.60 (s, 1H), 8.41 (s, 1H), 7.61-7.32 (m, 7H), 7.30-7.24 (m, 1H), 6.74 (s, 1H), 5.13 (s, 2H), 3.47-3.43 (m, 1H), 2.31 (s, 3H), 1.10-1.06 (m, 6H). | 2-(2-isopropylphenyl)-9-(4-(5-methyl-3-(trifluoromethyl)-1H-pyrazol-1-yl)benzyl)-7,9-dihydro-8H-purin-8-one |
| I-195 | m/z: 493.413 [M + H]⁺ Rt (min): 1.8133 | ¹H NMR (400 MHz, DMSO-d₆) δ 11.60 (s, 1H), 8.40 (s, 1H), 7.52-7.32 (m, 7H), 7.28-7.17 (m, 1H), 6.91 (s, 1H), 5.11 (s, 2H), 3.43-3.39 (m, 1H), 2.25 (s, 3H), 1.06 (d, J = 6.8 Hz, 6H). | 2-(2-isopropylphenyl)-9-(4-(3-methyl-5-(trifluoromethyl)-1H-pyrazol-1-yl)benzyl)-7,9-dihydro-8H-purin-8-one |
| I-196 | m/z: 436.3293 [M + H]⁺ Rt (min): 1.5983 | ¹H NMR (400 MHz, CD₃OD) δ 8.43 (s, 1H), 8.35 (s, 1H), 7.83-7.81 (m, 2H), 7.62-7.59 (m, 2H), 7.48-7.41 (m, 3H), 7.29-7.25 (m, 1H), 7.01 (d, J = 2.4 Hz, 1H), 5.22 (s, 2H), 3.30-3.26 (m, 1H), 1.15 (d, J = 7.2 Hz, 6H). | 1-(4-((2-(2-isopropylphenyl)-8-oxo-7,8-dihydro-9H-purin-9-yl)methyl)phenyl)-1H-pyrazole-3-carbonitrile |
| I-197 | m/z: 411.3013 [M + H]⁺ Rt (min): 1.525 | | 9-(3-(1H-pyrazol-1-yl)benzyl)-2-(2-isopropylphenyl)-7,9-dihydro-8H-purin-8-one |
| I-198 | m/z: 459.34 [M + H]⁺ Rt (min): 1.465 | ¹H NMR (400 MHz, DMSO-d₆) δ 11.65 (br s, 1H), 8.41 (s, 1H), 7.65 (d, J = 8.0 Hz, 2H), 7.52-7.50 (m, 1H), 7.48-7.34 (m, 5H), 7.26-7.23 (m, 1H), 5.10 (s, 2H), 3.69 (s, 3H), 3.48-3.41 (m, 1H), 1.10 (d, J = 6.8 Hz, 6H). | 9-(4-(4-chloro-1-methyl-1H-imidazol-2-yl)benzyl)-2-(2-isopropylphenyl)-7,9-dihydro-8H-purin-8-one |
| I-199 | m/z: 461.3603 [M + H]⁺ Rt (min): 1.61 | ¹H NMR (400 MHz, CD₃OD) δ 8.36 (s, 1H), 7.80-7.73 (m, 3H), 7.70-7.61 (m, 2H), 7.50-7.37 (m, 3H), 7.28-7.24 (m, 1H), 5.27 (s, 2H), 3.29-3.24 (m, 1H), 1.14 (d, J = 7.2 Hz, 6H). | 1-(4-((2-(2-isopropylphenyl)-8-oxo-7,8-dihydro-9H-purin-9-yl)methyl)phenyl)-1H-pyrazole-3,5-dicarbonitrile |
| I-200 | m/z: 440.36 [M + H]⁺ Rt (min): 1.595 | ¹H NMR (300 MHz, DMSO-d₆) δ 11.59 (br s, 1H), 8.40 (s, 1H), 7.60-7.58 (m, 2H), 7.52-7.50 (m, 1H), 7.43-7.37 (m, 4H), 7.27-7.23 (m, 1H), 5.05 (s, 2H), 3.46-3.42 (m, 1H), 2.45 (s, 3H), 2.38 (s, 3H), 1.08 (d, J = 6.8 Hz, 6H). | 9-(4-(2,5-dimethyloxazol-4-yl)benzyl)-2-(2-isopropylphenyl)-7,9-dihydro-8H-purin-8-one |
| I-201 | m/z: 553.5312 [M + H]⁺ Rt (min): 1.5633 | ¹H NMR (400 MHz, CD₃OD) δ 8.33 (s, 1H), 8.28 (s, 1H), 7.59 (d, J = 8.0 Hz, 2H), 7.47 (d, J = 8.0 Hz, 2H), 7.32-7.21 (m, 2H), 7.17-7.08 (m, 1H), 5.55-5.43 (m, 1H), 5.22 (s, 2H), 4.99-4.91 (m, 2H), 4.84-4.78 (m, 2H), 3.23-3.11 (m, 1H), 1.28 (d, J = 6.8 Hz, 6H). | 2-(3-fluoro-2-isopropylphenyl)-9-(4-(1-(oxetan-3-yl)-4-(trifluoromethyl)-1H-imidazol-2-yl)benzyl)-7,9-dihydro-8H-purin-8-one |
| I-202 | m/z: 499.46 [M + H]⁺ Rt (min): 0.86 | ¹H NMR (400 MHz, CD₃OD) δ 8.33 (s, 1H), 7.55 (d, J = 8.0 Hz, 2H), 7.50-7.38 (m, 3H), 7.34-7.24 (m, 2H), 7.19-7.09 (m, 1H), 5.49-5.37 (m, 1H), 5.22 (s, 2H), 5.02-4.90 (m, 2H), 4.88-4.78 (m, 2H), 3.24-3.12 (m, 1H), 2.27 (s, 3H), 1.30 (d, J = 6.8 Hz, 6H). | 2-(3-fluoro-2-isopropylphenyl)-9-(4-(4-methyl-1-(oxetan-3-yl)-1H-imidazol-2-yl)benzyl)-7,9-dihydro-8H-purin-8-one |
| I-203 | m/z: 440.36 [M + H]⁺ Rt (min): | | 9-((6-(1,4-dimethyl-1H-imidazol-2-yl)pyridin-3-yl)methyl)-2-(2-isopropylphenyl)-7,9-dihydro-8H-purin-8-one |
| I-204 | m/z: 441.4002 [M + H]⁺ Rt (min): | ¹H NMR (400 MHz, CD₃OD) δ 8.33 (s, 1H), 8.02 (d, J = 2.8 Hz, 1H), 7.66-7.62 (m, 2H), 7.55-7.41 (m, 5H), 7.29-7.26 (m, 1H), 5.94 | 2-(2-isopropylphenyl)-9-(4-(3-methoxy-1H-pyrazol-1-yl)benzyl)-7,9-dihydro-8H-purin-8-one |

TABLE 4-continued

| Cmpd no. | LCMS | ¹H NMR (300 MHz) δ ppm | Chemical Name |
|---|---|---|---|
| | 1.6167 | (d, J = 2.8 Hz, 1H), 5.16 (s, 2H), 3.94 (d, J = 2.8 Hz, 3H), 3.34-3.24 (m, 1H), 1.16 (d, J = 6.8 Hz, 6H). | |
| I-205 | m/z: 441.4 [M + H]⁺ Rt (min): 1.1117 | ¹H NMR (400 MHz, CD₃OD) δ 8.32 (s, 1H), 7.76 (d, J = 3.60 Hz, 1H), 7.63 (d, J = 8.40 Hz, 2H), 7.46-7.41 (m, 3H), 7.39-7.34 (m, 2H), 7.27-7.23 (m, 1H), 5.48 (d, J = 3.60 Hz, 1H), 5.20 (s, 2H), 3.35-3.32 (m, 1H), 3.22 (s, 3H), 1.23-1.13 (m, 6H). | 2-(2-isopropylphenyl)-9-(4-(2-methyl-5-oxo-2,5-dihydro-1H-pyrazol-1-yl)benzyl)-7,9-dihydro-8H-purin-8-one |
| I-206 | m/z: 441.4005 [M + H]⁺ Rt (min): 1.505 | ¹H NMR (400 MHz, CD₃OD) δ 8.34 (s, 1H), 7.61 (d, J = 8.8 Hz, 2H), 7.54-7.41 (m, 6H), 7.30-7.26 (m, 1H), 5.85 (d, J = 2.0 Hz, 1H), 5.19 (s, 2H), 3.97 (s, 3H), 3.32-3.27 (m, 1H), 1.15 (d, J = 6.8 Hz, 6H). | 2-(2-isopropylphenyl)-9-(4-(5-methoxy-1H-pyrazol-1-yl)benzyl)-7,9-dihydro-8H-purin-8-one |
| I-207 | m/z: 450.401 [M + H]⁺ Rt (min): 1.625 | ¹H NMR (300 MHz, DMSO-d₆) δ 11.52 (br s, 1H), 8.43 (s, 1H), 7.58 (d, J = 8.4 Hz, 2H), 7.52-7.50 (m, 3H), 7.44-7.37 (m, 2H), 7.28-7.22 (m, 1H), 6.98 (s, 1H), 5.14 (s, 2H), 3.48-3.35 (m, 1H), 2.32 (s, 3H), 1.09 (d, J = 6.90 Hz, 6H). | 1-(4-((2-(2-isopropylphenyl)-8-oxo-7,8-dihydro-9H-purin-9-yl)methyl)phenyl)-5-methyl-1H-pyrazole-3-carbonitrile |
| I-208 | m/z: 450.3727 [M + H]⁺ Rt (min): 1.6683 | ¹H NMR (300 MHz, DMSO-d₆) δ 8.42 (s, 1H), 7.67 (d, J = 8.4 Hz, 2H), 7.55-7.52 (m, 3H), 7.44-7.37(m, 2H), 7.27-7.22 (m, 2H), 5.13 (s, 2H), 3.48-3.37 (m, 1H), 2.32 (s, 3H), 1.08 (d, J = 6.9 Hz, 6H). | 1-(4-((2-(2-isopropylphenyl)-8-oxo-7,8-dihydro-9H-purin-9-yl)methyl)phenyl)-3-methyl-1H-pyrazole-5-carbonitrile |
| I-209 | m/z: 494.3882 [M + H]⁺ Rt (min): 1.6516 | | 2-(2-isopropylphenyl)-9-(4-(1-methyl-3-(trifluoromethyl)-1H-1,2,4-triazol-5-yl)benzyl)-7,9-dihydro-8H-purin-8-one |
| I-210 | m/z: 459.3448 [M + H]⁺ Rt (min): 1.7817 | ¹H NMR (400 MHz, DMSO-d₆) δ 11.58 (br s, 1H), 8.39 (s, 1H), 7.50-7.44 (m, 5H), 7.41-7.37 (m, 2H), 7.24-7.20 (m, 1H), 6.34 (s, 1H), 5.09 (s, 2H), 3.45-3.38 (m, 1H), 2.25 (s, 3H), 1.08-1.02 (m, 6H). | 9-(4-(3-chloro-5-methyl-1H-pyrazol-1-yl)benzyl)-2-(2-isopropylphenyl)-7,9-dihydro-8H-purin-8-one |
| I-211 | m/z: 459.3448 [M + H]⁺ Rt (min): 1.7864 | ¹H NMR (400 MHz, CD₃OD) δ 8.33 (s, 1H), 7.59-7.57 (m, 2H), 7.49-7.38 (m, 5H), 7.27-7.23 (m, 1H), 6.32 (s, 1H), 5.21 (s, 2H), 3.35-3.31 (m, 1H), 2.26 (s, 3H), 1.19-1.13 (m, 6H). | 9-(4-(5-chloro-3-methyl-1H-pyrazol-1-yl)benzyl)-2-(2-isopropylphenyl)-7,9-dihydro-8H-purin-8-one |
| I-212 | m/z: 445.4 [M + H]⁺ Rt (min): 1.5142 | ¹H NMR (400 MHz, CD₃OD) δ 8.30 (s, 1H), 7.48-7.40 (m, 3H), 7.28-7.24(m, 1H), 5.76 (s, 1H), 4.04-4.00 (m, 1H), 3.87-3.85 (m, 2H), 3.39-3.30 (m, 1H), 2.21 (s, 3H), 2.08-2.01 (m, 4H), 1.88-1.84 (m, 6H), 1.39-1.32 (m, 8H). | 9-(((1s,4s)-4-(3,5-dimethyl-1H-pyrazol-1-yl)cyclohexyl)methyl)-2-(2-isopropylphenyl)-7,9-dihydro-8H-purin-8-one |
| I-213 | m/z: 445.4 [M + H]⁺ Rt (min): 1.5667 | ¹H NMR (400 MHz, CDCl₃) δ 8.29 (s, 1H), 7.44-7.37 (m, 3H), 7.25-7.20 (m, 1H), 5.79 (s, 1H), 4.17-4.15 (m, 2H), 4.09-4.02 (m, 1H), 3.56-3.29 (m, 1H), 2.40-2.38 (m, 1H), 2.33-2.22 (m, 5H), 2.15 (s, 3H), 1.84-1.81 (m, 2H), 1.76-1.70 (m, 4H), 1.17 (d, J = 6.80 Hz, 6H). | 9-(((1r,4r)-4-(3,5-dimethyl-1H-pyrazol-1-yl)cyclohexyl)methyl)-2-(2-isopropylphenyl)-7,9-dihydro-8H-purin-8-one |
| I-214 | m/z: 507.4 [M + H]⁺ Rt (min): 1.6617 | ¹H NMR (400 MHz, CD₃OD) δ 8.31 (d, J = 2.80 Hz, 1H), 7.67-7.61 (m, 5H), 7.45-7.38 (m, 3H), 7.27-7.22 (m, 1H), 5.91-5.83 (m, 1H), 3.75 (s, 3H), 3.42-3.32 (m, 1H), 2.10 (d, J = 7.20 Hz, 3H), 1.21-1.10 (m, 6H). | (R)-2-(2-isopropylphenyl)-9-(1-(4-(1-methyl-4-(trifluoromethyl)-1H-imidazol-2-yl)phenyl)ethyl)-7,9-dihydro-8H-purin-8-one |
| I-215 | m/z: 507.4 [M + H]⁺ Rt (min): 1.6609 | ¹H NMR (400 MHz, CD₃OD) δ 8.31 (s, 1H), 7.70-7.59 (m, 5H), 7.47-7.36 (m, 3H), 7.29-7.20 (m, 1H), 5.93-5.83 (m, 1H), 3.75 (s, 3H), 3.42-3.32 (m, 1H), 2.10 (d, J = 7.60 Hz, 3H), 1.21-1.10 (m, 6H). | (S)-2-(2-isopropylphenyl)-9-(1-(4-(1-methyl-4-(trifluoromethyl)-1H-imidazol-2-yl)phenyl)ethyl)-7,9-dihydro-8H-purin-8-one |

TABLE 4-continued

| Cmpd no. | LCMS | ¹H NMR (300 MHz) δ ppm | Chemical Name |
|---|---|---|---|
| I-216 | m/z: 429.2632 [M + H]⁺ Rt (min): 1.7009 | | 9-(4-(3,3-dimethyloxetan-2-yl)benzyl)-2-(2-isopropylphenyl)-7,9-dihydro-8H-purin-8-one |
| I-217 | m/z: 402.1073 [M + H]⁺ Rt (min): 1.26 | | N-(3-((2-(2-isopropylphenyl)-8-oxo-7,8-dihydro-9H-purin-9-yl)methyl)phenyl)acetamide |
| I-218 | m/z: 402.1415 [M + H]⁺ Rt (min): 1.22 | | N-(4-((2-(2-isopropylphenyl)-8-oxo-7,8-dihydro-9H-purin-9-yl)methyl)phenyl)acetamide |
| I-219 | m/z: 493.35 [M + H]⁺ Rt (min): 1.5436 | ¹H NMR (400 MHz, CD₃OD) δ 8.33 (s, 1H), 7.63-7.58 (m, 4H), 7.53-7.52 (m, 1H), 7.46-7.38 (m, 3H), 7.26-7.22 (m, 1H), 5.22 (s, 2H), 3.75 (s, 3H), 3.35-3.28 (m, 1H), 1.15 (d, J = 7.2 Hz, 6H). | 2-(2-isopropylphenyl)-9-(4-(1-methyl-5-(trifluoromethyl)-1H-imidazol-2-yl)benzyl)-7,9-dihydro-8H-purin-8-one |
| I-220 | m/z: 470.4105 [M + H]⁺ Rt (min): 1.6785 | ¹H NMR (300 MHz, CDCl₃): δ 9.47 (s, 1H), 8.30 (s, 1H), 7.49 (d, J = 7.3 Hz, 1H), 7.39-7.31 (m, 2H), 7.21 (br d, J = 7.9 Hz, 1H), 4.09 (br d, J = 18.5 Hz, 2H), 3.94 (br s, 2H), 3.40 (br d, J = 6.7 Hz, 1H), 2.97 (br s, 2H), 1.78 (m, 2H), 1.72-1.57 (m, 2H), 1.37 (s, 9H), 1.16 (d, J = 6.7 Hz, 6H). | tert-butyl 4-fluoro-4-((2-(2-isopropylphenyl)-8-oxo-7,8-dihydro-9H-purin-9-yl)methyl)piperidine-1-carboxylate |
| I-221 | m/z: 494.3265 [M + H]⁺ Rt (min): 1.06 | | 2-(2-isopropylphenyl)-9-(4-(4-(piperidin-4-yl)-1H-pyrazol-1-yl)benzyl)-7,9-dihydro-8H-purin-8-one |
| I-222 | m/z: 480.19 [M + H]⁺ Rt (min): 0.88 | ¹H NMR (400 MHz, CDCl₃) δ 8.30 (s, 1H), 7.77 (s, 1H), 7.57-7.50 (m, 5H), 7.45-7.40 (m, 2H), 7.29-7.26 (m, 1H), 6.26 (s, 1H), 5.14 (s, 2H), 3.54-3.45 (m, 2H), 3.44-3.30 (m, 1H), 3.20-3.15 (m, 1H), 3.13-2.91 (m, 2H), 2.27-2.18 (m, 2H), 2.04-1.95 (m, 1H), 1.25-1.21 (m, 6H). | 2-(2-isopropylphenyl)-9-(4-(3-(pyrrolidin-3-yl)-1H-pyrazol-1-yl)benzyl)-7,9-dihydro-8H-purin-8-one |
| I-223 | m/z: 494.23 [M + H]⁺ Rt (min): 0.92 | ¹H NMR (400 MHz, CD₃OD) δ 8.30 (s, 1H), 8.10 (s, 1H), 7.69-7.67 (m, 2H), 7.53-7.50 (m, 2H), 7.45-7.38 (m, 3H), 7.27-7.23 (m, 1H), 6.37 (s, 1H), 5.16 (s, 2H), 3.30-3.24 (m, 1H), 3.13-3.10 (m, 1H), 2.98-2.88 (m, 2H), 2.76-2.73 (m, 1H), 2.14-2.11 (m, 1H), 1.85-1.83 (m, 1H), 1.78-1.66 (m, 2H), 1.29 (s, 1H), 1.14-1.12 (m, 6H). | 2-(2-isopropylphenyl)-9-(4-(3-(piperidin-3-yl)-1H-pyrazol-1-yl)benzyl)-7,9-dihydro-8H-purin-8-one |
| I-224 | m/z: 494.21 [M + H]⁺ Rt (min): 0.92 | | (R)-2-(2-isopropylphenyl)-9-(4-(3-(piperidin-3-yl)-1H-pyrazol-1-yl)benzyl)-7,9-dihydro-8H-purin-8-one |
| I-225 | m/z: 494.23 [M + H]⁺ Rt (min): 0.92 | | (S)-2-(2-isopropylphenyl)-9-(4-(3-(piperidin-3-yl)-1H-pyrazol-1-yl)benzyl)-7,9-dihydro-8H-purin-8-one |
| I-226 | m/z: 437.3696 [M + H]⁺ Rt (min): 1.5706 | ¹H NMR (300 MHz, CDCl₃) δ 10.03-9.90 (m, 1H), 8.29 (s, 1H), 7.77 (d, J = 2.3 Hz, 1H), 7.61 (d, J = 1.2 Hz, 1H), 7.57-7.47 (m, 5H), 7.42-7.33 (m, 2H), 7.26-7.19 (m, 1H), 6.35 (d, J = 2.1 Hz, 1H), 3.46 (br d, J = 6.7 Hz, 1H), 1.70-1.51 (m, 4H), 1.17 (d, J = 6.7 Hz, 6H). | 9-(1-(4-(1H-pyrazol-1-yl)phenyl)cyclopropyl)-2-(2-isopropylphenyl)-7,9-dihydro-8H-purin-8-one |
| I-227 | m/z: 389.2778 [M + H]⁺ | ¹H NMR (300 MHz, CDCl₃) δ 9.62 (br s, 1H), 8.22 (s, 1H), 7.55 (d, J = 7.6 Hz, 1H), 7.51-7.43 (m, 2H), | 9-(1-(4-fluorophenyl)cyclopropyl)-2-(2-isopropylphenyl)-7,9- |

TABLE 4-continued

| Cmpd no. | LCMS | ¹H NMR (300 MHz) δ ppm | Chemical Name |
|---|---|---|---|
| | Rt (min): 1.6785 | 7.43-7.34 (m, 2H), 7.27-7.20 (m, 1H), 6.91-6.86 (m, 2H), 3.57-3.45 (m, 1H), 1.65-1.58 (m, 4H), 1.19 (d, J = 6.7 Hz, 6H). | dihydro-8H-purin-8-one |

Library Protocol A.

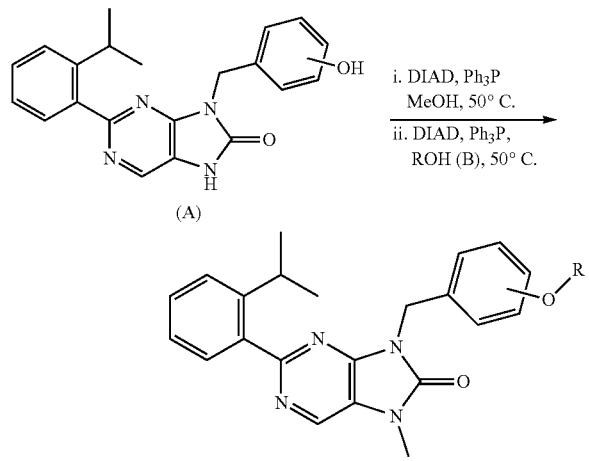

Note: All reagents in this protocol were used as 0.2M solutions in anhydrous THF. Under an atmosphere of nitrogen, a mixture of phenol (A) (either Intermediate B-94 or B-96) (150 μL, 0.030 mmol), MeOH (165 μL, 0.033 mmol) and triphenylphosphine (180 μL, 0.036 mmol) was treated with diisopropyl azodicarboxylate (180 μL, 0.036 mmol) and the mixture was heated to 50° C. After 2 h, additional triphenylphosphine (180 μL, 0.036 mmol) and diisopropyl azodicarboxylate (180 μL, 0.036 mmol) were added and the mixture heated to 50° C. for 2 h. The solution was concentrated, taken up in anhydrous THF (400 uL), and alcohol (B) (150 μl, 30.0 μmol) and triphenylphosphine (150 μl, 30.0 μmol) were added. The vial was flushed with nitrogen, diisopropyl azodicarboxylate (180 μL, 0.036 mmol) was added, and the reaction mixture was heated to 50° C. After 2 h, additional triphenylphosphine (180 μL, 0.036 mmol) and diisopropyl azodicarboxylate (180 μL, 0.036 mmol) were added and the mixture stirred another 2 h at 50° C. The reaction mixture was concentrated and partitioned between 1N NaOH (0.5 mL) and EtOAc (0.5 mL). The organic layer was separated and the aqueous phase was extracted with EtOAc. The combined organic extracts were concentrated to afford the crude product, which was purified by mass-triggered preparatory HPLC. The product-containing fractions were combined and concentrated in a Genevac to afford the desired product.

TABLE 5

The following compounds were synthesized according to Library Protocol A:

| Cmpd no. | LCMS | Chemical Name |
|---|---|---|
| I-228 | m/z: 429.2763 [M + H]⁺ Rt (min): 1.91 | 9-(4-(cyclopropylmethoxy)benzyl)-2-(2-isopropylphenyl)-7-methyl-7,9-dihydro-8H-purin-8-one |
| I-229 | m/z: 459.2066 [M + H]⁺ Rt (min): 1.7 | 2-(2-isopropylphenyl)-7-methyl-9-(4-((tetrahydrofuran-3-yl)methoxy)benzyl)-7,9-dihydro-8H-purin-8-one |
| I-230 | m/z: 486.3091 [M + H]⁺ Rt (min): 1.21 | 2-(2-isopropylphenyl)-7-methyl-9-(4-((1-methylpiperidin-3-yl)methoxy)benzyl)-7,9-dihydro-8H-purin-8-one |
| I-231 | m/z: 466.2258 [M + H]⁺ Rt (min): 1.64 | 2-(2-isopropylphenyl)-7-methyl-9-(4-(pyridin-2-ylmethoxy)benzyl)-7,9-dihydro-8H-purin-8-one |
| I-232 | m/z: 469.2157 [M + H]⁺ Rt (min): 1.16 | 2-(2-isopropylphenyl)-7-methyl-9-(4-((1-methyl-1H-imidazol-5-yl)methoxy)benzyl)-7,9-dihydro-8H-purin-8-one |
| I-233 | m/z: 446.2729 [M + H]⁺ Rt (min): 1.11 | 9-(4-(2-(dimethylamino)ethoxy)benzyl)-2-(2-isopropylphenyl)-7-methyl-7,9-dihydro-8H-purin-8-one |
| I-234 | m/z: 460.2465 [M + H]⁺ Rt (min): 1.16 | 9-(4-(3-(dimethylamino)propoxy)benzyl)-2-(2-isopropylphenyl)-7-methyl-7,9-dihydro-8H-purin-8-one |
| I-235 | m/z: 470.2162 [M + H]⁺ Rt (min): 1.73 | 2-(2-isopropylphenyl)-7-methyl-9-(4-((5-methylisoxazol-3-yl)methoxy)benzyl)-7,9-dihydro-8H-purin-8-one |
| I-236 | m/z: 447.2477 [M + H]⁺ Rt (min): 1.76 | 9-(4-(2-ethoxyethoxy)benzyl)-2-(2-isopropylphenyl)-7-methyl-7,9-dihydro-8H-purin-8-one |
| I-237 | m/z: 429.2447 [M + H]⁺ Rt (min): 1.99 | 9-(4-cyclobutoxybenzyl)-2-(2-isopropylphenyl)-7-methyl-7,9-dihydro-8H-purin-8-one |
| I-238 | m/z: 459.2066 [M + H]⁺ Rt (min): 1.7 | 2-(2-isopropylphenyl)-7-methyl-9-(4-((tetrahydro-2H-pyran-4-yl)oxy)benzyl)-7,9-dihydro-8H-purin-8-one |

TABLE 5-continued

The following compounds were synthesized according to Library Protocol A:

| Cmpd no. | LCMS | Chemical Name |
| --- | --- | --- |
| I-239 | m/z: 429.2409 [M + H]+ Rt (min): 1.93 | 9-(3-(cyclopropylmethoxy)benzyl)-2-(2-isopropylphenyl)-7-methyl-7,9-dihydro-8H-purin-8-one |
| I-240 | m/z: 459.24 [M + H]+ Rt (min): 1.73 | 2-(2-isopropylphenyl)-7-methyl-9-(3-((tetrahydrofuran-3-yl)methoxy)benzyl)-7,9-dihydro-8H-purin-8-one |
| I-241 | m/z: 486.3091 [M + H]+ Rt (min): 1.23 | 2-(2-isopropylphenyl)-7-methyl-9-(3-((1-methylpiperidin-3-yl)methoxy)benzyl)-7,9-dihydro-8H-purin-8-one |
| I-242 | m/z: 466.226 [M + H]+ Rt (min): 1.66 | 2-(2-isopropylphenyl)-7-methyl-9-(3-(pyridin-2-ylmethoxy)benzyl)-7,9-dihydro-8H-purin-8-one |
| I-243 | m/z: 469.2407 [M + H]+ Rt (min): 1.18 | 2-(2-isopropylphenyl)-7-methyl-9-(3-((1-methyl-1H-imidazol-5-yl)methoxy)benzyl)-7,9-dihydro-8H-purin-8-one |
| I-244 | m/z: 446.2659 [M + H]+ Rt (min): 1.12 | 9-(3-(2-(dimethylamino)ethoxy)benzyl)-2-(2-isopropylphenyl)-7-methyl-7,9-dihydro-8H-purin-8-one |
| I-245 | m/z: 460.2729 [M + H]+ Rt (min): 1.17 | 9-(3-(3-(dimethylamino)propoxy)benzyl)-2-(2-isopropylphenyl)-7-methyl-7,9-dihydro-8H-purin-8-one |
| I-246 | m/z: 429.2447 [M + H]+ Rt (min): 2.01 | 9-(3-cyclobutoxybenzyl)-2-(2-isopropylphenyl)-7-methyl-7,9-dihydro-8H-purin-8-one |

Library Protocol B.

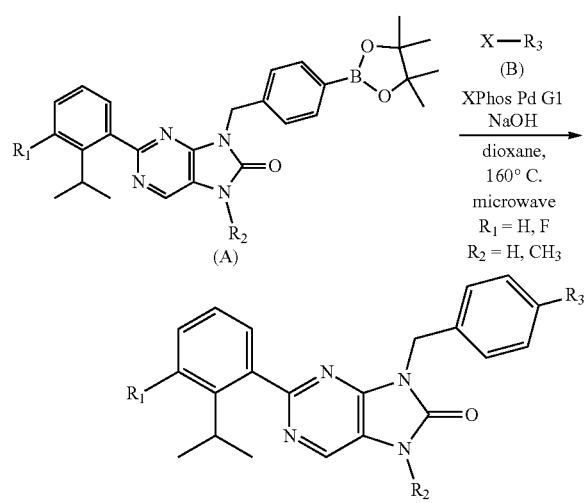

Under nitrogen, a mixture of boronic ester (A) (either Intermediate B-79, B-83, B-86 or B-101) (0.2M in dioxane, 150 μL, 30.0 μmol), aryl halide (B) (0.2M in dioxane, 225 μL, 45.0 μmol), 1N NaOH (100 μL, 100 μmol) and XPhos Pd G1 (0.02M in dioxane, 70 μL, 1.400 mol) was heated for 20 min at 160° C. in a Biotage Initiator microwave. The reaction mixture was concentrated and partitioned between 1N NaOH (0.5 mL) and EtOAc (0.5 mL). The organic layer was separated and the aqueous phase was extracted with EtOAc. The combined organic extracts were concentrated to afford the crude product, which was purified by mass-triggered preparatory HPLC. The product-containing fractions were combined and concentrated in a Genevac to afford the desired product.

Table 6. The following compounds were synthesized according to Library Protocol B.

TABLE 6

| Cmpd no. | LCMS | Chemical Name |
| --- | --- | --- |
| I-247 | m/z: 423.0857 [M + H]+ Rt (min): 1.43 | 2-(2-isopropylphenyl)-9-(4-(pyrazin-2-yl)benzyl)-7,9-dihydro-8H-purin-8-one |
| I-248 | m/z: 492.2152 [M + H]+ Rt (min): 1.23 | 9-((3'-(2-(dimethylamino)ethyl)-[1,1'-biphenyl]-4-yl)methyl)-2-(2-isopropylphenyl)-7,9-dihydro-8H-purin-8-one |
| I-249 | m/z: 492.2184 [M + H]+ Rt (min): 1.19 | 9-((4'-(2-(dimethylamino)ethyl)-[1,1'-biphenyl]-4-yl)methyl)-2-(2-isopropylphenyl)-7,9-dihydro-8H-purin-8-one |
| I-250 | m/z: 508.2132 [M + H]+ Rt (min): 1.27 | 2-(2-isopropylphenyl)-9-(4-(6-morpholinopyrimidin-4-yl)benzyl)-7,9-dihydro-8H-purin-8-one |
| I-251 | m/z: 425.1005 [M + H]+ Rt (min): 1.01 | 2-(2-isopropylphenyl)-9-(4-(1-methyl-1H-imidazol-5-yl)benzyl)-7,9-dihydro-8H-purin-8-one |

TABLE 6-continued

| Cmpd no. | LCMS | Chemical Name |
|---|---|---|
| I-252 | m/z: 439.1402 [M + H]+ Rt (min): 1.42 | 9-(4-(1,5-dimethyl-1H-pyrazol-4-yl)benzyl)-2-(2-isopropylphenyl)-7,9-dihydro-8H-purin-8-one |
| I-253 | m/z: 440.0798 [M + H]+ Rt (min): 1.59 | 9-(4-(3,5-dimethylisoxazol-4-yl)benzyl)-2-(2-isopropylphenyl)-7,9-dihydro-8H-purin-8-one |
| I-254 | m/z: 483.1449 [M + H]+ Rt (min): 1.22 | 2-(4-(4-((2-(2-isopropylphenyl)-8-oxo-7,8-dihydro-9H-purin-9-yl)methyl)phenyl)-1-methyl-1H-pyrazol-5-yl)acetic acid |
| I-255 | m/z: 423.0856 [M + H]+ Rt (min): 1.48 | 2-(2-isopropylphenyl)-9-(4-(pyrimidin-2-yl)benzyl)-7,9-dihydro-8H-purin-8-one |
| I-256 | m/z: 425.1726 [M + H]+ Rt (min): 1.02 | 2-(2-isopropylphenyl)-9-(4-(1-methyl-1H-pyrazol-5-yl)benzyl)-7,9-dihydro-8H-purin-8-one |
| I-257 | m/z: 439.1 [M + H]+ Rt (min): 1.04 | 2-(2-isopropylphenyl)-7-methyl-9-(4-(1-methyl-1H-imidazol-2-yl)benzyl)-7,9-dihydro-8H-purin-8-one |
| I-258 | m/z: 453.16 [M + H]+ Rt (min): 0.88 | 9-(4-(1,4-dimethyl-1H-imidazol-2-yl)benzyl)-2-(2-isopropylphenyl)-7-methyl-7,9-dihydro-8H-purin-8-one |
| I-259 | m/z: 522.29 [M + H]+ Rt (min): 1.11 | 9-((2'-(2-(dimethylamino)ethoxy)-[1,1'-biphenyl]-4-yl)methyl)-2-(2-isopropylphenyl)-7-methyl-7,9-dihydro-8H-purin-8-one |
| I-260 | m/z: 522.29 [M + H]+ Rt (min): 1.08 | 9-((3'-(2-(dimethylamino)ethoxy)-[1,1'-biphenyl]-4-yl)methyl)-2-(2-isopropylphenyl)-7-methyl-7,9-dihydro-8H-purin-8-one |
| I-261 | m/z: 522.24 [M + H]+ Rt (min): 1.06 | 9-((4'-(2-(dimethylamino)ethoxy)-[1,1'-biphenyl]-4-yl)methyl)-2-(2-isopropylphenyl)-7-methyl-7,9-dihydro-8H-purin-8-one |
| I-262 | m/z: 506.25 [M + H]+ Rt (min): 1.06 | 9-((4'-(2-(dimethylamino)ethyl)-[1,1'-biphenyl]-4-yl)methyl)-2-(2-isopropylphenyl)-7-methyl-7,9-dihydro-8H-purin-8-one |
| I-263 | m/z: 522.24 [M + H]+ Rt (min): 1.1 | 2-(2-isopropylphenyl)-7-methyl-9-(4-(6-morpholinopyrimidin-4-yl)benzyl)-7,9-dihydro-8H-purin-8-one |
| I-264 | m/z: 439.18 [M + H]+ Rt (min): 0.88 | 2-(2-isopropylphenyl)-7-methyl-9-(4-(1-methyl-1H-imidazol-5-yl)benzyl)-7,9-dihydro-8H-purin-8-one |
| I-265 | m/z: 481.2228 [M + H]+ Rt (min): 1.54 | 9-(4-(6,7-dihydro-4H-pyrazolo[5,1-c][1,4]oxazin-3-yl)benzyl)-2-(2-isopropylphenyl)-7-methyl-7,9-dihydro-8H-purin-8-one |
| I-266 | m/z: 476.16 [M + H]+ Rt (min): 1.54 | 9-(4-([1,2,4]triazolo[1,5-a]pyridin-5-yl)benzyl)-2-(2-isopropylphenyl)-7-methyl-7,9-dihydro-8H-purin-8-one |
| I-267 | m/z: 476.1638 [M + H]+ Rt (min): 1.77 | 9-(4-(benzo[d]isoxazol-7-yl)benzyl)-2-(2-isopropylphenyl)-7-methyl-7,9-dihydro-8H-purin-8-one |
| I-268 | m/z: 475.189 [M + H]+ Rt (min): 1.76 | 9-(4-(1H-indazol-7-yl)benzyl)-2-(2-isopropylphenyl)-7-methyl-7,9-dihydro-8H-purin-8-one |
| I-269 | m/z: 475.19 [M + H]+ Rt (min): 0.94 | 9-(4-(imidazo[1,2-a]pyridin-8-yl)benzyl)-2-(2-isopropylphenyl)-7-methyl-7,9-dihydro-8H-purin-8-one |
| I-270 | m/z: 475.19 [M + H]+ Rt (min): 0.95 | 9-(4-(imidazo[1,2-a]pyridin-5-yl)benzyl)-2-(2-isopropylphenyl)-7-methyl-7,9-dihydro-8H-purin-8-one |
| I-271 | m/z: 439.18 [M + H]+ Rt (min): | 2-(2-isopropylphenyl)-7-methyl-9-(4-(1-methyl-1H-imidazol-4-yl)benzyl)-7,9-dihydro-8H-purin-8-one |
| I-272 | m/z: 440.1596 [M + H]+ Rt (min): 1.38 | 2-(2-isopropylphenyl)-7-methyl-9-(4-(1-methyl-1H-1,2,4-triazol-3-yl)benzyl)-7,9-dihydro-8H-purin-8-one |
| I-273 | m/z: 425.2638 [M + H]+ Rt (min): 2.3761 | 2-(2-isopropylphenyl)-9-(4-(1-methyl-1H-imidazol-4-yl)benzyl)-7,9-dihydro-8H-purin-8-one |
| I-274 | m/z: 426.12 [M + H]+ Rt (min): | 2-(2-isopropylphenyl)-9-(4-(1-methyl-1H-1,2,4-triazol-3-yl)benzyl)-7,9-dihydro-8H-purin-8-one |
| I-275 | m/z: 453.36 [M + H]+ Rt (min): 0.9183 | 9-(4-(1-isopropyl-1H-imidazol-4-yl)benzyl)-2-(2-isopropylphenyl)-7,9-dihydro-8H-purin-8-one |
| I-276 | m/z: 453.36 [M + H]+ Rt (min): 0.8827 | 9-(4-(1,2-dimethyl-1H-imidazol-4-yl)benzyl)-2-(2-isopropylphenyl)-7-methyl-7,9-dihydro-8H-purin-8-one |
| I-277 | m/z: 467.38 [M + H]+ Rt (min): 0.9771 | 9-(4-(1-isopropyl-1H-imidazol-4-yl)benzyl)-2-(2-isopropylphenyl)-7-methyl-7,9-dihydro-8H-purin-8-one |

TABLE 6-continued

| Cmpd no. | LCMS | Chemical Name |
|---|---|---|
| I-278 | m/z: 483.4002 [M + H]+ Rt (min): 1.4357 | 3-(4-((2-(2-isopropylphenyl)-7-methyl-8-oxo-7,8-dihydro-9H-purin-9-yl)methyl)phenyl)-1-methyl-1H-1,2,4-triazole-5-carboxamide |
| I-279 | m/z: 454.34 [M + H]+ Rt (min): 1.3892 | 9-(4-(1,5-dimethyl-1H-1,2,4-triazol-3-yl)benzyl)-2-(2-isopropylphenyl)-7-methyl-7,9-dihydro-8H-purin-8-one |
| I-280 | m/z: 508.3663 [M + H]+ Rt (min): 1.8404 | 2-(2-isopropylphenyl)-7-methyl-9-(4-(1-methyl-5-(trifluoromethyl)-1H-1,2,4-triazol-3-yl)benzyl)-7,9-dihydro-8H-purin-8-one |
| I-281 | m/z: 470.3911 [M + H]+ Rt (min): 1.62 | 2-(2-isopropylphenyl)-9-(4-(5-methoxy-1-methyl-1H-1,2,4-triazol-3-yl)benzyl)-7-methyl-7,9-dihydro-8H-purin-8-one |
| I-282 | m/z: 525.47 [M + H]+ Rt (min): 1.5302 | 2-(2-isopropylphenyl)-7-methyl-9-(4-(1-methyl-5-morpholino-1H-1,2,4-triazol-3-yl)benzyl)-7,9-dihydro-8H-purin-8-one |
| I-283 | m/z: 454.34 [M + H]+ Rt (min): 1.3517 | 9-(4-(1,3-dimethyl-1H-1,2,4-triazol-5-yl)benzyl)-2-(2-isopropylphenyl)-7-methyl-7,9-dihydro-8H-purin-8-one |
| I-284 | m/z: 467.37 [M + H]+ Rt (min): 1.773 | 9-(4-(1-isopropyl-1H-pyrazol-5-yl)benzyl)-2-(2-isopropylphenyl)-7-methyl-7,9-dihydro-8H-purin-8-one |
| I-285 | m/z: 440.2952 [M + H]+ Rt (min): 1.4334 | 2-(2-isopropylphenyl)-7-methyl-9-(4-(1-methyl-1H-1,2,3-triazol-5-yl)benzyl)-7,9-dihydro-8H-purin-8-one |
| I-286 | m/z: 476.38 [M + H]+ Rt (min): | 9-(4-([1,2,4]triazolo[4,3-a]pyridin-3-yl)benzyl)-2-(2-isopropylphenyl)-7-methyl-7,9-dihydro-8H-purin-8-one |
| I-287 | m/z: 440.2953 [M + H]+ Rt (min): 1.4222 | 2-(2-isopropylphenyl)-7-methyl-9-(4-(1-methyl-1H-1,2,3-triazol-4-yl)benzyl)-7,9-dihydro-8H-purin-8-one |
| I-288 | m/z: 469.36 [M + H]+ Rt (min): 0.825 | 9-(4-(5-(hydroxymethyl)-1-methyl-1H-imidazol-4-yl)benzyl)-2-(2-isopropylphenyl)-7-methyl-7,9-dihydro-8H-purin-8-one |
| I-289 | m/z: 476.31 [M + H]+ Rt (min): 1.4959 | 9-(4-(imidazo[1,2-a]pyrazin-8-yl)benzyl)-2-(2-isopropylphenyl)-7-methyl-7,9-dihydro-8H-purin-8-one |
| I-290 | m/z: 440.3368 [M + H]+ Rt (min): 1.7325 | 2-(2-isopropylphenyl)-7-methyl-9-(4-(4-methyloxazol-2-yl)benzyl)-7,9-dihydro-8H-purin-8-one |
| I-291 | m/z: 462.34 [M + H]+ Rt (min): 1.3534 | 9-(4-(imidazo[1,2-a]pyrazin-8-yl)benzyl)-2-(2-isopropylphenyl)-7,9-dihydro-8H-purin-8-one |
| I-292 | m/z: 511.42 [M + H]+ Rt (min): 1.3952 | 2-(2-isopropylphenyl)-9-(4-(1-methyl-5-morpholino-1H-1,2,4-triazol-3-yl)benzyl)-7,9-dihydro-8H-purin-8-one |
| I-293 | m/z: 494.3611 [M + H]+ Rt (min): 1.7055 | 2-(2-isopropylphenyl)-9-(4-(1-methyl-5-(trifluoromethyl)-1H-1,2,4-triazol-3-yl)benzyl)-7,9-dihydro-8H-purin-8-one |
| I-294 | m/z: 440.36 [M + H]+ Rt (min): 1.27 | 9-(4-(1,5-dimethyl-1H-1,2,4-triazol-3-yl)benzyl)-2-(2-isopropylphenyl)-7,9-dihydro-8H-purin-8-one |
| I-295 | m/z: 456.3541 [M + H]+ Rt (min): 1.4762 | 2-(2-isopropylphenyl)-9-(4-(5-methoxy-1-methyl-1H-1,2,4-triazol-3-yl)benzyl)-7,9-dihydro-8H-purin-8-one |
| I-296 | m/z: 440.36 [M + H]+ Rt (min): 1.2334 | 9-(4-(1,3-dimethyl-1H-1,2,4-triazol-5-yl)benzyl)-2-(2-isopropylphenyl)-7,9-dihydro-8H-purin-8-one |
| I-297 | m/z: 455.35 [M + H]+ Rt (min): 0.7613 | 9-(4-(5-(hydroxymethyl)-1-methyl-1H-imidazol-4-yl)benzyl)-2-(2-isopropylphenyl)-7,9-dihydro-8H-purin-8-one |
| I-298 | m/z: 426.3171 [M + H]+ Rt (min): 1.719 | 2-(2-isopropylphenyl)-9-(4-(1-methyl-1H-1,2,3-triazol-5-yl)benzyl)-7,9-dihydro-8H-purin-8-one |
| I-299 | m/z: 453.37 [M + H]+ Rt (min): 1.638 | 9-(4-(1-isopropyl-1H-pyrazol-5-yl)benzyl)-2-(2-isopropylphenyl)-7,9-dihydro-8H-purin-8-one |
| I-300 | m/z: 442.34 [M + H]+ Rt (min): 1.638 | 2-(2-isopropylphenyl)-9-(4-(5-methylthiazol-4-yl)benzyl)-7,9-dihydro-8H-purin-8-one |
| I-301 | m/z: 456.35 [M + H]+ Rt (min): 1.7083 | 9-(4-(2,5-dimethylthiazol-4-yl)benzyl)-2-(2-isopropylphenyl)-7,9-dihydro-8H-purin-8-one |
| I-302 | m/z: 458.34 [M + H]+ Rt (min): 1.2917 | 9-(4-(5-(hydroxymethyl)thiazol-4-yl)benzyl)-2-(2-isopropylphenyl)-7,9-dihydro-8H-purin-8-one |
| I-303 | m/z: 456.3541 [M + H]+ Rt (min): 1.7476 | 2-(2-isopropylphenyl)-7-methyl-9-(4-(5-methylthiazol-4-yl)benzyl)-7,9-dihydro-8H-purin-8-one |

TABLE 6-continued

| Cmpd no. | LCMS | Chemical Name |
|---|---|---|
| I-304 | m/z: 470.4 [M + H]+ Rt (min): 1.86 | 9-(4-(2,5-dimethylthiazol-4-yl)benzyl)-2-(2-isopropylphenyl)-7-methyl-7,9-dihydro-8H-purin-8-one |
| I-305 | m/z: 472.39 [M + H]+ Rt (min): 1.4183 | 9-(4-(5-(hydroxymethyl)thiazol-4-yl)benzyl)-2-(2-isopropylphenyl)-7-methyl-7,9-dihydro-8H-purin-8-one |
| I-306 | m/z: 476.38 [M + H]+ Rt (min): 1.4184 | 2-(2-isopropylphenyl)-9-(4-(6-methylimidazo[1,2-a]pyrazin-8-yl)benzyl)-7,9-dihydro-8H-purin-8-one |
| I-307 | m/z: 457.38 [M + H]+ Rt (min): 0.88 | 9-(4-(1,4-dimethyl-1H-imidazol-2-yl)benzyl)-2-(3-fluoro-2-isopropylphenyl)-7,9-dihydro-8H-purin-8-one |
| I-308 | m/z: 443.3 [M + H]+ Rt (min): 0.8783 | 2-(3-fluoro-2-isopropylphenyl)-9-(4-(1-methyl-1H-imidazol-4-yl)benzyl)-7,9-dihydro-8H-purin-8-one |
| I-309 | m/z: 439.32 [M + H]+ Rt (min): 0.85 | (R)-2-(2-isopropylphenyl)-9-(1-(4-(1-methyl-1H-imidazol-2-yl)phenyl)ethyl)-7,9-dihydro-8H-purin-8-one |
| I-310 | m/z: 439.32 [M + H]+ Rt (min): | (S)-2-(2-isopropylphenyl)-9-(1-(4-(1-methyl-1H-imidazol-2-yl)phenyl)ethyl)-7,9-dihydro-8H-purin-8-one |

Library Protocol C.

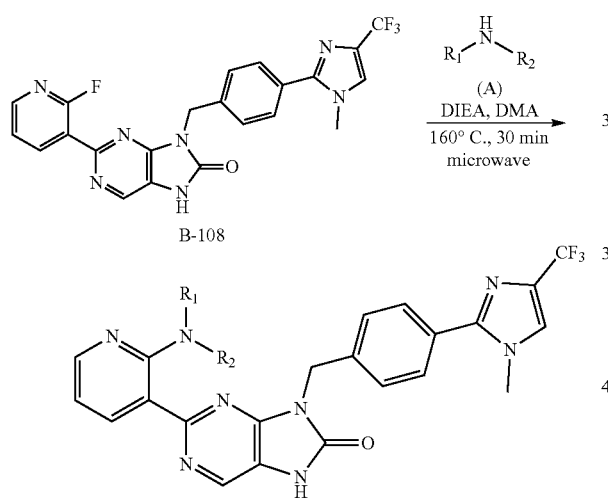

A microwave reaction vial was charged with Intermediate B-108 (0.2M in DMF, 150 µL, 30.0 µmol), amine (A) (0.2 M in dioxane, 300 µL, 60 µmol) and DIEA (15 µL, 86 mol) and was heated for 30 min at 160° C. in a Biotage microwave reactor. The volatiles were removed under reduced pressure and the residue was partitioned between 1N NaOH (0.5 mL) and EtOAc (0.5 mL). The organic layer was separated and the aqueous phase was extracted with EtOAc. The combined organic extracts were concentrated to afford the crude product, which was purified by mass-triggered preparatory HPLC. The product-containing fractions were combined and concentrated in a Genevac to afford the desired product.

Table 7. The following compounds were synthesized according to Library Protocol C.

TABLE 7

| Cmpd no. | LCMS | Chemical Name |
|---|---|---|
| I-311 | m/z: 481.3203 [M + H]+ Rt (min): 0.7747 | 9-(4-(1-methyl-4-(trifluoromethyl)-1H-imidazol-2-yl)benzyl)-2-(2-(methylamino)pyridin-3-yl)-7,9-dihydro-8H-purin-8-one |
| I-312 | m/z: 495.3634 [M + H]+ Rt (min): 0.8287 | 2-(2-(ethylamino)pyridin-3-yl)-9-(4-(1-methyl-4-(trifluoromethyl)-1H-imidazol-2-yl)benzyl)-7,9-dihydro-8H-purin-8-one |
| I-313 | m/z: 509.4066 [M + H]+ [M + H]+ Rt (min): 0.8692 | 2-(2-(isopropylamino)pyridin-3-yl)-9-(4-(1-methyl-4-(trifluoromethyl)-1H-imidazol-2-yl)benzyl)-7,9-dihydro-8H-purin-8-one |
| I-314 | m/z: 507.378 [M + H]+ Rt (min): 0.8258 | 2-(2-(cyclopropylamino)pyridin-3-yl)-9-(4-(1-methyl-4-(trifluoromethyl)-1H-imidazol-2-yl)benzyl)-7,9-dihydro-8H-purin-8-one |
| I-315 | m/z: 539.4428 [M + H]+ Rt (min): 0.8827 | 2-(2-((2-ethoxyethyl)amino)pyridin-3-yl)-9-(4-(1-methyl-4-(trifluoromethyl)-1H-imidazol-2-yl)benzyl)-7,9-dihydro-8H-purin-8-one |
| I-316 | m/z: 521.4239 [M + H]+ Rt (min): 0.9097 | 2-(2-(cyclobutylamino)pyridin-3-yl)-9-(4-(1-methyl-4-(trifluoromethyl)-1H-imidazol-2-yl)benzyl)-7,9-dihydro-8H-purin-8-one |

TABLE 7-continued

| Cmpd no. | LCMS | Chemical Name |
| --- | --- | --- |
| I-317 | m/z: 539.4428 [M + H]+ Rt (min): 0.8827 | 2-(2-((1-methoxypropan-2-yl)amino)pyridin-3-yl)-9-(4-(1-methyl-4-(trifluoromethyl)-1H-imidazol-2-yl)benzyl)-7,9-dihydro-8H-purin-8-one |
| I-318 | m/z: 552.4452 [M + H]+ Rt (min): 0.8283 | N,N-dimethyl-2-((3-(9-(4-(1-methyl-4-(trifluoromethyl)-1H-imidazol-2-yl)benzyl)-8-oxo-8,9-dihydro-7H-purin-2-yl)pyridin-2-yl)amino)acetamide |
| I-319 | m/z: 539.4429 [M + H]+ Rt (min): 0.8827 | (R)-2-(2-((1-methoxypropan-2-yl)amino)pyridin-3-yl)-9-(4-(1-methyl-4-(trifluoromethyl)-1H-imidazol-2-yl)benzyl)-7,9-dihydro-8H-purin-8-one |
| I-320 | m/z: 551.47 [M + H]+ Rt (min): 0.8692 | 9-(4-(1-methyl-4-(trifluoromethyl)-1H-imidazol-2-yl)benzyl)-2-(2-(((tetrahydrofuran-2-yl)methyl)amino)pyridin-3-yl)-7,9-dihydro-8H-purin-8-one |
| I-321 | m/z: 551.47 [M + H]+ Rt (min): 0.8533 | 9-(4-(1-methyl-4-(trifluoromethyl)-1H-imidazol-2-yl)benzyl)-2-(2-((tetrahydro-2H-pyran-4-yl)amino)pyridin-3-yl)-7,9-dihydro-8H-purin-8-one |
| I-322 | m/z: 537.4274 [M + H]+ Rt (min): 0.8667 | (S)-9-(4-(1-methyl-4-(trifluoromethyl)-1H-imidazol-2-yl)benzyl)-2-(2-((tetrahydrofuran-3-yl)amino)pyridin-3-yl)-7,9-dihydro-8H-purin-8-one |
| I-323 | m/z: 495.3634 [M + H]+ Rt (min): 0.7567 | 2-(2-(dimethylamino)pyridin-3-yl)-9-(4-(1-methyl-4-(trifluoromethyl)-1H-imidazol-2-yl)benzyl)-7,9-dihydro-8H-purin-8-one |
| I-324 | m/z: 523.4182 [M + H]+ Rt (min): 0.8827 | 2-(2-(diethylamino)pyridin-3-yl)-9-(4-(1-methyl-4-(trifluoromethyl)-1H-imidazol-2-yl)benzyl)-7,9-dihydro-8H-purin-8-one |
| I-325 | m/z: 521.4343 [M + H]+ Rt (min): 0.7442 | 9-(4-(1-methyl-4-(trifluoromethyl)-1H-imidazol-2-yl)benzyl)-2-(2-(pyrrolidin-1-yl)pyridin-3-yl)-7,9-dihydro-8H-purin-8-one |
| I-326 | m/z: 535.4121 [M + H]+ Rt (min): 0.8827 | 9-(4-(1-methyl-4-(trifluoromethyl)-1H-imidazol-2-yl)benzyl)-2-(2-(piperidin-1-yl)pyridin-3-yl)-7,9-dihydro-8H-purin-8-one |
| I-327 | m/z: 539.4428 [M + H]+ Rt (min): 0.8287 | 2-(2-((2-methoxyethyl)(methyl)amino)pyridin-3-yl)-9-(4-(1-methyl-4-(trifluoromethyl)-1H-imidazol-2-yl)benzyl)-7,9-dihydro-8H-purin-8-one |
| I-328 | m/z: 550.5 [M + H]+ Rt (min): 0.7342 | 9-(4-(1-methyl-4-(trifluoromethyl)-1H-imidazol-2-yl)benzyl)-2-(2-(4-methylpiperazin-1-yl)pyridin-3-yl)-7,9-dihydro-8H-purin-8-one |
| I-329 | m/z: 603.5 (M + H) + [M + H]+ Rt (min): 1.166 | 9-(4-(1-methyl-4-(trifluoromethyl)-1H-imidazol-2-yl)benzyl)-2-(2-(4-(trifluoromethyl)piperidin-1-yl)pyridin-3-yl)-7,9-dihydro-8H-purin-8-one |
| I-330 | m/z: 523.3847 [M + H]+ Rt (min): 0.8692 | 2-(2-(isopropyl(methyl)amino)pyridin-3-yl)-9-(4-(1-methyl-4-(trifluoromethyl)-1H-imidazol-2-yl)benzyl)-7,9-dihydro-8H-purin-8-one |
| I-331 | m/z: 509.4065 [M + H]+ Rt (min): 0.8287 | 2-(2-(ethyl(methyl)amino)pyridin-3-yl)-9-(4-(1-methyl-4-(trifluoromethyl)-1H-imidazol-2-yl)benzyl)-7,9-dihydro-8H-purin-8-one |
| I-332 | m/z: 563.4 [M + H]+ Rt (min): 1.4357 | 2-(2-(methyl(2,2,2-trifluoroethyl)amino)pyridin-3-yl)-9-(4-(1-methyl-4-(trifluoromethyl)-1H-imidazol-2-yl)benzyl)-7,9-dihydro-8H-purin-8-one |
| I-333 | m/z: 537.3624 [M + H]+ Rt (min): 0.9317 | 9-(4-(1-methyl-4-(trifluoromethyl)-1H-imidazol-2-yl)benzyl)-2-(2-morpholinopyridin-3-yl)-7,9-dihydro-8H-purin-8-one |
| I-334 | m/z: 525.4 [M + H]+ Rt (min): 0.8827 | 2-(2-(3-fluoroazetidin-1-yl)pyridin-3-yl)-9-(4-(1-methyl-4-(trifluoromethyl)-1H-imidazol-2-yl)benzyl)-7,9-dihydro-8H-purin-8-one |
| I-335 | m/z: 507.3261 [M + H]+ Rt (min): 0.7325 | 2-(2-(azetidin-1-yl)pyridin-3-yl)-9-(4-(1-methyl-4-(trifluoromethyl)-1H-imidazol-2-yl)benzyl)-7,9-dihydro-8H-purin-8-one |
| I-336 | m/z: 543.3436 [M + H]+ Rt (min): 1.2334 | 2-(2-(3,3-difluoroazetidin-1-yl)pyridin-3-yl)-9-(4-(1-methyl-4-(trifluoromethyl)-1H-imidazol-2-yl)benzyl)-7,9-dihydro-8H-purin-8-one |
| I-337 | m/z: 575.329 [M + H]+ Rt (min): 1.1255 | 9-(4-(1-methyl-4-(trifluoromethyl)-1H-imidazol-2-yl)benzyl)-2-(2-(3-(trifluoromethyl)azetidin-1-yl)pyridin-3-yl)-7,9-dihydro-8H-purin-8-one |

Library Protocol D.

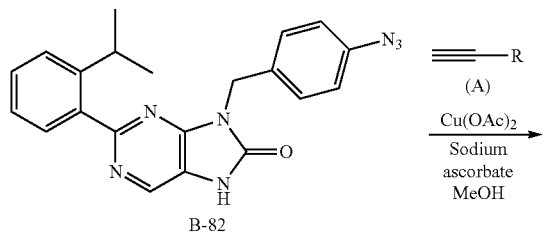

B-82 and sodium ascorbate (0.2M in water, 30 μL, 6 μmol) was stirred at ambient temperature for 16 h. The reaction mixture was concentrated and partitioned between 1N NaOH (0.5 mL) and EtOAc (0.5 mL). The organic layer was separated and the aqueous phase was extracted with EtOAc. The combined organic fractions were placed on a 500 mg SiliaPrepMB TAAcONa column (purchased from Silicycle) and eluted with MeOH (3 mL) to scavenge residual copper, followed by purification by mass-triggered preparatory HPLC. The product-containing fractions were combined and concentrated in a Genevac to afford the desired product.

Table 8. The following compounds were synthesized according to Library Protocol D.

TABLE 8

| Cmpd no. | LCMS | Chemical Name |
|---|---|---|
| I-338 | m/z: 469.1699 [M + H]⁺ Rt (min): 1.02 | 9-(4-(4-(2-aminopropan-2-yl)-1H-1,2,3-triazol-1-yl)benzyl)-2-(2-isopropylphenyl)-7,9-dihydro-8H-purin-8-one |
| I-339 | m/z: 469.159 [M + H]⁺ Rt (min): 1 | 9-(4-(4-((dimethylamino)methyl)-1H-1,2,3-triazol-1-yl)benzyl)-2-(2-isopropylphenyl)-7,9-dihydro-8H-purin-8-one |
| I-340 | m/z: 488.1128 [M + H]⁺ Rt (min): 1.7 | 2-(2-isopropylphenyl)-9-(4-(4-phenyl-1H-1,2,3-triazol-1-yl)benzyl)-7,9-dihydro-8H-purin-8-one |
| I-341 | m/z: 518.1495 [M + H]⁺ Rt (min): 1.66 | 2-(2-isopropylphenyl)-9-(4-(4-(4-methoxyphenyl)-1H-1,2,3-triazol-1-yl)benzyl)-7,9-dihydro-8H-purin-8-one |
| I-342 | m/z: 456.1049 [M + H]⁺ Rt (min): 1.16 | 9-(4-(4-(2-hydroxyethyl)-1H-1,2,3-triazol-1-yl)benzyl)-2-(2-isopropylphenyl)-7,9-dihydro-8H-purin-8-one |
| I-343 | m/z: 452.075 [M + H]⁺ Rt (min): 1.5 | 9-(4-(4-cyclopropyl-1H-1,2,3-triazol-1-yl)benzyl)-2-(2-isopropylphenyl)-7,9-dihydro-8H-purin-8-one |
| I-344 | m/z: 456.1049 [M + H]⁺ Rt (min): 1.33 | 2-(2-isopropylphenyl)-9-(4-(4-(methoxymethyl)-1H-1,2,3-triazol-1-yl)benzyl)-7,9-dihydro-8H-purin-8-one |
| I-345 | m/z: 470.1449 [M + H]⁺ Rt (min): 1.26 | 9-(4-(4-(2-hydroxypropan-2-yl)-1H-1,2,3-triazol-1-yl)benzyl)-2-(2-isopropylphenyl)-7,9-dihydro-8H-purin-8-one |
| I-346 | m/z: 497.1849 [M + H]⁺ Rt (min): 1.07 | 9-(4-(4-((diethylamino)methyl)-1H-1,2,3-triazol-1-yl)benzyl)-2-(2-isopropylphenyl)-7,9-dihydro-8H-purin-8-one |
| I-347 | m/z: 456.0592 [M + H]⁺ Rt (min): 1.2 | (R)-9-(4-(4-(1-hydroxyethyl)-1H-1,2,3-triazol-1-yl)benzyl)-2-(2-isopropylphenyl)-7,9-dihydro-8H-purin-8-one |
| I-348 | m/z: 497.1848 [M + H]⁺ [M + H]⁺ Rt (min): 1.08 | 9-(4-(4-(3-aminopentan-3-yl)-1H-1,2,3-triazol-1-yl)benzyl)-2-(2-isopropylphenyl)-7,9-dihydro-8H-purin-8-one |
| I-349 | m/z: 489.1244 [M + H]⁺ Rt (min): 1.48 | 2-(2-isopropylphenyl)-9-(4-(4-(pyridin-2-yl)-1H-1,2,3-triazol-1-yl)benzyl)-7,9-dihydro-8H-purin-8-one |
| I-350 | m/z: 504.0749 [M + H]⁺ Rt (min): 1.23 | 2-(2-isopropylphenyl)-9-(4-(4-((methylsulfonyl)methyl)-1H-1,2,3-triazol-1-yl)benzyl)-7,9-dihydro-8H-purin-8-one |

-continued

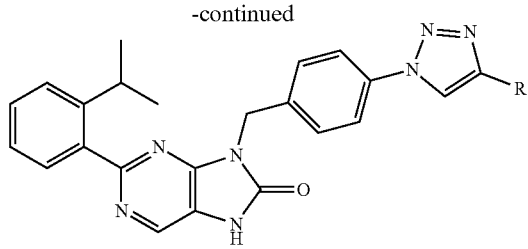

A mixture of Intermediate B-82 (0.2M in MeOH, 150 μL, 30 μmol), alkyne (A) (0.2M in MeOH, 150 μL, 30 μmol), copper (II) acetate (0.2M solution in water, 30 μL, 6 μmol)

Library Protocol E.

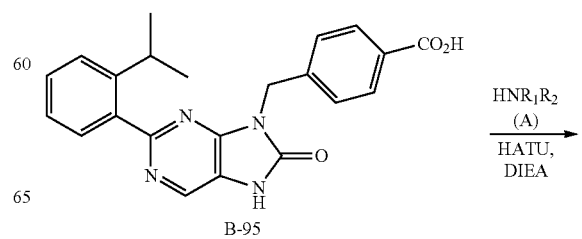

B-95

-continued

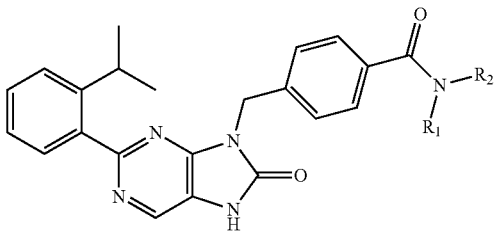

Note: All reagents were prepared as solutions in DMF unless specifically noted. A mixture of Intermediate B-95 (0.2M, 100 µL, 20 µmol), DIEA (6.99 µL, 40 µmol), HATU (0.2M, 100 µL, 20 µmol) and amine (A) (0.2M, 110 µL, 22 µmol) was heated to 50° C. for 16 h, then concentrated under a stream of nitrogen. The residue was treated with saturated sodium bicarbonate (600 µL) and extracted with EtOAc (2×600 µL). The combined organic extracts were concentrated under a stream of nitrogen and purified by mass-directed preparative HPLC to afford the final product.

Table 9. The following compounds were synthesized according to Library Protocol E.

TABLE 9

| Cmpd no. | LCMS | Chemical Name |
|---|---|---|
| I-351 | m/z: 402.1415 (M + H)+ Rt (min): 1.1767 | 4-((2-(2-isopropylphenyl)-8-oxo-7,8-dihydro-9H-purin-9-yl)methyl)-N-methylbenzamide |
| I-352 | m/z: 446.1387 [M + H]+ Rt (min): 1.22 | 4-((2-(2-isopropylphenyl)-8-oxo-7,8-dihydro-9H-purin-9-yl)methyl)-N-(2-methoxyethyl)benzamide |
| I-353 | m/z: 428.1366 [M + H]+ Rt (min): 1.2833 | N-cyclopropyl-4-((2-(2-isopropylphenyl)-8-oxo-7,8-dihydro-9H-purin-9-yl)methyl)benzamide |
| I-354 | m/z: 496.1805 [M + H]+ Rt (min): 1.5277 | N-(4-fluorobenzyl)-4-((2-(2-isopropylphenyl)-8-oxo-7,8-dihydro-9H-purin-9-yl)methyl)benzamide |
| I-355 | m/z: 416.1788 [M + H]+ Rt (min): 1.2582 | 4-((2-(2-isopropylphenyl)-8-oxo-7,8-dihydro-9H-purin-9-yl)methyl)-N,N-dimethylbenzamide |
| I-356 | m/z: 430.283 [M + H]+ Rt (min): 1.3683 | N-isopropyl-4-((2-(2-isopropylphenyl)-8-oxo-7,8-dihydro-9H-purin-9-yl)methyl)benzamide |
| I-357 | m/z: 444.3262 [M + H]+ Rt (min): 1.47 | N-isobutyl-4-((2-(2-isopropylphenyl)-8-oxo-7,8-dihydro-9H-purin-9-yl)methyl)benzamide |
| I-358 | m/z: 456.2891 [M + H]+ Rt (min): 1.5031 | N-cyclopentyl-4-((2-(2-isopropylphenyl)-8-oxo-7,8-dihydro-9H-purin-9-yl)methyl)benzamide |
| I-359 | m/z: 532.4214 [M + H]+ Rt (min): 1.7842 | 4-((2-(2-isopropylphenyl)-8-oxo-7,8-dihydro-9H-purin-9-yl)methyl)-N-(1-phenylcyclopentyl)benzamide |
| I-360 | m/z: 482.36 [M + H]+ Rt (min): 0.7833 | 4-((2-(2-isopropylphenyl)-8-oxo-7,8-dihydro-9H-purin-9-yl)methyl)-N-((1-methyl-1H-imidazol-2-yl)methyl)benzamide |
| I-361 | m/z: 482.34 [M + H]+ Rt (min): 1.166 | 4-((2-(2-isopropylphenyl)-8-oxo-7,8-dihydro-9H-purin-9-yl)methyl)-N-((1-methyl-1H-pyrazol-4-yl)methyl)benzamide |
| I-362 | m/z: 444.3262 [M + H]+ Rt (min): 1.4492 | N,N-diethyl-4-((2-(2-isopropylphenyl)-8-oxo-7,8-dihydro-9H-purin-9-yl)methyl)benzamide |
| I-363 | m/z: 458.3045 [M + H]+ Rt (min): 1.2334 | 2-(2-isopropylphenyl)-9-(4-(morpholine-4-carbonyl)benzyl)-7,9-dihydro-8H-purin-8-one |
| I-364 | m/z: 484.3758 [M + H]+ Rt (min): 1.6784 | N-cyclohexyl-4-((2-(2-isopropylphenyl)-8-oxo-7,8-dihydro-9H-purin-9-yl)methyl)-N-methylbenzamide |
| I-365 | m/z: 510.3818 [M + H]+ Rt (min): 1.6059 | N-(4-fluorobenzyl)-4-((2-(2-isopropylphenyl)-8-oxo-7,8-dihydro-9H-purin-9-yl)methyl)-N-methylbenzamide |
| I-366 | m/z: 470.3748 [M + H]+ Rt (min): 1.6092 | 2-(2-isopropylphenyl)-9-(4-(4-methylpiperidine-1-carbonyl)benzyl)-7,9-dihydro-8H-purin-8-one |
| I-367 | m/z: 486.3594 [M + H]+ Rt (min): 1.2817 | 4-((2-(2-isopropylphenyl)-8-oxo-7,8-dihydro-9H-purin-9-yl)methyl)-N-methyl-N-(tetrahydro-2H-pyran-4-yl)benzamide |
| I-368 | m/z: 500.4251 [M + H]+ Rt (min): 1.475 | 2-(2-isopropylphenyl)-9-(4-(3-(methoxymethyl)piperidine-1-carbonyl)benzyl)-7,9-dihydro-8H-purin-8-one |
| I-369 | m/z: 456.3232 [M + H]+ Rt (min): 1.4575 | (R)-2-(2-isopropylphenyl)-9-(4-(2-methylpyrrolidine-1-carbonyl)benzyl)-7,9-dihydro-8H-purin-8-one |
| I-370 | m/z: 488.3418 [M + H]+ Rt (min): 1.4834 | N-isopropyl-4-((2-(2-isopropylphenyl)-8-oxo-7,8-dihydro-9H-purin-9-yl)methyl)-N-(2-methoxyethyl)benzamide |

TABLE 9-continued

| Cmpd no. | LCMS | Chemical Name |
|---|---|---|
| I-371 | m/z: 513.31 [M + H]+ Rt (min): 1.3683 | 4-((2-(2-isopropylphenyl)-8-oxo-7,8-dihydro-9H-purin-9-yl)methyl)-N-methyl-N-((2-methylthiazol-4-yl)methyl)benzamide |
| I-372 | m/z: 468.32 [M + H]+ Rt (min): 0.8692 | 4-((2-(2-isopropylphenyl)-8-oxo-7,8-dihydro-9H-purin-9-yl)methyl)-N-(1-methyl-1H-imidazol-2-yl)benzamide |
| I-373 | m/z: 430.3313 [M + H]+ Rt (min): 1.3548 | N-ethyl-4-((2-(2-isopropylphenyl)-8-oxo-7,8-dihydro-9H-purin-9-yl)methyl)-N-methylbenzamide |
| I-374 | m/z: 444.3262 [M + H]+ Rt (min): 1.4592 | 4-((2-(2-isopropylphenyl)-8-oxo-7,8-dihydro-9H-purin-9-yl)methyl)-N-methyl-N-propylbenzamide |
| I-375 | m/z: 444.326 [M + H]+ Rt (min): 1.4357 | N-isopropyl-4-((2-(2-isopropylphenyl)-8-oxo-7,8-dihydro-9H-purin-9-yl)methyl)-N-methylbenzamide |
| I-376 | m/z: 446.2997 [M + H]+ Rt (min): 1.1117 | N-(2-hydroxyethyl)-4-((2-(2-isopropylphenyl)-8-oxo-7,8-dihydro-9H-purin-9-yl)methyl)-N-methylbenzamide |
| I-377 | m/z: 444.3262 [M + H]+ Rt (min): 1.0833 | 9-(4-(3-hydroxyazetidine-1-carbonyl)benzyl)-2-(2-isopropylphenyl)-7,9-dihydro-8H-purin-8-one |
| I-378 | m/z: 458.3495 [M + H]+ Rt (min): 1.085 | (S)-9-(4-(3-hydroxypyrrolidine-1-carbonyl)benzyl)-2-(2-isopropylphenyl)-7,9-dihydro-8H-purin-8-one |
| I-379 | m/z: 442.3694 [M + H]+ Rt (min): 1.3952 | N-cyclopropyl-4-((2-(2-isopropylphenyl)-8-oxo-7,8-dihydro-9H-purin-9-yl)methyl)-N-methylbenzamide |
| I-380 | m/z: 487.4315 [M + H]+ Rt (min): 1.15 | N-(2-(dimethylamino)-2-oxoethyl)-4-((2-(2-isopropylphenyl)-8-oxo-7,8-dihydro-9H-purin-9-yl)methyl)-N-methylbenzamide |
| I-381 | m/z: 444.3262 [M + H]+ Rt (min): 1.166 | 4-((2-(2-isopropylphenyl)-8-oxo-7,8-dihydro-9H-purin-9-yl)methyl)-N-(oxetan-3-yl)benzamide |
| I-382 | m/z: 472.413 [M + H]+ Rt (min): 1.2198 | (S)-9-(4-(2-(hydroxymethyl)pyrrolidine-1-carbonyl)benzyl)-2-(2-isopropylphenyl)-7,9-dihydro-8H-purin-8-one |
| I-383 | m/z: 499.4594 [M + H]+ Rt (min): 1.112 | 9-(4-(4-acetylpiperazine-1-carbonyl)benzyl)-2-(2-isopropylphenyl)-7,9-dihydro-8H-purin-8-one |
| I-384 | m/z: 516.4446 [M + H]+ Rt (min): 1.2603 | (S)-2-(2-isopropylphenyl)-9-(4-(3-(2-methoxyethoxy)pyrrolidine-1-carbonyl)benzyl)-7,9-dihydro-8H-purin-8-one |
| I-385 | m/z: 486.3949 [M + H]+ Rt (min): 1.42 | 9-(4-((2R,6S)-2,6-dimethylmorpholine-4-carbonyl)benzyl)-2-(2-isopropylphenyl)-7,9-dihydro-8H-purin-8-one |
| I-386 | m/z: 446.3416 [M + H]+ Rt (min): 1.2975 | 9-(4-(3-fluoroazetidine-1-carbonyl)benzyl)-2-(2-isopropylphenyl)-7,9-dihydro-8H-purin-8-one |
| I-387 | m/z: 472.3547 [M + H]+ Rt (min): 1.2317 | N-((1R,2S)-2-hydroxycyclopentyl)-4-((2-(2-isopropylphenyl)-8-oxo-7,8-dihydro-9H-purin-9-yl)methyl)benzamide |
| I-388 | m/z: 492.3783 [M + H]+ Rt (min): 1.4884 | 9-(4-(4,4-difluoropiperidine-1-carbonyl)benzyl)-2-(2-isopropylphenyl)-7,9-dihydro-8H-purin-8-one |
| I-389 | m/z: 442.3446 [M + H]+ Rt (min): 1.3412 | 2-(2-isopropylphenyl)-9-(4-(pyrrolidine-1-carbonyl)benzyl)-7,9-dihydro-8H-purin-8-one |
| I-390 | m/z: 456.3541 [M + H]+ Rt (min): 1.4567 | 2-(2-isopropylphenyl)-9-(4-(2-methylpyrrolidine-1-carbonyl)benzyl)-7,9-dihydro-8H-purin-8-one |
| I-391 | m/z: 486.3912 [M + H]+ Rt (min): 1.4159 | 4-((2-(2-isopropylphenyl)-8-oxo-7,8-dihydro-9H-purin-9-yl)methyl)-N-(1-(methoxymethyl)cyclopropyl)-N-methylbenzamide |
| I-392 | m/z: 478.3459 [M + H]+ Rt (min): 1.4217 | 9-(4-(3,3-difluoropyrrolidine-1-carbonyl)benzyl)-2-(2-isopropylphenyl)-7,9-dihydro-8H-purin-8-one |
| I-393 | m/z: 484.4402 [M + H]+ Rt (min): 1.325 | 9-(4-(5-oxa-2-azaspiro[3.4]octane-2-carbonyl)benzyl)-2-(2-isopropylphenyl)-7,9-dihydro-8H-purin-8-one |
| I-394 | m/z: 484.3758 [M + H]+ Rt (min): 1.2233 | 9-(4-(6-oxa-2-azaspiro[3.4]octane-2-carbonyl)benzyl)-2-(2-isopropylphenyl)-7,9-dihydro-8H-purin-8-one |
| I-395 | m/z: 456.4191 [M + H]+ Rt (min): 1.4467 | (S)-2-(2-isopropylphenyl)-9-(4-(2-methylpyrrolidine-1-carbonyl)benzyl)-7,9-dihydro-8H-purin-8-one |
| I-396 | m/z: 486.4564 [M + H]+ Rt (min): 1.4 | (S)-2-(2-isopropylphenyl)-9-(4-(2-(methoxymethyl)pyrrolidine-1-carbonyl)benzyl)-7,9-dihydro-8H-purin-8-one |

TABLE 9-continued

| Cmpd no. | LCMS | Chemical Name |
|---|---|---|
| I-397 | m/z: 484.4806 [M + H]+ Rt (min): 1.66 | 9-(4-(2-ethylpiperidine-1-carbonyl)benzyl)-2-(2-isopropylphenyl)-7,9-dihydro-8H-purin-8-one |
| I-398 | m/z: 470.4625 [M + H]+ Rt (min): 1.565 | 2-(2-isopropylphenyl)-9-(4-(2-methylpiperidine-1-carbonyl)benzyl)-7,9-dihydro-8H-purin-8-one |
| I-399 | m/z: 470.4625 [M + H]+ Rt (min): 1.59 | 2-(2-isopropylphenyl)-9-(4-(3-methylpiperidine-1-carbonyl)benzyl)-7,9-dihydro-8H-purin-8-one |
| I-400 | m/z: 500.4996 [M + H]+ Rt (min): 1.4933 | 2-(2-isopropylphenyl)-9-(4-(2-(methoxymethyl)piperidine-1-carbonyl)benzyl)-7,9-dihydro-8H-purin-8-one |
| I-401 | m/z: 486.4564 [M + H]+ Rt (min): 1.3683 | 2-(2-isopropylphenyl)-9-(4-(3-methoxypiperidine-1-carbonyl)benzyl)-7,9-dihydro-8H-purin-8-one |
| I-402 | m/z: 472.4281 [M + H]+ Rt (min): 1.25 | 4-((2-(2-isopropylphenyl)-8-oxo-7,8-dihydro-9H-purin-9-yl)methyl)-N-methyl-N-(tetrahydrofuran-3-yl)benzamide |
| I-403 | m/z: 486.4688 [M + H]+ Rt (min): 1.3983 | (R)-2-(2-isopropylphenyl)-9-(4-(2-(methoxymethyl)pyrrolidine-1-carbonyl)benzyl)-7,9-dihydro-8H-purin-8-one |
| I-404 | m/z: 472.4637 [M + H]+ Rt (min): 1.3033 | (R)-2-(2-isopropylphenyl)-9-(4-(3-methylmorpholine-4-carbonyl)benzyl)-7,9-dihydro-8H-purin-8-one |
| I-405 | m/z: 472.4321 [M + H]+ Rt (min): 1.305 | (S)-2-(2-isopropylphenyl)-9-(4-(3-methylmorpholine-4-carbonyl)benzyl)-7,9-dihydro-8H-purin-8-one |
| I-406 | m/z: 484.4408 [M + H]+ Rt (min): 1.51 | 4-((2-(2-isopropylphenyl)-8-oxo-7,8-dihydro-9H-purin-9-yl)methyl)-N-methyl-N-(2,2,2-trifluoroethyl)benzamide |
| I-407 | m/z: 460.2274 [M + H]+ Rt (min): 1.3 | 4-((2-(2-isopropylphenyl)-8-oxo-7,8-dihydro-9H-purin-9-yl)methyl)-N-(2-methoxyethyl)-N-methylbenzamide |
| I-408 | m/z: 459.2 [M + H]+ Rt (min): 0.77 | N-(2-(dimethylamino)ethyl)-4-((2-(2-isopropylphenyl)-8-oxo-7,8-dihydro-9H-purin-9-yl)methyl)benzamide |
| I-409 | m/z: 499.24 [M + H]+ Rt (min): 0.83 | 4-((2-(2-isopropylphenyl)-8-oxo-7,8-dihydro-9H-purin-9-yl)methyl)-N-(2-(piperidin-1-yl)ethyl)benzamide |
| I-410 | m/z: 471.38 [M + H]+ Rt (min): 0.7583 | 2-(2-isopropylphenyl)-9-(4-(4-methylpiperazine-1-carbonyl)benzyl)-7,9-dihydro-8H-purin-8-one |
| I-411 | m/z: 484.4166 [M + H]+ Rt (min): 1.3117 | 9-(4-(2-oxa-5-azaspiro[3.4]octane-5-carbonyl)benzyl)-2-(2-isopropylphenyl)-7,9-dihydro-8H-purin-8-one |

Library Protocol F.

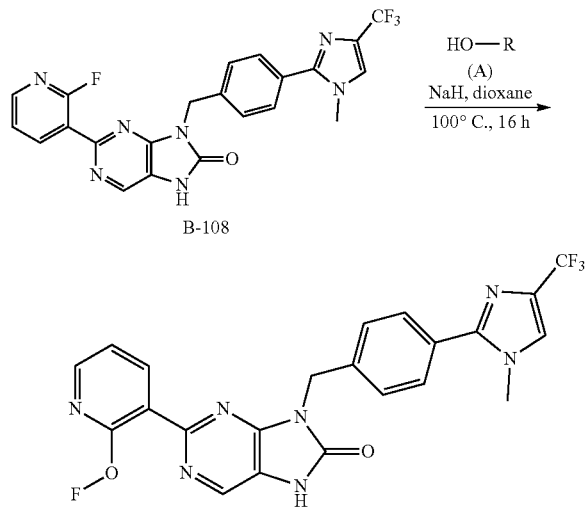

A reaction vial was charged with alcohol (A) (0.2M solution in dioxane, 165 µl, 33.0 µmol) and sodium hydride (1.0 M suspension in dioxane, 60 µL, 60.0 µmol) and the vial was capped and shaken at ambient temperature for 15 min. Intermediate B-108 (0.2 M solution in dioxane, 150 µL, 30.0 µmol) was then added and the mixture was heated for 16 h at 100° C. The reaction mixture was cooled to ambient temperature and the volatiles were removed under reduced pressure. The residue was partitioned between 1N NaOH (0.5 mL) and EtOAc (0.5 mL). The organic layer was separated and combined with a second extraction of the aqueous layer with EtOAc (0.5 mL). After concentration, the product was collected using mass-triggered preparatory HPLC and product-containing fractions were combined and concentrated in a Genevac.

Table 10. The following compounds were synthesized according to Library Protocol F.

TABLE 10

| Cmpd no. | LCMS | Chemical Name |
|---|---|---|
| I-412 | m/z: 482.3 [M + H]+ Rt (min): 1.1608 | 2-(2-methoxypyridin-3-yl)-9-(4-(1-methyl-4-(trifluoromethyl)-1H-imidazol-2-yl)benzyl)-7,9-dihydro-8H-purin-8-one |
| I-413 | m/z: 510.4 [M + H]+ Rt (min): 1.3683 | 9-(4-(1-methyl-4-(trifluoromethyl)-1H-imidazol-2-yl)benzyl)-2-(2-propoxypyridin-3-yl)-7,9-dihydro-8H-purin-8-one |
| I-414 | m/z: 522.4 [M + H]+ Rt (min): 1.3817 | 2-(2-(cyclopropylmethoxy)pyridin-3-yl)-9-(4-(1-methyl-4-(trifluoromethyl)-1H-imidazol-2-yl)benzyl)-7,9-dihydro-8H-purin-8-one |
| I-415 | m/z: 540.4 [M + H]+ Rt (min): 1.2709 | 2-(2-(2-ethoxyethoxy)pyridin-3-yl)-9-(4-(1-methyl-4-(trifluoromethyl)-1H-imidazol-2-yl)benzyl)-7,9-dihydro-8H-purin-8-one |
| I-416 | m/z: 510.2 [M + H]+ Rt (min): 1.3517 | 2-(2-isopropoxypyridin-3-yl)-9-(4-(1-methyl-4-(trifluoromethyl)-1H-imidazol-2-yl)benzyl)-7,9-dihydro-8H-purin-8-one |
| I-417 | m/z: 524.4 [M + H]+ Rt (min): 1.4762 | 2-(2-(sec-butoxy)pyridin-3-yl)-9-(4-(1-methyl-4-(trifluoromethyl)-1H-imidazol-2-yl)benzyl)-7,9-dihydro-8H-purin-8-one |
| I-418 | m/z: 564.4 [M + H]+ Rt (min): 1.5559 | 9-(4-(1-methyl-4-(trifluoromethyl)-1H-imidazol-2-yl)benzyl)-2-(2-((1,1,1-trifluoropropan-2-yl)oxy)pyridin-3-yl)-7,9-dihydro-8H-purin-8-one |
| I-419 | m/z: 522.4 [M + H]+ Rt (min): 1.42 | 2-(2-cyclobutoxypyridin-3-yl)-9-(4-(1-methyl-4-(trifluoromethyl)-1H-imidazol-2-yl)benzyl)-7,9-dihydro-8H-purin-8-one |
| I-420 | m/z: 508.4 [M + H]+ Rt (min): 1.2334 | 2-(2-cyclopropoxypyridin-3-yl)-9-(4-(1-methyl-4-(trifluoromethyl)-1H-imidazol-2-yl)benzyl)-7,9-dihydro-8H-purin-8-one |
| I-421 | m/z: 496.3 [M + H]+ Rt (min): 1.2469 | 2-(2-ethoxypyridin-3-yl)-9-(4-(1-methyl-4-(trifluoromethyl)-1H-imidazol-2-yl)benzyl)-7,9-dihydro-8H-purin-8-one |
| I-422 | m/z: 524.4 [M + H]+ Rt (min): 1.4762 | 2-(2-isobutoxypyridin-3-yl)-9-(4-(1-methyl-4-(trifluoromethyl)-1H-imidazol-2-yl)benzyl)-7,9-dihydro-8H-purin-8-one |
| I-423 | m/z: 526.4 [M + H]+ Rt (min): 1.1929 | 2-(2-(2-methoxyethoxy)pyridin-3-yl)-9-(4-(1-methyl-4-(trifluoromethyl)-1H-imidazol-2-yl)benzyl)-7,9-dihydro-8H-purin-8-one |
| I-424 | m/z: 552.5 [M + H]+ Rt (min): 1.2558 | 9-(4-(1-methyl-4-(trifluoromethyl)-1H-imidazol-2-yl)benzyl)-2-(2-((tetrahydrofuran-2-yl)methoxy)pyridin-3-yl)-7,9-dihydro-8H-purin-8-one |
| I-425 | m/z: 552.5 [M + H]+ Rt (min): 1.2198 | 9-(4-(1-methyl-4-(trifluoromethyl)-1H-imidazol-2-yl)benzyl)-2-(2-((tetrahydrofuran-3-yl)methoxy)pyridin-3-yl)-7,9-dihydro-8H-purin-8-one |
| I-426 | m/z: 554.4605 [M + H]+ Rt (min): 1.2675 | 2-(2-(3-methoxybutoxy)pyridin-3-yl)-9-(4-(1-methyl-4-(trifluoromethyl)-1H-imidazol-2-yl)benzyl)-7,9-dihydro-8H-purin-8-one |
| I-427 | m/z: 538.5 [M + H]+ Rt (min): 1.5942 | 9-(4-(1-methyl-4-(trifluoromethyl)-1H-imidazol-2-yl)benzyl)-2-(2-(pentan-3-yloxy)pyridin-3-yl)-7,9-dihydro-8H-purin-8-one |
| I-428 | m/z: 554.5 [M + H]+ Rt (min): 1.395 | 2-(2-((1-methoxybutan-2-yl)oxy)pyridin-3-yl)-9-(4-(1-methyl-4-(trifluoromethyl)-1H-imidazol-2-yl)benzyl)-7,9-dihydro-8H-purin-8-one |
| I-429 | m/z: 539.4 [M + H]+ Rt (min): 0.7882 | 2-(2-(2-(dimethylamino)ethoxy)pyridin-3-yl)-9-(4-(1-methyl-4-(trifluoromethyl)-1H-imidazol-2-yl)benzyl)-7,9-dihydro-8H-purin-8-one |

Example 36. 9-(4-(1-(azetidin-3-yl)-4-(trifluoromethyl)-1H-imidazol-2-yl)benzyl)-2-(2-isopropylphenyl)-7,9-dihydro-8H-purin-8-one (I-430)

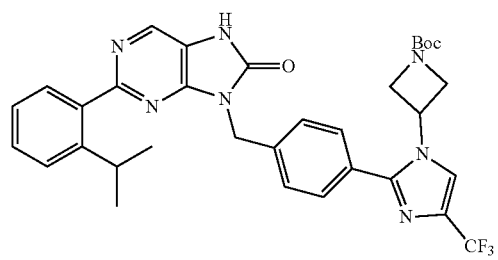

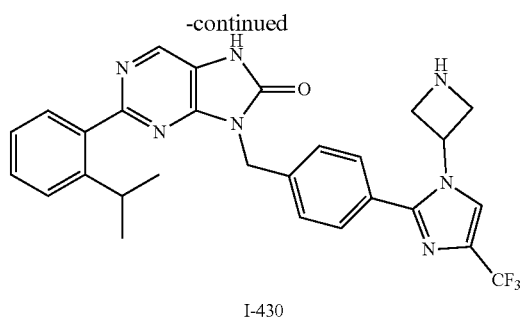

A mixture of tert-butyl 3-(2-(4-((2-(2-isopropylphenyl)-8-oxo-7,8-dihydro-9H-purin-9-yl)methyl)phenyl)-4-(trifluoromethyl)-1H-imidazol-1-yl)azetidine-1-carboxylate (prepared from Intermediate B-36 following Example 35)

(100 mg, 0.16 mmol), DCM (10 mL) and TFA (3 mL) was stirred for 1 h at 40° C. then was concentrated under vacuum. The residue was dissolved in DCM (20 mL) and was washed with saturated aqueous sodium bicarbonate solution (10 mL). The aqueous layer was extracted with DCM (2×20 mL), and the combined organic layers were dried over anhydrous sodium sulfate, filtered and concentrated under vacuum. The residue was purified by prep-HPLC to afford 9-(4-(1-(azetidin-3-yl)-4-(trifluoromethyl)-1H-imidazol-2-yl)benzyl)-2-(2-isopropylphenyl)-7,9-dihydro-8H-purin-8-one (I-430) (24.8 mg, 29%) as a white solid.

Table 11. The following compounds were synthesized from compounds described herein and by sequentially following Examples 35 and 36.

TABLE 11

| Cmpd no. | LCMS | 1H NMR (300 MHz) δ ppm | Chemical Name |
|---|---|---|---|
| I-430 | m/z: 534.44 [M + H]$^+$ Rt (min): 0.9333 | 1H NMR (400 MHz, DMSO-d$_6$) δ 8.38 (s, 1H), 8.31 (s, 1H), 7.53-7.31 (m, 7H), 7.27-7.18 (m, 1H), 5.12-4.98 (m, 3H), 3.75-3.63 (m, 4H), 3.45-3.35 (m, 1H), 1.08 (d, J = 6.8 Hz, 6H). | 9-(4-(1-(azetidin-3-yl)-4-(trifluoromethyl)-1H-imidazol-2-yl)benzyl)-2-(2-isopropylphenyl)-7,9-dihydro-8H-purin-8-one |
| I-431 | m/z: 494.3326 [M + H]$^+$ Rt (min): 1.08 | 1H NMR (400 MHz, CDCl$_3$) δ 8.30 (s, 1H), 7.76 (d, J = 2.4 Hz, 1H), 7.61-7.56 (m, 5H), 7.46-7.40 (m, 2H), 7.30-7.26 (m, 1H), 6.25 (d, J = 2.0 Hz, 1H), 5.16 (s, 2H), 4.43 (br s, 2H), 3.53-3.46 (m, 1H), 3.23-3.20 (m, 2H), 2.92-2.76 (m, 3H), 2.02-2.00 (m, 2H), 1.76-1.67 (m, 2H), 1.25-1.15 (m, 6H). | 2-(2-isopropylphenyl)-9-(4-(3-(piperidin-4-yl)-1H-pyrazol-1-yl)benzyl)-7,9-dihydro-8H-purin-8-one |
| I-432 | m/z: 495.2782 [M + H]$^+$ Rt (min): 1.08 | 1H NMR (300 MHz, DMSO-d$_6$) δ 8.38 (s, 1H), 8.23 (d, J = 2.4 Hz, 1H), 7.65 (d, J = 8.4 Hz, 2H), 7.51 (d, J = 6.9 Hz, 1H), 7.44-7.36 (m, 4H), 7.27-7.23 (m, 1H), 6.05 (d, J = 2.7 Hz, 1H), 5.02 (s, 2H), 3.48-3.44 (m, 1H), 3.12-3.09 (m, 4H), 2.81-2.78 (m, 4H), 1.12-1.09 (m, 6H). | 2-(2-isopropylphenyl)-9-(4-(3-(piperazin-1-yl)-1H-pyrazol-1-yl)benzyl)-7,9-dihydro-8H-purin-8-one |
| I-433 | m/z: 508.1736 [M + H]$^+$ Rt (min): 1.18 | | 2-(2-isopropylphenyl)-7-methyl-9-(4-(3-(piperidin-4-yl)-1H-pyrazol-1-yl)benzyl)-7,9-dihydro-8H-purin-8-one |
| I-434 | m/z: 512.23 [M + H]$^+$ Rt (min): 0.94 | 1H NMR (400 MHz, CD$_3$OD) δ 8.30 (s, 1H), 8.10 (s, 1H), 7.68-7.66 (m, 2H), 7.52-7.50 (m, 2H), 7.28-7.23 (m, 2H), 7.14-7.09 (m, 1H), 6.38 (s, 1H), 5.16 (s, 2H), 3.36-3.35 (m, 2H), 3.14-3.10 (m, 1H), 3.03-2.96 (m, 3H), 2.16-2.11 (m, 2H), 1.90-1.85 (m, 2H), 1.27-1.24 (m, 6H). | 2-(3-fluoro-2-isopropylphenyl)-9-(4-(3-(piperidin-4-yl)-1H-pyrazol-1-yl)benzyl)-7,9-dihydro-8H-purin-8-one |
| I-435 | m/z: 495.21 [M + H]$^+$ Rt (min): 0.54 | | 2-(2-isopropylpyridin-3-yl)-9-(4-(3-(piperidin-4-yl)-1H-pyrazol-1-yl)benzyl)-7,9-dihydro-8H-purin-8-one |
| I-436 | m/z: 548.5 [M + H]$^+$ Rt (min): 0.9906 | 1H NMR (400 MHz, CD$_3$OD) δ 8.46 (s, 1H), 8.19-8.17 (m, 1H), 7.63-7.56 (m, 2H), 7.52-7.37 (m, 5H), 7.30-7.21 (m, 1H), 5.27-5.12 (m, 3H), 3.92-3.80 (m, 4H), 3.56-3.51 (m, 3H), 3.37-3.32 (m, 1H), 1.17 (d, J = 6.80 Hz, 6H). | 9-(4-(1-(azetidin-3-yl)-4-(trifluoromethyl)-1H-imidazol-2-yl)benzyl)-2-(2-isopropylphenyl)-7-methyl-7,9-dihydro-8H-purin-8-one |
| I-437 | m/z: 411.11 [M + H]$^+$ Rt (min): 0.76 | | 9-(4-(1H-imidazol-2-yl)benzyl)-2-(2-isopropylphenyl)-7,9-dihydro-8H-purin-8-one |

Example 37. 2-(2-Isopropylpyridin-3-yl)-9-(4-(1-(1-methylazetidin-3-yl)-4-(trifluoromethyl)-1H-imidazol-2-yl)benzyl)-7,9-dihydro-8H-purin-8-one (I-438)

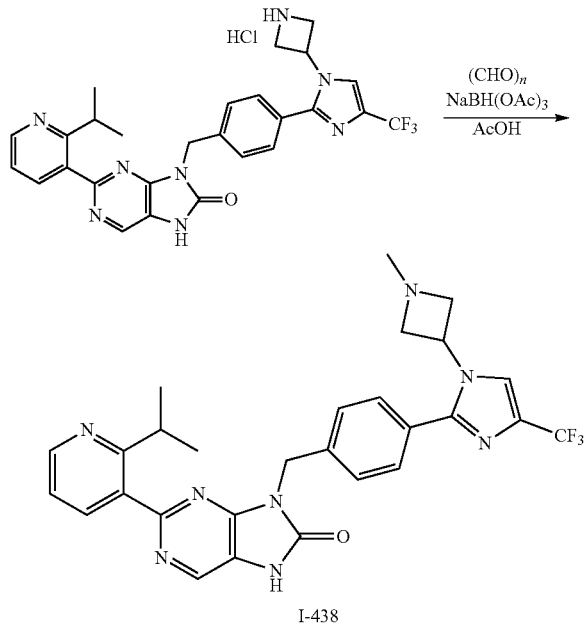

I-438

A mixture of 9-(4-(1-(azetidin-3-yl)-4-(trifluoromethyl)-1H-imidazol-2-yl)benzyl)-2-(2-isopropylpyridin-3-yl)-7,9-dihydro-8H-purin-8-one hydrochloride (prepared from Intermediate B-36 following sequentially Examples 35 and 36) (100 mg, 0.18 mmol), MeOH (3 mL) and paraformaldehyde (78 mg, 0.87 mmol) was stirred for 16 h at ambient temperature, then acetic acid (22 mg, 0.37 mmol) and sodium triacetoxyborohydride (118 mg, 0.56 mmol) were added and the resulting mixture was stirred for 1 h at ambient temperature. The reaction mixture was concentrated, brine (10 mL) was added, and the mixture extracted with EtOAc (3×10 mL). The organic layers were combined, dried over anhydrous sodium sulfate, filtered and concentrated under vacuum. The residue was purified by prep-HPLC to afford 14.2 mg (15%) of 2-(2-isopropylpyridin-3-yl)-9-(4-(1-(1-methylazetidin-3-yl)-4-(trifluoromethyl)-1H-imidazol-2-yl)benzyl)-7,9-dihydro-8H-purin-8-one (I-438) as a white solid. $^1$H NMR (400 MHz, CD$_3$OD) δ 8.56-8.55 (m, 1H), 8.38 (s, 1H), 8.13 (s, 1H), 8.00-7.98 (m, 1H), 7.59 (d, J=8.0 Hz, 2H), 7.50 (d, J=8.4 Hz, 2H), 7.35-7.32 (m, 1H), 5.23 (s, 2H), 4.93-4.87 (m, 1H), 3.72-3.62 (m, 2H), 3.61-3.55 (m, 1H), 3.42-3.38 (m, 2H), 2.38 (s, 3H), 1.23 (d, J=6.8 Hz, 6H). MS (ESI) m/z 549.2 [M+H]$^+$.

Table 12. The following compounds were synthesized according to Example 37.

TABLE 12

| Cmpd no. | LCMS | $^1$H NMR (300 MHz) δ ppm | Chemical Name |
|---|---|---|---|
| I-438 | m/z: 549.5 [M + H]$^+$ Rt (min): 0.5367 | $^1$H NMR (400 MHz, CD$_3$OD) δ 8.56-8.55 (m, 1H), 8.38 (s, 1H), 8.13 (s, 1H), 8.00-7.98 (m, 1H), 7.59 (d, J = 8.0 Hz, 2H), 7.50 (d, J = 8.4 Hz, 2H), 7.35-7.32 (m, 1H), 5.23 (s, 2H), 4.93-4.87 (m, 1H), 3.72-3.62 (m, 2H), 3.61-3.55 (m, 1H), 3.42-3.38 (m, 2H), 2.38 (s, 3H), 1.23 (d, J = 6.8 Hz, 6H). | 2-(2-isopropylpyridin-3-yl)-9-(4-(1-(1-methylazetidin-3-yl)-4-(trifluoromethyl)-1H-imidazol-2-yl)benzyl)-7,9-dihydro-8H-purin-8-one |
| I-439 | m/z: 508.2337 [M + H]$^+$ Rt (min): 1.1 | $^1$H NMR (400 MHz, CDCl$_3$) δ 8.34 (s, 1H), 7.78-7.77 (m, 1H), 7.62-7.52 (m, 5H), 7.46-7.39 (m, 2H), 7.30-7.26 (m, 1H), 6.27 (s, 1H), 5.16 (s, 2H), 3.54-3.47 (m, 1H), 3.18-3.14 (m, 2H), 2.93-2.86 (m, 1H), 2.51-2.30 (m, 5H), 2.12-2.00 (m, 4H), 1.25-1.17 (m, 6H). | 2-(2-isopropylphenyl)-9-(4-(3-(1-methylpiperidin-4-yl)-1H-pyrazol-1-yl)benzyl)-7,9-dihydro-8H-purin-8-one |
| I-440 | m/z: 494.23 [M + H]$^+$ Rt (min): 0.91 | | 2-(2-isopropylphenyl)-9-(4-(3-(1-methylpyrrolidin-3-yl)-1H-pyrazol-1-yl)benzyl)-7,9-dihydro-8H-purin-8-one |
| I-441 | m/z: 526.22 [M + H]$^+$ Rt (min): 0.95 | $^1$H NMR (300 MHz, CD$_3$OD) δ 8.29 (s, 1H), 8.04 (s, 1H), 7.67-7.64 (m, 2H), 7.51-7.49 (m, 2H), 7.29-7.22 (m, 2H), 7.14-7.07 (m 1H), 6.35 (s, 1H), 5.14 (s, 2H), 3.16-3.07 (m, 1H), 3.00-2.96 (m, 2H), 2.77-2.69 (m, 1H), 2.33 (s, 3H), 2.25-2.18 (m, 2H), 2.01-1.97 (m, 2H), 1.97-1.74 (m, 2H), 1.31-1.24 (m, 6H). | 2-(3-fluoro-2-isopropylphenyl)-9-(4-(3-(1-methylpiperidin-4-yl)-1H-pyrazol-1-yl)benzyl)-7,9-dihydro-8H-purin-8-one |
| I-442 | m/z: 509.25 [M + H]$^+$ Rt (min): 0.54 | | 2-(2-isopropylpyridin-3-yl)-9-(4-(3-(1-methylpiperidin-4-yl)-1H-pyrazol-1-yl)benzyl)-7,9-dihydro-8H-purin-8-one |

TABLE 12-continued

| Cmpd no. | LCMS | $^1$H NMR (300 MHz) δ ppm | Chemical Name |
|---|---|---|---|
| I-443 | m/z: 565.2 [M + H]$^+$ Rt (min): 0.83 | $^1$H NMR (300 MHz, CD$_3$OD) δ 8.32-8.26 (m, 2H), 8.16-8.15 (m, 1H), 8.05 (m, 1H), 7.73-7.56 (m, 4H), 7.20-7.16 (m 1H), 6.35 (s, 1H), 5.16 (s, 2H), 5.10-4.95 (m, 2H), 3.06-3.02 (m, 2H), 2.76-2.73 (m, 1H), 2.47-2.29 (m, 5H), 2.15-2.00 (m, 2H), 1.89-1.74 (m, 2H). | 9-(4-(3-(1-methylpiperidin-4-yl)-1H-pyrazol-1-yl)benzyl)-2-(2-(2,2,2-trifluoroethoxy)pyridin-3-yl)-7,9-dihydro-8H-purin-8-one |
| I-444 | m/z: 508.24 [M + H]$^+$ Rt (min): 0.92 | | 2-(2-isopropylphenyl)-9-(4-(3-(1-methylpiperidin-3-yl)-1H-pyrazol-1-yl)benzyl)-7,9-dihydro-8H-purin-8-one |
| I-445 | m/z: 522.47 [M + H]$^+$ Rt (min): 0.5975 | $^1$H NMR (300 MHz, CD$_3$OD) δ 8.29 (s, 1H), 7.57 (s, 4H), 7.55-7.34 (m, 3H), 7.24-7.18 (m, 1H), 6.88 (s, 1H), 5.17 (s, 2H), 3.61 (s, 3H), 3.34-3.29 (m, 1H), 3.05-2.98 (m, 2H), 2.60-2.50 (m, 1H), 2.41 (s, 3H), 2.36-2.24 (m, 2H), 2.06-1.95 (m, 2H), 1.74-1.61 (m, 2H), 1.12 (d, J = 6.9 Hz, 6H). | 2-(2-isopropylphenyl)-9-(4-(1-methyl-4-(1-methylpiperidin-4-yl)-1H-imidazol-2-yl)benzyl)-7,9-dihydro-8H-purin-8-one |
| I-446 | m/z: 522.47 [M + H]$^+$ Rt (min): 0.5724 | $^1$H NMR (300 MHz, CD$_3$OD) δ 8.28 (s, 1H), 7.51 (s, 4H), 7.47-7.30 (m, 3H), 7.24-7.18 (m, 1H), 6.78 (s, 1H), 5.16 (s, 2H), 3.57 (s, 3H), 3.33-3.24 (m, 1H), 2.99-2.94 (m, 2H), 2.67-2.59 (m, 1H), 2.31 (s, 3H), 2.22-1.97 (m, 4H), 1.77-1.63 (m, 2H), 1.12 (d, J = 6.9 Hz, 6H). | 2-(2-isopropylphenyl)-9-(4-(1-methyl-5-(1-methylpiperidin-4-yl)-1H-imidazol-2-yl)benzyl)-7,9-dihydro-8H-purin-8-one |
| I-447 | m/z: 548.48 [M + H]$^+$ Rt (min): 0.9467 | $^1$H NMR (400 MHz, CD$_3$OD) δ 8.36 (s, 1H), 8.15 (d, J = 1.4 Hz, 1H), 7.62-7.60 (m, 2H), 7.55-7.39 (m, 5H), 7.30-7.25 (m, 1H), 5.24 (s, 2H), 4.99-4.85 (m, 1H), 3.74-3.69 (m, 2H), 3.47-3.34 (m, 3H), 2.40 (s, 3H), 1.19 (d, J = 7.2 Hz, 6H). | 2-(2-isopropylphenyl)-9-(4-(1-(1-methylazetidin-3-yl)-4-(trifluoromethyl)-1H-imidazol-2-yl)benzyl)-7,9-dihydro-8H-purin-8-one |
| I-448 | m/z: 562.5 [M + H]$^+$ Rt (min): 1.0041 | $^1$H NMR (400 MHz, CD$_3$OD) δ 8.46 (s, 1H), 8.13 (s, 1H), 7.63-7.56 (m, 2H), 7.53-7.36 (m, 5H), 7.30-7.21 (m, 1H), 5.24 (s, 2H), 4.93-4.85 (m, 1H), 3.71-3.66 (m, 2H), 3.54 (s, 3H), 3.44-3.32 (m, 3H), 2.37 (s, 3H), 1.18-1.12 (m, 6H). | 2-(2-isopropylphenyl)-7-methyl-9-(4-(1-(1-methylazetidin-3-yl)-4-(trifluoromethyl)-1H-imidazol-2-yl)benzyl)-7,9-dihydro-8H-purin-8-one |

Example 38: General Preparation of Sulfonamides

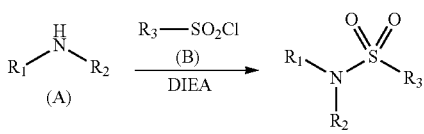

A reaction vial was treated with a 0.2 M solution of the appropriate amine (A) (prepared following Example 30) (150 μL, 30 μmol) in DCE, DIEA (10.48 μL, 60.0 μmol) and a 0.2 M solution of the appropriate isocyanate (180 μL, 36.0 μmol) in DCE. The mixture was heated at 50° C. for 72 h, then was concentrated under a stream of nitrogen. The residue was partitioned between saturated NaHCO$_3$ and EtOAc (600 μL). The organic phase was separated and combined with a second extract of EtOAc (600 μL). The combined extracts were dried under a stream of nitrogen and the crude material purified by mass-directed preparative reverse phase HPLC.

Table 13. The following compounds were synthesized according to Example 38.

TABLE 13

| Cmpd no. | LCMS | $^1$H NMR (300 MHz) δ ppm | Chemical Name |
|---|---|---|---|
| I-449 | m/z: 507.1297 [M + H]$^+$ Rt (min): 1.46 | | 2-(2-isopropylphenyl)-7-methyl-9-((1-(pyridin-3-ylsulfonyl)piperidin-4-yl)methyl)-7,9-dihydro-8H-purin-8-one |
| I-450 | m/z: 472.0951 [M + H]$^+$ Rt (min): 1.55 | | 2-(2-isopropylphenyl)-9-((1-(isopropylsulfonyl)piperidin-4-yl)methyl)-7-methyl-7,9-dihydro-8H-purin-8-one |

TABLE 13-continued

| Cmpd no. | LCMS | ¹H NMR (300 MHz) δ ppm | Chemical Name |
|---|---|---|---|
| I-451 | m/z: 510.1644 [M + H]⁺ Rt (min): 1.44 | | 2-(2-isopropylphenyl)-7-methyl-9-((1-((1-methyl-1H-imidazol-2-yl)sulfonyl)piperidin-4-yl)methyl)-7,9-dihydro-8H-purin-8-one |
| I-452 | m/z: 456.178 [M + H]⁺ Rt (min): 1.53 | ¹H NMR (400 MHz, CD₃OD) δ 8.33 (s, 1H), 7.48-7.41 (m, 3H), 7.29-7.25 (m, 1H), 5.04-5.00 (m, 1H), 4.10-4.05 (m, 1H), 3.99-3.96 (m, 1H), 3.84-3.81 (m, 2H), 3.49-3.35 (m, 2H), 3.08-3.02 (m, 1H), 2.34-2.15 (m, 3H), 1.24-1.16 (m, 12H). | 2-(2-isopropylphenyl)-9-(2-(isopropylsulfonyl)-2-azaspiro[3.3]heptan-5-yl)-7,9-dihydro-8H-purin-8-one |
| I-453 | m/z: 518.3786 [M + H]⁺ Rt (min): 1.43 | | N-(4-((2-(2-isopropylphenyl)-7-methyl-8-oxo-7,8-dihydro-9H-purin-9-yl)methyl)phenyl)-1-methyl-1H-pyrazole-3-sulfonamide |
| I-454 | m/z: 518.38 [M + H]⁺ Rt (min): 1.3952 | | N-(4-((2-(2-isopropylphenyl)-7-methyl-8-oxo-7,8-dihydro-9H-purin-9-yl)methyl)phenyl)-1-methyl-1H-imidazole-2-sulfonamide |
| I-455 | m/z: 532.4203 [M + H]⁺ Rt (min): 1.5706 | | N-(4-((2-(2-isopropylphenyl)-7-methyl-8-oxo-7,8-dihydro-9H-purin-9-yl)methyl)phenyl)-1,2-dimethyl-1H-imidazole-4-sulfonamide |
| I-456 | m/z: 532.4215 [M + H]⁺ Rt (min): 1.5706 | | N-(4-((2-(2-isopropylphenyl)-7-methyl-8-oxo-7,8-dihydro-9H-purin-9-yl)methyl)phenyl)-N,1-dimethyl-1H-pyrazole-3-sulfonamide |
| I-457 | m/z: 532.42 [M + H]⁺ Rt (min): 1.5571 | | N-(4-((2-(2-isopropylphenyl)-7-methyl-8-oxo-7,8-dihydro-9H-purin-9-yl)methyl)phenyl)-N,1-dimethyl-1H-imidazole-2-sulfonamide |
| I-458 | m/z: 546.46 [M + H]⁺ Rt (min): 1.4492 | | N-(4-((2-(2-isopropylphenyl)-7-methyl-8-oxo-7,8-dihydro-9H-purin-9-yl)methyl)phenyl)-N,1,2-trimethyl-1H-imidazole-4-sulfonamide |
| I-459 | m/z: 466.3665 [M + H]⁺ Rt (min): 1.5166 | | N-(4-((2-(2-isopropylphenyl)-7-methyl-8-oxo-7,8-dihydro-9H-purin-9-yl)methyl)phenyl)-N-methylmethanesulfonamide |
| I-460 | m/z: 474.3634 [M + H]⁺ Rt (min): 1.3867 | ¹H NMR (300 MHz, CDCl₃) δ = 8.33 (s, 1H), 7.50 (d, J = 7.3 Hz, 1H), 7.39-7.32 (m, 2H), 7.22 (br d, J = 7.0 Hz, 1H), 4.12 (d, J = 17.0 Hz, 2H), 3.65 (br d, J = 11.7 Hz, 2H), 3.41 (br d, J = 6.4 Hz, 1H), 3.03 (br s, 2H), 2.24-2.11 (m, 1H), 2.01-1.80 (m, 4H), 1.17 (d, J = 6.7 Hz, 6H), 1.09 (br d, J = 4.4 Hz, 2H), 0.91 (br d, J = 5.9 Hz, 2H) | 9-((1-(cyclopropylsulfonyl)-4-fluoropiperidin-4-yl)methyl)-2-(2-isopropylphenyl)-7,9-dihydro-8H-purin-8-one |
| I-461 | m/z: 456.4192 [M + H]⁺ Rt (min): 1.3733 | | 9-((1-(cyclopropylsulfonyl)piperidin-4-yl)methyl)-2-(2-isopropylphenyl)-7,9-dihydro-8H-purin-8-one |

Example 39. General Preparation of Amides

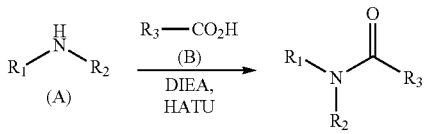

A reaction vial containing purinone-amine (A) (0.2M in dioxane, 150 μL, 0.030 mmol), carboxylic acid (B) (0.2M in dioxane, 165 μL, 0.033 mmol), DIEA (15 μL, 0.086 mmol) and HATU (0.2M in dioxane, 165 μL, 0.033 mmol) was stirred at ambient temperature for 4 h. The reaction mixture was concentrated and partitioned between 1N NaOH (0.5 mL) and EtOAc (0.5 mL). The organic layer was separated and the aqueous phase was extracted with EtOAc. The combined organic extracts were concentrated to afford the crude product, which was purified by mass-triggered preparatory HPLC. The product-containing fractions were combined and concentrated in a Genevac to afford the desired product.

Table 14. The following compounds were synthesized according to Example 39.

TABLE 14

| Cmpd no. | LCMS | $^1$H NMR (300 MHz) δ ppm | Chemical Name |
|---|---|---|---|
| I-462 | m/z: 436.1503 [M + H]$^+$ Rt (min): 1.47 | | 9-((1-isobutyrylpiperidin-4-yl)methyl)-2-(2-isopropylphenyl)-7-methyl-7,9-dihydro-8H-purin-8-one |
| I-463 | m/z: 536.184 [M + H]$^+$ Rt (min): 1.38 | $^1$H NMR (400 MHz, CDCl$_3$) δ 9.25 (br s, 1H), 8.45 (s, 1H), 7.79 (s, 1H), 7.62-7.57 (m, 5H), 7.47-7.44 (m, 2H), 7.32-7.26 (m, 1H), 6.25 (s, 1H), 5.17 (m, 2H), 4.65-4.62 (m, 1H), 3.91-3.87 (m, 1H), 3.51-3.47 (m, 1H), 3.24-3.20 (m, 1H), 3.18-2.95 (m, 1H), 2.81-2.74 (m, 1H), 2.13 (s, 3H), 2.08-2.00 (m, 2H), 1.73-1.64 (m, 2H), 1.25-1.23 (m, 6H). | 9-(4-(3-(1-acetylpiperidin-4-yl)-1H-pyrazol-1-yl)benzyl)-2-(2-isopropylphenyl)-7,9-dihydro-8H-purin-8-one |
| I-464 | m/z: 554.2792 [M + H]$^+$ Rt (min): 1.49 | 1H NMR (300 MHz, CD$_3$OD) δ 8.30 (s, 1H), 8.06 (s, 1H), 7.67-7.64 (m, 2H), 7.51-7.49 (m, 2H), 7.29-7.22 (m, 2H), 7.14-7.07 (m 1H), 6.35 (s, 1H), 5.15 (s, 2H), 4.55-4.51 (m, 1H), 4.01-3.96 (m, 1H), 3.30-3.22 (m, 1H), 3.22-3.10 (m, 1H), 3.10-2.95 (m, 1H), 2.95-2.86 (m, 1H), 2.11 (s, 3H), 2.11-1.96 (m, 2H), 1.60-1.75 (m, 2H), 1.26-1.24 (m, 6H). | 9-(4-(3-(1-acetylpiperidin-4-yl)-1H-pyrazol-1-yl)benzyl)-2-(3-fluoro-2-isopropylphenyl)-7,9-dihydro-8H-purin-8-one |
| I-465 | m/z: 537.2531 [M + H]$^+$ Rt (min): 0.83 | | 9-(4-(3-(1-acetylpiperidin-4-yl)-1H-pyrazol-1-yl)benzyl)-2-(2-isopropylpyridin-3-yl)-7,9-dihydro-8H-purin-8-one |
| I-466 | m/z: 593.2041 [M + H]$^+$ Rt (min): 1.31 | | 9-(4-(3-(1-acetylpiperidin-4-yl)-1H-pyrazol-1-yl)benzyl)-2-(2-(2,2,2-trifluoroethoxy)pyridin-3-yl)-7,9-dihydro-8H-purin-8-one |
| I-467 | m/z: 522.241 [M + H]$^+$ Rt (min): 1.35 | $^1$H NMR (400 MHz, CD$_3$OD) δ 8.32 (s, 1H), 8.12 (s, 1H), 7.70-7.68 (m, 2H), 7.54-7.51 (m, 2H), 7.46-7.39 (m, 3H), 7.24-7.23 (m, 1H), 6.43-6.40 (m, 1H), 5.16 (s, 2H), 3.93-3.86 (m, 1H), 3.71-3.53 (m, 4H), 3.27-3.25 (m, 1H), 2.48-2.08 (m, 2H), 2.09-2.07 (m, 3H), 1.14-1.12 (m, 6H). | 9-(4-(3-(1-acetylpyrrolidin-3-yl)-1H-pyrazol-1-yl)benzyl)-2-(2-isopropylphenyl)-7,9-dihydro-8H-purin-8-one |
| I-468 | m/z: 536.2782 [M + H]$^+$ Rt (min): 1.47 | $^1$H NMR (400 MHz, CD$_3$OD) δ 8.32 (s, 1H), 8.11-8.09 (m, 1H), 7.71-7.68 (m, 2H), 7.54-7.51 (m, 2H), 7.44-7.43 (m, 3H), 7.21-7.19 (m, 1H), 6.41-6.39 (m, 1H), 5.17 (s, 2H), 4.62-4.58 (m, 0.5H), 4.28-4.22 (m, 0.5H), 4.04-3.98 (m, 0.5H), 3.92-3.80 (m, 0.5H), 3.42-3.39 (m, 1H), 3.28-3.15 (m, 1H), 3.00-2.82 (m, 2H), 2.21-2.19 (m, 4H), 1.90-1.77 (m, 2H), 1.71-1.50 (m, 1H), 1.15-1.13 (m, 6H) | 9-(4-(3-(1-acetylpiperidin-3-yl)-1H-pyrazol-1-yl)benzyl)-2-(2-isopropylphenyl)-7,9-dihydro-8H-purin-8-one |

TABLE 14-continued

| Cmpd no. | LCMS | ¹H NMR (300 MHz) δ ppm | Chemical Name |
|---|---|---|---|
| I-469 | m/z: 496.1985 [M + H]⁺ Rt (min): 1.5533 | | N-(4-((2-(2-isopropylphenyl)-7-methyl-8-oxo-7,8-dihydro-9H-purin-9-yl)methyl)phenyl)-1,3-dimethyl-1H-pyrazole-5-carboxamide |
| I-470 | m/z: 496.2198 [M + H]⁺ Rt (min): 1.3633 | | N-(4-((2-(2-isopropylphenyl)-7-methyl-8-oxo-7,8-dihydro-9H-purin-9-yl)methyl)phenyl)-N,5-dimethyl-1H-pyrazole-3-carboxamide |
| I-471 | m/z: 510.2578 [M + H]⁺ Rt (min): 1.4873 | | N-(4-((2-(2-isopropylphenyl)-7-methyl-8-oxo-7,8-dihydro-9H-purin-9-yl)methyl)phenyl)-N,1,3-trimethyl-1H-pyrazole-5-carboxamide |
| I-472 | m/z: 550.52 [M + H]⁺ Rt (min): 0.8152 | ¹H NMR (300 MHz, CD₃OD) δ 8.27 (s, 1H), 7.55-7.51 (m, 4H), 7.48-7.34 (m, 3H), 7.24-7.18 (m, 1H), 6.88 (s, 1H), 5.17 (s, 2H), 4.53 (d, J = 13.5 Hz, 1H), 3.94 (d, J = 13.8 Hz, 1H), 3.61 (s, 3H), 3.33-3.15 (m, 2H), 2.82-2.63 (m, 2H), 2.08 (s, 3H), 2.00-1.84 (m, 2H), 1.64-1.56 (m, 2H), 1.10 (d, J = 6.9 Hz, 6H). | 9-(4-(4-(1-acetylpiperidin-4-yl)-1-methyl-1H-imidazol-2-yl)benzyl)-2-(2-isopropylphenyl)-7,9-dihydro-8H-purin-8-one |
| I-473 | m/z: 550.49 [M + H]⁺ Rt (min): 0.8152 | ¹H NMR (300 MHz, CD₃OD) δ 8.28 (s, 1H), 7.51 (s, 4H), 7.43-7.34 (m, 3H), 7.24-7.18 (m, 1H), 6.78 (s, 1H), 5.17 (s, 2H), 4.53 (d, J = 13.4 Hz, 1H), 3.94 (d, J = 13.5 Hz, 1H), 3.61 (s, 3H), 3.33-3.19 (m, 2H), 2.96-2.70 (m, 2H), 2.08 (s, 3H), 2.06-1.97 (m, 2H), 1.69-1.44 (m, 2H), 1.12 (d, J = 6.9 Hz, 6H). | 9-(4-(5-(1-acetylpiperidin-4-yl)-1-methyl-1H-imidazol-2-yl)benzyl)-2-(2-isopropylphenyl)-7,9-dihydro-8H-purin-8-one |
| I-474 | m/z: 554.5907 [M + H]⁺ Rt (min): 1.3933 | ¹H NMR (400 MHz, DMSO-d₆) δ 11.66 (s, 1H), 8.41 (s, 1H), 8.34 (d, J = 2.5 Hz, 1H), 7.76-7.69 (m, 2H), 7.50-7.38 (m, 3H), 7.24 (d, J = 7.6 Hz, 1H), 7.11-7.02 (m, 1H), 6.41 (d, J = 2.4 Hz, 1H), 5.04 (s, 2H), 4.40 (d, J = 13.5 Hz, 1H), 3.87 (d, J = 13.7 Hz, 1H), 3.23-3.10 (m, 1H), 2.93 (m, 1H), 2.75-2.62 (m, 2H), 2.02 (s, 3H), 1.92 (t, J = 15.6 Hz, 2H), 1.68-1.54 (m, 1H), 1.53-1.40 (m, 1H), 1.04 (d, J = 6.8 Hz, 6H). | 9-(4-(3-(1-acetylpiperidin-4-yl)-1H-pyrazol-1-yl)benzyl)-2-(2-fluoro-6-isopropylphenyl)-7,9-dihydro-8H-purin-8-one |
| I-475 | m/z: 440.4162 [M + H]⁺ Rt (min): 1.345 | | 9-((4-fluoro-1-isobutyrylpiperidin-4-yl)methyl)-2-(2-isopropylphenyl)-7,9-dihydro-8H-purin-8-one |
| I-476 | m/z: 576.564 [M + H]⁺ Rt (min): 1.375 | ¹H NMR (400 MHz, CD₃OD) δ 8.23 (s, 1H), 8.15 (s, 1H), 7.53-7.51 (m, 2H), 7.43-7.41 (m, 2H), 7.35-7.33 (m, 3H), 7.18-7.13 (m, 1H), 5.13-5.08 (m, 3H), 4.51-4.46 (m, 1H), 4.35-4.26 (m, 2H), 4.09-4.05 (m, 1H), 3.22-3.20 (m, 1H), 1.78 (s, 3H), 1.08 (d, J = 6.8 Hz, 6H). | 9-(4-(1-(1-acetylazetidin-3-yl)-4-(trifluoromethyl)-1H-imidazol-2-yl)benzyl)-2-(2-isopropylphenyl)-7,9-dihydro-8H-purin-8-one |
| I-477 | m/z: 577.5391 [M + H]⁺ Rt (min): 0.8067 | | 9-(4-(1-(1-acetylazetidin-3-yl)-4-(trifluoromethyl)-1H-imidazol-2-yl)benzyl)-2-(2-isopropylpyridin-3-yl)-7,9-dihydro-8H-purin-8-one |

Example 40: General Preparation of Ureas

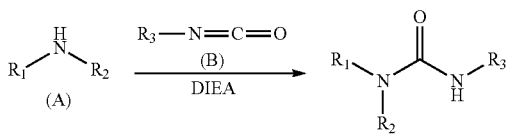

A reaction vial containing 0.2 M solution of the appropriate purinone amine (A) (150 µL, 30 µmol) in 10% DIEA/DCE, DIEA (10.48 µL, 60.0 µmol) and a 0.2 M solution of the appropriate isocyanate (B) (180 µL, 36.0 µmol) was stirred at ambient temperature for 20 hours, then was treated with additional DIEA (10.48 µL, 60.0 µmol) and a 0.2 M solution of the appropriate isocyanate (180 µL, 36.0 µmol) in DCE. The mixture was heated at 50° C. for 24 h, then was concentrated under a stream of nitrogen and the crude material purified by mass-directed preparative reverse phase HPLC.

Table 15. The following compounds were synthesized according to Example 40.

TABLE 15

| Cmpd no. | LCMS | $^1$H NMR (300 MHz) δ ppm | Chemical Name |
|---|---|---|---|
| I-478 | m/z: 451.1649 [M + H]$^+$ Rt (min): 1.38 | | N-isopropyl-4-((2-(2-isopropylphenyl)-7-methyl-8-oxo-7,8-dihydro-9H-purin-9-yl)methyl)piperidine-1-carboxamide |
| I-479 | m/z: 449.15 [M + H]$^+$ Rt (min): 1.29 | | N-cyclopropyl-4-((2-(2-isopropylphenyl)-7-methyl-8-oxo-7,8-dihydro-9H-purin-9-yl)methyl)piperidine-1-carboxamide |
| I-480 | m/z: 551.3 [M + H]$^+$ Rt (min): 1.36 | $^1$H NMR (300 MHz, CD$_3$OD) δ 8.33 (s, 1H), 8.09 (d, J = 2.4 Hz, 1H), 7.69 (d, J = 8.4 Hz, 2H), 7.56-7.40 (m, 5H), 7.30-7.25 (m, 1H), 6.37 (d, J = 2.4 Hz, 1H), 5.18 (s, 2H), 4.10-4.05 (m, 2H), 3.31-3.25 (m, 1H), 3.02-2.87 (m, 3H), 2.75 (s, 3H), 2.05-1.98 (m, 2H), 1.74-1.60 (m, 2H), 1.16 (d, J = 6.9 Hz, 6H). | 4-(1-(4-((2-(2-isopropylphenyl)-8-oxo-7,8-dihydro-9H-purin-9-yl)methyl)phenyl)-1H-pyrazol-3-yl)-N-methylpiperidine-1-carboxamide |
| I-481 | m/z: 459.3812 [M + H]$^+$ Rt (min): 1.4897 | | 1-isopropyl-3-(4-((2-(2-isopropylphenyl)-7-methyl-8-oxo-7,8-dihydro-9H-purin-9-yl)methyl)phenyl)urea |
| I-482 | m/z: 475.4037 [M + H]$^+$ Rt (min): 1.3534 | | 1-(4-((2-(2-isopropylphenyl)-7-methyl-8-oxo-7,8-dihydro-9H-purin-9-yl)methyl)phenyl)-3-(2-methoxyethyl)urea |
| I-483 | m/z: 457.3714 [M + H]$^+$ Rt (min): 1.4059 | | 1-cyclopropyl-3-(4-((2-(2-isopropylphenyl)-7-methyl-8-oxo-7,8-dihydro-9H-purin-9-yl)methyl)phenyl)urea |
| I-484 | m/z: 473.4262 [M + H]$^+$ Rt (min): 1.5436 | | 3-isopropyl-1-(4-((2-(2-isopropylphenyl)-7-methyl-8-oxo-7,8-dihydro-9H-purin-9-yl)methyl)phenyl)-1-methylurea |
| I-485 | m/z: 489.447 [M + H]$^+$ Rt (min): 1.3942 | | 1-(4-((2-(2-isopropylphenyl)-7-methyl-8-oxo-7,8-dihydro-9H-purin-9-yl)methyl)phenyl)-3-(2-methoxyethyl)-1-methylurea |
| I-486 | m/z: 471.3727 [M + H]$^+$ Rt (min): 1.445 | | 3-cyclopropyl-1-(4-((2-(2-isopropylphenyl)-7-methyl-8-oxo-7,8-dihydro-9H-purin-9-yl)methyl)phenyl)-1-methylurea |
| I-487 | m/z: 455.4436 [M + H]$^+$ | | 4-fluoro-N-isopropyl-4-((2-(2-isopropylphenyl)- |

TABLE 15-continued

| Cmpd no. | LCMS | ¹H NMR (300 MHz) δ ppm | Chemical Name |
|---|---|---|---|
| | Rt (min): 1.2767 | | 8-oxo-7,8-dihydro-9H-purin-9-yl)methyl)piperidine-1-carboxamide |

Example 41: General Protocol for Alkylation of Anilines

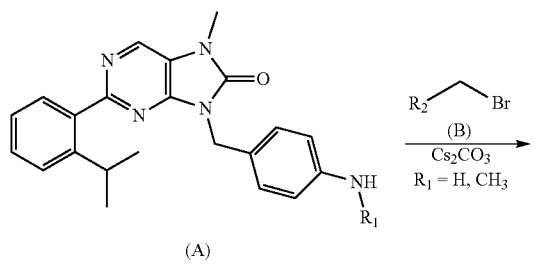

(A)

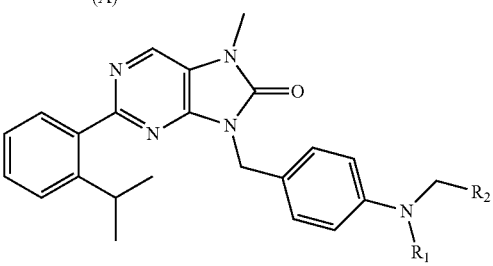

A mixture of aniline (A) (either Intermediate B-104 or B-105) (0.2M in DMF, 150 μL, 30 μmol), cesium carbonate (19.55 mg, 60.0 μmol), and alkyl halide (B) (0.2M in DMF, 225 μL, 45.0 μmol) was heated either at 80° C. for 20 h (if $R_1$=H) or 110° C. (if $R_1$=CH$_3$). If a reaction was not complete after 20 h, additional alkyl halide (B) (0.2M in DMF, 225 μL, 45.0 μmol) was added and the reaction heated at the appropriate temperature for an additional 20 h. The reaction mixture was concentrated and partitioned between saturated sodium bicarbonate (0.6 mL) and EtOAc (0.6 mL). The organic layer was separated and the aqueous phase was extracted with EtOAc. The combined extracts were concentrated and purified by mass-triggered preparative reverse-phase HPLC to afford the desired product.

Table 16. The following compounds were synthesized according to Example 41.

TABLE 16

| Cmpd no. | LCMS | Chemical Name |
|---|---|---|
| I-488 | m/z: 428.37 [M + H]⁺ Rt (min): 1.5976 | 9-(4-((cyclopropylmethyl)amino)benzyl)-2-(2-isopropylphenyl)-7-methyl-7,9-dihydro-8H-purin-8-one |
| I-489 | m/z: 432.36 [M + H]⁺ Rt (min): 1.5659 | 2-(2-isopropylphenyl)-9-(4-((2-methoxyethyl)amino)benzyl)-7-methyl-7,9-dihydro-8H-purin-8-one |
| I-490 | m/z: 442.37 [M + H]⁺ Rt (min): 1.57 | 9-(4-((cyclopropylmethyl)(methyl)amino)benzyl)-2-(2-isopropylphenyl)-7-methyl-7,9-dihydro-8H-purin-8-one |

TABLE 16-continued

| Cmpd no. | LCMS | Chemical Name |
|---|---|---|
| I-491 | m/z: 446.34 [M + H]⁺ Rt (min): 1.6785 | 2-(2-isopropylphenyl)-9-(4-((2-methoxyethyl)(methyl)amino)benzyl)-7-methyl-7,9-dihydro-8H-purin-8-one |

Example 42: General Protocol for Amine Arylation

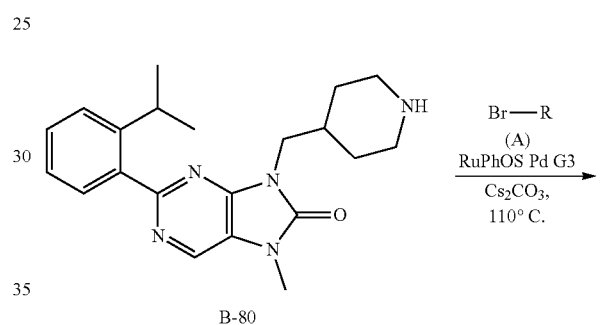

B-80

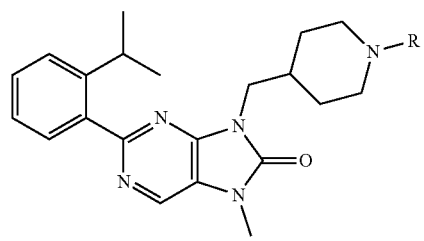

A mixture of Intermediate B-80 (0.2M in DMF, 150 μL, 30 μmol), heteroaryl bromide (A) (0.2M in DMF, 300 μL, 60 μmol), cesium carbonate (48 mg, 150 μmol), and RuPhos Pd G3 (0.02M in DMF, 300 μL, 6 μmol) was heated for 16 h at 110° C. The reaction mixture was cooled to ambient temperature, concentrated and partitioned between 1N NaOH (0.5 mL) and EtOAc (0.5 mL). The organic layer was separated and the aqueous phase was extracted with EtOAc. The combined organic extracts were concentrated to afford the crude product, which was purified by mass-triggered preparatory HPLC. The product-containing fractions were combined and concentrated in a Genevac to afford the desired product.

Table 17. The following compounds were synthesized according to Example 42.

TABLE 17

| Cmpd no. | LCMS | Chemical Name |
|---|---|---|
| I-492 | m/z: 450.103 (M + H)+ Rt (min): 1.34 | 9-((1-(1,3,4-thiadiazol-2-yl)piperidin-4-yl)methyl)-2-(2-isopropylphenyl)-7-methyl-7,9-dihydro-8H-purin-8-one |
| I-493 | m/z: 444.12 (M + H)+ Rt (min): 1.58 | 2-(2-isopropylphenyl)-7-methyl-9-((1-(pyrimidin-2-yl)piperidin-4-yl)methyl)-7,9-dihydro-8H-purin-8-one |
| I-494 | m/z: 477.4 (M + H)+ Rt (min): 1.8135 | 9-((1-(2,5-dimethylthiazol-4-yl)piperidin-4-yl)methyl)-2-(2-isopropylphenyl)-7-methyl-7,9-dihydro-8H-purin-8-one |
| I-495 | m/z: 427.16 (M + H)+ Rt (min): 0.92 | 2-(2-isopropylphenyl)-9-(2-(pyridin-3-yl)-2-azaspiro[3.3]heptan-5-yl)-7-methyl-7,9-dihydro-8H-purin-8-one |

Example 43: General Protocol for Imidazole Alkylation

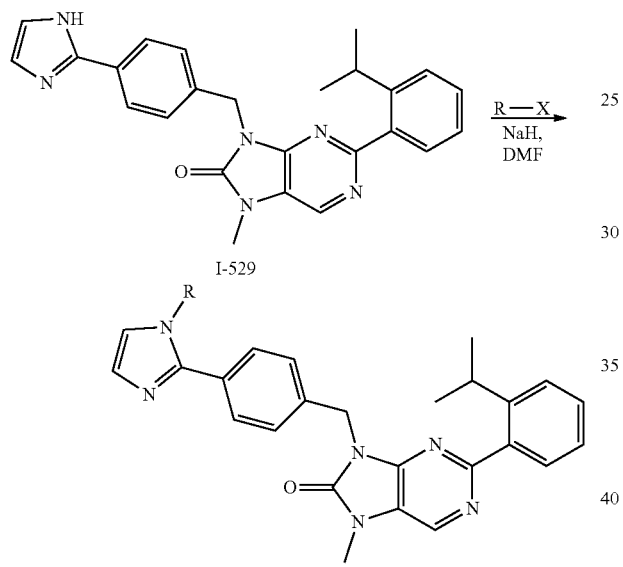

A mixture of 9-(4-(1H-imidazol-2-yl)benzyl)-2-(2-isopropylphenyl)-7-methyl-7,9-dihydro-8H-purin-8-one (I-529) (80 mg, 0.19 mmol) in DMF (5 mL) was treated with sodium hydride (60% dispersion in mineral oil, 22 mg, 0.57 mmol) at 0° C. After stirring the resulting mixture for 0.5 h at room temperature, the appropriate alkyl halide (1.2 equiv) was added. The resulting mixture was stirred for 2 h at room temperature, then was poured into water (20 mL) and was extracted with EtOAc (3×20 mL). The organic layers were combined, washed with brine (20 mL), dried over anhydrous sodium sulfate, filtered and concentrated under vacuum. The product was purified by prep-HPLC.

Table 18. The following compounds were synthesized according to Example 43 employing the appropriate alkyl halide. Note: I-499 was subjected to an additional step (Example 36) to remove the Boc group.

TABLE 18

| Cmpd no. | LCMS | $^1$H NMR (300 MHz) δ ppm | Chemical Name |
|---|---|---|---|
| I-496 | m/z: 453.16 [M + H]+ Rt (min): 0.89 | $^1$H NMR (300 MHz, CD$_3$OD) δ 8.44 (s, 1H), 7.58-7.31 (m, 7H), 7.27-7.22 (m, 2H), 7.01 (d, J = 1.20 Hz, 1H), 5.22 (s, 2H), 4.07 (q, J = 7.2 Hz, 2H), 3.53 (s, 3H), 3.35-3.26 (m, 1H), 1.32 (t, J = 7.2 Hz, 3H), 1.14 (d, J = 6.9 Hz, 6H). | 9-(4-(1-ethyl-1H-imidazol-2-yl)benzyl)-2-(2-isopropylphenyl)-7-methyl-7,9-dihydro-8H-purin-8-one |
| I-497 | m/z: 467.2 [M + H]+ Rt (min): 0.95 | $^1$H NMR (300 MHz, CD$_3$OD) δ 8.47 (s, 1H), 7.63-7.36 (m, 7H), 7.38-7.21 (m, 2H), 7.03 (d, J = 1.2 Hz, 1H), 5.25 (s, 2H), 4.53-4.44 (m, 1H), 3.53 (s, 3H), 3.35-3.30 (m, 1H), 1.39 (d, J = 6.9 Hz, 6H), 1.14 (d, J = 6.9 Hz, 6H). | 9-(4-(1-isopropyl-1H-imidazol-2-yl)benzyl)-2-(2-isopropylphenyl)-7-methyl-7,9-dihydro-8H-purin-8-one |
| I-498 | m/z: 483.18 [M + H]+ Rt (min): 0.89 | | 2-(2-isopropylphenyl)-9-(4-(1-(2-methoxyethyl)-1H-imidazol-2-yl)benzyl)-7-methyl-7,9-dihydro-8H-purin-8-one |
| I-499 | m/z: 508.27 [M + H]+ | | 2-(2-isopropylphenyl)-7-methyl-9-(4-(1- |

TABLE 18-continued

| Cmpd no. | LCMS | ¹H NMR (300 MHz) δ ppm | Chemical Name |
|---|---|---|---|
| | Rt (min): 0.56 | | (piperidin-4-yl)-1H-imidazol-2-yl)benzyl)-7,9-dihydro-8H-purin-8-one |
| I-500 | m/z: 475.14 [M + H]⁺ Rt (min): 1.5 | ¹H NMR (400 MHz, CDCl₃) δ 8.32 (s, 1H), 7.65 (d, J = 8.0 Hz, 2H), 7.59-7.53 (m, 3H), 7.46-7.36 (m, 3H), 7.38-7.15 (m, 2H), 7.00 (t, J = 59.6 Hz, 1H), 5.22 (s, 2H), 3.54-3.45 (m, 4H), 1.77-1.28 (m, 6H). | 9-(4-(1-(difluoromethyl)-1H-imidazol-2-yl)benzyl)-2-(2-isopropylphenyl)-7-methyl-7,9-dihydro-8H-purin-8-one |

9-((1-(1,4-Dimethyl-1H-imidazol-2-yl)piperidin-4-yl)methyl)-2-(2-isopropylphenyl)-7-methyl-7,9-dihydro-8H-purin-8-one (I-501)

2-(2-Isopropylphenyl)-9-((1-(4-(trifluoromethyl)pyrimidin-2-yl)azetidin-3-yl)methyl)-7,9-dihydro-8H-purin-8-one (I-502)

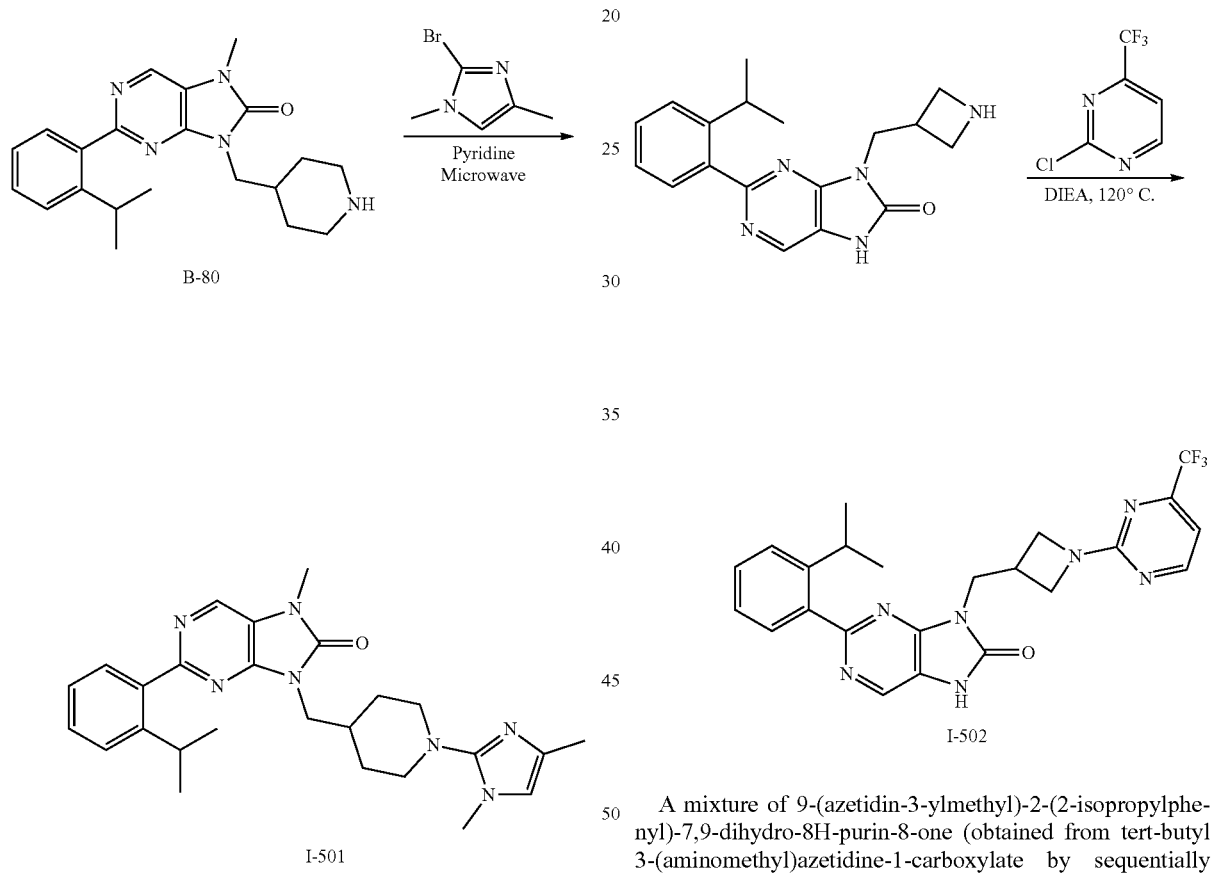

A mixture of Intermediate B-80 (0.2M solution in pyridine, 150 µl, 30 µmol) and 2-bromo-1,4-dimethyl-1H-imidazole (0.2M solution in pyridine, 300 µl, 60 µmol) was heated for 30 min at 220° C. in a Biotage Initiator microwave. After cooling to ambient temperature, the volatiles were removed under reduced pressure. The residue was treated with 1N NaOH (0.5 mL) and the mixture extracted with EtOAc (2×0.5 mL). The volatiles were removed under reduced pressure and the residue was purified using mass-triggered preparatory HPLC to afford 9-((1-(1,4-Dimethyl-1H-imidazol-2-yl)piperidin-4-yl)methyl)-2-(2-isopropylphenyl)-7-methyl-7,9-dihydro-8H-purin-8-one (I-501). LCMS Rt (min): 0.9096, m/z 460.48 [M+H]⁺.

A mixture of 9-(azetidin-3-ylmethyl)-2-(2-isopropylphenyl)-7,9-dihydro-8H-purin-8-one (obtained from tert-butyl 3-(aminomethyl)azetidine-1-carboxylate by sequentially following Example 35 and Example 36) (0.2M in DMF, 150 µL, 30 µmol), 2-chloro-4-(trifluoromethyl)pyrimidine (0.2M in DMF, 300 µL, 60 µmol), and DIEA (17.4 µL, 100 µmol) was heated for 30 min at 120° C. in a Biotage Initiator microwave reactor. The reaction mixture was cooled to room temperature, concentrated and partitioned between 1N NaOH (0.5 mL) and EtOAc (0.5 mL). The organic layer was separated and the aqueous phase was extracted with EtOAc. The combined organic extracts were concentrated to afford the crude product, which was purified by mass-triggered preparatory HPLC. The product-containing fractions were combined and concentrated in a Genevac to afford 2-(2-isopropylphenyl)-9-((1-(4-(trifluoromethyl)pyrimidin-2-yl)azetidin-3-yl)methyl)-7,9-dihydro-8H-purin-8-one (I-502). LCMS Rt (min): 1.6367, m/z 470.3975 [M+H]⁺.

383

Example 44. 1-(4-((2-(2-Isopropylphenyl)-8-oxo-7,8-dihydro-9H-purin-9-yl)methyl)phenyl)-N,N,5-trimethyl-1H-pyrazole-3-carboxamide (I-503)

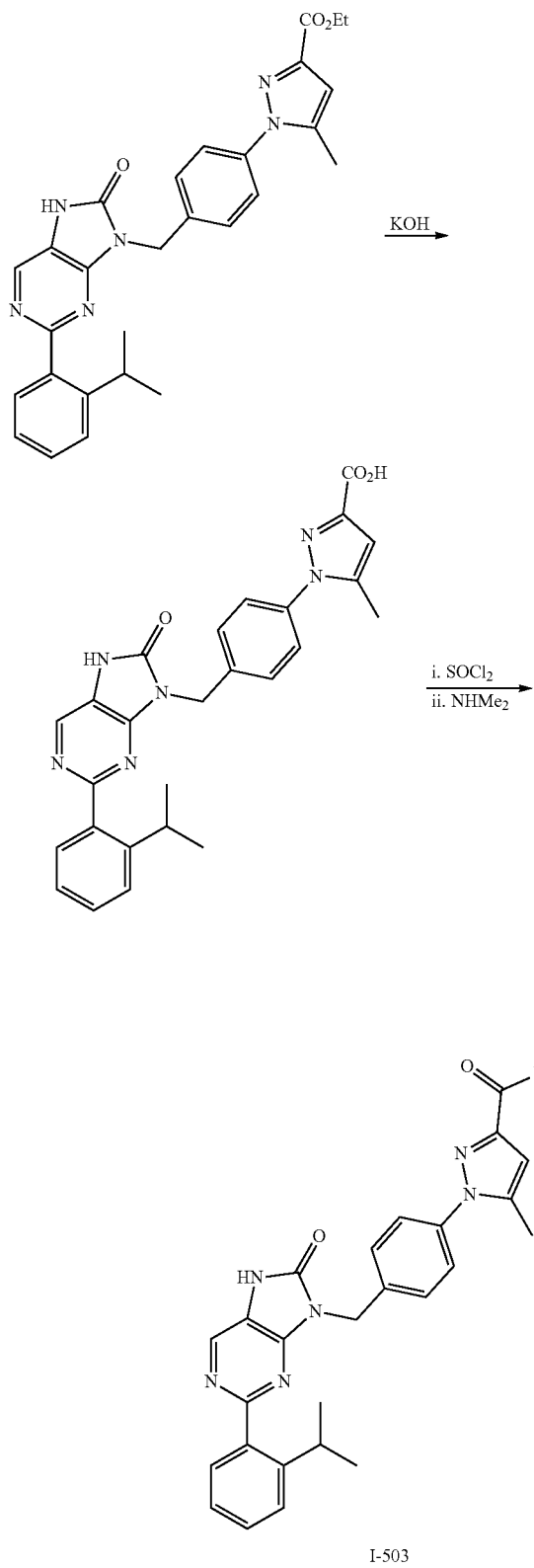

384

Step 1. 1-(4-((2-(2-Isopropylphenyl)-8-oxo-7,8-dihydro-9H-purin-9-yl)methyl)phenyl)-5-methyl-1H-pyrazole-3-carboxylic acid A mixture of ethyl 1-(4-((2-(2-isopropylphenyl)-8-oxo-7,8-dihydro-9H-purin-9-yl)methyl)phenyl)-5-methyl-1H-pyrazole-3-carboxylate (prepared from Intermediate B-32 following Example 35) (500 mg, 1.01 mmol), THF (15 mL), MeOH (15 mL), water (15 mL) and potassium hydroxide (170 mg, 3.03 mmol) was stirred for 18 h at room temperature. The reaction mixture was concentrated under vacuum and diluted with water (50 mL). The pH value was adjusted to 4 with diluted hydrochloric acid (1 N) and the solids were collected by filtration and dried under vacuum to afford 420 mg (89%) of 1-(4-((2-(2-isopropylphenyl)-8-oxo-7,8-dihydro-9H-purin-9-yl)methyl)phenyl)-5-methyl-1H-pyrazole-3-carboxylic acid as a yellow solid. MS (ESI) m/z 469.2 [M+H]$^+$.

Step 2. 1-(4-((2-(2-Isopropylphenyl)-8-oxo-7,8-dihydro-9H-purin-9-yl)methyl)phenyl)-N,N,5-trimethyl-1H-pyrazole-3-carboxamide A mixture of 1-(4-((2-(2-isopropylphenyl)-8-oxo-7,8-dihydro-9H-purin-9-yl)methyl)phenyl)-5-methyl-1H-pyrazole-3-carboxylic acid (100 mg, 0.21 mmol) and thionyl chloride (10 mL) was stirred for 0.5 h at 80° C. After cooling to room temperature, the resulting mixture was concentrated under vacuum and dissolved in DCM (15 mL). To this solution triethylamine (65 mg, 0.64 mmol) and dimethylamine hydrochloride (19 mg, 0.23 mmol) was added successively at 0° C. The resulting solution was stirred for 1 h at 0° C. then was concentrated under vacuum. The residue was purified by prep-TLC (eluting with 20/1 DCM/MeOH) and further purified by prep-HPLC to afford 15.6 mg (15%) of 1-(4-((2-(2-isopropylphenyl)-8-oxo-7,8-dihydro-9H-purin-9-yl)methyl)phenyl)-N,N, 5-trimethyl-1H-pyrazole-3-carboxamide (I-503) as a white solid. $^1$H NMR (400 MHz, CDCl$_3$) δ 8.60 (s, 1H), 7.62-7.59 (m, 3H), 7.52-7.47 (m, 2H), 7.41-7.38 (m, 2H), 7.37-7.28 (m, 1H), 6.58 (s, 1H), 5.20 (s, 2H), 3.48-3.39 (m, 1H), 3.34 (s, 3H), 3.10 (s, 3H), 2.32 (s, 3H), 1.24 (d, J=6.80 Hz, 6H). LCMS Rt (min): 1.3817, m/z 496.5323 [M+H]$^+$.

1-(4-((2-(2-Cyclopropylphenyl)-8-oxo-7,8-dihydro-9H-purin-9-yl)methyl)phenyl)-N,N,5-trimethyl-1H-pyrazole-3-carboxamide (I-504)

I-504

Ethyl 1-(4-((2-(2-cyclopropylphenyl)-8-oxo-7,8-dihydro-9H-purin-9-yl)methyl)phenyl)-5-methyl-1H-pyrazole-3-carboxylate (prepared from Intermediates B-32 and B-8 following Example 31) was used to prepare 1-(4-((2-(2-cyclopropylphenyl)-8-oxo-7,8-dihydro-9H-purin-9-yl)

methyl)phenyl)-N,N,5-trimethyl-1H-pyrazole-3-carboxamide (I-504) following Example 44. LCMS Rt (min): 1.2917, m/z 494.5584 [M+H]$^+$ 9-((4-Fluoro-1-(pyridin-3-yl)piperidin-4-yl)methyl)-2-(2-isopropylphenyl)-7,9-dihydro-8H-purin-8-one (I-505)

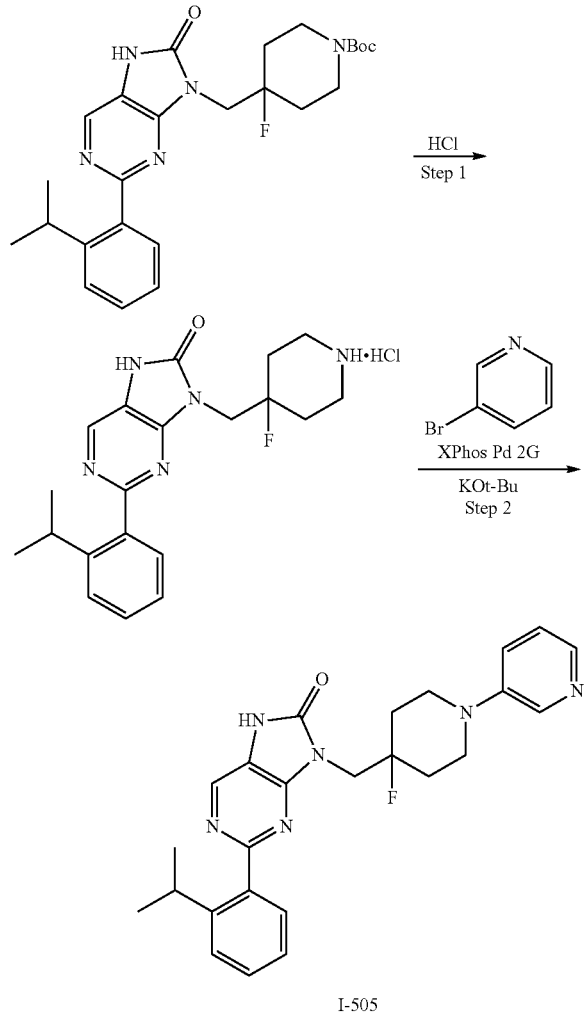

I-505

Step 1. 9-((4-Fluoropiperidin-4-yl)methyl)-2-(2-isopropylphenyl)-7,9-dihydro-8H-purin-8-one hydrochloride To a solution of tert-butyl 4-fluoro-4-((2-(2-isopropylphenyl)-8-oxo-7,8-dihydro-9H-purin-9-yl)methyl)piperidine-1-carboxylate (prepared from tert-butyl 4-(aminomethyl)-4-fluoropiperidine-1-carboxylate following Example 35) (0.18 g, 0.383 mmol) in 1,4-dioxane (2 mL) was added HCl (4M in 1,4-dioxane, 1.725 mL, 6.90 mmol) at ambient temperature. The reaction mixture was heated to 50° C. for 1 h, then was cooled to ambient temperature. The resulting white solids were collected by vacuum filtration, washed with ether and dried under reduced pressure to afford 9-((4-fluoropiperidin-4-yl)methyl)-2-(2-isopropylphenyl)-7,9-dihydro-8H-purin-8-one hydrochloride (151 mg, 97%). MS (ESI) m/z 370.12 [M+H]$^+$.

Step 2. 9-((4-Fluoro-1-(pyridin-3-yl)piperidin-4-yl)methyl)-2-(2-isopropylphenyl)-7,9-dihydro-8H-purin-8-one A mixture of 9-((4-fluoropiperidin-4-yl)methyl)-2-(2-isopropylphenyl)-7H-purin-8(9H)-one (20 mg, 0.054 mmol), 3-bromopyridine (17 mg, 0.11 mmol), sodium tert-butoxide (16 mg, 0.162 mmol), and XPhos Pd G2 (4.26 mg, 5.41 µmol) was evacuated and backfilled with nitrogen three times before 1,4-dioxane (1.2 mL) was added and nitrogen was bubbled through the reaction mixture. The reaction vial was sealed and heated to 100° C. for 48 h. After cooling to ambient temperature, the mixture was diluted with EtOAc, sequentially washed with water and brine, dried over sodium sulfate, filtered, concentrated and purified by reverse phase HPLC to afford 9-((4-fluoro-1-(pyridin-3-yl)piperidin-4-yl)methyl)-2-(2-isopropylphenyl)-7,9-dihydro-8H-purin-8-one (I-505) (10.8 mg, 45% yield). $^1$H NMR (300 MHz, CDCl$_3$): δ 8.31 (s, 1H), 7.51 (br d, J=7.6 Hz, 1H), 7.39-7.31 (m, 2H), 7.25-7.16 (m, 5H), 7.12 (br s, 1H), 4.15 (s, 1H), 4.09 (s, 1H), 3.47 (m, 3H), 3.11-2.99 (m, 2H), 1.97 (m, 4H), 1.16 (d, J=7.0 Hz, 6H). LCMS Rt (min): 0.835, m/z 447.38 [M+H]$^+$.

9-(4-(1-(2-hydroxyethyl)-4-(trifluoromethyl)-1H-imidazol-2-yl)benzyl)-2-(2-isopropylphenyl)-7,9-dihydro-8H-purin-8-one (I-506)

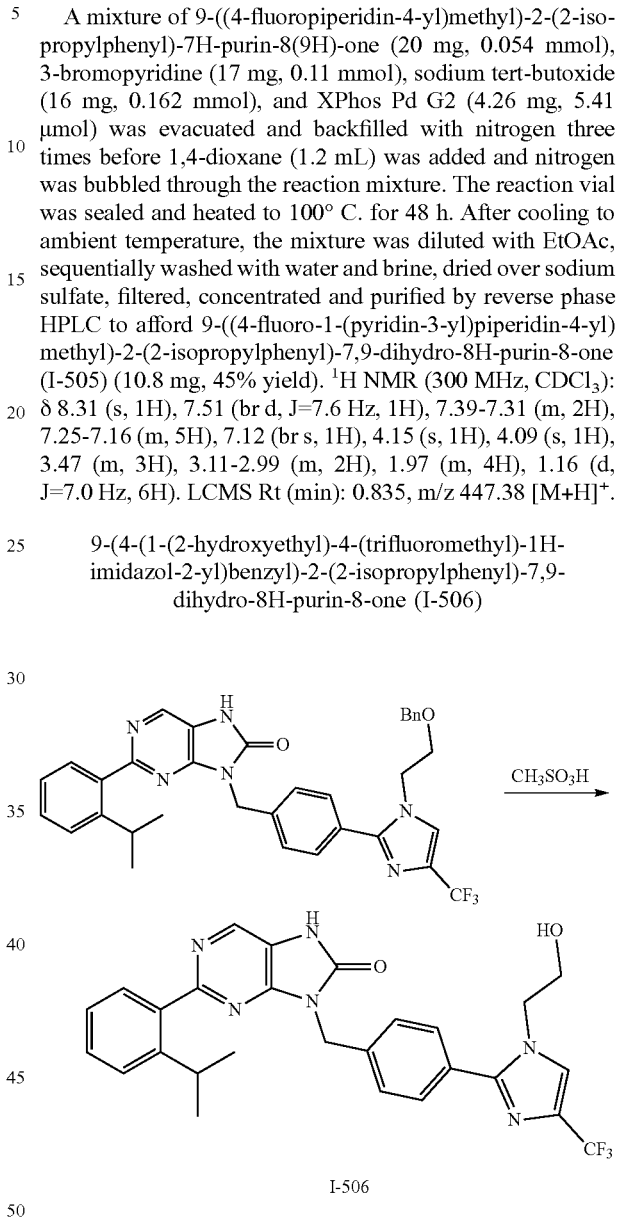

I-506

A solution of 9-(4-(1-(2-(benzyloxy)ethyl)-4-(trifluoromethyl)-1H-imidazol-2-yl)benzyl)-2-(2-isopropylphenyl)-7,9-dihydro-8H-purin-8-one (prepared from Intermediate B-34 following Example 35) (100 mg, 0.16 mmol), DCM (5 mL) and methanesulfonic acid (1 mL) was stirred for 18 h at ambient temperature. The reaction mixture was concentrated under vacuum and the residue was purified by prep-HPLC to afford 9-(4-(1-(2-hydroxyethyl)-4-(trifluoromethyl)-1H-imidazol-2-yl)benzyl)-2-(2-isopropylphenyl)-7,9-dihydro-8H-purin-8-one (I-506) (22.0 mg, 26%) as a white solid. $^1$H NMR (400 MHz, DMSO-d$_6$) δ 8.37 (d, J=1.2 Hz, 1H), 7.94 (s, 1H), 7.66-7.64 (m, 2H), 7.54-7.33 (m, 5H), 7.28-7.19 (m, 1H), 5.09 (s, 2H), 5.05 (br s, 1H), 4.05 (t, J=5.6 Hz, 2H), 3.67 (t, J=5.6 Hz, 2H), 3.47-3.45 (m, 1H), 1.08 (d, J=6.8 Hz, 6H). LCMS Rt (min): 1.405, m/z 523.41 [M+H]$^+$.

7-Ethyl-2-(2-isopropylpyridin-3-yl)-9-(4-(1-methyl-4-(trifluoromethyl)-1H-imidazol-2-yl)benzyl)-7,9-dihydro-8H-purin-8-one (I-507)

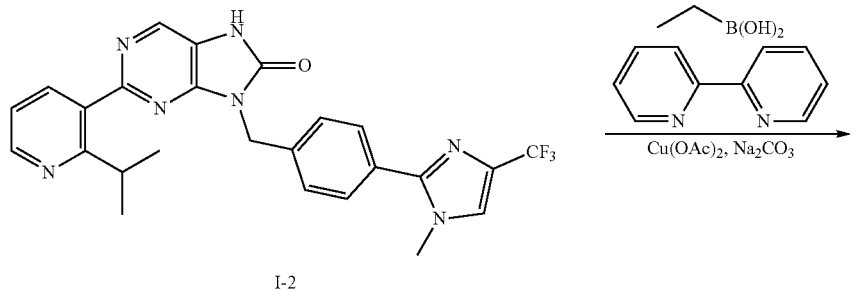

A mixture of ethylboronic acid (14.97 mg, 0.203 mmol), 2-(2-isopropylpyridin-3-yl)-9-(4-(1-methyl-4-(trifluoromethyl)-1H-imidazol-2-yl)benzyl)-7,9-dihydro-8H-purin-8-one (I-2) (50 mg, 0.101 mmol) and sodium carbonate (21.48 mg, 0.203 mmol) in DCE (1 mL) and DMF (0.3 mL) was treated with a suspension of copper (II) acetate (18.40 mg, 0.101 mmol) and 2,2'-bipyridine (15.82 mg, 0.101 mmol) in hot DCE (0.5 mL) and the mixture was stirred at 70° C. for 24 h. The reaction mixture was cooled to room temperature and was washed with successively with saturated aqueous ammonium chloride and water. The organic layer was separated and the aqueous layer was extracted with DCM (3×). The combined organic layers were washed with brine, dried over sodium sulfate, filtered, concentrated under reduced pressure and purified by prep-HPLC to afford 7-ethyl-2-(2-isopropylpyridin-3-yl)-9-(4-(1-methyl-4-(trifluoromethyl)-1H-imidazol-2-yl)benzyl)-7,9-dihydro-8H-purin-8-one (I-507) (2.0 mg, 4% yield). $^1$H NMR (300 MHz, CDCl$_3$) δ 8.59 (dd, J=1.5, 4.7 Hz, 1H), 8.26 (s, 1H), 7.90-7.84 (m, 1H), 7.53 (m, 4H), 7.21 (s, 1H), 7.16-7.12 (m, 1H), 5.12 (s, 2H), 3.95 (d, J=7.3 Hz, 2H), 3.66 (s, 3H), 3.63-3.56 (m, 1H), 1.36 (t, J=7.3 Hz, 3H), 1.23 (d, J=6.7 Hz, 6H). LCMS Rt (min): 1.112, m/z 522.4744 [M+H]$^+$.

Example 45. 9-((5-(1H-Pyrazol-1-yl)pyrazin-2-yl)methyl)-2-(2-isopropylphenyl)-7,9-dihydro-8H-purin-8-one (I-508)

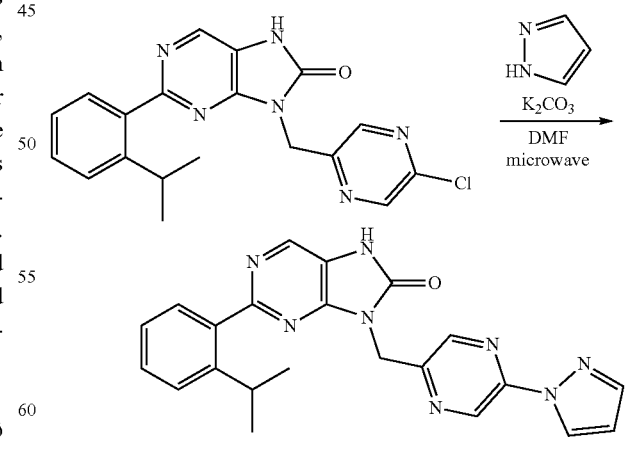

A mixture of 9-((5-chloropyrazin-2-yl)methyl)-2-(2-isopropylphenyl)-7H-purin-8(9H)-one (prepared from (5-chloropyrazin-2-yl)methanamine following Example 35) (150

µL of a 0.2M solution in DMF, 30 µmol), potassium carbonate (20 mg, 145 µmol) and 1H-pyrazole (500 µL of a 0.2M solution in DMF, 100 µmol) was sequentially heated for 10 min at 150° C. and 30 min at 160° C. in a Biotage microwave. The volatiles were removed under reduced pressure, 1N NaOH (0.5 mL) was added, and the mixture extracted with EtOAc (2×0.5 mL). The combined organic extracts were concentrated and purified by mass-triggered preparatory HPLC to afford 9-((5-(1H-pyrazol-1-yl)pyrazin-2-yl)methyl)-2-(2-isopropylphenyl)-7,9-dihydro-8H-purin-8-one (I-508). LCMS Rt (min): 1.425, m/z 413.3142 [M+H]$^+$.

9-((5-(1H-pyrazol-1-yl)pyrimidin-2-yl)methyl)-2-(2-isopropylphenyl)-7,9-dihydro-8H-purin-8-one (I-509)

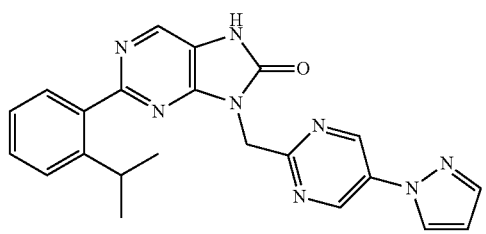

I-509

9-((5-Chloropyrimidin-2-yl)methyl)-2-(2-isopropylphenyl)-7,9-dihydro-8H-purin-8-one (prepared from (5-chloropyrimidin-2-yl)methanamine following Example 35) was used to prepare 9-((5-(1H-pyrazol-1-yl)pyrimidin-2-yl)methyl)-2-(2-isopropylphenyl)-7,9-dihydro-8H-purin-8-one (I-509) according to Example 45. LCMS Rt (min): 1.2867, m/z 413.3143 [M+H]$^+$.

9-((5-(3,5-Dimethyl-1H-pyrazol-1-yl)pyrazin-2-yl)methyl)-2-(2-isopropylphenyl)-7,9-dihydro-8H-purin-8-one (I-510)

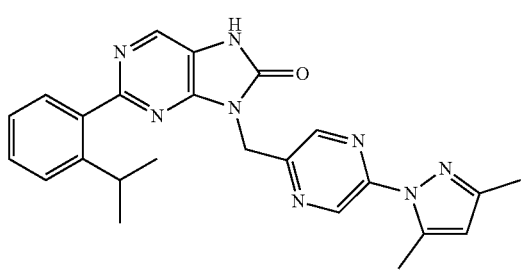

I-510

9-((5-(3,5-Dimethyl-1H-pyrazol-1-yl)pyrazin-2-yl)methyl)-2-(2-isopropylphenyl)-7,9-dihydro-8H-purin-8-one (I-510) was prepared according to Example 45, substituting 3,5-dimethyl-1H-pyrazole for 1H-pyrazole. LCMS Rt (min): 1.595, m/z 441.3356 [M+H]$^+$.

9-((5-(3,5-Dimethyl-1H-pyrazol-1-yl)pyrimidin-2-yl)methyl)-2-(2-isopropylphenyl)-7,9-dihydro-8H-purin-8-one (I-511)

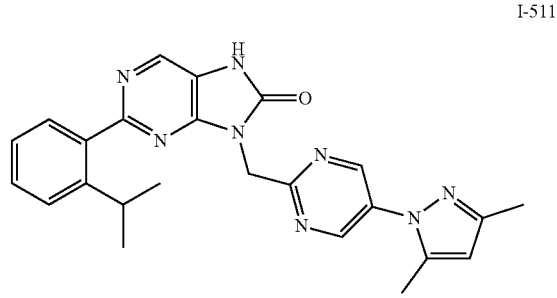 [SMILES: Cc1cc(C)n(-c2cnc(Cn3c(=O)[nH]c4cnc(-c5ccccc5C(C)C)nc43)nc2)n1]

I-511

9-((5-(3,5-dimethyl-1H-pyrazol-1-yl)pyrimidin-2-yl)methyl)-2-(2-isopropylphenyl)-7,9-dihydro-8H-purin-8-one was prepared in an analogous fashion to 9-((5-(1H-pyrazol-1-yl)pyrimidin-2-yl)methyl)-2-(2-isopropylphenyl)-7,9-dihydro-8H-purin-8-one (I-511), substituting 3,5-dimethyl-1H-pyrazole for 1H-pyrazole. LCMS Rt (min): 1.3917, m/z 441.3604 [M+H]$^+$.

2-(2-Isopropylphenyl)-9-(4-(2-oxopyrrolidin-1-yl)benzyl)-7,9-dihydro-8H-purin-8-one (I-512)

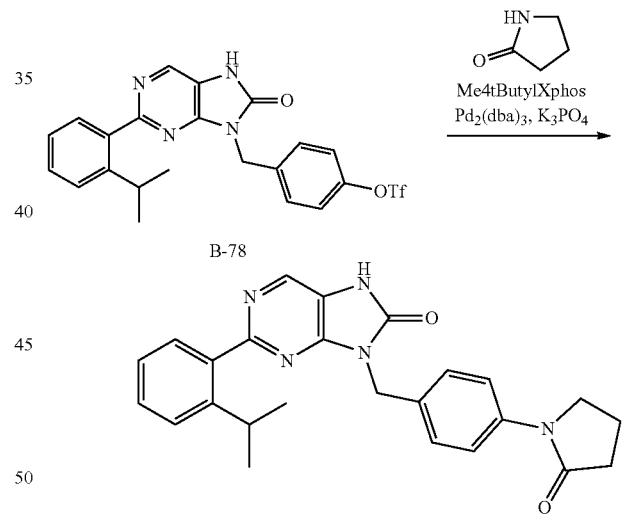

I-512

Note: All solutions are in tert-butanol unless specifically noted. Under a nitrogen atmosphere, a mixture of 0.2M Intermediate B-78 (150 µL, 30 µmol), 0.2M pyrrolidin-2-one (225 µl, 45.0 µmol), 0.02M Pd$_2$(dba)$_3$ (37.5 µl, 0.750 µmol) and 0.02 M Me4tButylXPhos (75 µl, 1.500 µmol) and potassium phosphate (9.55 mg, 45.0 µmol) was heated to 110° C. After 2 h, additional solutions of pyrrolidin-2-one (225 µl, 45.0 µmol), Pd$_2$(dba)$_3$ (37.5 µl, 0.750 µmol) and Me4tButylXPhos (75 µl, 1.500 µmol) were added and the reaction mixture heated 16 h at 110° C. After cooling to ambient temperature, the reaction mixture was concentrated to dryness, treated with saturated sodium bicarbonate (600 µL) and extracted with EtOAc (2×600 µL). The combined extracts were applied to a SiliaMetS® Dimercaptotriazine (DMT) resin and eluted with 10% MeOH/EtOAc (3 mL). The eluent was dried under a stream of nitrogen and the residue was purified by mass-directed preparative reverse phase HPLC to afford 0.8 mg (6% yield) of 2-(2-isopropylphenyl)-9-(4-(2-oxopyrrolidin-1-yl)benzyl)-7,9-dihydro-8H-purin-8-one (I-512). LCMS Rt (min): 1.3542, m/z 428.3326 [M+H]$^+$.

9-(4-(1H-tetrazol-5-yl)benzyl)-2-(2-isopropylphenyl)-7,9-dihydro-8H-purin-8-one (I-513)

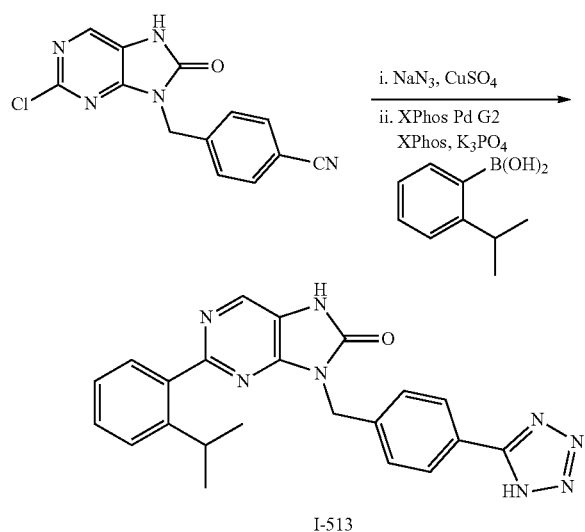

I-513

A mixture of 4-((2-chloro-8-oxo-7,8-dihydro-9H-purin-9-yl)methyl)benzonitrile (prepared from 4-(aminomethyl)benzonitrile following Example 18) (0.2M in DMSO, 150 µL, mol), sodium azide (1.950 mg, 30.0 µmol) and copper(II) sulfate pentahydrate (0.02M in DMSO, 30.0 µL, 0.600 µmol) was heated at 110° C. for 2.5 h then at 140° C. for 2 h. The reaction was cooled, treated with 1N HCl (600 µL) and the mixture extracted with EtOAc (2×600 µL). The combined organic extracts were concentrated, dissolved in dioxane (150 µL) and treated sequentially with (2-isopropylphenyl)boronic acid (0.2M in dioxane, 225 µL, 45.0 µmol), 1M potassium phosphate, XPhos Pd G2 (0.02M in dioxane, 30.0 µL, 0.600 µmol) and XPhos (0.02M in dioxane, 45.0 µL, 0.900 µmol). The mixture was placed under an atmosphere of nitrogen, then was heated to 80° C. for 16 h. The reaction mixture was recharged with (2-isopropylphenyl)boronic acid (0.2M in dioxane, 225 µL, 45.0 µmol), 1M potassium phosphate, XPhos Pd G2 (0.02M in dioxane, 30.0 µL, 0.600 µmol) and XPhos (0.02M in dioxane, 45.0 µL, 0.900 µmol) and was heated at 110° C. starting for an additional 7.5 h. The reaction mixture was concentrated, treated with 1N HCl (600 µL) and extracted with EtOAc (2×600 µL). The combined organic extracts were applied to a SiliaMetS® Dimercaptotriazine (DMT) resin and eluted with 10% MeOH/EtOAc (3 mL). The eluent concentrated and purified by mass-directed preparative reverse phase HPLC to afford 0.5 mg (4%) of 9-(4-(1H-tetrazol-5-yl)benzyl)-2-(2-isopropylphenyl)-7,9-dihydro-8H-purin-8-one (I-513). LCMS Rt (min): 1.2317, m/z 413.3142 [M+H]$^+$.

9-((1-(2,5-Dimethylthiazol-4-yl)-4-fluoropiperidin-4-yl)methyl)-2-(2-isopropylphenyl)-7,9-dihydro-8H-purin-8-one (I-514)

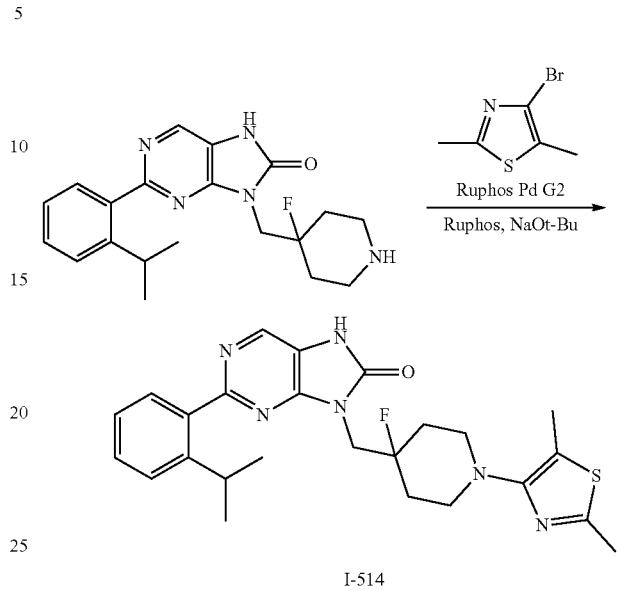

I-514

Note: All reagents are solutions in THF unless specifically noted. Under an atmosphere of nitrogen, a mixture of 9-((4-fluoropiperidin-4-yl)methyl)-2-(2-isopropylphenyl)-7,9-dihydro-8H-purin-8-one (11.08 mg, 30 µmol), sodium tert-butoxide (5.77 mg, 60.0 µmol), THF (250 µL), 4-bromo-2,5-dimethylthiazole (0.2M, 165 µL, 33.0 µmol), RuPhos precatalyst (0.02M, 75 µL, 1.500 µmol) and RuPhos (0.02M, 75 µL, 1.500 µmol) was heated to 100° C. for 20 h. The reaction was concentrated, treated with saturated sodium bicarbonate (600 µL) and extracted with EtOAc (2×600 µL). The combined extracts were concentrated and purified by mass-directed preparative reverse phase HPLC to afford 1.0 mg (7% yield) of 9-((1-(2,5-dimethylthiazol-4-yl)-4-fluoropiperidin-4-yl)methyl)-2-(2-isopropylphenyl)-7,9-dihydro-8H-purin-8-one (I-514). LCMS Rt (min): 1.6817, m/z 481.44 [M+H]$^+$.

9-(4-(4-cyclopropyl-1-methyl-1H-imidazol-2-yl)benzyl)-2-(2-isopropylpyridin-3-yl)-7-methyl-7,9-dihydro-8H-purin-8-one (I-515)

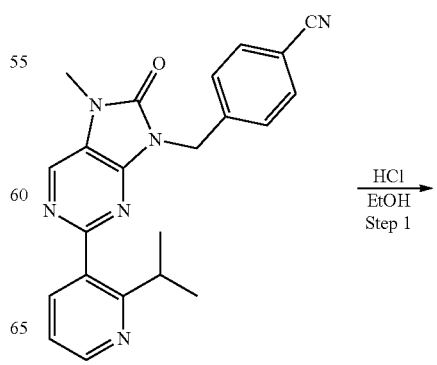

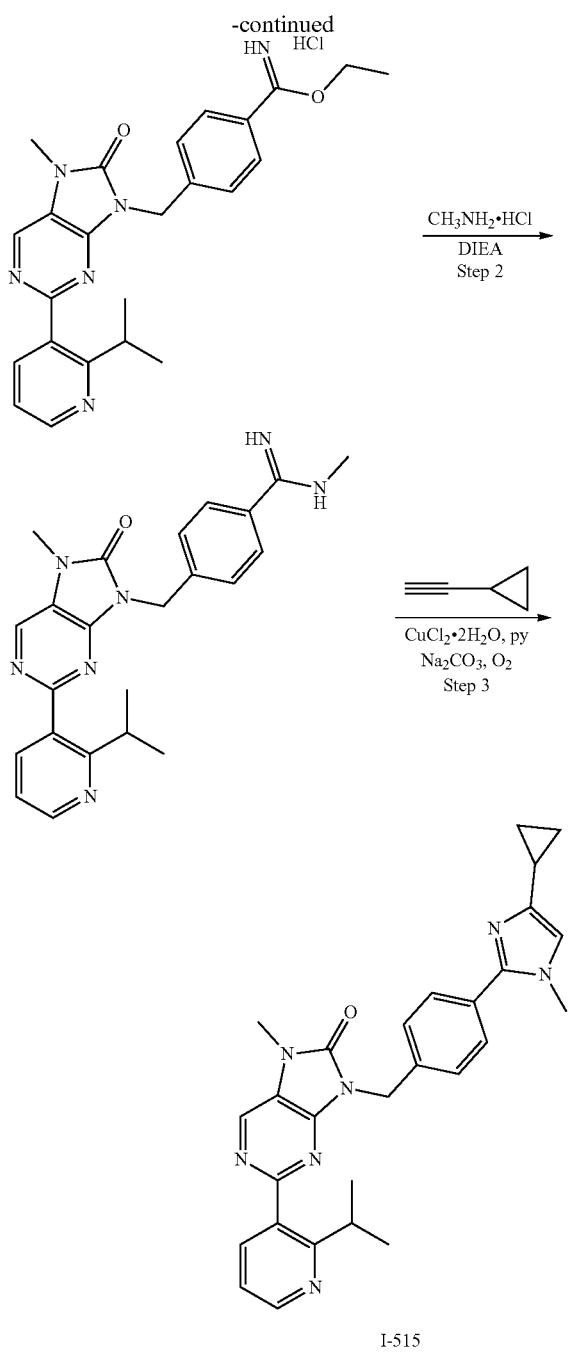

Step 2. 4-((2-(2-Isopropylpyridin-3-yl)-7-methyl-8-oxo-7,8-dihydro-9H-purin-9-yl)methyl)-N-methyl-benzimidamide A mixture of methanamine hydrochloride (349 mg, 5.17 mmol), MeOH (10 mL), DIEA (1.34 g, 10.37 mmol) and ethyl 4-((2-(2-isopropylpyridin-3-yl)-7-methyl-8-oxo-7,8-dihydro-9H-purin-9-yl)methyl)benzimidate hydrochloride (540 mg, 1.15 mmol) was stirred overnight at ambient temperature. The reaction mixture was concentrated under vacuum and the residue was purified by prep-TLC (eluting with 1/5 MeOH/DCM) to afford 200 mg (38%) of 4-((2-(2-isopropylpyridin-3-yl)-7-methyl-8-oxo-7,8-dihydro-9H-purin-9-yl)methyl)-N-methylbenzimidamide as a white solid. MS (ESI) m/z: 416.4 [M+H]$^+$.

Step 3. 9-(4-(4-Cyclopropyl-1-methyl-1H-imidazol-2-yl)benzyl)-2-(2-isopropylpyridin-3-yl)-7-methyl-7,9-dihydro-8H-purin-8-one A sealed tube was charged with 4-((2-(2-isopropylpyridin-3-yl)-7-methyl-8-oxo-7,8-dihydro-9H-purin-9-yl)methyl)-N-methylbenzimidamide (100 mg, 0.24 mmol), copper(II) chloride dihydrate (8 mg, 0.05 mmol), sodium carbonate (51 mg, 0.48 mmol), DCE (0.5 mL) and pyridine (38 mg, 0.48 mmol). To this mixture oxygen was introduced, followed by slow addition of a solution of ethynylcyclopropane (32 mg, 0.48 mmol) in DCE (2 mL) over 10 h using a syringe pump (0.2 mL/h) at 70° C. The resulting solution was stirred for 24 h at 70° C. then was cooled to room temperature and the reaction mixture filtered and concentrated. The residue was purified by prep-TLC (eluting with 1/5 MeOH/DCM) and the product was further purified by prep-HPLC resulting in 3.6 mg (3%) of 9-(4-(4-cyclopropyl-1-methyl-1H-imidazol-2-yl)benzyl)-2-(2-isopropylpyridin-3-yl)-7-methyl-7,9-dihydro-8H-purin-8-one (I-515) as a white solid. $^1$H NMR (400 MHz, CD$_3$OD) δ 8.71 (br s, 1H), 8.59-8.51 (m, 2H), 7.76-7.71 (m, 5H), 7.34 (s, 1H), 5.32 (s, 2H), 4.01-3.97 (m, 1H), 3.87 (s, 3H), 3.81 (s, 3H), 1.98-1.94 (m, 1H), 1.37-1.28 (m, 6H), 1.09-1.08 (m, 2H), 0.84-0.83 (m, 2H). LCMS Rt (min): 0.5475, m/z 480.4 [M+H]$^+$.

Example 46. 9-(4-(1H-Pyrazol-1-yl)benzyl)-2-(3-isopropylpyridin-4-yl)-7-methyl-7,9-dihydro-8H-purin-8-one (I-516)

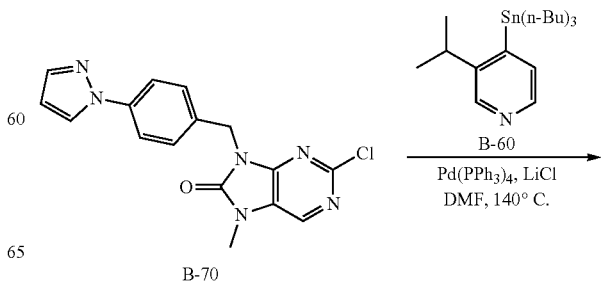

Step 1. Ethyl 4-((2-(2-isopropylpyridin-3-yl)-7-methyl-8-oxo-7,8-dihydro-9H-purin-9-yl)methyl)benzimidate hydrochloride A mixture of 4-((2-(2-isopropylpyridin-3-yl)-7-methyl-8-oxo-7,8-dihydro-9H-purin-9-yl)methyl)benzonitrile (prepared from 4-(aminomethyl)benzonitrile following sequentially Examples 31 and 33) (400 mg, 1.04 mmol) and a solution of HCl in EtOH (33% wt/v, 2 mL) was stirred for 3 h at ambient temperature. The reaction mixture was concentrated under vacuum to afford ethyl 4-((2-(2-isopropylpyridin-3-yl)-7-methyl-8-oxo-7,8-dihydro-9H-purin-9-yl)methyl)benzimidate hydrochloride as a yellow solid. MS (ESI) m/z: 431.4 [M+H-HCl]$^+$.

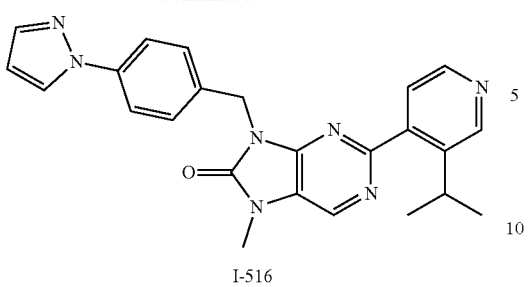

I-516

In an 8 mL round-bottom flask purged and maintained with an inert atmosphere of nitrogen, a mixture of Intermediate B-60 (80 mg, 0.20 mmol), DMF (2 mL), Intermediate B-70 (66 mg, 0.19 mmol), tetrakis(triphenylphosphine)palladium(0) (23 mg, 0.02 mmol) and lithium chloride (25 mg, 0.60 mmol) was stirred for 16 h at 140° C. After cooling to room temperature, the reaction mixture was concentrated under vacuum and purified by prep-TLC (eluting with 1:1 EtOAc/PE) followed by prep-HPLC to afford 1.6 mg (2%) of 9-(4-(1H-pyrazol-1-yl)benzyl)-2-(3-isopropylpyridin-4-yl)-7-methyl-7,9-dihydro-8H-purin-8-one (I-516) as a white solid. $^1$H NMR (300 MHz, CD$_3$OD) δ 8.64 (s, 1H), 8.52-8.46 (m, 2H), 8.20 (d, J=2.40 Hz, 1H), 7.74-7.09 (m, 3H), 7.63-7.54 (m, 3H), 6.52-6.51 (m, 1H), 5.22 (s, 2H), 3.62-3.53 (m, 4H), 1.22 (d, J=6.90 Hz, 6H). LCMS Rt (min): 1.08, m/z 426.19 [M+H]$^+$.

9-(4-(1H-Pyrazol-1-yl)benzyl)-2-(3-isopropylpyridin-2-yl)-7-methyl-7,9-dihydro-8H-purin-8-one (I-517)

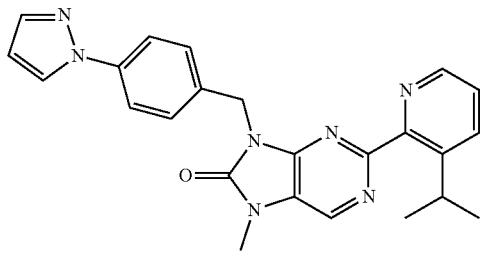

I-517

9-(4-(1H-Pyrazol-1-yl)benzyl)-2-(3-isopropylpyridin-2-yl)-7-methyl-7,9-dihydro-8H-purin-8-one (I-517) was prepared as a white solid following Example 46. $^1$H NMR (300 MHz, CD$_3$OD) δ 8.52-8.46 (m, 2H), 8.20-8.19 (m, 1H), 7.99-7.96 (m, 1H), 7.72-7.69 (m, 3H), 7.57-7.50 (m, 3H), 6.52-6.50 (m, 1H), 5.22 (s, 2H), 3.56 (s, 3H), 3.17-3.08 (m, 1H), 1.16 (d, J=6.90 Hz, 6H). LCMS Rt (min): 1.17, m/z 426.255 [M+H]$^+$.

Example 47. 2-(2-Isopropylphenyl)-9-(4-(1-(2-methoxyethyl)-1H-pyrazol-4-yl)benzyl)-7,9-dihydro-8H-purin-8-one (I-518)

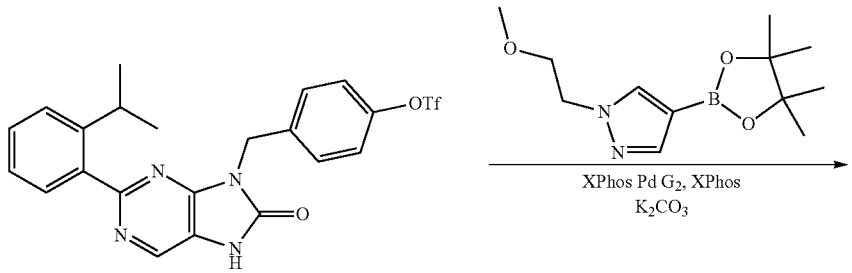

B-78

XPhos Pd G$_2$, XPhos
K$_2$CO$_3$

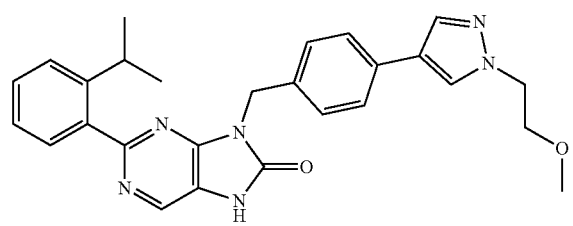

I-518

In a microwave reaction vial were combined Intermediate B-78 (14.77 mg, 30 mol), 1-(2-methoxyethyl)-4-(4,4,5,5-tetramethyl-1,3,2-dioxaborolan-2-yl)-1H-pyrazole (11.35 mg, 45.0 µmol), THF (1.5 ml), 1 M potassium carbonate (150 µL, 150 µmol), a 0.02 M solution of XPhos Pd G2 in THF (30.0 µl, 0.600 µmol), and a 0.02 M solution XPhos in THF (45.0 µl, 0.900 µmol). The vial was sealed and repeatedly evacuated and back-filled with nitrogen, then was heated at 160° C. for 20 min in a microwave reactor. The reaction was dried down under nitrogen and the residue was partitioned between saturated sodium bicarbonate (600 µL) of and EtOAc (600 µL). The organic layer was separated and combined with a second EtOAc extract, and the combined extracts applied to a Silicycle SilicaMetSDMT resin and eluted with 10% MeOH/EtOAc (3 mL). The eluent was dried under nitrogen and the residue was purified by mass-directed preparative reverse phase HPLC to afford 6.7 mg (47% yield) of 2-(2-isopropylphenyl)-9-(4-(1-(2-methoxyethyl)-1H-pyrazol-4-yl)benzyl)-7,9-dihydro-8H-purin-8-one (I-518). LCMS Rt (min): 1.43, m/z 469.21 [M+H]+.

2-(2-Isopropylphenyl)-9-(4-(1-(tetrahydro-2H-pyran-4-yl)-1H-pyrazol-4-yl)benzyl)-7,9-dihydro-8H-purin-8-one (I-519)

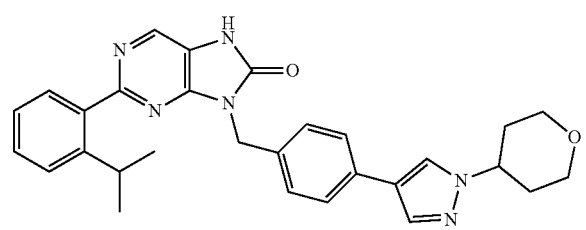

I-519

2-(2-Isopropylphenyl)-9-(4-(1-(tetrahydro-2H-pyran-4-yl)-1H-pyrazol-4-yl)benzyl)-7,9-dihydro-8H-purin-8-one (I-519) was synthesized from 1-(tetrahydro-2H-pyran-4-yl)-4-(4,4,5,5-tetramethyl-1,3,2-dioxaborolan-2-yl)-1H-pyrazole following Example 47. LCMS Rt (min): 1.4575, m/z 495.4285 [M+H]+.

9-(4-(1-(2-(Dimethylamino)ethyl)-1H-pyrazol-4-yl)benzyl)-2-(2-isopropylphenyl)-7,9-dihydro-8H-purin-8-one (I-520)

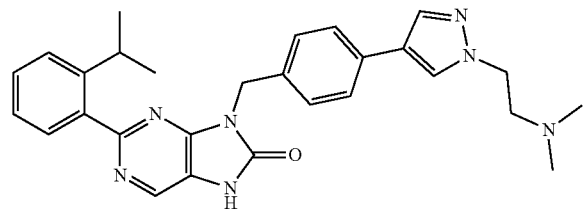

I-520

9-(4-(1-(2-(Dimethylamino)ethyl)-1H-pyrazol-4-yl)benzyl)-2-(2-isopropylphenyl)-7,9-dihydro-8H-purin-8-one (I-520) was obtained following Example 47. LCMS Rt (min): 0.87, m/z 482.27 [M+H]+.

9-(4-(1-(2-(Dimethylamino)ethyl)-1H-1,2,3-triazol-4-yl)benzyl)-2-(2-isopropylphenyl)-7,9-dihydro-8H-purin-8-one (I-521)

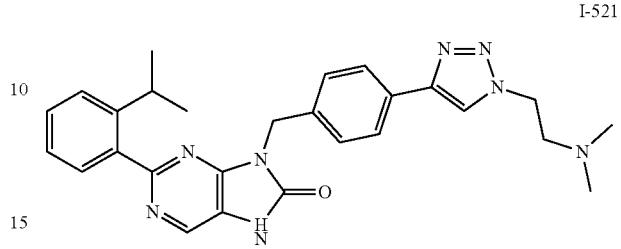

I-521

A solution of (2-bromoethyl)dimethylamine hydrobromide (2 g, 8.59 mmol) in acetone (12 mL), water (4 mL), 1,8-diazabicyclo[5.4.0]undec-7-ene (2.6 g, 17.08 mmol) and sodium azide (1.12 g, 17.23 mmol) was stirred for 4 h at 50° C., which after cooling to room temperature resulted in a solution of 2-azido-N,N-dimethylethanamine in acetone and water (0.53 M, 16 mL) which was used in the preparation of 9-(4-(1-(2-(dimethylamino)ethyl)-1H-1,2,3-triazol-4-yl)benzyl)-2-(2-isopropylphenyl)-7,9-dihydro-8H-purin-8-one (I-521) following Example 48. 1H NMR (400 MHz, CD3OD) δ 8.33 (d, J=7.20 Hz, 2H), 7.79 (d, J=7.20 Hz, 2H), 7.50-7.38 (m, 5H), 7.23-7.20 (m, 1H), 5.17 (s, 2H), 4.57 (t, J=6.40 Hz, 2H), 3.26-3.25 (m, 1H), 2.88 (t, J=6.40 Hz, 2H), 2.30 (s, 6H), 1.11 (d, J=6.80 Hz, 6H). LCMS Rt (min): 0.82, m/z 483.19 [M+H]+.

Example 48. 9-(4-(1-(2-Hydroxyethyl)-1H-1,2,3-triazol-4-yl)benzyl)-2-(2-isopropylphenyl)-7,9-dihydro-8H-purin-8-one (I-522)

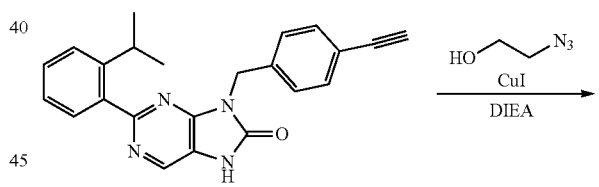

B-135

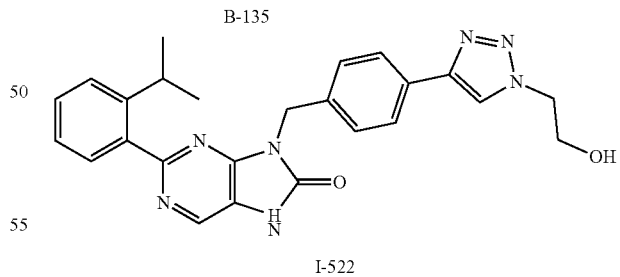

I-522

A mixture of 2-iodoethan-1-ol (500 mg, 2.91 mmol), acetone (6 mL), water (2 mL) and sodium azide (378 mg, 5.81 mmol) was stirred for 4 h at 50° C., which after cooling to room temperature resulted in a solution of 2-azidoethan-1-ol in acetone and water (0.36 M, 8 mL) which was used directly in the next step.

In a vial purged and maintained with an inert atmosphere of nitrogen, a mixture of 2-azidoethan-1-ol solution in acetone and water (0.36 M, 2 mL, 0.73 mmol), Intermediate B-135 (15 mg, 0.04 mmol), copper(I) iodide (0.77 mg, 0.004 mmol) and DIEA (10.6 mg, 0.08 mmol) was stirred for 1 h at 20° C. The reaction mixture was concentrated under vacuum and the residue was purified by prep-HPLC to afford 8 mg (42%) of 9-(4-(1-(2-hydroxyethyl)-1H-1,2,3-triazol-4-yl)benzyl)-2-(2-isopropylphenyl)-7,9-dihydro-8H-purin-8-one (I-522) as a white solid. $^1$H NMR (400 MHz, CD$_3$OD) δ 8.32 (s, 2H), 7.80-7.78 (m, 2H), 7.50-7.38 (m, 5H), 7.27-7.23 (m, 1H), 5.16 (s, 2H), 4.52 (t, J=5.20 Hz, 2H), 3.97 (t, J=5.20 Hz, 2H), 3.27-3.25 (m, 1H), 1.13 (d, J=7.20 Hz, 6H). LCMS Rt (min): 1.16, m/z 456.147 [M+H]$^+$.

9-(4-(1H-1,2,3-triazol-5-yl)benzyl)-2-(2-isopropylphenyl)-7,9-dihydro-8H-purin-8-one (I-523)

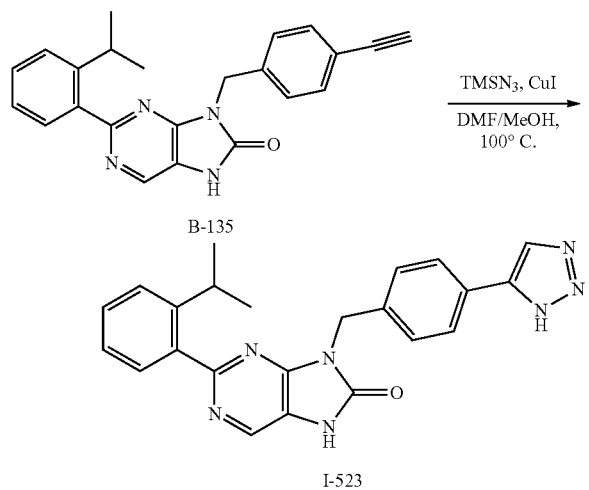

In a flask purged and maintained with an inert atmosphere of nitrogen, a mixture of Intermediate B-135 (30 mg, 0.08 mmol), azidotrimethylsilane (88 mg, 0.76 mmol), copper(I) iodide (1.45 mg, 0.01 mmol), DMF (2.8 mL) and MeOH (0.4 mL) was stirred for 18 h at 100° C. The reaction mixture was concentrated under vacuum and the residue was purified by prep-HPLC to afford 25 mg (74%) of 9-(4-(1H-1,2,3-triazol-5-yl)benzyl)-2-(2-isopropylphenyl)-7,9-dihydro-8H-purin-8-one (I-523) as a white solid. $^1$H NMR (400 MHz, CD$_3$OD) δ 8.32 (s, 1H), 8.13 (s, 1H), 7.80 (d, J=8.40 Hz, 2H), 7.50-7.38 (m, 5H), 7.27-7.23 (m, 1H), 5.17 (s, 2H), 3.30-3.24 (m, 1H), 1.11 (d, J=6.80 Hz, 6H). LCMS Rt (min): 1.24, m/z 412.1518 [M+H]$^+$.

Methyl 2-(9-(4-(1-Methyl-4-(trifluoromethyl)-1H-imidazol-2-yl)benzyl)-8-oxo-8,9-dihydro-7H-purin-2-yl)benzoate (I-524)

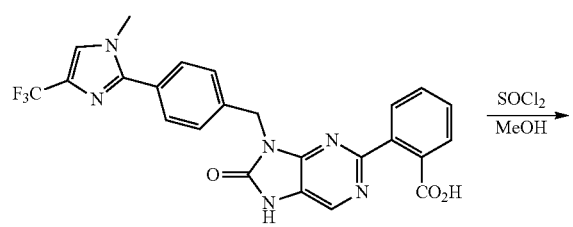

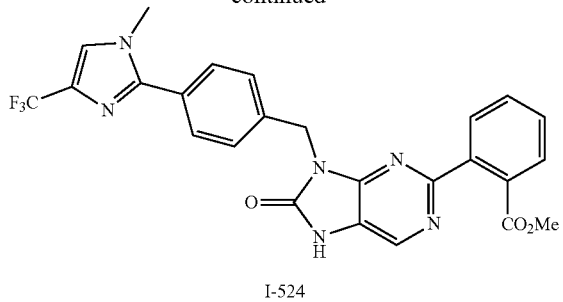

I-524

A mixture of 2-(9-(4-(1-methyl-4-(trifluoromethyl)-1H-imidazol-2-yl)benzyl)-8-oxo-8,9-dihydro-7H-purin-2-yl)benzoic acid (prepared from Intermediate B-49 and (2-(methoxycarbonyl)phenyl)boronic acid following the conditions of Example 32) (64 mg, 0.13 mmol), thionyl chloride (20 mg, 0.15 mmol) and MeOH (1 mL) was stirred overnight at ambient temperature then was concentrated under vacuum. The residue was purified by prep-HPLC to afford 60 mg (91%) of methyl 2-(9-(4-(1-methyl-4-(trifluoromethyl)-1H-imidazol-2-yl)benzyl)-8-oxo-8,9-dihydro-7H-purin-2-yl)benzoate (I-524) as a white solid. $^1$H NMR (400 MHz, CD$_3$OD) δ 8.32 (s, 1H), 7.93 (d, J=7.60 Hz, 1H), 7.69-7.60 (m, 7H), 7.55-7.52 (m, 1H), 5.20 (s, 2H), 3.75 (s, 3H), 3.58 (s, 3H). LCMS Rt (min): 1.3548, m/z 509.4 [M+H]$^+$.

2-(2-(2-hydroxypropan-2-yl)phenyl)-9-(4-(1-methyl-4-(trifluoromethyl)-1H-imidazol-2-yl)benzyl)-7,9-dihydro-8H-purin-8-one (I-525)

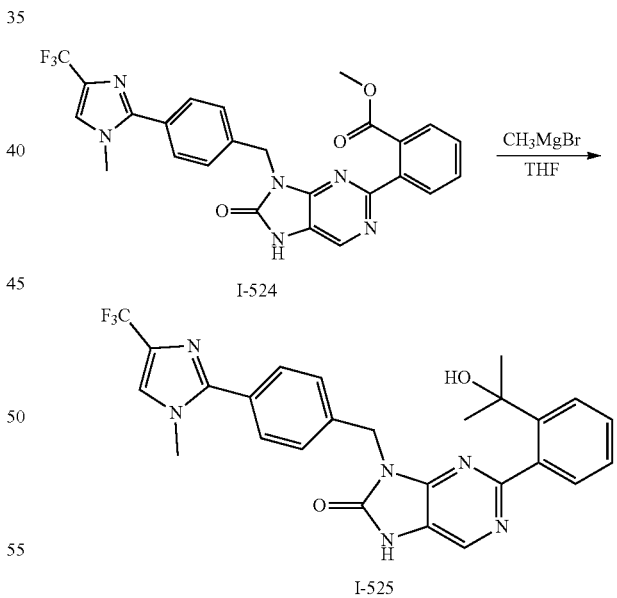

In a 25 mL round-bottom flask purged and maintained with an inert atmosphere of nitrogen at 0° C., a mixture of I-524 (100 mg, 0.20 mmol) and THF (3 mL) was treated dropwise with a 1M solution of methyl magnesium bromide in THF (1.96 mL, 1.96 mmol). The resulting solution was stirred for 5 h while warming to ambient temperature, then was quenched by the addition of water (5 mL). The mixture was extracted with EtOAc (3×5 mL) and the organic layers were combined, dried over anhydrous sodium sulfate, filtered and concentrated under vacuum. The residue was purified by silica gel chromatography (eluting with 0-100% EtOAc/PE) and further purified by prep-HPLC to afford 17.3 mg (17%) of 2-(2-(2-hydroxypropan-2-yl)phenyl)-9-(4-(1-methyl-4-(trifluoromethyl)-1H-imidazol-2-yl)benzyl)-7,9-dihydro-8H-purin-8-one (I-525) as a white solid. $^1$H NMR (400 MHz, CD$_3$OD) δ 8.31 (s, 1H), 7.70-7.66 (m, 1H), 7.66-7.56 (m, 6H), 7.48-7.39 (m, 1H), 7.39-7.31 (m, 1H), 5.22 (s, 2H), 3.75 (s, 3H), 1.43 (s, 6H). LCMS Rt (min): 1.2983, m/z 509.4 [M+H]$^+$.

2-(2-(1-Hydroxycyclopropyl)phenyl)-9-(4-(1-methyl-4-(trifluoromethyl)-1H-imidazol-2-yl)benzyl)-7,9-dihydro-8H-purin-8-one (I-526) and 9-(4-(1-methyl-4-(trifluoromethyl)-1H-imidazol-2-yl)benzyl)-2-(2-propionylphenyl)-7,9-dihydro-8H-purin-8-one (I-527)

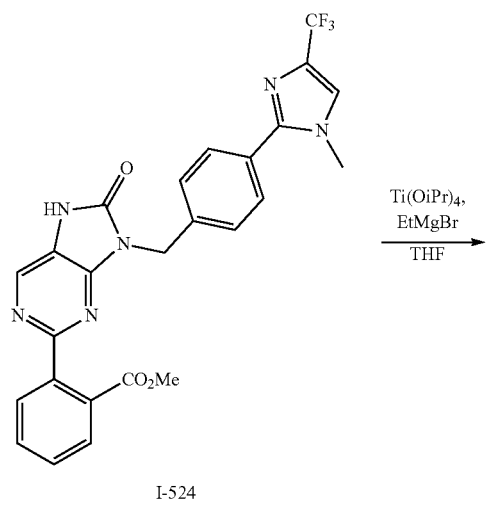

I-524

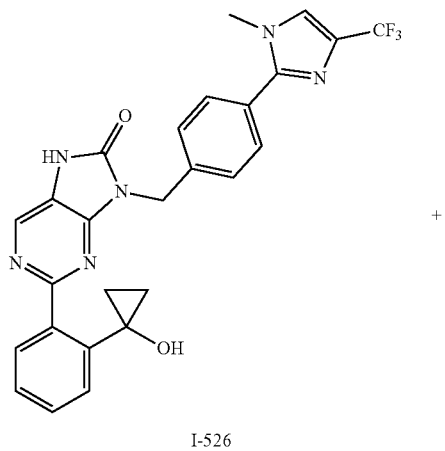

I-526

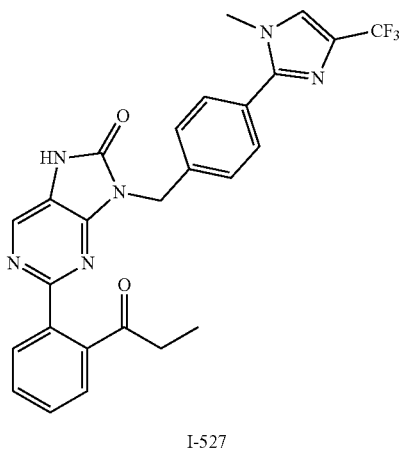

I-527

A mixture of I-524 (40 mg, 0.08 mmol), THF (1 mL) and titanium isopropoxide (22 mg, 0.08 mmol) was treated with dropwise addition of a solution of ethyl magnesium bromide in diethyl ether (3M, 0.13 mL 0.39 mmol) and the resulting solution was stirred for 18 h at ambient temperature. The reaction was then quenched by the addition of water (2 mL) and the mixture was extracted with EtOAc (3×2 mL). The organic layers were combined, dried over anhydrous sodium sulfate, filtered and concentrated under vacuum. The residue was purified by prep-HPLC to afford 1.4 mg (4%) of 2-(2-(1-hydroxycyclopropyl)phenyl)-9-(4-(1-methyl-4-(trifluoromethyl)-1H-imidazol-2-yl)benzyl)-7,9-dihydro-8H-purin-8-one (I-526) as an off-white solid and 1.3 mg (3%) of 9-(4-(1-methyl-4-(trifluoromethyl)-1H-imidazol-2-yl)benzyl)-2-(2-propionylphenyl)-7,9-dihydro-8H-purin-8-one (I-527) as an off-white solid.

I-526: $^1$H NMR (300 MHz, CD$_3$OD) δ 8.43 (s, 1H), 7.96-7.92 (m, 1H), 7.68-7.56 (m, 6H), 7.46-7.41 (m, 2H), 5.29 (s, 2H), 3.77 (s, 3H), 0.88-0.84 (m, 2H), 0.67-0.63 (m, 2H). LCMS Rt (min): 1.3952, m/z 507.4 [M+H]$^+$.

I-527: $^1$H NMR (300 MHz, CD$_3$OD) δ 8.29 (s, 1H), 8.19-8.16 (m, 1H), 7.67-7.52 (m, 7H), 7.41-7.38 (m, 1H), 5.22 (s, 2H), 3.75 (s, 3H), 2.64 (q, J=9.00 Hz, 2H), 1.05 (t, J=9.00 Hz, 3H). LCMS Rt (min): 1.031, m/z 507.4 [M+H]$^+$.

9-(4-(1H-Pyrazol-1-yl)benzyl)-2-(2-(2-hydroxypropan-2-yl)phenyl)-7,9-dihydro-8H-purin-8-one (I-528)

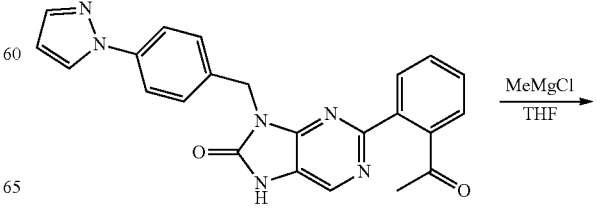

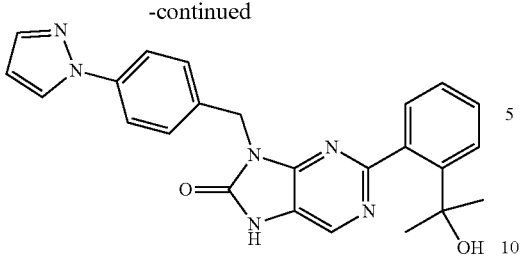

I-528

Into an 8 mL vial purged and maintained with an inert atmosphere of nitrogen, a solution of 9-(4-(1H-pyrazol-1-yl)benzyl)-2-(2-acetylphenyl)-7,9-dihydro-8H-purin-8-one (prepared according to Example 31) (50 mg, 0.12 mmol) in THF (2 mL) was treated with dropwise addition of a solution of methyl magnesium chloride in THF (3 M, 0.4 mL, 1.20 mmol) at −30° C. The resulting solution was stirred for 2 h at 0° C. then was quenched by the addition of saturated ammonium chloride solution (5 mL) and was extracted with EtOAc (2×5 mL). The organic layers were combined, dried over anhydrous sodium sulfate, filtered and concentrated under vacuum. The residue was purified prep-TLC (eluting with 1/1 EtOAc/PE) and further purified by prep-HPLC resulting in 5.6 mg (11%) of 9-(4-(1H-pyrazol-1-yl)benzyl)-2-(2-(2-hydroxypropan-2-yl)phenyl)-7,9-dihydro-8H-purin-8-one (I-528) as a white solid. $^1$H NMR (300 MHz, CD$_3$OD) δ 8.31 (s, 1H), 8.20 (d, J=2.70 Hz, 1H), 7.77-7.67 (m, 3H), 7.70-7.53 (m, 4H), 7.48-7.35 (m, 2H), 6.52-6.51 (m, 1H) 5.19 (s, 2H), 1.44 (s, 6H). LCMS Rt (min): 1.2, m/z 427.1617 [M+H]$^+$.

9-(4-(1H-Imidazol-2-yl)benzyl)-2-(2-isopropylphenyl)-7-methyl-7,9-dihydro-8H-purin-8-one (I-529)

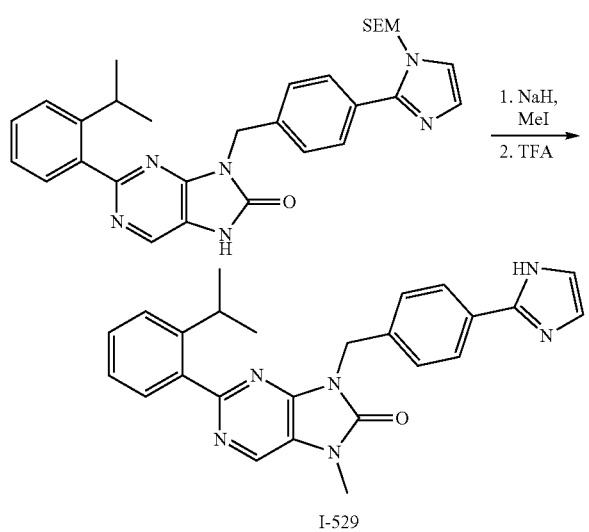

I-529

2-(2-Isopropylphenyl)-9-(4-(1-((2-(trimethylsilyl)ethoxy)methyl)-1H-imidazol-2-yl)benzyl)-7,9-dihydro-8H-purin-8-one (prepared from Intermediate B-31 following Example 31) was transformed into 9-(4-(1H-imidazol-2-yl)benzyl)-2-(2-isopropylphenyl)-7-methyl-7,9-dihydro-8H-purin-8-one (I-529) by sequentially following Example 33 (step 1)

and Example 36 (step 2). $^1$H NMR (300 MHz, CD$_3$OD) δ 8.30 (s, 1H), 8.06 (s, 1H), 7.67-7.64 (m, 2H), 7.51-7.49 (m, 2H), 7.29-7.22 (m, 2H), 7.14-7.07 (m 1H), 6.35 (s, 1H), 5.15 (s, 2H), 4.55-4.51 (m, 1H), 4.01-3.96 (m, 1H), 3.32-3.12 (m, 1H), 1.13-1.10 (m, 6H). LCMS Rt (min): 0.82, m/z 425.11 [M+H]$^+$.

2-(9-(4-(1H-Pyrazol-1-yl)benzyl)-2-(2-isopropylphenyl)-8-oxo-8,9-dihydro-7H-purin-7-yl)propanoic acid (I-530)

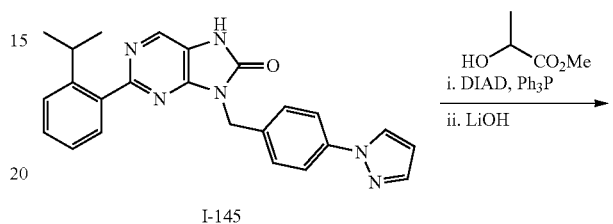

I-145

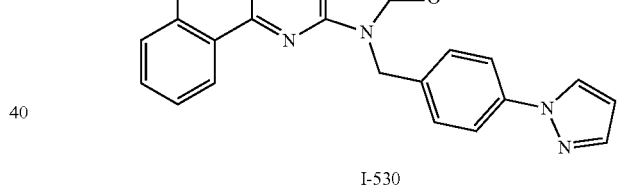

I-530

Note: All reagents are 0.2M in anhydrous THF. Under nitrogen, a solution of I-145 (150 µL, 0.030 mmol), methyl 2-hydroxypropanoate (165 µL, 0.033 mmol) and triphenylphosphine (180 µL, 0.036 mmol) was treated with diisopropyl azodicarboxylate (180 µL, 0.036 mmol) and heated to 50° C. After 2 h, additional triphenylphosphine (180 µL, 0.036 mmol) and diisopropyl azodicarboxylate (180 µL, 0.036 mmol) were added and heating at 50° C. was continued for 2 h. The solution was concentrated under reduced pressure, the residue treated with 1N NaOH (0.5 mL) and the mixture extracted with EtOAc (2×0.5 mL). The combined extracts were concentrated and the residue was taken up in EtOH (300 uL) and 10M aqueous lithium hydroxide (30 µL, 300 µmol) and heated at 50° C. for 4 h. The reaction mixture was concentrated under reduced pressure, diluted with water (200 uL) and titrated to pH 6 with 1N HCl. The mixture was extracted with EtOAc (2×0.5 mL), the volatiles removed under reduced pressure, and the residue purified by mass-triggered preparatory HPLC to afford 2-(9-(4-(1H-pyrazol-1-yl)benzyl)-2-(2-isopropylphenyl)-8-oxo-8,9-dihydro-7H-purin-7-yl)propanoic acid (I-530). LCMS Rt (min): 1.62, m/z 483.1173 [M+H]$^+$.

Example 49. 2-(2-(Difluoromethoxy)pyridin-3-yl)-9-(4-(1-methyl-4-(trifluoromethyl)-1H-imidazol-2-yl)benzyl)-6-(methylamino)-7,9-dihydro-8H-purin-8-one (I-531)

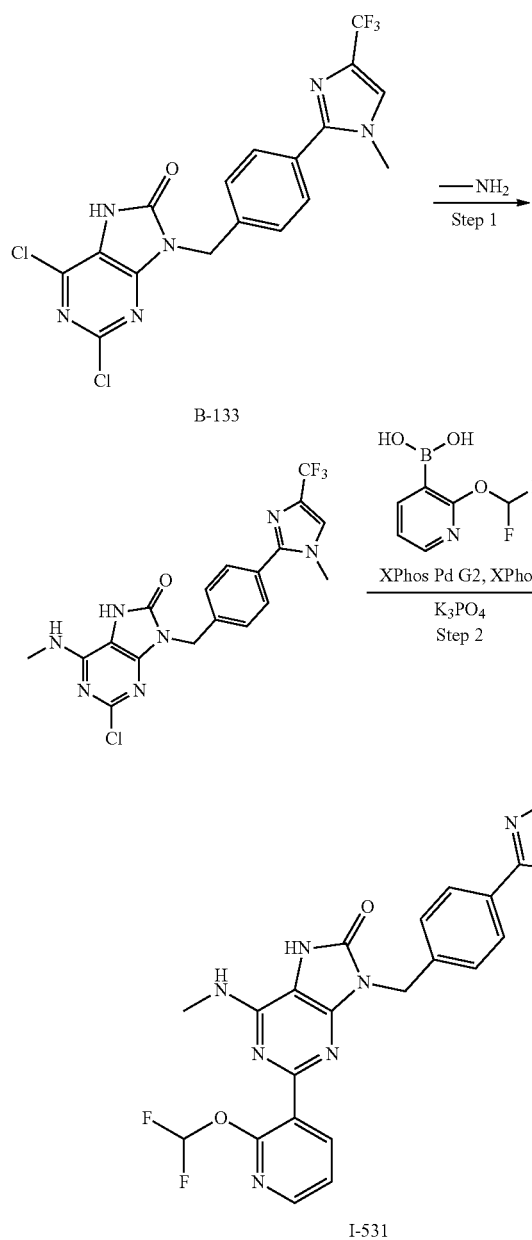

Step 1. 2-Chloro-9-(4-(1-methyl-4-(trifluoromethyl)-1H-imidazol-2-yl)benzyl)-6-(methylamino)-7,9-dihydro-8H-purin-8-one A suspension of Intermediate B-133 (13.30 mg, 0.030 mmol) in EtOH (200 uL) was treated with a solution methylamine (33 wt. % in EtOH, 1.0 mL, 8.0 mmol) and the reaction was heated at 50° C. for 96 h. After cooling to room temperature, the volatiles were removed under a stream of nitrogen and the residue partitioned between saturated sodium bicarbonate (600 μL) and EtOAc (600 μL). The organic layer was separated and combined with a second extract of EtOAc (600 μL). The combined extracts were concentrated under a stream of nitrogen to afford crude 2-chloro-9-(4-(1-methyl-4-(trifluoromethyl)-1H-imidazol-2-yl)benzyl)-6-(methylamino)-7,9-dihydro-8H-purin-8-one.

Step 2. 2-(2-(Difluoromethoxy)pyridin-3-yl)-9-(4-(1-methyl-4-(trifluoromethyl)-1H-imidazol-2-yl)benzyl)-6-(methylamino)-7,9-dihydro-8H-purin-8-one 2-(2-(Difluoromethoxy)pyridin-3-yl)-9-(4-(1-methyl-4-(trifluoromethyl)-1H-imidazol-2-yl)benzyl)-6-(methylamino)-7,9-dihydro-8H-purin-8-one (I-531) was obtained from 2-chloro-9-(4-(1-methyl-4-(trifluoromethyl)-1H-imidazol-2-yl)benzyl)-6-(methylamino)-7,9-dihydro-8H-purin-8-one following Example 27. LCMS Rt (min): 1.4897, m/z 547.4393 [M+H]$^+$.

2-(2-Isopropylphenyl)-9-(4-(1-methyl-4-(trifluoromethyl)-1H-imidazol-2-yl)benzyl)-6-(methylamino)-7,9-dihydro-8H-purin-8-one (I-532)

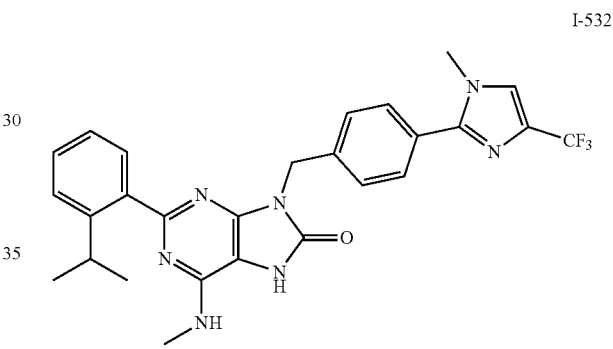

2-(2-Isopropylphenyl)-9-(4-(1-methyl-4-(trifluoromethyl)-1H-imidazol-2-yl)benzyl)-6-(methylamino)-7,9-dihydro-8H-purin-8-one (I-532) was prepared according to Example 49. LCMS Rt (min): 1.719, m/z 522.4 [M+H]$^+$.

6-(Dimethylamino)-2-(2-isopropylphenyl)-9-(4-(1-methyl-4-(trifluoromethyl)-1H-imidazol-2-yl)benzyl)-7,9-dihydro-8H-purin-8-one (I-533)

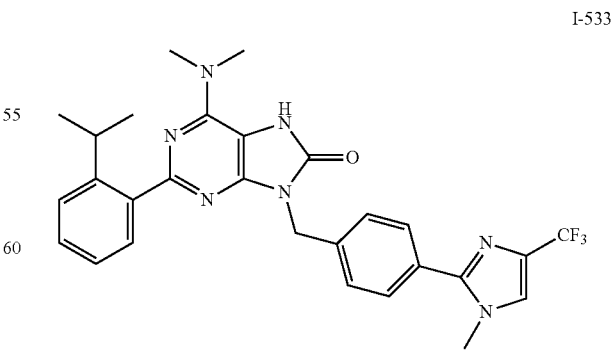

6-(Dimethylamino)-2-(2-isopropylphenyl)-9-(4-(1-methyl-4-(trifluoromethyl)-1H-imidazol-2-yl)benzyl)-7,9- dihydro-8H-purin-8-one (I-533) was prepared according to Example 49. LCMS Rt (min): 1.8268, m/z 536.5 [M+H]+.

6-Acetyl-2-(2-isopropylphenyl)-9-(4-(1-methyl-4-(trifluoromethyl)-1H-imidazol-2-yl)benzyl)-7,9-dihydro-8H-purin-8-one (I-534)

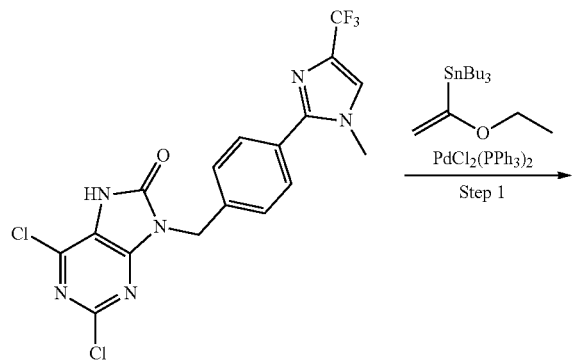

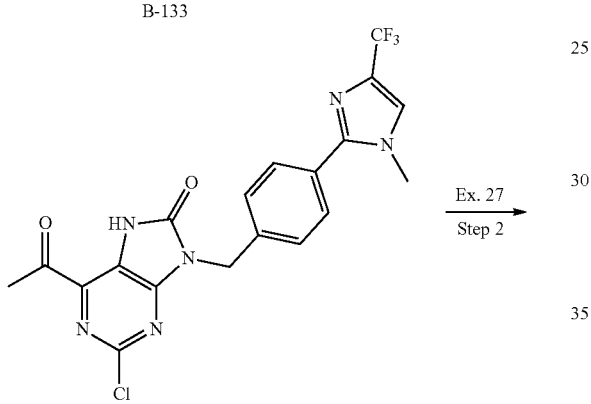

Step 1. 6-Acetyl-2-chloro-9-(4-(1-methyl-4-(trifluoromethyl)-1H-imidazol-2-yl)benzyl)-7,9-dihydro-8H-purin-8-one In a reaction vial a mixture of Intermediate B-133 (13.30 mg, 30 µmol), PdCl$_2$(PPh$_3$)$_2$ (4.21 mg, 6.00 µmol), dioxane (200 µL) and tributyl(1-ethoxyvinyl)stannane (10.97 µl, 31.5 µmol) was placed under an atmosphere of nitrogen and heated at 100° C. for 20 h. The reaction mixture was cooled to room temperature and was treated with EtOAc (600 uL), water (600 uL), and potassium fluoride (80 µl, 39.9 µmol). The reaction was stirred at ambient temperature for 1 h then was filtered and the filter cake was washed with EtOAc. The organic layer was separated from the filtrate, and was combined with a second extract of EtOAc. The combined organics were concentrated under a stream of nitrogen and the residue was dissolved in acetone (150 µL) and treated with p-toluenesulfonic acid monohydrate (30.0 µmol). The reaction was heated at 80° C. for 2.5 h, then was concentrated to afford crude 6-acetyl-2-chloro-9-(4-(1-methyl-4-(trifluoromethyl)-1H-imidazol-2-yl)benzyl)-7,9-dihydro-8H-purin-8-one.

Step 2. 6-Acetyl-2-(2-isopropylphenyl)-9-(4-(1-methyl-4-(trifluoromethyl)-1H-imidazol-2-yl)benzyl)-7,9-dihydro-8H-purin-8-one 6-Acetyl-2-(2-isopropylphenyl)-9-(4-(1-methyl-4-(trifluoromethyl)-1H-imidazol-2-yl)benzyl)-7,9-dihydro-8H-purin-8-one (I-534) was obtained from 6-acetyl-2-chloro-9-(4-(1-methyl-4-(trifluoromethyl)-1H-imidazol-2-yl)benzyl)-7,9-dihydro-8H-purin-8-one following Example 27. LCMS Rt (min): 1.8742, m/z 535.449 [M+H]+.

2-(2-Isopropylphenyl)-6-methoxy-9-(4-(1-methyl-4-(trifluoromethyl)-1H-imidazol-2-yl)benzyl)-7,9-dihydro-8H-purin-8-one (I-535)

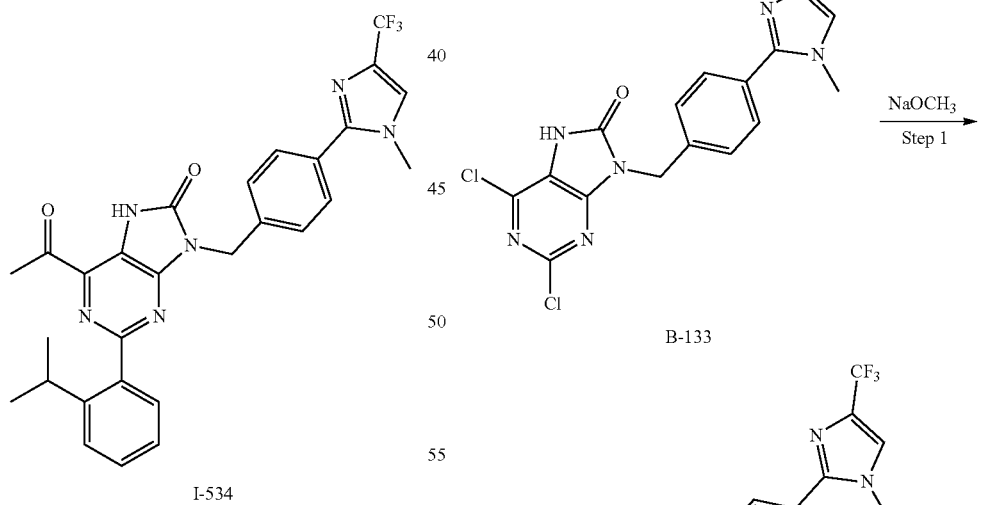

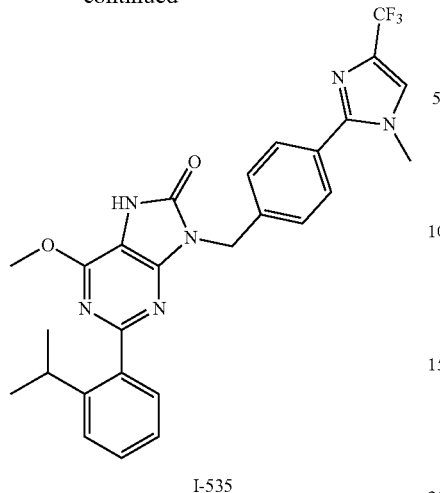

I-535

Step 1. 2-Chloro-6-methoxy-9-(4-(1-methyl-4-(trifluoromethyl)-1H-imidazol-2-yl)benzyl)-7,9-dihydro-8H-purin-8-one In a reaction vial a mixture of Intermediate B-133 (12.2 mg, 0.028 mmol), MeOH (200 µL) and sodium methoxide (62.9 µl, 0.275 mmol) was heated at 80° C. for 3 h. After cooling to room temperature, the volatiles were removed under a stream of nitrogen and the residue partitioned between saturated sodium bicarbonate (600 µL) and EtOAc (600 µL). The organic layer was separated and combined with a second extract of EtOAc (600 µL). The combined extracts were concentrated under a stream of nitrogen to afford crude 2-chloro-6-methoxy-9-(4-(1-methyl-4-(trifluoromethyl)-1H-imidazol-2-yl)benzyl)-7,9-dihydro-8H-purin-8-one.

Step 2. 2-(2-Isopropylphenyl)-6-methoxy-9-(4-(1-methyl-4-(trifluoromethyl)-1H-imidazol-2-yl)benzyl)-7,9-dihydro-8H-purin-8-one 2-(2-Isopropylphenyl)-6-methoxy-9-(4-(1-methyl-4-(trifluoromethyl)-1H-imidazol-2-yl)benzyl)-7,9-dihydro-8H-purin-8-one (I-535) was synthesized from 2-chloro-6-methoxy-9-(4-(1-methyl-4-(trifluoromethyl)-1H-imidazol-2-yl)benzyl)-7,9-dihydro-8H-purin-8-one following Example 26. LCMS Rt (min): 1.8267, m/z 523.4315 [M+H]⁺.

Example 50. 9-(4-(1-Isopropyl-5-methyl-1H-imidazol-2-yl)benzyl)-2-(2-isopropylphenyl)-7,9-dihydro-8H-purin-8-one (I-536) and 9-(4-(1-isopropyl-4-methyl-1H-imidazol-2-yl)benzyl)-2-(2-isopropylphenyl)-7,9-dihydro-8H-purin-8-one (I-537)

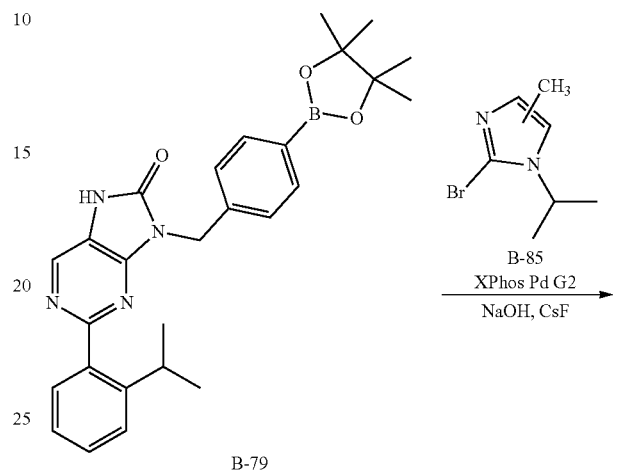

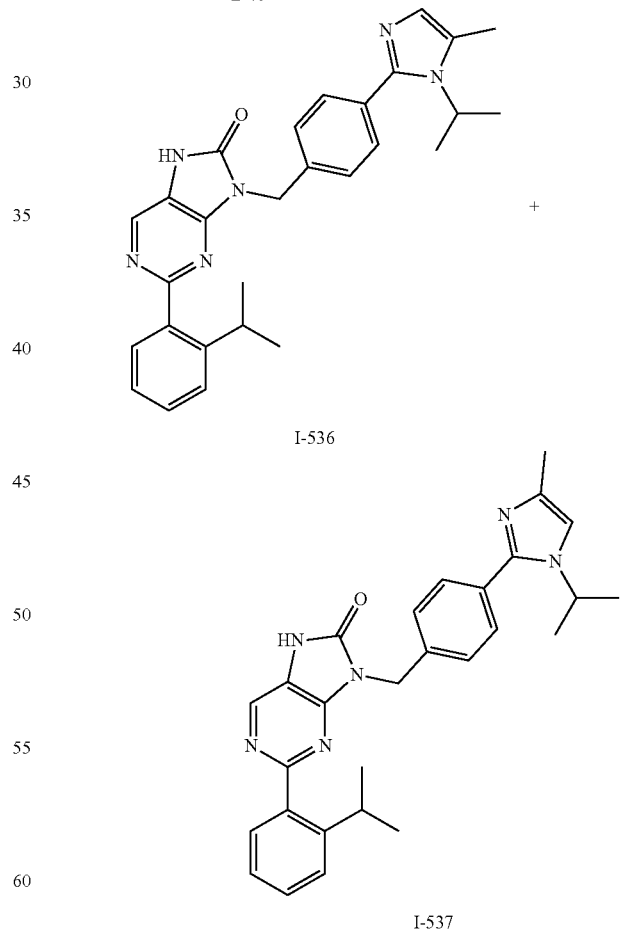

In a 20 mL sealed tube purged and maintained with an inert atmosphere of nitrogen, a mixture of Intermediate B-85 (200 mg, 0.99 mmol), Intermediate B-79 (50% purity, 931 mg, 1.98 mmol), XPhos Pd G2 (31 mg, 0.04 mmol), NaOH (120 mg, 3.00 mmol), cesium fluoride (300 mg, 1.98 mmol), 1,4-dioxane (8 mL) and water (2 mL) was stirred for 30 minutes at 160° C. After cooling to room temperature, the resulting mixture was concentrated under vacuum and was purified by prep-TLC (eluting with 10:1 DCM/MeOH), with further purification by prep-HPLC. The regioisomers were separated by prep-Chiral HPLC resulting in 4.2 mg (2%) of I-536 as a white solid and 24.2 mg (11%) of I-537 as a white solid.

I-536 (Chiral HPLC retention time=23.6 min): $^1$H NMR (400 MHz, CDCl$_3$) δ 12.24 (br s, 1H), 8.19 (s, 1H), 7.56-7.51 (m, 5H), 7.48-7.36 (m, 2H), 7.34-7.23 (m, 1H), 6.96 (s, 1H), 5.14 (s, 2H), 4.65-4.58 (m, 1H), 3.48-3.41 (m, 1H), 2.43 (s, 3H), 1.48 (d, J=7.20 Hz, 6H), 1.18 (d, J=6.80 Hz, 6H). LCMS Rt (min): 0.94, m/z 467.2 [M+H]$^+$.

I-537 (Chiral HPLC retention time=11.37 min): $^1$H NMR (400 MHz, CDCl$_3$) δ 8.14-8.12 (m, 1H), 7.70-7.62 (m, 2H), 7.62-7.50 (m, 3H), 7.47-7.35 (m, 2H), 7.26-7.21 (m, 1H), 6.84 (s, 1H), 5.20 (s, 2H), 4.55-4.49 (m, 1H), 3.46-3.39 (m, 1H), 2.31 (s, 3H), 1.42 (d, J=6.40 Hz, 6H), 1.17 (d, J=6.80 Hz, 6H). LCMS Rt (min): 0.94, m/z 467.2 [M+H]$^+$.

Example 51. N-(2-(4-((2-(2-Isopropylphenyl)-8-oxo-7,8-dihydro-9H-purin-9-yl)methyl)phenyl)-1-methyl-1H-imidazol-4-yl)acetamide (I-538)

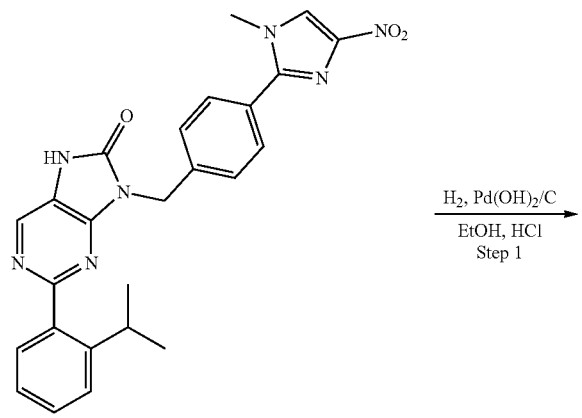

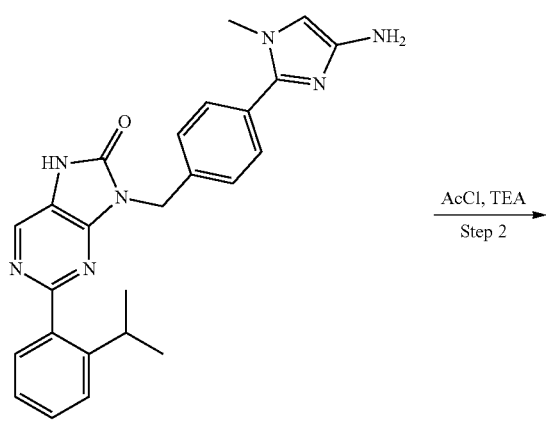

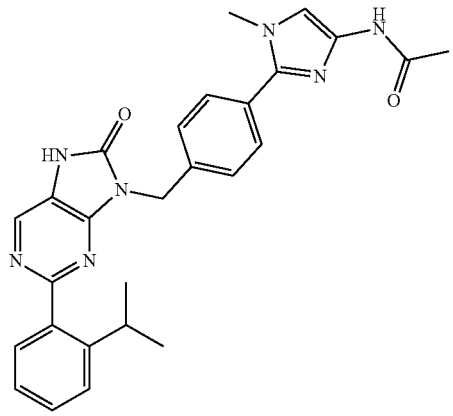

I-538

Step 1. 9-(4-(4-Amino-1-methyl-1H-imidazol-2-yl)benzyl)-2-(2-isopropylphenyl)-7,9-dihydro-8H-purin-8-one Into a 25 mL round-bottom flask was placed 2-(2-isopropylphenyl)-9-(4-(1-methyl-4-nitro-1H-imidazol-2-yl)benzyl)-7,9-dihydro-8H-purin-8-one (obtained from Intermediates B-79 and B-122 following Example 50) (80 mg, 0.17 mmol), EtOH (2 mL), Pd(OH)$_2$/C (20 percent wt Pd(OH)$_2$ on activated carbon, 55 mg) and concentrated hydrochloric acid (0.05 mL). To the above hydrogen was introduced in. The resulting mixture was stirred for 18 h at 25° C. The reaction mixture was filtered and concentrated under vacuum to afford 80 mg (crude) of 9-(4-(4-amino-1-methyl-1H-imidazol-2-yl)benzyl)-2-(2-isopropylphenyl)-7,9-dihydro-8H-purin-8-one as a yellow solid. MS (ESI) m/z 440.2 [M+H]$^+$.

Step 2. N-(2-(4-((2-(2-Isopropylphenyl)-8-oxo-7,8-dihydro-9H-purin-9-yl)methyl)phenyl)-1-methyl-1H-imidazol-4-yl)acetamide Into a 25 mL round-bottom flask was placed 9-(4-(4-amino-1-methyl-1H-imidazol-2-yl)benzyl)-2-(2-isopropylphenyl)-7,9-dihydro-8H-purin-8-one (80 mg, 0.17 mmol), DCM (2 mL), triethylamine (52 mg, 0.51 mmol) and acetyl chloride (16 mg, 0.20 mmol). The resulting solution was stirred for 0.5 h at 25° C. The reaction mixture was diluted with DCM (10 mL) and then washed with water (5 mL×3), dried over anhydrous sodium sulfate, filtered and concentrated under vacuum. The residue was purified by prep-TLC (eluting with 1/20 MeOH/DCM) and the product was further purified by prep-HPLC to afford 3.6 mg (4%) of N-(2-(4-((2-(2-isopropylphenyl)-8-oxo-7,8-dihydro-9H-purin-9-yl)methyl)phenyl)-1-methyl-1H-imidazol-4-yl)acetamide (I-538) as a white solid. $^1$H NMR (400 MHz, DMSO-d$_6$) δ 10.35 (s, 1H), 8.40 (s, 1H), 7.66-7.59 (m, 2H), 7.51-7.48 (m, 1H), 7.45-7.34 (m, 4H), 7.29-7.19 (m, 2H), 5.08 (s, 2H), 3.68 (s, 3H), 3.49-3.37 (m, 1H), 1.97 (s, 3H), 1.08 (d, J=7.20 Hz, 6H). LCMS Rt (min): 1.0041, m/z 482.43 [M+H]$^+$.

Example 52. 9-(4-(1H-Pyrazol-4-yl)benzyl)-2-(2-isopropylphenyl)-7,9-dihydro-8H-purin-8-one (I-539)

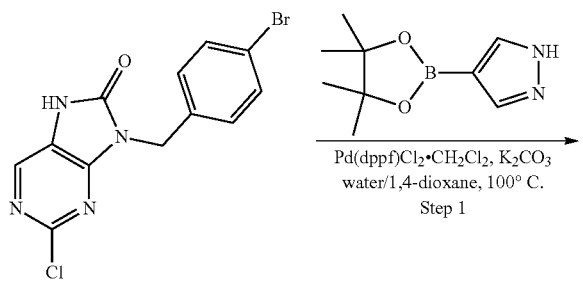

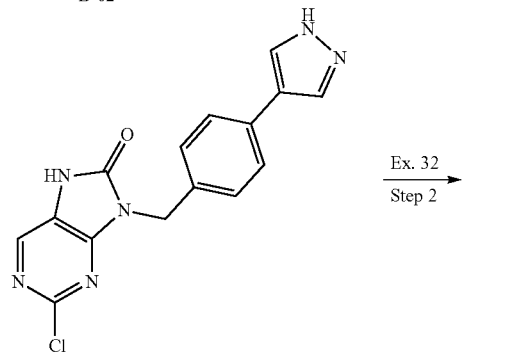

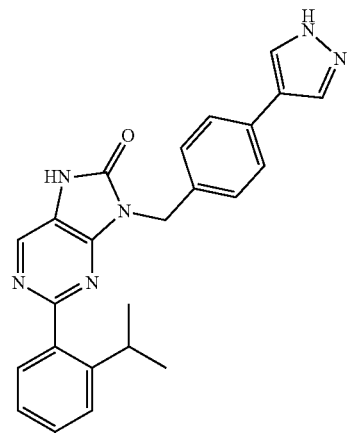

Step 1. 9-(4-(1H-Pyrazol-4-yl)benzyl)-2-chloro-7,9-dihydro-8H-purin-8-one

To a 100-mL round-bottom flask purged and maintained with an inert atmosphere of nitrogen, a mixture of Intermediate B-62 (150 mg, 0.44 mmol), 4-(4,4,5,5-tetramethyl-1,3,2-dioxaborolan-2-yl)-1H-pyrazole (103 mg, 0.53 mmol), Pd(dppf)Cl₂·CH₂Cl₂ (40 mg, 0.049 mmol), potassium carbonate (190 mg, 1.37 mmol), water (2 mL) and 1,4-dioxane (20 mL) was stirred for 24 h at 100° C. After cooled to room temperature, the reaction mixture was concentrated under vacuum and purified by silica gel chromatography (eluting with 3:1 EtOAc/PE) to give 115 mg (80%) of 9-(4-(1H-pyrazol-4-yl)benzyl)-2-chloro-7,9-dihydro-8H-purin-8-one. MS (ESI) m/z 327[M+H]⁺.

Step 2. 9-(4-(1H-Pyrazol-4-yl)benzyl)-2-(2-isopropylphenyl)-7,9-dihydro-8H-purin-8-one 9-(4-(1H-Pyrazol-4-yl)benzyl)-2-(2-isopropylphenyl)-7,9-dihydro-8H-purin-8-one (I-539) was obtained from 9-(4-(1H-pyrazol-4-yl)benzyl)-2-chloro-7,9-dihydro-8H-purin-8-one following Example 32. ¹H NMR (400 MHz, CD₃OD) δ 8.31 (s, 1H), 8.05-7.77 (m, 2H), 7.56-7.49 (m, 2H), 7.49-7.35 (m, 5H), 7.30-7.20 (m, 1H), 5.13 (s, 2H), 3.31-3.20 (m, 1H), 1.12 (d, J=6.80 Hz, 6H). LCMS Rt (min): 1.27, m/z 411.2419 [M+H]⁺.

2-(2-isopropylphenyl)-9-(4-(1-(piperidin-4-yl)-1H-pyrazol-4-yl)benzyl)-7,9-dihydro-8H-purin-8-one (I-540)

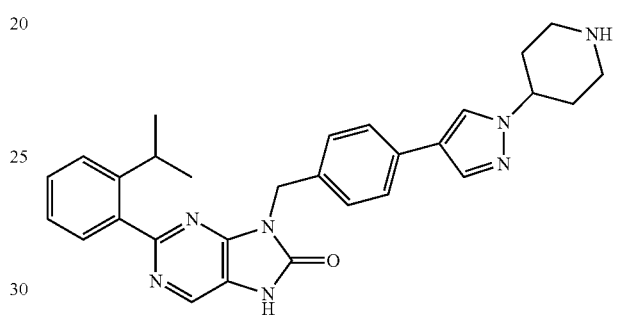

2-(2-Isopropylphenyl)-9-(4-(1-(piperidin-4-yl)-1H-pyrazol-4-yl)benzyl)-7,9-dihydro-8H-purin-8-one (I-540) was obtained from tert-butyl 4-(4-(4,4,5,5-tetramethyl-1,3,2-dioxaborolan-2-yl)-1H-pyrazol-1-yl)piperidine-1-carboxylate by sequentially following Example 51 and Example 36. ¹H-NMR (300 MHz, CD₃OD) δ 8.32 (s, 1H), 8.04 (s, 1H), 7.83 (s, 1H), 7.58-7.49 (m, 2H), 7.49-7.35 (m, 5H), 7.31-7.20 (m, 1H), 5.12 (s, 2H), 4.42-4.27 (m, 1H), 3.31-3.20 (m, 3H), 2.94-2.75 (m, 2H), 2.24-1.90 (m, 4H), 1.12 (d, J=7.2 Hz, 6H). LCMS Rt (min): 1.06, m/z 494.3673 [M+H]⁺.

2-(4-((2-(2-Isopropylphenyl)-7-methyl-8-oxo-7,8-dihydro-9H-purin-9-yl)methyl)phenyl)-1-methyl-1H-imidazole-4-carbonitrile (I-541)

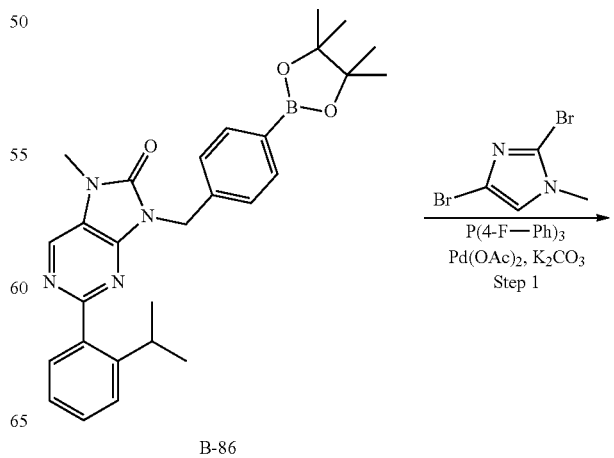

-continued

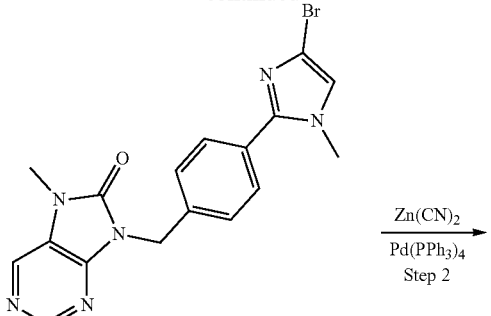

Step 1. 9-(4-(4-Bromo-1-methyl-1H-imidazol-2-yl)benzyl)-2-(2-isopropylphenyl)-7-methyl-7,9-dihydro-8H-purin-8-one Under an atmosphere of nitrogen, a solution of palladium (II) acetate (3.99 mg, 0.018 mmol) and tris(4-fluorophenyl)phosphine (11.23 mg, 0.036 mmol) in THF was added to a 1.5 mL reaction vial containing a solution of Intermediate B-86 (172 mg, 0.355 mmol), 2,4-dibromo-1-methyl-1H-imidazole (85 mg, 0.355 mmol), and potassium phosphate (377 mg, 1.775 mmol) in THF. The mixture was heated at 80° C. for 16 h, then at 110° C. for 16 h. The volatiles were removed under reduced pressure and the residue was partitioned between 1N NaOH (0.5 mL) and EtOAc (0.5 mL). The organic layer was separated and combined with a second extract of the aqueous layer using EtOAc (0.5 mL). The volatiles were removed under reduced pressure affording crude 9-(4-(4-bromo-1-methyl-1H-imidazol-2-yl)benzyl)-2-(2-isopropylphenyl)-7-methyl-7,9-dihydro-8H-purin-8-one which was used directly in the next step.

Step 2. 2-(4-((2-(2-Isopropylphenyl)-7-methyl-8-oxo-7,8-dihydro-9H-purin-9-yl)methyl) phenyl)-1-methyl-1H-imidazole-4-carbonitrile 2-(4-((2-(2-isopropylphenyl)-7-methyl-8-oxo-7,8-dihydro-9H-purin-9-yl)methyl)phenyl)-1-methyl-1H-imidazole-4-carbonitrile (I-541) was prepared as a white solid from 9-(4-(4-bromo-1-methyl-1H-imidazol-2-yl)benzyl)-2-(2-isopropylphenyl)-7-methyl-7,9-dihydro-8H-purin-8-one following Step 5 of Example 25. LCMS Rt (min): 1.5166, m/z 464.416 [M+H]$^+$ 2-(2-Cyclopropylphenyl)-9-(4-(5-(hydroxymethyl)-3-methyl-1H-pyrazol-1-yl)benzyl)-7,9-dihydro-8H-purin-8-one (I-542)

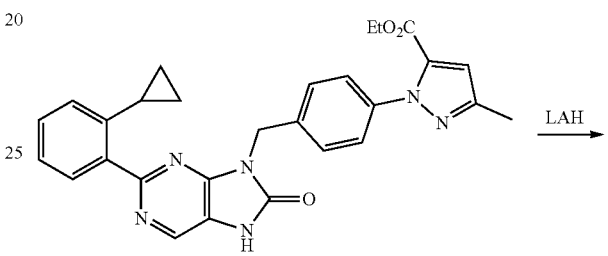

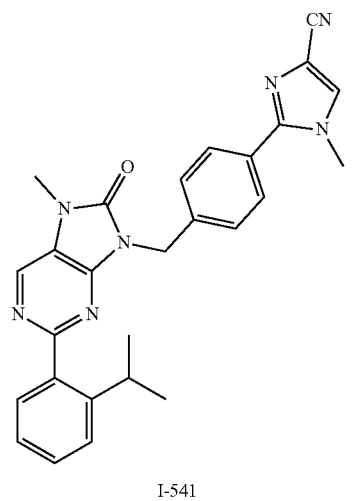

I-541

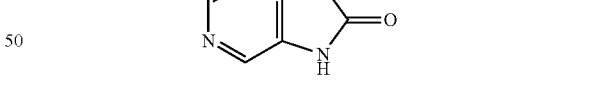

I-542

Ethyl 1-(4-((2-(2-cyclopropylphenyl)-8-oxo-7,8-dihydro-9H-purin-9-yl)methyl)phenyl)-3-methyl-1H-pyrazole-5-carboxylate (prepared from Intermediate B-33 following sequentially Examples 18 and 32) was used in the preparation of 2-(2-cyclopropylphenyl)-9-(4-(5-(hydroxymethyl)-3-methyl-H-pyrazol-1-yl)benzyl)-7,9-dihydro-8H-purin-8-one (I-542) following Example 3. $^1$H NMR (400 MHz, CD$_3$OD) δ 8.33 (s, 1H), 7.58-7.49 (m, 5H), 7.35-7.32 (m, 1H), 7.26-7.22 (m, 1H), 7.09 (d, J=7.60 Hz, 1H), 6.28 (s, 1H), 5.21 (s, 2H), 4.48 (s, 2H), 2.29-2.23 (m, 4H), 0.67-0.62 (m, 2H), 0.52-0.49 (m, 2H). LCMS Rt (min): 1.2017, m/z 453.41 [M+H]$^+$.

Methyl 4-(1-(4-((2-(2-isopropylphenyl)-8-oxo-7,8-dihydro-9H-purin-9-yl)methyl)phenyl)-1H-pyrazol-3-yl)piperidine-1-carboxylate (I-543)

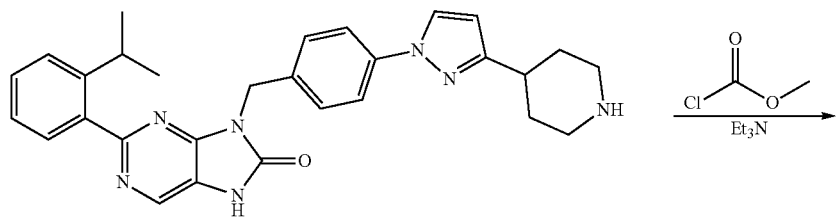

I-431

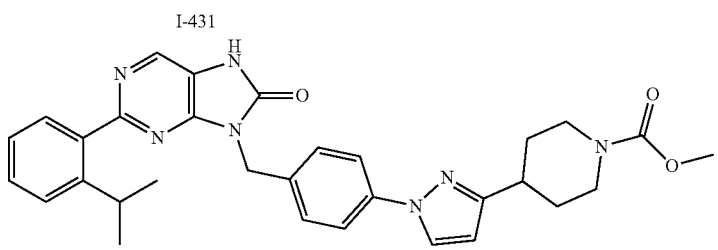

I-543

A solution of 2-(2-isopropylphenyl)-9-(4-(3-(piperidin-4-yl)-1H-pyrazol-1-yl)benzyl)-7,9-dihydro-8H-purin-8-one (I-431) (50 mg, 0.10 mmol), triethylamine (30 mg, 0.30 mmol), dichloromethane (10 mL) and methyl chloroformate (11.3 mg, 0.12 mmol) was stirred for 30 min at 0° C. then was concentrated under vacuum. The residue was purified by prep-HPLC to afford 20 mg (35%) of methyl 4-(1-(4-((2-(2-isopropylphenyl)-8-oxo-7,8-dihydro-9H-purin-9-yl)methyl)phenyl)-1H-pyrazol-3-yl)piperidine-1-carboxylate (I-543) as a white solid. $^1$H NMR (400 MHz, CDCl$_3$) δ 9.75 (br s, 1H), 8.35 (s, 1H), 7.78 (d, J=2.5 Hz, 1H), 7.59-7.56 (m, 5H), 7.47-7.41 (m, 2H), 7.31-7.26 (m, 1H), 6.24 (d, J=2.40 Hz, 1H), 5.17 (s, 2H), 4.20 (br s, 2H), 3.71 (s, 3H), 3.52-3.45 (m, 1H), 2.97-2.87 (m, 3H), 2.05-1.96 (m, 2H), 1.75-1.59 (m, 2H), 1.23 (d, J=6.80 Hz, 6H). LCMS Rt (min): 1.66, m/z 552.3149 [M+H]$^+$.

2-(2-(1-Hydroxyethyl)phenyl)-9-(4-(1-methyl-4-(trifluoromethyl)-1H-imidazol-2-yl)benzyl)-7,9-dihydro-8H-purin-8-one (I-544)

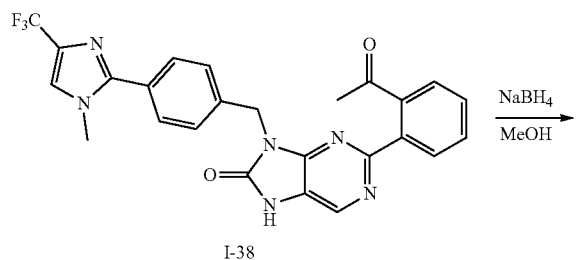

I-38

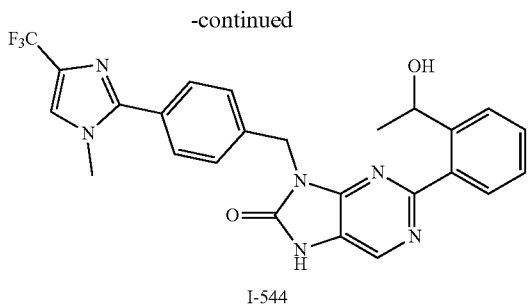

I-544

A mixture of 2-(2-acetylphenyl)-9-(4-(1-methyl-4-(trifluoromethyl)-1H-imidazol-2-yl)benzyl)-7,9-dihydro-8H-purin-8-one (I-38) (50 mg, 0.10 mmol) and methanol (1 mL) was treated with sodium borohydride (3.9 mg, 0.10 mmol) and the resulting solution was stirred for 18 h at ambient temperature. The reaction mixture was treated with water (1 mL) and was extracted with DCM (3×2 mL). The organic layers were combined, dried over anhydrous sodium sulfate, filtered and concentrated under vacuum. The residue was purified by prep-HPLC to afford 13.9 mg (28%) of 2-(2-(1-hydroxyethyl)phenyl)-9-(4-(1-methyl-4-(trifluoromethyl)-1H-imidazol-2-yl)benzyl)-7,9-dihydro-8H-purin-8-one (I-544) as an off-white solid. $^1$H NMR (300 MHz, CD$_3$OD) δ 8.38 (s, 1H), 7.75-7.60 (m, 7H), 7.52-7.47 (m, 1H), 7.41-7.38 (m, 1H), 5.27-5.23 (m, 3H), 3.78 (s, 3H), 1.40 (d, J=6.60 Hz, 3H). LCMS Rt (min): 1.2633, m/z 495.4 [M+H]$^+$.

Example 53: Ubitquin-Rhodamine 110 Assay for USP1 Activity

The HTS assay was performed in a final volume of 20 μL in assay buffer containing 20 mM Tris-HCl (pH 8.0, (1M Tris-HCl, pH 8.0 solution; Corning 46-031-CM)), 2 mM CaCl$_2$) (1M Calcium Chloride solution; Sigma #21114) 1 mM GSH (L-Glutathione reduced; Sigma #G4251), 0.01%

Prionex (0.22 µM filtered, Sigma #G-0411), and 0.01% Triton X-100. Stock compound solutions were stored at −20° C. as 10 mM in DMSO. Up to 1 month prior to the assay, 2 mM test compounds were pre-dispensed into assay plates (Black, low volume; Corning #3820) and frozen at −20° C. Prestamped assay plates were allowed to come to room temperature on the day of the assay. For the screen, 100 nL of 2 mM was pre-dispensed for a final screening concentration of 10 µM (DMSO$_{(fc)}$=0.5%). The final concentration of the enzyme (USP1, construct USP1 (1-785, GG670, 671AA)/UAF1 (1-677)-Flag; Viva) in the assay was 100 pM. Final substrate (Ub-Rh110; Ubiquitin-Rhodamine 110, R&D Systems #U-555) concentration was 25 nM with [Ub-Rh110]<<Km. 10 µL of 2× enzyme was added to assay plates (pre-stamped with compound) either simultaneously with 2× Ub-Rh110 or preincubated with USP1 40 minutes prior to the addition of 10 µL of 2× Ub-Rh110 to compound plates. Plates were incubated stacked for 45 minutes at room temperature before fluorescence was read on the Envision (Excitation at 485 nm and Emission at 535 nm; Perkin Elmer) or on the PheraSTAR (Excitation at 485 nm and Emission at 535 nm; BMG Labtech)

For follow-up IC$_{50}$ studies, each assay was performed in a final volume of 15 µL in assay buffer containing 20 mM Tris-HCl (pH 8.0, (1M Tris-HCl, pH 8.0 solution; Corning 46-031-CM)), 1 mM GSH (L-Glutathione reduced; Sigma #G4251), 0.03% BGG (0.22 µM filtered, Sigma, #G7516-25G), and 0.01% Triton X-100 (Sigma, #T9284-10L). Nanoliter quantities of either an 8-point or 10-point, 3-fold serial dilution in DMSO was pre-dispensed into assay plates (Perkin Elmer, ProxiPlate-384 F Plus, #6008269) for a final test concentration range of either 25 µM to 11 nM or 25 µM to 1.3 nM, respectively. The final concentration of the enzyme (USP1, construct USP1 (1-785, GG670, 671AA)/UAF1 (1-677)-Flag; Viva) in the assay was 25 pM. Final substrate (Ub-Rh110; Ubiquitin-Rhodamine 110, R&D Systems #U-555) concentration was 25 nM with [Ub-Rh110]<<Km. 5 µL of 2× enzyme was added to assay plates (pre-stamped with compound) preincubated with USP1 for 30 minutes and then 5 µL of 2× Ub-Rh110 was added to assay plates. Plates were incubated stacked for 20 minutes at room temperature before 5 µL of stop solution (final concentration of 10 mM citric acid in assay buffer (Sigma, #251275-500G)). Fluorescence was read on the Envision (Excitation at 485 nm and Emission at 535 nm; Perkin Elmer) or on the PheraSTAR (Excitation at 485 nm and Emission at 535 nm; BMG Labtech).

For both assay formats data were reported as percent inhibition compared with control wells based on the following equation: % inh=[1−((FLU−Ave$_{Low}$)/(Ave$_{High}$−Ave$_{Low}$))]×100 where FLU=measured Fluorescence, Ave$_{Low}$=average Fluorescence of no enzyme control (n=16), and Ave$_{High}$=average Fluorescence of DMSO control (n=16). IC$_{50}$ values were determined by curve fitting of the standard 4 parameter logistic fitting algorithm included in the Activity Base software package: IDBS XE Designer Model205. Data is fitted using the Levenburg Marquardt algorithm.

Table 19. USP1 activity of compounds of the present disclosure in the USP1 assay. ++++ indicates an IC$_{50}$ of less than about 50 nM, +++ indicates an IC$_{50}$ between about 50 nM and about 200 nM, ++ indicates an IC$_{50}$ between about 200 nM and about 2 µM, and + indicates an IC$_{50}$ greater than 2 µM.

TABLE 19

| Cmpd no. | USP1 IC$_{50}$ |
|---|---|
| I-1 | ++++ |
| I-2 | ++++ |
| I-3 | ++ |
| I-4 | + |
| I-5 | + |
| I-6 | +++ |
| I-7 | ++ |
| I-8 | ++++ |
| I-9 | ++ |
| I-10 | ++ |
| I-11 | ++++ |
| I-12 | ++ |
| I-13 | ++ |
| I-14 | +++ |
| I-15 | + |
| I-16 | + |
| I-17 | + |
| I-18 | ++ |
| I-19 | ++ |
| I-20 | ++ |
| I-21 | +++ |
| I-22 | ++ |
| I-23 | +++ |
| I-24 | +++ |
| I-25 | +++ |
| I-26 | ++++ |
| I-27 | +++ |
| I-28 | + |
| I-29 | ++ |
| I-30 | ++++ |
| I-31 | ++++ |
| I-32 | +++ |
| I-33 | ++++ |
| I-34 | ++++ |
| I-35 | ++++ |
| I-36 | ++ |
| I-37 | ++++ |
| I-38 | ++++ |
| I-39 | +++ |
| I-40 | ++++ |
| I-41 | +++ |
| I-42 | ++++ |
| I-43 | +++ |
| I-44 | ++++ |
| I-45 | ++++ |
| I-46 | ++ |
| I-47 | ++ |
| I-48 | ++++ |
| I-49 | ++++ |
| I-50 | ++++ |
| I-51 | ++++ |
| I-52 | ++++ |
| I-53 | ++++ |
| I-54 | ++ |
| I-55 | ++++ |
| I-56 | ++++ |
| I-57 | ++ |
| I-58 | ++++ |
| I-59 | +++ |
| I-60 | ++++ |
| I-61 | +++ |
| I-62 | ++ |
| I-63 | ++++ |
| I-64 | +++ |
| I-65 | ++++ |
| I-66 | ++ |
| I-67 | ++++ |
| I-68 | +++ |
| I-69 | ++++ |
| I-70 | ++++ |
| I-71 | ++++ |
| I-72 | ++ |
| I-73 | ++++ |
| I-74 | ++ |
| I-75 | +++ |
| I-76 | ++++ |
| I-77 | ++++ |

TABLE 19-continued

| Cmpd no. | USP1 IC$_{50}$ |
|---|---|
| I-78 | ++++ |
| I-79 | ++++ |
| I-80 | ++++ |
| I-81 | ++++ |
| I-82 | ++++ |
| I-83 | ++++ |
| I-84 | ++++ |
| I-85 | +++ |
| I-86 | ++ |
| I-87 | +++ |
| I-88 | ++ |
| I-89 | ++ |
| I-90 | ++++ |
| I-91 | ++++ |
| I-92 | ++ |
| I-93 | +++ |
| I-94 | ++++ |
| I-95 | ++++ |
| I-96 | ++++ |
| I-97 | ++ |
| I-98 | ++++ |
| I-99 | ++++ |
| I-100 | ++++ |
| I-101 | ++++ |
| I-102 | ++ |
| I-103 | +++ |
| I-104 | ++ |
| I-105 | ++++ |
| I-106 | ++++ |
| I-107 | ++ |
| I-108 | ++++ |
| I-109 | +++ |
| I-110 | ++++ |
| I-111 | +++ |
| I-112 | + |
| I-113 | ++++ |
| I-114 | ++++ |
| I-115 | ++++ |
| I-116 | ++++ |
| I-117 | ++++ |
| I-118 | ++++ |
| I-119 | +++ |
| I-120 | ++++ |
| I-121 | ++ |
| I-122 | ++ |
| I-123 | +++ |
| I-124 | +++ |
| I-125 | +++ |
| I-126 | ++++ |
| I-127 | +++ |
| I-128 | +++ |
| I-129 | ++++ |
| I-130 | ++++ |
| I-131 | ++++ |
| I-132 | ++++ |
| I-133 | ++ |
| I-134 | +++ |
| I-135 | +++ |
| I-136 | +++ |
| I-137 | ++++ |
| I-138 | ++++ |
| I-139 | +++ |
| I-140 | +++ |
| I-141 | ++ |
| I-142 | ++ |
| I-143 | ++ |
| I-144 | + |
| I-145 | ++++ |
| I-146 | +++ |
| I-147 | +++ |
| I-148 | ++ |
| I-149 | +++ |
| I-150 | ++++ |
| I-151 | ++ |
| I-152 | ++++ |
| I-153 | + |
| I-154 | + |
| I-155 | +++ |
| I-156 | + |
| I-157 | +++ |
| I-158 | ++++ |
| I-159 | ++ |
| I-160 | ++++ |
| I-161 | ++ |
| I-162 | +++ |
| I-163 | ++++ |
| I-164 | ++ |
| I-165 | +++ |
| I-166 | +++ |
| I-167 | ++ |
| I-168 | +++ |
| I-169 | ++++ |
| I-170 | ++++ |
| I-171 | +++ |
| I-172 | ++++ |
| I-173 | ++++ |
| I-174 | ++++ |
| I-175 | ++++ |
| I-176 | ++++ |
| I-177 | ++++ |
| I-178 | ++++ |
| I-179 | +++ |
| I-180 | +++ |
| I-181 | ++ |
| I-182 | + |
| I-183 | + |
| I-184 | ++++ |
| I-185 | ++++ |
| I-186 | +++ |
| I-187 | ++++ |
| I-188 | ++++ |
| I-189 | ++++ |
| I-190 | ++++ |
| I-191 | ++++ |
| I-192 | ++++ |
| I-193 | ++++ |
| I-194 | ++++ |
| I-195 | ++++ |
| I-196 | ++++ |
| I-197 | +++ |
| I-198 | ++++ |
| I-199 | ++++ |
| I-200 | ++++ |
| I-201 | ++++ |
| I-202 | ++++ |
| I-203 | ++++ |
| I-204 | ++++ |
| I-205 | +++ |
| I-206 | ++++ |
| I-207 | ++++ |
| I-208 | ++++ |
| I-209 | ++++ |
| I-210 | ++++ |
| I-211 | ++++ |
| I-212 | ++++ |
| I-213 | ++ |
| I-214 | ++++ |
| I-215 | ++++ |
| I-216 | +++ |
| I-217 | ++ |
| I-218 | ++ |
| I-219 | ++++ |
| I-220 | +++ |
| I-221 | ++ |
| I-222 | ++ |
| I-223 | +++ |
| I-224 | +++ |
| I-225 | +++ |
| I-226 | ++++ |
| I-227 | ++++ |
| I-228 | +++ |
| I-229 | +++ |
| I-230 | ++ |
| I-231 | ++++ |

TABLE 19-continued

| Cmpd no. | USP1 IC$_{50}$ |
|---|---|
| I-232 | ++ |
| I-233 | +++ |
| I-234 | + |
| I-235 | ++ |
| I-236 | ++++ |
| I-237 | +++ |
| I-238 | ++ |
| I-239 | + |
| I-240 | ++ |
| I-241 | ++ |
| I-242 | + |
| I-243 | ++ |
| I-244 | + |
| I-245 | + |
| I-246 | + |
| I-247 | +++ |
| I-248 | ++ |
| I-249 | ++ |
| I-250 | +++ |
| I-251 | ++ |
| I-252 | +++ |
| I-253 | ++ |
| I-254 | + |
| I-255 | +++ |
| I-256 | ++++ |
| I-257 | ++++ |
| I-258 | ++++ |
| I-259 | ++++ |
| I-260 | +++ |
| I-261 | +++ |
| I-262 | +++ |
| I-263 | ++ |
| I-264 | +++ |
| I-265 | ++ |
| I-266 | +++ |
| I-267 | ++ |
| I-268 | +++ |
| I-269 | ++++ |
| I-270 | ++ |
| I-271 | ++++ |
| I-272 | +++ |
| I-273 | ++++ |
| I-274 | +++ |
| I-275 | ++++ |
| I-276 | ++++ |
| I-277 | ++++ |
| I-278 | +++ |
| I-279 | ++++ |
| I-280 | ++++ |
| I-281 | ++++ |
| I-282 | +++ |
| I-283 | ++++ |
| I-284 | ++ |
| I-285 | ++ |
| I-286 | ++++ |
| I-287 | ++++ |
| I-288 | ++ |
| I-289 | ++++ |
| I-290 | ++++ |
| I-291 | ++++ |
| I-292 | +++ |
| I-293 | ++++ |
| I-294 | ++++ |
| I-295 | ++++ |
| I-296 | ++++ |
| I-297 | ++ |
| I-298 | + |
| I-299 | +++ |
| I-300 | ++++ |
| I-301 | ++++ |
| I-302 | ++++ |
| I-303 | ++++ |
| I-304 | ++++ |
| I-305 | ++++ |
| I-306 | ++++ |
| I-307 | ++++ |
| I-308 | ++++ |
| I-309 | ++++ |
| I-310 | ++++ |
| I-311 | ++++ |
| I-312 | ++++ |
| I-313 | ++++ |
| I-314 | ++++ |
| I-315 | ++++ |
| I-316 | +++ |
| I-317 | +++ |
| I-318 | ++ |
| I-319 | ++ |
| I-320 | +++ |
| I-321 | ++ |
| I-322 | +++ |
| I-323 | ++++ |
| I-324 | ++++ |
| I-325 | ++++ |
| I-326 | ++++ |
| I-327 | +++ |
| I-328 | ++ |
| I-329 | ++++ |
| I-330 | +++ |
| I-331 | ++++ |
| I-332 | ++++ |
| I-333 | +++ |
| I-334 | ++++ |
| I-335 | +++ |
| I-336 | ++++ |
| I-337 | ++++ |
| I-338 | + |
| I-339 | + |
| I-340 | ++ |
| I-341 | ++ |
| I-342 | ++ |
| I-343 | +++ |
| I-344 | ++ |
| I-345 | ++ |
| I-346 | + |
| I-347 | + |
| I-348 | + |
| I-349 | ++ |
| I-350 | + |
| I-351 | +++ |
| I-352 | ++ |
| I-353 | +++ |
| I-354 | +++ |
| I-355 | ++++ |
| I-356 | ++++ |
| I-357 | +++ |
| I-358 | +++ |
| I-359 | +++ |
| I-360 | ++ |
| I-361 | ++ |
| I-362 | ++++ |
| I-363 | +++ |
| I-364 | ++++ |
| I-365 | +++ |
| I-366 | +++ |
| I-367 | +++ |
| I-368 | +++ |
| I-369 | ++++ |
| I-370 | +++ |
| I-371 | +++ |
| I-372 | +++ |
| I-373 | ++++ |
| I-374 | ++++ |
| I-375 | ++++ |
| I-376 | ++ |
| I-377 | + |
| I-378 | ++ |
| I-379 | ++++ |
| I-380 | +++ |
| I-381 | ++ |
| I-382 | ++ |
| I-383 | ++ |
| I-384 | ++ |
| I-385 | +++ |

TABLE 19-continued

| Cmpd no. | USP1 IC$_{50}$ |
|---|---|
| I-386 | +++ |
| I-387 | +++ |
| I-388 | ++ |
| I-389 | ++++ |
| I-390 | ++++ |
| I-391 | ++++ |
| I-392 | ++++ |
| I-393 | ++ |
| I-394 | ++ |
| I-395 | ++++ |
| I-396 | ++ |
| I-397 | ++++ |
| I-398 | ++++ |
| I-399 | ++++ |
| I-400 | +++ |
| I-401 | +++ |
| I-402 | ++ |
| I-403 | ++ |
| I-404 | ++ |
| I-405 | ++ |
| I-406 | +++ |
| I-407 | +++ |
| I-408 | + |
| I-409 | + |
| I-410 | + |
| I-411 | ++++ |
| I-412 | ++++ |
| I-413 | ++++ |
| I-414 | ++++ |
| I-415 | ++++ |
| I-416 | ++++ |
| I-417 | ++++ |
| I-418 | ++++ |
| I-419 | ++++ |
| I-420 | ++++ |
| I-421 | ++++ |
| I-422 | ++++ |
| I-423 | +++ |
| I-424 | ++++ |
| I-425 | ++++ |
| I-426 | ++++ |
| I-427 | ++++ |
| I-428 | +++ |
| I-429 | ++ |
| I-430 | ++++ |
| I-431 | +++ |
| I-432 | ++ |
| I-433 | ++ |
| I-434 | +++ |
| I-435 | + |
| I-436 | ++++ |
| I-437 | ++++ |
| I-438 | ++++ |
| I-439 | +++ |
| I-440 | ++ |
| I-441 | +++ |
| I-442 | + |
| I-443 | ++ |
| I-444 | ++++ |
| I-445 | ++++ |
| I-446 | ++++ |
| I-447 | ++++ |
| I-448 | ++++ |
| I-449 | + |
| I-450 | +++ |
| I-451 | ++ |
| I-452 | ++ |
| I-453 | + |
| I-454 | ++ |
| I-455 | + |
| I-456 | +++ |
| I-457 | +++ |
| I-458 | ++ |
| I-459 | ++ |
| I-460 | ++ |
| I-461 | +++ |
| I-462 | + |
| I-463 | ++++ |
| I-464 | +++ |
| I-465 | ++ |
| I-466 | ++ |
| I-467 | +++ |
| I-468 | ++++ |
| I-469 | ++ |
| I-470 | + |
| I-471 | + |
| I-472 | ++++ |
| I-473 | ++++ |
| I-474 | ++++ |
| I-475 | + |
| I-476 | ++++ |
| I-477 | ++++ |
| I-478 | + |
| I-479 | + |
| I-480 | ++++ |
| I-481 | +++ |
| I-482 | ++ |
| I-483 | ++ |
| I-484 | ++ |
| I-485 | + |
| I-486 | ++ |
| I-487 | + |
| I-488 | +++ |
| I-489 | +++ |
| I-490 | ++ |
| I-491 | ++ |
| I-492 | + |
| I-493 | + |
| I-494 | +++ |
| I-495 | ++ |
| I-496 | ++++ |
| I-497 | ++++ |
| I-498 | ++++ |
| I-499 | ++++ |
| I-500 | ++++ |
| I-501 | +++ |
| I-502 | + |
| I-503 | ++++ |
| I-504 | +++ |
| I-505 | ++ |
| I-506 | ++++ |
| I-507 | ++++ |
| I-508 | + |
| I-509 | + |
| I-510 | +++ |
| I-511 | ++ |
| I-512 | +++ |
| I-513 | + |
| I-514 | ++++ |
| I-515 | +++ |
| I-516 | + |
| I-517 | + |
| I-518 | +++ |
| I-519 | ++ |
| I-520 | ++ |
| I-521 | ++ |
| I-522 | ++ |
| I-523 | +++ |
| I-524 | ++++ |
| I-525 | ++++ |
| I-526 | ++++ |
| I-527 | ++ |
| I-528 | ++ |
| I-529 | +++ |
| I-530 | ++ |
| I-531 | ++++ |
| I-532 | ++++ |
| I-533 | ++++ |
| I-534 | +++ |
| I-535 | ++++ |
| I-536 | ++++ |
| I-537 | ++++ |
| I-538 | +++ |
| I-539 | ++ |

TABLE 19-continued

| Cmpd no. | USP1 IC$_{50}$ |
|---|---|
| I-540 | ++ |
| I-541 | ++++ |
| I-542 | ++++ |
| I-543 | ++++ |
| I-544 | +++ |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound I-2:

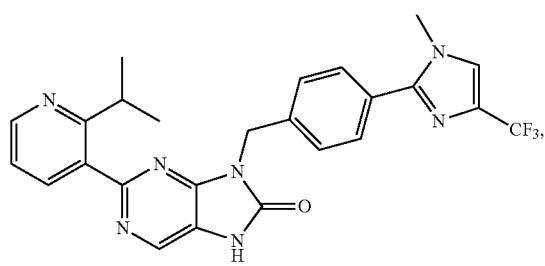
(I-2)

or a pharmaceutically acceptable salt thereof.

2. A pharmaceutical composition comprising the compound of claim 1, or a pharmaceutically acceptable salt thereof, and a pharmaceutically acceptable carrier in a unit dosage form.

3. A composition comprising a compound I-2:

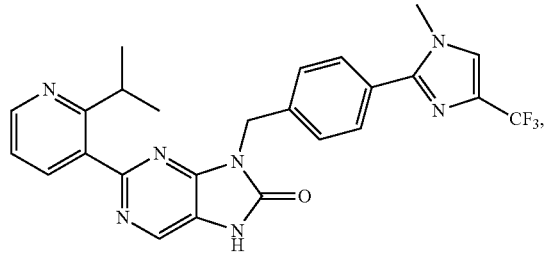
(I-2)

or a pharmaceutically acceptable salt thereof, wherein the compound I-2 is obtained by a process comprising a step of treating a compound B-49:

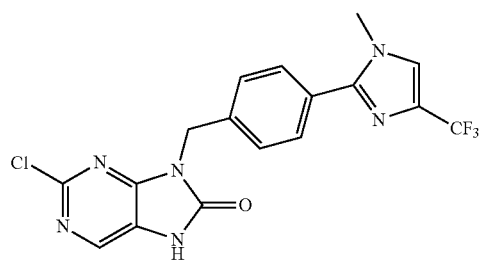
(B-49)

with a compound B-2:

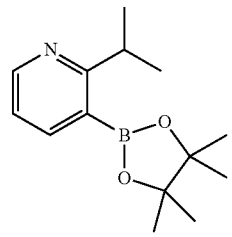
(B-2)

in the presence of a first base and a catalytic amount of a palladium catalyst to provide the compound I-2.

4. The composition of claim 3, wherein the first base is K$_2$CO$_3$.

5. The composition of claim 3, wherein the palladium catalyst is Pd(dppf)Cl$_2$.CH$_2$Cl$_2$.

6. The composition of claim 3, wherein the process further comprises a step of treating a compound:

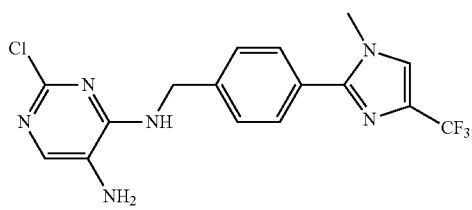 [SMILES: Cn1cc(C(F)(F)F)nc1-c1ccc(CNc2nc(Cl)ncc2[N+](=O)[O-])cc1]

with carbonyldiimidazole (CDI) to provide the compound B-49.

7. The composition of claim 6, wherein the process further comprises a step of treating a compound:

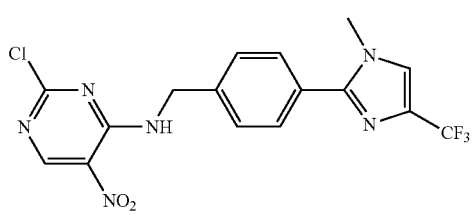

with a metal and ammonium chloride to provide the compound:

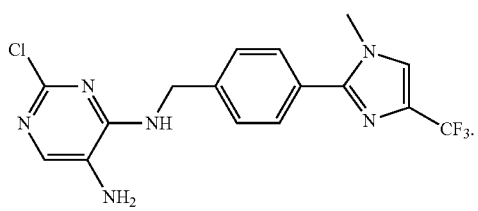 [SMILES: Cn1cc(C(F)(F)F)nc1-c1ccc(CNc2nc(Cl)ncc2N)cc1]

8. The composition of claim 7, wherein the metal is iron powder.

9. The composition of claim 7, wherein the process further comprises a step of treating a compound B-23:

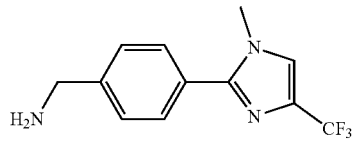

(B-23)

with a compound:

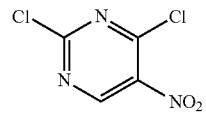

in the presence of a second base to provide the compound:

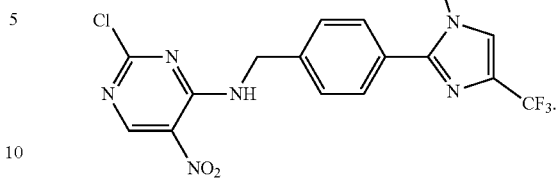

10. The composition of claim 9, wherein the second base is N,N-diisopropylethylamine (DIEA).

11. A composition comprising a compound I-2:

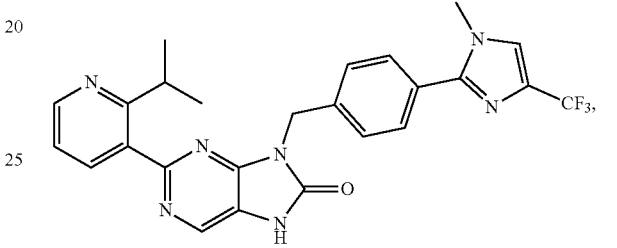

(I-2)

or a pharmaceutically acceptable salt thereof, and a pharmaceutically acceptable carrier.

* * * * *